US009440952B2

(12) United States Patent
Miller et al.

(10) Patent No.: US 9,440,952 B2
(45) Date of Patent: Sep. 13, 2016

(54) COMPOUNDS INHIBITING LEUCINE-RICH REPEAT KINASE ENZYME ACTIVITY

(71) Applicant: Merck Sharp & Dohme Corp., Rahway, NJ (US)

(72) Inventors: Michael Miller, Scotch Plains, NJ (US); Kallol Basu, Hillsborough, NJ (US); Duane DeMong, Somerset, NJ (US); Jack Scott, Scotch Plains, NJ (US); Hong Liu, Hillsborough, NJ (US); Xing Dai, Cranford, NJ (US); Joel M. Harris, Blaine, MN (US); Bernard Neustadt, West Orange, NJ (US); Andrew Stamford, Chatham, NJ (US); Marc Poirier, Stewartsville, NJ (US); John A. McCauley, Maple Glen, PA (US); Thomas Greshock, Harleysville, PA (US); Heather Stevenson, Ardmore, PA (US); John Sanders, Hatfield, PA (US); Jonathan Kern, West Point, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/772,589

(22) PCT Filed: Feb. 27, 2014

(86) PCT No.: PCT/US2014/018929
§ 371 (c)(1),
(2) Date: Sep. 3, 2015

(87) PCT Pub. No.: WO2014/137728
PCT Pub. Date: Sep. 12, 2014

(65) Prior Publication Data
US 2016/0009682 A1  Jan. 14, 2016

Related U.S. Application Data

(60) Provisional application No. 61/772,009, filed on Mar. 4, 2013.

(51) Int. Cl.
*C07D 401/04* (2006.01)
*C07D 401/14* (2006.01)
*C07D 405/14* (2006.01)
*C07D 409/14* (2006.01)
*C07D 413/14* (2006.01)
*C07D 417/14* (2006.01)
*C07D 471/10* (2006.01)
*C07D 451/02* (2006.01)
*C07D 487/10* (2006.01)
*C07D 491/04* (2006.01)
*C07D 491/08* (2006.01)
*C07D 491/056* (2006.01)
*C07D 498/04* (2006.01)
*C07D 498/08* (2006.01)
*C07D 403/04* (2006.01)
*C07D 491/10* (2006.01)
*C07D 487/04* (2006.01)
*C07D 491/107* (2006.01)
*C07D 491/113* (2006.01)

(52) U.S. Cl.
CPC .......... *C07D 401/04* (2013.01); *C07D 401/14* (2013.01); *C07D 403/04* (2013.01); *C07D 405/14* (2013.01); *C07D 409/14* (2013.01); *C07D 413/14* (2013.01); *C07D 417/14* (2013.01); *C07D 451/02* (2013.01); *C07D 471/10* (2013.01); *C07D 487/04* (2013.01); *C07D 487/10* (2013.01); *C07D 491/04* (2013.01); *C07D 491/056* (2013.01); *C07D 491/08* (2013.01); *C07D 491/10* (2013.01); *C07D 491/107* (2013.01); *C07D 491/113* (2013.01); *C07D 498/04* (2013.01); *C07D 498/08* (2013.01)

(58) Field of Classification Search
CPC  C07D 401/04; C07D 401/14; C07D 405/14; C07D 409/14; C07D 413/14; C07D 417/14; C07D 451/03; C07D 471/10; C07D 487/10; C07D 491/04; C07D 491/08; C07D 491/056; C07D 498/04; C07D 498/08
See application file for complete search history.

(56) References Cited

U.S. PATENT DOCUMENTS

| | | | |
|---|---|---|---|
| 7,211,594 B2 * | 5/2007 | Bhagwat | A61K 31/416 514/381 |
| 7,776,890 B2 | 8/2010 | Oinuma et al. | |
| 2004/0127536 A1 | 7/2004 | Bhagwat et al. | |
| 2006/0079564 A1 | 4/2006 | Jansen et al. | |
| 2009/0203690 A1 | 8/2009 | Akritopoulou-Zanze et al. | |
| 2009/0221602 A1 | 9/2009 | Charrier et al. | |
| 2012/0329780 A1 | 12/2012 | Thormann et al. | |

FOREIGN PATENT DOCUMENTS

| | | |
|---|---|---|
| EP | 1380576 B1 | 1/2004 |
| EP | 1510516 | 3/2005 |

(Continued)

OTHER PUBLICATIONS

Buckley et al., Bioorg. Med. Chem. Lett. 18 (2008) 3291-3295.*

*Primary Examiner* — Rebecca Anderson
(74) *Attorney, Agent, or Firm* — Keith D. MacMillan; John C. Todaro

(57) ABSTRACT

The present invention is directed to indazole compounds which are potent inhibitors of LRRK2 kinase and useful in the treatment or prevention of diseases in which the LRRK2 kinase is involved, such as Parkinson's Disease. The invention is also directed to pharmaceutical compositions comprising these compounds and the use of these compounds and compositions in the prevention or treatment of such diseases in which LRRK-2 kinase is involved.

19 Claims, No Drawings

(56) References Cited

FOREIGN PATENT DOCUMENTS

| WO | 0153268 A2 | 7/2001 |
|---|---|---|
| WO | 0210137 | 2/2002 |
| WO | 02083648 | 10/2002 |
| WO | 03035005 | 5/2003 |
| WO | 2006081230 | 8/2006 |
| WO | 2008068171 | 6/2008 |
| WO | 2008137105 | 11/2008 |
| WO | 2008154241 | 12/2008 |
| WO | 2009054984 | 4/2009 |
| WO | 2010017046 A1 | 2/2010 |
| WO | 2010083145 A1 | 7/2010 |
| WO | 2011141756 | 11/2011 |
| WO | 2012038743 | 3/2012 |
| WO | 2012058193 | 5/2012 |
| WO | 2012078777 | 6/2012 |
| WO | 2014137719 A1 | 9/2014 |
| WO | 2014137723 A1 | 9/2014 |
| WO | 2014137725 A1 | 9/2014 |
| WO | 2014137728 | 9/2014 |
| WO | 2015026683 A1 | 2/2015 |
| WO | 2015073344 A1 | 5/2015 |
| WO | 2016036586 A1 | 3/2016 |

* cited by examiner

COMPOUNDS INHIBITING LEUCINE-RICH REPEAT KINASE ENZYME ACTIVITY

CROSS-REFERENCE TO RELATED APPLICATIONS

This Application is a U.S. National Stage Application under 35 U.S.C. 371 of PCT Application No. PCT/US2014/018929, filed Feb. 27, 2014, which claims priority to U.S. Provisional Application Ser. No. 61/772,009, filed Mar. 4, 2013.

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 protein has also been demonstrated to be associated with Lewy bodies, a pathological hallmark of PD as well as other neurodegenerative diseases such as Lewy body dementia (Zhu et al., Molecular Neurodegeneration, Vol 30, 2006, pp. 1-17) thereby suggesting that LRRK2 may be associated with the pathogenesis of these diseases.

A growing body of evidence also suggests a role for LRRK2 in immune cell function in the brain with LRRK2 inhibition demonstrated to attenuate microglial inflammatory responses (Moehle et al., The Journal of Neuroscience Vol 32, 2012, pp. 1602-1611). Neuroinflammation is a hallmark of a number of neurodegenerative diseases such as PD and Alzheimer's disease, thereby suggesting that LRRK2 inhibitors may have utility in the treatment of neuroinflammation in these disorders.

Genome-wide association studies also highlight LRRK2 in the modification of susceptibility to the chronic autoimmune Crohn's disease and leprosy (Zhang et al., The New England Journal of Medicine, Vol 361, 2009, pp. 2609-2618; Umeno et al., Inflammatory Bowel Disease Vol 17, 2011, pp. 2407-2415). LRRK2 is also associated with certain types of cancer, e.g. melanoma as well as renal and thyroid carcinomas (Saunders-Pullman et al., Movement Disorders, Vol 25, 2010, pp. 2536-2541; Looyenga, et al., Proceedings of the National Academy of Sciences, USA, Vol 108, 2011, pp. 1439-1444).

Accordingly, compounds and compositions effective at modulating LRRK2 activity may provide a treatment for neurodegenerative diseases such as Parkinson's disease, Lewy body dementia, neuroinflammation, and for disease such as Crohn's disease, leprosy and cancer.

SUMMARY OF THE INVENTION

The present invention is directed to indazole compounds which are potent inhibitors of LRRK2 kinase and may be useful in the treatment or prevention of diseases in which the LRRK2 kinase is involved, such as Parkinson's Disease. The invention is also directed to pharmaceutical compositions comprising these compounds and the use of these compounds and compositions in the prevention or treatment of such diseases in which LRRK-2 kinase is involved.

DETAILED DESCRIPTION OF THE INVENTION

The present invention is directed to compounds of Formula I:

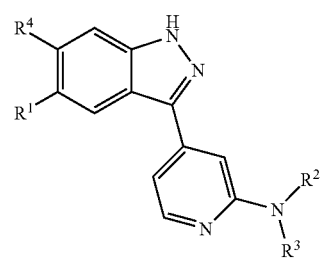

or a pharmaceutically acceptable salt thereof, wherein:
$R^1$ is selected from the group consisting of:
  a) hydrogen,
  b) halo,
  c) cyano,
  d) hydroxyl,
  e) $C_{2-6}$ alkenyl, which is optionally substituted with one to three substitutents independently selected from the group consisting of halo, cyano and $R^5$;
  f) $OC_{2-6}$ alkenyl, which is optionally substituted with one to three substitutents independently selected from the group consisting of halo, cyano and $R^5$;
  g) $R^5$,
  h) $OR^5$,
  i) $R^7$,
  j) $S(O)_m R^5$,
  k) $S(O)_m R^7$,
  l) $(C=O)R^7$,
  m) $(C=O)R^5$,
  n) $(C=O)OR^5$, and
  o) $NR^cR^d$;
$R^2$ is selected from the group consisting of hydrogen and $C_{1-6}$ alkyl, which is optionally substituted with one to three substitutents independently selected from the group consisting of:
  a) halo,
  b) cyano,
  c) $R^5$,
  d) $R^7$,
  e) $OR^5$, and
  f) $NR^cR^d$;
$R^3$ is selected from the group consisting of:
  a) hydrogen,
  b) $C_{1-6}$ alkyl, which is optionally substituted with one to three substitutents independently selected from the group consisting of halo, cyano, $OR^5$ and $NR^cR^d$,
  c) $C_{3-8}$ cycloalkyl, which is optionally substituted with one to three substitutents independently selected from the group consisting of halo, cyano, $OR^5$ and $NR^cR^d$,
  d) heterocyclyl, which is optionally substituted with one to three substitutents independently selected from the group consisting of halo, cyano, oxo, $R^5$, $OR^5$ and $NR^cR^d$,
  e) heteroaryl, which is optionally substituted with one to three substitutents independently selected from the group consisting of halo, cyano, oxo, $R^5$, $OR^5$ and $NR^cR^d$,
  f) $C_{4-8}$ cycloalkenyl, which is optionally substituted with one to three substitutents independently selected from the group consisting of halo, cyano, $OR^5$ and $NR^cR^d$,
  g) $(C=O)R^7$,
  h) $(C=O)R^5$,
  i) $S(O)_mR^5$, and
  j) $S(O)_mR^7$;
or $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) cyano,
  d) $OR^5$,
  e) $NR^cR^d$,
  f) $SO_3H$,
  g) $S(O)_mR^5$,
  h) $S(O)_mR^7$
  i) $R^5$,
  j) $R^6$,
  k) $R^7$,
  l) $(C=O)R^5$,
  m) $(C=O)OR^5$,
  n) $(C=O)R^7$, and
  o) $(C=O)NR^cR^d$;
$R^4$ is selected from the group consisting of hydrogen, halo, cyano, $OR^5$, aryl, heteroaryl, $C_{3-8}$ cycloalkyl, $C_{4-8}$ cycloalkenyl, $C_{4-8}$ heterocyclyl and $C_{1-6}$ alkyl, which is optionally substituted with one to three substitutents independently selected from the group consisting of halo, cyano, $OC_{1-3}$ alkyl, $NR^cR^d$ and hydroxyl;
or $R^1$ and $R^4$ can be taken together with the atoms to which they are attached to form a 5 to 10 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) cyano,
  d) $R^5$, and
  e) $R^7$;
$R^5$ is selected from the group consisting of hydrogen and $C_{1-6}$ alkyl, which is optionally substituted with one to three substitutents independently selected from the group consisting of:
  a) halo,
  b) hydroxyl,
  c) $OC_{1-6}$ alkyl,
  d) $NR^cR^d$,
  e) $(C=O)NR^cR^d$,
  f) $S(O)_mR^8$,
  g) $S(O)_mR^7$,
  h) $R^7$, and
  i) $OR^7$;
$R^6$ is $C_{1-6}$ alkyl, which is optionally substituted with one to three substitutents independently selected from the group consisting of halo and hydroxyl;
or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of:
  a) halo,
  b) oxo,
  c) cyano,
  d) hydroxyl,
  e) $C_{1-3}$ alkyl, which is optionally substituted with one to three halo,
  f) $C_{3-8}$ cycloalkyl,
  g) $OC_{1-3}$ alkyl, which is optionally substituted with one to three halo, and
  h) $OC_{3-8}$ cycloalkyl;
$R^7$ is selected from the group consisting of $C_{4-8}$ heterocyclyl, $C_{3-8}$ cycloalkyl, $C_{4-8}$ cycloalkenyl, aryl or heteroaryl, wherein said heterocyclyl, cycloalkyl, cycloalkenyl, aryl and heteroaryl groups are optionally substituted with one to three substituents independently selected from the group consisting of:
  a) halo,
  b) cyano,
  c) hydroxyl,
  d) oxo,
  e) $C_{1-3}$ alkyl, which is optionally substituted with one to four substituents independently selected from the group consisting of hydroxyl, halo, cyano, heterocyclyl, $OC_{1-3}$ alkyl and $NR^cR^d$,
  f) $OC_{1-3}$ alkyl, which is optionally substituted with one to four substituents independently selected from the group consisting of hydroxyl, halo, cyano, heterocyclyl, $OC_{1-3}$ alkyl $NR^cR^d$ and aryl,
  g) $C_{3-8}$ cycloalkyl, which is optionally substituted with one to four substituents independently selected from the group consisting of hydroxyl, halo, cyano, heterocyclyl, $OC_{1-3}$ alkyl and $NR^cR^d$,
  h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
  i) heteroaryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
  j) heterocyclyl, which is optionally substituted with one to four substituents independently selected from the group consisting of hydroxyl, halo, cyano, $OC_{1-3}$ alkyl and $NR^cR^d$,
  k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$;

$R^8$ is hydrogen or $C_{1-6}$ alkyl, which is optionally substituted with one to three substituents independently selected from the group consisting of:
  a) halo,
  b) cyano,
  c) hydroxyl,
  d) $OC_{1-3}$ alkyl, which is optionally substituted with one to four substituents independently selected from the group consisting of hydroxyl, halo and $NR^cR^d$, and
  e) $C_{3-8}$ cycloalkyl;

$R^c$ is selected from the group consisting of:
  a) hydrogen and
  b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl$)_2$, $OC_{1-6}$ alkyl, and $C_{3-8}$ cycloalkyl;

$R^d$ is selected from the group consisting of:
  a) hydrogen,
  b) $C_{3-8}$ cycloalkyl,
  c) $C_{3-6}$ heterocyclyl,
  d) $C_{1-3}$ alkyl,
  e) (C=O)$C_{1-3}$ alkyl,
  f) aryl, and
  g) heteroaryl;

wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl;

or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl; m is an integer from zero to two.

In a class of the invention, $R^1$ is selected from the group consisting of $R^5$, $OR^5$ and $R^7$. In a subclass of the invention, $R^1$ is selected from the group consisting of $OR^5$ and $R^7$. In another subclass of the invention, $R^1$ is $R^5$. In another subclass of the invention, $R^1$ is $OR^5$. In another subclass of the invention, $R^1$ is and $R^7$. In another subclass of the invention, $R^1$ is selected from the group consisting of: $OC_{1-3}$ alkyl, aryl and heteroaryl, wherein said aryl and heteroaryl groups are optionally substituted with one to three substituents independently selected from the group consisting of halo, hydroxyl, $C_{1-3}$ alkyl and $OC_{1-3}$ alkyl.

In a class of the invention, $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) cyano,
  d) $OR^5$,
  e) $NR^cR^d$,
  f) $SO_3H$
  g) $S(O)_mR^5$,
  h) $S(O)_mR^7$,
  i) $R^5$,
  j) $R^6$,
  k) $R^7$,
  l) (C=O)$R^5$,
  m) (C=O)$OR^5$,
  n) (C=O)$R^7$, and
  o) (C=O)$NR^cR^d$.

In a subclass of the invention, $R^2$ and $R^3$ can be taken together with the atoms to which they are attached to form a 6 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) $OR^5$,
  d) $NR^cR^d$,
  e) $S(O)_mR^5$,
  f) $S(O)_mR^7$,
  g) $R^5$,
  h) $R^6$,
  i) $R^7$,
  j) (C=O)$R^5$,
  k) (C=O)$OR^5$, and
  l) (C=O)$R^7$.

In a class of the invention, $R^4$ is selected from the group consisting of hydrogen and halo. In a subclass of the invention, $R^4$ is hydrogen. In a subclass of the invention, $R^4$ is halo.

In a class of the invention, $R^5$ is selected from the group consisting of hydrogen or $C_{1-6}$ alkyl. In a subclass of the invention, $R^5$ is hydrogen. In another subclass of the invention, $R^5$ is $C_{1-6}$ alkyl.

In a class of the invention, $R^6$ is $C_{1-6}$ alkyl.

In a class of the invention, $R^8$ is selected from the group consisting of hydrogen or $C_{1-6}$ alkyl. In a subclass of the invention, $R^8$ is hydrogen. In another subclass of the invention, $R^8$ is $C_{1-6}$ alkyl.

In a class of the invention, $R^c$ is selected from the group consisting of hydrogen or $C_{1-3}$ alkyl. In a subclass of the invention, $R^c$ is hydrogen. In another subclass of the invention, $R^c$ is $C_{1-3}$ alkyl.

In a class of the invention, $R^d$ is hydrogen.

Reference to the preferred classes and subclasses set forth above is meant to include all combinations of particular and preferred groups unless stated otherwise.

Specific embodiments of the present invention include, but are not limited to the compounds identified herein as Examples 1 to 402, or pharmaceutically acceptable salts thereof.

The invention also encompasses a pharmaceutical composition which comprises an inert carrier and the compound of Formula I, or a pharmaceutically acceptable salt thereof.

The invention may also encompass a method of treating Parkinson's Disease in a mammalian patient in need of such treatment, which comprises administering to the patient a therapeutically effective amount of the compound of Formula I, or a pharmaceutically acceptable salt thereof.

The invention may also encompass the use of a compound of Formula I, or a pharmaceutically acceptable salt thereof, and a pharmaceutically acceptable carrier, for the manufacture of a medicament for the treatment of Parkinson's Disease.

The invention is also directed to medicaments or pharmaceutical compositions which may be useful for treating diseases or disorders in which LRRK2 is involved, such as Parkinson's Disease, which comprise a compound of Formula I, or a pharmaceutically acceptable salt thereof, and a pharmaceutically acceptable carrier.

The invention is also directed to the use of a compound of Formula I which may be useful for treating diseases or disorders in which LRRK2 is involved, such as Parkinson's Disease.

The invention is further directed to a method for the manufacture of a medicament or a composition which may be useful for treating diseases or disorders in which LRRK2 is involved, such as Parkinson's Disease, comprising combining a compound of Formula I with one or more pharmaceutically acceptable carriers.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Tautomers of compounds defined in Formula I are also included within the scope of the present invention. For example, compounds including carbonyl —CH2C(O)— groups (keto forms) may undergo tautomerism to form hydroxyl —CH=C(OH)— groups (enol forms). Both keto and enol forms are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

As used herein, "alkyl" is intended to mean linear or branched structures having no carbon-to-carbon double or triple bonds. Thus, $C_{1-4}$ alkyl is defined to identify the group as having 1, 2, 3 or 4 carbons in a linear or branched arrangement, such that $C_{1-4}$ alkyl specifically includes, but is not limited to, methyl, ethyl, n-propyl, iso-propyl, n-butyl, iso-butyl and tert-butyl.

As appreciated by those of skill in the art, "halo" or "halogen" as used herein is intended to include chloro (Cl), fluoro (F), bromo (Br) and iodo (I).

The term "cycloalkyl" shall mean cyclic rings of alkanes of three to eight total carbon atoms, unless otherwise indicated, or any number within this range (i.e., cyclopropyl, cyclobutyl, cyclopentyl, cyclohexyl, cycloheptyl, methylcyclopropyl, 2,2-dimethyl-cyclobutyl, 2-ethyl-cyclopentyl or cyclooctyl) and also includes bicyclic or fused spirocyclic compounds.

The term "cycloalkenyl" shall mean cyclic rings of four to eight total carbon atoms, unless otherwise indicated, or any number within this range where one or two degrees of unsaturation are present. Non-limiting examples of said cycloalkenyl groups are: cyclohexenyl, cyclopentenyl, cyclooctadienyl.

The term "carbocycle" shall mean cyclic rings of three to eight total carbon atoms, unless otherwise indicated, or any number within this range, where zero, one or two degrees of unsaturation are present and where said "carbocycle" can be bicyclic or fused spirocyclic in nature. Non-limiting examples of said carbocyclyl groups are: cyclohexenyl, cyclopentenyl, cyclooctadienyl, cyclohexyl or cyclopropyl.

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "C2-C6 alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. The heterocyclic group also includes rings that possess one or two degrees of unsaturation. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also emcompassed by this definition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which may be selected from the group consisting of the compounds disclosed in the following Examples and pharmaceutically acceptable salts thereof and individual diastereomers thereof.

The subject compounds are useful in a method of inhibition of LRRK2 receptors in a patient such as a mammal in need of such antagonism comprising the administration of an effective amount of the compound. The present invention is directed to the use of the compounds disclosed herein as inhibitors of LRRK2 receptors. In addition to primates, especially humans, a variety of other mammals can be treated according to the method of the present invention.

Another embodiment of the present invention is directed to a method for the treatment, control, amelioration, or reduction of risk of a disease or disorder in which the LRRK2 kinase is involved in a patient that comprises administering to the patient a therapeutically effective amount of a compound that is an inhibitor of LRRK2 kinase.

The present invention is further directed to a method for the manufacture of a medicament for inhibition of LRRK2 receptors activity in humans and animals comprising combining a compound of the present invention with a pharmaceutical carrier or diluent.

The subject treated in the present methods is generally a mammal, for example a human being, male or female, in whom inhibition of LRRK2 kinase activity is desired. The term "therapeutically effective amount" means the amount of the subject compound that will elicit the biological or medical response of a tissue, system, animal or human that is being sought by the researcher, veterinarian, medical doctor or other clinician.

The terms "treating" or "treatment" of a disease as used herein includes: inhibiting the disease, i.e., arresting or reducing the development of the disease or its clinical symptoms; or relieving the disease, i.e., causing regression of the disease or its clinical symptoms. The term "preventing" or "prevention" of a disease as used herein includes: causing the clinical symptoms of the disease not to develop in a mammal that may be exposed to or predisposed to the disease but does not yet experience or display symptoms of the disease, and the like.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as LRRK2 kinase inhibitors may make them useful pharmacological agents for disorders that involve LRRK2 kinase in humans and animals, but particularly in humans.

In another embodiment the invention provides a method of inhibiting LRRK2 Kinase activity (this is to say, inhibiting the kinase activity associated with Leucine-Rich Repeat Kinase 2 [LRRK2], a multidomain protein containing kinase and GTPase enzymatic activities) in a patient in need of therapy for a condition amenable to treatment by such kinase activity inhibition, for example, treatment or prevention of neurologic damage associated with Parkinson's disease, for example, improvement in dopaminergic tone and in providing symptomatic benefit, for example, in treating, alleviating, ameliorating, or managing motor and non-motor symptoms of Parkinson's disease, and other conditions that may be treated or prevented by inhibition of LRRK2 kinase. Of particular importance is the acute or prophylactic treatment of Parkinson's Disease.

The subject compounds may be further useful in a method for the prevention, treatment, control, amelioration, or reduction of risk of the diseases, disorders and conditions noted herein.

The subject compounds may be further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation.

In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of Parkinson's Disease, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

General Schemes:

A general procedure for the preparation of alkoxy substituted indazoles such as x is shown in Scheme 1. Treatment of a suitable bromo-indazole i with iodine/KOH and the like in a solvent such as MeCN and the like will provide compound ii. The indazole can be protected with SEM-Cl and the like to provide the protected indazole iii. The iodo group in iii can be subjected to palladium-mediated cross coupling with a boronic acid such as iv and the like to provide indazole v. The bromide in v can be converted into the pinacol boronic ester vii using vi under palladium catalyzed conditions and the like. The boronic ester v can be oxidized to the alcohol viii using acetic acid/$H_2O_2$ and the like. The alcohol in viii can be reacted with electrophiles such as ix (LG=leaving group) in the presence of $K_2CO_3$ followed by removal of the indazole protecting group with TBAF and the like to provide examples such as x. Alternatively, compounds such as viii can be treated with DIAD, $PPh_3$ and an $R^5OH$, followed by removal of the indazole protecting group with TBAF and the like to provide examples such as x.

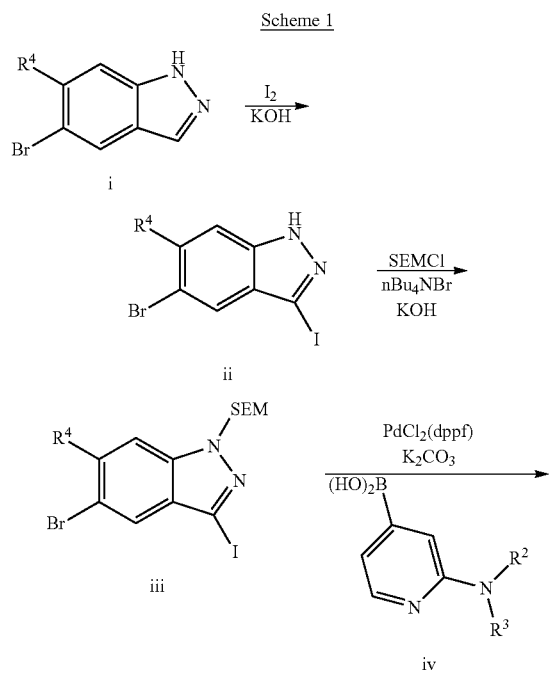

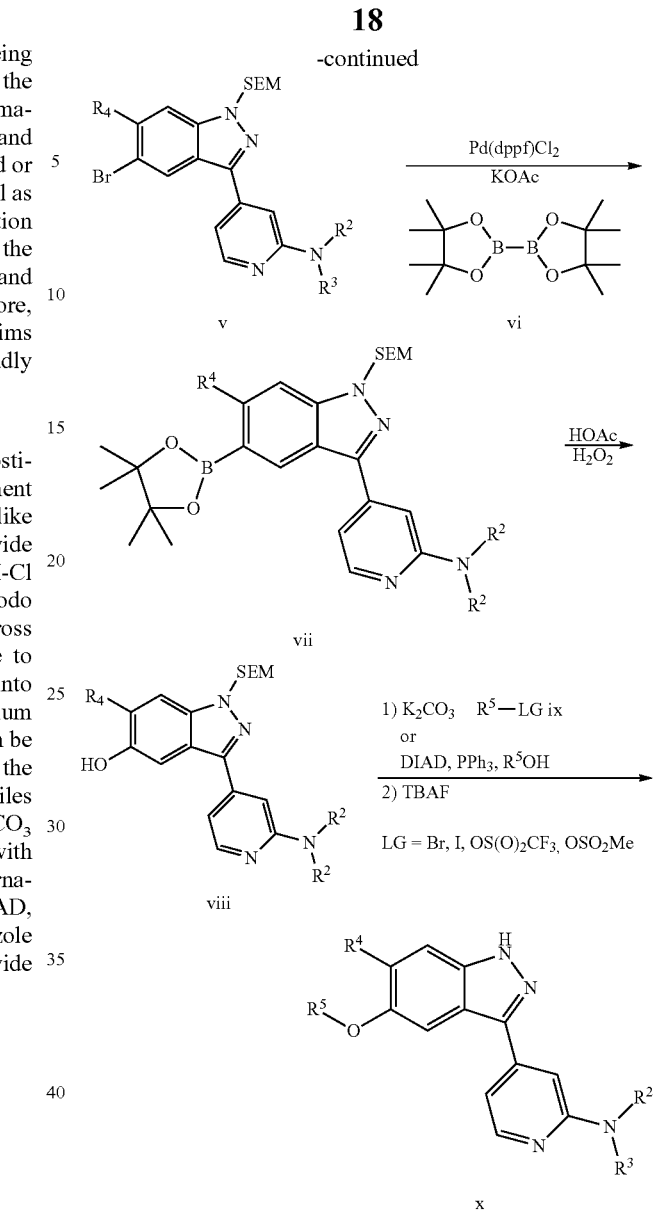

Treatment of i with NIS followed by TrCl and the like will provide xi (Scheme 2). The iodo indazole xi can be converted into the pyridyl substituted indazole xii via palladium-mediated cross-coupling with a suitable boronic acid iv or analogous boronate. The aryl bromide xii can be converted into the alcohol xiii via cross-coupling of the bromide with pinacol diborane and a palladium catalyst and the like, followed by oxidation of the resulting boronate with a method such as hydrogen peroxide in acetic acid and the like. The alcohol xiii can be converted into alkoxyindazoles such as x by first using a base and appropriate electrophile such as $R^5$-LG (LG=leaving group) and the like, followed by removal of the trityl protecting group with triethylsilane and the like. Alternatively, compounds such as xiii can be treated with DIAD, $PPh_3$ and an $R^5OH$, followed by removal of the trityl protecting group to provide examples such as x. Alternatively, the trityl group can be removed with aqueous HCl and the like in a solvent such as ethanol and the like or aqueous TFA and the like with a solvent such as dichloromethane and the like.

Scheme 2

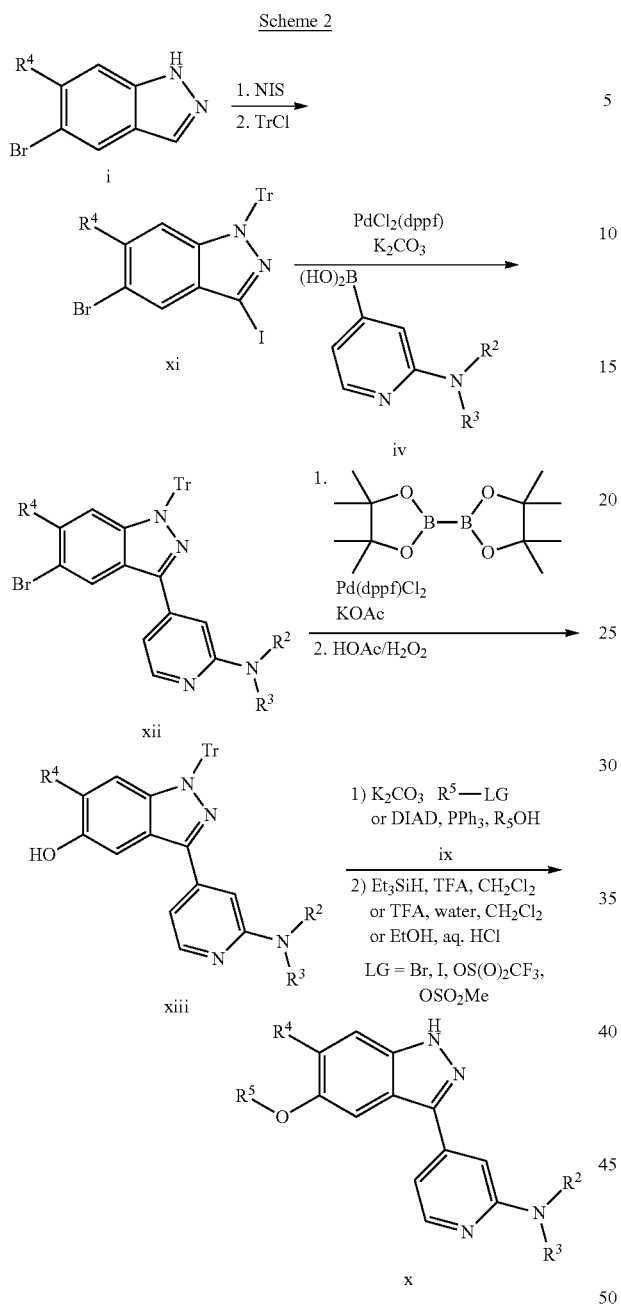

protected intermediate. The cross-coupling that is outlined in the conversion of xv to xvi can be performed on the SEM-protected material as well and removal of the SEM group to provide compounds x can be accomplished in the same manner as that described in Scheme 1.

Scheme 3

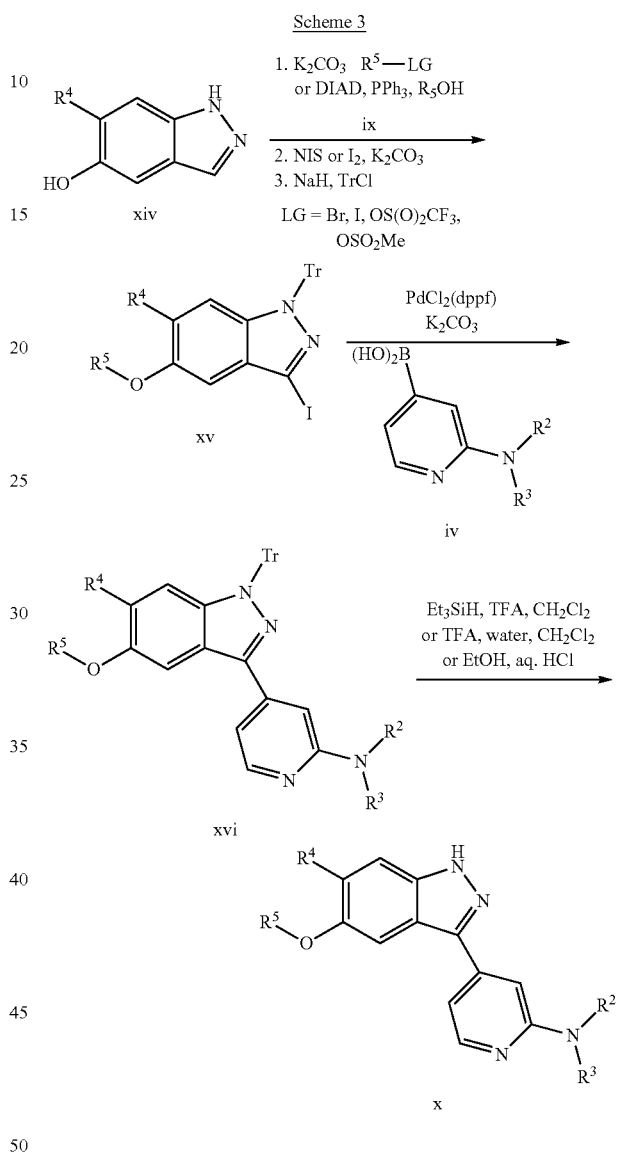

Alternatively, a hydroxyindazole such as xiv can be converted to the alkoxyindazole by using a base and an appropriate electrophile such as $R^5$-LG (LG=leaving group) and the like or by treatment with DIAD, $PPh_3$ and an $R^5OH$ and the like (Scheme 1). Iodination of the indazole with NIS or a mixture of iodine and potassium carbonate and the like, followed by protection of the indazole nitrogen by treatment with a base such as NaH and the like followed by trityl chloride will afford compounds xv. Palladium-catalyzed cross coupling of xv with boronic acids such as iv and the like or their corresponding boronate esters will provide compounds xvi. Removal of the trityl group from xvi can be accomplished via methods similar to that described in Scheme 2 to afford compounds x. In an alternative protecting group scheme, NaH/TrCl can be replaced with SEM-Cl and a base such as $Et_3N$ and the like to afford the SEM- An additional approach to compounds such as x is outlined in Scheme 4. Treatment of an appropriate alcohol $R^5$—OH and a base such as NaH and the like, followed by addition of xvii will provide the ether xviii. The bromide xviii can be converted into the methylated intermediate xix via palladium-mediated cross coupling with $Me_3B_3O_3$ and the like. The nitro derivative xix can be treated with Pd/C in the presence of $HCOONH_4$ to produce the amine xx. The amine xx can be acylated to provide xxi. The acylated amine xxi can be treated with iso-amyl nitrate in the presence of $Ac_2O/KOAc$ and the like to provide the N-acyl indazole xxii. Compounds such as xxii can be treated with ammonia and the like to produce indazoles xxi. The indazole xxi can be treated with iodine and KOH and the like to provide the iodo-indazole xxii. The indazole nitrogen can be protected with trityl chloride and base and the like to provide xxiii. The iodo-indazole xxiii can be converted into xxiv via cross coupling using the appropriate boronic acid and the like and an appropriate palladium catalyst. The chloro-pyridine xxiv can be converted into examples such as x using the appropriate amine (HN(R²)R³), palladium catalyst, and ligand followed by deprotection of the trityl group using standard conditions.

Scheme 5 demonstrates an alternative approach to intermediates such as v. The iodo-indazole iii can be converted into the fluoro-pyridine xxv using an appropriate palladium catalyst and boronic acid and the like. The fluoro-pyridine xxv can be converted into the amino-pyridine v using the appropriate amine (HN(R2)R3) and a base in a solvent such

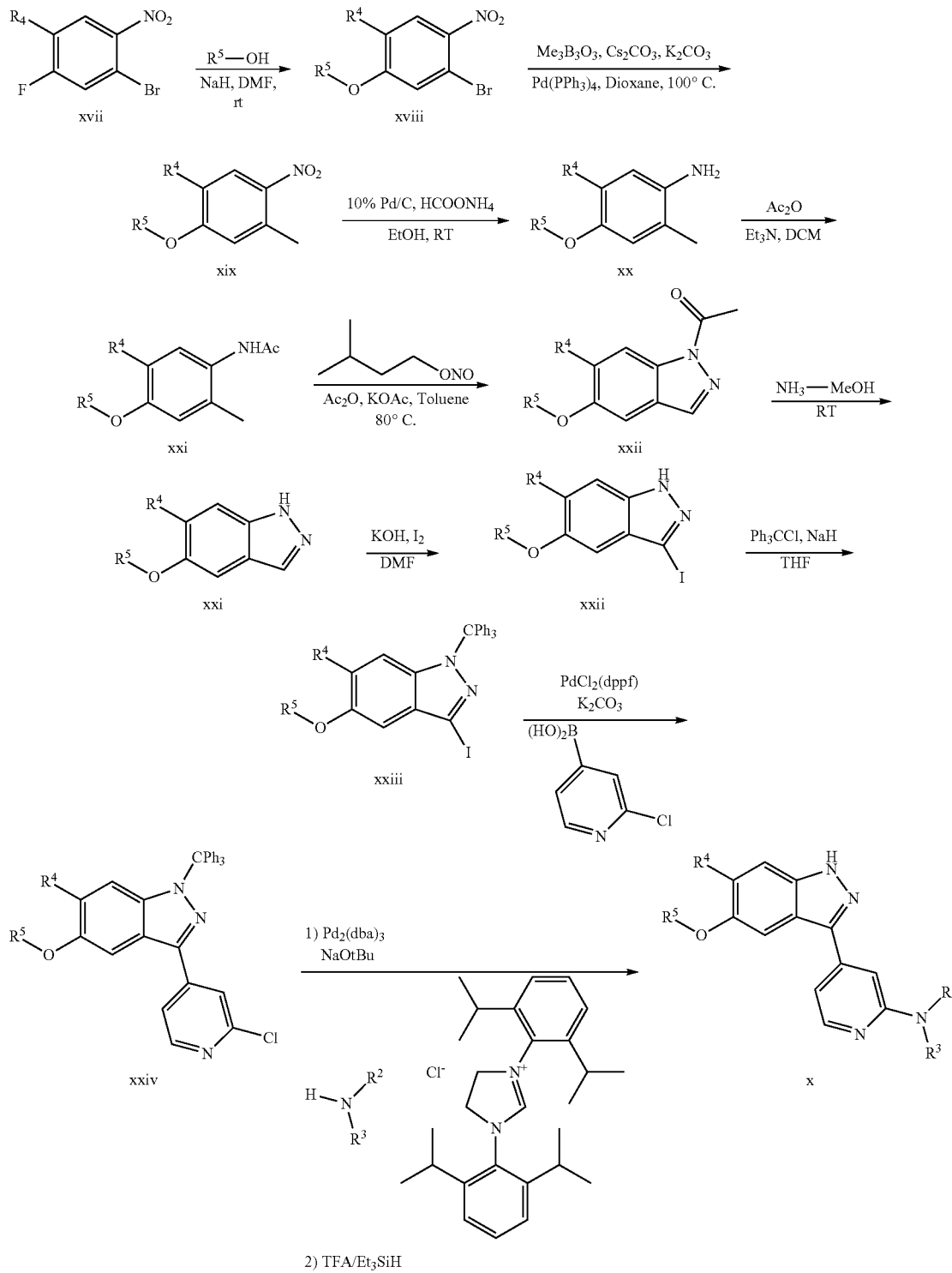

as DMSO and the like. The bromo-indazole v can be converted into examples such as x via methods previously described in Scheme 1.

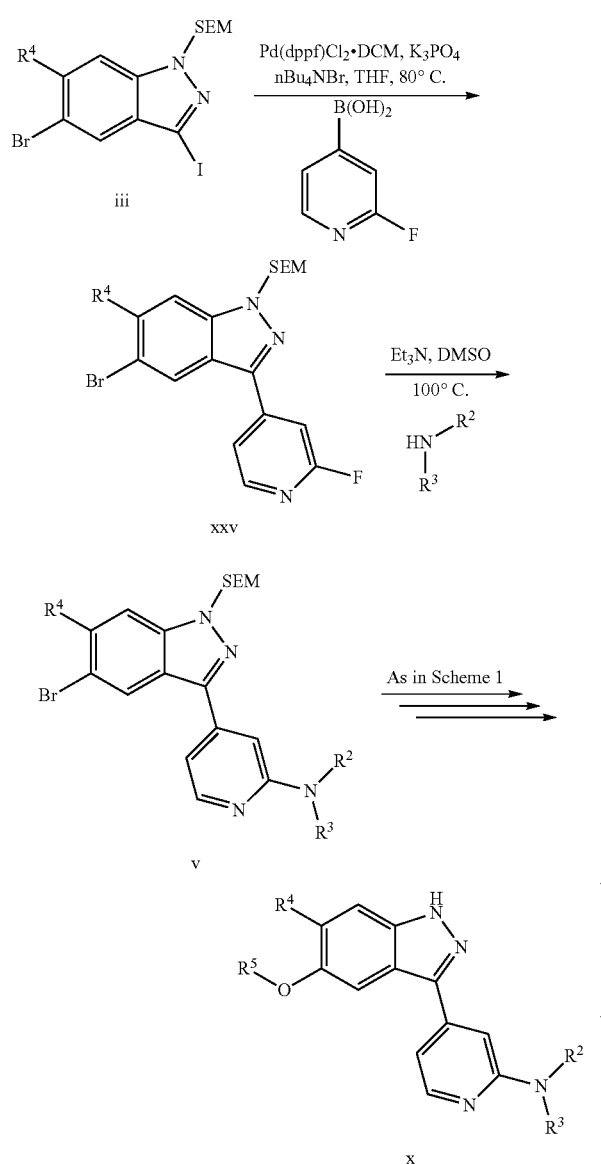

Scheme 5

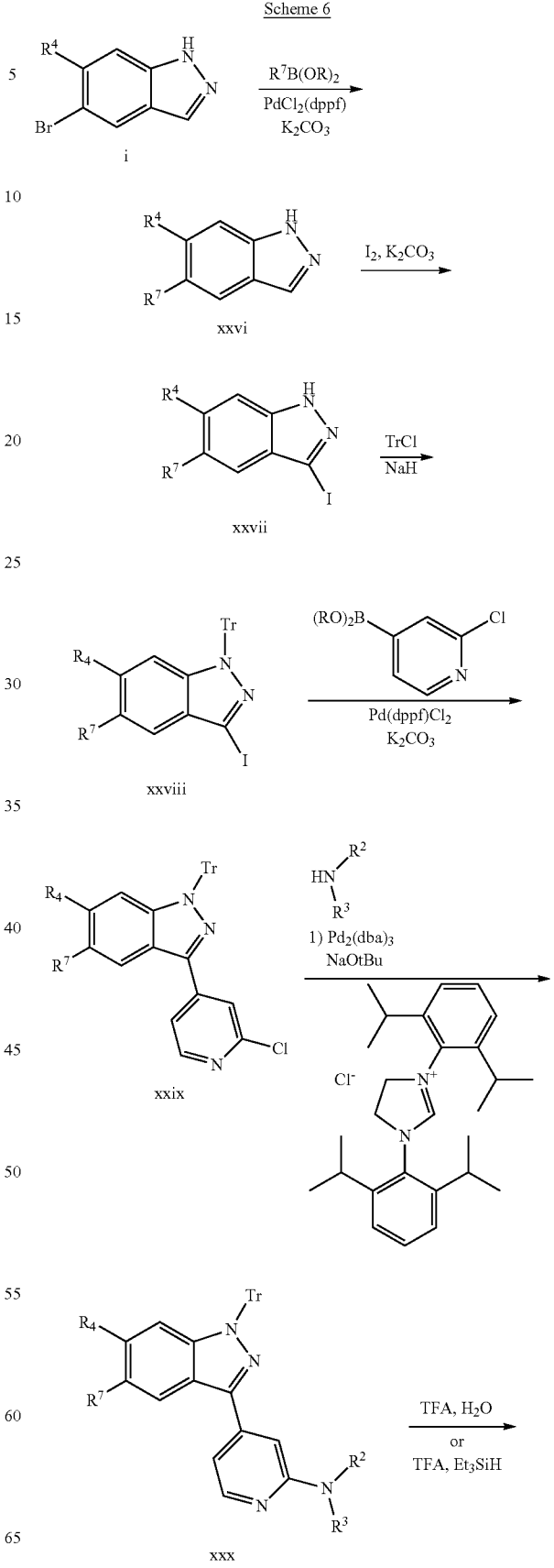

Scheme 6

A general procedure for the preparation of certain $R^7$ substituted indazoles such as xxxi is shown in Scheme 6. Treatment of a suitable bromo-indazole i under palladium catalyzed cross coupling conditions with a boronic acid and the like will afford xxvi. Treatment with iodine/$K_2CO_3$ and the like in a solvent such as MeCN and the like will provide compound xxvii. The indazole can be treated with a base such as NaH and the like, followed by trityl chloride to provide the protected indazole xxviii. Compound xxviii can the undergo palladium-catalyzed cross coupling with the requisite boromic acid to afford xxix. Palladium or nickel mediated amination with the appropriate amines will provide compounds xxx. Removal of the trityl group via methods outlined in Scheme 2 will provide compounds xxxi.

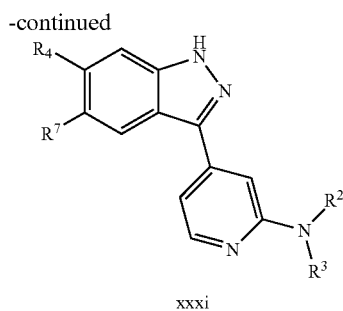

xxxi

An alternate approach to compounds xxxi is outlined in Scheme 7. Palladium mediated cross-coupling between compounds v and a suitable boronic acid or ester $R^7B(OR)_2$ will afford compounds xxxii. Removal of the SEM protecting group from xxxii via treatment with TBAF or a two-step protocol consisting of treatment with TFA in $CH_2Cl_2$ and the like, followed by a mixture of ammonium hydroxide, methanol and $CH_2Cl_2$ and the like will afford compounds xxxi. The analogous trityl-protected bromoindazole xii can be subjected to the first step of Scheme 7, followed by removal of the trityl group via a method outlined in Scheme 2 to afford compounds xxxi.

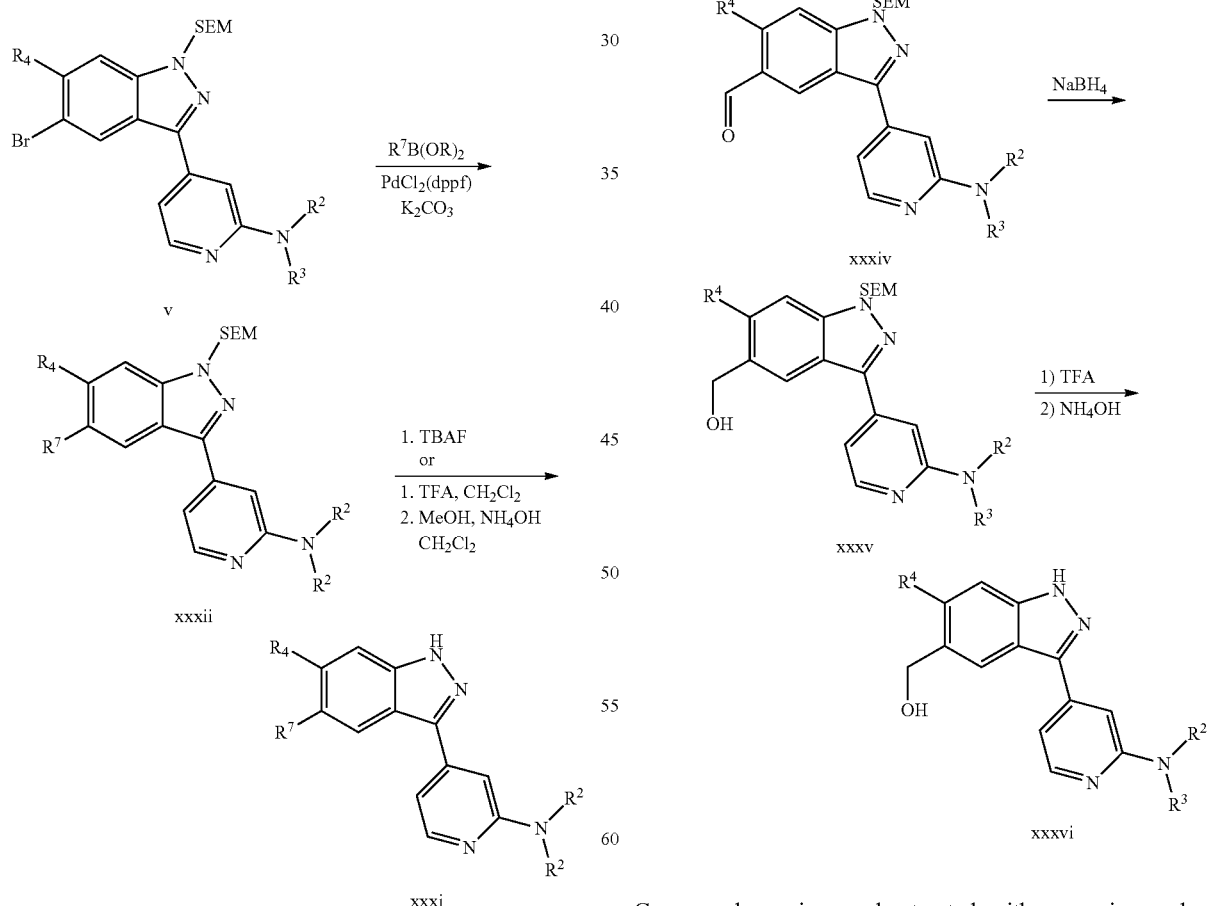

Lithiation of the bromoindazole xxv followed by addition of DMF will afford xxxiii (Scheme 8). Treatment of xxxiii with amines $HN(R^2)R^3$ will provide compounds xxxiv. Reduction of the aldehyde with $NaBH_4$ and the like will provide xxxv which can be deprotected under standard conditions to afford compounds xxxvi.

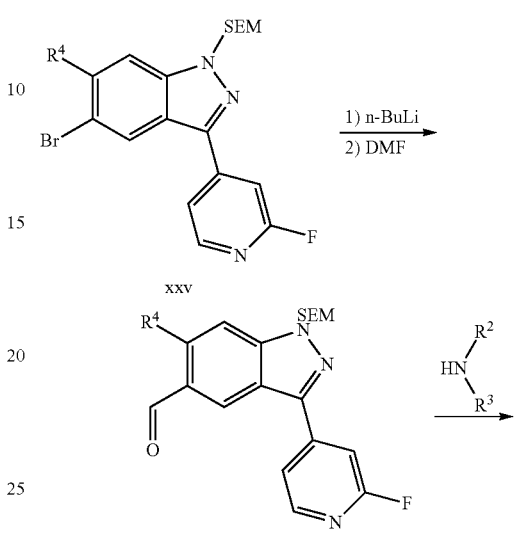

Compounds xxxiv can be treated with an amine and a reducing agent such as $NaCNBH_3$ and the like to afford compounds xxxvii (Scheme 9). Removal of the SEM group using the previously described conditions can afford compounds xxxviii.

Scheme 9

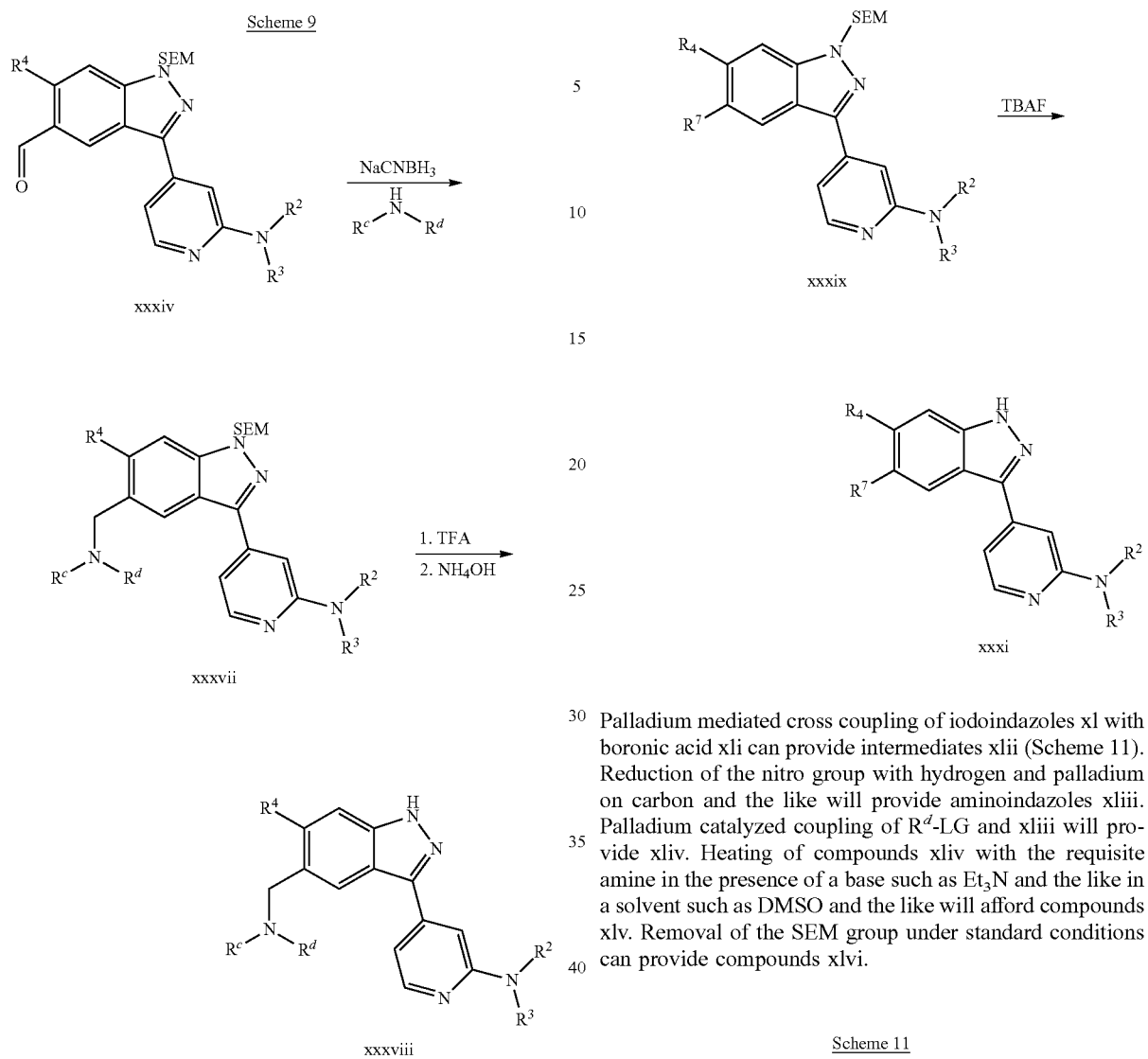

Compounds xxxi can also be prepared from an intermediate such as vii (Scheme 10). Palladium catalyzed cross-coupling of vii with an appropriate R⁷-LG will provide compounds xxxix. Removal of the SEM group under standard conditions will result in compounds xxxi.

Palladium mediated cross coupling of iodoindazoles xl with boronic acid xli can provide intermediates xlii (Scheme 11). Reduction of the nitro group with hydrogen and palladium on carbon and the like will provide aminoindazoles xliii. Palladium catalyzed coupling of R$^d$-LG and xliii will provide xliv. Heating of compounds xliv with the requisite amine in the presence of a base such as Et₃N and the like in a solvent such as DMSO and the like will afford compounds xlv. Removal of the SEM group under standard conditions can provide compounds xlvi.

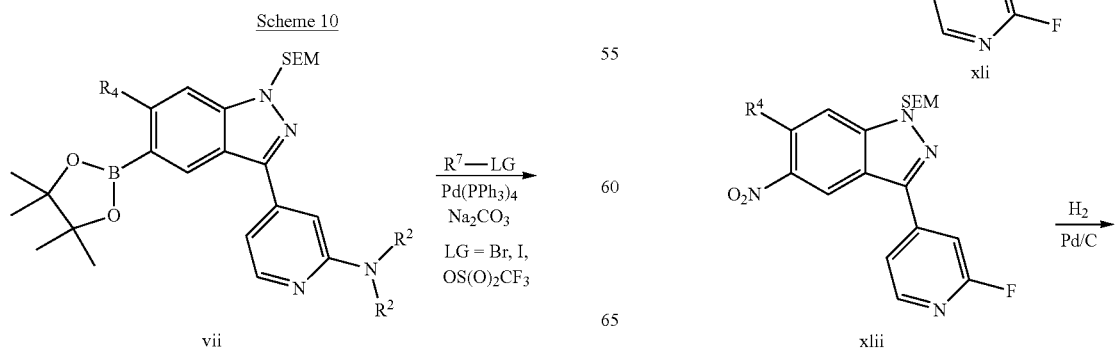

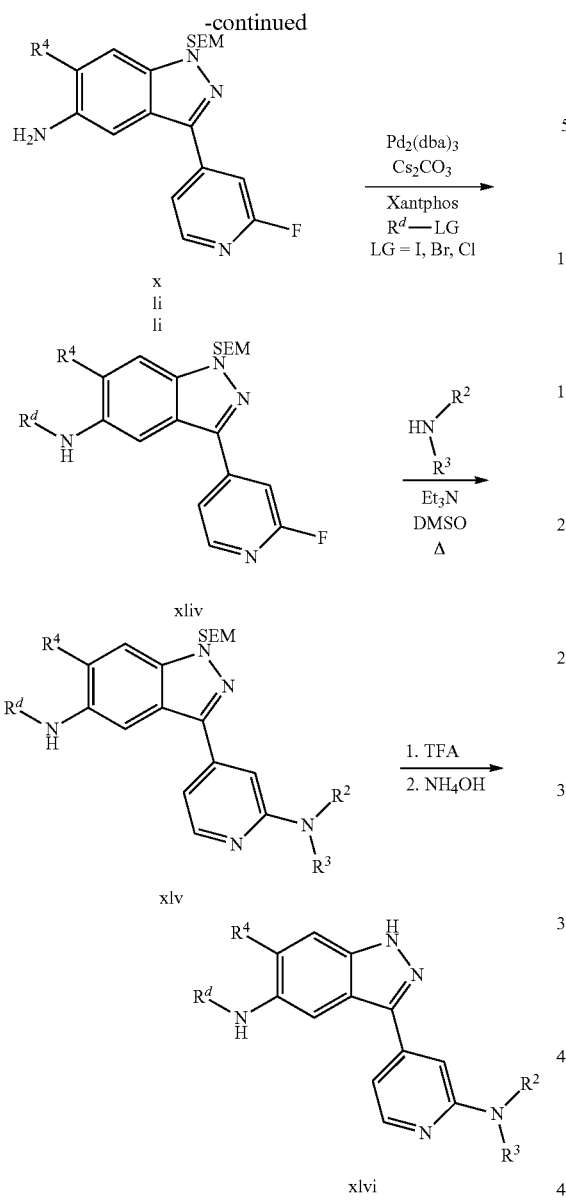

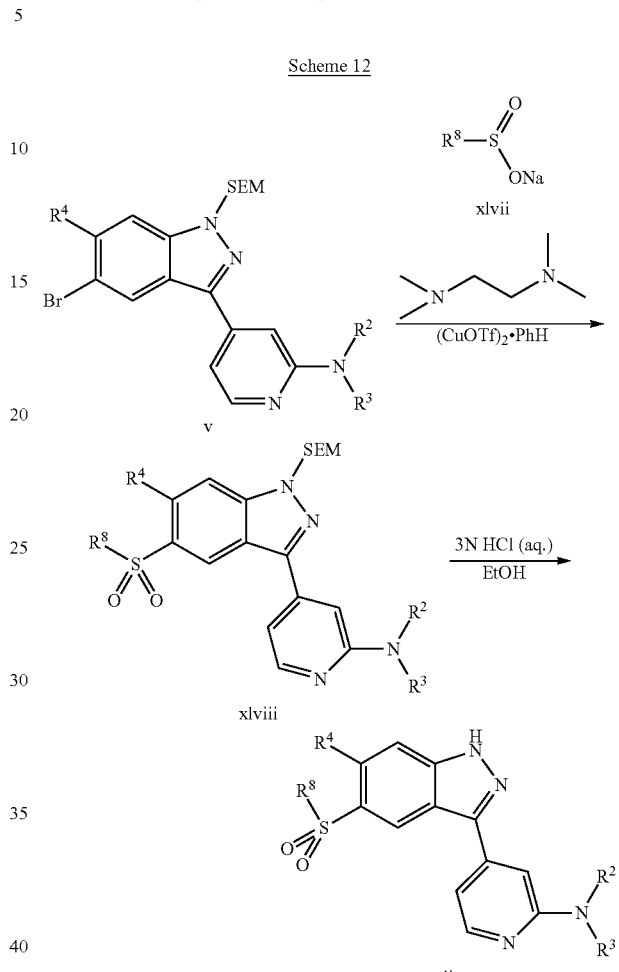

Intermediate v can be heated in the presence of a sodium sulfinate xlvii, a diamine such as N,N,N',N'-tetramethylethylenediamine and the like and a catalyst such as copper(I) triflate and the like to provide compounds xlviii (Scheme 12). Removal of the SEM protecting group under standard conditions will provide compounds xlix.

EXPERIMENTALS

Abbreviations used in the experimentals may include the following:

| | | | |
|---|---|---|---|
| ACN | Acetonitrile | AcOH | Acetic acid |
| Aq | Aqueous | Bn | Benzyl |
| BOC | tert-Butoxycarbonyl | BOC$_2$O, Boc$_2$O | BOC Anhydride |
| Bu | Butyl | C. (or ° C.) | degrees Celsius |
| Cbz | benzyloxycarbonyl | DBU | 1,8-Diazabicyclo[5.4.0]undec-7-ene |
| dba | dibenzylideneacetone | COD | 1,5-cyclooctodiene |
| DCM | Dichloromethane | DIPEA | Diisopropylethylamine |
| DMA | N,N-Dimethylacetamide | DMAP | 4-Dimethylaminopyridine |
| DME | 1,2-dimethoxyethane | DMF | Dimethylformamide |
| DMSO | Dimethyl sulfoxide | DPPF | 1,1'-(bis-diphenylphosphino)ferrocene |
| EDCI | 1-(3-Dimethylaminopropyl)-3-ethylcarbodiimide hydrochloride | EDC | 1-(3-Dimethylaminopropyl)-3-ethylcarbodiimide hydrochloride |
| EI | Electron ionization | Eq | Equivalents |
| Et | Ethyl | EtOAc | Ethyl acetate |
| EtOH | Ethanol | g | grams |
| h, hr | hours | $^1$H | proton |

| | | | |
|---|---|---|---|
| HATU | N,N,N',N'-Tetramethyl-O-(7-Azabenzotriazol-1-yl)uronium hexafluorophosphate | Hex | hexanes |
| HOBT | 1-Hydroxybenzotriazole | HOBT•$H_2O$ | 1-Hydroxybenzotriazole hydrate |
| HOTS | para-toluene sulfonic acid (see also TsOH) | HOTS•$H_2O$ | para-toluene sulfonic acid hydrate (see also TsOH•$H_2O$) |
| HMPA | hexamethylphosphoramide | HPLC | High pressure liquid chromatography |
| IPA | isopropanol, 2-propanol | LDA | lithium diisopropylamide |
| M | Molar | mmol | milimolar |
| mCPBA | meta-Chloroperoxy benzoic acid | Me | Methyl |
| MeCN | Acetonitrile | MeOH | Methanol |
| min | Minutes | mg | Milligrams |
| MHZ | Megahertz | mL (or ml) | Milliliter |
| Mol sieves | molecular sieves | N | normal |
| NMR | Nuclear Magnetic Resonance | MS | Mass Spectroscopy |
| NBS | N-Bromosuccinimide | NMM | N-Methylmorpholine |
| NMP | 1-methyl-2-pyrrolidone | ON | Overnight |
| PE | Petroleum ether | | |
| PTLC | Preparative thin layer chromatography | PyBrOP | Bromo-tris-pyrrolidino-phosphonium hexafluorophosphate |
| PyBOP | (Benzotriazol-1-yloxy)tripyrrolidinophosphonium hexafluorophosphate | Pyr | Pyridine |
| Quant | quantitative | RT or rt | Room temperature |
| sat (or sat. or sat'd.) | Saturated | SFC | supercritical fluid chromatography |
| sgc | Silica gel 60 chromatography | $SiO_2$ | Silica gel |
| tBOC | tert-Butoxycarbonyl | t-Bu | tert-butyl |
| TEA | Triethylamine | Tf | Trifluoromethane sulfonyl |
| TFA | Trifluoroacetic acid | THF | Tetrahydrofuran |
| TLC | Thin layer chromatography | Ts | Toluene sulfonyl |
| TsOH | para-toluene sulfonic acid | TsOH•$H_2O$ | para-toluene sulfonic acid hydrate |

General Experimental Information:

Unless otherwise noted, all reactions are magnetically stirred.

Unless otherwise noted, when diethyl ether is used in the experiments described below, it is Fisher ACS certified material and is stabilized with BHT.

Unless otherwise noted, "concentrated to dryness" means evaporating the solvent from a solution or mixture using a rotary evaporator.

Unless otherwise noted, flash chromatography is carried out on an Isco, Analogix, or Biotage automated chromatography system using a commercially available cartridge as the column. Columns may be purchased from Isco, Analogix, Biotage, Varian, or Supelco and are usually filled with silica gel as the stationary phase.

Unless otherwise noted, all LRRK2 $IC_{50}$ data presented in tables refers to the LRRK2 Km ATP LanthaScreen™ Assay that is described in the Biological Assay section.

Scheme A

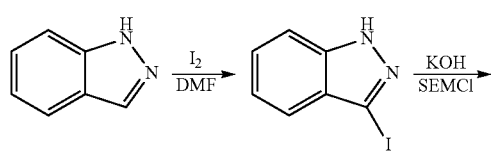

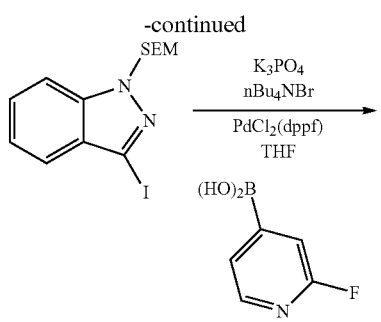

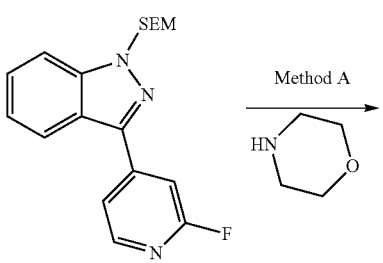

-continued

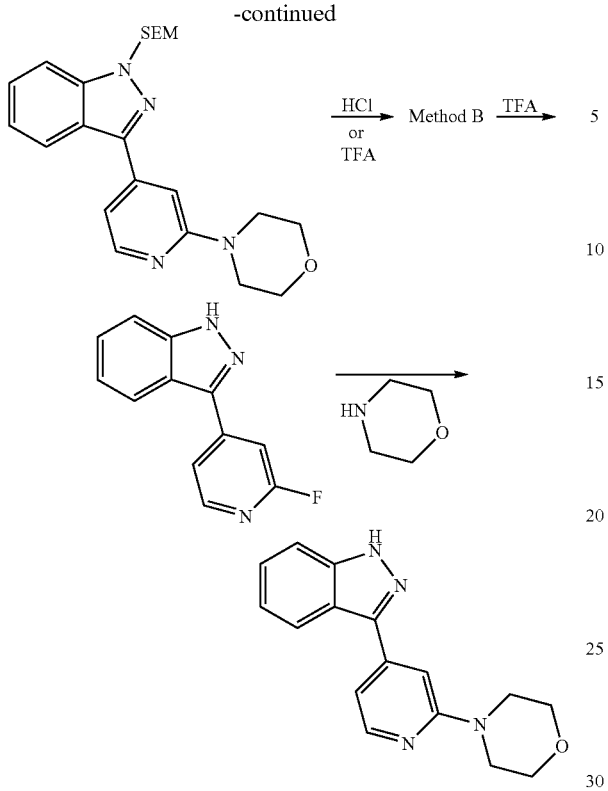

Example 1

Step 1

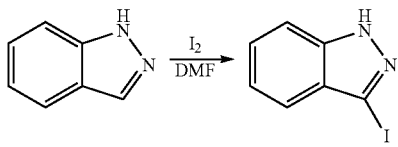

To a suspension of indazole (5.56 g, 47.1 mmol) and potassium hydroxide (5.28 g, 94.0 mmol) in DMF (77 mL) at rt was added iodine (17.92 g, 70.6 mmol). After 24 h, the resulting mixture was diluted with EtOAc and washed with 10% aq. sodium metabisulfite, water, and brine. The organic layer was dried (Na₂SO₄) and concentrated to afford the title compound which was used without further purification; LRMS (ESI) m/z 245.0 [(M+H)⁺ calcd for C₇H₆IN₂: 245].

Step 2

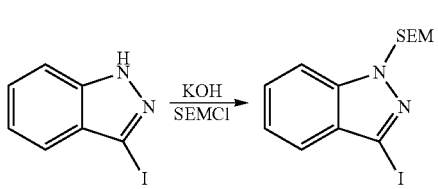

To a suspension of 3-iodo-1H-indazole (9.36 g, 38.4 mmol), tetrabutylammonium bromide (0.12 g, 0.38 mmol), and potassium hydroxide (19.37 g, 345 mmol) in water (20 mL) and CH₂Cl₂ (50 mL) at 0° C. was added SEM-Cl (7.5 mL, 42.2 mmol). The mixture was stirred at rt for 2 h then diluted with CH₂Cl₂, washed with water and brine, dried (Na₂SO₄) and concentrated. Purification by silica gel chromatography (gradient elution, 0-10% EtOAc/hexanes) afforded the title compound; LRMS (ESI) m/z 374.9 [(M+H)⁺ calcd for C₁₃H₂₀IN₂OSi: 375].

Step 3

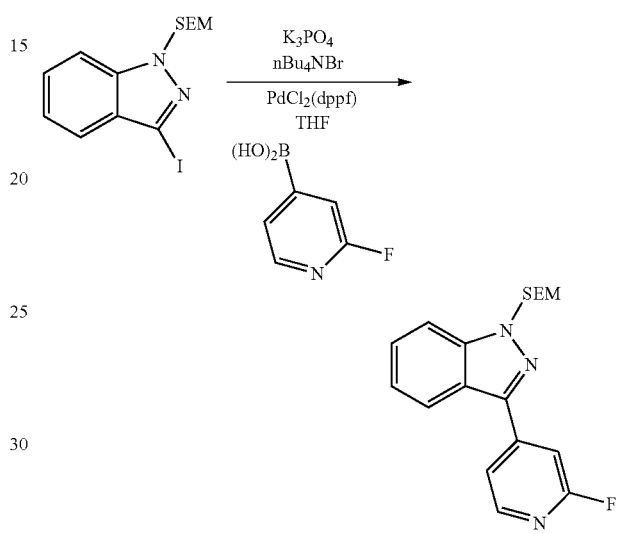

To a suspension of 3-iodo-1-{[2-(trimethylsilyl)ethoxy]methyl}-1H-indazole (5.0 g, 13.4 mmol), 2-fluoropyridine-4-boronic acid (1.88 g, 13.4 mmol), tri-potassium phosphate trihydrate (10.7 g, 40.1 mmol), and tetrabutylammonium bromide (0.86 g, 2.67 mmol) in THF (121 mL) at rt under N₂ was added 1,1'-bis(diphenylphosphino)ferrocene-palladium(II) dichloride dichloromethane complex (2.18 g, 2.67 mmol). The resulting mixture was heated at 80° C. for 48 h. After cooling to rt, the mixture was filtered through Celite, diluted with EtOAc, washed with water, dried (Na₂SO₄), and concentrated. Purification by silica gel chromatography (gradient elution, 0-35% EtOAc/hexanes) afforded the title compound; LRMS (ESI) m/z 344.0 [(M+H)⁺ calcd for C₁₈H₂₃FN₃OSi: 344].

Example 1 can be prepared by either Method A or Method B below.

Method A:

Step 4

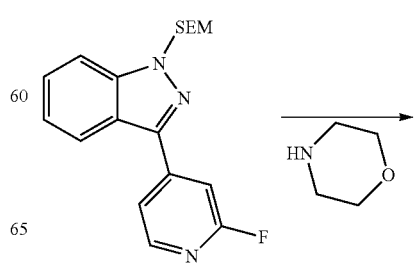

-continued

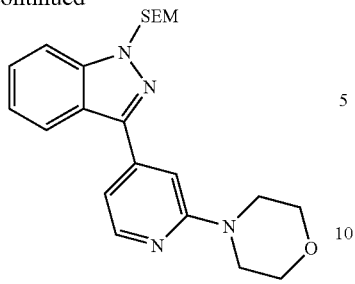

Combined 3-(2-fluoropyridin-4-yl)-1-{[2-(trimethylsilyl)ethoxy]methyl}-1H-indazole (0.30 g, 0.87 mmol) and morpholine (0.76 g, 8.73 mmol) at rt, either using morpholine as the solvent or in DMF with a few drops of triethylamine. The mixture was heated at 90° C. overnight. After cooling to rt, the mixture was diluted with EtOAc and washed with 10% aq. citric acid (brought to pH 5 with 1N NaOH), water, and brine. The organics were dried (Na$_2$SO$_4$), concentrated and purified by silica gel chromatography (gradient elution, 0-100% EtOAc/hexanes) to afford the title compound; LRMS (ESI) m/z 411.1 [(M+H)$^+$ calcd for C$_{22}$H$_{31}$N$_4$O$_2$Si: 411].

Step 5

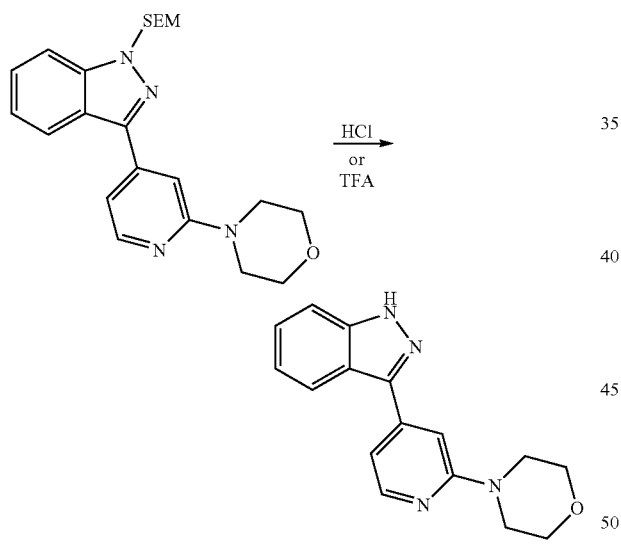

Example 1

Bubbled HCl (g) through a solution of 3-[2-(morpholin-4-yl)pyridin-4-yl]-1-{[2-(trimethylsilyl)ethoxy]methyl}-1H-indazole (50 mg, 0.12 mmol) in MeOH (1.2 mL) at 0° C. for 5 min. The resulting solution was heated at 60° C. in a sealed tube overnight. After cooling to 0° C., the mixture was diluted with EtOAc and quenched with saturated aq. NaHCO$_3$. The mixture was extracted with EtOAc, dried (Na$_2$SO$_4$), and concentrated. Purification by silica gel chromatography (gradient elution, 0-7% MeOH/CH$_2$Cl$_2$) afforded the title compound; HRMS (ES+) m/z 281.1395 [(M+H)$^+$ calcd for C$_{16}$H$_{17}$N$_4$O: 281.1397]; LCMS (ESI) m/z 281.1 (Ret.=1.27 min, LCMS condition a).

Alternatively, deprotection of the SEM could be accomplished by stirring 3-[2-(morpholin-4-yl)pyridin-4-yl]-1-{[2-(trimethylsilyl)ethoxy]methyl}-1H-indazole (50 mg, 0.12 mmol) in CH$_2$Cl$_2$ (1.2 mL) and TFA (2.4 mL) at rt. After 12, the solution was concentrated and redissolved in MeOH (1.2 mL) and CH$_2$Cl$_2$ (1.2 mL) and NH$_4$OH (1.2 mL) was added. After 5 h, the resulting solution was quenched with water and extracted with CH$_2$Cl$_2$. The combined extracts were dried (Na$_2$SO$_4$), concentrated and purified as above to afford the title compound.

Method B:

Step 4

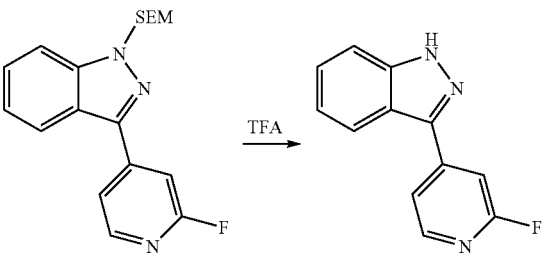 [SMILES: C[Si](C)(C)CCOCn1nc(-c2ccnc(F)c2)c2ccccc21 ; Fc1cc(-c2n[nH]c3ccccc23)ccn1]

To a solution of 3-(2-fluoropyridin-4-yl)-1-{[2-(trimethylsilyl)ethoxy]methyl}-1H-indazole (20 mg, 0.058 mmol) in CH$_2$Cl$_2$ (0.58 mL) at rt was added TFA (0.58 mL). The mixture was stirred at rt for 5 h then concentrated. To the resulting oil was added MeOH (1 mL), CH$_2$Cl$_2$ (1 mL) and NH$_4$OH (1 mL). After 5 h, the resulting solution was quenched with water and extracted with CH$_2$Cl$_2$. The combined extracts were dried (Na$_2$SO$_4$), concentrated, and purified by silica gel chromatography (gradient elution, 0-50% EtOAc/hexanes) to afford the title compound; LRMS (ESI) m/z 214.1 [(M+H)$^+$ calcd for C$_{12}$H$_9$FN$_3$: 214].

Step 5

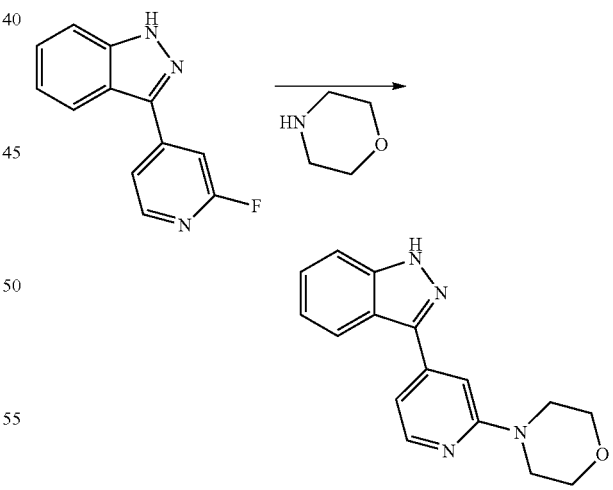

Example 1

Combined 3-(2-fluoropyridin-4-yl)-1H-indazole (319 mg, 1.50 mmol) and morpholine (652 mg, 7.48 mmol) at rt, either using morpholine as the solvent or in DMF with a few drops of triethylamine. The mixture was heated at 90° C. overnight. After cooling to rt, the mixture was diluted with EtOAc and washed with 10% aq. citric acid (brought to pH 5 with 1N NaOH), water, and brine. The organics were dried ($Na_2SO_4$), concentrated and purified by silica gel chromatography (gradient elution, 0-80% EtOAc/hexanes) to afford the title compound; LRMS (ESI) m/z 281.1 [(M+H)$^+$ calcd for $C_{16}H_{17}N_4O$: 281].

By following the procedure outlined in Scheme A for Example 1, using the appropriate amine and either Method A or Method B, the following compounds can be prepared (Examples 2-74).

| Ex | Structure | Cond. | LCMS RT (min) | m/z | Method (Prep) | LRRK2 IC$_{50}$ (nM) |
|---|---|---|---|---|---|---|
| 2 | | a | 1.58 | 293.1 | A | 76 |
| 3 | | a | 1.51 | 283.1 | A | 48 |
| 4 | | a | 1.51 | 269.2 | A | 46 |
| 5 | | a | 1.51 | 265.2 | A | 17 |
| 6 | | a | 1.52 | 279.2 | A | 16 |

-continued

| Ex | Structure | LCMS Cond. | RT (min) | m/z | Method (Prep) | LRRK2 IC$_{50}$ (nM) |
|---|---|---|---|---|---|---|
| 7 | 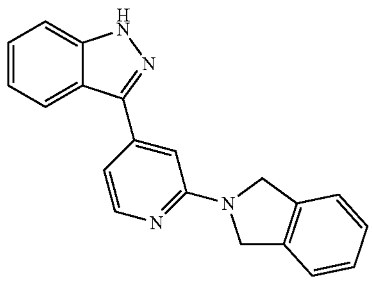 [SMILES: c1ccc2c(c1)CN(c1cc(-c3n[nH]c4ccccc34)ccn1)C2] | a | 1.70 | 313.1 | A | 87 |
| 8 | 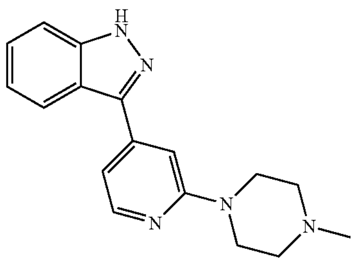 [SMILES: CN1CCN(c2cc(-c3n[nH]c4ccccc34)ccn2)CC1] | a | 2.24 | 294.2 | A | 42 |
| 9 | 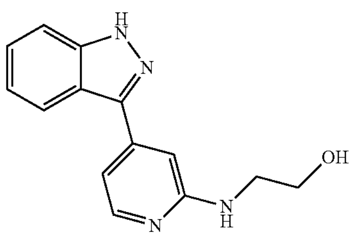 [SMILES: OCCNc1cc(-c2n[nH]c3ccccc23)ccn1] | a | 1.47 | 255.1 | A | 54 |
| 10 | 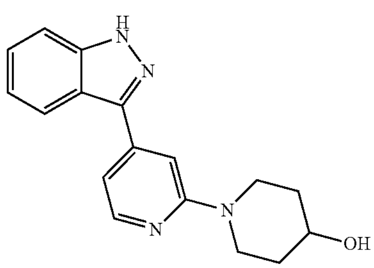 [SMILES: OC1CCN(c2cc(-c3n[nH]c4ccccc34)ccn2)CC1] | a | 1.33 | 295.2 | A | 24 |
| 11 | 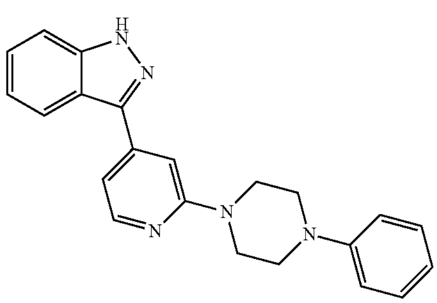 [SMILES: c1ccc(N2CCN(c3cc(-c4n[nH]c5ccccc45)ccn3)CC2)cc1] | a | 2.27 | 356.0 | A | 49 |

| Ex | Structure | LCMS Cond. | RT (min) | m/z | Method (Prep) | LRRK2 IC$_{50}$ (nM) |
|---|---|---|---|---|---|---|
| 12 | 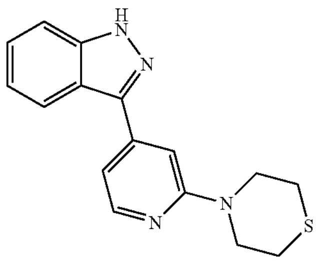 [SMILES: c1ccc2c(-c3ccnc(N4CCSCC4)c3)n[nH]c2c1] | a | 1.69 | 297.0 | A | 46 |
| 13 | 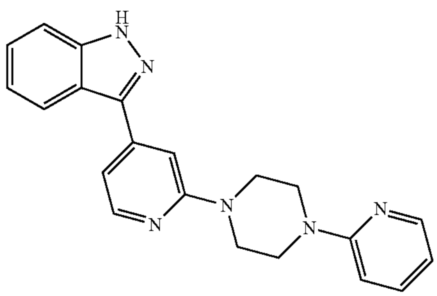 [SMILES: c1ccc(N2CCN(c3cc(-c4n[nH]c5ccccc45)ccn3)CC2)nc1] | a | 2.26 | 357.0 | A | 22 |
| 14 | 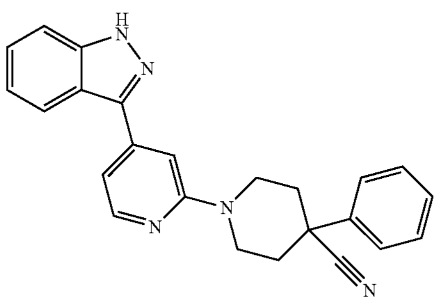 [SMILES: N#CC1(c2ccccc2)CCN(c2cc(-c3n[nH]c4ccccc34)ccn2)CC1] | a | 1.87 | 380.0 | A | 67 |
| 15 | 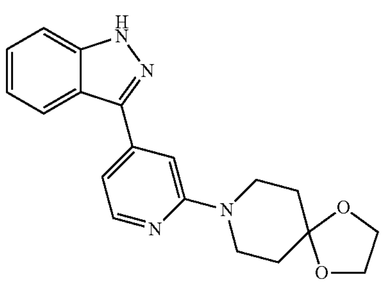 [SMILES: c1ccc2c(-c3ccnc(N4CCC5(CC4)OCCO5)c3)n[nH]c2c1] | a | 1.52 | 337.0 | A | 36 |
| 16 | 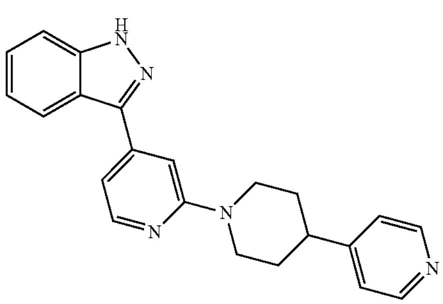 [SMILES: c1ccc2c(-c3ccnc(N4CCC(c5ccncc5)CC4)c3)n[nH]c2c1] | a | 0.80 | 356.0 | A | 186 |

-continued

| | | | LCMS | | | LRRK2 |
|---|---|---|---|---|---|---|
| Ex | Structure | Cond. | RT (min) | m/z | Method (Prep) | IC$_{50}$ (nM) |
| 17 | | a | 1.78 | 381.0 | A | 16 |
| 18 | | a | 1.84 | 358.0 | B | 17 |
| 19 | | a | 0.72 | 371.0 | B | 18 |
| 20 | | a | 1.67 | 424.0 | B | 27 |
| 21 | | a | 1.63 | 297.1 | B | 22 |

-continued

| Ex | Structure | LCMS Cond. | RT (min) | m/z | Method (Prep) | LRRK2 IC$_{50}$ (nM) |
|---|---|---|---|---|---|---|
| 22 | | a | 0.92 | 356.1 | B | 20 |
| 23 | | a | 0.75 | 372.1 | B | 20 |
| 24 | | a | 0.77 | 357.1 | B | 18 |
| 25 | | a | 0.72 | 372.1 | B | 21 |

-continued

| Ex | Structure | LCMS Cond. | RT (min) | m/z | Method (Prep) | LRRK2 IC$_{50}$ (nM) |
|---|---|---|---|---|---|---|
| 26 | 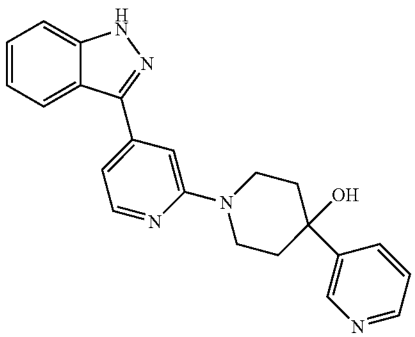 [SMILES: OC1(c2cccnc2)CCN(c2cc(-c3n[nH]c4ccccc34)ccn2)CC1] | a | 0.82 | 372.1 | B | 19 |
| 27 | 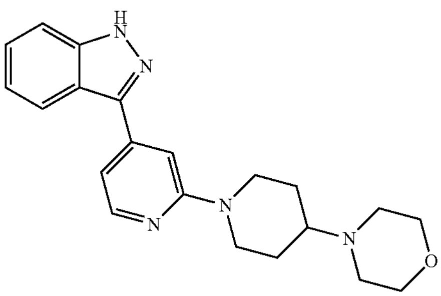 [SMILES: c1ccc2c(-c3ccnc(N4CCC(N5CCOCC5)CC4)c3)n[nH]c2c1] | a | 0.78 | 364.1 | B | 32 |
| 28 | 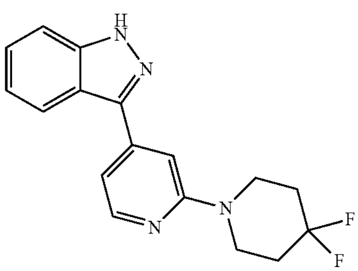 [SMILES: FC1(F)CCN(c2cc(-c3n[nH]c4ccccc34)ccn2)CC1] | a | 2.42 | 315.1 | B | 57 |
| 29 | 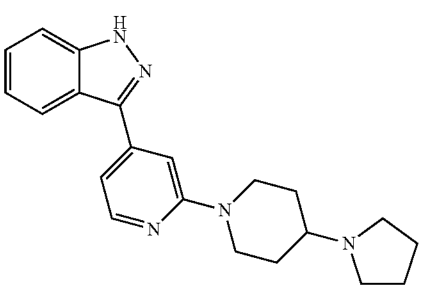 [SMILES: c1ccc2c(-c3ccnc(N4CCC(N5CCCC5)CC4)c3)n[nH]c2c1] | a | 0.59 | 348.1 | B | 45 |
| 30 | 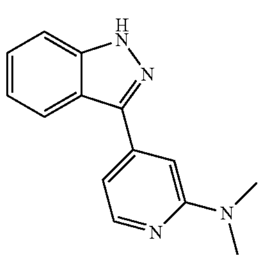 [SMILES: CN(C)c1cc(-c2n[nH]c3ccccc23)ccn1] | a | 1.45 | 239.1 | B | 33 |

-continued
| Ex | Structure | LCMS Cond. | RT (min) | m/z | Method (Prep) | LRRK2 IC$_{50}$ (nM) |
|---|---|---|---|---|---|---|
| 31 | 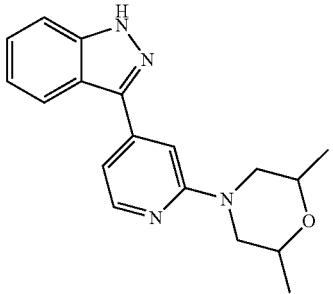 [SMILES: CC1CN(c2cc(-c3n[nH]c4ccccc34)ccn2)CC(C)O1] | a | 2.51 | 309.2 | B | 12 |
| 32 | 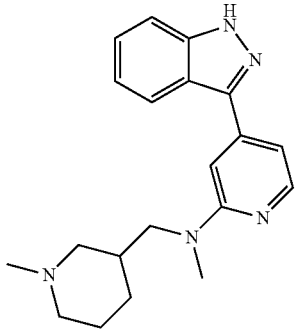 [SMILES: CN1CCCC(CN(C)c2cc(-c3n[nH]c4ccccc34)ccn2)C1] | b | 0.76 | 336.4 | B | 75 |
| 33 | 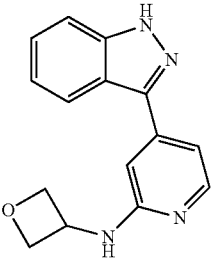 [SMILES: c1ccc2c(-c3ccnc(NC4COC4)c3)n[nH]c2c1] | b | 0.78 | 267.4 | B | 3507 |
| 34 | 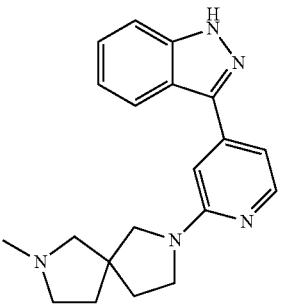 [SMILES: CN1CCC2(CCN(c3cc(-c4n[nH]c5ccccc45)ccn3)C2)C1] | b | 0.76 | 334.4 | B | 22 |

| | | | LCMS | | | LRRK2 |
|---|---|---|---|---|---|---|
| Ex | Structure | Cond. | RT (min) | m/z | Method (Prep) | IC$_{50}$ (nM) |
| 35 | | b | 0.73 | 308.4 | B | 28 |
| 36 | | b | 0.90 | 326.4 | B | 27 |
| 37 | | b | 0.83 | 325.4 | B | 64 |
| 38 | | b | 0.87 | 299.3 | B | 79 |

|     |           | LCMS |           |     |                  | LRRK2              |
|-----|-----------|------|-----------|-----|------------------|--------------------|
| Ex  | Structure | Cond.| RT (min)  | m/z | Method (Prep)    | IC$_{50}$ (nM)     |
| 39  |           | b    | 0.86      | 299.3 | B              | 26                 |
| 39  |           | b    | 0.82      | 317.4 | B              | 280                |
| 40  |           | b    | 0.78      | 378.5 | B              | 28                 |

-continued
| Ex | Structure | LCMS Cond. | RT (min) | m/z | Method (Prep) | LRRK2 IC$_{50}$ (nM) |
|---|---|---|---|---|---|---|
| 41 | 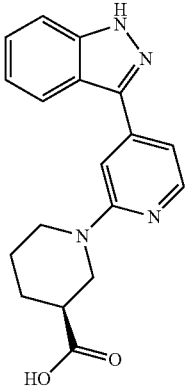 [SMILES: O=C(O)[C@H]1CCCN(c2cc(-c3n[nH]c4ccccc34)ccn2)C1] | b | 0.87 | 323.3 | B | 24 |
| 42 | 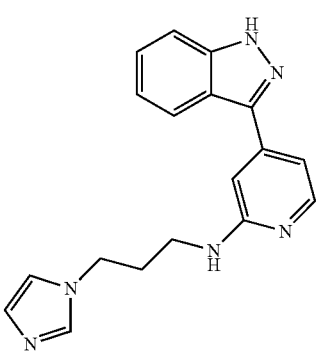 [SMILES: c1ccc2c(-c3ccnc(NCCCn4ccnc4)c3)n[nH]c2c1] | b | 0.76 | 319.4 | B | 31 |
| 43 | 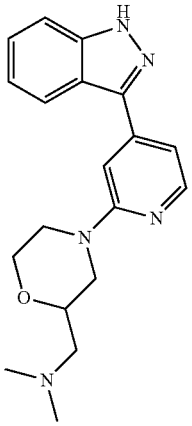 [SMILES: CN(C)CC1CN(c2cc(-c3n[nH]c4ccccc34)ccn2)CCO1] | b | 0.77 | 338.4 | B | 19 |
| 44 | 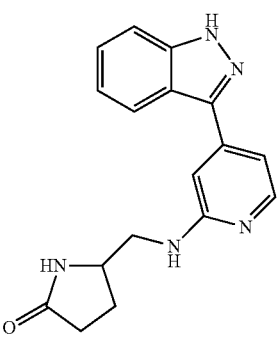 [SMILES: O=C1CCC(CNc2cc(-c3n[nH]c4ccccc34)ccn2)N1] | b | 0.81 | 308.4 | B | 26 |

-continued
| Ex | Structure | LCMS Cond. | RT (min) | m/z | Method (Prep) | LRRK2 IC$_{50}$ (nM) |
|---|---|---|---|---|---|---|
| 45 | 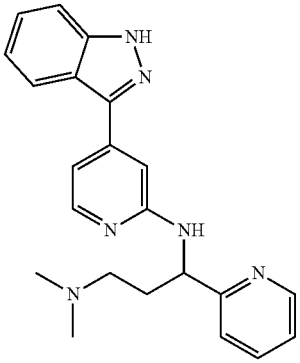 [SMILES: CN(C)CCC(Nc1cc(-c2n[nH]c3ccccc23)ccn1)c1ccccn1] | b | 0.82 | 373.4 | B | 72 |
| 46 | 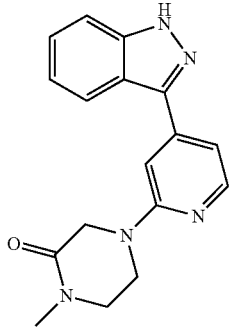 [SMILES: CN1CCN(c2cc(-c3n[nH]c4ccccc34)ccn2)CC1=O] | b | 0.82 | 308.4 | B | 21 |
| 47 | 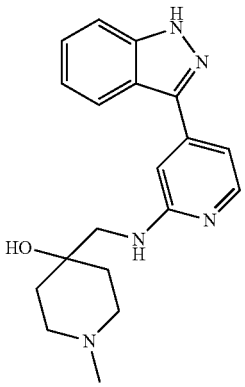 [SMILES: CN1CCC(O)(CNc2cc(-c3n[nH]c4ccccc34)ccn2)CC1] | b | 0.75 | 338.4 | B | 63 |
| 48 | 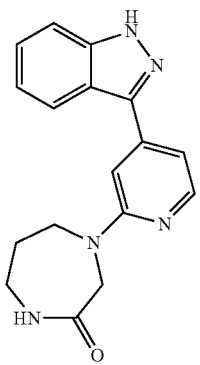 [SMILES: O=C1CN(c2cc(-c3n[nH]c4ccccc34)ccn2)CCCN1] | b | 0.79 | 308.4 | B | 54 |

-continued
| Ex | Structure | LCMS Cond. | RT (min) | m/z | Method (Prep) | LRRK2 IC$_{50}$ (nM) |
|---|---|---|---|---|---|---|
| 49 | 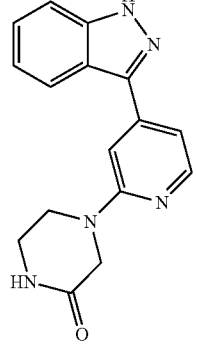 | b | 0.78 | 294.4 | B | 23 |
| 50 | 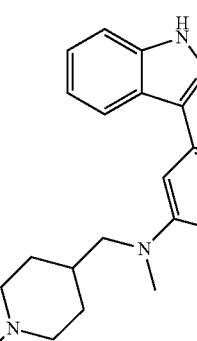 | b | 0.77 | 336.4 | B | 40 |
| 51 | 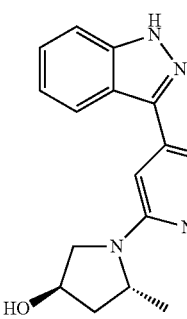 | b | 0.86 | 295.3 | B | 33 |
| 52 | 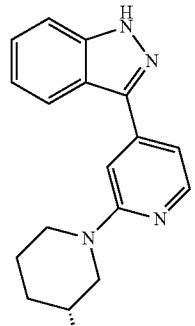 | b | 0.87 | 323.4 | B | 31 |

| | | LCMS | | | LRRK2 |
|---|---|---|---|---|---|
| Ex | Structure | Cond. | RT (min) | m/z | Method (Prep) | IC$_{50}$ (nM) |
| 53 | | b | 0.76 | 407.5 | B | 18 |
| 54 | | b | 0.75 | 308.2 | B | 47 |
| 55 | | b | 0.74 | 318.4 | B | 14 |
| 56 | | b | 0.76 | 352.4 | B | 25 |

-continued

| Ex | Structure | LCMS Cond. | RT (min) | m/z | Method (Prep) | LRRK2 IC$_{50}$ (nM) |
|---|---|---|---|---|---|---|
| 57 | | b | 0.78 | 407.5 | B | 6.1 |
| 58 | | b | 0.82 | 299.3 | B | 51 |
| 59 | | b | 0.84 | 315.3 | B | 37 |
| 60 | | b | 0.81 | 361.4 | B | 202 |

-continued
| Ex | Structure | LCMS Cond. | RT (min) | m/z | Method (Prep) | LRRK2 IC$_{50}$ (nM) |
|---|---|---|---|---|---|---|
| 61 | 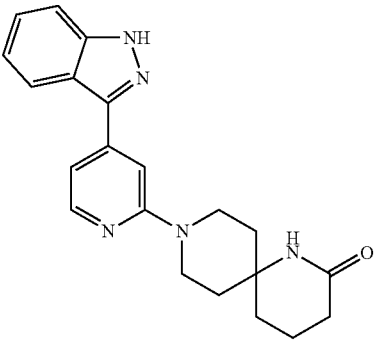 [SMILES: O=C1CCCC2(CCN(c3cc(-c4n[nH]c5ccccc45)ccn3)CC2)N1] | b | 0.85 | 362.4 | B | 14 |
| 62 | 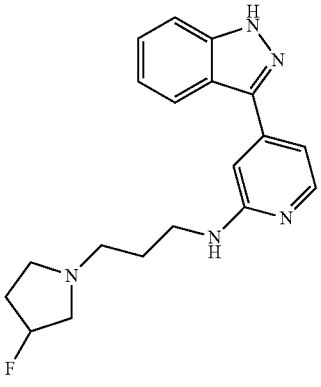 [SMILES: FC1CCN(CCCNc2cc(-c3n[nH]c4ccccc34)ccn2)C1] | b | 0.78 | 340.4 | B | 46 |
| 63 | 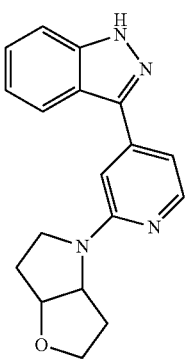 [SMILES: c1ccc2c(-c3ccnc(N4CCC5OCCC54)c3)n[nH]c2c1] | b | 0.88 | 307.4 | B | 40 |
| 64 | 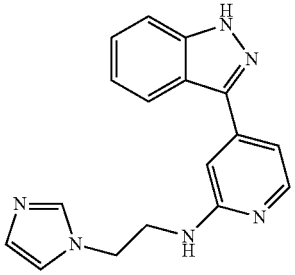 [SMILES: c1ccc2c(-c3ccnc(NCCn4ccnc4)c3)n[nH]c2c1] | b | 0.75 | 305.4 | B | 35 |

-continued

| Ex | Structure | LCMS Cond. | RT (min) | m/z | Method (Prep) | LRRK2 IC$_{50}$ (nM) |
|---|---|---|---|---|---|---|
| 65 | 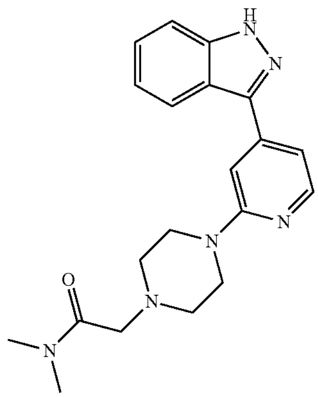 [SMILES: CN(C)C(=O)CN1CCN(c2cc(-c3n[nH]c4ccccc34)ccn2)CC1] | b | 0.78 | 365.4 | B | 6.8 |
| 66 | 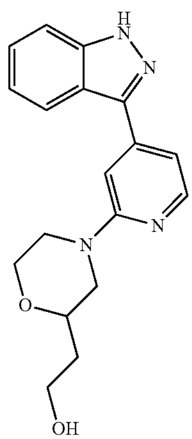 [SMILES: OCCC1CN(c2cc(-c3n[nH]c4ccccc34)ccn2)CCO1] | b | 0.82 | 325.2 | B | 15 |
| 67 | 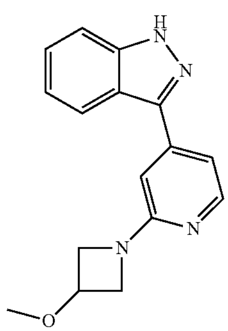 [SMILES: COC1CN(c2cc(-c3n[nH]c4ccccc34)ccn2)C1] | b | 0.89 | 281.4 | B | 31 |
| 68 | 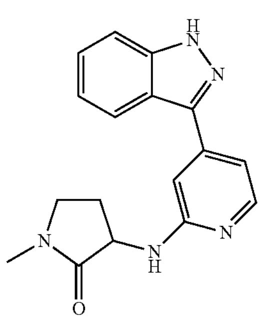 [SMILES: CN1CCC(Nc2cc(-c3n[nH]c4ccccc34)ccn2)C1=O] | b | 0.83 | 308.3 | B | 108 |

-continued

| Ex | Structure | LCMS Cond. | RT (min) | m/z | Method (Prep) | LRRK2 IC$_{50}$ (nM) |
|---|---|---|---|---|---|---|
| 69 | 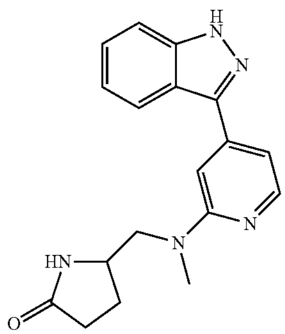 [SMILES: CN(CC1CCC(=O)N1)c1cc(-c2n[nH]c3ccccc23)ccn1] | b | 0.81 | 322.4 | B | 75 |
| 70 | 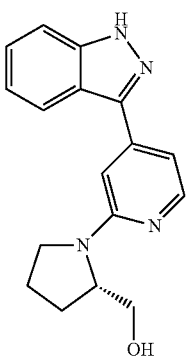 [SMILES: OC[C@@H]1CCCN1c1cc(-c2n[nH]c3ccccc23)ccn1] | b | 0.87 | 296.4 | B | 40 |
| 71 | 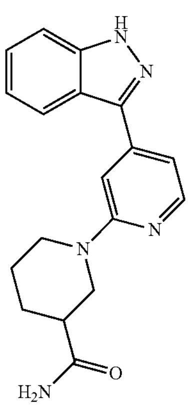 [SMILES: NC(=O)C1CCCN(c2cc(-c3n[nH]c4ccccc34)ccn2)C1] | b | 0.82 | 322.3 | B | 16 |
| 72 | 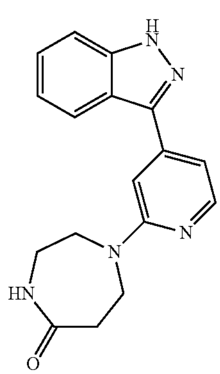 [SMILES: O=C1CCN(c2cc(-c3n[nH]c4ccccc34)ccn2)CCN1] | b | 0.79 | 308.4 | B | 57 |

-continued
| Ex | Structure | LCMS Cond. | RT (min) | m/z | Method (Prep) | LRRK2 IC$_{50}$ (nM) |
|---|---|---|---|---|---|---|
| 73 | 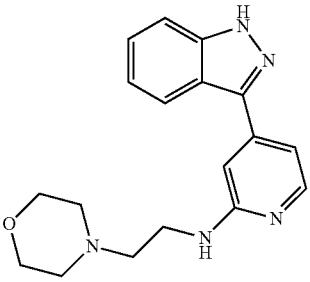 [SMILES: c1ccc2c(-c3ccnc(NCCN4CCOCC4)c3)n[nH]c2c1] | b | 0.74 | 324.4 | B | 35 |
| 74 | 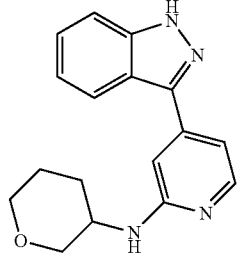 [SMILES: c1ccc2c(-c3ccnc(NC4CCCOC4)c3)n[nH]c2c1] | b | 0.89 | 295.4 | B | 57 |
| 401 | 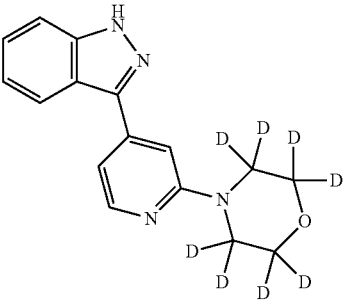 [SMILES: [2H]C1([2H])OC([2H])([2H])C([2H])([2H])N(c2cc(-c3n[nH]c4ccccc34)ccn2)C1([2H])[2H]] | e | 1.68 | 289 | A | 27 |
| 402 | 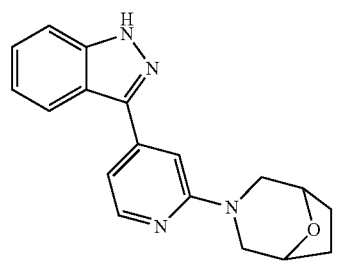 [SMILES: c1ccc2c(-c3ccnc(N4CC5CCC(C4)O5)c3)n[nH]c2c1] | e | 1.72 | 307 | A | 27 |
Scheme B
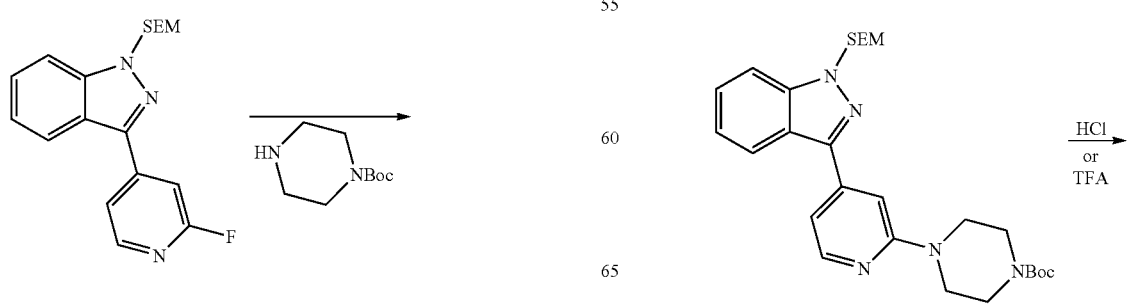

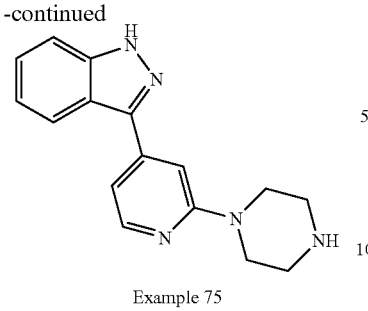

Example 75

Bubbled HCl (g) through a solution of tert-butyl 4-[4-(1-{[2-(trimethylsilyl)ethoxy]methyl}-1H-indazol-3-yl)pyridin-2-yl]piperazine-1-carboxylate (prepared using the procedure provided for Example 1, Method A) (15 mg, 0.029 mmol) in MeOH (0.3 mL) at 0° C. for 5 mins. The resulting solution was heated at 60° C. in a sealed tube overnight. After cooling to 0° C., the mixture was diluted with EtOAc and quenched with saturated aq. NaHCO₃. The mixture was extracted with EtOAc, dried (Na₂SO₄), and concentrated. Purification by medium pressure reverse phase chromatography afforded Example 75; LRMS (ESI) m/z 280.1 (Ret.=1.44 min, LCMS condition a) [(M+H)⁺ calcd for $C_{16}H_{18}N_5$: 280].

Scheme C

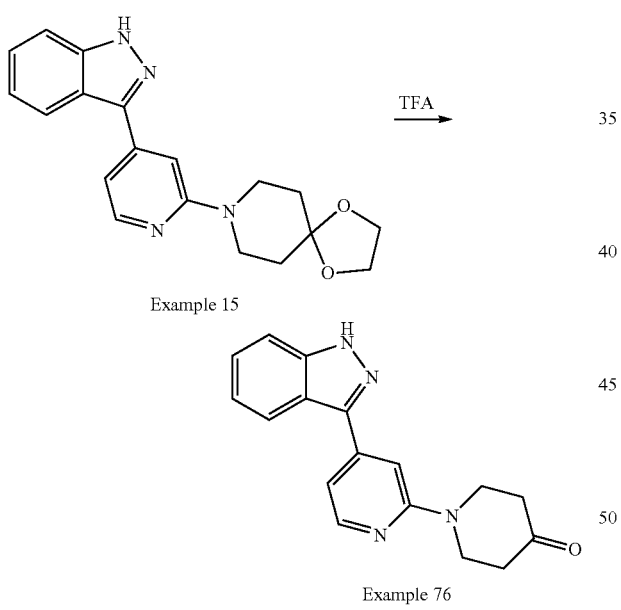

Example 15

Example 76

To a solution of 8-[4-(1H-indazol-3-yl)pyridin-2-yl]-1,4-dioxa-8-azaspiro[4.5]decane (Example 15) (20 mg, 0.06 mmol) in CH₂Cl₂ (0.6 mL) at rt was added TFA (0.5 mL). The mixture was stirred at rt for 5 h then concentrated. To the resulting oil was added MeOH (1 mL), CH₂Cl₂ (1 mL) and NH₄OH (1 mL). After 5 h, the resulting solution was quenched with water and extracted with CH₂Cl₂. The combined extracts were dried (Na₂SO₄), concentrated, and purified by silica gel chromatography (gradient elution, 0-5% MeOH/CH₂Cl₂) to afford Example 76; LRMS (ESI) m/z 293.1 (Ret.=1.39 min, LCMS condition a) [(M+H)⁺ calcd for $C_{17}H_{17}N_4O$: 293].

Scheme D

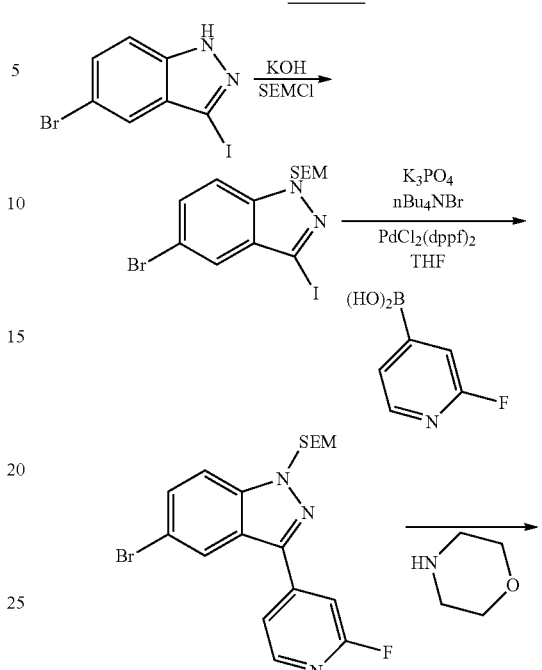

Example 77

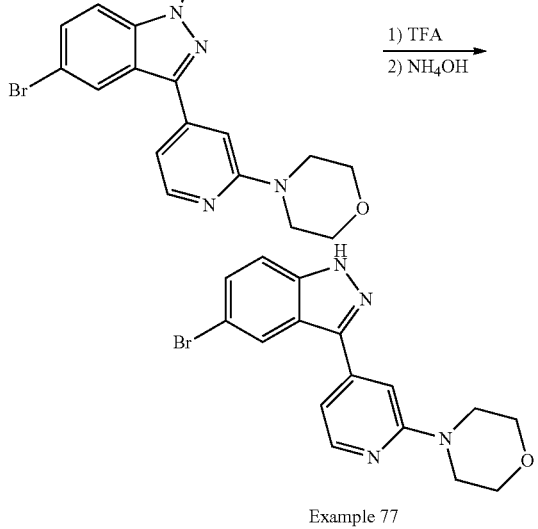

To a suspension of 5-bromo-3-iodo-1H-indazole (prepared from 5-bromo-1H-indazole using the procedure provided in Example 1) (16.58 g, 51.2 mmol), tetrabutylammonium bromide (0.165 g, 0.51 mmol), and potassium hydroxide (25.8 g, 46 mmol) in water (26 mL) and CH₂Cl₂ (68 mL) at 0° C. was added SEM-Cl (10 mL, 56.3 mmol). The mixture was stirred for 3 h at rt. The resulting mixture was diluted with CH₂Cl₂ and washed with water and brine.

The organics were dried (Na₂SO₄), concentrated and purified by silica gel chromatography (gradient elution, 0-20% EtOAc/hexanes) to afford the title compound; LRMS (ESI) m/z 453.8 [(M+H)⁺ calcd for $C_{13}H_{19}BrIN_2OSi$: 454].

Step 2

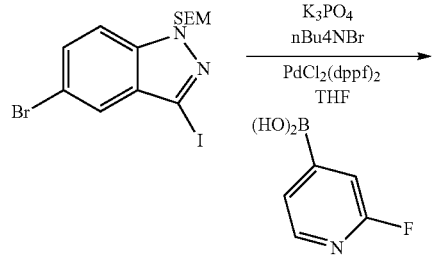

To a solution of 5-bromo-3-iodo-1-{[2-(trimethylsilyl)ethoxy]methyl}-1H-indazole (7.0 g, 15.45 mmol), 2-fluoropyridine-4-boronic acid (2.18 g, 15.45 mmol), tri-potassium phosphate trihydrate (12.34 g, 46.3 mmol), and tetrabutylammonium bromide (1.0 g, 3.09 mmol) in THF (140 mL) at rt under N₂ was added 1,1'-bis(diphenylphosphino)ferrocene-palladium(II) dichloride dichloromethane complex (2.52 g, 3.09 mmol). The resulting mixture was heated at 80° C. for 48 h. After cooling to rt, the mixture was filtered through Celite, diluted with EtOAc, washed with water, dried (Na₂SO₄), and concentrated. Purification by silica gel chromatography (gradient elution, 0-20% EtOAc/hexanes) afforded the title compound; LRMS (ESI) m/z 422.8 [(M+H)⁺ calcd for $C_{18}H_{22}BrFN_3OSi$: 423].

Step 3

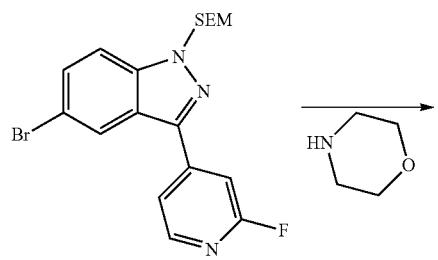

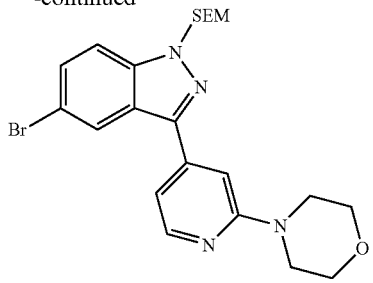

A solution of 5-bromo-3-(2-fluoropyridin-4-yl)-1-{[2-(trimethylsilyl)ethoxy]methyl}-1H-indazole (0.80 g, 1.89 mmol) and morpholine (1.32 g, 15.2 mmol) was heated at 70° C. overnight. After cooling to rt, the mixture was diluted with EtOAc and washed with 10% aq. citric acid (brought to pH 5 with 1 N NaOH), water, and brine. The organics were dried (Na₂SO₄), concentrated and purified by silica gel chromatography (gradient elution, 0-80% EtOAc/hexanes) to afford the title compound; LRMS (ESI) m/z 490.8 [(M+H)⁺ calcd for $C_{22}H_{30}BrN_4O_2Si$: 490].

Step 4

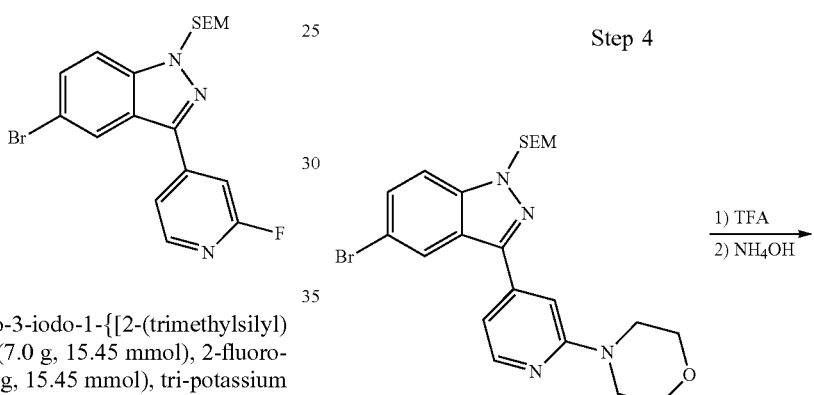

Example 77

To a solution of 5-bromo-3-[2-(morpholin-4-yl)pyridin-4-yl]-1-{[2-(trimethylsilyl)ethoxy]methyl}-1H-indazole (20 mg, 0.041 mmol) in CH₂Cl₂ (0.4 mL) at rt was added TFA (0.4 mL). The mixture was stirred at rt overnight then concentrated. To the resulting oil was added MeOH (1 mL), CH₂Cl₂ (1 mL) and NH₄OH (1 mL). After 5 h, the resulting solution was quenched with water and extracted with CH₂Cl₂. The combined extracts were dried (Na₂SO₄), concentrated, and purified by silica gel chromatography (gradient elution, 0-100% EtOAc/hexanes) to afford Example 77; LRMS (ESI) m/z 360.9 (Ret.=1.66 min, LCMS condition a).

Scheme E

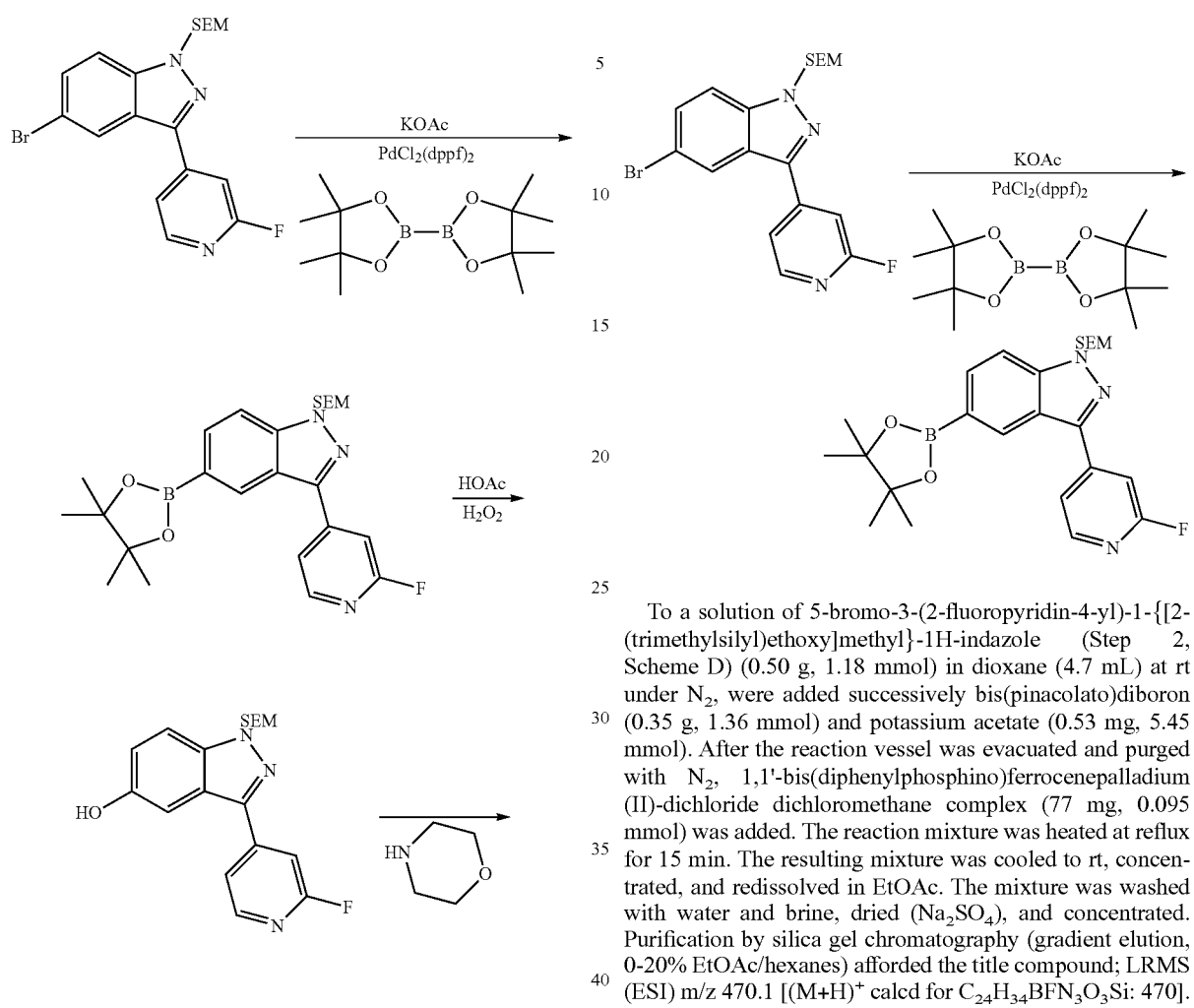

Example 78

Step 1

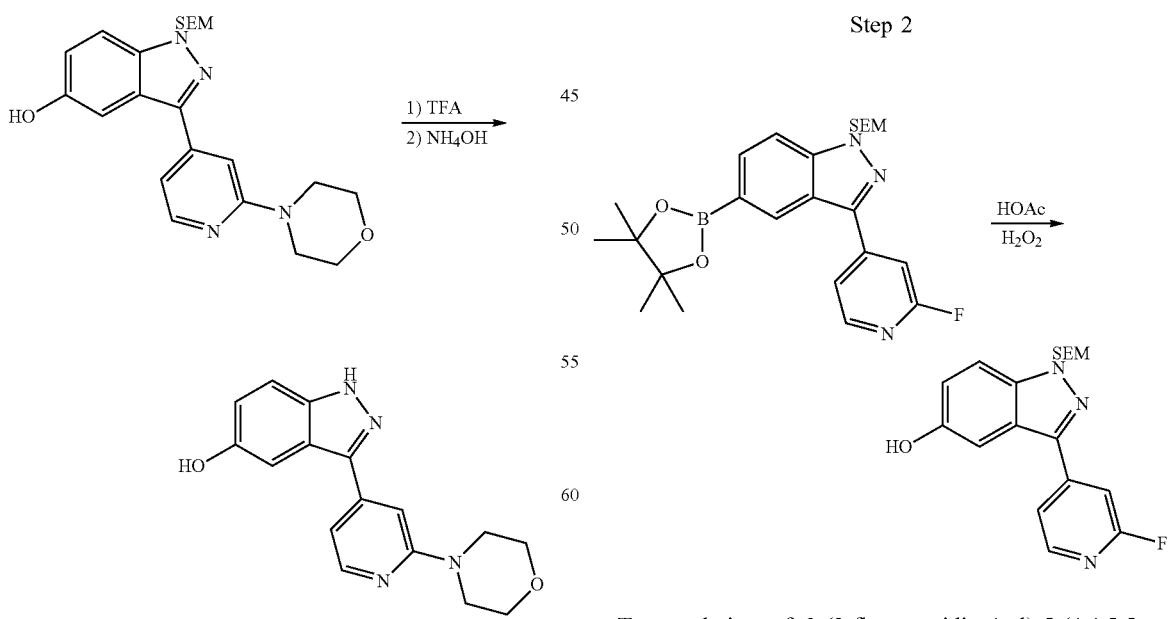

To a solution of 5-bromo-3-(2-fluoropyridin-4-yl)-1-{[2-(trimethylsilyl)ethoxy]methyl}-1H-indazole (Step 2, Scheme D) (0.50 g, 1.18 mmol) in dioxane (4.7 mL) at rt under $N_2$, were added successively bis(pinacolato)diboron (0.35 g, 1.36 mmol) and potassium acetate (0.53 mg, 5.45 mmol). After the reaction vessel was evacuated and purged with $N_2$, 1,1'-bis(diphenylphosphino)ferrocenepalladium (II)-dichloride dichloromethane complex (77 mg, 0.095 mmol) was added. The reaction mixture was heated at reflux for 15 min. The resulting mixture was cooled to rt, concentrated, and redissolved in EtOAc. The mixture was washed with water and brine, dried ($Na_2SO_4$), and concentrated. Purification by silica gel chromatography (gradient elution, 0-20% EtOAc/hexanes) afforded the title compound; LRMS (ESI) m/z 470.1 [(M+H)$^+$ calcd for $C_{24}H_{34}BFN_3O_3Si$: 470].

Step 2

To a solution of 3-(2-fluoropyridin-4-yl)-5-(4,4,5,5-tetramethyl-1,3,2-dioxaborolan-2-yl)-1-{[2-(trimethylsilyl)ethoxy]methyl}-1H-indazole (0.43 g, 0.92 mmol) in THF (3.7 mL) at rt were added successively acetic acid (0.10 mL, 1.84 mmol) and hydrogen peroxide (0.38 mL, 1.84 mmol). After 1 h, acetic acid (0.10 mL, 1.84 mmol) and hydrogen peroxide (0.38 mL, 1.84 mmol) were added. After another 1 h, acetic acid (0.10 mL, 1.84 mmol) and hydrogen peroxide (0.38 mL, 1.84 mmol) were added. After 6 h, the resulting mixture was quenched with water and extracted with $CH_2Cl_2$. The combined extracts were dried ($Na_2SO_4$), concentrated, and purified by silica gel chromatography (gradient elution, 0-60% EtOAc/hexanes) to afford the title compound; LRMS (ESI) m/z 360.0 [(M+H)$^+$ calcd for $C_{18}H_{23}FN_3O_2Si$: 360].

Step 3

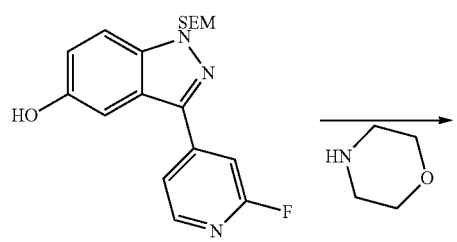

A mixture of 3-(2-fluoropyridin-4-yl)-1-{[2-(trimethylsilyl)ethoxy]methyl}-1H-indazol-5-ol (5 mg, 0.014 mmol) and morpholine (12 μL, 0.14 mmol) in DMSO (35 μL) was heated at 90° C. overnight. After cooling to rt, the mixture was diluted with EtOAc and washed with 10% aq. citric acid (brought to pH 5 with 1 N NaOH), water, and brine. The organics were dried ($Na_2SO_4$), concentrated and purified by silica gel chromatography (gradient elution, 0-7% MeOH/$CH_2Cl_2$) to afford the title compound; LRMS (ESI) m/z 427.0 [(M+H)$^+$ calcd for $C_{22}H_{31}N_4O_3Si$: 427].

Step 4

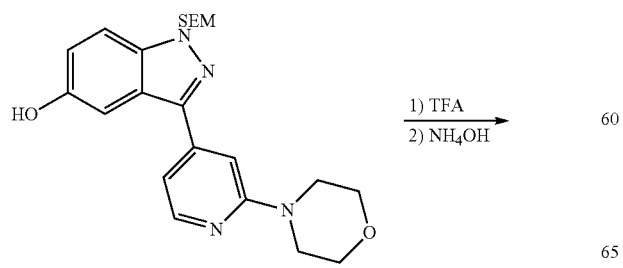

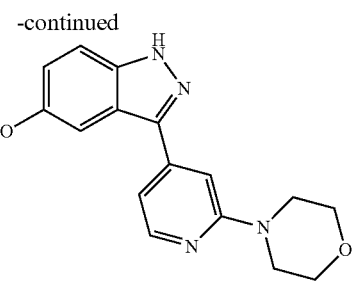

Example 78

To a solution of 3-[2-(morpholin-4-yl)pyridin-4-yl]-1-{[2-(trimethylsilyl)ethoxy]methyl}-1H-indazol-5-ol (50 mg, 0.12 mmol) in $CH_2Cl_2$ (1.2 mL) at rt was added TFA (0.9 mL). The mixture was stirred at rt overnight then concentrated. To the resulting oil was added MeOH (1 mL), $CH_2Cl_2$ (1 mL) and $NH_4OH$ (1 mL). After 5 h, the resulting solution was quenched with water and extracted with $CH_2Cl_2$. The combined extracts were dried ($Na_2SO_4$), concentrated, and purified by silica gel chromatography (gradient elution, 0-100% EtOAc/hexanes) to afford the title compound; LRMS (ESI) m/z 297.2 (Ret.=1.32 min, LCMS condition a).

Scheme F

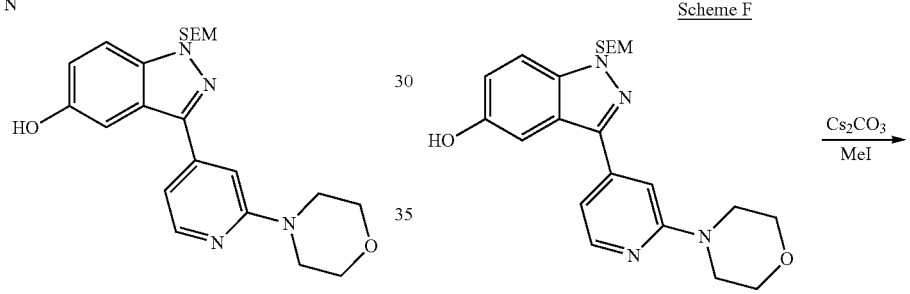

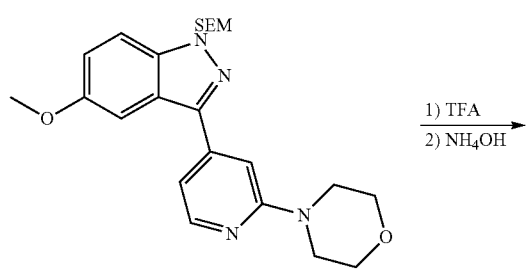

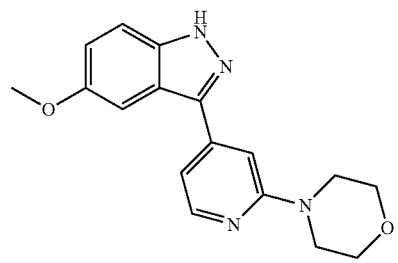

Example 79

Step 1

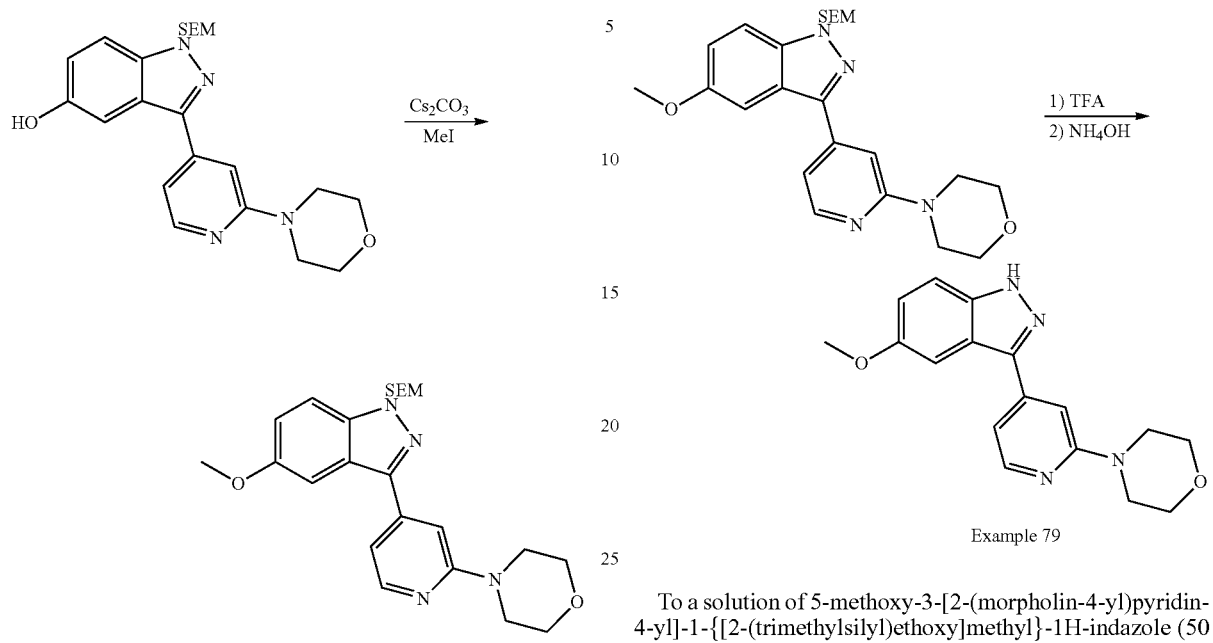

Step 2

To a solution of 3-[2-(morpholin-4-yl)pyridin-4-yl]-1-{[2-(trimethylsilyl)ethoxy]methyl}-1H-indazol-5-ol (Scheme E) (50 mg, 0.12 mmol) in DMF (1.2 mL) at 0° C., were added cesium carbonate (38.2 mg, 0.12 mmol) and methyl iodide (11 µL, 0.12 mmol). After 1 h, the resulting mixture was quenched with water and extracted with EtOAc. The combined extracts were dried ($Na_2SO_4$) and concentrated to afford the title compound without further purification; LRMS (ESI) m/z 441.0 [(M+H)$^+$ calcd for $C_{23}H_{33}N_4O_3Si$: 441].

To a solution of 5-methoxy-3-[2-(morpholin-4-yl)pyridin-4-yl]-1-{[2-(trimethylsilyl)ethoxy]methyl}-1H-indazole (50 mg, 0.11 mmol) in $CH_2Cl_2$ (1.1 mL) at rt was added TFA (0.9 mL). The mixture was stirred at rt overnight then concentrated. To the resulting oil was added MeOH (1 mL), $CH_2Cl_2$ (1 mL) and $NH_4OH$ (1 mL). After 5 h, the resulting solution was quenched with water and extracted with $CH_2Cl_2$. The combined extracts were dried ($Na_2SO_4$), concentrated, and purified by silica gel chromatography (gradient elution, 0-100% EtOAc/hexanes) to afford the title compound; LRMS (ESI) m/z 311.2 (Ret.=1.65 min, LCMS condition a).

By following the procedure outlined in Scheme F, using the appropriate alkyl halide, the following compounds can be prepared (Examples 80-84).

| Ex | Structure | HRMS Calcd. | HRMS Found | LRRK2 IC$_{50}$ (nM) |
|---|---|---|---|---|
| 80 | 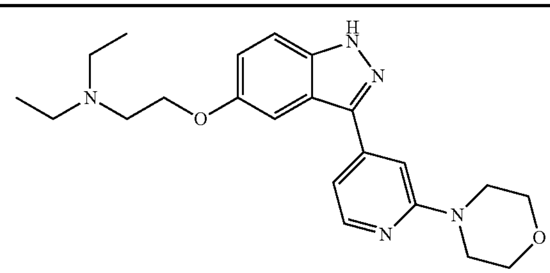 | 396.2394 | 396.2395 | 37 |
| 81 | 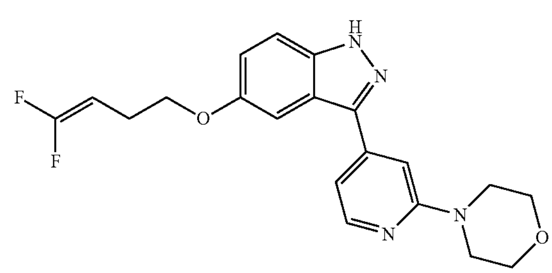 [SMILES: FC(F)=CCCOc1ccc2[nH]nc(-c3ccnc(N4CCOCC4)c3)c2c1] | 387.1627 | 387.1627 | 4.8 |

-continued
| Ex | Structure | HRMS Calcd. | HRMS Found | LRRK2 IC$_{50}$ (nM) |
|---|---|---|---|---|
| 82 | 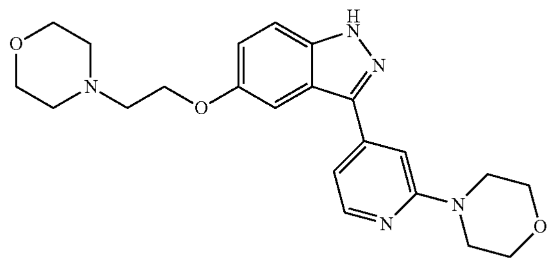 [SMILES: c1cc(-c2n[nH]c3ccc(OCCN4CCOCC4)cc23)cc(N2CCOCC2)n1] | 410.2187 | 410.2192 | 4.7 |
| 83 | 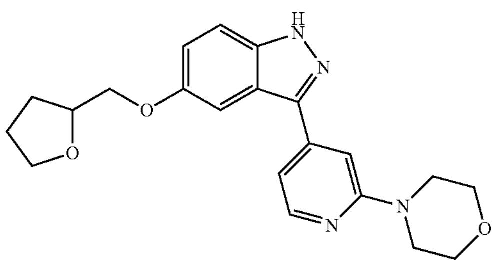 [SMILES: c1cc(-c2n[nH]c3ccc(OCC4CCCO4)cc23)cc(N2CCOCC2)n1] | 381.1921 | 381.1918 | 5.4 |
| 84 | 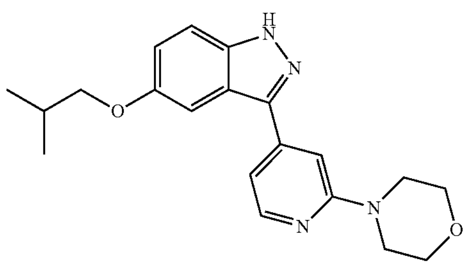 [SMILES: CC(C)COc1ccc2[nH]nc(-c3ccnc(N4CCOCC4)c3)c2c1] | 353.1972 | 353.1963 | 5.9 |
Scheme G
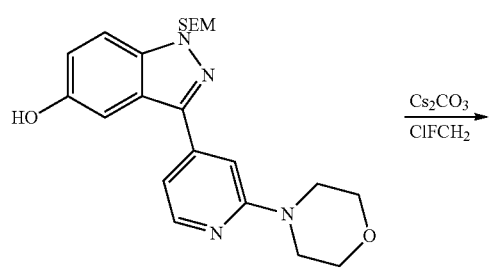
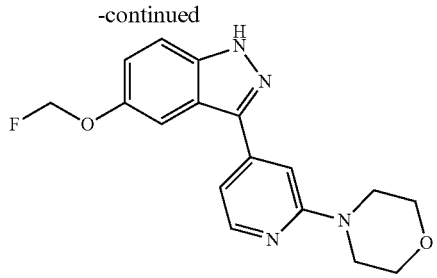
Example 85
Step 1
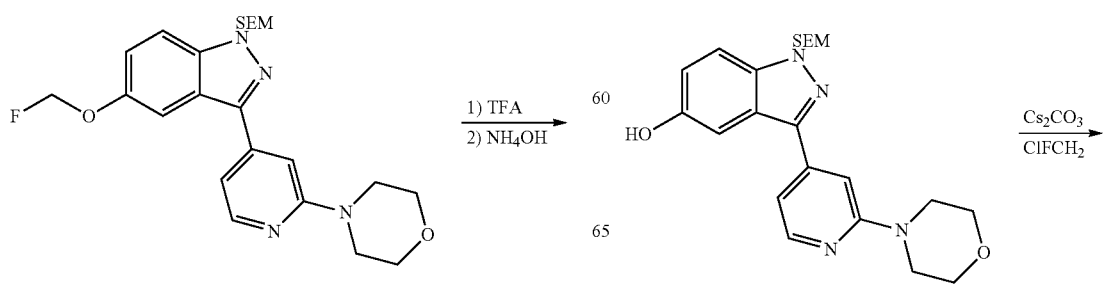

-continued

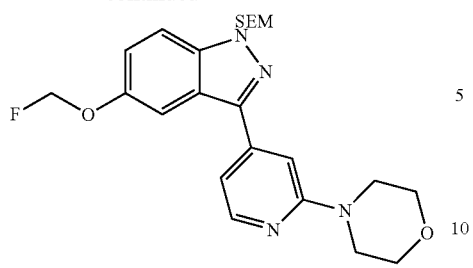

To a solution of 3-[2-(morpholin-4-yl)pyridin-4-yl]-1-{[2-(trimethylsilyl)ethoxy]methyl}-1H-indazol-5-ol (Scheme E) (50 mg, 0.12 mmol) in DMF (1.2 mL) at 0° C. was added cesium carbonate (42 mg, 0.13 mmol). Chloro(fluoro)methane (g) was bubbled through the solution for 1 min. The resulting mixture was stirred at rt for 5 h. The mixture was diluted with EtOAc and washed with water and brine. The organics were dried (Na$_2$SO$_4$), concentrated, and purified by silica gel chromatography (gradient elution, 0-80% EtOAc/hexanes); LRMS (ESI) m/z 459.1 [(M+H)$^+$ calcd for C$_{23}$H$_{32}$FN$_4$O$_3$Si: 459].

Step 2

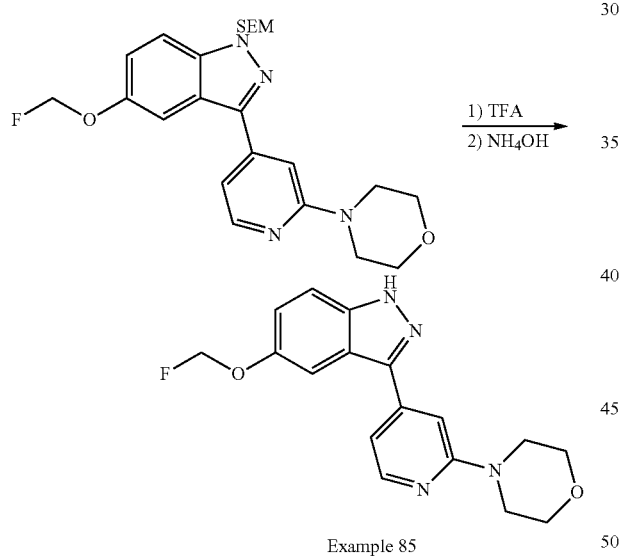

Example 85

To a solution of 5-(fluoromethoxy)-3-[2-(morpholin-4-yl)pyridin-4-yl]-1-{[2-(trimethylsilyl) ethoxy]methyl}-1H-indazole (36 mg, 0.078 mmol) in CH$_2$Cl$_2$ (0.8 mL) at rt was added TFA (61 μL). The mixture was stirred at rt overnight then concentrated. To the resulting oil was added MeOH (1 mL), CH$_2$Cl$_2$ (1 mL) and NH$_4$OH (1 mL). After 3 h, the resulting solution was quenched with water and extracted with CH$_2$Cl$_2$. The combined extracts were dried (Na$_2$SO$_4$), concentrated, and purified by silica gel chromatography (gradient elution, 0-100% EtOAc/hexanes) to afford the title compound; HRMS (ES+) m/z 329.1408 [(M+H)$^+$ calcd for C$_{17}$H$_{18}$FN$_4$O$_2$: 329.1408]; LRMS (ESI) m/z 329.2 (Ret.=1.45 min, LCMS condition a).

Scheme H

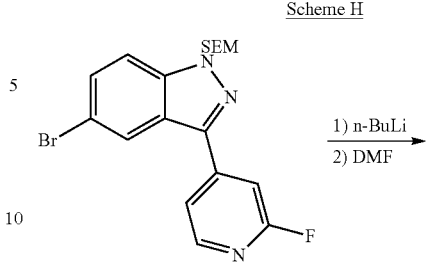

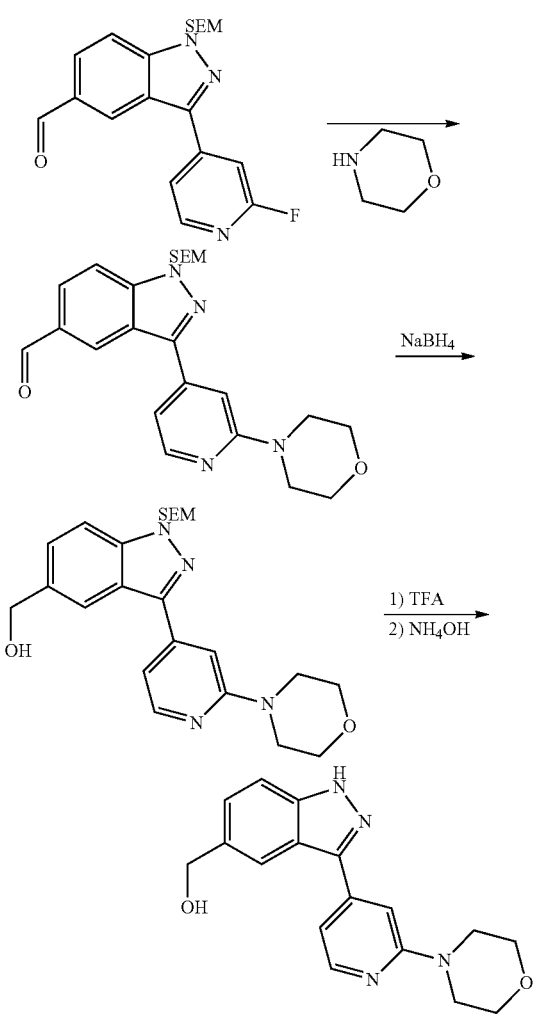

Example 86

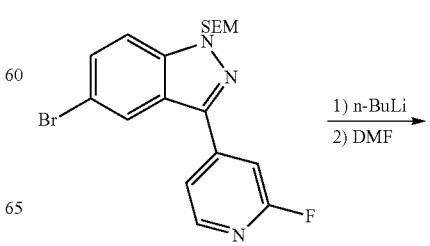

-continued

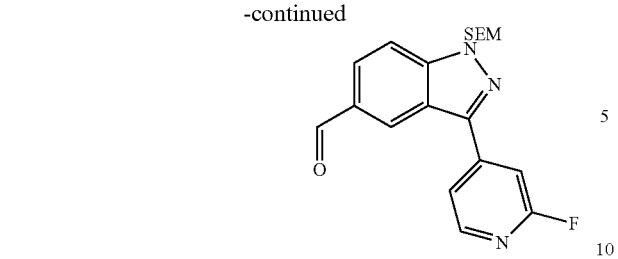

To a solution of 5-bromo-3-(2-fluoropyridin-4-yl)-1-{[2-(trimethylsilyl)ethoxy]methyl}-1H-indazole (Step 2, Scheme D) (200 mg, 0.47 mmol) in THF (2.4 mL) at −78° C. was added dropwise n-butyllithium (284 μL, 0.71 mmol). After 2 min, DMF (367 μL, 4.74 mmol) was added to the solution. The mixture was slowly warmed to rt over 1 h. The resulting mixture was quenched with water and 1 N HCl and extracted with $CH_2Cl_2$. The combined extracts were dried ($Na_2SO_4$) and concentrated. Purification by silica gel chromatography (gradient elution, 0-40% EtOAc/hexanes) afforded the title compound; LRMS (ESI) m/z 372.0 [(M+H)$^+$ calcd for $C_{19}H_{23}FN_3O_2Si$: 372].

Step 2

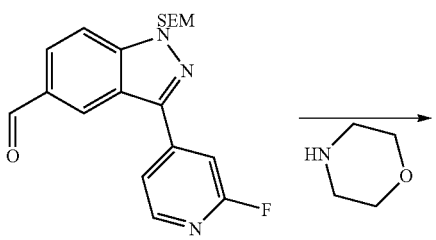

A mixture of 3-(2-fluoropyridin-4-yl)-1-{[2-(trimethylsilyl)ethoxy]methyl}-1H-indazole-5-carbaldehyde (519 mg, 1.40 mmol) and morpholine (1.2 mL, 14.0 mmol) was heated at 90° C. overnight. After cooling to rt, the mixture was diluted with EtOAc and washed with 10% aq. citric acid (brought to pH 5 with 1 N NaOH), water, and brine. The organics were dried ($Na_2SO_4$), concentrated and purified by silica gel chromatography (gradient elution, 0-3% MeOH/$CH_2Cl_2$) to afford the title compound; LRMS (ESI) m/z 439.0 [(M+H)$^+$ calcd for $C_{23}H_{31}N_4O_3Si$: 439].

Step 3

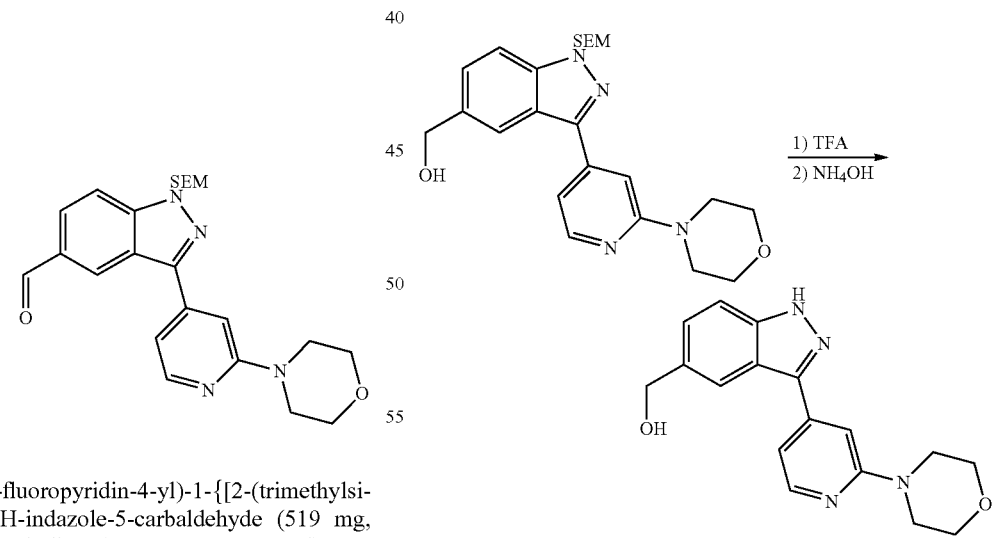

To a solution of 3-[2-(morpholin-4-yl)pyridin-4-yl]-1-{[2-(trimethylsilyl)ethoxy]methyl}-1H-indazole-5-carbaldehyde (160 mg, 0.37 mmol) in THF (3.6 mL) at 0° C. was added sodium borohydride (15.2 mg, 0.40 mmol). After 3 h, the mixture was filtered through Celite, diluted with EtOAc, and washed with water. The organics were dried ($Na_2SO_4$), concentrated, and purified by silica gel chromatography (gradient elution, 0-100% EtOAc/hexanes) to afford the title compound; LRMS (ESI) m/z 441.0 [(M+H)$^+$ calcd for $C_{23}H_{33}N_4O_3Si$: 441].

Step 4

Example 86

To a solution of (3-[2-(morpholin-4-yl)pyridin-4-yl]-1-{[2-(trimethylsilyl)ethoxy]methyl}-1H-indazol-5-yl)methanol (41 mg, 0.093 mmol) in $CH_2Cl_2$ (0.9 mL) at rt was added TFA (0.36 mL). The mixture was stirred at rt overnight and then concentrated. To the resulting oil was added MeOH (1 mL), CH$_2$Cl$_2$ (1 mL) and NH$_4$OH (1 mL). After 5 h, the resulting solution was quenched with water and extracted with CH$_2$Cl$_2$. The combined extracts were dried (Na$_2$SO$_4$), concentrated, and purified by silica gel chromatography (gradient elution, 0-100% EtOAc/hexanes) to afford the title compound; HRMS (ES+) m/z 311.1503 [(M+H)$^+$ calcd for C$_{17}$H$_{19}$N$_4$O$_2$: 311.1503]; LCMS (ESI) m/z 311.2 (Ret.=1.40 min, LCMS condition a).

Scheme I

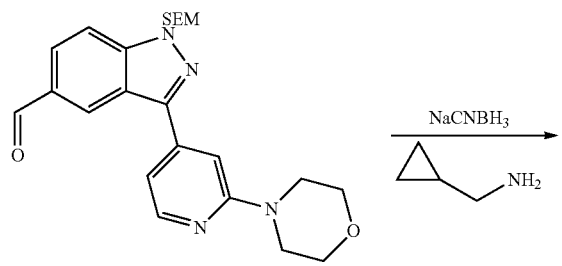

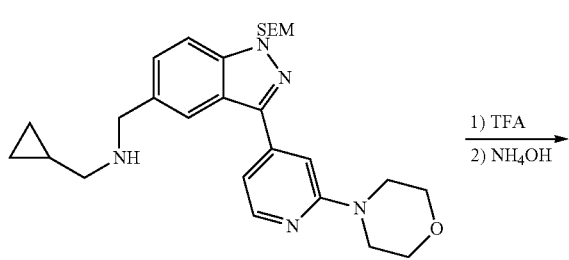

Example 87

Step 1

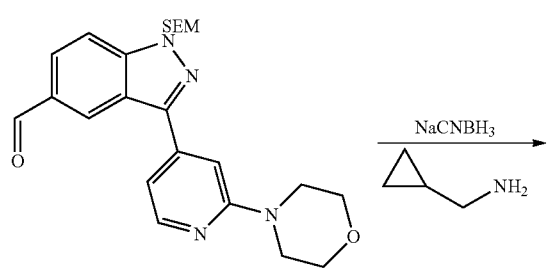

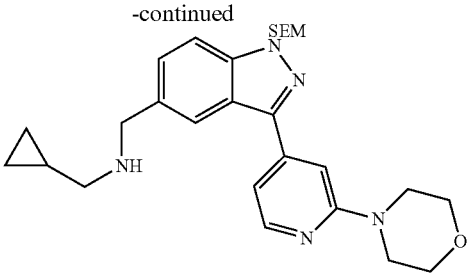

To a solution of 3-[2-(morpholin-4-yl)pyridin-4-yl]-1-{[2-(trimethylsilyl)ethoxy]methyl}-1H-indazole-5-carbaldehyde (Example 56) (100 mg, 0.23 mmol) in 1,2-dichloroethane (2.3 mL) at rt was added cyclopropylmethylamine (24 mg, 0.34 mmol). To this solution were added acetic acid (39 μL, 0.68 mmol) and sodium cyanoborohydride resin (101 mg, 0.23 mmol). The resulting mixture was heated in the microwave at 100° C. for 30 min. The reaction mixture was filtered through Celite and diluted with CH$_2$Cl$_2$ and water. The mixture was extracted with CH$_2$Cl$_2$, dried (Na$_2$SO$_4$), and concentrated. Purification by silica gel chromatography (gradient elution, 0-10% MeOH/CH$_2$Cl$_2$) afforded the title compound; LRMS (ESI) m/z 494.2 [(M+H)$^+$ calcd for C$_{27}$H$_{40}$N$_5$O$_2$Si: 494].

Example 87

To a solution of 1-cyclopropyl-N-[(3-[2-(morpholin-4-yl)pyridin-4-yl]-1-{[2-(trimethylsilyl) ethoxy]methyl}-1H-indazol-5-yl)methyl]methanamine (17 mg, 0.034 mmol) in CH$_2$Cl$_2$ (0.3 mL) at rt was added TFA (0.13 mL). The mixture was stirred at rt overnight then concentrated. To the resulting oil was added MeOH (1 mL), CH$_2$Cl$_2$ (1 mL) and NH$_4$OH (1 mL). After 5 h, the resulting solution was quenched with water and extracted with CH$_2$Cl$_2$. The combined extracts were dried (Na$_2$SO$_4$), concentrated, and purified by Gilson reverse phase chromatography to afford the title compound as a TFA salt; LCMS (ESI) m/z 364.2 (Ret.=1.49 min, LCMS condition a).

By following the procedure outlined in Scheme I, using the appropriate amine, the following compounds can be prepared (Examples 88-96).

| Ex | Structure | LCMS Cond. | RT (min) | m/z | LRRK2 IC$_{50}$ (nM) |
|---|---|---|---|---|---|
| 88 | 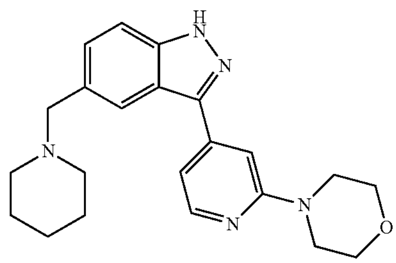 [SMILES: c1cc(-c2n[nH]c3ccc(CN4CCCCC4)cc23)cc(N2CCOCC2)n1] | a | 0.83 | 378.1 | 164 |
| 89 | 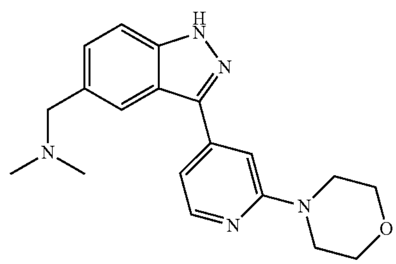 [SMILES: CN(C)Cc1ccc2[nH]nc(-c3ccnc(N4CCOCC4)c3)c2c1] | a | 1.59 | 338.2 | 35 |
| 90 | 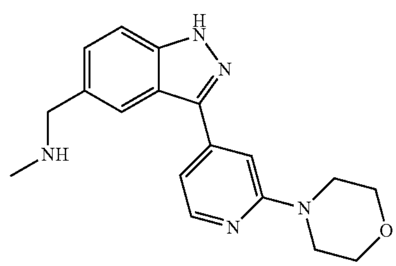 [SMILES: CNCc1ccc2[nH]nc(-c3ccnc(N4CCOCC4)c3)c2c1] | a | 1.58 | 324.1 | 302 |
| 91 | 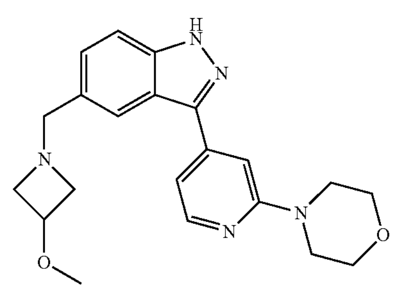 [SMILES: COC1CN(Cc2ccc3[nH]nc(-c4ccnc(N5CCOCC5)c4)c3c2)C1] | a | 0.79 | 380.1 | 161 |
| 92 | 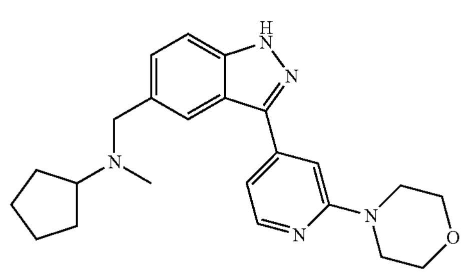 [SMILES: CN(Cc1ccc2[nH]nc(-c3ccnc(N4CCOCC4)c3)c2c1)C1CCCC1] | a | 1.47 | 392.2 | 54 |

-continued
| Ex | Structure | Cond. | LCMS RT (min) | m/z | LRRK2 IC$_{50}$ (nM) |
|---|---|---|---|---|---|
| 93 | 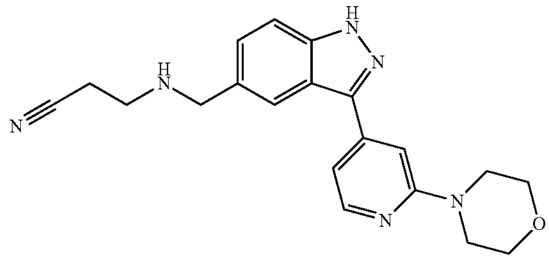 [SMILES: N#CCCNCc1ccc2[nH]nc(-c3ccnc(N4CCOCC4)c3)c2c1] | a | 1.42 | 363.1 | 30 |
| 94 | 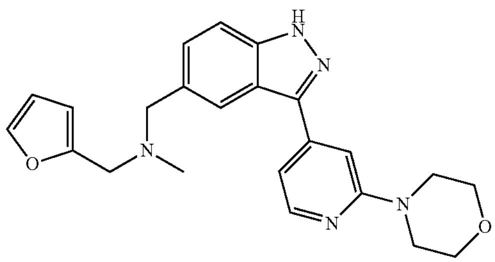 [SMILES: CN(Cc1ccc2[nH]nc(-c3ccnc(N4CCOCC4)c3)c2c1)Cc1ccco1] | a | 1.43 | 404.1 | 13 |
| 95 | 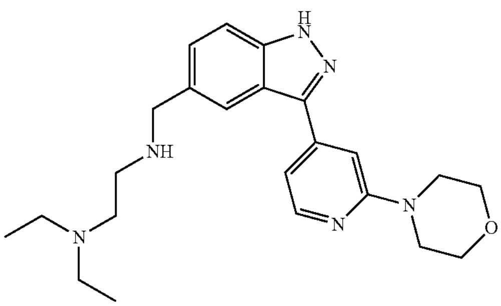 [SMILES: CCN(CC)CCNCc1ccc2[nH]nc(-c3ccnc(N4CCOCC4)c3)c2c1] | a | 0.76 | 409.2 | 273 |
| 96 | 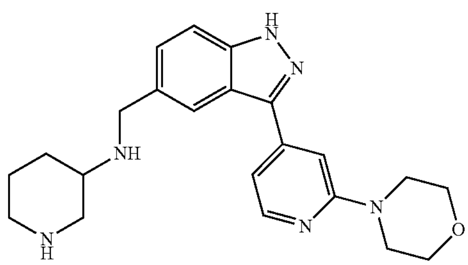 [SMILES: c1cc(-c2n[nH]c3ccc(CNC4CCCNC4)cc23)cc(N2CCOCC2)n1] | a | 0.74 | 393.2 | 110 |
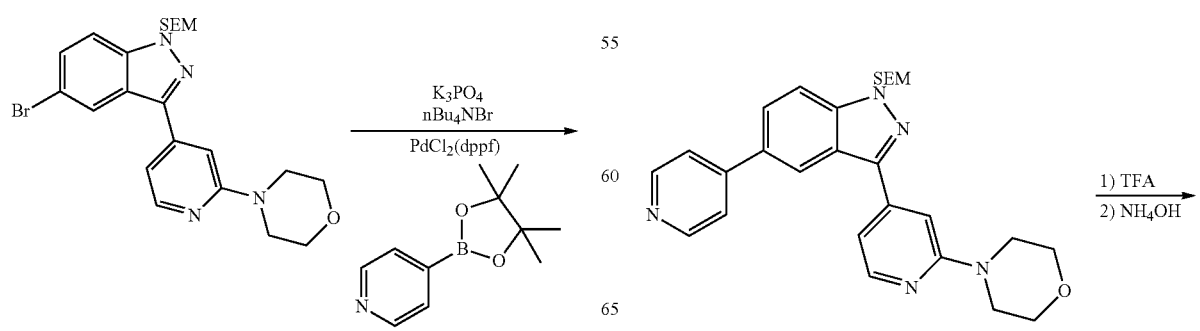
Scheme J

95
-continued

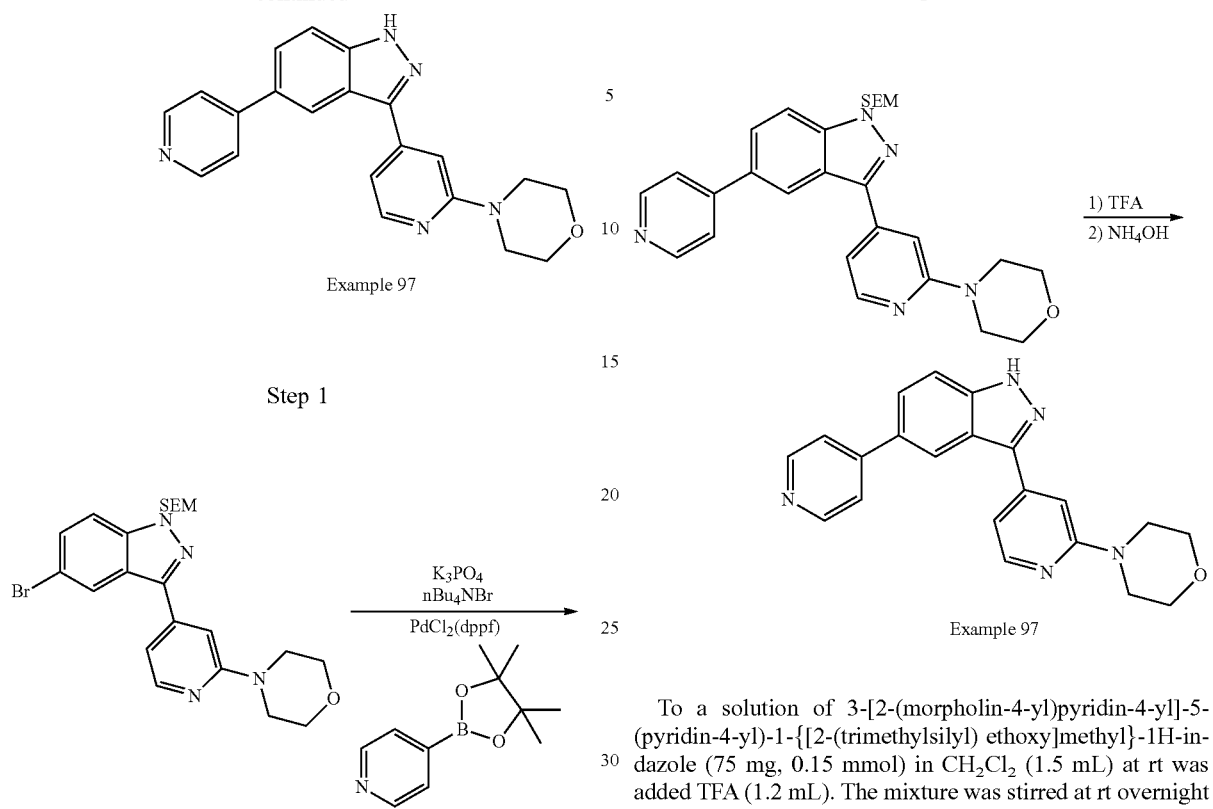

Example 97

Step 1

To a suspension of 5-bromo-3-[2-(morpholin-4-yl)pyridin-4-yl]-1-{[2-(trimethylsilyl) ethoxy]methyl}-1H-indazole (Step 3, Scheme D) (100 mg, 0.20 mmol), 4-(4,4,5,5-tetramethyl-1,3,2-dioxaborolan-2-yl)pyridine (42 mg, 0.20 mmol), tri-potassium phosphate trihydrate (163 mg, 0.61 mmol), and tetrabutylammonium bromide (13.2 mg, 0.041 mmol) in THF (1.9 mL) at rt under $N_2$ was added 1,1'-bis(diphenylphosphino)ferrocene-palladium(II)dichloride dichloromethane complex (33 mg, 0.041 mmol). The resulting mixture was heated at 80° C. for 48 h. After cooling to rt, the mixture was filtered through Celite, diluted with EtOAc, washed with water, dried ($Na_2SO_4$), and concentrated. Purification by silica gel chromatography (gradient elution, 0-100% EtOAc/hexanes) afforded the title compound; LRMS (ESI) m/z 488.0 [(M+H)$^+$ calcd for $C_{27}H_{34}N_5O_2Si$: 488].

96
Step 2

To a solution of 3-[2-(morpholin-4-yl)pyridin-4-yl]-5-(pyridin-4-yl)-1-{[2-(trimethylsilyl) ethoxy]methyl}-1H-indazole (75 mg, 0.15 mmol) in $CH_2Cl_2$ (1.5 mL) at rt was added TFA (1.2 mL). The mixture was stirred at rt overnight then concentrated. To the resulting oil was added MeOH (1 mL), $CH_2Cl_2$ (1 mL) and $NH_4OH$ (1 mL). After 5 h, the resulting solution was quenched with water and extracted with $CH_2Cl_2$. The combined extracts were dried ($Na_2SO_4$) and concentrated. Purification by medium pressure reverse phase chromatography afforded the title compound as a TFA salt; HRMS (ES+) m/z 358.1664 [(M+H)$^+$ calcd for $C_{21}H_{20}N_5O$: 358.1662]; LCMS (ESI) m/z 358.0 (Ret.=1.42 min, LCMS condition a).

Scheme K

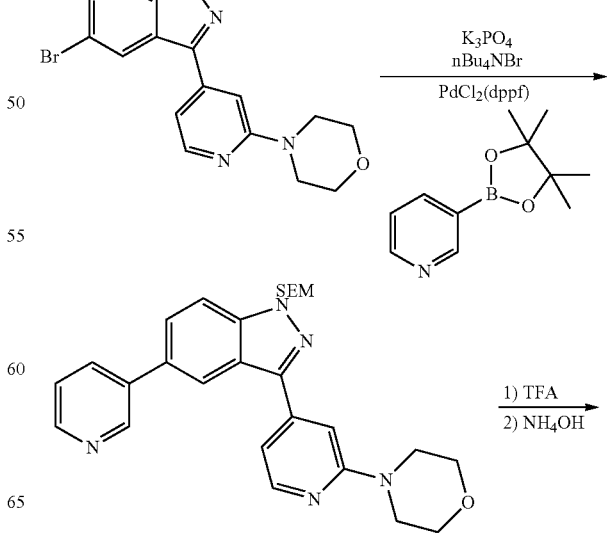

97

-continued

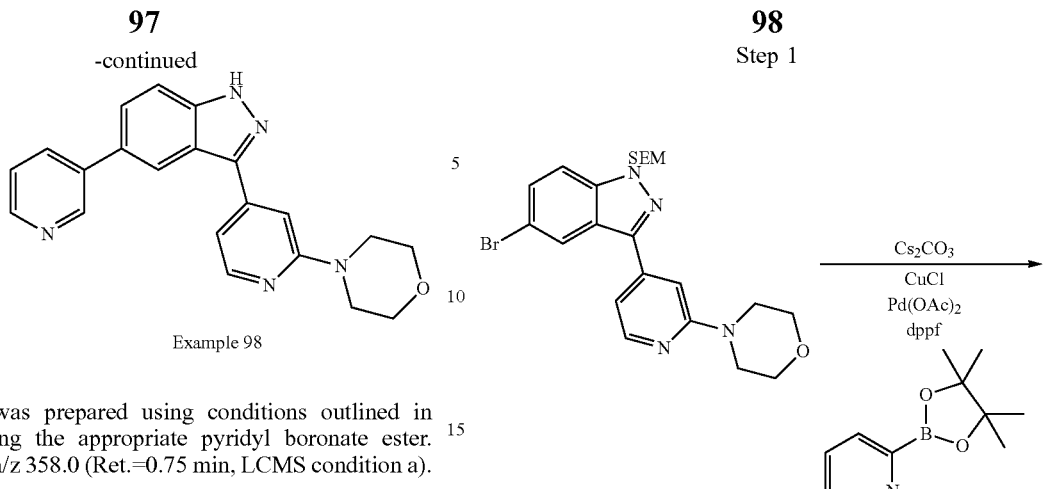

Example 98

Example 98 was prepared using conditions outlined in Scheme J using the appropriate pyridyl boronate ester. LCMS (ESI) m/z 358.0 (Ret.=0.75 min, LCMS condition a).

Scheme L

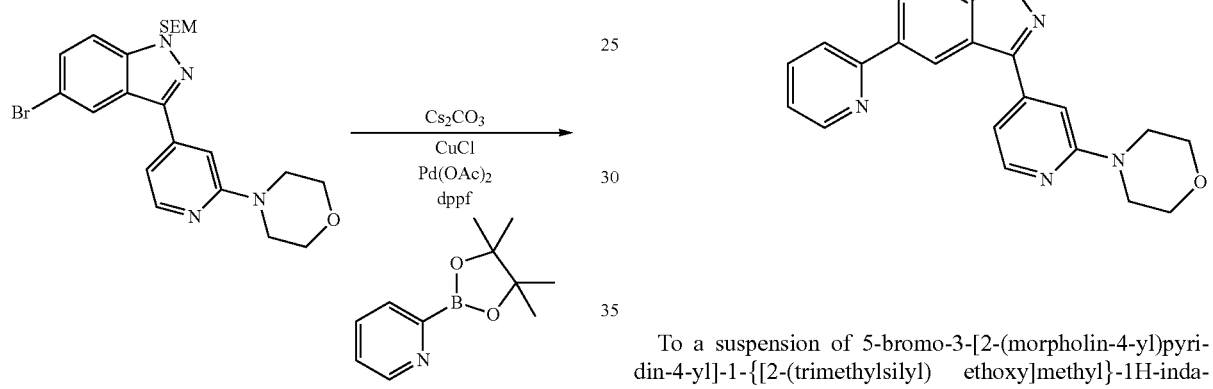

Example 99

98

Step 1

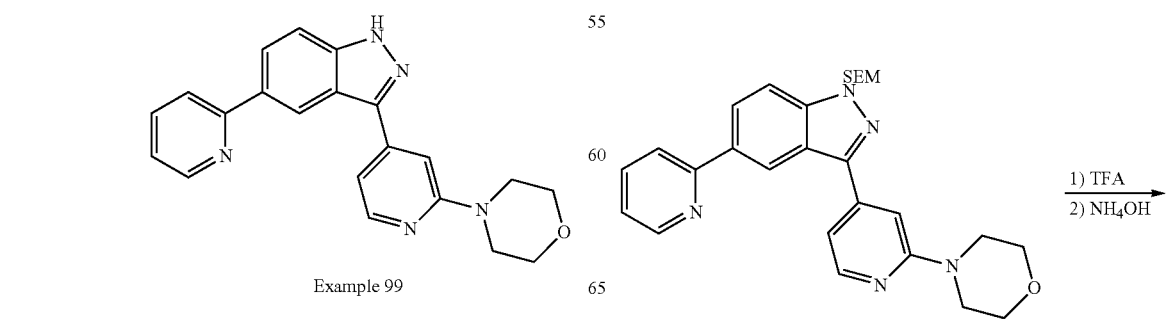

To a suspension of 5-bromo-3-[2-(morpholin-4-yl)pyridin-4-yl]-1-{[2-(trimethylsilyl) ethoxy]methyl}-1H-indazole (Step 3, Scheme D) (100 mg, 0.20 mmol), 2-(4,4,5,5-tetramethyl-1,3,2-dioxaborolan-2-yl)pyridine (84 mg, 0.41 mmol), and cesium carbonate (266 mg, 0.82 mmol) in DMF (1.9 mL) at rt under $N_2$ were added copper(I) chloride (20.2 mg, 0.20 mmol), palladium(II) acetate (2.3 mg, 0.01 mmol), and 1,1'-bis(diphenylphosphino)ferrocene (11 mg, 0.020 mmol). The resulting mixture was heated at 100° C. in a sealed vessel for 16 h. After cooling to rt, the mixture was filtered through Celite, diluted with EtOAc, washed with water, dried ($Na_2SO_4$), and concentrated. Purification by silica gel chromatography (gradient elution, 0-100% EtOAc/hexanes) afforded the title compound; LRMS (ESI) m/z 488.0 [(M+H)$^+$ calcd for $C_{27}H_{34}N_5O_2Si$: 488].

Step 2

99
-continued

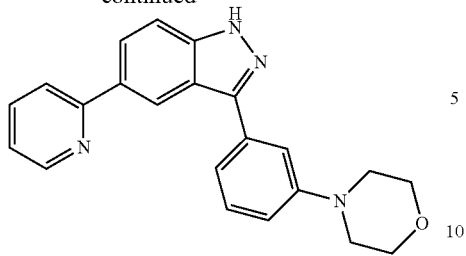

Example 99

100
-continued

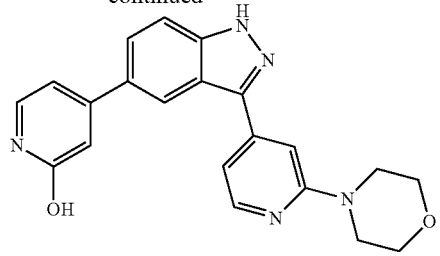

Example 100

To a solution of 3-[2-(morpholin-4-yl)pyridin-4-yl]-5-(pyridin-2-yl)-1-{[2-(trimethylsilyl) ethoxy]methyl}-1H-indazole (80 mg, 0.16 mmol) in $CH_2Cl_2$ (1.6 mL) at rt was added TFA (1.3 mL). The mixture was stirred at rt overnight then concentrated. To the resulting oil was added MeOH (1 mL), $CH_2Cl_2$ (1 mL) and $NH_4OH$ (1 mL). After 5 h, the resulting solution was quenched with water and extracted with $CH_2Cl_2$. The combined extracts were dried ($Na_2SO_4$) and concentrated. Purification by Gilson reverse phase chromatography afforded the title compound as a TFA salt; HRMS (ES+) m/z 358.1666 [(M+H)$^+$ calcd for $C_{21}H_{20}N_5O$: 358.1662]; LCMS (ESI) m/z 358.1 (Ret.=1.29 min, LCMS condition a).

Step 1

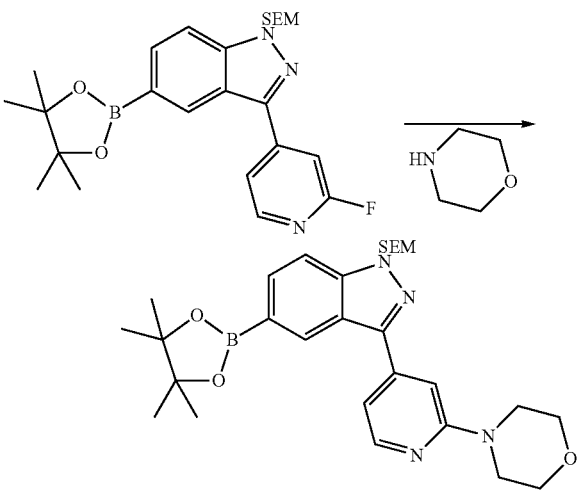

A mixture of 3-(2-fluoropyridin-4-yl)-5-(4,4,5,5-tetramethyl-1,3,2-dioxaborolan-2-yl)-1-{[2-(trimethylsilyl)ethoxy]methyl}-1H-indazole (Step 1, Scheme E) (0.70 g, 1.49 mmol) and morpholine (2.6 mL, 29.8 mmol) was heated at 70° C. overnight. After cooling to rt, the mixture was diluted with EtOAc and washed with 10% aq. citric acid (brought to pH 5 with 1 N NaOH), water, and brine. The organics were dried ($Na_2SO_4$), concentrated and purified by silica gel chromatography (gradient elution, 0-60% EtOAc/hexanes) to afford the title compound; LRMS (ESI) m/z 537.0 [(M+H)$^+$ calcd for $C_{28}H_{42}BN_4O_4Si$: 537].

Step 2

Scheme M

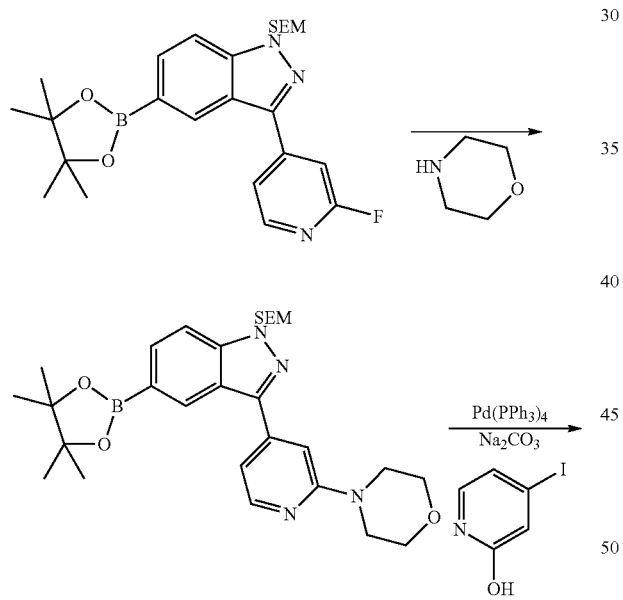

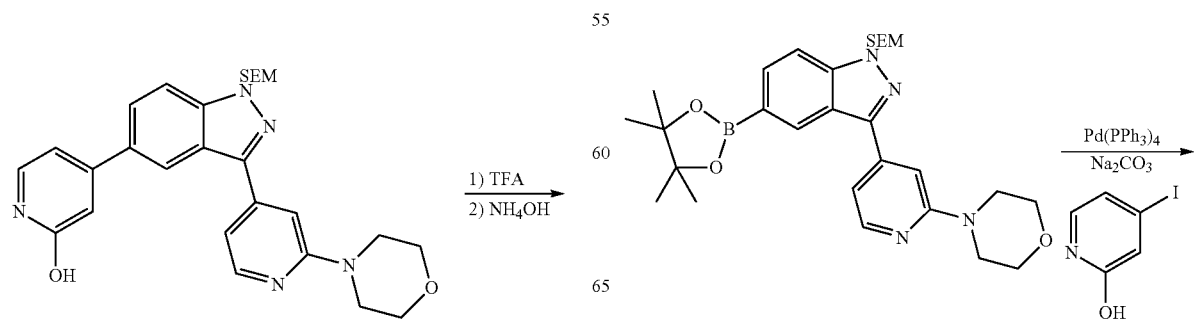

101

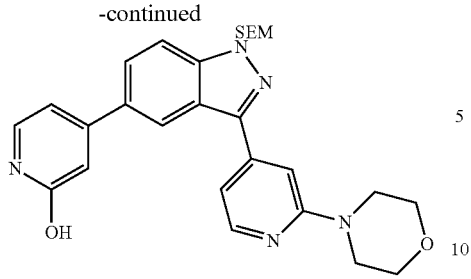

To a solution of 3-[2-(morpholin-4-yl)pyridin-4-yl]-5-(4,4,5,5-tetramethyl-1,3,2-dioxaborolan-2-yl)-1-{[2-(trimethylsilyl)ethoxy]methyl}-1H-indazole (215 mg, 0.40 mmol), 4-iodopyridin-2-ol (89 mg, 0.40 mmol), and 2 M aqueous sodium carbonate (401 μL, 0.80 mmol) in THF (3.6 mL) at rt, was added tetrakis(triphenylphosphine)palladium(0) (9.2 mg, 0.008 mmol). The resulting mixture was heated at 100° C. in a sealed vessel for 16 h. After cooling to rt, the mixture was filtered through Celite, diluted with EtOAc, washed with water, dried (Na$_2$SO$_4$), and concentrated. Purification by silica gel chromatography (gradient elution, 0-10% MeOH/CH$_2$Cl$_2$) afforded the title compound; LRMS (ESI) m/z 504.0 [(M+H)$^+$ calcd for C$_{27}$H$_{34}$N$_5$O$_3$Si: 504].

Step 3

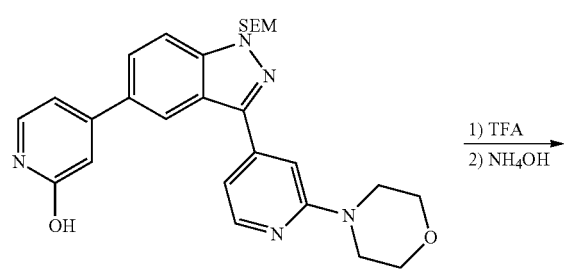

1) TFA
2) NH$_4$OH

102

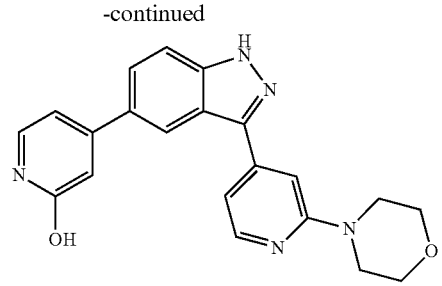

Example 100

To a solution of 5-(3-[2-(morpholin-4-yl)pyridin-4-yl]-1-{[2-(trimethylsilyl)ethoxy]methyl}-1H-indazol-5-yl)pyridin-2-ol (182 mg, 0.36 mmol) in CH$_2$Cl$_2$ (3.6 mL) at rt was added TFA (0.6 mL). The mixture was stirred at rt overnight then concentrated. To the resulting oil was added MeOH (1 mL), CH$_2$Cl$_2$ (1 mL) and NH$_4$OH (1 mL). After 5 h, the resulting solution was quenched with water and extracted with CH$_2$Cl$_2$. The combined extracts were dried (Na$_2$SO$_4$) and concentrated. Purification by silica gel chromatography (gradient elution, 0-15% MeOH/CH$_2$Cl$_2$) afforded the title compound; HRMS (ES+) m/z 374.1607 [(M+H)$^+$ calcd for C$_{21}$H$_{20}$N$_5$O$_2$: 374.1612]; LCMS (ESI) m/z 374.1 (Ret.=1.37 min, LCMS condition a).

By following the procedure outlined in Scheme M, using the appropriate aryl halide, the following compounds can be prepared (Examples 101-102).

| Ex | Structure | Cond. | LCMS RT (min) | m/z | LRRK2 IC$_{50}$ (nM) |
|---|---|---|---|---|---|
| 101 | | a | 2.4 | 465.1 | 182 |
| 102 | | a | 1.4 | 388.1 | 0.2 |

Scheme N

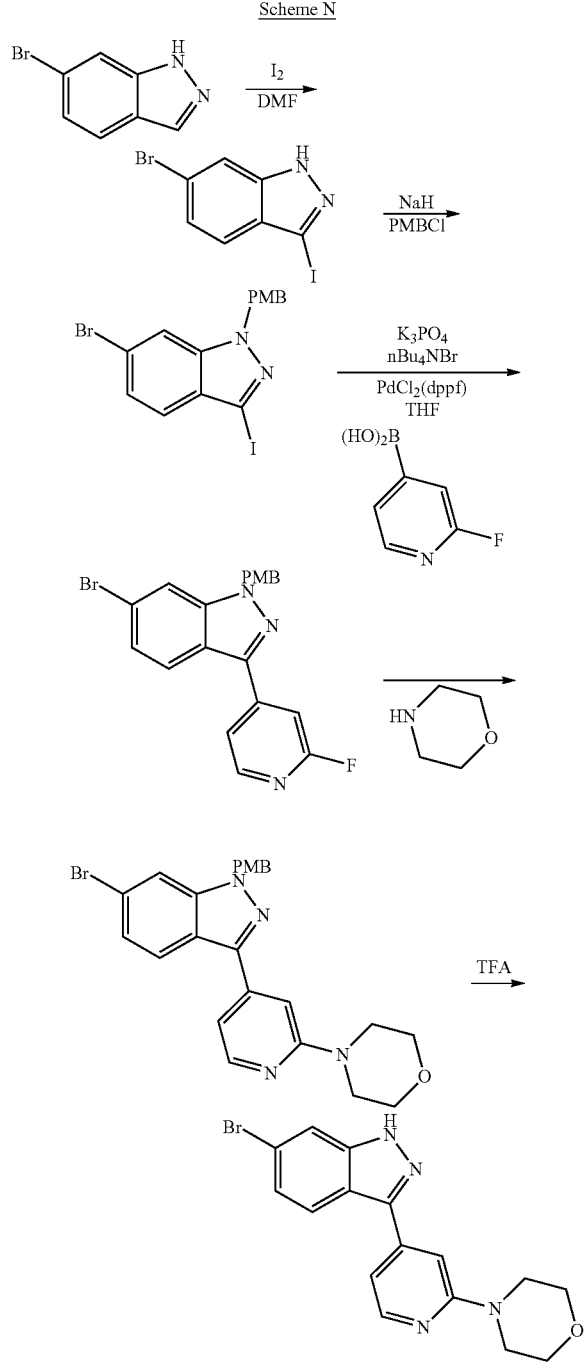

Example 103

Step 1

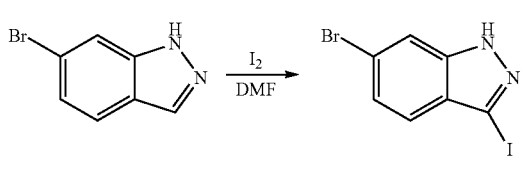

6-Bromo-3-iodo-1H-indazole was prepared from 6-bromo-1H-indazole using the procedure provided in Example 1; LRMS (ESI) m/z 322.8 [(M+H)$^+$ calcd for $C_7H_5BrIN_2$: 323].

Step 2

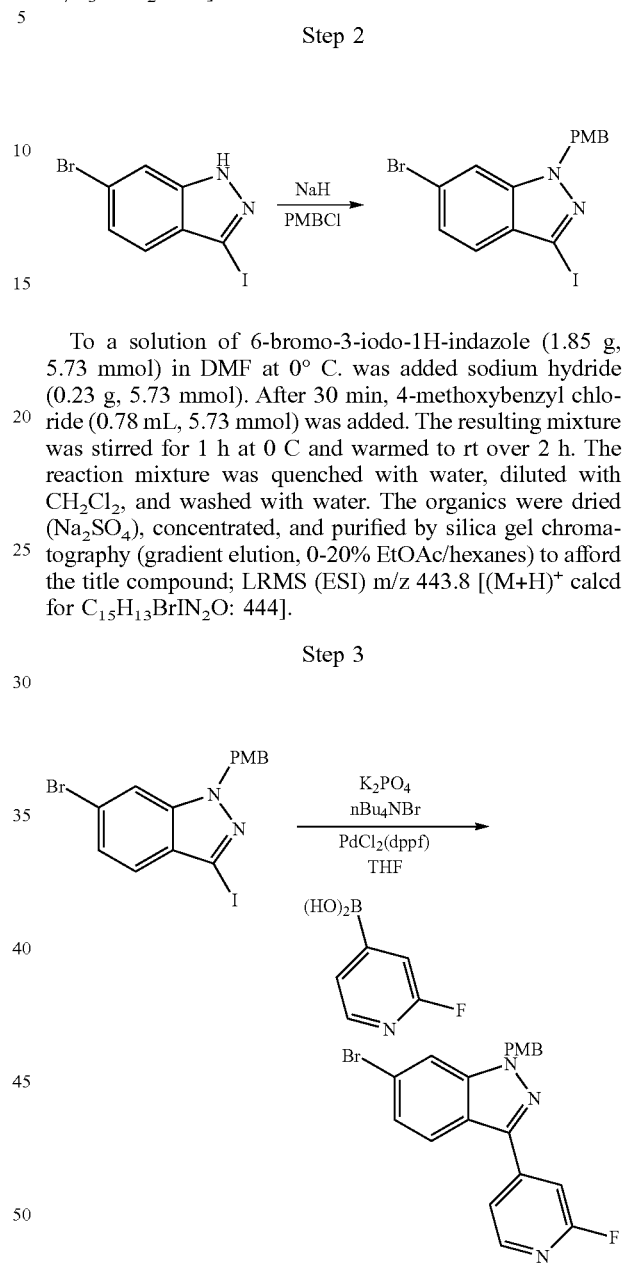

To a solution of 6-bromo-3-iodo-1H-indazole (1.85 g, 5.73 mmol) in DMF at 0° C. was added sodium hydride (0.23 g, 5.73 mmol). After 30 min, 4-methoxybenzyl chloride (0.78 mL, 5.73 mmol) was added. The resulting mixture was stirred for 1 h at 0 C and warmed to rt over 2 h. The reaction mixture was quenched with water, diluted with $CH_2Cl_2$, and washed with water. The organics were dried ($Na_2SO_4$), concentrated, and purified by silica gel chromatography (gradient elution, 0-20% EtOAc/hexanes) to afford the title compound; LRMS (ESI) m/z 443.8 [(M+H)$^+$ calcd for $C_{15}H_{13}BrIN_2O$: 444].

Step 3

To a suspension of 6-bromo-3-iodo-1-(4-methoxybenzyl)-1H-indazole (2.15 g, 4.85 mmol), 2-fluoropyridine-4-boronic acid (0.68 g, 4.85 mmol), tri-potassium phosphate trihydrate (3.88 g, 14.56 mmol), and tetrabutylammonium bromide (0.31 g, 0.97 mmol) in THF (44 mL) at rt under $N_2$ was added 1,1'-bis(diphenylphosphino)ferrocene-palladium (II) dichloride dichloromethane complex (0.79 g, 0.97 mmol). The resulting mixture was heated at 80° C. for 48 h. After cooling to rt, the mixture was filtered through Celite, diluted with EtOAc, washed with water, dried ($Na_2SO_4$), and concentrated. Purification by silica gel chromatography (gradient elution, 0-20% EtOAc/hexanes) afforded the title compound; LRMS (ESI) m/z 412.8 [(M+H)$^+$ calcd for $C_{18}H_{23}ClN_3OSi$: 413].

Step 4

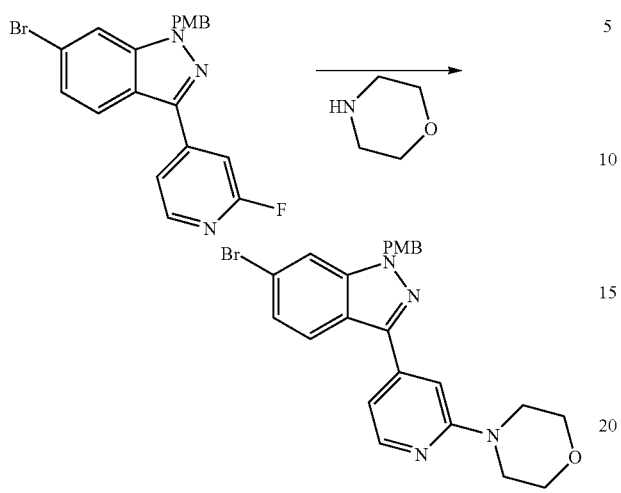

To a solution of 6-bromo-3-(2-fluoropyridin-4-yl)-1-(4-methoxybenzyl)-1H-indazole (0.55 g, 1.32 mmol) in DMSO (2.6 mL) at rt was added morpholine (1.1 mL, 13.22 mmol). The resulting solution was heated at 80° C. overnight. After cooling to rt, the mixture was diluted with EtOAc and washed with 10% aq. citric acid (brought to pH 5 with 1 N NaOH), water, and brine. The organics were dried (Na$_2$SO$_4$), concentrated and purified by silica gel chromatography (gradient elution, 0-80% EtOAc/hexanes) to afford the title compound; LRMS (ESI) m/z 479.9 [(M+H)$^+$ calcd for C$_{24}$H$_{24}$BrN$_4$O$_2$: 480].

Step 5

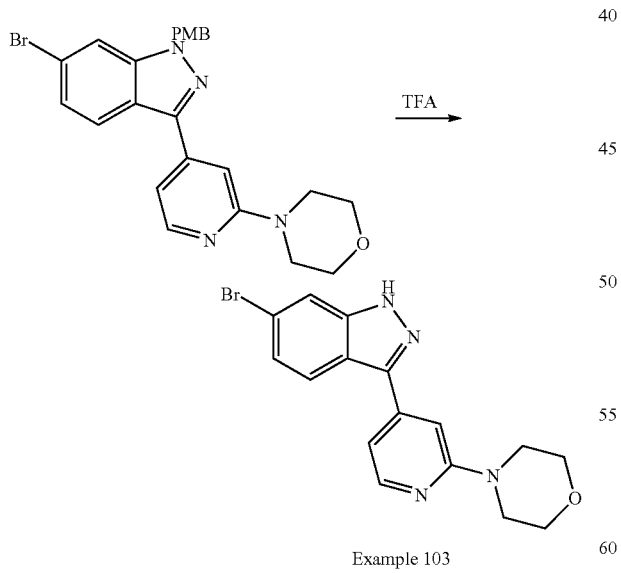

Example 103

6-Bromo-1-(4-methoxybenzyl)-3-[2-(morpholin-4-yl) pyridin-4-yl]-1H-indazole (50 mg, 0.10 mmol) was dissolved in TFA (0.4 mL) and heated at 100° C. for 3 h. The solution was concentrated and purified by medium pressure reverse phase chromatography to afford the title compound;

HRMS (ES+) m/z 359.0492 [(M+H)$^+$ calcd for C$_{16}$H$_{16}$BrN$_4$O: 359.0502]; LCMS (ESI) m/z 361.0 (Ret.=1.56 min, LCMS condition a).

Scheme O

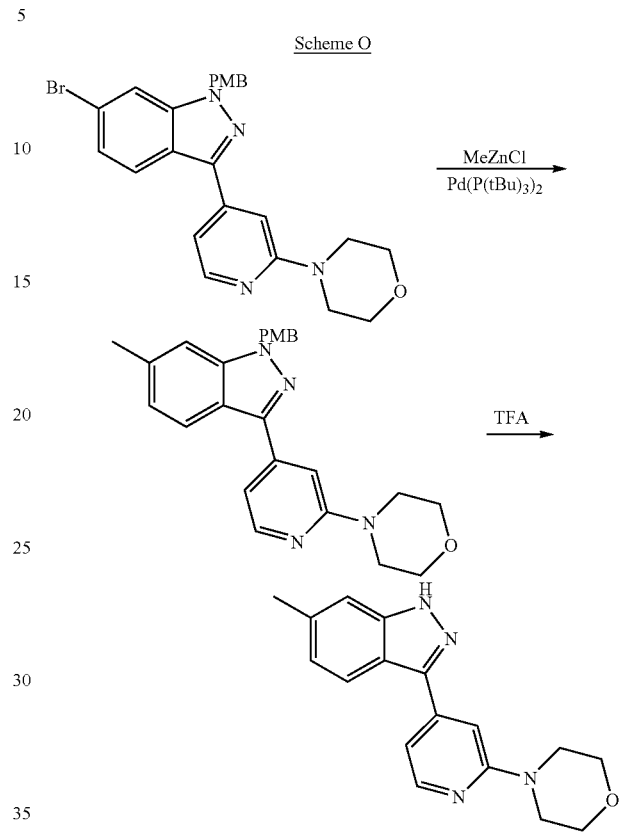

Example 104

Step 1

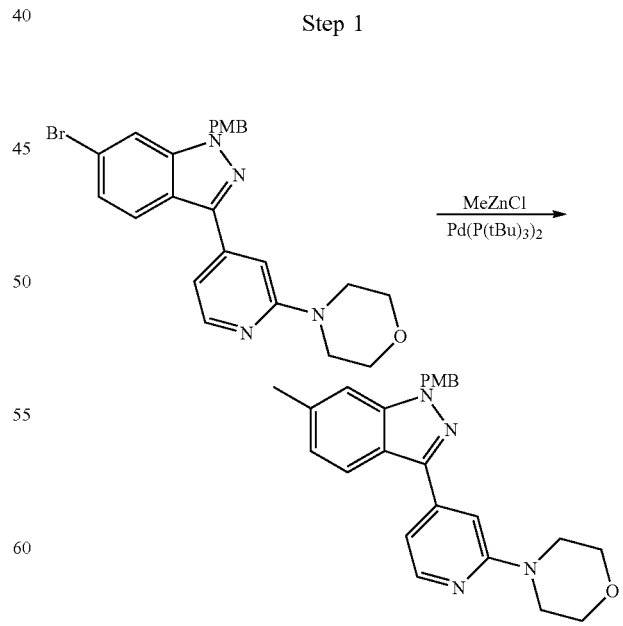

To a suspension of 6-bromo-1-(4-methoxybenzyl)-3-[2-(morpholin-4-yl)pyridin-4-yl]-1H-indazole (Example 73) (70 mg, 0.15 mmol) and 2 M methylzinc chloride (73 µL, 0.15 mmol) in THF (292 μL) at rt was added bis(tri-t-butylphosphine)palladium(0) (2.1 mg, 0.004 mmol). The mixture was stirred at rt overnight. After cooling to 0° C., the resulting mixture was quenched with water, diluted with CH$_2$Cl$_2$, and filtered through Celite. The filtrate was extracted with CH$_2$Cl$_2$, dried (Na$_2$SO$_4$), and concentrated to afford the title compound without further purification; LRMS (ESI) m/z 415.1 [(M+H)$^+$ calcd for C$_{25}$H$_{27}$N$_4$O$_2$: 415].

Step 2

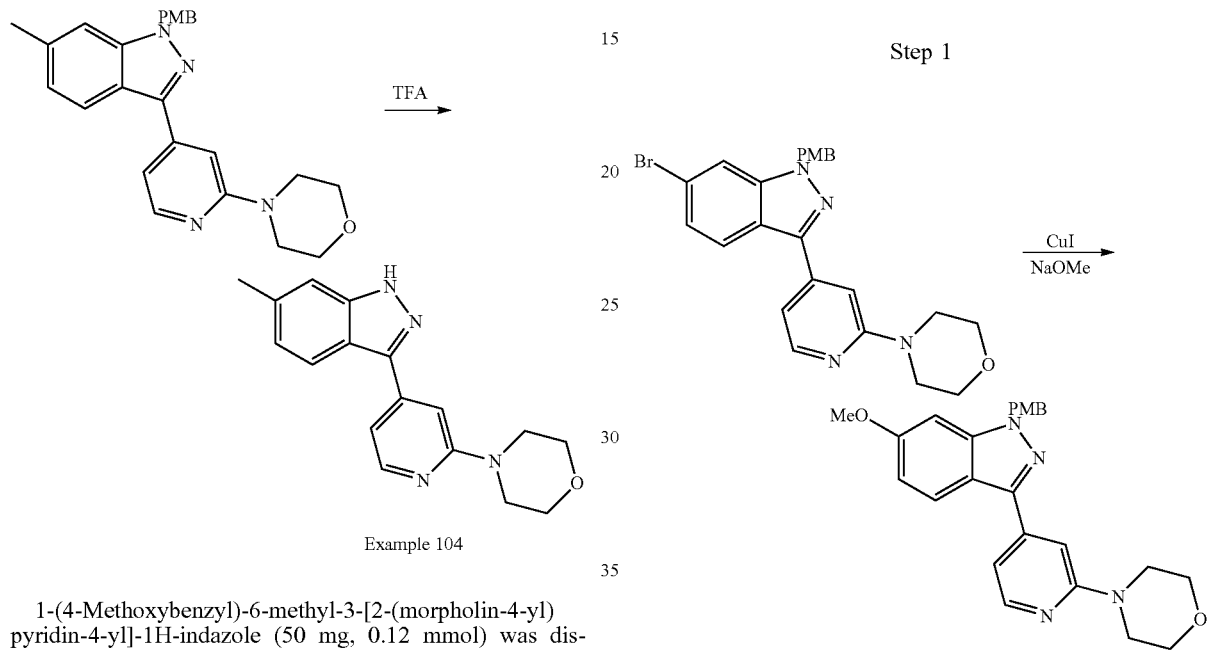

Example 104

1-(4-Methoxybenzyl)-6-methyl-3-[2-(morpholin-4-yl)pyridin-4-yl]-1H-indazole (50 mg, 0.12 mmol) was dissolved in TFA (0.47 mL) and heated at 100° C. for 3 h. The solution was concentrated and purified by Gilson reverse phase chromatography to afford the title compound; HRMS (ES+) m/z 295.1546 [(M+H)$^+$; calcd for C$_{17}$H$_{19}$N$_4$O: 295.1553]; LCMS (ESI) m/z 295.2 (Ret.=1.46 min, LCMS condition a).

Scheme P

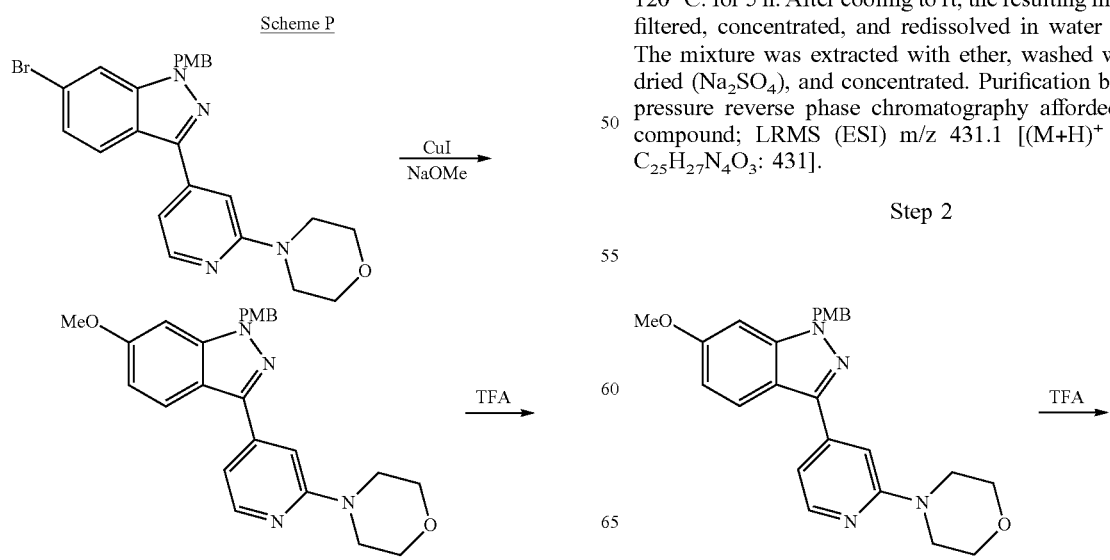

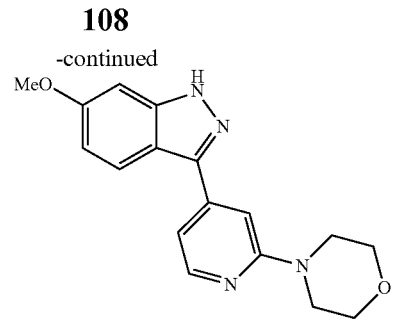

Example 105

Step 1

To a suspension of 6-bromo-1-(4-methoxybenzyl)-3-[2-(morpholin-4-yl)pyridin-4-yl]-1H-indazole (Example 73) (20 mg, 0.042 mmol) and copper(I) iodide (8 mg, 0.042 mmol) in DMF (0.2 mL) at rt was added 2 M sodium methoxide (209 μL, 0.42 mmol). The mixture was stirred at 120° C. for 5 h. After cooling to rt, the resulting mixture was filtered, concentrated, and redissolved in water and ether. The mixture was extracted with ether, washed with brine, dried (Na$_2$SO$_4$), and concentrated. Purification by medium pressure reverse phase chromatography afforded the title compound; LRMS (ESI) m/z 431.1 [(M+H)$^+$ calcd for C$_{25}$H$_{27}$N$_4$O$_3$: 431].

Step 2

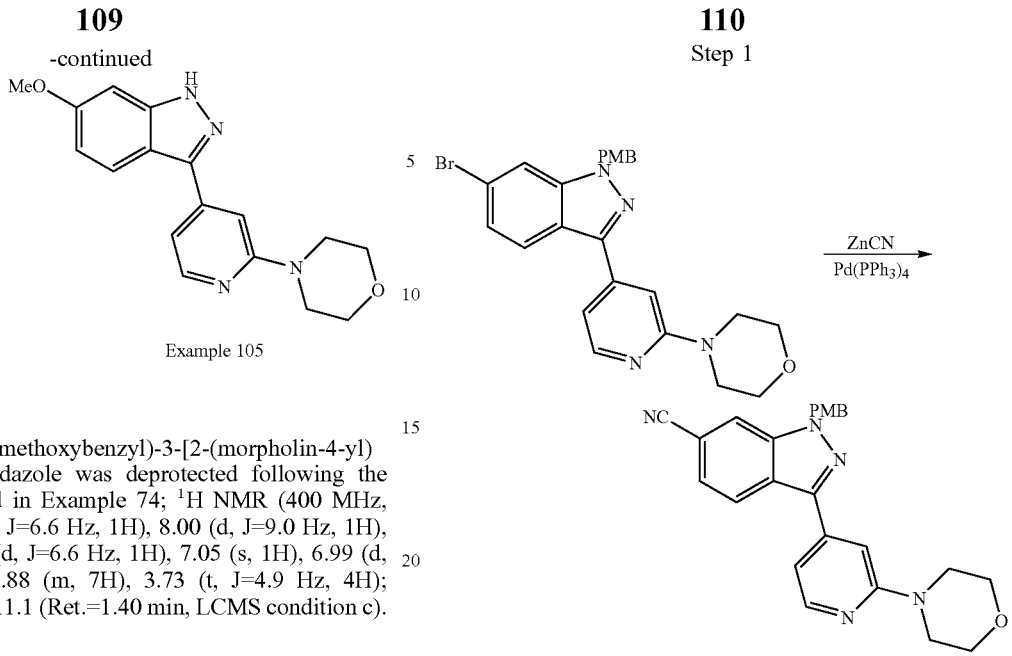

Example 105

6-Methoxy-1-(4-methoxybenzyl)-3-[2-(morpholin-4-yl)pyridin-4-yl]-1H-indazole was deprotected following the procedure provided in Example 74; $^1$H NMR (400 MHz, CD$_3$OD) δ 8.04 (d, J=6.6 Hz, 1H), 8.00 (d, J=9.0 Hz, 1H), 7.77 (s, 1H), 7.68 (d, J=6.6 Hz, 1H), 7.05 (s, 1H), 6.99 (d, J=9.0, 1H), 3.93-3.88 (m, 7H), 3.73 (t, J=4.9 Hz, 4H); LCMS (ESI) m/z 311.1 (Ret.=1.40 min, LCMS condition c).

Scheme Q

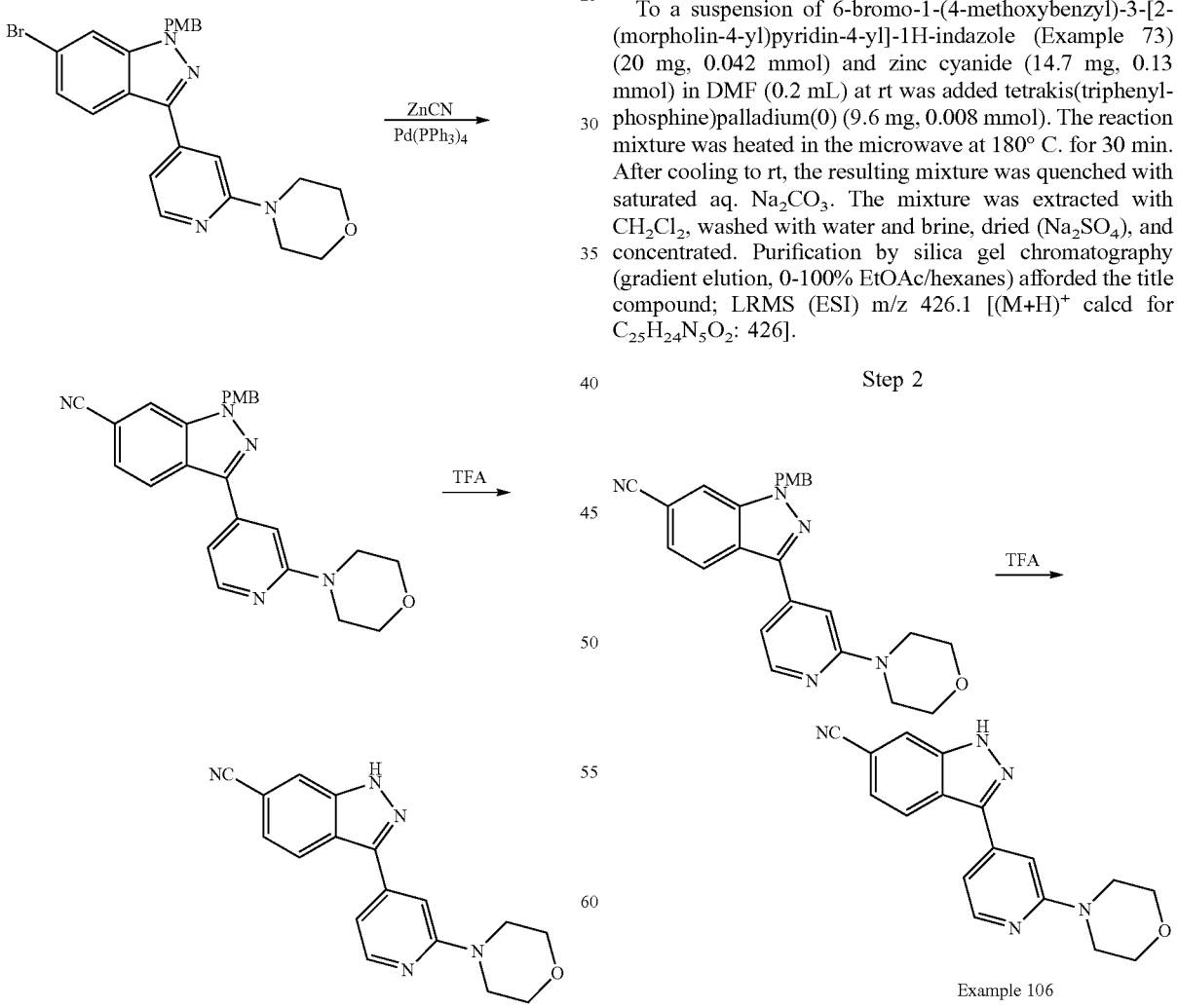

Example 106

Step 1

To a suspension of 6-bromo-1-(4-methoxybenzyl)-3-[2-(morpholin-4-yl)pyridin-4-yl]-1H-indazole (Example 73) (20 mg, 0.042 mmol) and zinc cyanide (14.7 mg, 0.13 mmol) in DMF (0.2 mL) at rt was added tetrakis(triphenylphosphine)palladium(0) (9.6 mg, 0.008 mmol). The reaction mixture was heated in the microwave at 180° C. for 30 min. After cooling to rt, the resulting mixture was quenched with saturated aq. Na$_2$CO$_3$. The mixture was extracted with CH$_2$Cl$_2$, washed with water and brine, dried (Na$_2$SO$_4$), and concentrated. Purification by silica gel chromatography (gradient elution, 0-100% EtOAc/hexanes) afforded the title compound; LRMS (ESI) m/z 426.1 [(M+H)$^+$ calcd for C$_{25}$H$_{24}$N$_5$O$_2$: 426].

Step 2

Example 106

1-(4-Methoxybenzyl)-3-[2-(morpholin-4-yl)pyridin-4-yl]-1H-indazole-6-carbonitrile was deprotected following the procedure provided in Example 74; ¹H NMR (400 MHz, CD₃OD) δ 8.34 (d, J=8.6 Hz, 1H), 8.15 (s, 1H), 8.09 (d, J=6.6 Hz, 1H), 7.84 (s, 1H), 7.72 (d, J=6.6 Hz, 1H), 7.59 (d, J=8.6 Hz, 1H), 3.92 (t, J=4.8 Hz, 4H), 3.77 (t, J=4.8 Hz, 4H); LCMS (ESI) m/z 306.1 (Ret.=1.33 min, LCMS condition c).

extracted with CH₂Cl₂, dried (Na₂SO₄), and concentrated. Purification by silica gel chromatography (gradient elution, 0-35% EtOAc/hexanes) afforded the title compound; LRMS (ESI) m/z 515.0 [(M+H)⁺ calcd for C₂₉H₃₅N₄O₃Si: 515].

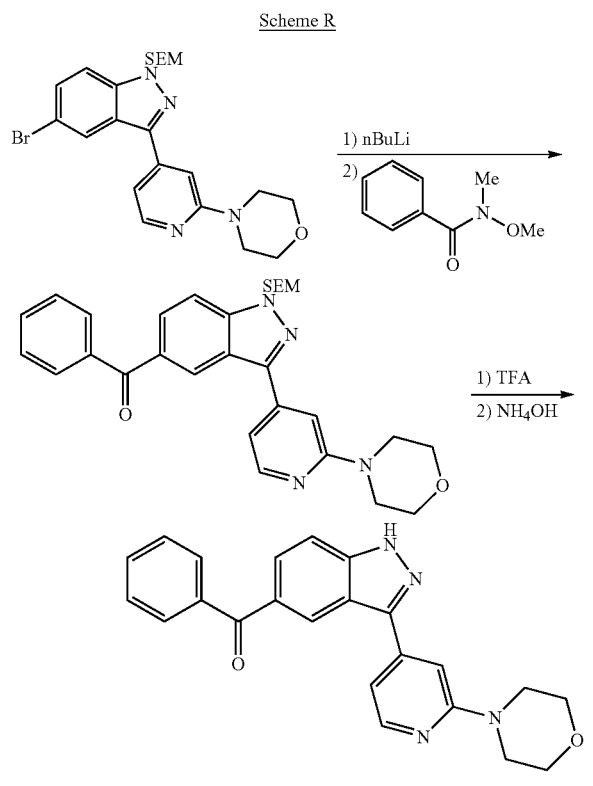

Scheme R

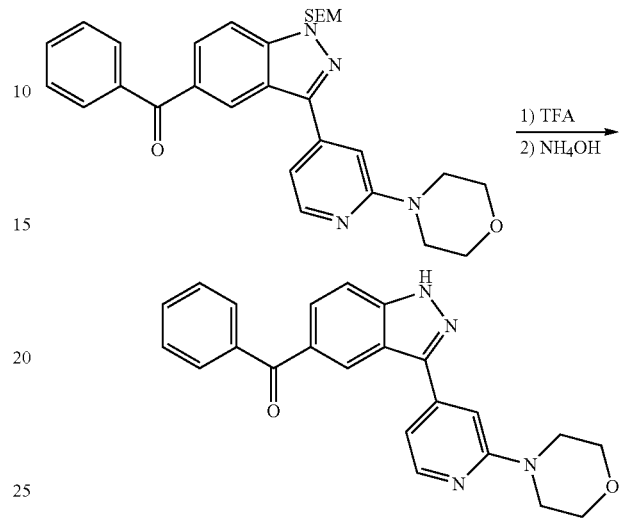

Example 107

To a solution of (3-[2-(morpholin-4-yl)pyridin-4-yl]-1-{[2-(trimethylsilyl)ethoxy]methyl}-1H-indazol-5-yl)(phenyl)methanone (20 mg, 0.039 mmol) in CH₂Cl₂ (0.4 mL) at rt was added TFA (90 The mixture was stirred at rt overnight then concentrated. To the resulting oil was added MeOH (1 mL), CH₂Cl₂ (1 mL) and NH₄OH (1 mL). After 5 h, the resulting solution was quenched with water and extracted with CH₂Cl₂. The combined extracts were dried (Na₂SO₄) and concentrated. Purification by silica gel chromatography (gradient elution, 0-100% EtOAc/hexanes) afforded the title compound; LCMS (ESI) m/z 385.0 (Ret.=2.30 min, LCMS condition a).

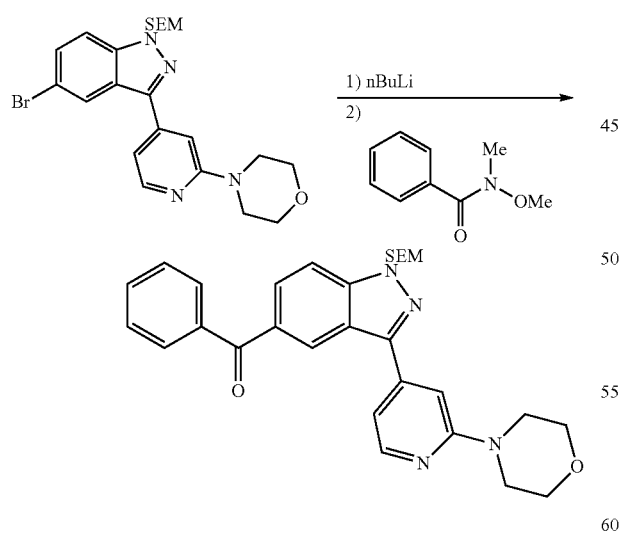

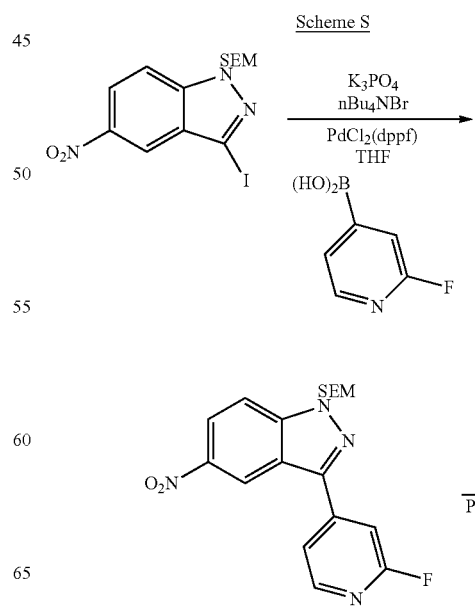

Scheme S

To a solution of 5-bromo-3-[2-(morpholin-4-yl)pyridin-4-yl]-1-{[2-(trimethylsilyl)ethoxy]methyl}-1H-indazole (Step 3, Scheme D) (100 mg, 0.20 mmol) in THF (1 mL) at −78° C. was added dropwise n-butyllithium (204 μL, 0.51 mmol). After 2 min, N-methoxy-N-methylbenzamide (169 mg, 1.02 mmol) was added and the mixture was warmed to rt over 1 h. The resulting mixture was quenched with water,

113

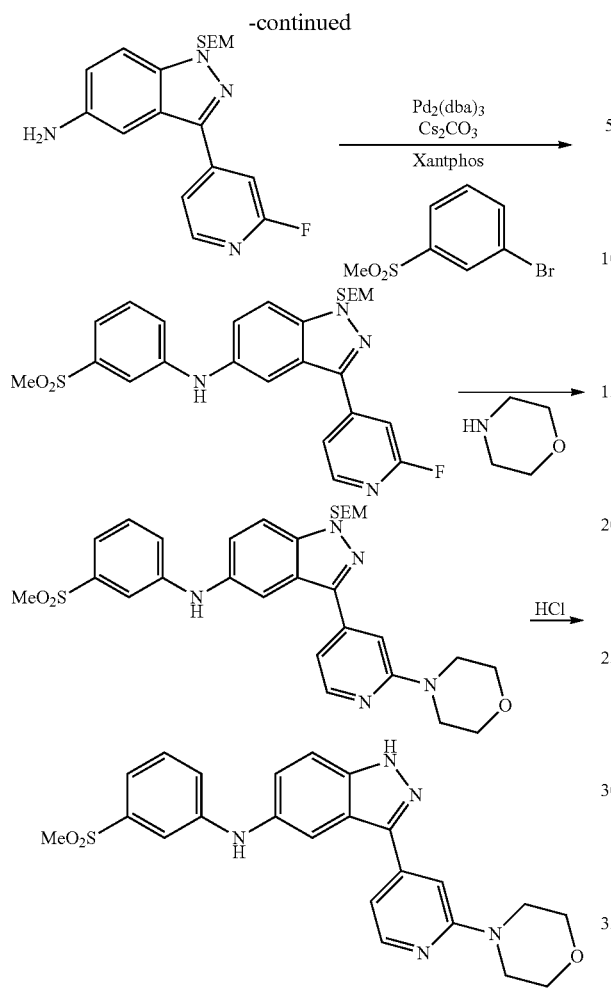

Example 108

Step 1

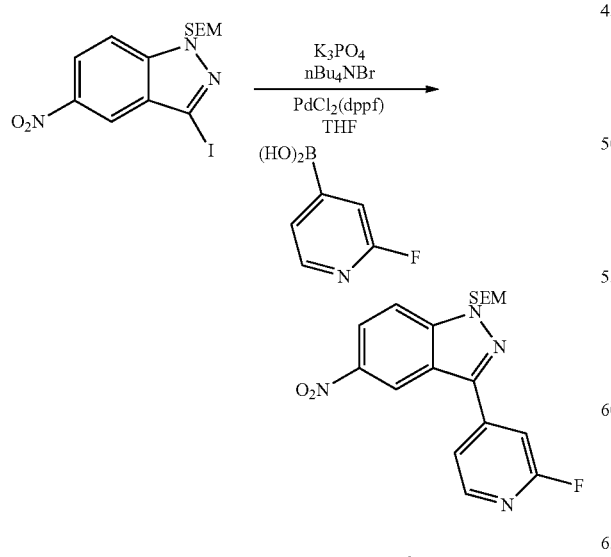

To a suspension of 3-iodo-5-nitro-1-{[2-(trimethylsilyl)ethoxy]methyl}-1H-indazole (Synthesis (2006), 20, 3506-3514) (3.0 g, 7.15 mmol) and (2-fluoropyridin-4-yl)boronic acid (2.02 g, 14.3 mmol), potassium phosphate trihydrate (5.72 g, 21.5 mmol), and tetrabutylammonium bromide (0.46 g, 1.43 mmol) in THF (65 mL) at rt under $N_2$ was added 1,1'-bis(diphenylphosphino)ferrocene-palladium(II) dichloride dichlormethane complex (1.17 g, 1.43 mmol). The reaction mixture was heated at 80° C. for 48 h. After cooling to rt, the resulting mixture was filtered through Celite, diluted with EtOAc, washed with water, dried ($Na_2SO_4$), and concentrated. Purification by silica gel chromatography (gradient elution, 0-100% EtOAc/hexanes) afforded the title compound; LRMS (ESI) m/z 388.9 [(M+H)$^+$ calcd for $C_{18}H_{22}FN_4O_3Si$: 389].

Step 2

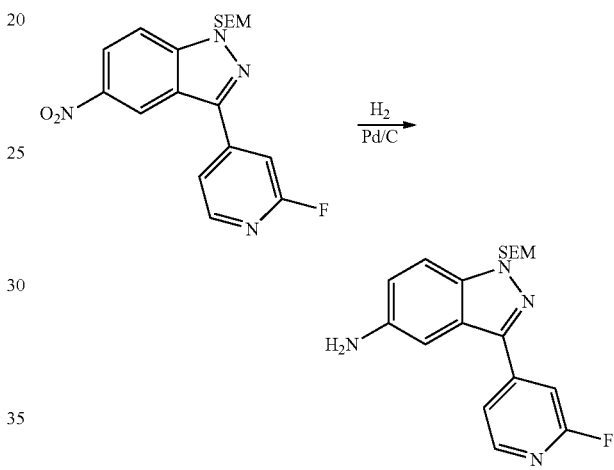

A vessel containing a solution of 3-(2-fluoropyridin-4-yl)-5-nitro-1-{[2-(trimethylsilyl)ethoxy]methyl}-1H-indazole (0.34 g, 0.87 mmol) in anhydrous MeOH (8.7 mL) at rt was evacuated and purged with $N_2$. The reaction vessel was charged with 10% palladium on carbon (32 mg, 0.30 mmol), evacuated, purged with $N_2$, evacuated, and put under a hydrogen balloon. The reaction mixture was stirred at rt under $H_2$ for 2 h. The resulting suspension was filtered through Celite and the filtrate was concentrated to afford the title compound which was used without further purification; LRMS (ESI) m/z 359.0 [(M+H)$^+$ calcd for $C_{18}H_{24}FN_4OSi$: 359].

Step 3

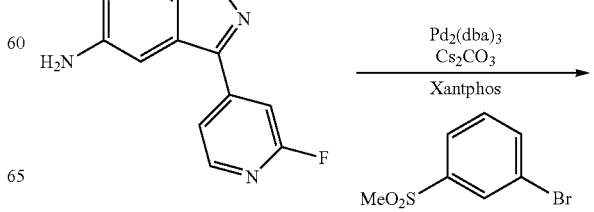

-continued

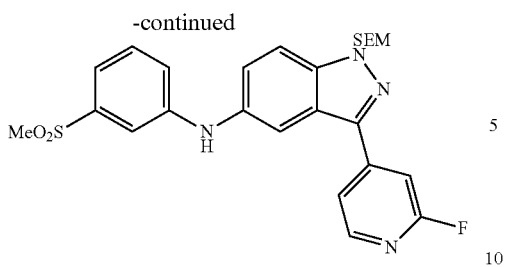

To a mixture of 3-(2-fluoropyridin-4-yl)-1-{[2-(trimethylsilyl)ethoxy]methyl}-1H-indazol-5-amine (0.30 g, 0.84 mmol), 3-bromophenyl methyl sulphone (0.20 g, 0.84 mmol), Xantphos (0.53 g, 0.92 mmol), and cesium carbonate (0.38 g, 1.2 mmol) in THF (22 mL) at rt under $N_2$ was added $Pd_2(dba)_3$ (380 mg, 0.42 mmol). The reaction mixture was purged with $N_2$ and heated at 80° C. for 48 h. After cooling to rt, the resulting mixture was filtered through Celite, diluted with EtOAc, washed with water, dried ($Na_2SO_4$), and concentrated. Purification by silica gel chromatography (gradient elution, 0-100% EtOAc/hexanes) afforded the title compound; LRMS (ESI) m/z 512.9 [(M+H)$^+$ calcd for $C_{25}H_{30}FN_4O_3SSi$: 513].

Step 4

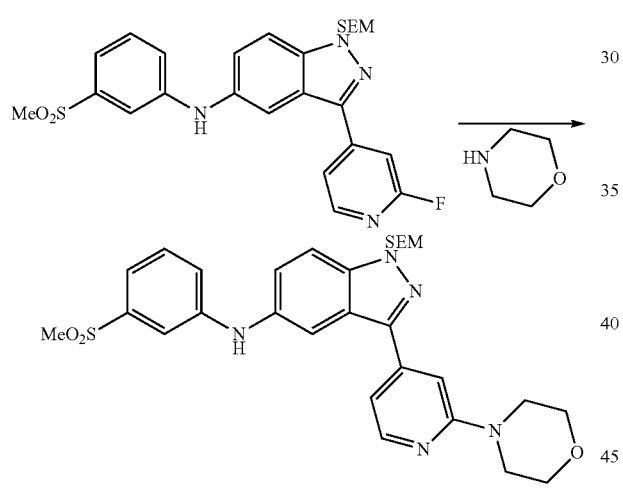

A mixture of 3-(2-fluoropyridin-4-yl)-N-[3-(methylsulfonyl)phenyl]-1-{[2-(trimethylsilyl)ethoxy]methyl}-1H-indazol-5-amine (20 mg, 0.04 mmol) in morpholine (34 mg, 0.39 mmol) was heated at 150° C. overnight. After cooling to rt, the mixture was diluted with EtOAc, washed with 10% aq. citric acid (brought to pH 5 with 1 N NaOH), dried ($Na_2SO_4$), and concentrated to afford the title compound which was used without further purification; LRMS (ESI) m/z 580.0 [(M+H)$^+$ calcd for $C_{29}H_{38}N_5O_4SSi$: 580].

Step 5

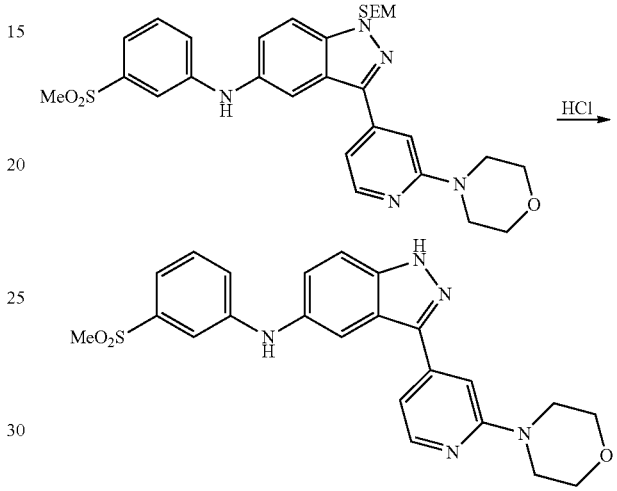

Example 108

HCl (g) was bubbled through a solution of N-[3-(methylsulfonyl)phenyl]-3-[2-(morpholin-4-yl)pyridin-4-yl]-1-{[2-(trimethylsilyl)ethoxy]methyl}-1H-indazol-5-amine (50 mg, 0.086 mmol) in MeOH (0.9 mL) at 0° C. for 5 min. The reaction mixture was heated at 60° C. for 2 h The resulting solution was concentrated and purified by medium pressure reverse phase chromatography to afford the title compound as a TFA salt; HRMS (ES+) m/z 450.1598 [(M+H)$^+$ calcd for $C_{23}H_{24}N_5O_3S$: 450.1594]; LCMS (ESI) m/z 449.9 (Ret.=0.96 min, LCMS condition a).

By following the procedure outlined in Scheme S, using the appropriate amine, the following compounds can be prepared (Examples 109-112).

| Ex | Structure | LCMS Cond. | RT (min) | m/z | LRRK2 IC$_{50}$ (nM) |
|---|---|---|---|---|---|
| 109 | | a | 1.63 | 408.0 | 34 |

-continued

| Ex | Structure | LCMS Cond. | RT (min) | m/z | LRRK2 IC$_{50}$ (nM) |
|---|---|---|---|---|---|
| 110 | | a | 1.81 | 449.9 | 83 |
| 111 | | a | 1.36 | 408.0 | 35 |
| 112 | | a | 2.17 | 419.9 | 11 |

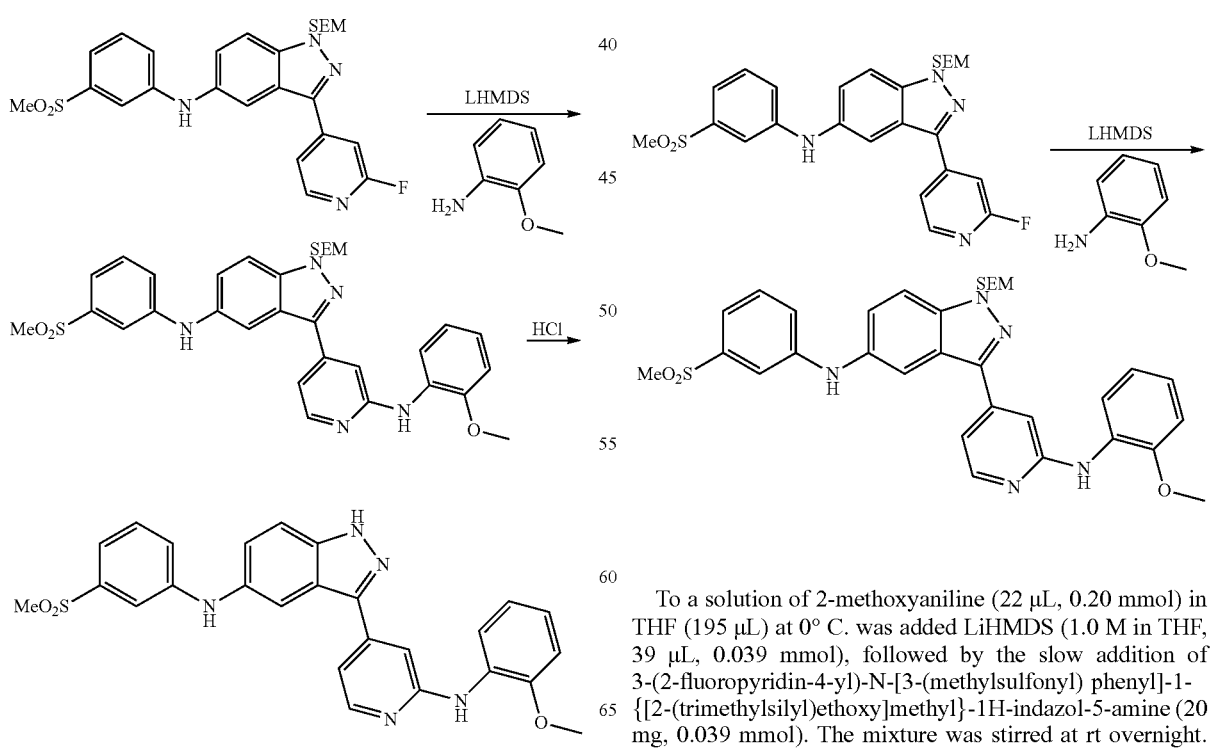

Step 1

To a solution of 2-methoxyaniline (22 μL, 0.20 mmol) in THF (195 μL) at 0° C. was added LiHMDS (1.0 M in THF, 39 μL, 0.039 mmol), followed by the slow addition of 3-(2-fluoropyridin-4-yl)-N-[3-(methylsulfonyl) phenyl]-1-{[2-(trimethylsilyl)ethoxy]methyl}-1H-indazol-5-amine (20 mg, 0.039 mmol). The mixture was stirred at rt overnight. The resulting mixture was filtered and concentrated to afford the title compound which was used without further purification; LRMS (ESI) m/z 616.0 [(M+H)$^+$ calcd for C$_{32}$H$_{38}$N$_5$O$_4$SSi: 616].

Step 2

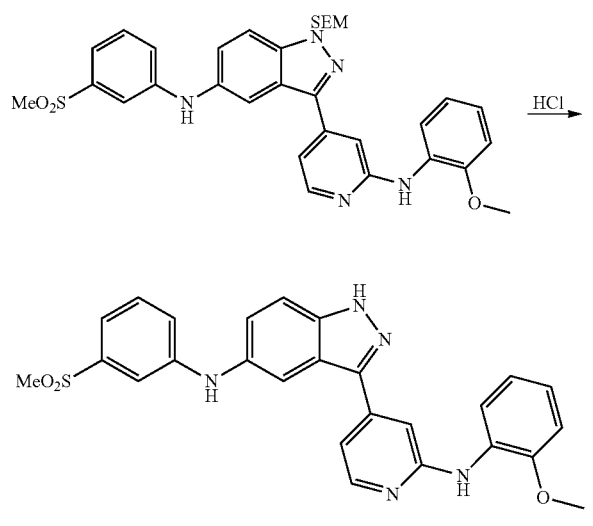

Example 113

HCl (g) was bubbled through a solution of 3-{2-[(2-methoxyphenyl)amino]pyridin-4-yl}-N-[3-(methylsulfonyl)phenyl]-1-{[2-(trimethylsilyl)ethoxy]methyl}-1H-indazol-5-amine (20 mg, 0.032 mmol) in MeOH (5 mL) at 0° C. for 5 min. The resulting solution was heated at 80° C. in a sealed tube overnight. After cooling to 0° C., the mixture was concentrated and purified by medium pressure reverse phase chromatography to afford the title compound as a TFA salt; HRMS (ES+) m/z 486.1597 [(M+H)$^+$ calcd for C$_{26}$H$_{24}$N$_5$O$_3$S: 486.1594]; LCMS (ESI) m/z 485.9 (Ret.=2.05 min, LCMS condition a).

Scheme U

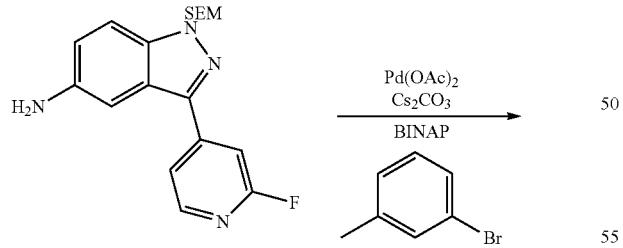

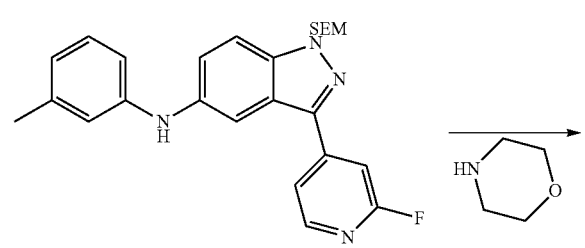

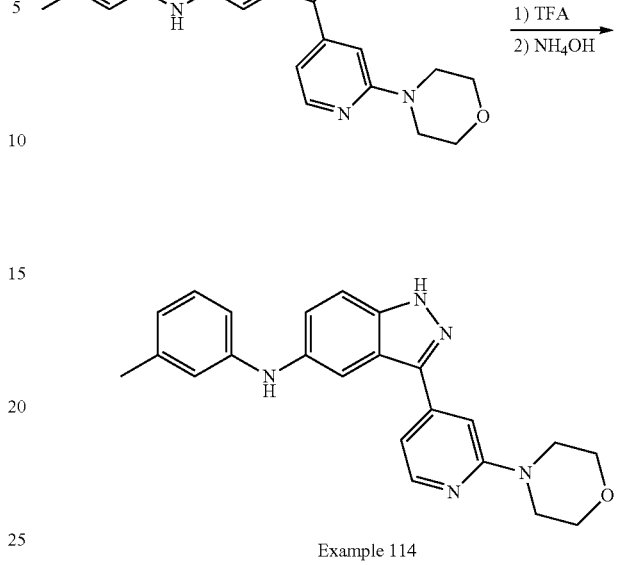

Example 114

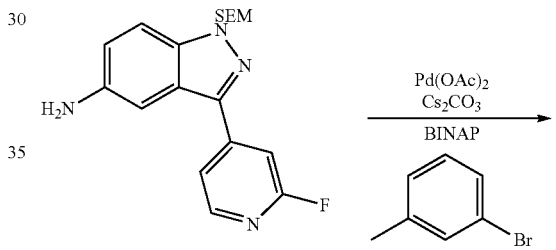

To a suspension of 3-(2-fluoropyridin-4-yl)-1-{[2-(trimethylsilyl)ethoxy]methyl}-1H-indazol-5-amine (Example 120) (1.63 g, 4.55 mmol), 1-bromo-3-methylbenzene (1.17 g, 6.82 mmol), and cesium carbonate (4.44 g, 13.64 mmol) in THF (46 mL) at rt under N$_2$ were added racemic BINAP (0.85 g, 1.36 mmol) and palladium(II) acetate (204 mg, 0.91 mmol). The reaction mixture was purged with N$_2$ and heated at 80° C. for 48 h. After cooling to rt, the resulting mixture was filtered through Celite, diluted with EtOAc, washed with water, dried (Na$_2$SO$_4$), and concentrated. Purification by silica gel chromatography (gradient elution, 0-30% EtOAc/hexanes) afforded the title compound; LRMS (ESI) m/z 449.0 [(M+H)$^+$ calcd for C$_{25}$H$_{30}$FN$_4$OSi: 449].

Step 2

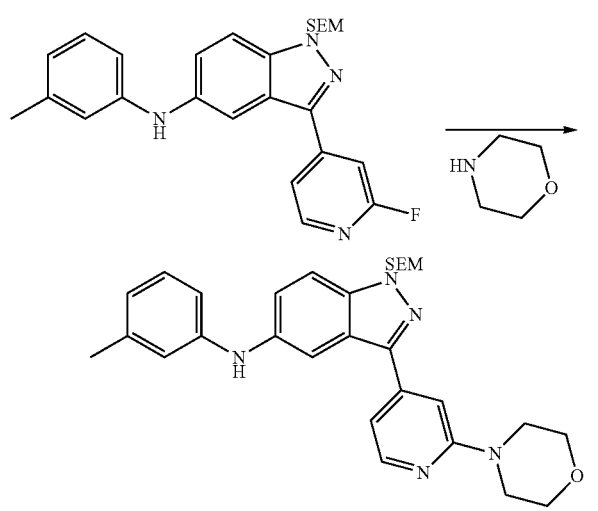

A mixture of 3-(2-fluoropyridin-4-yl)-N-(3-methylphenyl)-1-{[2-(trimethylsilyl)ethoxy]methyl}-1H-indazol-5-amine (100 mg, 0.22 mmol) in morpholine (194 μL, 2.23 mmol) was heated at 150° C. overnight. After cooling to rt, the mixture was diluted with EtOAc, washed with 10% aq. citric acid (brought to pH 5 with 1 N NaOH), dried (Na$_2$SO$_4$), and concentrated to afford the title compound which was used without further purification; LRMS (ESI) m/z 516.0 [(M+H)$^+$ calcd for C$_{29}$H$_{38}$N$_5$O$_2$Si: 516].

Step 3

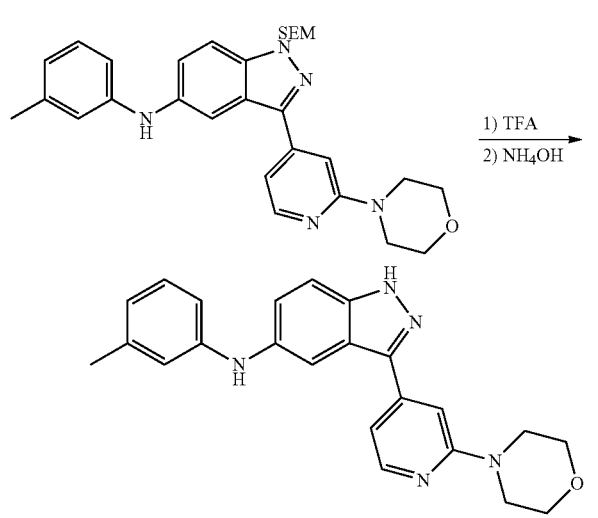

Example 114

N-(3-Methylphenyl)-3-[2-(morpholin-4-yl)pyridin-4-yl]-1-{[2-(trimethylsilyl)ethoxy]methyl}-1H-indazol-5-amine was deprotected using the procedure provided in Example 88; HRMS (ES+) m/z 386.1966 [(M+H)$^+$ calcd for C$_{23}$H$_{24}$N$_5$O: 386.1975].

Scheme V

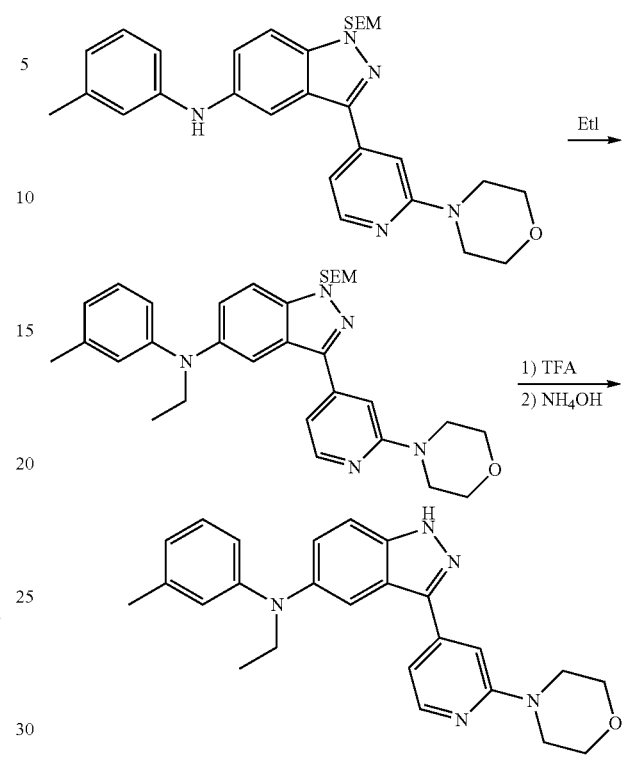

Example 115

Step 1

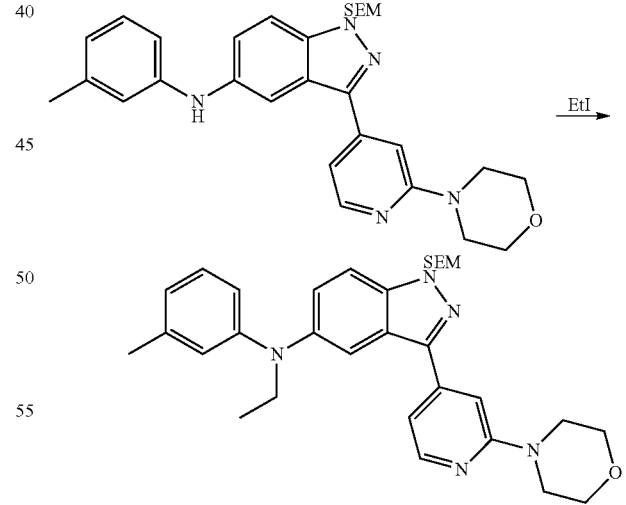

The SEM protected indazole (10 mg, 0.02 mmol) was taken up in DMF (0.2 mL). The solution was cooled to 0° C. Sodium hydride (1 mg, 0.02 mmol) and ethyl iodide (1.6 μL, 0.02 mmol) were added. The solution was stirred at RT for 12 hours. The solution was quenched with water and extracted with DCM. The combined organic layers were dried (MgSO$_4$), filtered, and concentrated. The residue was purified by ISCO flash chromatography (0-80% EtOAc in hexane gradient) which furnished the desired product.

Step 2

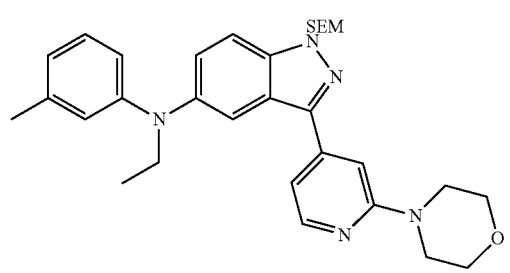

HCl

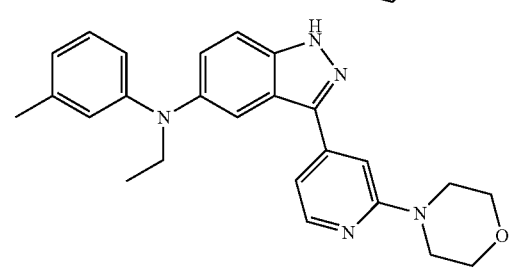

Example 115

The SEM protected indazole was deprotected using conditions outline in Scheme T which provided Example 115; LCMS (ESI) m/z 414.0 (Ret.=2.03 min, LCMS condition a).

Scheme W

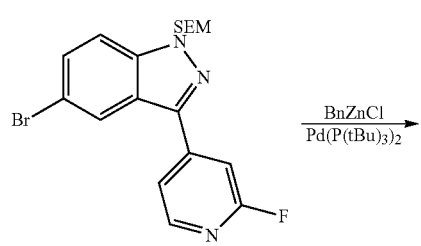

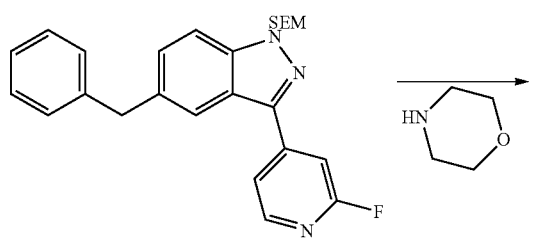

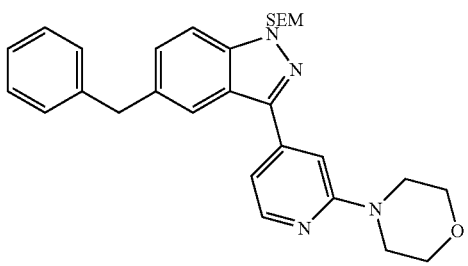

HCl

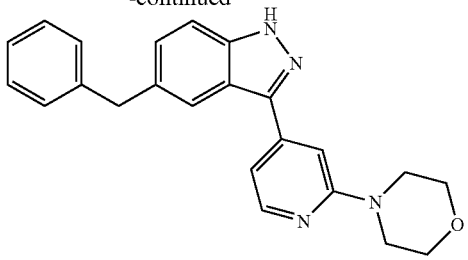

Example 116

Step 1

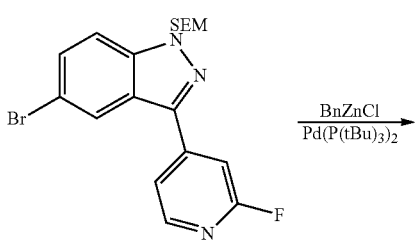

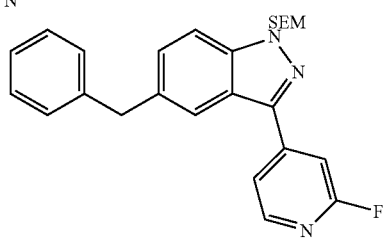

5-Benzyl-3-(2-fluoropyridin-4-yl)-1-{[2-(trimethylsilyl)ethoxy]methyl}-1H-indazole was prepared from 5-bromo-3-(2-fluoropyridin-4-yl)-1-{[2-(trimethylsilyl)ethoxy]methyl}-1H-indazole, using the procedure provided in Step 1 of Scheme O.

Step 2

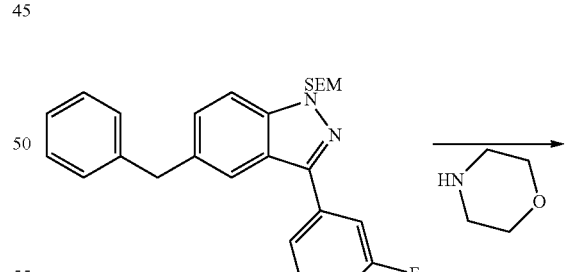

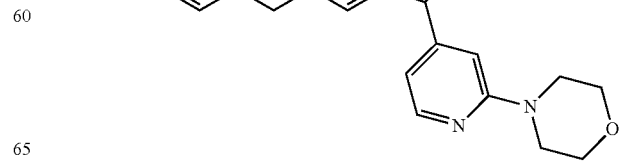

125

The fluoro-pyridine was converted into the morpholine analog using conditions outlined in Step 2 of Scheme U.

Step 3

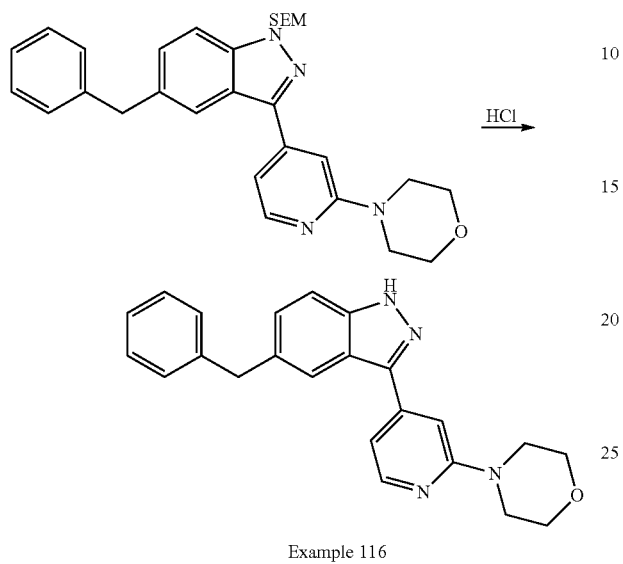

Example 116

The SEM protected indazole was converted into Example 116 using conditions outlined in Step 2 of Scheme T; HRMS (ES+) m/z 371.1858 [(M+H)+ calcd for $C_{23}H_{23}N_4O$: 371.1866]; LCMS (ESI) m/z 371.0 (Ret.=1.83 min, LCMS condition a).

Scheme X

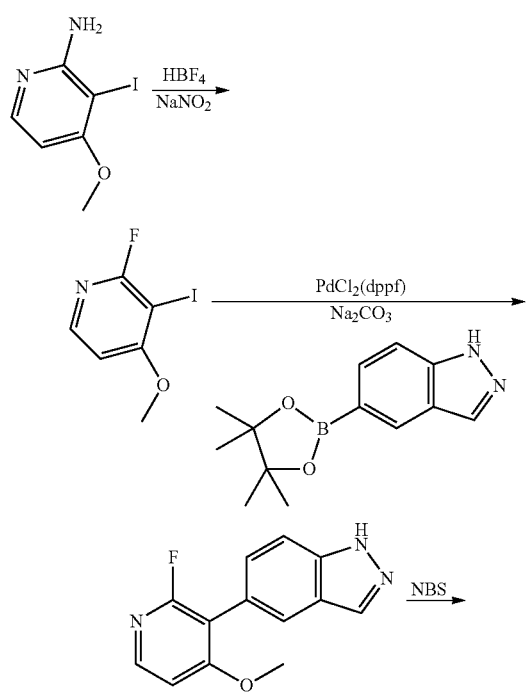

126

-continued

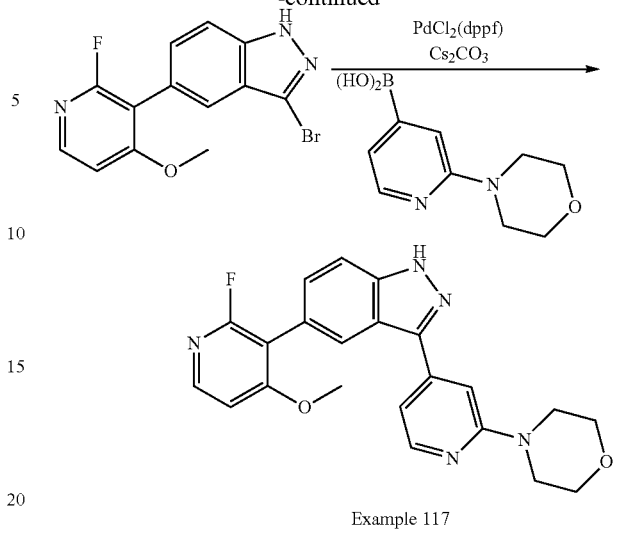

Example 117

Step 1

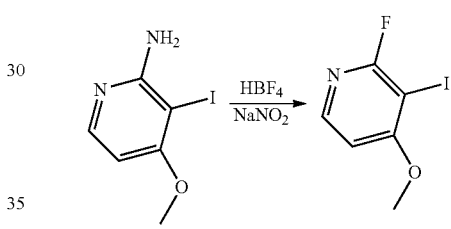

A mixture of 3-iodo-4-methoxypyridin-2-amine (2.5 g, 10 mmol) in tetrafluoroboric acid (70 mL) was cooled to −20° C. and a solution of sodium nitrite (1.38 g, 20 mmol) in water (6 mL) was added over 30 minutes. The reaction was stirred at −20° C. for 3 hours and additional amounts of sodium nitrite were added until all starting material was consumed. After 4 hours, the mixture was neutralized with saturated aqueous sodium carbonate and saturated aqueous sodium bicarbonate and extracted with ether (3×). The combined extracts were dried ($Na_2SO_4$), filtered. Purification by silica gel chromatography (gradient elution, 40-100% EtOAc/hexanes) afforded the title compound; LRMS (ESI) m/z 254.1 [(M+H)+ calcd for $C_6H_6FINO$: 254].

Step 2

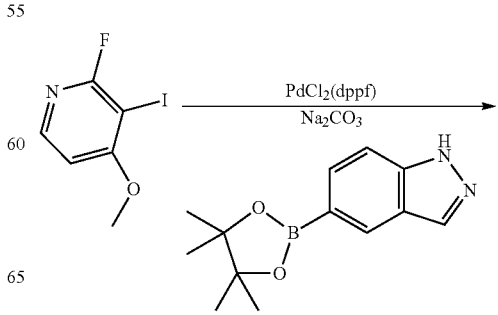

-continued

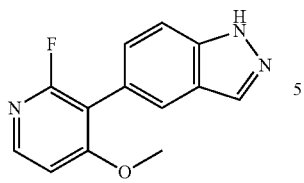

A mixture of 2-fluoro-3-iodo-4-methoxypyridine (1.00 g, 3.95 mmol), 5-(4,4,5,5-tetramethyl-1,3,2-dioxaborolan-2-yl)-1H-indazole (1.54 g, 6.32 mmol) and sodium carbonate (2 M in water, 4.0 mL, 8.0 mmol) in DMF (5 mL) and 1,2-dimethoxyethane (5 mL) was saturated with a gentle stream of $N_2$ for 5 min. 1,1'-bis(diphenylphosphino)ferrocene-palladium(II)dichloride dichloromethane complex (323 mg, 0.40 mmol) was added and the mixture was heated at 105° C. overnight. The resulting mixture was diluted with 1 M aqueous HCl and extracted with ethyl acetate (3×). The combined extracts were dried ($Na_2SO_4$), filtered, and concentrated. Purification by silica gel chromatography (gradient elution, 10-100% EtOAc/hexanes) afforded title compound in pure form; HRMS (ES+) m/z 244.0884 [(M+H)$^+$ calcd for $C_{13}H_{11}FN_3O$: 244.0881].

Step 3

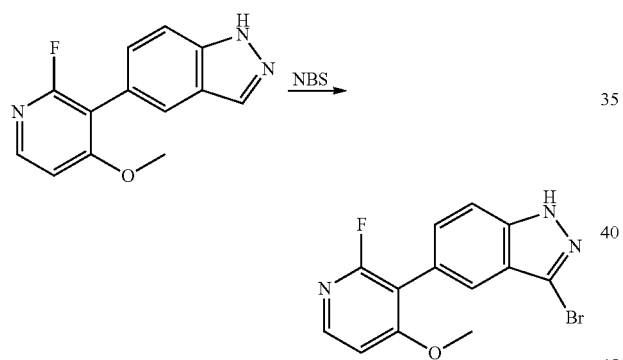

The indazole (30 mg, 0.12 mmol) and NBS (24 mg, 0.14 mmol) were allowed to stir at RT in $CH_3CN$ (15 ml). The solution was concentrated. The residue was purified via ISCO flash chromatography (0-100% EtOAc in hexanes gradient) which provided the desired product.

Step 4

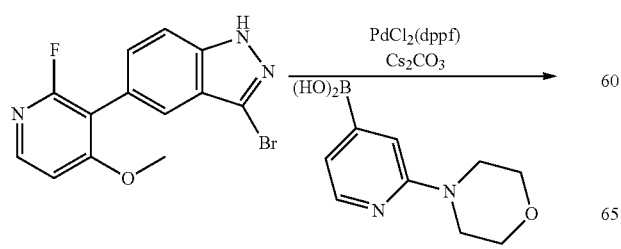

-continued

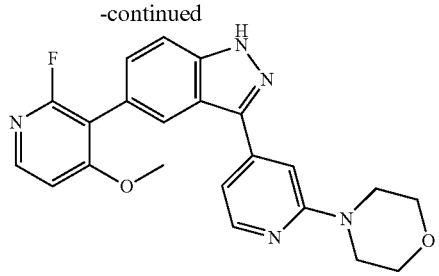

Example 117

The bromide (50 mg, 0.16 mmol), boronic acid (48 mg, 0.23 mmol), PdCl2(dppf) (13 mg, 0.016 mmol), and $Cs_2CO_3$ (0.16 ml of a 2 M aqueous solution) were taken up in THF (1 ml). The solution was flushed with nitrogen, and it was heated at 100° C. for 12 hours. The solution was partitioned between DCM and water. The aqueous layer was extracted with DCM. The combined organic layers were dried, filtered, and concentrated. The residue was purified via flash chromatography (0-100% EtOAc in hexanes gradient) which provided Example 117; LCMS (ESI) m/z 406.1 (Ret.=1.98 min, LCMS condition a).

Scheme Y

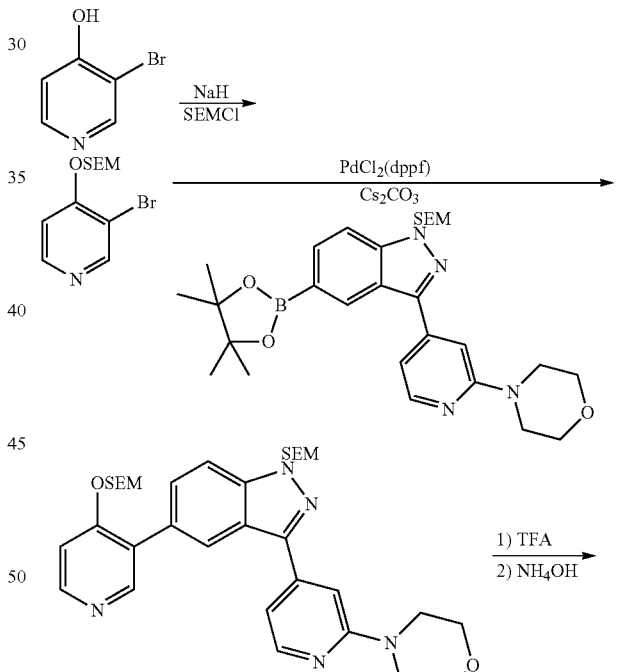

Example 118

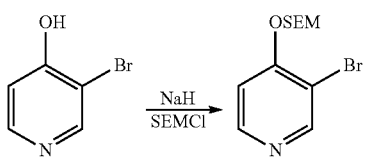

To a solution of 3-bromopyridin-4-ol (0.50 g, 2.87 mmol) in DMF (29 mL) at 0° C. was added sodium hydride (0.48 g, 2.87 mmol). After 15 min, SEM-Cl (0.51 mL, 2.87 mmol) was added and the resulting solution was stirred at rt for 1 h. The reaction mixture was quenched with water, extracted with EtOAc, and washed with water and brine. The organics were dried ($Na_2SO_4$), concentrated, and purified by silica gel chromatography (gradient elution, 0-100% EtOAc/hexanes) to afford the title compound; LRMS (ESI) m/z 305.1 [(M+H)$^+$ calcd for $C_{11}H_{19}BrNO_2Si$: 305].

Step 2

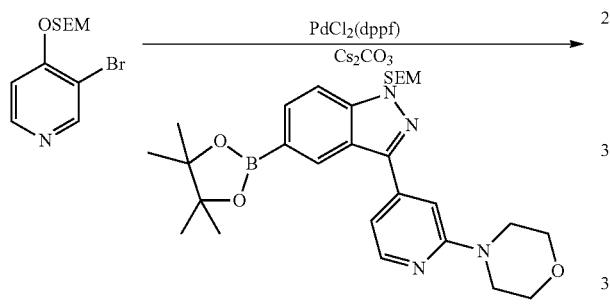

A mixture of 3-[2-(morpholin-4-yl)pyridin-4-yl]-5-(4,4,5,5-tetramethyl-1,3,2-dioxaborolan-2-yl)-1-{[2-(trimethylsilyl)ethoxy]methyl}-1H-indazole (prepared from Example 70, Step 1) (40 mg, 0.074 mmol), 3-bromo-4-{[2-(trimethylsilyl)ethoxy]methoxy}pyridine (23 mg, 0.074 mmol), [1,1'-bis(diphenylphosphino)ferrocene]dichloro-palladium (II), 1:1 complex with dichloromethane (6.1 mg, 0.007 mmol), 2 M cesium carbonate in water (74 µL, 0.15 mmol) and THF (0.37 mL) was flushed with a stream of $N_2$ and heated to 100° C. for 16 h. The resulting reaction mixture was diluted with water and extracted with $CH_2Cl_2$. The organic layers were dried ($Na_2SO_4$), concentrated and purified by silica gel chromatography (gradient elution, 0-50% EtOAc/hexanes) to afford the title compound; LRMS (ESI) m/z 634.1 [(M+H)$^+$ calcd for $C_{33}H_{48}N_5O_4Si_2$: 634].

Step 3

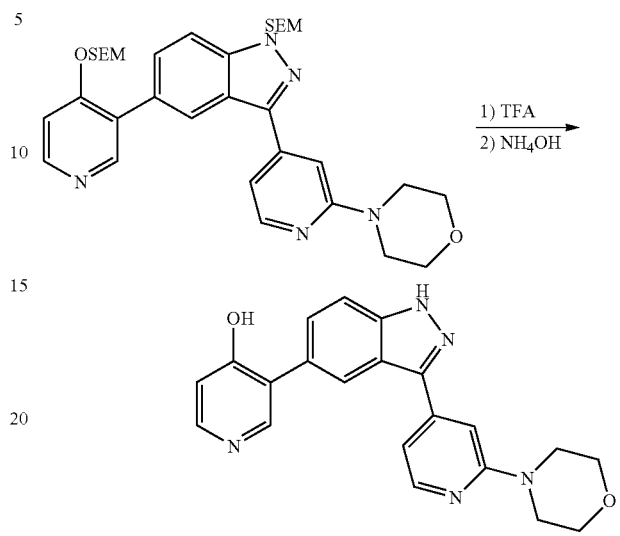

Example 118

To a solution of 3-[2-(morpholin-4-yl)pyridin-4-yl]-5-(4-{[2-(trimethylsilyl)ethoxy]methoxy}pyridin-3-yl)-1-{[2-(trimethylsilyl)ethoxy]methyl}-1H-indazole (14 mg, 0.022 mmol) in $CH_2Cl_2$ (44 µL) at rt was added TFA (51 µL). The mixture was stirred at rt for 3 h then concentrated. To the resulting oil was added MeOH (1 mL), $CH_2Cl_2$ (1 mL) and $NH_4OH$ (1 mL). After 5 h, the resulting solution was quenched with water and extracted with $CH_2Cl_2$. The combined extracts were dried ($Na_2SO_4$), concentrated, and purified by Gilson reverse phase chromatography to afford the title compound as a TFA salt; $^1$HRMS (ES+) m/z 374.1606 [(M+H)$^+$ calcd for $C_{21}H_{20}N_5O_2$: 374.1612]; LCMS (ESI) m/z 374.1 (Ret.=1.09 min, LCMS condition a).

Scheme Z

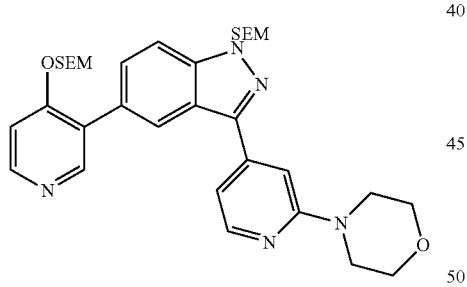

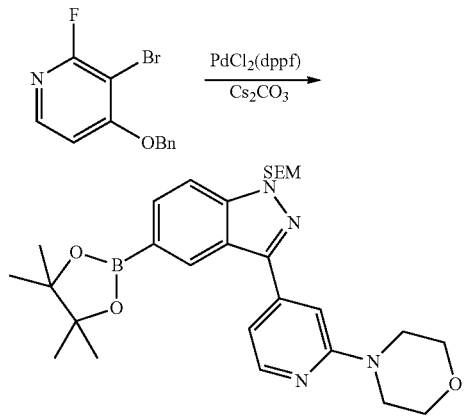

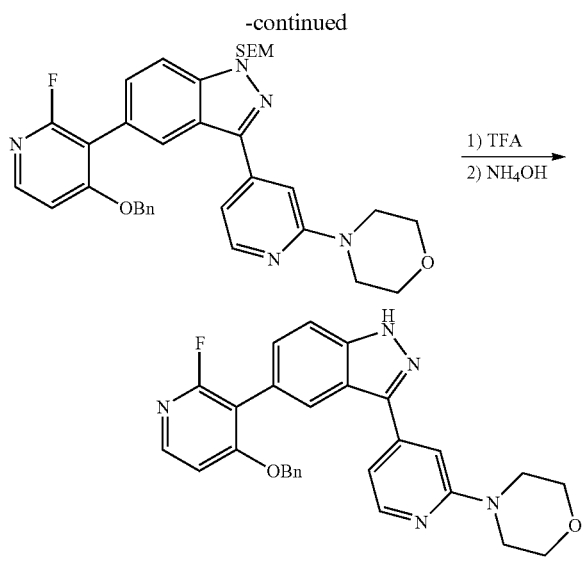

Step 1

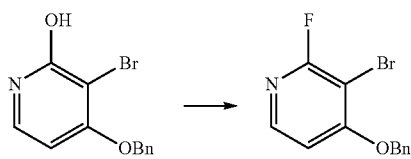 [SMILES: Oc1nccc(OCc2ccccc2)c1Br ; Fc1nccc(OCc2ccccc2)c1Br]

To a solution of 4-(benzyloxy)-3-bromopyridin-2-ol (252 mg, 0.90 mmol) in acetonitrile (9 mL) at rt were added perfluoro-2-methyl-2-pentene (0.17 mL, 0.90 mmol) and triethylamine (0.13 mL, 0.90 mmol). The resulting solution was heated at reflux for 16 h. The reaction mixture was concentrated and purified by medium pressure reverse phase chromatography to afford the title compound; LRMS (ESI) m/z 283.0 [(M+H)$^+$ calcd for $C_{12}H_{20}BrFNO$: 283].

Step 2

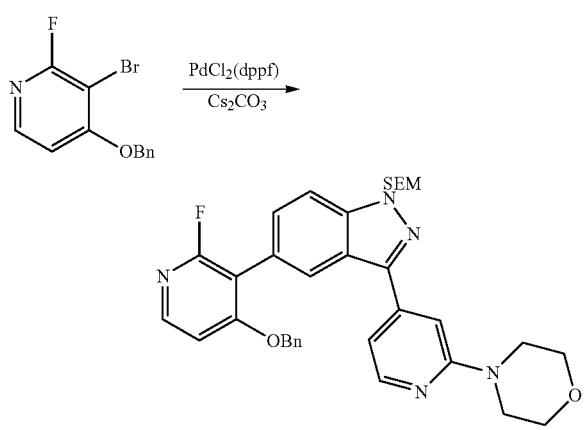

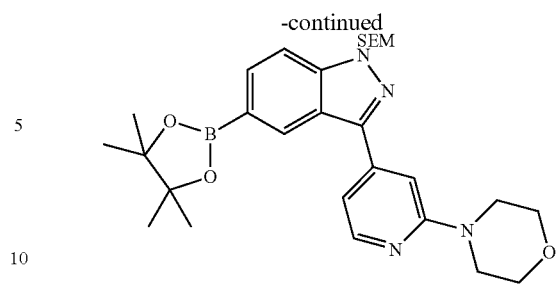

A mixture of 3-[2-(morpholin-4-yl)pyridin-4-yl]-5-(4,4,5,5-tetramethyl-1,3,2-dioxaborolan-2-yl)-1-{[2-(trimethylsilyl)ethoxy]methyl}-1H-indazole (prepared from Example 70, Step 1) (130 mg, 0.24 mmol), 4-(benzyloxy)-3-bromo-2-fluoropyridine (68 mg, 0.24 mmol), [1,1'-bis(diphenylphosphino)ferrocene]dichloro-palladium(II), 1:1 complex with dichloromethane (19.7 mg, 0.024 mmol), 2 M cesium carbonate in water (241 µL, 0.48 mmol) and THF (1.2 mL) was flushed with a stream of $N_2$ and heated to 100° C. for 16 h. The resulting reaction mixture was diluted with water and extracted with $CH_2Cl_2$. The organic layers were dried ($Na_2SO_4$), concentrated and purified by silica gel chromatography (gradient elution, 0-10% MeOH/$CH_2Cl_2$) to afford the title compound; LRMS (ESI) m/z 612.0 [(M+H)$^+$ calcd for $C_{34}H_{39}FN_5O_3Si$: 612].

Step 3

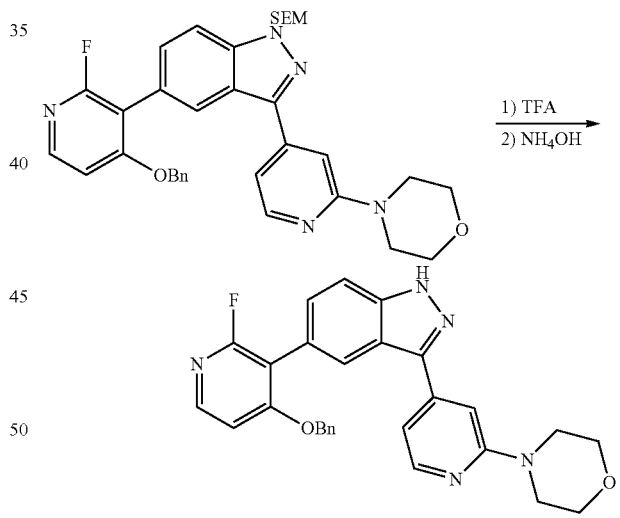

To a solution of 5-[4-(benzyloxy)-2-fluoropyridin-3-yl]-3-[2-(morpholin-4-yl)pyridin-4-yl]-1-{[2-(trimethylsilyl)ethoxy]methyl}-1H-indazole (41 mg, 0.067 mmol) in $CH_2Cl_2$ (134 µL) at rt was added TFA (155 µL). The mixture was stirred at rt for 3 h then concentrated. To the resulting oil was added MeOH (1 mL), $CH_2Cl_2$ (1 mL) and $NH_4OH$ (1 mL). After 5 h, the resulting solution was quenched with water and extracted with $CH_2Cl_2$. The combined extracts were dried ($Na_2SO_4$), concentrated, and purified by basic alumina chromatography (gradient elution, 0-10% MeOH/$CH_2Cl_2$) to afford the title compound; LRMS (ESI) m/z 482.1 [(M+H)$^+$ calcd for $C_{28}H_{25}FN_5O_2$: 482].

Step 4

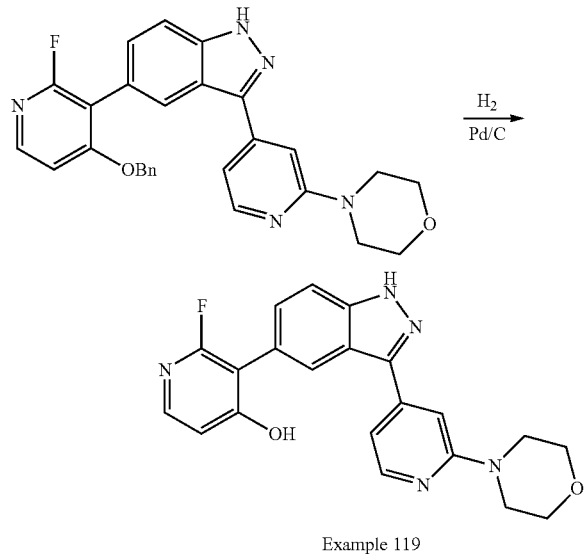

Example 119

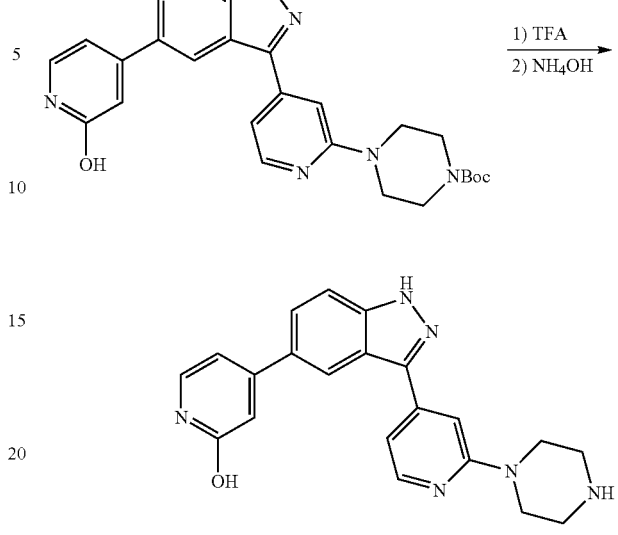

Example 120

A vessel containing a solution of 5-[4-(benzyloxy)-2-fluoropyridin-3-yl]-3-[2-(morpholin-4-yl)pyridin-4-yl]-1H-indazole (6 mg, 0.012 mmol) in anhydrous MeOH (125 μL) at rt was evacuated and purged with $N_2$. The reaction vessel was charged with 10% palladium on carbon (1.3 mg, 0.012 mmol), evacuated, purged with $N_2$, evacuated, and put under a hydrogen balloon. The reaction mixture was stirred at rt under $H_2$ for 16 h. The resulting suspension was filtered through Celite and the filtrate was concentrated. Purification by medium pressure reverse phase chromatography afforded the title compound as a TFA salt; HRMS (ES+) m/z 392.1507 [(M+H)$^+$ calcd for $C_{21}H_{19}FN_5O_2$: 392.1517]; LCMS (ESI) m/z 392.1 (Ret.=0.72 min, LCMS condition c).

Step 1

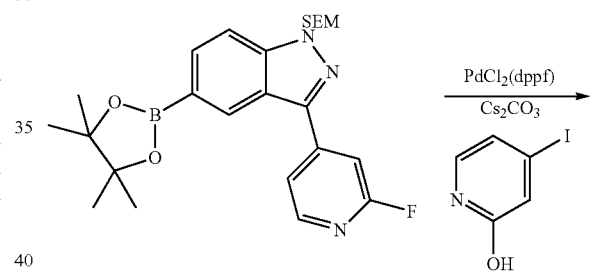

Scheme AA

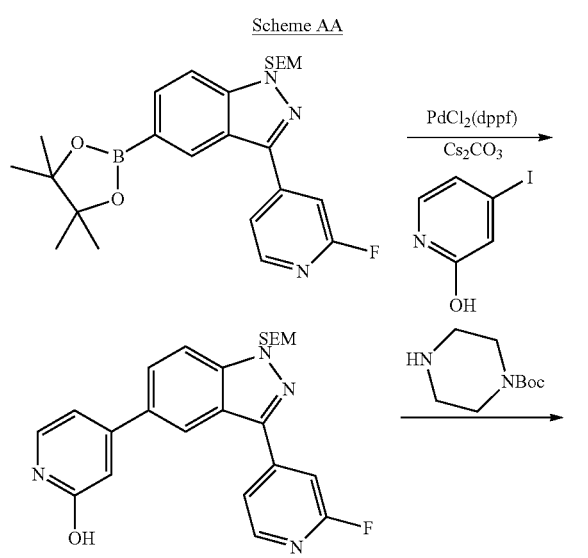

A mixture of 3-(2-fluoropyridin-4-yl)-5-(4,4,5,5-tetramethyl-1,3,2-dioxaborolan-2-yl)-1-{[2-(trimethylsilyl)ethoxy]methyl}-1H-indazole (Step 1, Scheme E) (371 mg, 0.79 mmol), 4-iodopyridin-2-ol (174 mg, 0.79 mmol), [1,1′-bis(diphenylphosphino)ferrocene]dichloro-palladium(II), 1:1 complex with dichloromethane (64.2 mg, 0.079 mmol), 2 M cesium carbonate in water (787 μL, 1.57 mmol) and THF (3.9 mL) was flushed with a stream of $N_2$ and heated to 100° C. for 16 h. The resulting reaction mixture was diluted with water and extracted with $CH_2Cl_2$. The organic layers were dried ($Na_2SO_4$), concentrated and purified by silica gel chromatography (gradient elution, 0-60% EtOAc/hexanes) to afford the title compound; LRMS (ESI) m/z 437.0 [(M+H)$^+$ calcd for $C_{23}H_{26}FN_4O_2Si$: 437].

Step 2

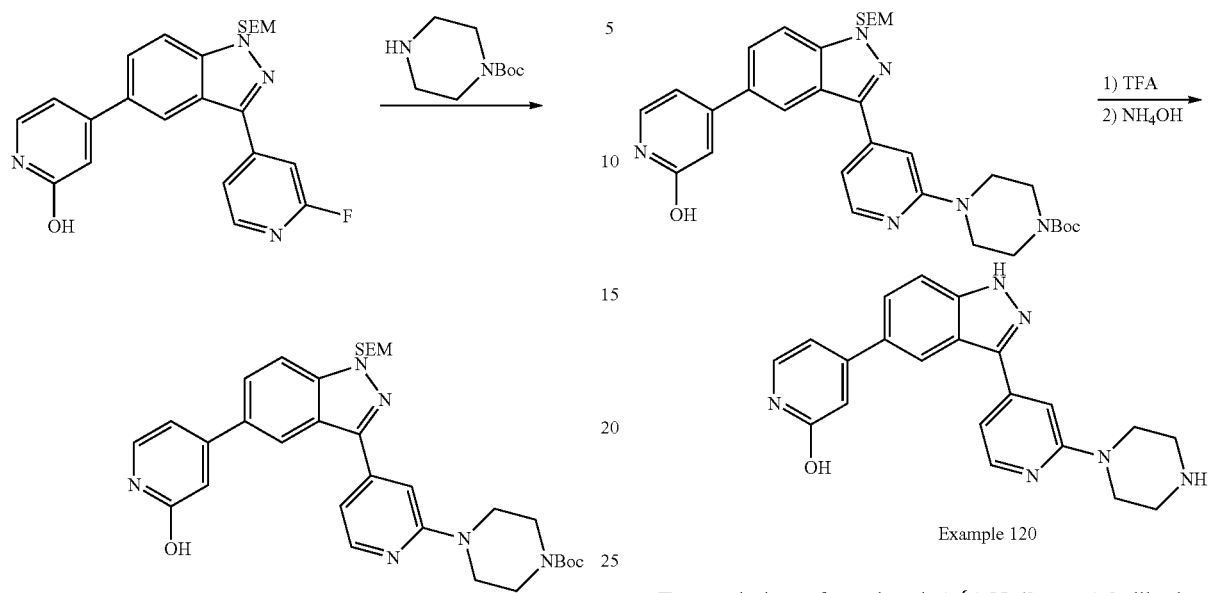

To a solution of 4-[3-(2-fluoropyridin-4-yl)-1-{[2-(trimethylsilyl)ethoxy]methyl}-1H-indazol-5-yl]pyridin-2(1H)-one (50 mg, 0.12 mmol) in DMSO (573 μL) at rt was added tert-butyl piperazine-1-carboxylate (213 mg, 1.15 mmol) and triethylamine (16 μL, 0.12 mmol). The resulting solution was heated at 100° C. for 16 h. After cooling to rt, the mixture was diluted with EtOAc and washed with 10% aq. citric acid (brought to pH 5 with 1N NaOH), water, and brine. The organics were dried ($Na_2SO_4$), concentrated and purified by medium pressure reverse phase chromatography to afford the title compound; LRMS (ESI) m/z 603.2 [(M+H)$^+$ calcd for $C_{32}H_{43}N_6O_4Si$: 603].

Step 3

To a solution of tert-butyl 4-{4-[5-(2-oxo-1,2-dihydro-pyridin-4-yl)-1-{[2-(trimethylsilyl)ethoxy]-methyl}-1H-indazol-3-yl]pyridin-2-yl}piperazine-1-carboxylate (43 mg, 0.071 mmol) in $CH_2Cl_2$ (143 μL) at rt was added TFA (165 μL). The mixture was stirred at rt for 3 h then concentrated. To the resulting oil was added MeOH (1 mL), $CH_2Cl_2$ (1 mL) and $NH_4OH$ (1 mL). After 5 h, the resulting solution was quenched with water and extracted with $CH_2Cl_2$. The combined extracts were dried ($Na_2SO_4$), concentrated, and purified by basic alumina chromatography (gradient elution, 0-12% MeOH/$CH_2Cl_2$) to afford the title compound; LCMS (ESI) m/z 373.1 (Ret.=0.72 min, LCMS condition a).

By following the procedure outlined in Scheme AA, using the appropriate amine, the following compounds can be prepared (Examples 121-123).

| Ex | Structure | LCMS Cond. | RT (min) | m/z | LRRK2 IC$_{50}$ (nM) |
|---|---|---|---|---|---|
| 121 | | a | 0.66 | 388.0 | 1.4 |
| 122 | | a | 0.79 | 402.1 | 1.1 |

-continued

| Ex | Structure | Cond. | LCMS RT (min) | m/z | LRRK2 IC$_{50}$ (nM) |
|---|---|---|---|---|---|
| 123 | 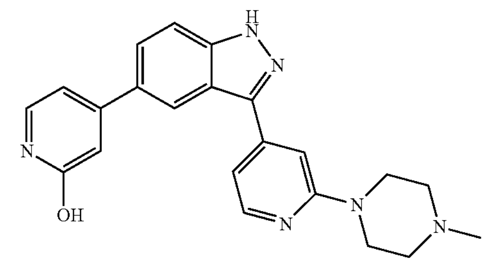 [SMILES: CN1CCN(c2cc(-c3n[nH]c4ccc(-c5ccnc(O)c5)cc34)ccn2)CC1] | a | 0.34 | 387.1 | 2.7 |

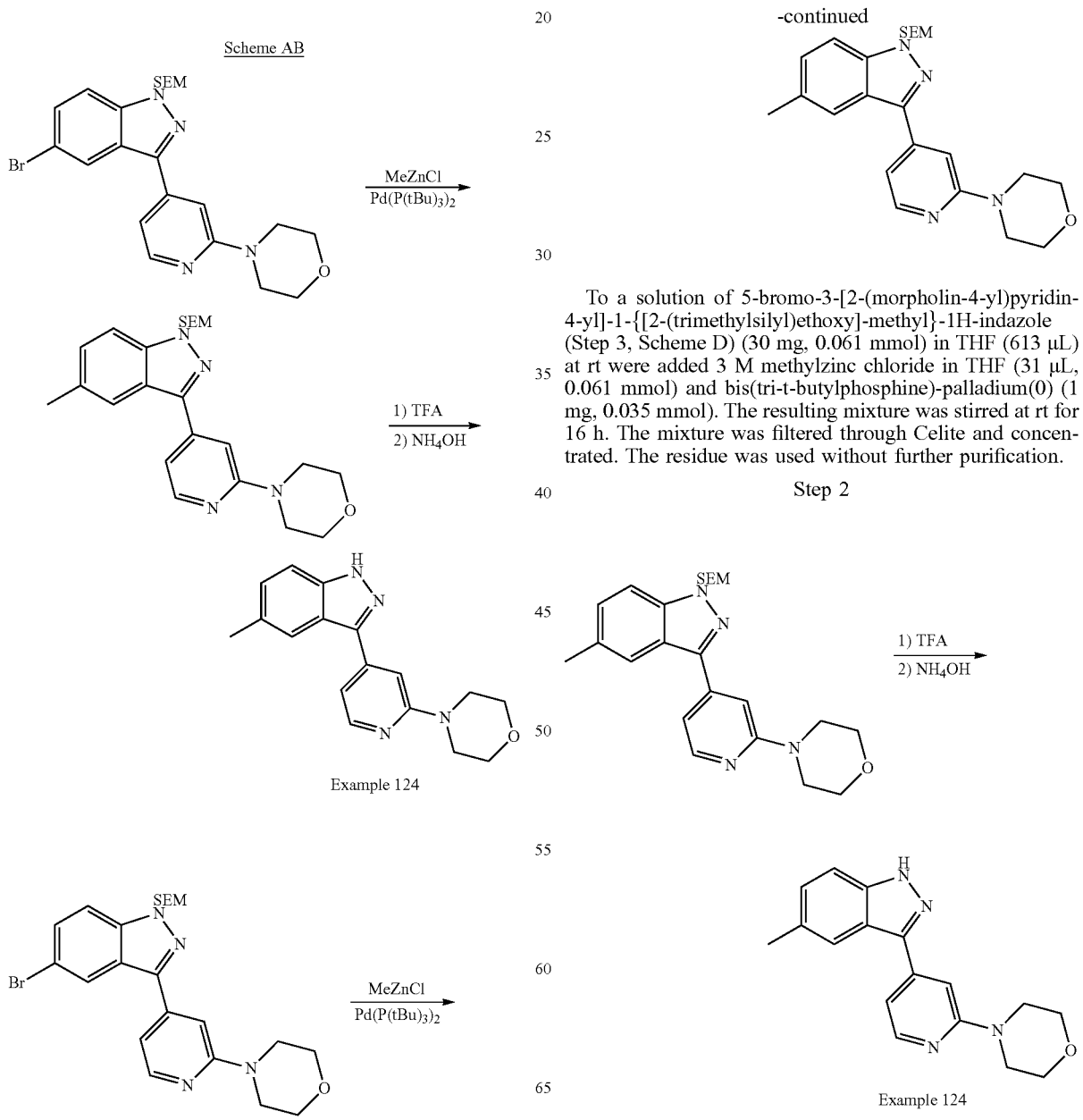

To a solution of 5-bromo-3-[2-(morpholin-4-yl)pyridin-4-yl]-1-{[2-(trimethylsilyl)ethoxy]-methyl}-1H-indazole (Step 3, Scheme D) (30 mg, 0.061 mmol) in THF (613 μL) at rt were added 3 M methylzinc chloride in THF (31 μL, 0.061 mmol) and bis(tri-t-butylphosphine)-palladium(0) (1 mg, 0.035 mmol). The resulting mixture was stirred at rt for 16 h. The mixture was filtered through Celite and concentrated. The residue was used without further purification.

Step 2

To the resulting oil was added MeOH (1 mL), CH$_2$Cl$_2$ (1 mL) and NH$_4$OH (1 mL). After 4 h, the resulting solution was quenched with water and extracted with CH$_2$Cl$_2$. The combined extracts were dried (Na$_2$SO$_4$), concentrated, and purified by Gilson reverse phase chromatography to afford the title compound as a TFA salt; HRMS (ES+) m/z 295.1550 [(M+H)$^+$ calcd for C$_{17}$H$_{19}$N$_4$O: 295.1553].

Scheme AC

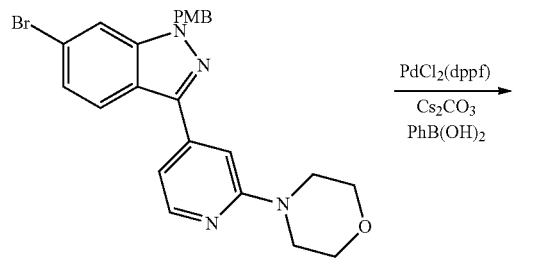

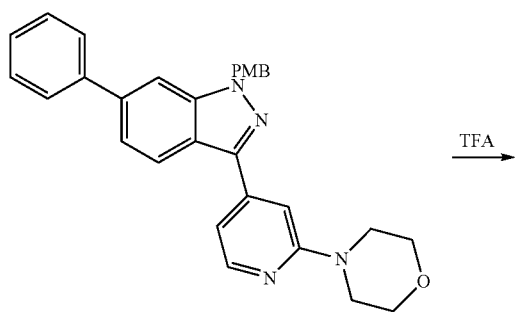

Example 125

Step 1

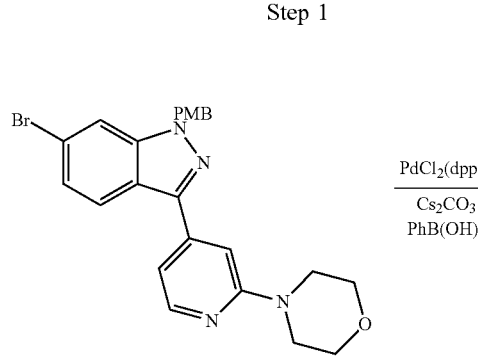

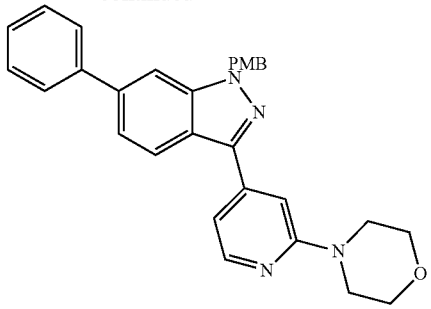

A mixture of 6-bromo-1-(4-methoxybenzyl)-3-[2-(morpholin-4-yl)pyridin-4-yl]-1H-indazole (prepared from Example 73, Step 4) (50 mg, 0.10 mmol), phenylboronic acid (12.7 mg, 0.10 mmol), [1,1'-bis(diphenylphosphino)ferrocene]dichloro-palladium(II), 1:1 complex with dichloromethane (7.6 mg, 0.010 mmol), 2 M cesium carbonate in water (104 μL, 0.21 mmol) and THF (1 mL) was flushed with a stream of N$_2$ and heated to 100° C. for 16 h. The resulting reaction mixture was diluted with water and extracted with CH$_2$Cl$_2$. The organic layers were dried (Na$_2$SO$_4$), concentrated and purified by silica gel chromatography (gradient elution, 0-10% MeOH/CH$_2$Cl$_2$) to afford the title compound; LRMS (ESI) m/z 477.0 [(M+H)$^+$ calcd for C$_{30}$H$_{29}$N$_4$O$_2$: 477].

Step 2

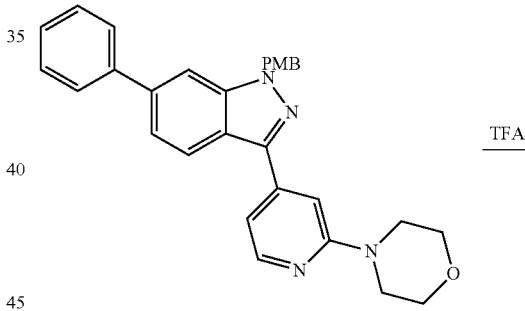

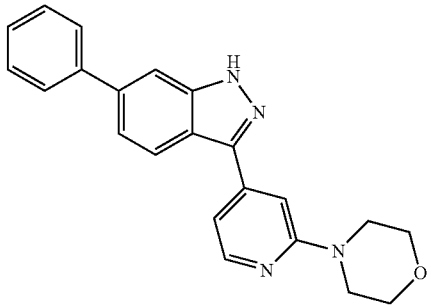

Example 125

1-(4-Methoxybenzyl)-3-[2-(morpholin-4-yl)pyridin-4-yl]-6-phenyl-1H-indazole (34 mg, 0.071 mmol) was dissolved in TFA (275 μL) and heated at 100° C. for 3 h. The solution was concentrated and purified by medium pressure reverse phase chromatography to afford the title compound as a TFA salt; HRMS (ES+) m/z 357.1705 [(M+H)$^+$ calcd for C$_{22}$H$_{19}$N$_4$O: 357.1710]; LCMS (ESI) m/z 357.1 (Ret.=1.20 min, LCMS condition a).

Scheme AD

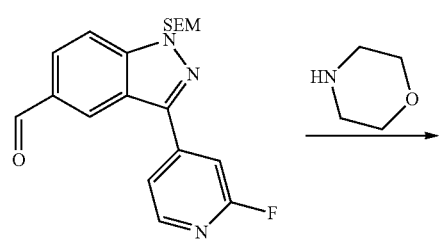

MeMgBr →

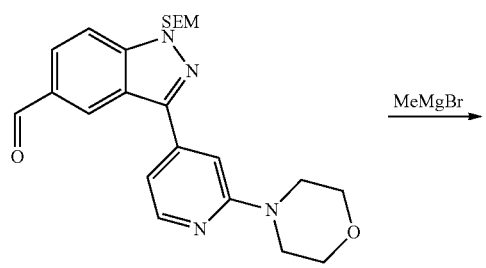

1) TFA
2) NH₄OH →

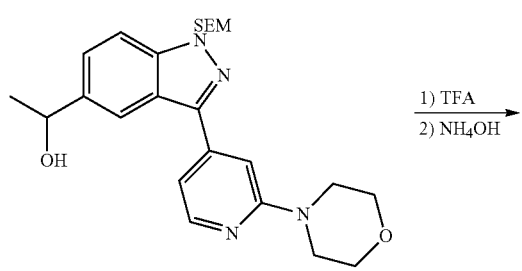

Example 126

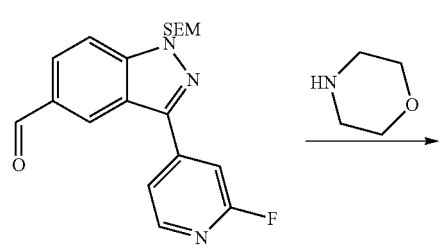

-continued

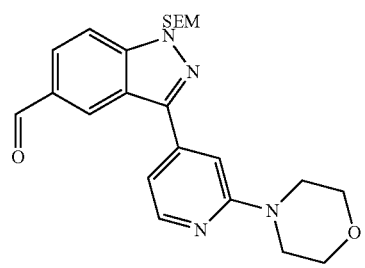

To a solution of 3-(2-fluoropyridin-4-yl)-1-{[2-(trimethylsilyl)ethoxy]methyl}-1H-indazole-5-carbaldehyde (prepared from Example 56, Step 1) (40 mg, 0.11 mmol) in DMSO (538 µL) at rt was added morpholine (94 µL). The resulting solution was heated at 100° C. for 16 h. After cooling to rt, the mixture was diluted with EtOAc and washed with 10% aq. citric acid (brought to pH 5 with 1N NaOH), water, and brine. The organics were dried (Na₂SO₄), concentrated and purified by silica gel chromatography (gradient elution, 0-5% MeOH/CH₂Cl₂) to afford the title compound; LRMS (ESI) m/z 439.0 [(M+H)⁺ calcd for $C_{23}H_{31}N_4O_3Si$: 439].

Step 2

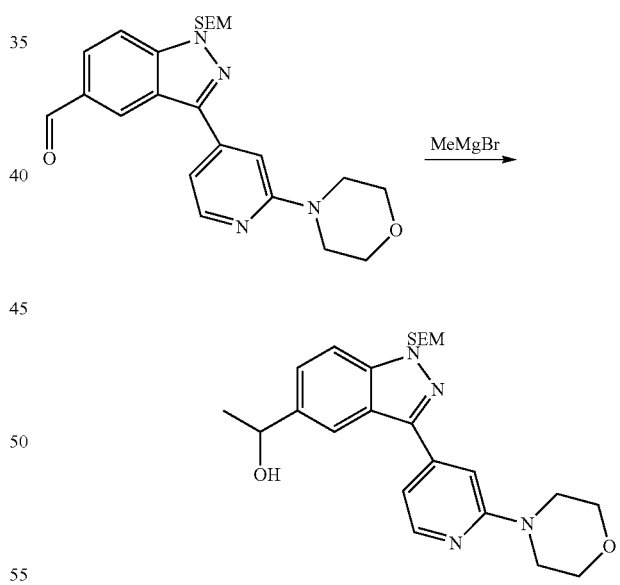

To a solution of 3-[2-(morpholin-4-yl)pyridin-4-yl]-1-{[2-(trimethylsilyl)ethoxy]methyl}-1H-indazole-5-carbaldehyde (41 mg, 0.093 mmol) in THF (1 mL) at −78° C. was added 3 M methylmagnesium bromide in THF (31 µL). The reaction mixture was stirred 1 h, then quenched with NH₄OH and extracted with ether. The organics were dried (Na₂SO₄), concentrated, and purified by silica gel chromatography (gradient elution, 0-10% MeOH/CH₂Cl₂) to afford the title compound; LRMS (ESI) m/z 455.1 [(M+H)⁺ calcd for $C_{24}H_{35}N_4O_3Si$: 455].

Step 3

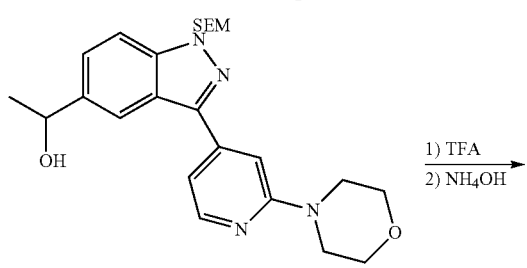

1) TFA
2) NH₄OH

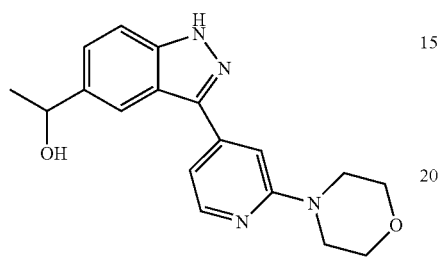

Example 126

To a solution 1-(3-[2-(morpholin-4-yl)pyridin-4-yl]-1-{[2-(trimethylsilyl)ethoxy]methyl}-1H-indazol-5-yl)ethanol (29 mg, 0.064 mmol) in $CH_2Cl_2$ (128 μL) at rt was added TFA (246 μL). The mixture was stirred at rt for 4 h then concentrated. To the resulting oil was added MeOH (1 mL), $CH_2Cl_2$ (1 mL) and $NH_4OH$ (1 mL). After 4 h, the resulting solution was quenched with water and extracted with $CH_2Cl_2$. The combined extracts were dried ($Na_2SO_4$), concentrated, and purified by medium pressure reverse phase chromatography to afford the title compound as a TFA salt; HRMS (ES+) m/z 325.1657 [(M+H)$^+$ calcd for $C_{18}H_{21}N_4O_2$: 325.1659]; LCMS (ESI) m/z 325.1 (Ret.=1.43 min, LCMS condition a).

By following the procedure outlined in Scheme AD, using the appropriate amine in step 1, the following compound can be prepared (Example 127).

| Ex | Structure | HRMS Calc'd | HRMS Found | LRRK2 IC$_{50}$ (nM) |
|---|---|---|---|---|
| 127 | (structure shown) | 369.1921 | 369.1915 | 17 |

By following the procedure outlined in Scheme H, using the appropriate amine, the following compound can be prepared (Example 128).

| Ex | Structure | HRMS Calc'd | HRMS Found | LRRK2 IC$_{50}$ (nM) |
|---|---|---|---|---|
| 128 | (structure shown) | 355.1765 | 355.1758 | 10 |

Parallel preparation of Examples 129-140: (Scheme AE) A set of microwave vials containing a mixture of the fluoropyridine prepared in Scheme AN (40 mg, 0.078 mmol) and the requisite amine (0.78 mmol) in pyridine (0.2 ml) was heated in a microwave reactor at 200° C. for 4 hour. After that time, the solvent was removed in vacuo. To the residue in each vial was added DCM (1 mL), TFA (0.5 mL) and H$_2$O (0.05 mL) and the mixtures were shaken at RT for 1.5 hours. Additional TFA (0.5 ml) and H$_2$O (0.05 mL) were added and the mixtures were shaken at RT overnight. The solvents were then removed in vacuo. The crude residue from each vial was dissolved in DMSO (1 mL) and filtered. The crude products were purified by mass triggered HPLC using the following conditions: [Waters Sunfire C18 column, 5 nm, 30×100 mm, gradient 10% initial to a range of 30-50% final MeCN (0.1% formic acid) in water (0.1% formic acid) 70 mL/min, 8 min run time] to afford Examples 129-140.

Scheme AE

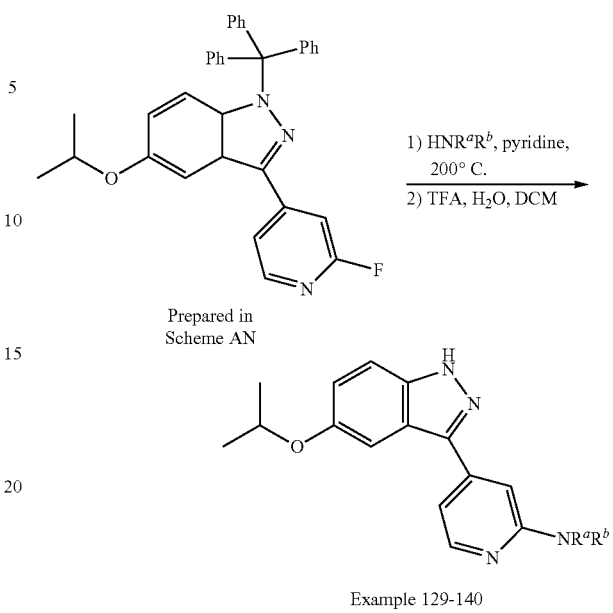

| Ex | Structure | Cond. | LCMS RT (min) | m/z | LRRK2 IC$_{50}$ (nM) |
|---|---|---|---|---|---|
| 129 | 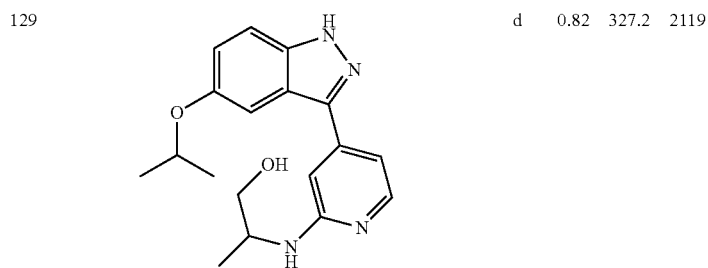 | d | 0.82 | 327.2 | 2119 |
| 130 | 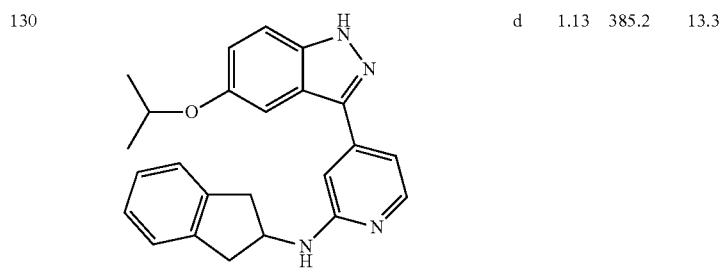 | d | 1.13 | 385.2 | 13.3 |

-continued
| Ex | Structure | LCMS Cond. | RT (min) | m/z | LRRK2 IC$_{50}$ (nM) |
|---|---|---|---|---|---|
| 131 | 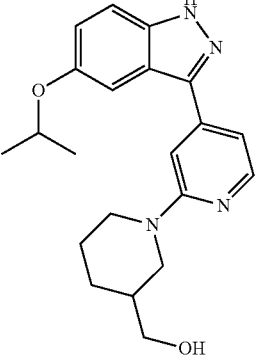 | d | 0.94 | 367.2 | 1.5 |
| 132 | 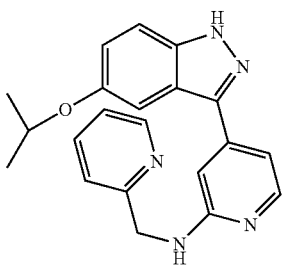 [SMILES: CC(C)Oc1ccc2[nH]nc(-c3ccnc(NCc4ccccn4)c3)c2c1] | d | 0.89 | 360.2 | 2.2 |
| 133 | 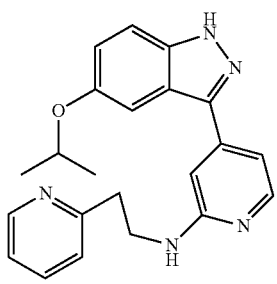 [SMILES: CC(C)Oc1ccc2[nH]nc(-c3ccnc(NCCc4ccccn4)c3)c2c1] | d | 0.91 | 374.2 | 0.8 |
| 134 | 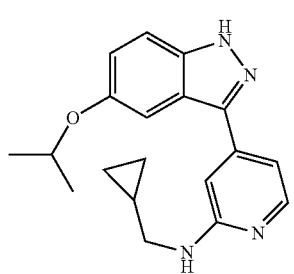 [SMILES: CC(C)Oc1ccc2[nH]nc(-c3ccnc(NCC4CC4)c3)c2c1] | d | 0.99 | 323.3 | 2 |
| 135 | 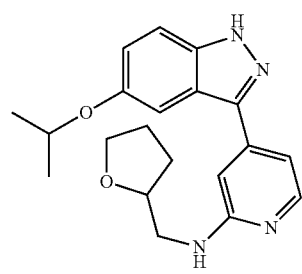 [SMILES: CC(C)Oc1ccc2[nH]nc(-c3ccnc(NCC4CCCO4)c3)c2c1] | d | 0.93 | 353.2 | 3.2 |

| | | | LCMS | | LRRK2 |
|---|---|---|---|---|---|
| Ex | Structure | Cond. | RT (min) | m/z | IC$_{50}$ (nM) |
| 136 | | d | 0.99 | 341.2 | 4.9 |
| 137 | | d | 0.93 | 309.2 | 24.3 |
| 138 | | d | 1.04 | 367.2 | 11.4 |
| 139 | | d | 1.20 | 385.2 | 18.1 |
| 140 | | d | 0.76 | 313.2 | 7.3 |

Parallel preparation of Examples 141-169: To a set of vials containing a solution of the aminopyridine XX (30 mg, 0.059 mmol) in DCE (1 mL) was added T3P (50% in EtOAc, 0.087 mL, 0.15 mmol) and iPr$_2$NEt (0.041 mL, 0.24 mmol). The requisite carboxylic acid (0.082 mmol) was then added individually to each vial. The vials were capped and the mixtures were then heated at 70° C. with stirring overnight. After that time, the mixtures were allowed to cool to RT. To each vial was added TFA (0.5 mL) and water (0.05 mL). The mixtures were shaken at RT for 1.5 hours. The solvent was removed in vacuo. The crude residue from each vial was dissolved in DMSO (1 mL) and filtered. The crude products were purified by mass triggered HPLC using the following conditions: [Waters XBridge C18 column, 5 μm, 19×100 mm, gradient ranges from 10-40% initial to 30-80% MeCN (0.1% NH$_4$OH) in water (0.1% NH$_4$OH) 50 mL/min, 8 min run time] to provide Examples 141-151. Examples 152-168 were repurified by mass triggered HPLC using the following conditions: [Waters Sunfire C18 column, 5 μm, 19×100 mm, gradient range 10-40% initial to 55-80% final MeCN (0.1% formic acid) in water (0.1% formic acid) 70 mL/min, 8 min run time].

Example 169 was repurified by mass triggered HPLC using the following conditions: [Waters Sunfire C18 column, 5 μm, 19×100 mm, gradient range 40-45% initial to 70% final MeCN (0.1% formic acid) in water (0.1% formic acid) 70 mL/min, 8 min run time].

Scheme AF

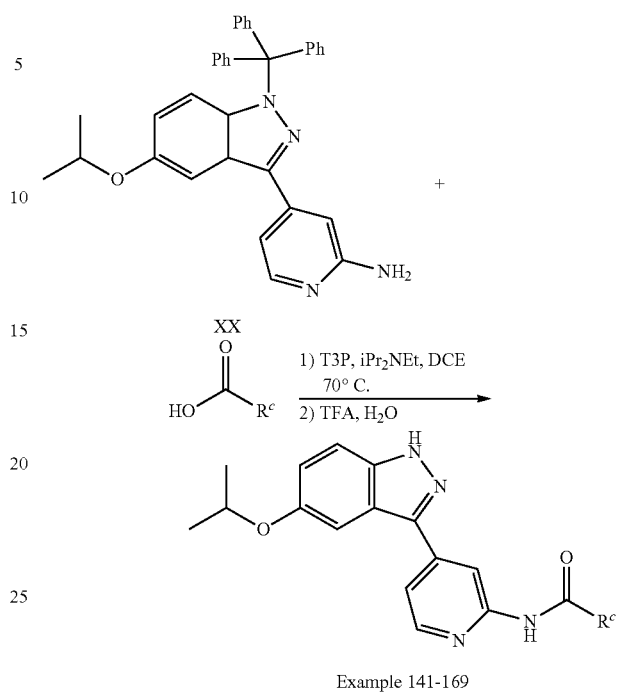

Example 141-169

| Ex | Structure | LCMS Cond. | RT (min) | m/z | LRRK2 IC$_{50}$ (nM) |
|---|---|---|---|---|---|
| 141 | 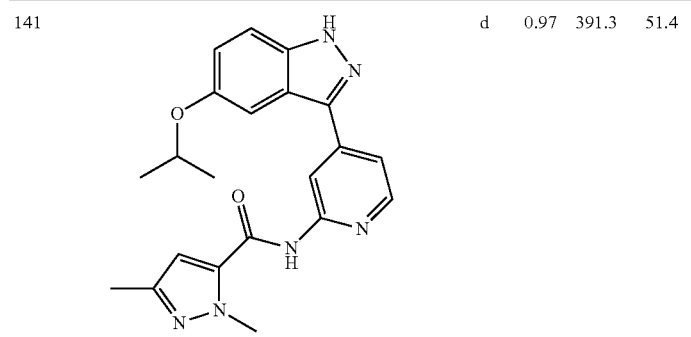 | d | 0.97 | 391.3 | 51.4 |
| 142 | 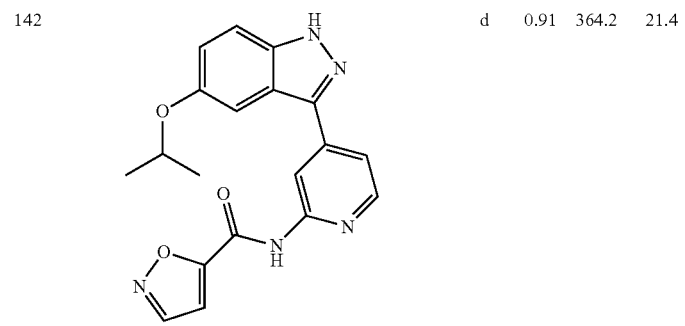 | d | 0.91 | 364.2 | 21.4 |

-continued
| Ex | Structure | Cond. | LCMS RT (min) | m/z | LRRK2 IC$_{50}$ (nM) |
|---|---|---|---|---|---|
| 143 | 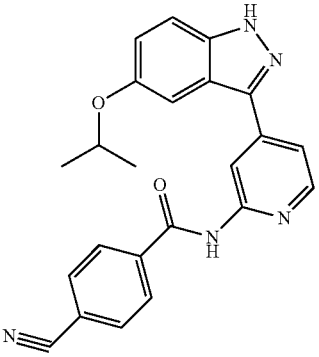 [SMILES: CC(C)Oc1ccc2[nH]nc(-c3ccnc(NC(=O)c4ccc(C#N)cc4)c3)c2c1] | d | 1.02 | 398.3 | 113.3 |
| 144 | 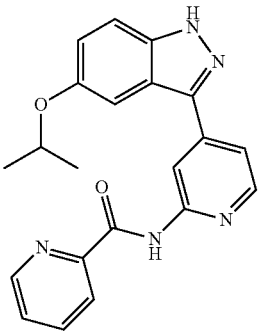 [SMILES: CC(C)Oc1ccc2[nH]nc(-c3ccnc(NC(=O)c4ccccn4)c3)c2c1] | d | 1.08 | 374.3 | 29.2 |
| 145 | 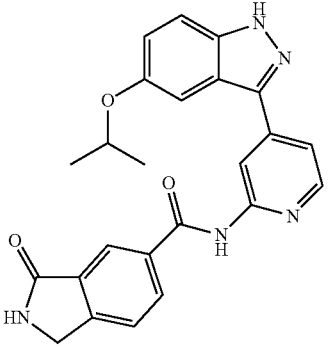 [SMILES: CC(C)Oc1ccc2[nH]nc(-c3ccnc(NC(=O)c4ccc5c(c4)C(=O)NC5)c3)c2c1] | d | 0.83 | 428.3 | 52 |
| 146 | 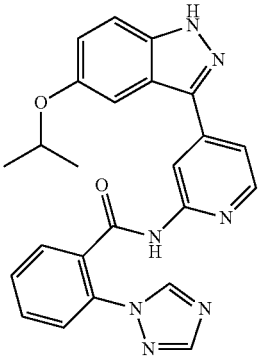 [SMILES: CC(C)Oc1ccc2[nH]nc(-c3ccnc(NC(=O)c4ccccc4-n4cncn4)c3)c2c1] | d | 0.86 | 440.3 | 36.8 |

-continued
| Ex | Structure | LCMS Cond. | RT (min) | m/z | LRRK2 IC$_{50}$ (nM) |
|---|---|---|---|---|---|
| 147 | 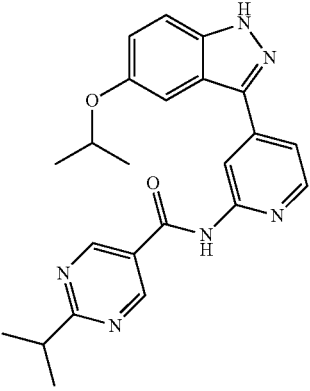 [SMILES: CC(C)Oc1ccc2[nH]nc(-c3ccnc(NC(=O)c4cnc(C(C)C)nc4)c3)c2c1] | d | 1.04 | 417.3 | 70.8 |
| 148 | 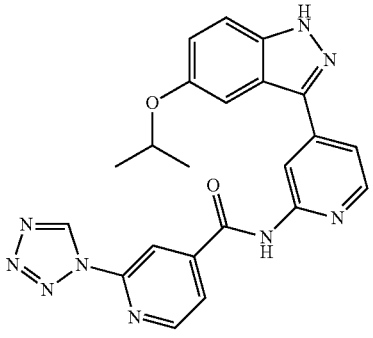 [SMILES: CC(C)Oc1ccc2[nH]nc(-c3ccnc(NC(=O)c4ccnc(-n5cnnn5)c4)c3)c2c1] | d | 0.93 | 442.3 | 23.9 |
| 149 | 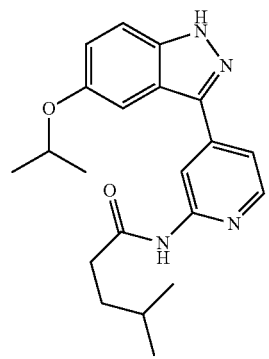 [SMILES: CC(C)CCC(=O)Nc1cc(-c2n[nH]c3ccc(OC(C)C)cc23)ccn1] | d | 1.12 | 367.3 | 79.6 |
| 150 | 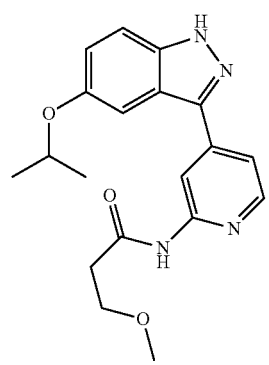 [SMILES: COCCC(=O)Nc1cc(-c2n[nH]c3ccc(OC(C)C)cc23)ccn1] | d | 0.87 | 355.3 | 51.7 |

-continued
| Ex | Structure | LCMS Cond. | RT (min) | m/z | LRRK2 IC$_{50}$ (nM) |
|---|---|---|---|---|---|
| 151 | 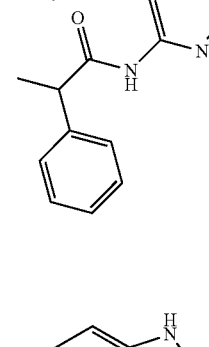 | d | 1.12 | 401.3 | 51.9 |
| 152 | 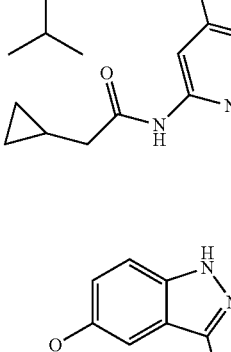 | d | 0.98 | 351.3 | 35.8 |
| 153 | 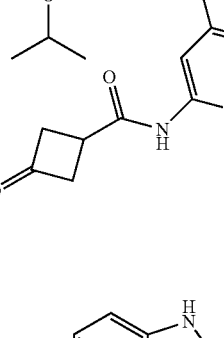 | d | 0.85 | 365.3 | 29.7 |
| 154 | 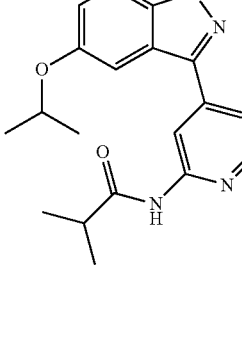 | d | 0.98 | 339.3 | 39.4 |

-continued

| Ex | Structure | LCMS Cond. | RT (min) | m/z | LRRK2 IC$_{50}$ (nM) |
|---|---|---|---|---|---|
| 155 | 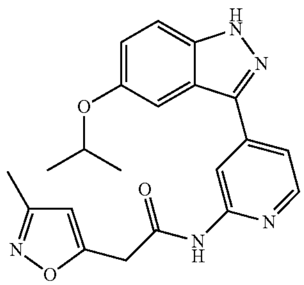 [SMILES: Cc1cc(CC(=O)Nc2cc(-c3n[nH]c4ccc(OC(C)C)cc34)ccn2)on1] | d | 0.89 | 392.4 | 13.4 |
| 156 | 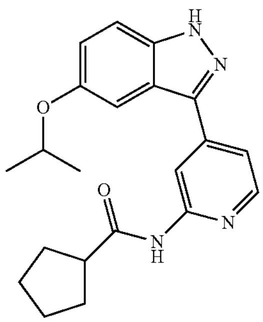 [SMILES: CC(C)Oc1ccc2[nH]nc(-c3ccnc(NC(=O)C4CCCC4)c3)c2c1] | d | 1.07 | 365.3 | 53.1 |
| 157 | 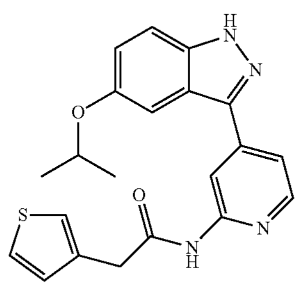 [SMILES: CC(C)Oc1ccc2[nH]nc(-c3ccnc(NC(=O)Cc4ccsc4)c3)c2c1] | d | 1.02 | 393.3 | 34.4 |
| 158 | 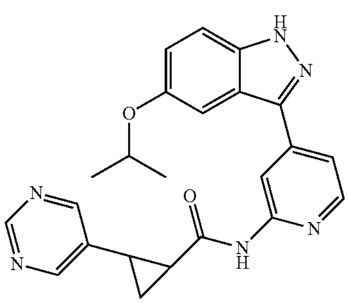 [SMILES: CC(C)Oc1ccc2[nH]nc(-c3ccnc(NC(=O)C4CC4c4cncnc4)c3)c2c1] | d | 0.86 | 415.4 | 30.9 |
| 159 | 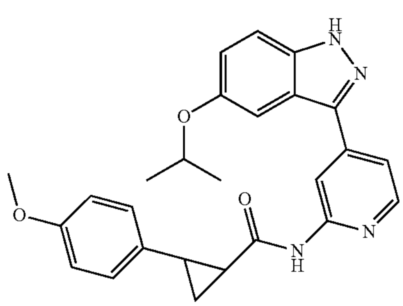 [SMILES: COc1ccc(C2CC2C(=O)Nc2cc(-c3n[nH]c4ccc(OC(C)C)cc34)ccn2)cc1] | d | 1.12 | 443.4 | 781.6 |

-continued
| Ex | Structure | LCMS Cond. | RT (min) | m/z | LRRK2 IC$_{50}$ (nM) |
|---|---|---|---|---|---|
| 160 | 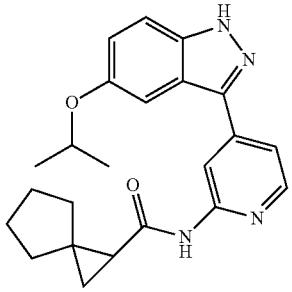 [SMILES: CC(C)Oc1ccc2[nH]nc(-c3ccnc(NC(=O)C4CC45CCCC5)c3)c2c1] | d | 1.17 | 391.4 | 140 |
| 161 | 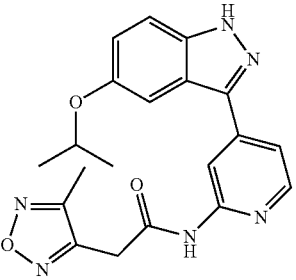 [SMILES: Cc1nonc1CC(=O)Nc1cc(-c2n[nH]c3ccc(OC(C)C)cc23)ccn1] | d | 0.94 | 393.3 | 32 |
| 162 | 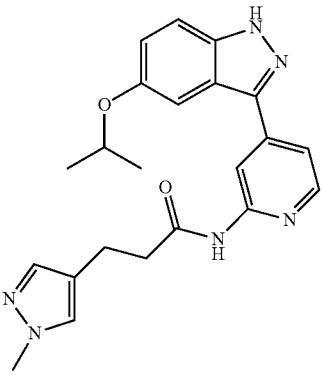 [SMILES: CC(C)Oc1ccc2[nH]nc(-c3ccnc(NC(=O)CCc4cnn(C)c4)c3)c2c1] | d | 0.85 | 405.4 | 27.2 |
| 163 | 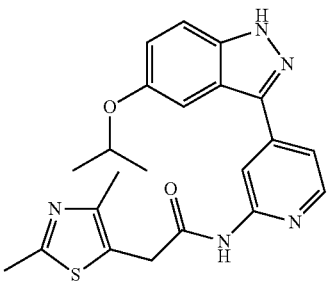 [SMILES: Cc1nc(C)c(CC(=O)Nc2cc(-c3n[nH]c4ccc(OC(C)C)cc34)ccn2)s1] | d | 0.91 | 422.4 | 34.9 |

|     |           | LCMS | | | LRRK2 |
|-----|-----------|------|------|------|-------|
| Ex  | Structure | Cond. | RT (min) | m/z | IC$_{50}$ (nM) |
| 164 | | d | 0.87 | 381.3 | 27.7 |
| 165 | | d | 0.76 | 394.4 | 23.4 |
| 166 | | d | 1.00 | 387.3 | 73.5 |
| 167 | | d | 0.99 | 443.4 | 78 |

-continued

| Ex | Structure | LCMS Cond. | RT (min) | m/z | LRRK2 IC$_{50}$ (nM) |
|---|---|---|---|---|---|
| 168 | 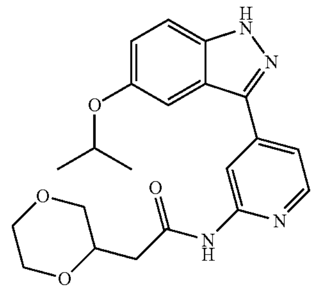 [SMILES: CC(C)Oc1ccc2[nH]nc(-c3ccnc(NC(=O)CC4COCCO4)c3)c2c1] | d | 0.84 | 397.4 | 33.4 |
| 169 | 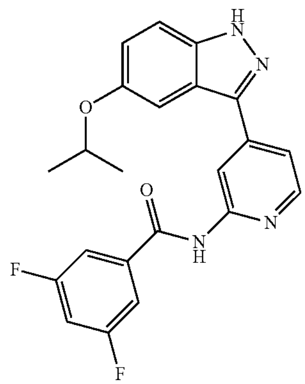 [SMILES: CC(C)Oc1ccc2[nH]nc(-c3ccnc(NC(=O)c4cc(F)cc(F)c4)c3)c2c1] | d | 1.12 | 409.3 | 169.3 |

Parallel preparation of Examples 170-184: In a glove bag under an atmosphere of nitrogen to a set of vials was added bis(cyclooctadiene)nickel (0) (2.1 mg, 0.0075 mmol), 1,3-bis-(2,6-diisopropylphenyl)imidazolinium chloride (6.4 mg, 0.015 mmol), sodium t-butoxide (29 mg, 0.30 mmol) followed by the requisite amine (0.15 mmol). To each vial was then added a solution of the chloropyridine prepared in Scheme AM (40 mg, 0.075 mmol) in dioxane (0.50 mL). The vials were capped and removed from the glove bag. The vials were placed into a pre-heated aluminium block at 80° C. The mixtures were stirred at that temperature overnight. Water (0.3 mL) was added to each reaction followed by DCM (1.2 mL). The vials were shaken at RT for 5 min. The mixture was transferred to a fritted barrel filter. The organic layer from each vial was drained into a clean vial. Additional DCM (1 mL) was added to the aqueous layer and the layers were separated. The solvent from the combined organic layers was removed in vacuo. To each vial was then added DCM (1 mL) followed by TFA (0.50 mL) and water (0.050 mL). The vials were shaken at RT for 1.5 hours. The solvent was removed in vacuo. Each crude product was redissolved in 1 mL of DMSO and filtered. The crude products were purified by mass triggered HPLC. [Waters XBridge C18 column, 5 μm, 19×100 mm, gradient ranges from 10-35% initial to 40-65% MeCN (0.1% NH$_4$OH) in water (0.1% NH$_4$OH) 50 mL/min, 8 min run time] to provide the examples 170-183. Example 184 was repurified using the following conditions: [Waters Sunfire C18 column, 5 μm, 19×100 mm, gradient 10% initial to 23% final MeCN (0.1% formic acid) in water (0.1% formic acid) 50 mL/min, 8 min run time].

Scheme AG

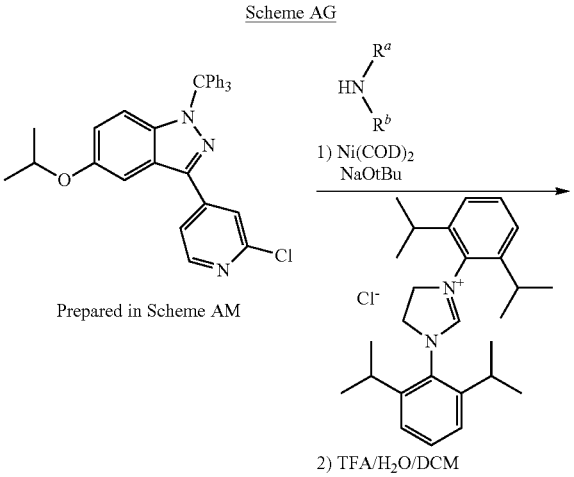

Prepared in Scheme AM

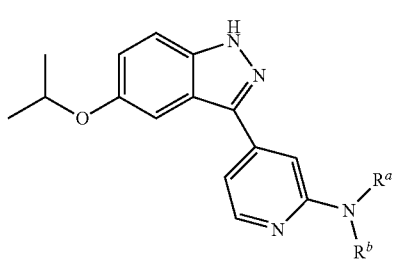

Examples 170-184

-continued

| Ex | Structure | Cond. | LCMS RT (min) | m/z | LRRK2 IC$_{50}$ (nM) |
|---|---|---|---|---|---|
| 170 | 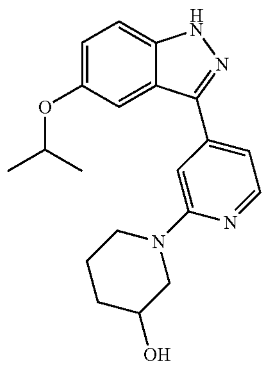 [SMILES: CC(C)Oc1ccc2[nH]nc(-c3ccnc(N4CCCC(O)C4)c3)c2c1] | d | 0.88 | 353.3 | 6.4 |
| 171 | 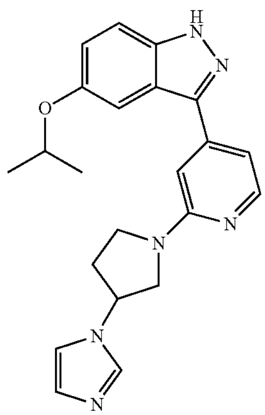 [SMILES: CC(C)Oc1ccc2[nH]nc(-c3ccnc(N4CCC(n5ccnc5)C4)c3)c2c1] | d | 0.84 | 389.3 | 3.1 |
| 172 | 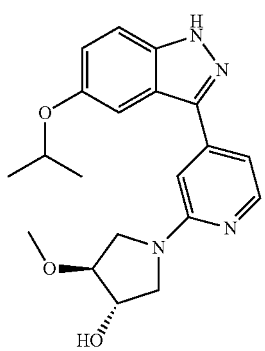 [SMILES: CO[C@H]1CN(c2cc(-c3n[nH]c4ccc(OC(C)C)cc34)ccn2)C[C@@H]1O] | d | 0.89 | 369.3 | 27.1 |
| 173 | 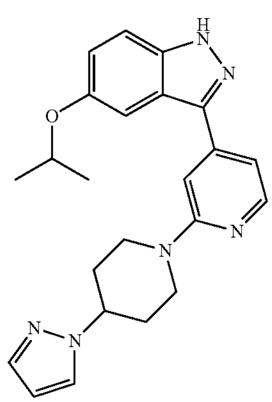 [SMILES: CC(C)Oc1ccc2[nH]nc(-c3ccnc(N4CCC(n5cccn5)CC4)c3)c2c1] | d | 1.00 | 403.4 | 4.9 |
| 174 | | d | 0.98 | 359.3 | 6.6 |
| 175 | | d | 0.94 | 400.4 | 2.2 |
| 176 | | d | 0.87 | 351.3 | 7.1 |
| 177 | | d | 0.94 | 353.3 | 5.2 |

| Ex | Structure | Cond. | LCMS RT (min) | m/z | LRRK2 IC$_{50}$ (nM) |
|---|---|---|---|---|---|
| 178 | | d | 0.94 | 353.3 | 5 |
| 179 | | d | 1.16 | 363.4 | 17.7 |
| 180 | | d | 0.79 | 376.3 | 10.2 |
| 181 | | d | 0.80 | 339.3 | 8.2 |
| 182 | | d | 0.94 | 393.3 | 10.8 |
| 183 | | d | 0.90 | 339.3 | 5.3 |
| 184 | | d | 0.80 | 387.3 | 5.4 |

Examples 185-215 were prepared in parallel using a method similar to that described in Scheme AG except the requisite amines and 3-bis-(2,6diisopropylphenyl)imidazolinium chloride were added to the vials prior to transfer into the glove bag. The crude products were purified by mass triggered HPLC. [Waters XBridge C18 column, 5 μm, 19×100 mm, gradient ranges from 10-40% initial to 45-80% MeCN (0.1% NH$_4$OH) in water (0.1% NH$_4$OH) 50 mL/min, 8 min run time] to provide Examples 185-215.

| Ex | Structure | LCMS Cond. | RT (min) | m/z | LRRK2 IC$_{50}$ (nM) |
|---|---|---|---|---|---|
| 185 | 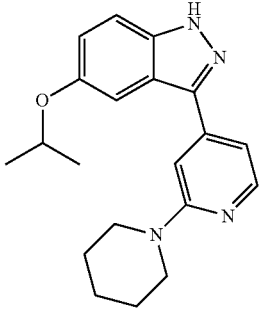 [SMILES: CC(C)Oc1ccc2[nH]nc(-c3ccnc(N4CCCCC4)c3)c2c1] | d | 1.13 | 373.4 | 7.5 |
| 186 | 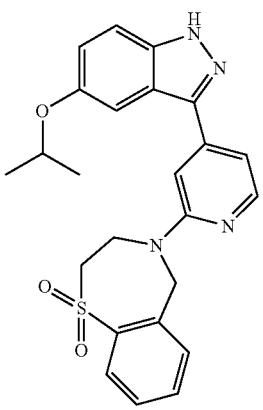 [SMILES: CC(C)Oc1ccc2[nH]nc(-c3ccnc(N4CCS(=O)(=O)c5ccccc5C4)c3)c2c1] | d | 1.04 | 449.4 | 154.2 |
| 187 | 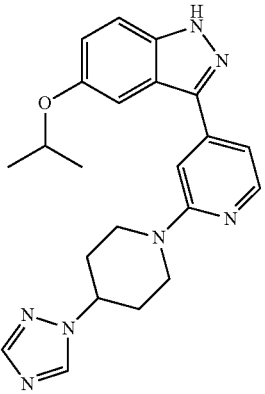 [SMILES: CC(C)Oc1ccc2[nH]nc(-c3ccnc(N4CCC(n5cncn5)CC4)c3)c2c1] | 4 | 0.88 | 404.4 | 4 |
| 188 | 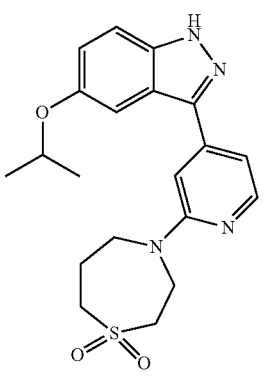 [SMILES: CC(C)Oc1ccc2[nH]nc(-c3ccnc(N4CCCS(=O)(=O)CC4)c3)c2c1] | d | 0.88 | 401.3 | 21.4 |

-continued

| Ex | Structure | LCMS Cond. | RT (min) | m/z | LRRK2 IC₅₀ (nM) |
|---|---|---|---|---|---|
| 189 | 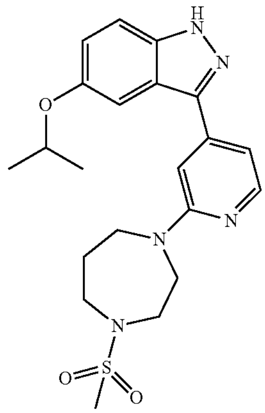 [SMILES: CC(C)Oc1ccc2[nH]nc(-c3ccnc(N4CCCN(S(C)(=O)=O)CC4)c3)c2c1] | d | 0.92 | 430.4 | 22.4 |
| 190 | 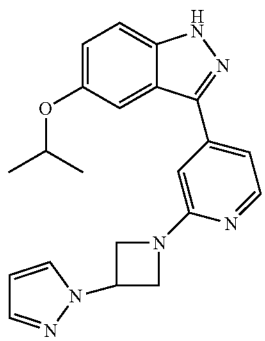 [SMILES: CC(C)Oc1ccc2[nH]nc(-c3ccnc(N4CC(n5cccn5)C4)c3)c2c1] | d | 0.90 | 375.4 | 13.2 |
| 191 | 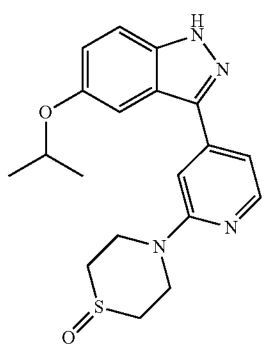 [SMILES: CC(C)Oc1ccc2[nH]nc(-c3ccnc(N4CCS(=O)CC4)c3)c2c1] | d | 0.79 | 371.3 | 7.4 |
| 192 | 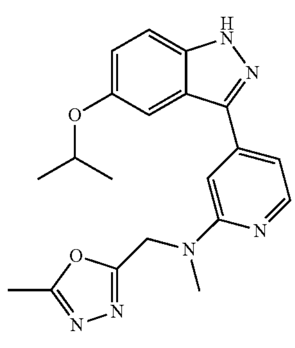 [SMILES: Cc1nnc(CN(C)c2cc(-c3n[nH]c4ccc(OC(C)C)cc34)ccn2)o1] | d | 0.89 | 379.4 | 25.3 |

-continued
| Ex | Structure | LCMS Cond. | RT (min) | m/z | LRRK2 IC$_{50}$ (nM) |
|---|---|---|---|---|---|
| 193 | 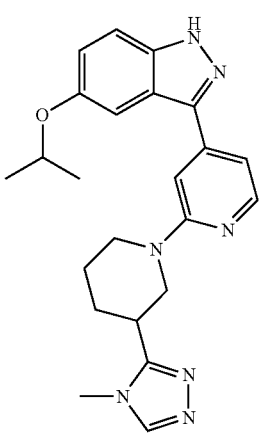 [SMILES: CC(C)Oc1ccc2[nH]nc(-c3ccnc(N4CCCC(c5nncn5C)C4)c3)c2c1] | d | 0.83 | 418.4 | 6.2 |
| 194 | 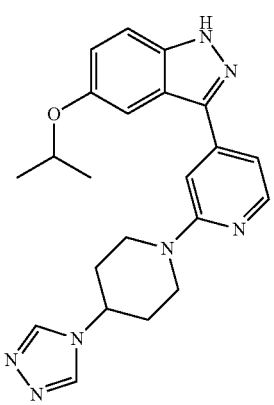 [SMILES: CC(C)Oc1ccc2[nH]nc(-c3ccnc(N4CCC(n5cnnc5)CC4)c3)c2c1] | d | 0.80 | 404.4 | 4.4 |
| 195 | 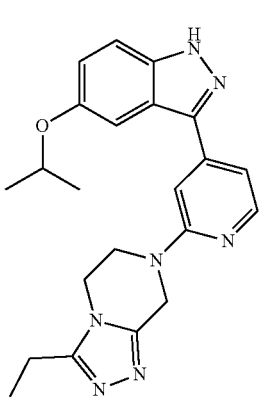 [SMILES: CCc1nnc2n1CCN(c1cc(-c3n[nH]c4ccc(OC(C)C)cc34)ccn1)C2] | d | 0.84 | 404.4 | 7.2 |

-continued

| Ex | Structure | LCMS Cond. | RT (min) | m/z | LRRK2 IC$_{50}$ (nM) |
|---|---|---|---|---|---|
| 196 | | d | 0.87 | 375.4 | 8.6 |
| 197 | | d | 1.00 | 390.4 | 12.8 |
| 198 | | d | 0.99 | 390.4 | 9.2 |

|     |           |       | LCMS |     | LRRK2 |
| --- | --------- | ----- | ---- | --- | ----- |
| Ex  | Structure | Cond. | RT (min) | m/z | IC$_{50}$ (nM) |
| 199 | | d | 1.00 | 428.4 | 8.9 |
| 200 | | d | 1.10 | 415.4 | 10.9 |
| 201 | | d | 1.03 | 323.4 | 5 |
| 202 | | d | 1.00 | 416.4 | 6.4 |

|     |           | LCMS |      |     | LRRK2 |
|-----|-----------|------|------|-----|-------|
| Ex  | Structure | Cond. | RT (min) | m/z | IC₅₀ (nM) |
| 203 | | d | 1.07 | 421.4 | 13.4 |
| 204 | | d | 1.06 | 416.4 | 7.9 |
| 205 | | d | 0.99 | 415.4 | 6.4 |
| 206 | | d | 1.06 | 435.4 | 10.5 |

-continued
| Ex | Structure | Cond. | LCMS RT (min) | m/z | LRRK2 IC$_{50}$ (nM) |
|---|---|---|---|---|---|
| 207 | 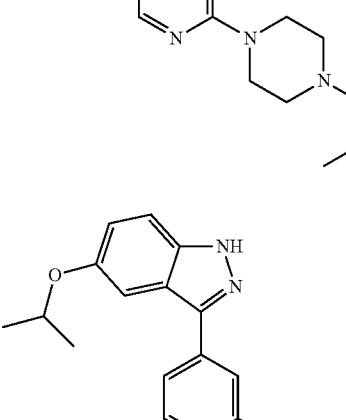 | d | 1.09 | 420.3 | 20.8 |
| 208 | 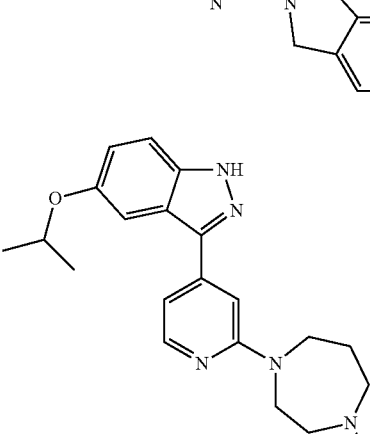 | d | 0.95 | 372.4 | 17.5 |
| 209 | 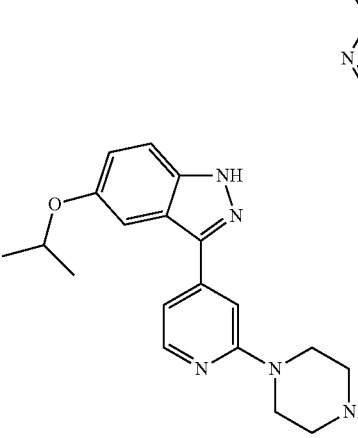 | d | 1.06 | 430.5 | 25.5 |
| 210 | 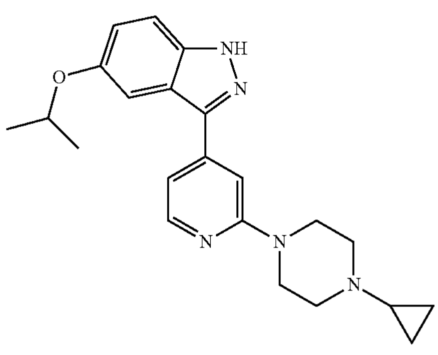 [SMILES: CC(C)Oc1ccc2[nH]nc(-c3ccnc(N4CCN(C5CC5)CC4)c3)c2c1] | d | 1.05 | 378.4 | 7.4 |

US 9,440,952 B2
-continued
| Ex | Structure | LCMS Cond. | RT (min) | m/z | LRRK2 IC50 (nM) |
|---|---|---|---|---|---|
| 211 | 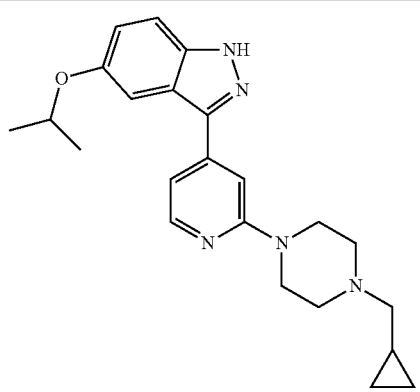 [SMILES: CC(C)Oc1ccc2[nH]nc(-c3ccnc(N4CCN(CC5CC5)CC4)c3)c2c1] | d | 1.08 | 392.4 | 6.2 |
| 212 | 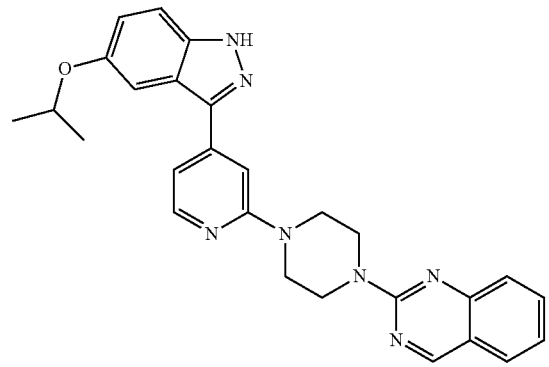 [SMILES: CC(C)Oc1ccc2[nH]nc(-c3ccnc(N4CCN(c5ncc6ccccc6n5)CC4)c3)c2c1] | d | 1.23 | 466.5 | 70.6 |
| 213 | 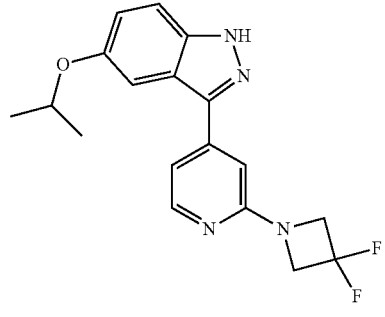 [SMILES: CC(C)Oc1ccc2[nH]nc(-c3ccnc(N4CC(F)(F)C4)c3)c2c1] | d | 1.01 | 345.3 | 16.7 |
| 214 | 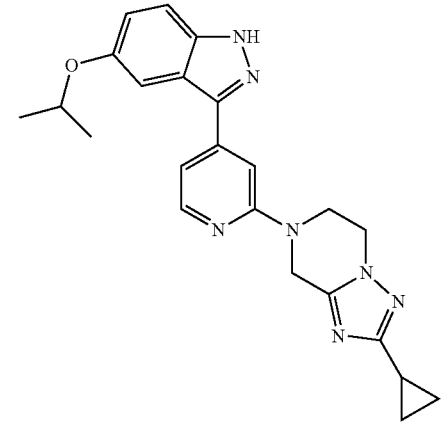 [SMILES: CC(C)Oc1ccc2[nH]nc(-c3ccnc(N4CCn5nc(C6CC6)nc5C4)c3)c2c1] | d | 0.95 | 416.4 | 15.4 |

| Ex | Structure | LCMS Cond. | RT (min) | m/z | LRRK2 IC$_{50}$ (nM) |
|---|---|---|---|---|---|
| 215 | 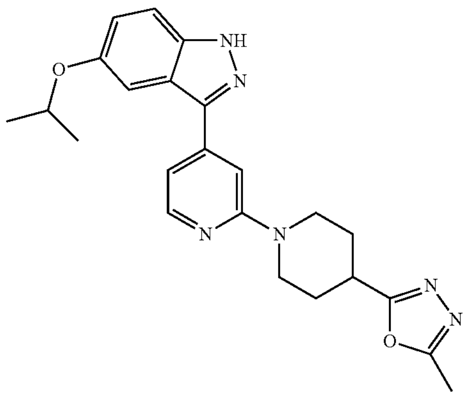 [SMILES: Cc1nnc(C2CCN(c3cc(-c4n[nH]c5ccc(OC(C)C)cc45)ccn3)CC2)o1] | d | 0.94 | 419.2 | 6 |

Examples 216-230 were prepared in parallel following the method described in Scheme AH. This procedure was similar to that described above for Scheme AG, utilizing the chloropyridine Intermediate AM.1.1. The crude products were purified by mass triggered HPLC. [Waters XBridge C18 column, 5 μm, 19×100 mm, gradient ranges from 10-30% initial to 35-65% MeCN (0.1% NH$_4$OH) in water (0.1% NH$_4$OH) 50 mL/min, 8 min run time] to provide Examples 216-230.

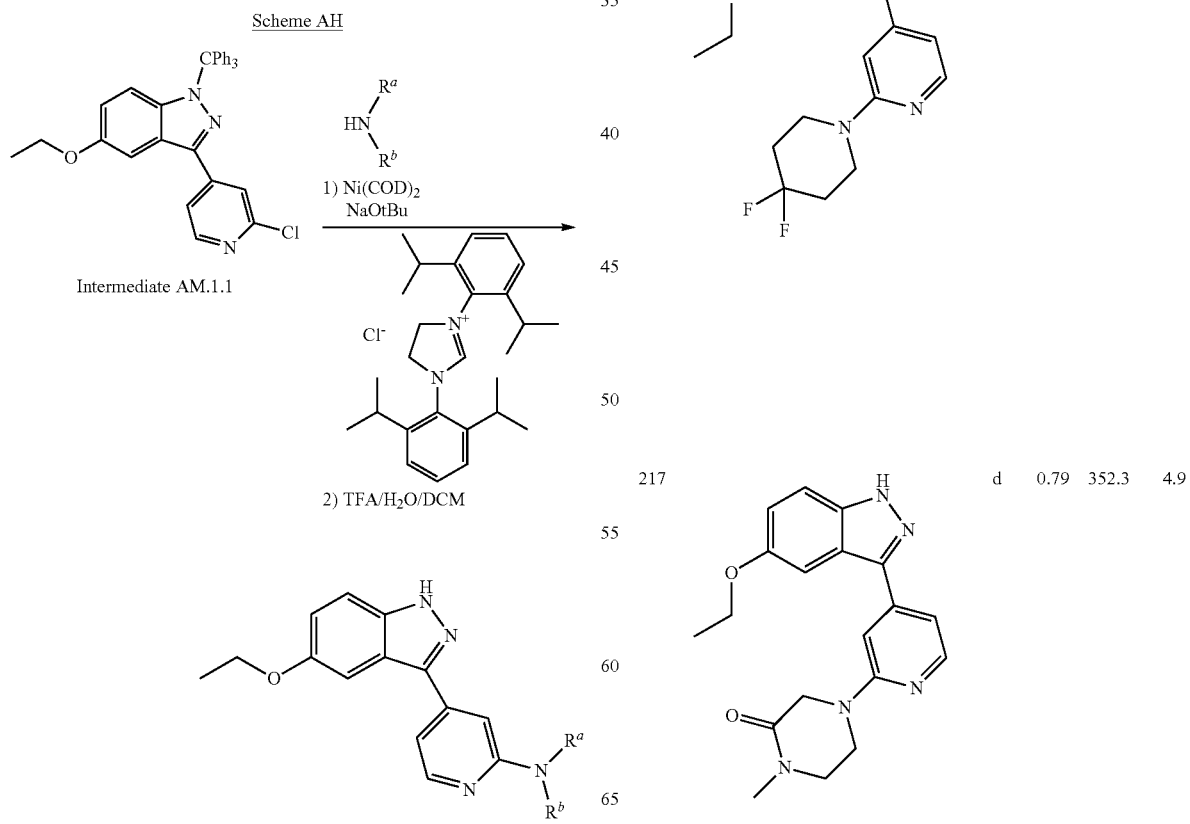

| Ex | Structure | LCMS Cond. | RT (min) | m/z | LRRK2 IC$_{50}$ (nM) |
|---|---|---|---|---|---|
| 216 | 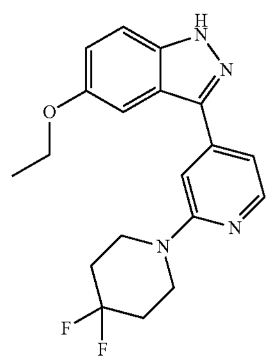 [SMILES: CCOc1ccc2[nH]nc(-c3ccnc(N4CCC(F)(F)CC4)c3)c2c1] | d | 1.06 | 359.3 | 5.4 |
| 217 | 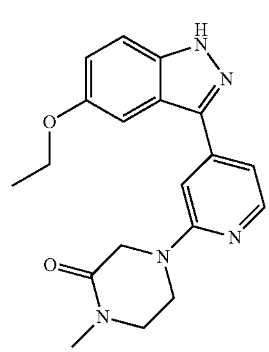 [SMILES: CCOc1ccc2[nH]nc(-c3ccnc(N4CCN(C)C(=O)C4)c3)c2c1] | d | 0.79 | 352.3 | 4.9 |

189
-continued

| Ex | Structure | LCMS Cond. | RT (min) | m/z | LRRK2 IC$_{50}$ (nM) |
|---|---|---|---|---|---|
| 218 | 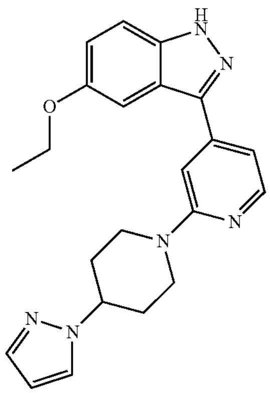 [SMILES: CCOc1ccc2[nH]nc(-c3ccnc(N4CCC(n5cccn5)CC4)c3)c2c1] | d | 0.95 | 389.4 | 14.4 |
| 219 | 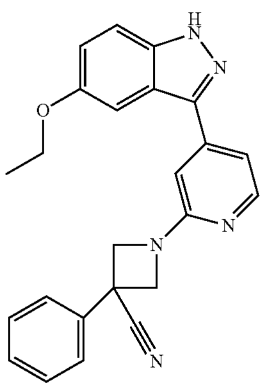 [SMILES: CCOc1ccc2[nH]nc(-c3ccnc(N4CC(C#N)(c5ccccc5)C4)c3)c2c1] | d | 1.05 | 396.4 | 70 |
| 220 | 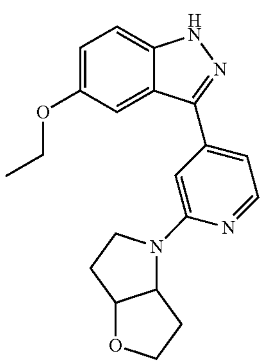 [SMILES: CCOc1ccc2[nH]nc(-c3ccnc(N4CCC5OCCC54)c3)c2c1] | d | 0.88 | 351.4 | 22.6 |
| 221 | 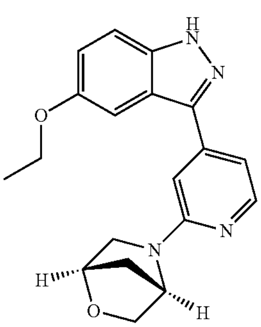 [SMILES: CCOc1ccc2[nH]nc(-c3ccnc(N4C[C@@H]5C[C@H]4CO5)c3)c2c1] | d | 0.82 | 337.3 | 20.9 |

190
-continued

| Ex | Structure | LCMS Cond. | RT (min) | m/z | LRRK2 IC$_{50}$ (nM) |
|---|---|---|---|---|---|
| 222 | | d | 0.89 | 375.4 | 9.3 |
| 223 | | d | 0.99 | 345.3 | 13.5 |
| 224 | | d | 0.89 | 339.4 | 18.8 |
| 225 | | d | 1.07 | 410.4 | 16.3 |

191
-continued
| Ex | Structure | Cond. | LCMS RT (min) | m/z | LRRK2 IC$_{50}$ (nM) |
|----|-----------|-------|---------------|-----|----------------------|
| 226 | | d | 0.82 | 361.3 | 18.9 |
| 227 | | d | 0.89 | 339.4 | 11.3 |
| 228 | | d | 1.10 | 349.4 | 48.9 |
| 229 | | d | 0.86 | 423.2 | 113 |
192
-continued
| Ex | Structure | Cond. | LCMS RT (min) | m/z | LRRK2 IC$_{50}$ (nM) |
|----|-----------|-------|---------------|-----|----------------------|
| 230 | | d | 0.88 | 295.3 | 29.4 |
Scheme AI
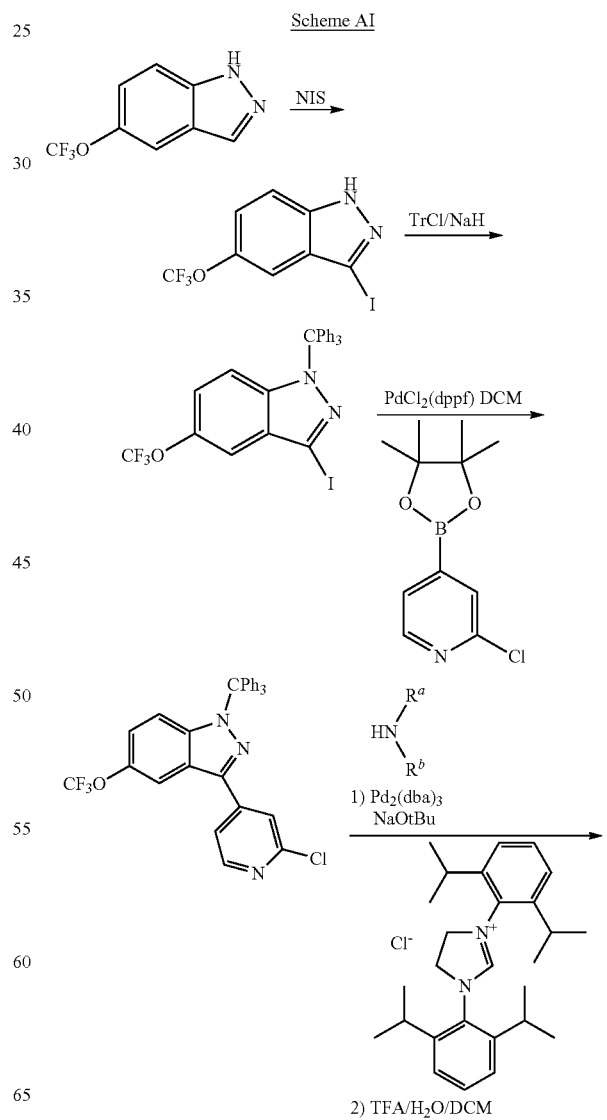

-continued

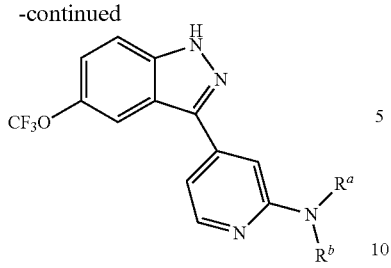

Examples 231-253

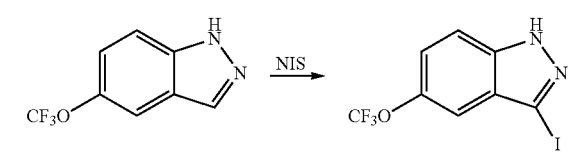

5-Trifluoromethoxy-indazole (1.4 g, 6.9 mmol) and K₂CO₃ (2.8 g, 20 mmol) were taken up in CH₃CN (38 ml). Iodine (3.9 g, 15.4 mmol) was added, and the solution was stirred at RT for 2 hours. The reaction was quenched with sat. Na₂S₂O₃$_{(aq)}$. The mixture was extracted with EtOAc. The aqueous layer was extracted with EtOAc. The combined organic layers were dried (Na₂SO₄), filtered, and concentrated. The solution was concentrated to provide the iodide.

Step 2

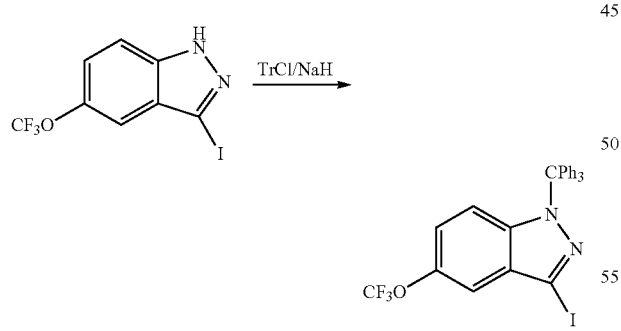

The iodide (2.6 g, 7.9 mmol) was taken up in THF (20 ml). NaH (0.44 g of a 60 wt % dispersion in oil, 11.1 mmol) was added at 0° C. Trityl chloride (2.65 g, 9.5 mmol) was added, and the solution was allowed to warm to RT. The solution was stirred at RT for 2 hours. Water was added, and the mixture was extracted with EtOAc. The combined organic layers were dried (Na₂SO₄), filtered, and concentrated. The residue was purified via gradient flash chromatography which provided the trityl protected indazole.

Step 3

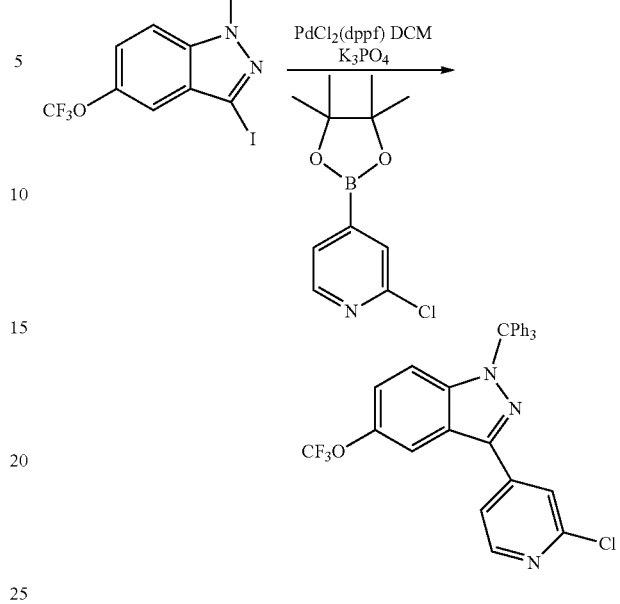

The trityl protected indazole (1.5 g, 2.6 mmol), boronate ester (0.76 g, 3.2 mmol), and K₃PO₄ (3.9 ml of a 2 M aq. solution) were taken up in 20 ml of DME. Argon was bubbled through the solution for 5 minutes, and then PdCl₂(dppf) DCM complex (0.22 g, 0.26 mmol) was added. The mixture was heated at 90° C. for 2 hours. The mixture was filtered through a celite pad and concentrated. The residue was purified via gradient flash chromatography which provided the chloro-pyridine as a white solid.

Step 4

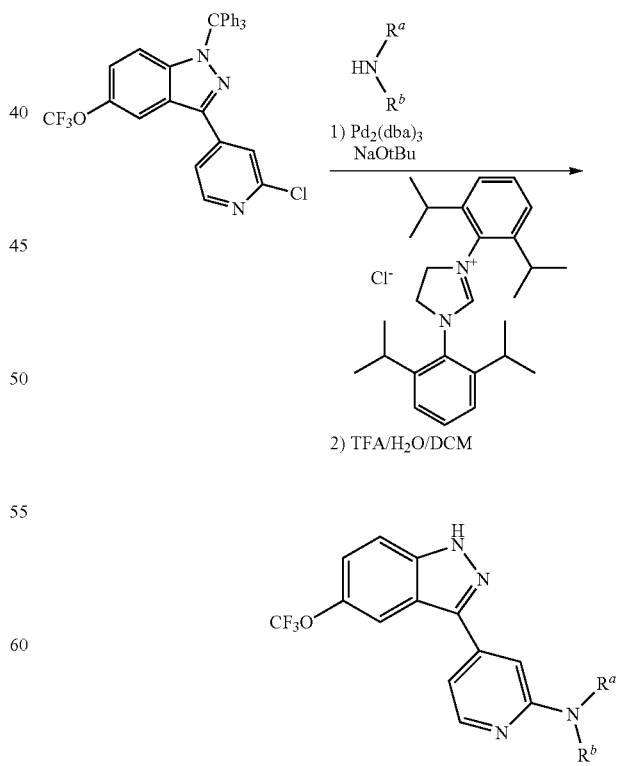

Examples 231-253

Parallel preparation of Examples 231-253 (Scheme AI): To a set of vials containing the requisite amine (0.13 mmol) if a solid, was added 1,3-bis-(2,6-diisopropylphenyl)imidazolinium chloride (5.4 mg, 0.013 mmol), Pd$_2$(dba)$_3$ (2.9 mg, 3.2 mop and sodium t-butoxide (24 mg, 0.25 mmol). The vials were transferred to a glove bag under an atmosphere of N$_2$. A solution of the chloropyridine (35 mg, 0.063 mmol) in dioxane (0.500 ml) was then added to each vial followed by the requisite amine (0.13 mmol) if it was a liquid. The vials were tightly capped and removed from the glove bag. The vials were placed into a pre-heated aluminium block at 90° C. The mixtures were stirred at that temperature for 4 hours. Water (2 mL) was added to each reaction followed by DCM (2.0 mL). The vials were shaken at RT for 5 min. The mixture was transferred to a fitted barrel filter. The organic layer from each vial was drained into a clean vial. Additional DCM (1 mL) was added to the aqueous layer and the layers were separated. The solvent from the combined organic layers was removed in vacuo. To each vial was then added DCM (1 mL) followed by TFA (0.50 mL) and water (0.050 mL). The vials were shaken at RT for 1.5 hours. The solvent was removed in vacuo. Each crude product was redissolved in 1 mL of DMSO and filtered. The crude products were purified by mass triggered HPLC using the following conditions: For Examples 231-235: [Waters Sunfire C18 column, 5 µm, 30×100 mm, gradient 10% initial to range of 45-60% final MeCN (0.1% formic acid) in water (0.1% formic acid) 70 mL/min, 8 min run time]. For Examples 236-239 and 241-253: [Waters Sunfire C18 column, 5 µm, 30×100 mm, gradient 10% initial to range of 45-60% final MeCN (0.1% TFA) in water (0.1% TFA) 70 mL/min, 8 min run time]. For Example 240: [Waters XBridge C18 column, 5 µm, 19×100 mm, gradient ranges from 10-30% initial to 30-70% MeCN (0.1% NH$_4$OH) in water (0.1% NH$_4$OH) 50 mL/min, 8 min run time].

| Ex | Structure | LCMS Cond. | RT (min) | m/z | LRRK2 IC$_{50}$ (nM) |
|---|---|---|---|---|---|
| 231 | | d | 0.89 | 379.2 | 82.7 |
| 232 | | d | 1.20 | 363.2 | 279 |
| 233 | | d | 1.08 | 349.2 | 130.4 |

-continued

| Ex | Structure | LCMS Cond. | RT (min) | m/z | LRRK2 IC$_{50}$ (nM) |
|---|---|---|---|---|---|
| 234 | 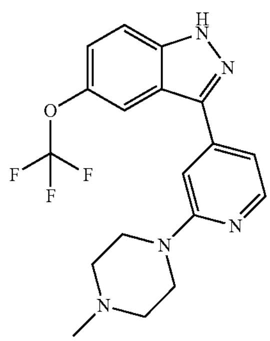 [SMILES: CN1CCN(c2cc(-c3n[nH]c4ccc(OC(F)(F)F)cc34)ccn2)CC1] | d | 0.97 | 378.2 | 82.5 |
| 235 | 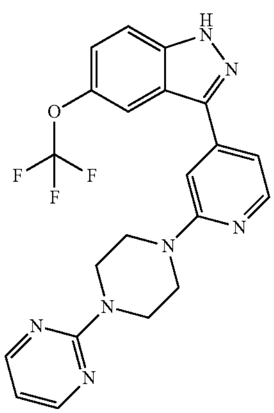 [SMILES: FC(F)(F)Oc1ccc2[nH]nc(-c3ccnc(N4CCN(c5ncccn5)CC4)c3)c2c1] | d | 1.11 | 442.2 | 476.3 |
| 236 | 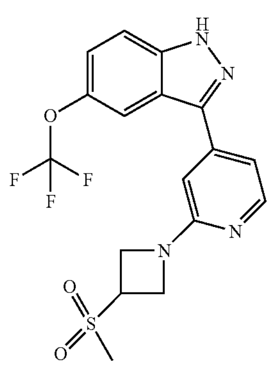 [SMILES: CS(=O)(=O)C1CN(c2cc(-c3n[nH]c4ccc(OC(F)(F)F)cc34)ccn2)C1] | d | 0.83 | 413.1 | 105.8 |
| 237 | 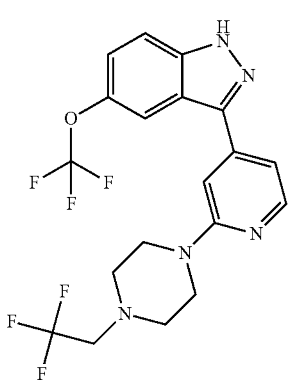 [SMILES: FC(F)(F)CN1CCN(c2cc(-c3n[nH]c4ccc(OC(F)(F)F)cc34)ccn2)CC1] | d | 1.16 | 446.2 | 279.3 |

-continued

| Ex | Structure | LCMS Cond. | RT (min) | m/z | LRRK2 IC$_{50}$ (nM) |
|---|---|---|---|---|---|
| 238 | | d | 0.84 | 395.2 | 164.7 |
| 239 | | d | 1.04 | 429.2 | 232.8 |
| 240 | | d | 1.01 | 367.2 | 206.2 |
| 241 | | d | 0.94 | 401.2 | 315.1 |

-continued

| Ex | Structure | LCMS Cond. | RT (min) | m/z | LRRK2 IC$_{50}$ (nM) |
|---|---|---|---|---|---|
| 242 | 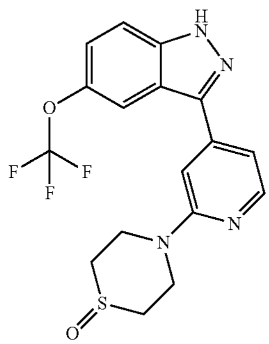 [SMILES: O=S1CCN(c2cc(-c3n[nH]c4ccc(OC(F)(F)F)cc34)ccn2)CC1] | d | 0.83 | 391.1 | 110.3 |
| 243 | 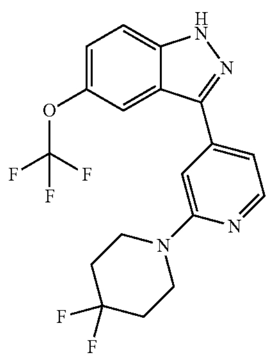 [SMILES: FC1(F)CCN(c2cc(-c3n[nH]c4ccc(OC(F)(F)F)cc34)ccn2)CC1] | d | 1.15 | 399.2 | 1063 |
| 244 | 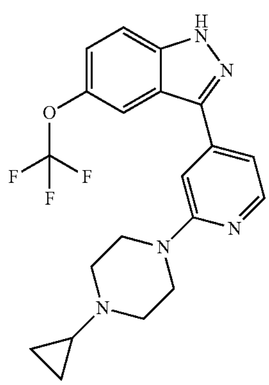 [SMILES: FC(F)(F)Oc1ccc2[nH]nc(-c3ccnc(N4CCN(C5CC5)CC4)c3)c2c1] | d | 1.09 | 404.2 | 187.7 |
| 245 | 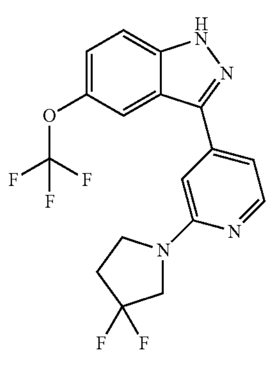 [SMILES: FC1(F)CCN(c2cc(-c3n[nH]c4ccc(OC(F)(F)F)cc34)ccn2)C1] | d | 1.08 | 385.1 | 1492 |

-continued

| Ex | Structure | LCMS Cond. | RT (min) | m/z | LRRK2 IC$_{50}$ (nM) |
|---|---|---|---|---|---|
| 246 | 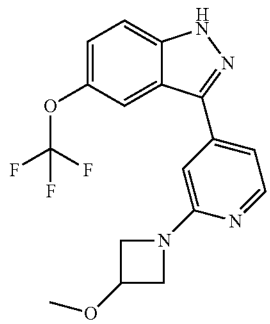 [SMILES: COC1CN(c2cc(-c3n[nH]c4ccc(OC(F)(F)F)cc34)ccn2)C1] | d | 0.95 | 365.1 | 288.9 |
| 247 | 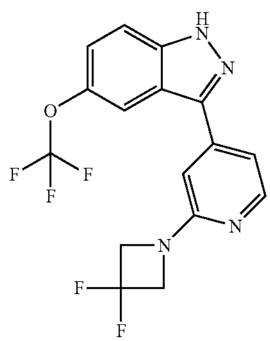 [SMILES: FC1(F)CN(c2cc(-c3n[nH]c4ccc(OC(F)(F)F)cc34)ccn2)C1] | d | 1.05 | 371.1 | 369.1 |
| 248 | 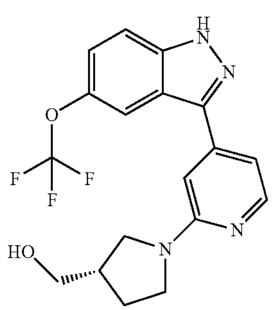 [SMILES: OC[C@H]1CCN(c2cc(-c3n[nH]c4ccc(OC(F)(F)F)cc34)ccn2)C1] | d | 0.87 | 379.2 | 96 |
| 249 | 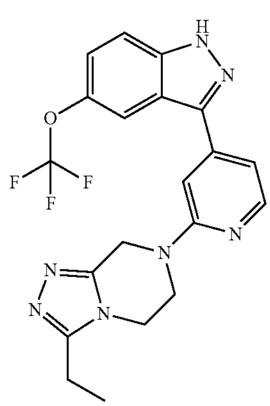 [SMILES: CCc1nnc2n1CCN(c1cc(-c3n[nH]c4ccc(OC(F)(F)F)cc34)ccn1)C2] | d | 0.88 | 430.2 | 190.2 |

-continued
| Ex | Structure | LCMS Cond. | RT (min) | m/z | LRRK2 IC$_{50}$ (nM) |
|---|---|---|---|---|---|
| 250 | 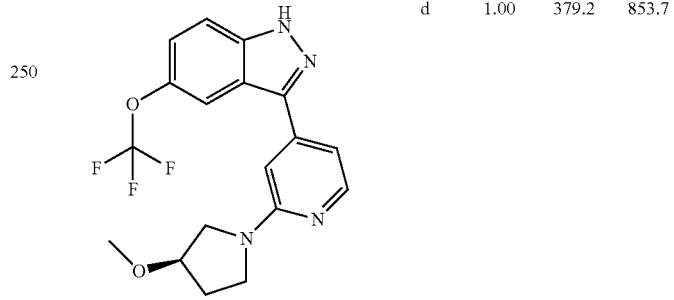 | d | 1.00 | 379.2 | 853.7 |
| 251 | 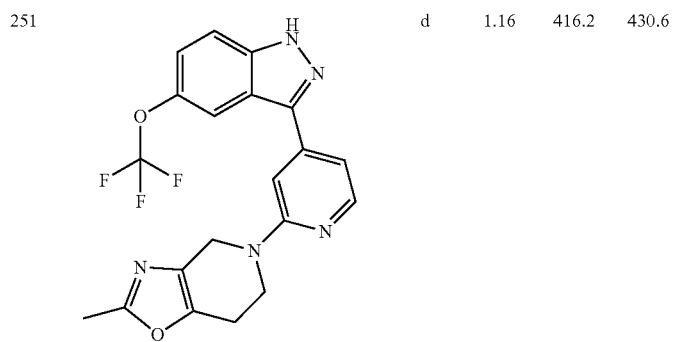 | d | 1.16 | 416.2 | 430.6 |
| 252 | 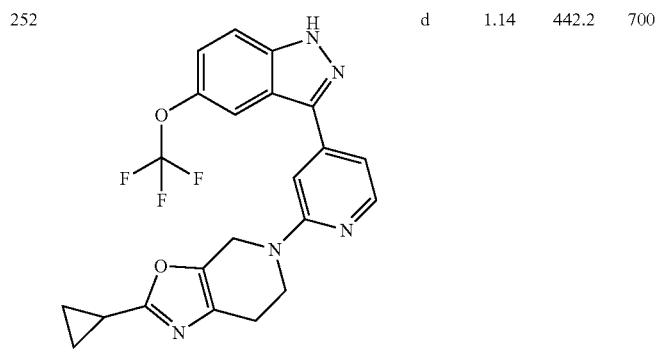 | d | 1.14 | 442.2 | 700 |
| 253 | 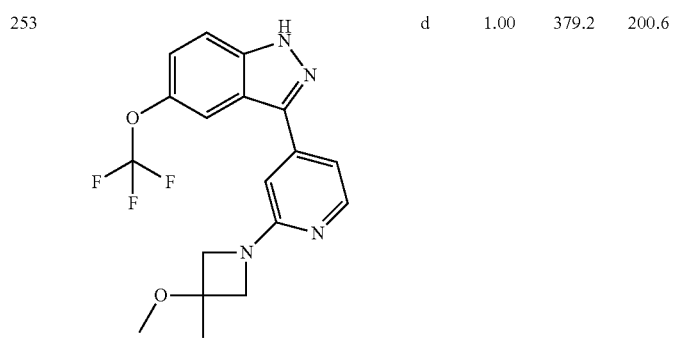 | d | 1.00 | 379.2 | 200.6 |

Scheme AJ

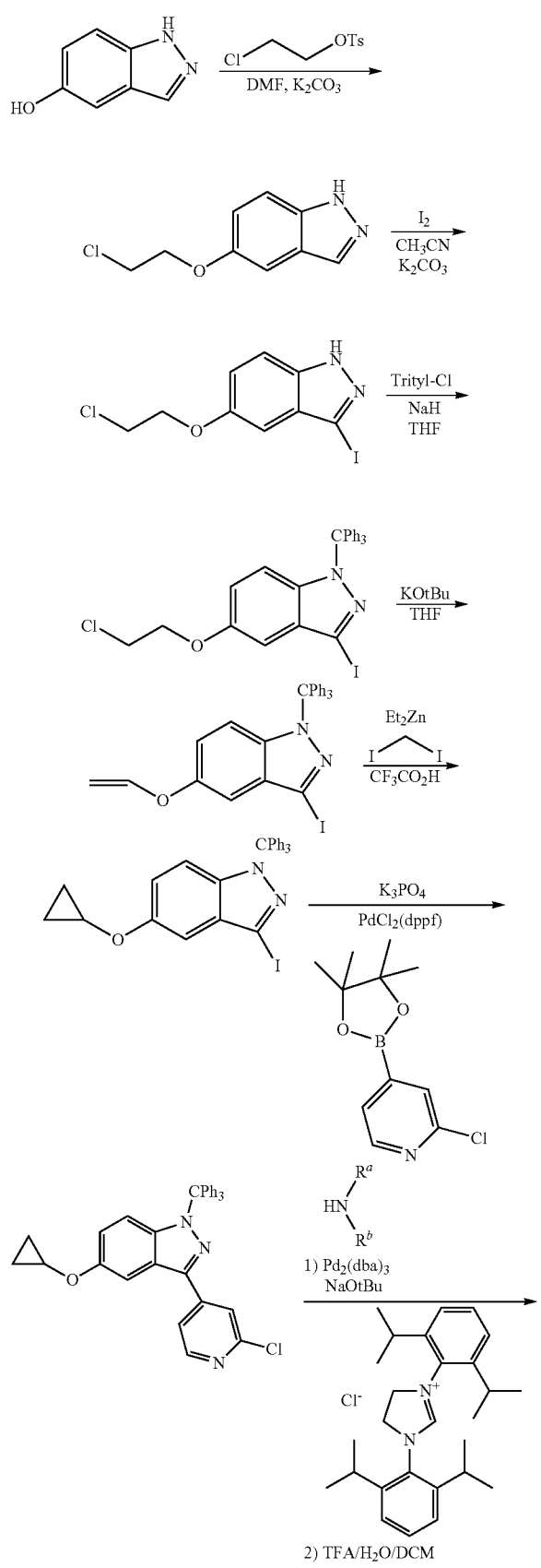

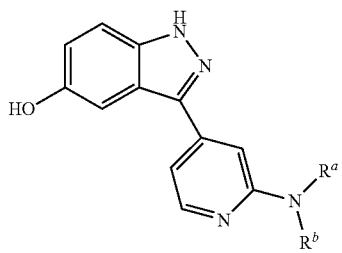

Examples 254 and 255

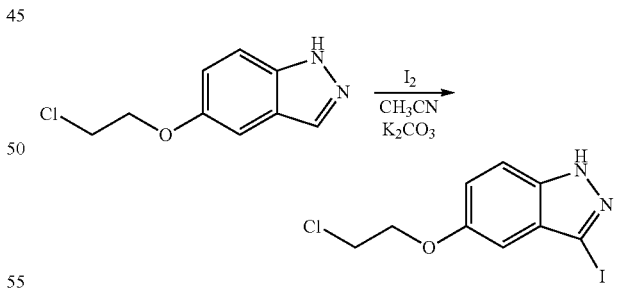

The hydroxyl-indazole (30 g) was taken up in DMF (200 ml). Potassium carbonate (62 g) was added to the solution, and the resulting mixture was stirred at RT for 15 minutes. 2-Chloroethyl-para-toluenesulfonate (43 ml) was added, and the resulting solution was heated at 50° C. for 20 h. The mixture was poured into water (600 ml) and quenched with acetic acid (26 ml). The mixture was filtered which provided a wet cake that was dried under reduced pressure. The brown solid was partitioned between EtOAc and water. The layers were separated and the organic layer was dried (MgSO$_4$), filtered, and concentrated. The resultant residue was slurried in MTBE followed by filtration to provide the desired product.

Step 2

The indazole (36 g) was taken up in CH$_3$CN (500 ml). Potassium carbonate (24 g) and iodine (3 g) were added, and the resulting solution was stirred at RT for 1 h. The mixture was poured into water (1 L), and extracted with MTBE. The organic layer was washed with 10% Na$_2$S$_2$O$_{3(aq.)}$ and dried over MgSO$_4$. The solution was filtered and concentrated. The residue was adsorbed onto SiO$_2$ (90 g) and purified on a short pad of SiO$_2$ eluting with a gradient of 10-30% EtOAc. The solution was concentrated which provided the desired iodide.

Step 3

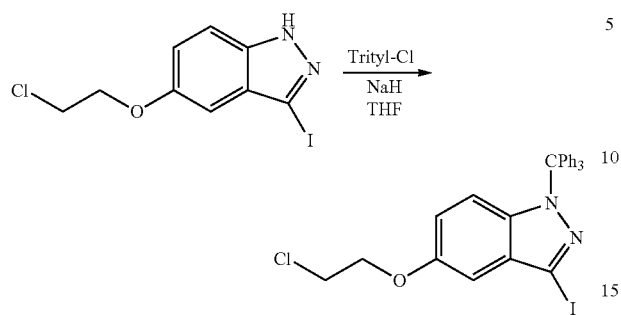

The indazole (17 g) was taken up in THF (100 ml) at 0° C. Sodium hydride (2.0 g) was added to the solution. After stirring at 0° C. for 10 minutes, trityl chloride (13.7 g) was added. The solution was warmed to RT for 2 hours. The solution was quenched with sat. NH$_4$Cl (aq.) and extracted with Et$_2$O. The combined organic layers were washed with brine and dried over MgSO$_4$. Filtration and concentration provided the crude product. The residue was slurried in hot MTBE. The solid was collected and dried. The solid was purified via gradient flash chromatography (0-10% MTBE in hexanes, SiO$_2$) which provided the trityl protected indazole.

Step 4

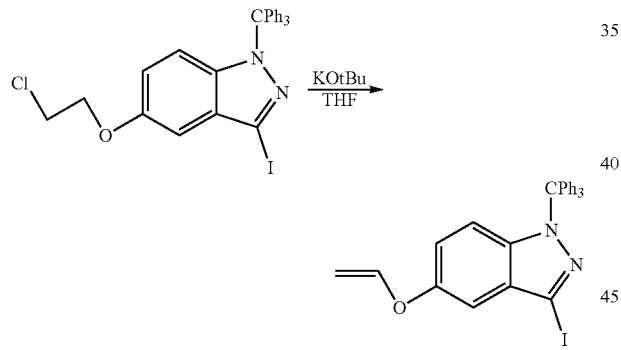

The indazole (20 g) was suspended in THF (120 mL), and potassium tert-butoxide (8.0 g) was added. After stirring at 2 hours at RT, the solution was partitioned between sat. NH$_4$Cl$_{(aq.)}$ and Et$_2$O. The aqueous layer was extracted with Et$_2$O. The combined organic layers were dried over MgSO$_4$. Filtration and concentration provided the desired alkene.

Step 5

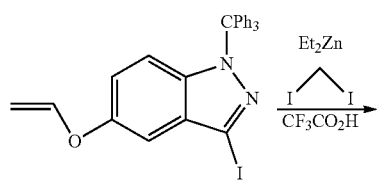

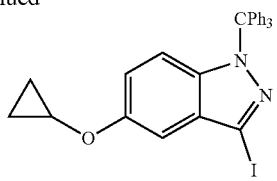

Diethyl zinc (57 ml of a 1.0M solution in hexane) and 20 ml of DCE were placed into a dry flask under nitrogen at RT. The solution was cooled to 0° C., and TFA (4.2 ml) in DCE (20 ml) was added over 30 minutes (exotherm/gas evolution). The white suspension was stirred at 0° C. for 15 minutes. Diiodomethane (4.6 ml) in DCE (20 ml) was added over 15 minutes at 0° C. The alkene (15.7 g) in DCE (100 ml) was added to the solution at 0° C. The solution was warmed to RT. After stirring at RT for 5 h, the solution was quenched with sat. NH$_4$Cl$_{(aq.)}$ and DCM. The aqueous layer was extracted with DCM. The combined organic layers were dried over MgSO$_4$. Filtration and concentration provided the crude product. The residue was purified via gradient flash chromatography (0-10% MTBE in hexanes, SiO$_2$) which provided the cyclopropoxy indazole.

Step 6

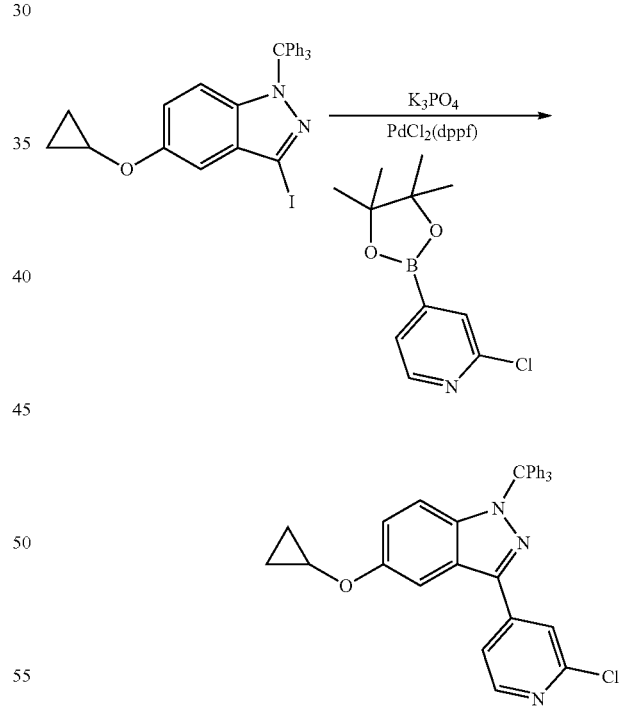

The indazole (1.4 g), boronate ester (742 mg), K$_3$PO$_4$ (3.8 ml of a 2 M aqueous solution), and PdCl$_2$(dppf)—DCM complex (211 mg) were taken up in 20 ml of DME. Argon was bubbled through the solution, and the mixture was placed into a sealed tube. The reaction was subjected to microwave irradiation (2 hours at 90° C.). The solution was cooled, filtered, and concentrated. The residue was purified by gradient flash chromatography (0-20% EtOAc in hexanes, SiO$_2$) which provided the chloro-pyridine.

Step 7

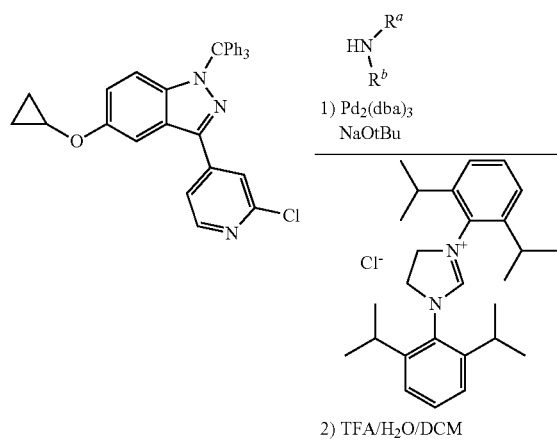

Examples 254 and 255

Parallel preparation of Examples 254 and 255: To a set of vials containing the requisite amine (0.152 mmol) if a solid, was added 1,3-bis-(2,6-diisopropylphenyl)imidazolinium chloride (6.47 mg, 0.015 mmol), Pd$_2$(dba)$_3$ (3.47 mg, 3.79 μmol) and sodium t-butoxide (29.1 mg, 0.303 mmol). The vials were transferred to a glove bag under an atmosphere of N$_2$. A solution of the chloro-pyridine (40 mg, 0.076 mmol) in dioxane (0.500 ml) was then added to each vial followed by the requisite amine (0.152 mmol) if it was a liquid. The vials were tightly capped and removed from the glove bag. The vials were placed into a pre-heated aluminium block at 90° C. The mixtures were stirred at that temperature overnight. Water (2 mL) was added to each reaction followed by DCM (2.0 mL). The vials were shaken at RT for 5 min. The mixture was transferred to a fritted barrel filter. The organic layer from each vial was drained into a clean vial. Additional DCM (1 mL) was added to the aqueous layer and the layers were separated. The solvent from the combined organic layers was removed in vacuo. To each vial was then added DCM (1 mL) followed by TFA (0.50 mL) and water (0.050 mL). The vials were shaken at RT for 1.5 hours. The solvent was removed in vacuo. Each crude product was redissolved in 1 mL of DMSO and filtered. The crude products were purified by mass triggered HPLC. [Waters XBridge C18 column, 5 μm, 19×100 mm, gradient from 10% initial to a range of 25-45% MeCN (0.1% NH$_4$OH) in water (0.1% NH$_4$OH) 50 mL/min, 8 min run time] to provide the Examples 254 and 255.

| Ex | Structure | LCMS Cond. | RT (min) | m/z | LRRK2 IC$_{50}$ (nM) |
|---|---|---|---|---|---|
| 254 | | d | 0.77 | 295.2 | 10.1 |
| 255 | | d | 0.48 | 345.2 | 30.8 |

Parallel preparation of Examples 256-264: To a set of vials containing a solution of the aminopyridine Intermediate AX.1 (40 mg, 0.078 mmol) in DCE (1 mL) was added diisopropylethylamine (0.027 mL, 0.16 mmol) and the requisite sulfonyl chloride (0.094 mmol). The resulting mixtures were heated at 75° C. overnight. Additional sulfonyl chloride (0.094 mmol) and diisopropylethyl amine (0.16 mmol) were added to the reactions that were not complete. These mixtures were allowed to stir at 75° C. for an additional 24 hours. After that time, the solvent from each vial was removed in vacuo. To each vial was added TFA (0.5 mL) and water (0.05 mL). The vials were shaken at RT for 2 hours. After that time the solvent was removed in vacuo. Each crude product was redissolved in 1 mL of DMSO and filtered. The crude products were purified by mass triggered HPLC using the following conditions: [Waters Sunfire C18 column, 5 μm, 19×100 mm, gradient ranges 10-20% initial to range of 35-55% final MeCN (0.1% formic acid) in water (0.1% formic acid) 50 mL/min, 8 min run time].

Scheme AK
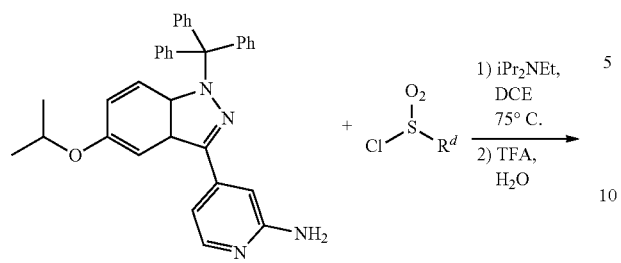 + 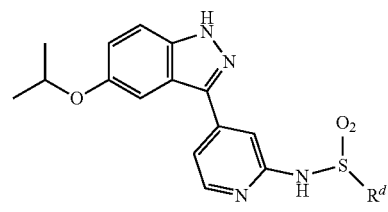
1) iPr₂NEt, DCE 75° C.
2) TFA, H₂O
Examples 256-264
| Ex | Structure | LCMS Cond. | RT (min) | m/z | LRRK2 IC₅₀ (nM) |
|---|---|---|---|---|---|
| 256 | 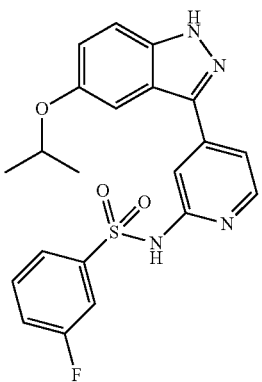 [SMILES: CC(C)Oc1ccc2[nH]nc(-c3ccnc(NS(=O)(=O)c4cccc(F)c4)c3)c2c1] | d | 0.60 | 427.3 | 42.5 |
| 257 | 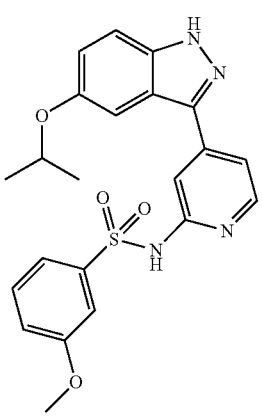 [SMILES: COc1cccc(S(=O)(=O)Nc2cc(-c3n[nH]c4ccc(OC(C)C)cc34)ccn2)c1] | d | 0.61 | 439.4 | 78.4 |

-continued

| Ex | Structure | LCMS Cond. | RT (min) | m/z | LRRK2 IC$_{50}$ (nM) |
|---|---|---|---|---|---|
| 258 | 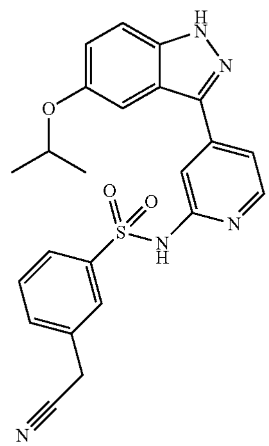 [SMILES: CC(C)Oc1ccc2[nH]nc(-c3ccnc(NS(=O)(=O)c4cccc(CC#N)c4)c3)c2c1] | d | 0.56 | 434.3 | 21.7 |
| 259 | 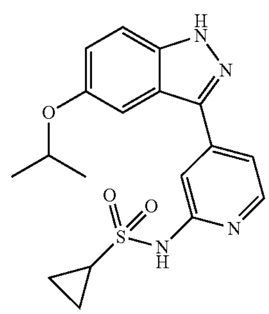 [SMILES: CC(C)Oc1ccc2[nH]nc(-c3ccnc(NS(=O)(=O)C4CC4)c3)c2c1] | d | 0.57 | 373.3 | 63.2 |
| 260 | 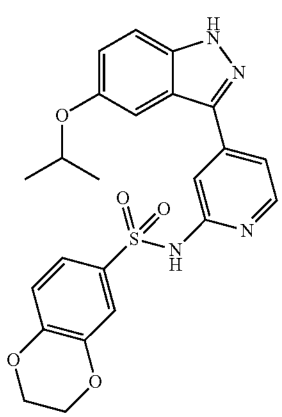 [SMILES: CC(C)Oc1ccc2[nH]nc(-c3ccnc(NS(=O)(=O)c4ccc5c(c4)OCCO5)c3)c2c1] | d | 0.60 | 467.4 | 52.3 |

-continued

| Ex | Structure | LCMS Cond. | RT (min) | m/z | LRRK2 IC$_{50}$ (nM) |
|---|---|---|---|---|---|
| 261 | 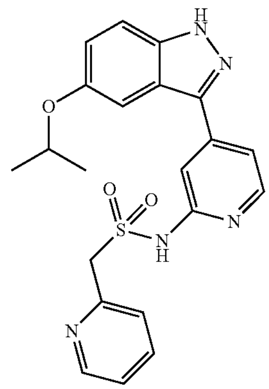 [SMILES: CC(C)Oc1ccc2[nH]nc(-c3ccnc(NS(=O)(=O)Cc4ccccn4)c3)c2c1] | d | 0.55 | 424.3 | 123.9 |
| 262 | 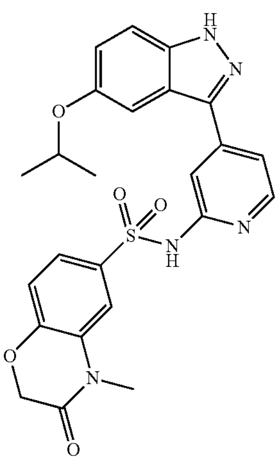 [SMILES: CC(C)Oc1ccc2[nH]nc(-c3ccnc(NS(=O)(=O)c4ccc5c(c4)N(C)C(=O)CO5)c3)c2c1] | d | 0.55 | 494.4 | 43.4 |
| 263 | 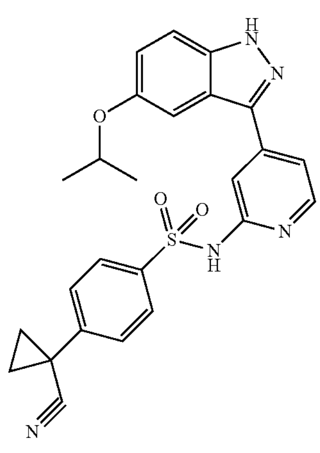 [SMILES: CC(C)Oc1ccc2[nH]nc(-c3ccnc(NS(=O)(=O)c4ccc(C5(C#N)CC5)cc4)c3)c2c1] | d | 0.60 | 474.4 | 60.8 |

-continued
| Ex | Structure | LCMS Cond. | RT (min) | m/z | LRRK2 IC$_{50}$ (nM) |
|---|---|---|---|---|---|
| 264 | 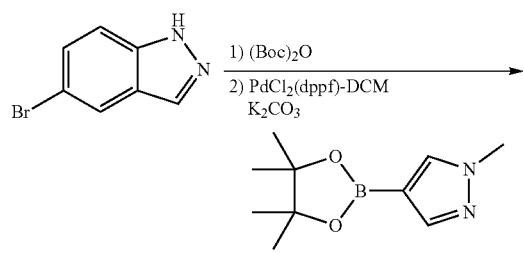 | d | 0.63 | 476.4 | 68.8 |
Scheme AL
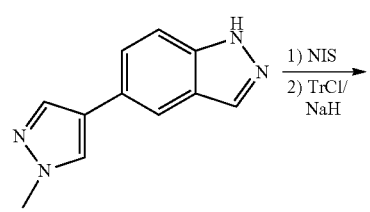
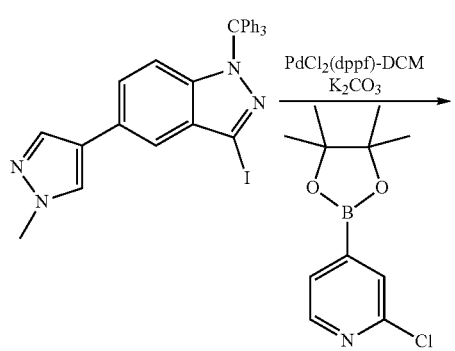
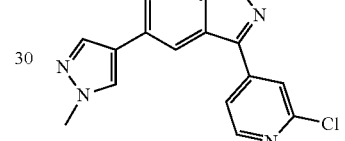
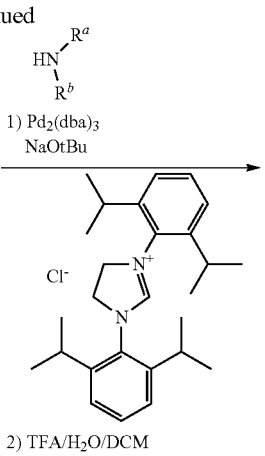
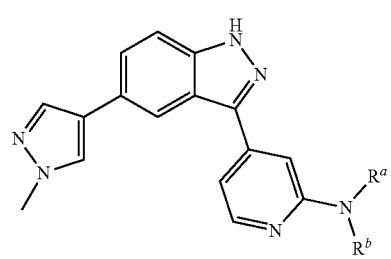
Examples 265-279
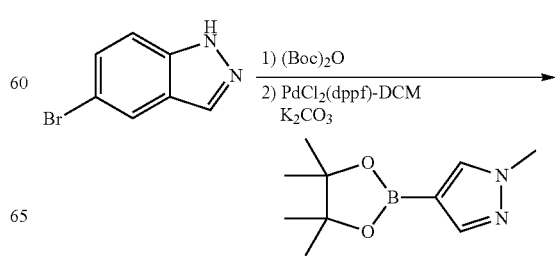

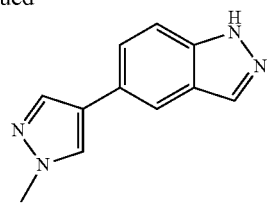

5-Bromo-indazole (2.0 g, 10.1 mmol) and (Boc)$_2$O (2.7 g, 12.2 mmol) were taken up in 20 ml of DCM. DMAP (150 mg) was added, and the solution was stirred at RT for 10 hours. The solution was concentrated. The residue was redissolved in 20 ml of dioxane. The boronic ester (3.2 g, 15.2 mmol), PdCl$_2$(dppf) DCM complex (1.7 g, 2 mmol), K$_2$CO$_3$ (2.8 g, 20.3 mmol), and water (0.4 ml) were added, and the resulting solution was heated at 100° C. for 10 hours. The mixture was concentrated, and the residue was taken up in DCM/MeOH (1/1, 15 ml). 4M Aqueous HCl (15 ml) was added, and the resulting solution was stirred at RT for 4 hours. The solution was concentrated. The residue was treated with 20 ml of 7 N NH$_3$ in MeOH. The resulting solution was concentrated. The residue was purified via gradient flash chromatography (DCM/MeOH) which provided the pyrazole as a yellow solid.

Step 2

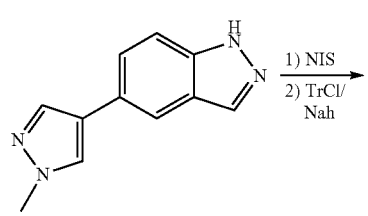

The pyrazole (1.5 g, 7.6 mmol) and NIS (2.0 g, 9.1 mmol) were taken up in 25 ml of DMF/CH$_3$CN (1/1). The mixture was heated at 90° C. for 4 hours. The solution was concentrated. The residue was dissolved in THF (30 ml). NaH (0.42 g, 17.4 mmol) and TrCl (4.6 g, 16.7 mmol) were added, and the resulting mixture was stirred at RT for 10 hours. The solution was partitioned between water and EtOAc. The aqueous layer was extracted with EtOAc. The combined organic layers were dried (MgSO$_4$), filtered, and concentrated. The residue was purified via gradient flash chromatography (DCM, SiO$_2$) which provided the iodide as a yellow solid.

Step 3

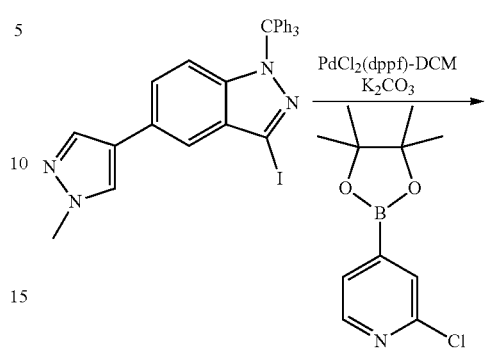

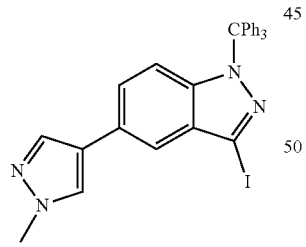

The iodide (1.0 g, 1.7 mmol), boronic acid (0.47 g, 1.9 mmol), PdCl$_2$(dppf) DCM complex (0.29 g, 0.35 mmol), and K$_2$CO$_3$ (0.49 g, 3.5 mmol) were taken up in 1,4-dioxane/water (10 ml/0.3 ml). The mixture was microwaved at 80° C. for 4 hours. The solution was concentrated. The residue was partitioned between water and EtOAc. The combined organic layers were dried, filtered, and concentrated. The residue was purified via gradient flash chromatography (DCM/MeOH) which provided the chloro-pyridine.

Step 4

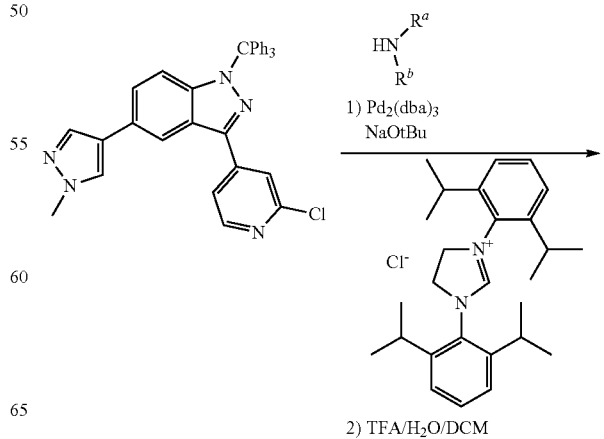

223
-continued

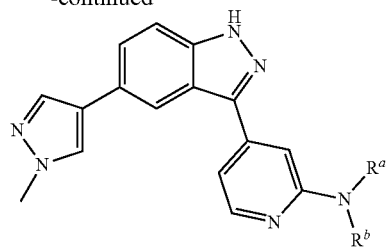

Examples 265-279

Parallel preparation of Examples 265-279: To a set of vials containing the requisite amine (0.067 mmol) if a solid, was added 1,3-Bis-(2,6-diisopropylphenyl)imidazolinium chloride (4.6 mg, 0.011 mmol), $Pd_2(dba)_3$ (5.0 mg, 5.4 μmol) and sodium t-butoxide (21 mg, 0.22 mmol). The vials were transferred to a glove bag under an atmosphere of $N_2$. A solution of the chloropyridine core (30 mg, 0.054 mmol) in Dioxane (0.500 ml) was then added to each vial followed by the requisite amine (0.152 mmol) if it was a liquid. The vials were tightly capped and removed from the glove bag. The vials were then placed into a pre-heated aluminium block at 90° C. The mixtures were stirred at that temperature for 4 hours. Water (2 mL) was added to each reaction mixture followed by DCM (2.0 mL). The vials were shaken at RT for 5 min. The mixture was transferred to a fritted barrel filter. The organic layer from each vial was drained into a clean vial. Additional DCM (1 mL) was added to the aqueous layer and the layers were separated. The solvent from the combined organic layers was removed in vacuo. To each vial was then added DCM (1 mL) followed by TFA (0.50 mL) and water (0.050 mL). The vials were shaken at RT for 1.5 hours. The solvent was removed in vacuo. Each crude product was redissolved in 1 mL of DMSO and filtered. The crude products were purified by mass triggered HPLC. [Waters Sunfire C18 column, 5 μm, 19×100 mm, gradient ranges 8-15% initial to range of 30-50% final MeCN (0.1% formic acid) in water (0.1% formic acid) 50 mL/min, 8 min run time] to afford Examples 265-279.

| Ex | Structure | LCMS Cond. | RT (min) | m/z | LRRK2 $IC_{50}$ (nM) |
|---|---|---|---|---|---|
| 265 | | d | 0.66 | 404.3 | 1.7 |
| 266 | | d | 0.92 | 359.2 | 2.4 |
| 267 | | d | 0.82 | 345.2 | 2.9 |

| Ex | Structure | Cond. | LCMS RT (min) | m/z | LRRK2 IC$_{50}$ (nM) |
|---|---|---|---|---|---|
| 268 | 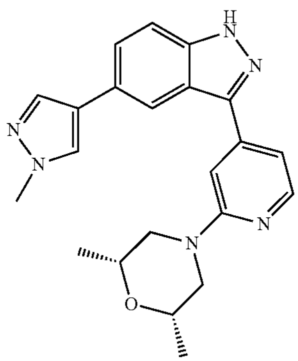 [SMILES: C[C@@H]1CN(c2cc(-c3n[nH]c4ccc(-c5cnn(C)c5)cc34)ccn2)C[C@H](C)O1] | d | 0.87 | 389.2 | 1.3 |
| 269 | 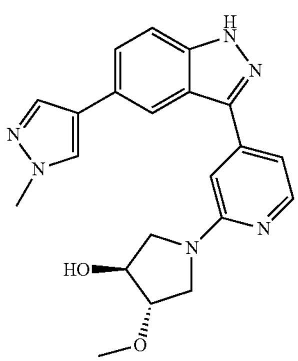 [SMILES: CO[C@H]1CN(c2cc(-c3n[nH]c4ccc(-c5cnn(C)c5)cc34)ccn2)C[C@@H]1O] | d | 0.64 | 391.2 | 4.2 |
| 270 | 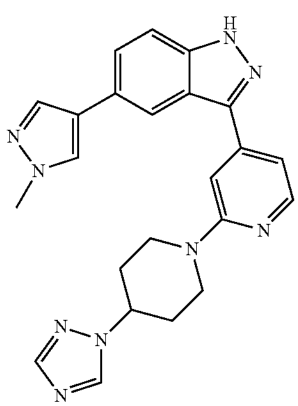 [SMILES: Cn1cc(-c2ccc3[nH]nc(-c4ccnc(N5CCC(n6cncn6)CC5)c4)c3c2)cn1] | d | 0.71 | 426.3 | 2.2 |
| 271 | 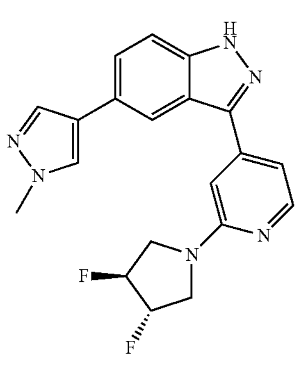 [SMILES: Cn1cc(-c2ccc3[nH]nc(-c4ccnc(N5C[C@H](F)[C@@H](F)C5)c4)c3c2)cn1] | d | 0.80 | 381.2 | 2.2 |

| Ex | Structure | LCMS Cond. | RT (min) | m/z | LRRK2 IC$_{50}$ (nM) |
|---|---|---|---|---|---|
| 272 | 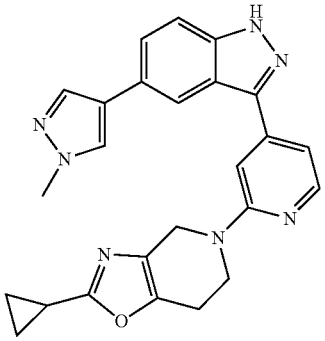 [SMILES: Cn1cc(-c2ccc3[nH]nc(-c4ccnc(N5CCc6oc(C7CC7)nc6C5)c4)c3c2)cn1] | d | 0.91 | 438.3 | 5.8 |
| 273 | 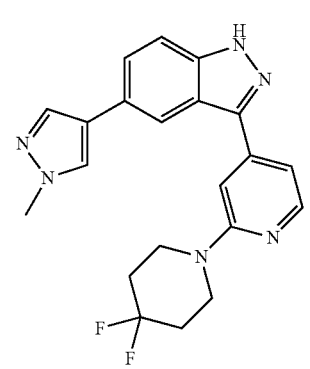 [SMILES: Cn1cc(-c2ccc3[nH]nc(-c4ccnc(N5CCC(F)(F)CC5)c4)c3c2)cn1] | d | 0.91 | 395.2 | 3 |
| 274 | 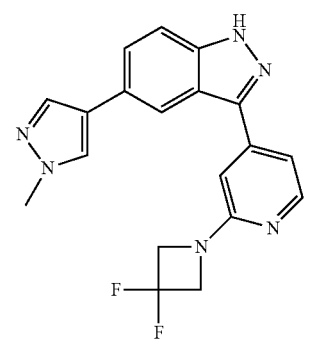 [SMILES: Cn1cc(-c2ccc3[nH]nc(-c4ccnc(N5CC(F)(F)C5)c4)c3c2)cn1] | d | 0.81 | 367.2 | 4.2 |
| 275 | 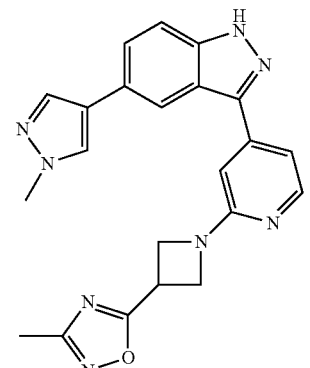 | d | 0.75 | 413.2 | 5.6 |

| Ex | Structure | LCMS Cond. | RT (min) | m/z | LRRK2 IC$_{50}$ (nM) |
|---|---|---|---|---|---|
| 276 | 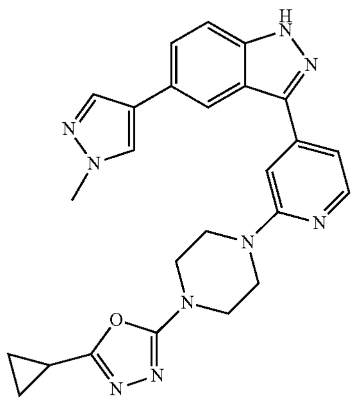 [SMILES: Cn1cc(-c2ccc3[nH]nc(-c4ccnc(N5CCN(c6nnc(C7CC7)o6)CC5)c4)c3c2)cn1] | d | 0.81 | 468.3 | 2.7 |
| 277 | 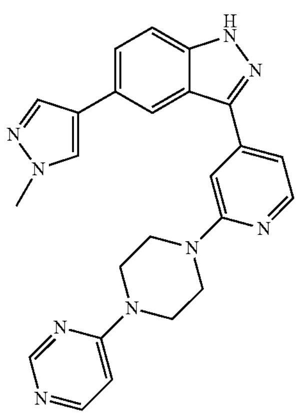 [SMILES: Cn1cc(-c2ccc3[nH]nc(-c4ccnc(N5CCN(c6ccncn6)CC5)c4)c3c2)cn1] | d | 0.76 | 438.3 | 2.1 |
| 278 | 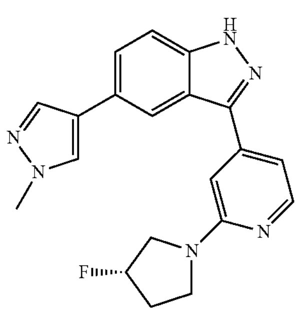 [SMILES: Cn1cc(-c2ccc3[nH]nc(-c4ccnc(N5CC[C@H](F)C5)c4)c3c2)cn1] | d | 0.78 | 363.2 | 1.9 |
| 279 | 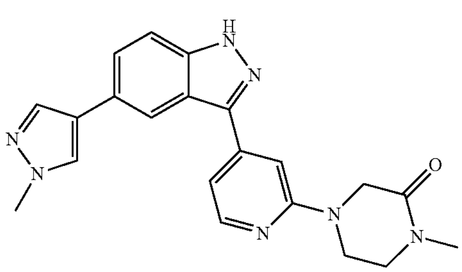 [SMILES: CN1CCN(c2cc(-c3n[nH]c4ccc(-c5cnn(C)c5)cc34)ccn2)CC1=O] | d | 0.67 | 388.2 | 2.9 |

Scheme AM

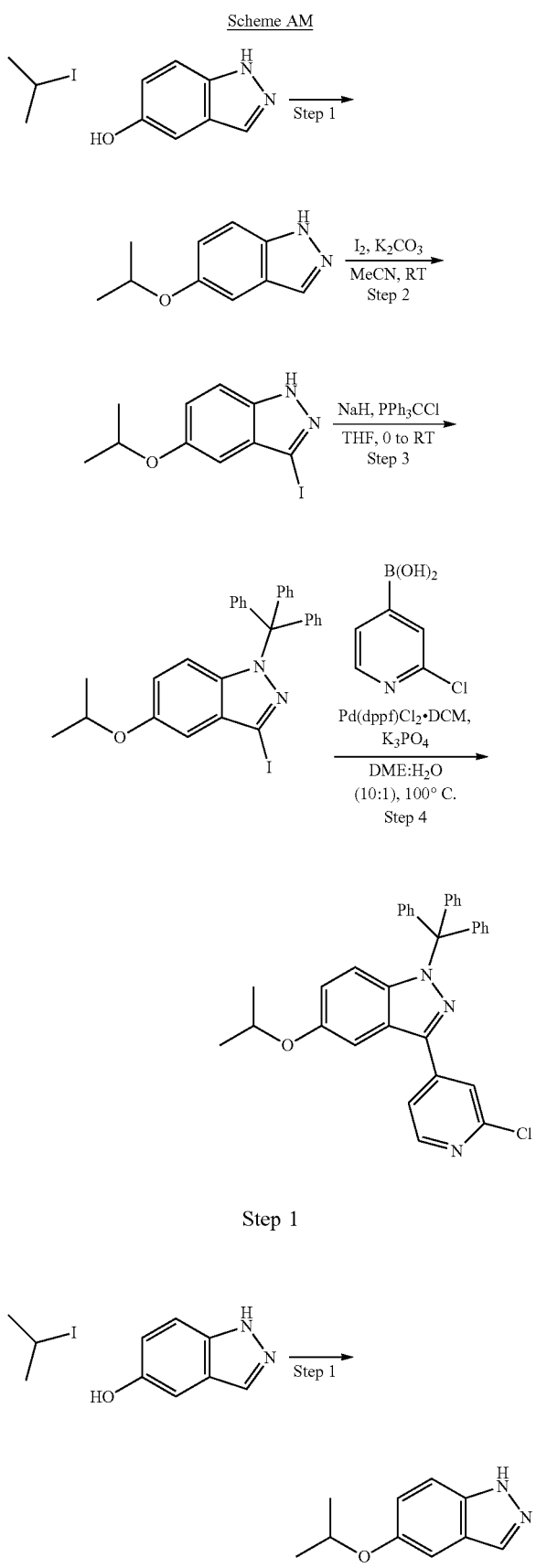

Step 1

Cesium carbonate (10.53 g, 32.3 mmol) was added to a suspension of the indazole (2.89 g, 21.55 mmol) in DMF (43 mL). After stirring this mixture for 15 minutes, 2-iodopropane (2.73 ml, 28.0 mmol) was added. The reaction vessel was sealed, and stirred at room temperature for 72 hours. The reaction mixture was partitioned between water and EtOAc. The layers were separated and the aqueous layer was extracted twice more with EtOAc. The organic layers were combined, dried over anhydrous $MgSO_4$, filtered, and concentrated to afford a crude residue which was subjected to silica gel chromatography (120 g ISCO gold column, $SiO_2$, gradient elution 0% to 60% EtOAc in hexanes, 50 mL/min, 24 minute run) to afford the desired product as an off-white solid.

Step 2

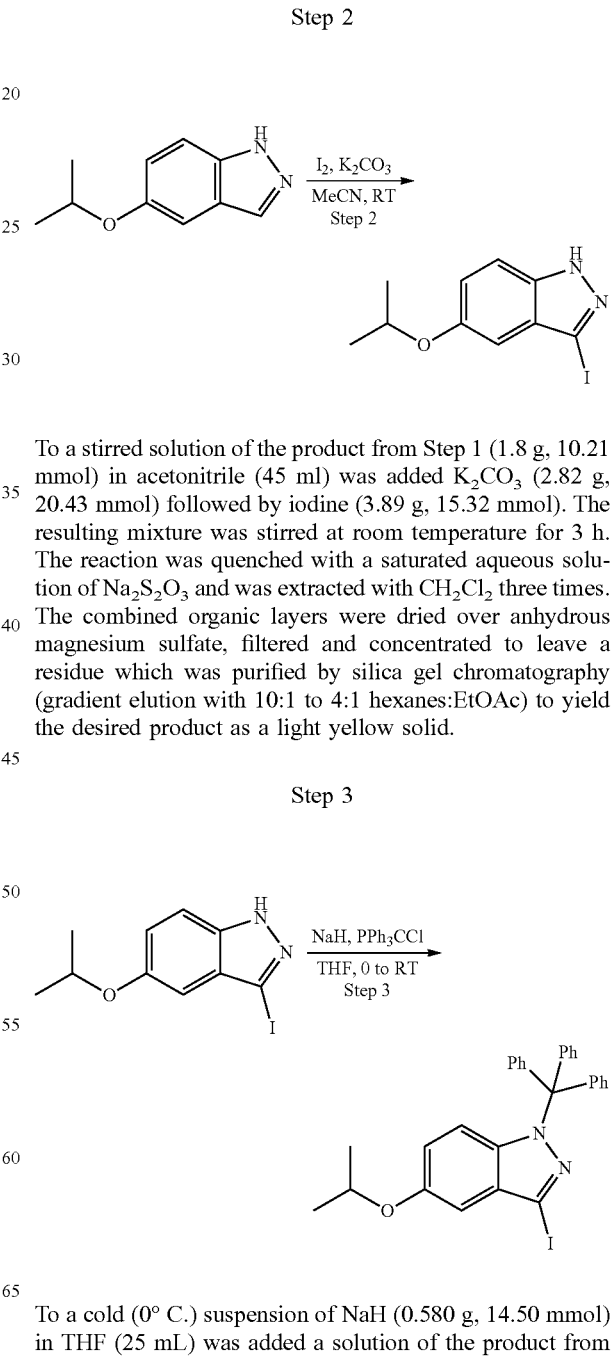

To a stirred solution of the product from Step 1 (1.8 g, 10.21 mmol) in acetonitrile (45 ml) was added $K_2CO_3$ (2.82 g, 20.43 mmol) followed by iodine (3.89 g, 15.32 mmol). The resulting mixture was stirred at room temperature for 3 h. The reaction was quenched with a saturated aqueous solution of $Na_2S_2O_3$ and was extracted with $CH_2Cl_2$ three times. The combined organic layers were dried over anhydrous magnesium sulfate, filtered and concentrated to leave a residue which was purified by silica gel chromatography (gradient elution with 10:1 to 4:1 hexanes:EtOAc) to yield the desired product as a light yellow solid.

Step 3

To a cold (0° C.) suspension of NaH (0.580 g, 14.50 mmol) in THF (25 mL) was added a solution of the product from Step 2 (3.65 g, 12.08 mmol) in THF (25 mL) dropwise via an addition funnel. After the addition was done, the mixture was stirred at 0° C. for 30 min. Trityl chloride (3.70 g, 13.29 mmol) was then added in one portion. The mixture was slowly warmed to room temperature and stirred for 6 h. The reaction was quenched with water and extracted with Et₂O (×3). The combined organic layers were dried over anhydrous magnesium sulfate, filtered, and concentrated under vacuum to leave a residue which was purified by silica gel chromatography (gradient elution, 100:0 to 20:1 hexanes:EtOAc) to yield the desired product as a white foam.

Step 4

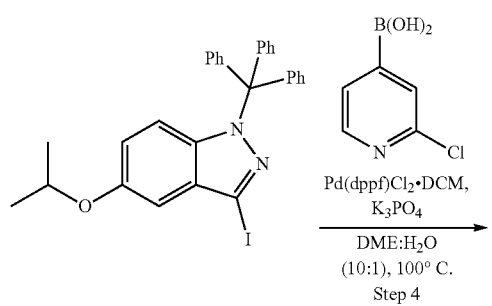

-continued

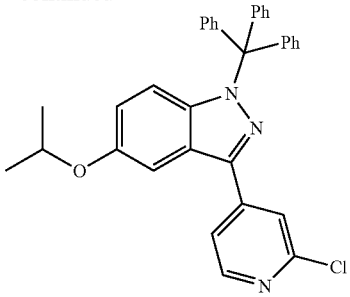

A mixture of the product from Step 3 (2.2 g, 4.04 mmol), (2-chloropyridin-4-yl)boronic acid (0.954 g, 6.06 mmol) and K₃PO₄ (2.57 g, 12.12 mmol) in DME (50 ml) and Water (5 ml) was purged with argon for 20 min. At that point, Pd(dppf)Cl₂-DCM complex (0.330 g, 0.404 mmol) was added and the mixture was heated to 100° C. for 15 h. The reaction was cooled to room temperature and concentrated under vacuum. Water was added and the mixture was extracted with CH₂Cl₂ (×3). The combined organic layers were dried over anhydrous magnesium sulfate, filtered and concentrated under vacuum to leave a residue which was purified by silica gel chromatography (isocratic elution with 10:1 hexane:EtOAc) to yield the desired product as a white solid.

TABLE AM.1

Using the method outlined in Scheme A and requisite alkyl halide, the following intermediates were prepared:

| Intermediate Number | Alkyl Halide | Intermediate |
|---|---|---|
| AM.1.1 | ethyl iodide | 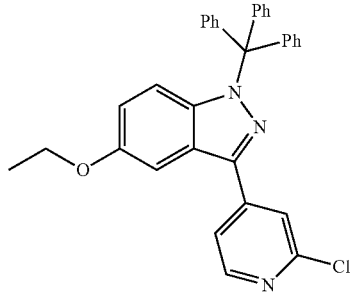 [SMILES: CCOc1ccc2c(c1)c(-c1ccnc(Cl)c1)nn2C(c1ccccc1)(c1ccccc1)c1ccccc1] |
| AM.1.2 | (+/−) 2-iodobutane | 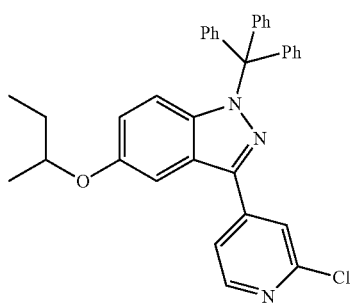 [SMILES: CCC(C)Oc1ccc2c(c1)c(-c1ccnc(Cl)c1)nn2C(c1ccccc1)(c1ccccc1)c1ccccc1] |

TABLE AM.1-continued

Using the method outlined in Scheme A and requisite alkyl halide, the following intermediates were prepared:

| Intermediate Number | Alkyl Halide | Intermediate |
|---|---|---|
| AM.1.3 | n-propyl iodide | 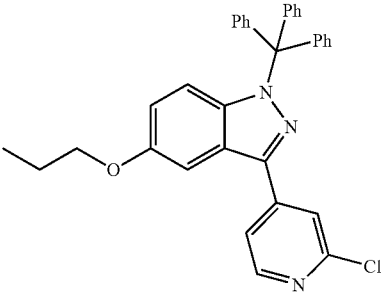 [SMILES: CCCOc1ccc2c(c1)c(-c1ccnc(Cl)c1)nn2C(c1ccccc1)(c1ccccc1)c1ccccc1] |

TABLE AM.2

Using the method outlined in Steps 1-3 in Scheme AM and the requisite alkyl halide, the following iodoindazole was prepared:

| Intermediate Number | Alkyl Halide | Intermediate |
|---|---|---|
| AM.2.1 | | |

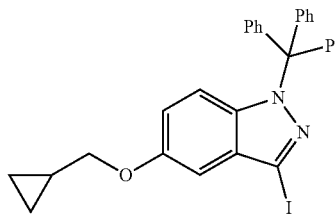

Scheme AN

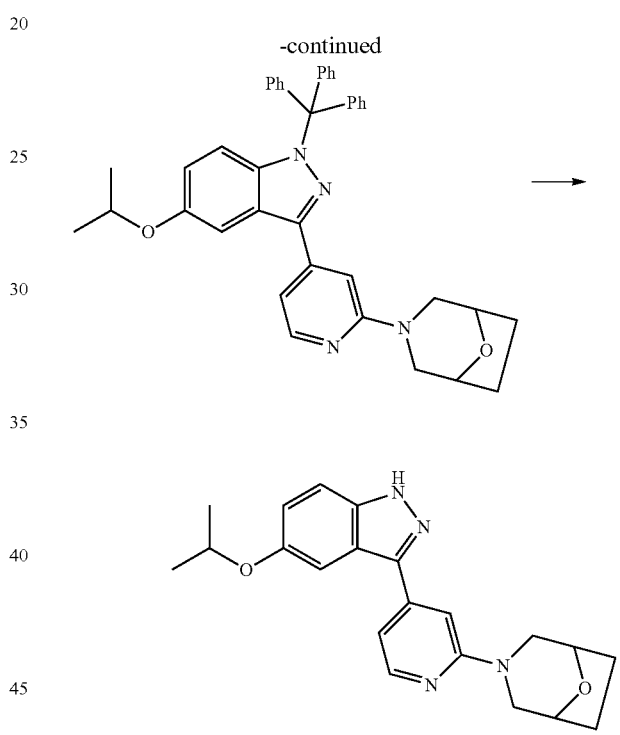

Example 280

Step 1

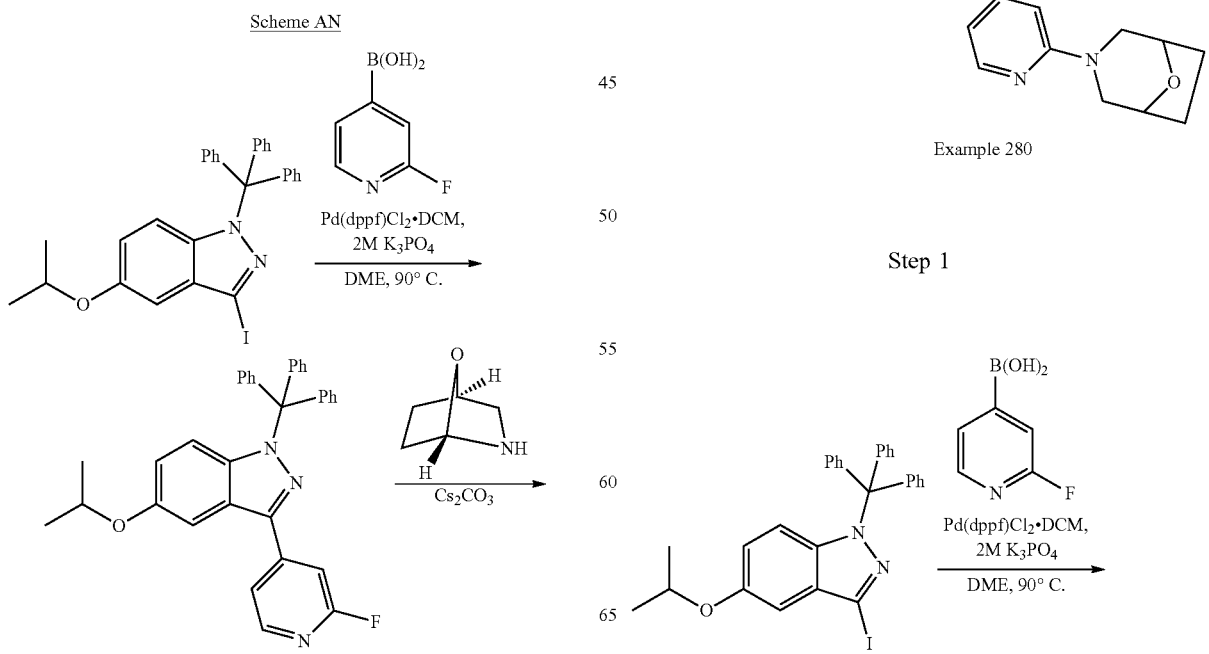

-continued

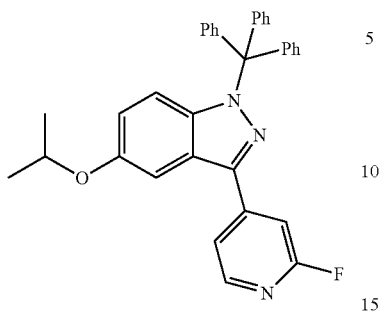

A stirred solution of the iodide prepared in Step 3 of Scheme AM (4 g, 7.35 mmol), (2-fluoropyridin-4-yl)boronic acid (1.242 g, 8.82 mmol) and 2M aqueous K₃PO₄ (11.02 ml, 22.04 mmol) in DME (73.5 ml) was purged with nitrogen. After a 15 min nitrogen purge Pd(dppf)Cl₂-DCM complex (0.600 g, 0.735 mmol) was added and the mixture was heated in a 90° C. oil bath under nitrogen for 1 hour. The reaction was then cooled to room temperature and filtered through a pad of silica gel. The silica gel pad was washed with EtOAc (200 mL) and the combined filtrates were concentrated to afford a residue which was purified by column chromatography on silica gel (ISCO RediSep Rf 80 g column, gradient elution with 0% to 50% EtOAc in hexanes) to give the desired product as a white solid.

Step 2

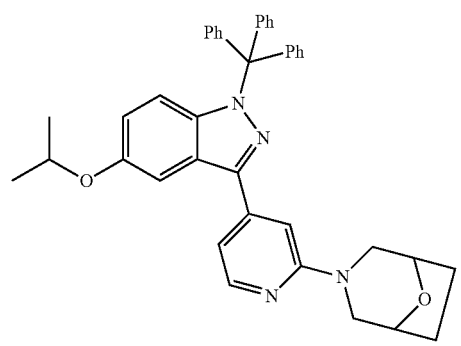

The fluoropyridine prepared in Step 1 (100 mg, 0.20 mmol), (1R,5S)-8-oxa-3-azabicyclo[3.2.1]octane (66 mg, 0.58 mmol) and cesium carbonate (254 mg, 0.78 mmol) were combined in DMSO (1 mL) in a microwave reaction vessel. The vessel was sealed and heated in a microwave reactor at 205° C. for 1 h. The reaction was cooled, unsealed, and partitioned between EtOAc and water. The layers were separated and the organic layer was concentrated to afford a yellow solid, which was used in the next step without further purification.

Step 3

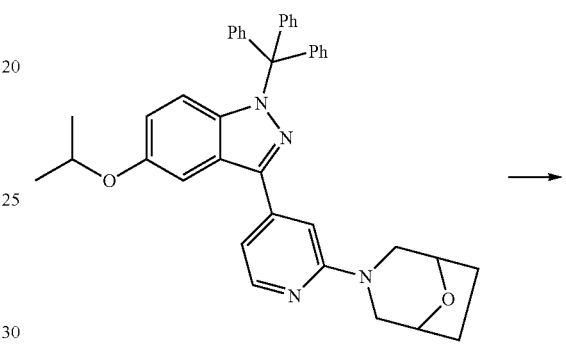

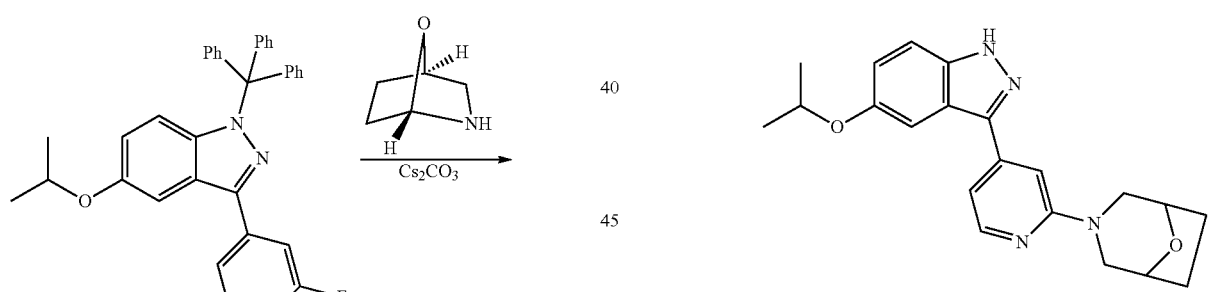

Example 280

The product from Step 2 was dissovled in TFA (1.5 mL) and water (300 μl). The resulting solution was stirred at room temperature for 2 h. The reaction was then concentrated. The residue was dissolved in MeOH (2 mL) and treated with a solution of ammonia (2 ml, 7N in MeOH). The solution was then concentrated and the residue was subjected to PTLC on silica gel to give Example 280 [LCMS (ESI) m/z 365 (Ret. time=2.07 min, LCMS method e)] as a yellow solid.

TABLE AN

Using the requisite amine and a method similar to that outlined in Scheme AN, the following Examples were prepared:

| Ex | Structure | Cond. | LCMS RT (min) | m/z | LRRK2 IC$_{50}$ (nM) |
|---|---|---|---|---|---|
| 281 | (structure) | e | 2.04 | 347 | 1.4 |
| 282 | (structure) | f | 1.57 | 365 | 7.7 |

TABLE AN.1

Using the method outlined in Steps 1 in Scheme AN and the requisite halide and boronate, the following intermediates were prepared:

| Intermediate Number | Halide | Boronate | Intermediate |
|---|---|---|---|
| AN.1.1 | (structure) | (structure) | (structure) |
| AN.1.2 | (structure) | (structure) | (structure) |

Scheme AO

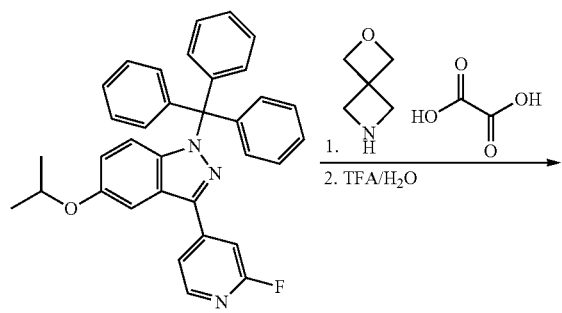

Example 283

Scheme AP

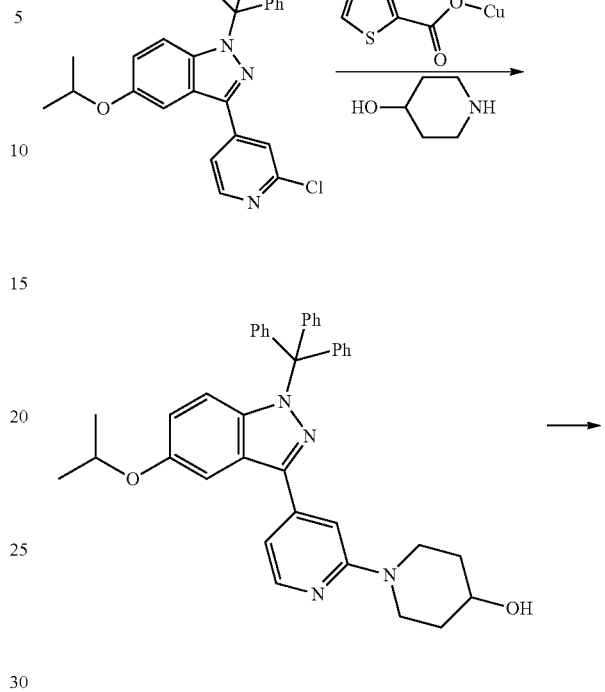

Example 285

The fluoropyridine prepared in Step 1 of Scheme AN (100 mg, 0.20 mmol), the spirocyclic amine (184 mg, 0.97 mmol) and triethylamine (493 mg, 4.87 mmol) were combined in DMSO (1.5 mL) in a glass reaction vessel. The vessel was sealed and heated at 125° C. for 18 h with stirring. The reaction was cooled, unsealed, and concentrated to afford a crude residue, which was subsequently dissolved in TFA (2 mL) and dichloromethane (1 mL). Triethylsilane (1 mL) was added and the reaction was stirred for 2 h. The reaction was concentrated to afford a residue, which was purified via C18 reversed phase chromatography (gradient elution, 0% to 100% MeCN in water with 0.1% TFA) to afford Example 283 (LCMS (ESI) m/z 351 (Ret.=2.02 min, LCMS method e)) as the TFA salt.

TABLE AO

Using the requisite amine and a method similar to that outlined in Scheme AO, the following Examples were prepared:

| Ex | Structure | LCMS Cond. | RT (min) | m/z | LRRK2 IC$_{50}$ (nM) |
|---|---|---|---|---|---|
| 284 | 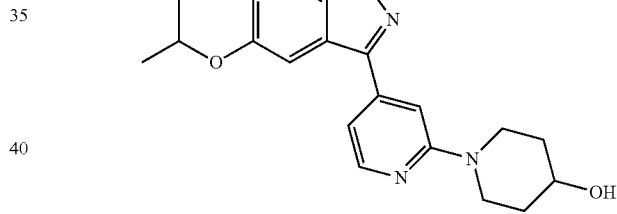 | e | 1.99 | 353 | 2.4 |

Step 1

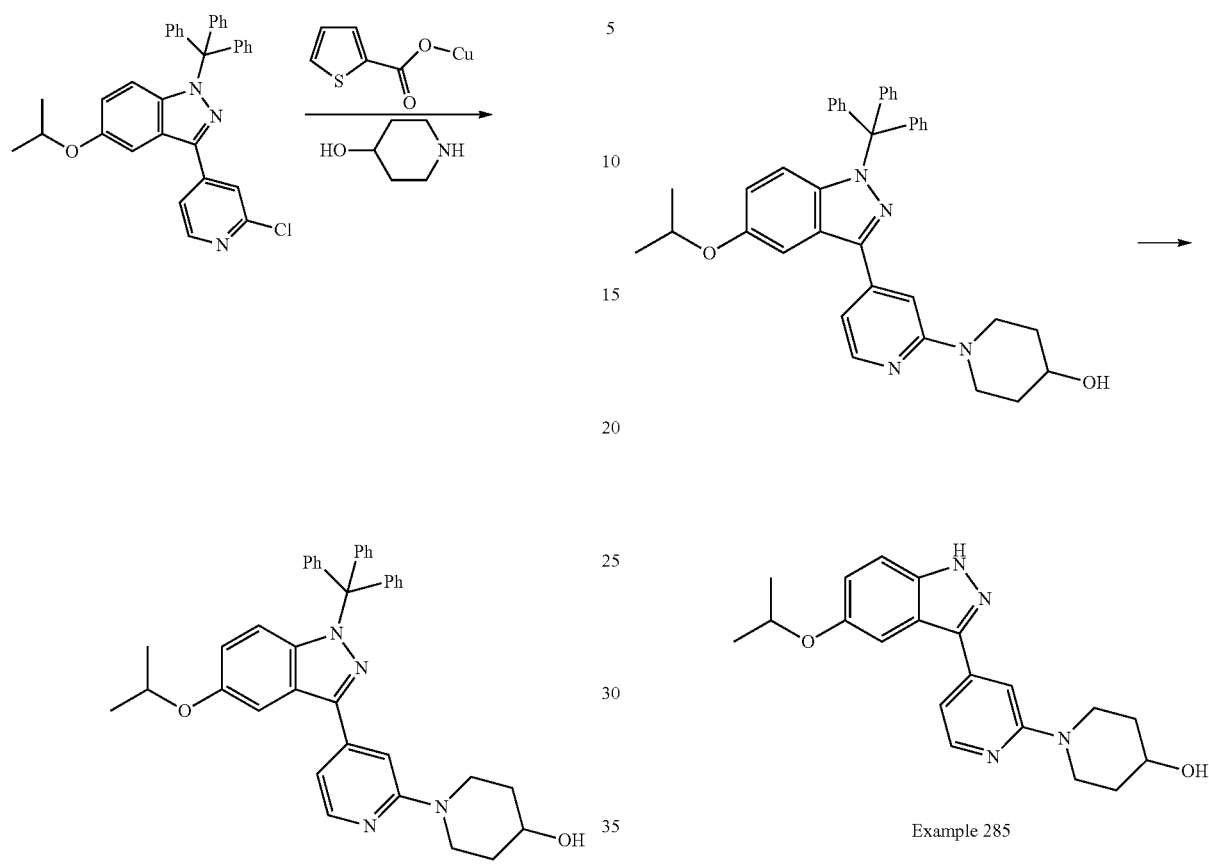

Step 2

Example 285

Copper(I) thiophene-2-carboxylate (250 mg, 1.311 mmol) was added to a stirred, room temperature mixture of the chloropyridine prepared in Step 4 of Scheme AM (2 g, 3.77 mmol), 4-hydroxypiperidine (1.22 g, 12.06 mmol) and i-Pr$_2$EtN (1.977 ml, 11.32 mmol) in DMSO (5 ml). The mixture was purged with nitrogen and was stirred in a sealed reaction vessel at 120° C. for 24 h. The reaction was then cooled to room temperature, unsealed and partitioned between EtOAc and 1:1 brine:water. The layers were separated and the aqueous layer was extracted with EtOAc. The combined organics were washed with brine, dried over anhydrous sodium sulfate, filtered and evaporated. The residue was purified by column chromatography on silica gel (ISCO RediSep Rf, 120 g column) gradient eluting with 0% to 100% EtOAc in hexanes to give the desired product as a colorless foam.

TFA (6 ml, 78 mmol) was added to a stirred, room temperature mixture of the compound prepared in Step 1 (135 mg, 0.227 mmol) and triethylsilane (3 ml, 18.78 mmol) in dichloromethane (18 ml). The resulting mixture was stirred at room temperature for 72 h. Methanol (30 ml, 742 mmol) was then added to the reaction, and the stirring was continued at room temperature. After 2 h, the reaction was warmed to 50° C. and stirred overnight. The mixture was then cooled and the solvent was evaporated under reduced pressure. The resulting residue was purified by reversed-phase column chromatography (Analogix 55 g C18 column, gradient elution 0% to 100% MeCN in water w/ 0.1% TFA) to give a mixture of the product and the 0-trifluoroacetate.

The material was then partitioned between dichloromethane and aqueous sodium hydrogen carbonate. The layers were separated and the aqueous layer was extracted with dichloromethane. The organic layers were combined, dried over anhydrous sodium sulfate, filtered and evaporated. The resulting residue was purified by column chromatography on silica gel (ISCO RediSep Rf, 24 g) eluting with a gradient of 0% to 75% MeOH in EtOAc to give the desired product as a colorless film. The material was then dissolved in 1,4-dioxane and treated with 4N HCl in 1,4-dioxane. A pale yellow precipitate formed, which was collected by filtration, washed with dioxane and dried under vacuum to afford Example 285 (LCMS (ESI) m/z 353 (Ret.=1.91 min, LCMS method e)) hydrochloride salt.

245
246
TABLE AP
Using a method similar to that outlined in Step 1 in Scheme AP and the requisite amine and chloropyridine, the following intermediate was prepared:
| Intermediate Number | Amine | Intermediate |
|---|---|---|
| AP.1 | 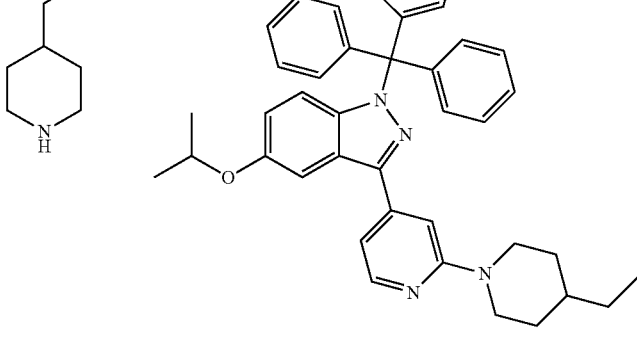 | 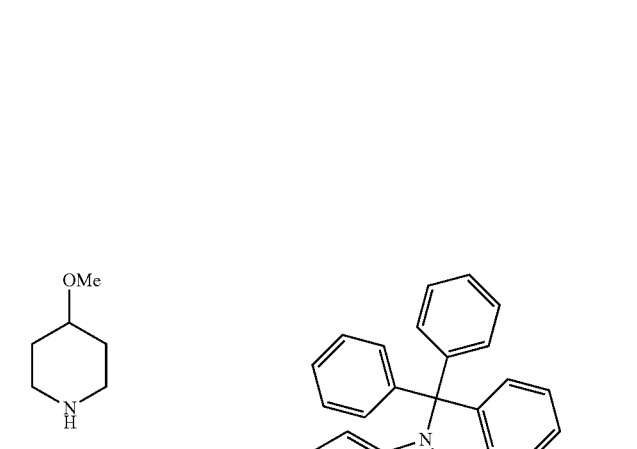 |
| AP.2 | | |
Scheme AQ
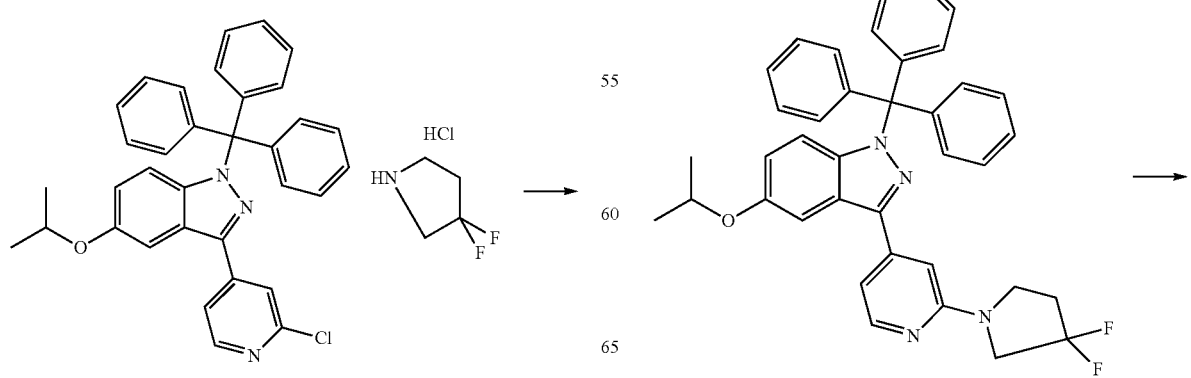
-continued

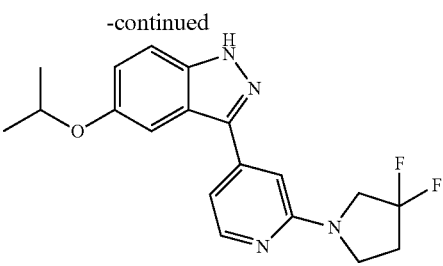

Example 286

Step 1

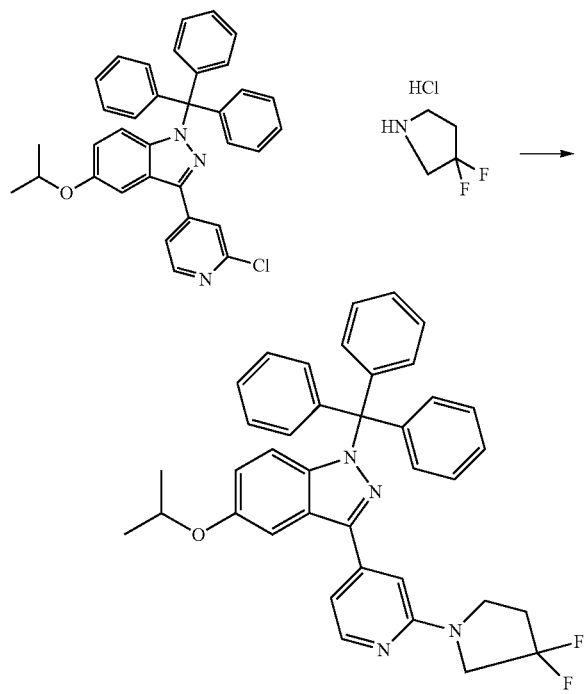

A solution of the chloropyridine prepared in Step 4 of Scheme AM (250 mg, 0.472 mmol) in 1,4-dioxane (4 ml) was treated with potassium tert-butoxide (132 mg, 1.179 mmol), 3,3-difluoropyrrolidine hydrochloride salt (74.5 mg, 0.519 mmol) 1,3-bis(2,6-diisopropylphenyl)-imidazolidinium chloride (40.3 mg, 0.094 mmol). The resulting mixture was purged with $N_2$ for 5 minutes. $Pd_2(dba)_3$ (43.2 mg, 0.047 mmol) was added and the reaction was sealed and heated overnight at 100° C. The reaction was then cooled to room temperature. The reaction mixture was diluted with EtOAc and filtered. The filtrate was concentrated in vacuo to afford a residue which was purified via silica gel chromatography (gradient elution, 0-30% EtOAc in hexanes to afford the desired product.

Step 2

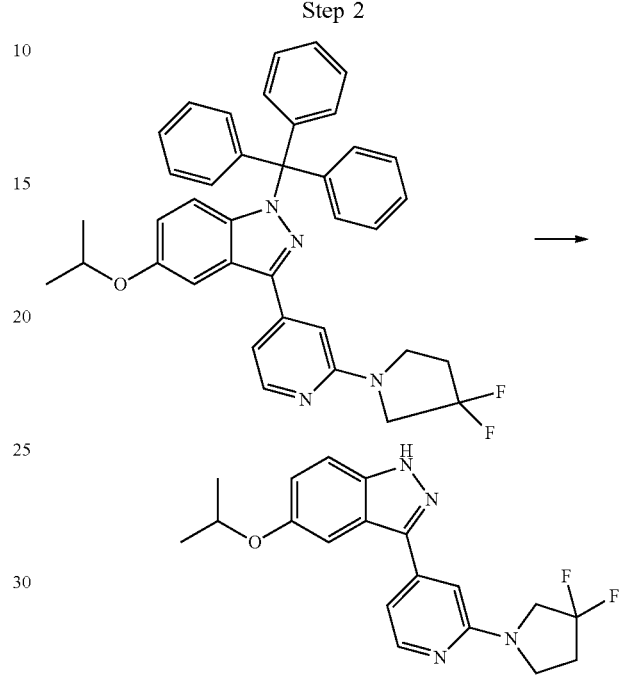

Example 286

The product from Step 1 (265 mg, 0.44 mmol) was dissolved in dichloromethane (6 mL). Water (4 mL) and TFA (4 mL) were added and the resulting mixture was stirred overnight at room temperature. The mixture was then concentrated under reduced pressure. The resulting residue was purified by reversed-phase column chromatography (Biotage SP1 MPLC, Analogix 30 g C18 column, gradient elution 0% to 100% MeCN in water w/ 0.1% TFA) to give Example 286 (LCMS (ESI) m/z 359 (Ret.=2.27 min, LCMS method e)) as the TFA salt.

TABLE AQ

Using the appropriate chloropyridine and amine and a method similar to that outlined in Scheme AQ, the following Examples were prepared:

| Ex | Structure | LCMS Cond. | RT (min) | m/z | LRRK2 IC$_{50}$ (nM) |
|---|---|---|---|---|---|
| 287 | | e | 2.13 | 373 | 14 |

TABLE AQ-continued

Using the appropriate chloropyridine and amine and a method similar to that outlined in Scheme AQ, the following Examples were prepared:

| Ex | Structure | LCMS Cond. | RT (min) | m/z | LRRK2 IC$_{50}$ (nM) |
|---|---|---|---|---|---|
| 288 | 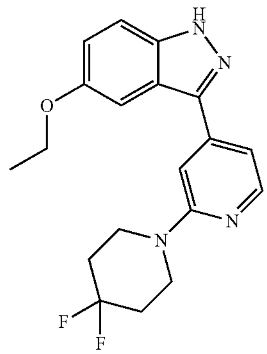 [SMILES: CCOc1ccc2[nH]nc(-c3ccnc(N4CCC(F)(F)CC4)c3)c2c1] | e | 2.09 | 359 | 22 |

TABLE AQ.1

Using the appropriate trityl protected indazole and a method similar to that outlined in Scheme AQ, Step 2, the following Examples were prepared:

| Ex | Structure | LCMS Cond. | RT (min) | m/z | LRRK2 IC$_{50}$ (nM) |
|---|---|---|---|---|---|
| 289 | 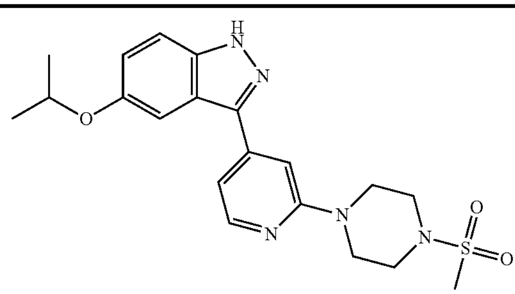 | e | 2.05 | 416 | 2.7 |
| 290 | 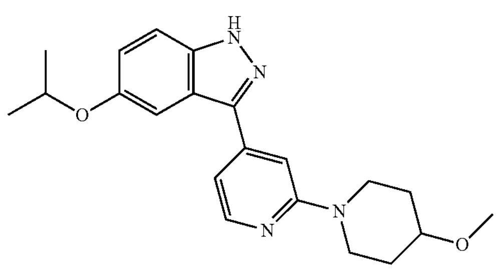 [SMILES: COC1CCN(c2cc(-c3n[nH]c4ccc(OC(C)C)cc34)ccn2)CC1] | e | 2.06 | 367 | 6.0 |
| 291 | 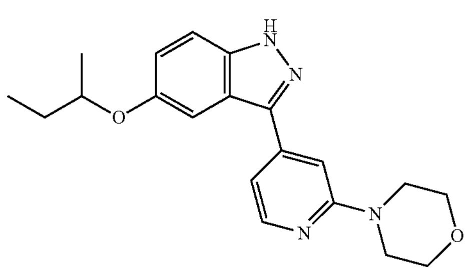 [SMILES: CCC(C)Oc1ccc2[nH]nc(-c3ccnc(N4CCOCC4)c3)c2c1] | e | 2.02 | 353 | 2.2 |

Scheme AR

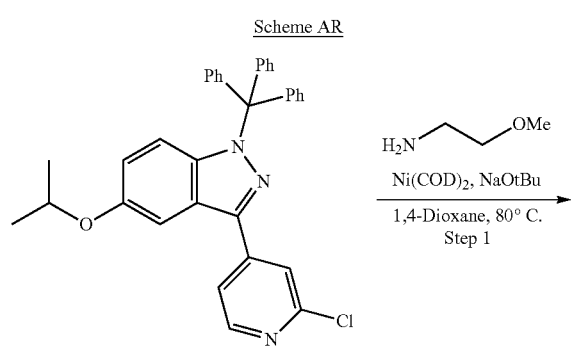

In a threaded glass reactor, a stirred mixture of the chloropyrimidine prepared in Step 4 of Scheme AM (1000 mg, 1.887 mmol), 2-methoxyethanolamine (0.325 ml, 3.77 mmol), potassium tert-butoxide (544 mg, 5.66 mmol), 1,3-bis(2,6-diisopropylphenyl)-imidazolidinium chloride (161 mg, 0.377 mmol) and Ni(COD)$_2$ (MW: 275.06, 52 mg, 0.19 mmol, 0.1 eq) in 1,4-dioxane (12 ml) was purged with nitrogen for 5 min. The reaction was then sealed and heated at 80° C. for 16 h. The reaction was then cooled to RT and unsealed. The reaction mixture was diluted with DCM, and filtered through a pad of celite. The filtrate was concentrated to leave a residue which was purified by column chromatography (ISCO RediSep Rf 40 g silica gel column, gradient elution with 0% to 100% hexanes in EtOAc) to yield the desired product as an oil.

Step 2

Trifluoroacetic acid (10 ml, 130 mmol) was added to a stirred, room temperature mixture of the product from Step 1 (560 mg, 0.985 mmol) in water (6 ml, 333 mmol) and dichloromethane (15 ml). The resulting mixture was stirred at room temperature for 18 h.

The reaction was subsequently evaporated and the resulting residue partitioned between methylene chloride and saturated aqueous sodium bicarbonate solution. The organic layer was then separated out, dried over anhydrous sodium sulfate, filtered and evaporated to give a crude product which was purified by silica gel column chromatography (Analogix Intelliflash system, ISCO RediSep Rf 12 g silica column, gradient elution from 0% to 100% EtOAc in dichloromethane) to afford the Example 292 (LCMS (ESI) m/z 327 (Ret.=2.04 min, LCMS method e)).

TABLE AR

Using the appropriate chloropyridine and amine and a method similar to that outlined in Scheme AR, the following Examples were prepared:

| Ex | Structure | LCMS Cond. | RT (min) | m/z | LRRK2 IC$_{50}$ (nM) |
|---|---|---|---|---|---|
| 293 | (structure) | e | 1.95 | 366 | 15 |

TABLE AR.1

Using the appropriate chloropyridine and amine and a method similar to that outlined in Step 1 of Scheme AR, followed by Step 2 of Scheme AQ, the following Examples were prepared:

| Ex | Structure | LCMS Cond. | RT (min) | m/z | LRRK2 IC$_{50}$ (nM) |
|---|---|---|---|---|---|
| 294 | (structure) | f | 1.37 | 352 | 17 |
| 295 | (structure) | e | 1.99 | 416 | 17 |
| 296 | (structure) | e | 1.99 | 353 | 7.5 |

TABLE AR.1-continued

Using the appropriate chloropyridine and amine and a method similar to that outlined in Step 1 of Scheme AR, followed by Step 2 of Scheme AQ, the following Examples were prepared:

| Ex | Structure | Cond. | LCMS RT (min) | m/z | LRRK2 IC$_{50}$ (nM) |
|---|---|---|---|---|---|
| 297 | 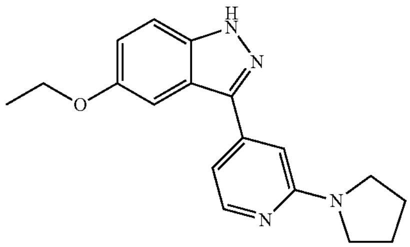 [SMILES: CCOc1ccc2[nH]nc(-c3ccnc(N4CCCC4)c3)c2c1] | e | 2.00 | 309 | 7.3 |
| 298 | 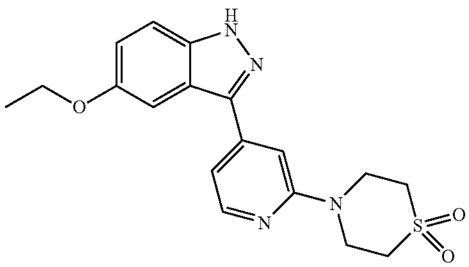 [SMILES: CCOc1ccc2[nH]nc(-c3ccnc(N4CCS(=O)(=O)CC4)c3)c2c1] | e | 1.91 | 373 | 51 |
| 299 | 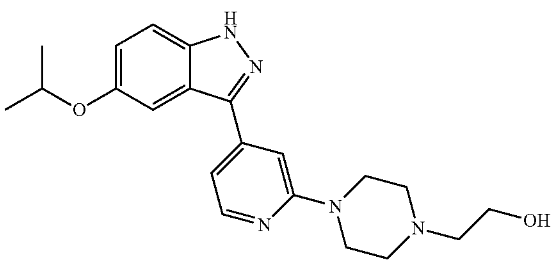 [SMILES: CC(C)Oc1ccc2[nH]nc(-c3ccnc(N4CCN(CCO)CC4)c3)c2c1] | j | 1.05 | 382 | 2.0 |

TABLE AR.2

Using the appropriate chloropyridine and amine and a method similar to that outlined in Step 1 of Scheme AR, followed by a method similar to that outlined in Step 2 of Scheme AV, the following Example was prepared:

| Ex | Structure | Cond. | LCMS RT (min) | m/z | LRRK2 IC$_{50}$ (nM) |
|---|---|---|---|---|---|
| 300 | 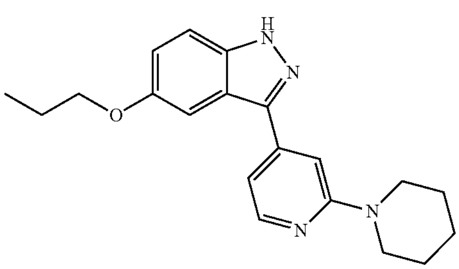 [SMILES: CCCOc1ccc2[nH]nc(-c3ccnc(N4CCCCC4)c3)c2c1] | e | 2.10 | 337 | 31 |

TABLE AR.3
Using the appropriate trityl protected indazole and a method similar to that outlined in Scheme AR, Step 2, the following Examples were prepared:
| Ex | Structure | LCMS Cond. | RT (min) | m/z | LRRK2 IC$_{50}$ (nM) |
|---|---|---|---|---|---|
| 301 | 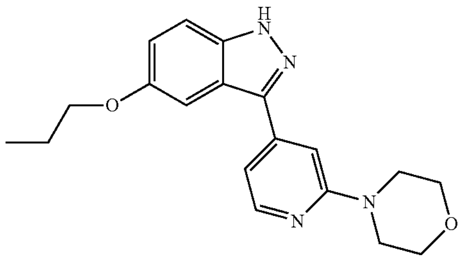 [SMILES: CCCOc1ccc2[nH]nc(-c3ccnc(N4CCOCC4)c3)c2c1] | e | 2.03 | 339 | 12 |
| 302 | 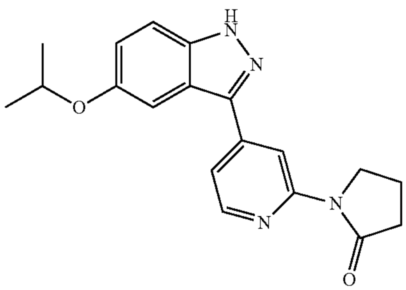 [SMILES: CC(C)Oc1ccc2[nH]nc(-c3ccnc(N4CCCC4=O)c3)c2c1] | e | 2.09 | 337 | 24 |
| 303 | 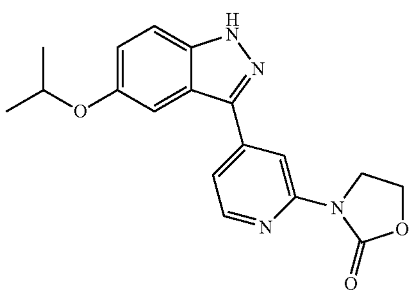 [SMILES: CC(C)Oc1ccc2[nH]nc(-c3ccnc(N4CCOC4=O)c3)c2c1] | e | 2.17 | 339 | 16 |
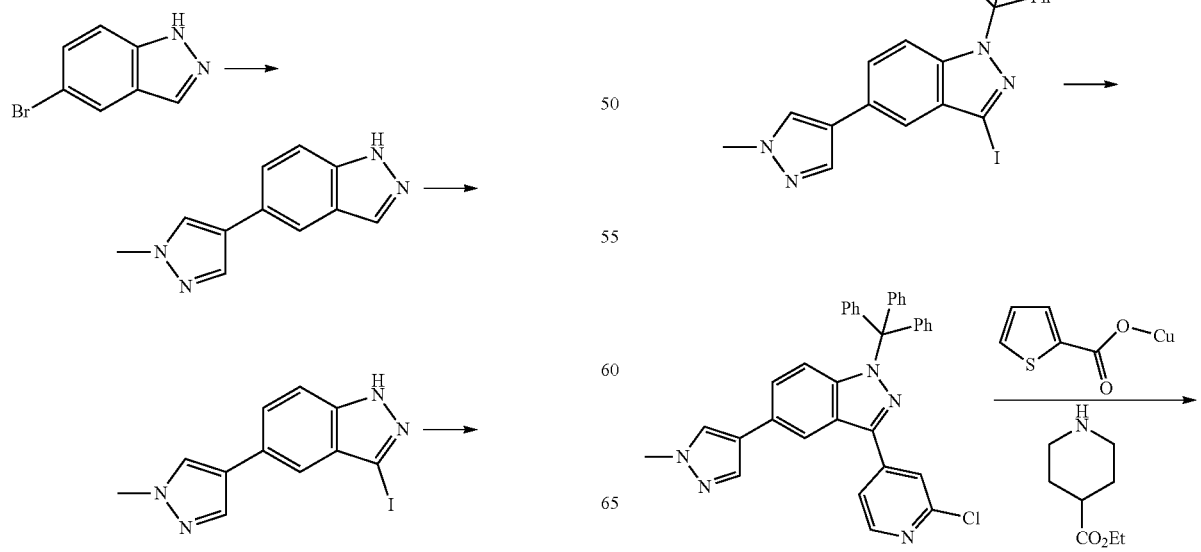

259 260

Step 2

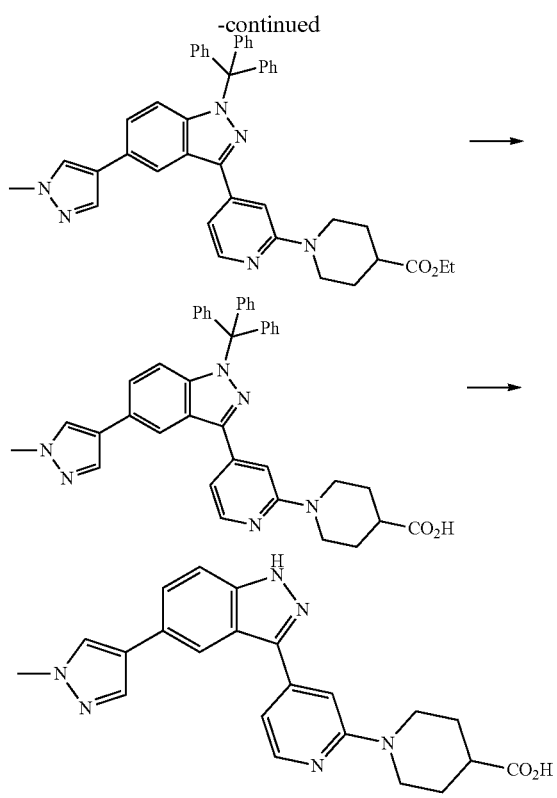

Example 304

Step 1

Into a 2000-mL 3-necked round-bottom flask was placed a solution of 5-(1-methyl-1H-pyrazol-4-yl)-1H-indazole (66 g, 332.96 mmol, 1.00 equiv) in $CH_3CN$ (700 mL) and potassium carbonate (68.9 g, 498.52 mmol, 1.50 equiv) at room temperature. This was followed by the addition of $I_2$ (101.6 g, 400.00 mmol, 1.20 equiv) in portions at room temperature. The resulting solution was stirred overnight at room temperature and then quenched by the addition of 1000 mL of water. The resulting solution was extracted with 4×500 mL of ethyl acetate. The organic layers were combined, washed with 1×1000 mL of brine, dried over anhydrous sodium sulfate and concentrated under vacuum. The crude product was re-crystallized from diethyl ether. This resulted in 3-iodo-5-(1-methyl-1H-pyrazol-4-yl)-1H-indazole as a yellow solid.

Step 3

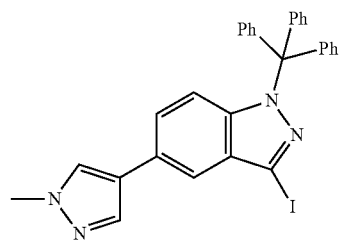

Into a 3000-mL 3-necked round-bottom flask purged and maintained with an inert atmosphere of nitrogen was placed a solution of 5-bromo-1H-indazole (130 g, 659.79 mmol, 1.00 equiv) in N,N-dimethylformamide (1300 mL) at room temperature. To this were added 1-methyl-4-(tetramethyl-1,3,2-dioxaborolan-2-yl)-1H-pyrazole (240 g, 1.15 mol, 1.70 equiv), potassium carbonate (247.1 g, 1.79 mol, 2.70 equiv) and Pd(dppf)$Cl_2$-DCM (26 g, 31.82 mmol, 0.05 equiv) at room temperature. The resulting solution was stirred overnight at 80° C. in an oil bath. The reaction mixture was cooled to 20° C., then quenched by the addition of 1500 mL of water. The resulting solution was extracted with 4×1000 mL of ethyl acetate. The organic layers were combined, washed with 2×1000 mL of brine, dried over anhydrous sodium sulfate and concentrated under vacuum. The crude product was re-crystallized from PE:EtOAc in the ratio of 10:1. This resulted in 5-(1-methyl-1H-pyrazol-4-yl)-1H-indazole as a yellow solid.

Into a 2000-mL 3-necked round-bottom flask purged and maintained with an inert atmosphere of nitrogen was placed a solution of 3-iodo-5-(1-methyl-1H-pyrazol-4-yl)-1H-indazole (71.5 g, 213.98 mmol, 1.00 equiv, 97%) in tetrahydrofuran (1000 mL) at room temperature. This was followed by the addition of sodium hydride (12.7 g, 317.50 mmol, 1.40 equiv, 60%) in portions at 0° C. The resulting solution was stirred for 15 min at 0° C., then added (chlorodiphenylmethyl)benzene (76 g, 272.62 mmol, 1.20 equiv) at 0° C. The resulting solution was stirred overnight at room temperature. The reaction was then quenched by the addition of 1000 mL of water. The resulting solution was extracted with 3×1000 mL of ethyl acetate. The organic layers were combined, washed with 2×1000 mL of brine, dried over anhydrous sodium sulfate and concentrated under vacuum. The residue was applied onto a silica gel column and eluted with ethyl acetate/petroleum ether (1:2). This resulted in 3-iodo-5-(1-methyl-1H-pyrazol-4-yl)-1-(triphenylmethyl)-1H-indazole as a orange solid.

Step 4

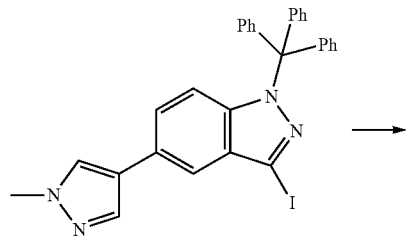

A mixture of 3-iodo-5-(1-methyl-1H-pyrazol-4-yl)-1-(triphenylmethyl)-1H-indazole (1.0 g, 1.77 mmol), 2-chloropyridine-4-boronic acid pinacol ester (465 mg, 1.94 mmol), 1,1'-Pd(dppf)Cl$_2$-DCM complex (288 mg, 0.353 mmol) and potassium carbonate (488 mg, 3.53 mmol) in 1,4-dioxane (10 mL) and water (0.3 mL) was sealed in a microwave reaction vessel and heated in a microwave reactor for 4 h at 80° C. The reaction was cooled and concentrated to afford a residue which was subjected to silica gel chromatography to afford the desired product as a yellow solid.

Step 5

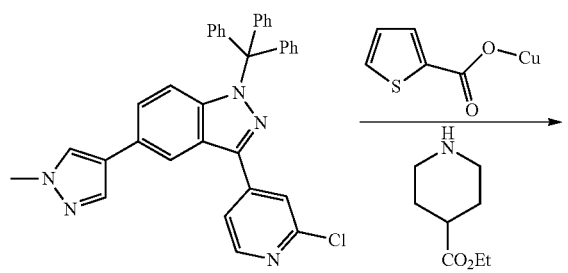

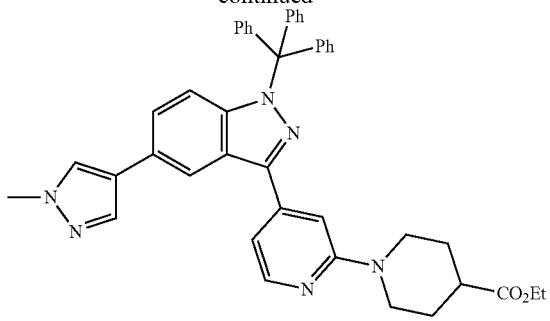

Copper(I) thiophene-2-carboxylate (27.6 mg, 0.145 mmol) was added to a stirred, room temperature mixture of the chloropyridine prepared in Step 4 (200 mg, 0.362 mmol), ethyl piperidine-4-carboxylate (85 mg, 0.543 mmol) and iPr$_2$EtN (0.190 ml, 1.087 mmol) in DMSO (500 µl). The mixture was purged with nitrogen and was stirred in a sealed reaction vessel at 120° C. 24 h. The reaction was cooled to room temperature and unsealed. The reaction mixture was partitioned between EtOAc and 1:1 brine:water. The layers were separated and the aqueous layer was extracted with EtOAc. The combined organic layers were washed with brine, dried over anhydrous sodium sulfate, filtered and evaporated. The resulting residue was purified by column chromatography on silica gel (ISCO RediSep Rf, 120 g column) gradient eluting with 0% to 100% EtOAc in hexanes to give the desired product as a colorless foam.

Step 6

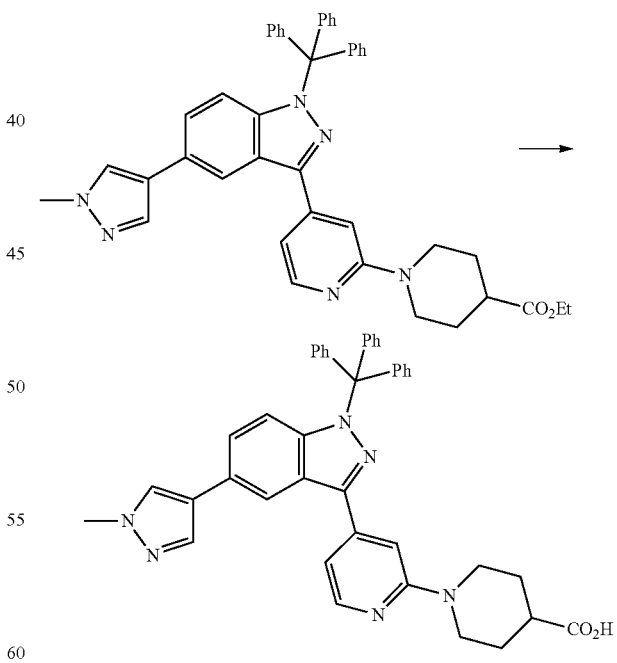

The product from Step 5 was dissolved in MeOH (10 ml) and THF (10 mL). Aqueous 2M NaOH (10 ml, 20.00 mmol) was added and the mixture was stirred overnight at room temperature. The pH of the reaction was then adjusted to ~pH 2 with 1N HCl (aq.). The reaction was then concentrated to a minimal volume and purified by reversed-phase column chromatography (Analogix 55 g C18 column), gradient eluting with 0% to 100% MeCN in water with 0.1% TFA to give the desired product as a colorless solid.

Step 7

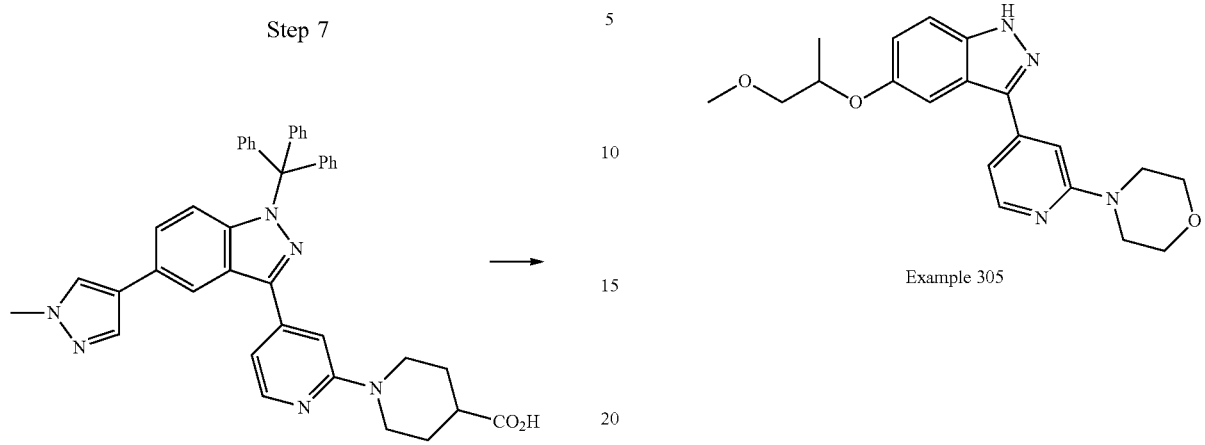

Example 304

Trifluoroacetic acid (10 ml, 130 mmol) was added to a stirred, room temperature mixture of the product from Step 6 (56 mg, 0.087 mmol) in CH$_2$Cl$_2$ (10 ml) and WATER (10 ml, 555 mmol) and the mixture was stirred at room temperature for 18 h.

The reaction was concentrated, the material was dissolved in MeCN and was purified by reversed-phase column chromatography (Biotage MPLC, Analogix 55 g C18 column), gradient eluting with 0% to 100% MeCN in water w/ 0.1% TFA to give Example 304 (LCMS (ESI) m/z 403 (Ret.=1.61 min, LCMS method e)).

Scheme AT

1. MsCl, Et$_3$N
2. Cs$_2$CO$_3$, DMF

Example 305

Methanesulfonyl chloride (0.145 mL, 1.88 mmol) was added to a solution of 1-methoxypropan-2-ol (254 mg, 2.81 mmol) and Et$_3$N (0.261 mL, 1.88 mmol) in CH$_2$Cl$_2$ (5 mL) at room temperature. The reaction was stirred at room temperature for 2 h. Diethyl ether (10 ml) was added and the reaction was filtered to remove the resulting solid. The filtrate was concentrated in vacuo. The resulting residue was dissovled in DMF (4 mL). Cesium carbonate (611 mg, 1.88 mmol) and the material prepared in Scheme E, Step 3 (200 mg, 0.47 mmol) were added to the DMF solution. The mixture was heated overnight at 40° C. Ethyl acetate (10 mL) was added and solution was filtered to remove the solid precipitate. The filtrate was concentrated to afford yellow solid. The solid was dissovled in DCM (2 mL), and treated with TFA (2 mL) and water (300 μl). The resulting solution was microwaved at 100° C. for 1 h. The reaction was cooled, then concentrated. Ammonia (5 ml, 7N in MeOH) was added to the resulting residue. The solution was then concentrated and the residue was subjected to PTLC on silica gel to give Example 305 (LCMS (ESI) m/z 369 (Ret.=1.91 min, LCMS method e)) as a yellow solid.

Scheme AU

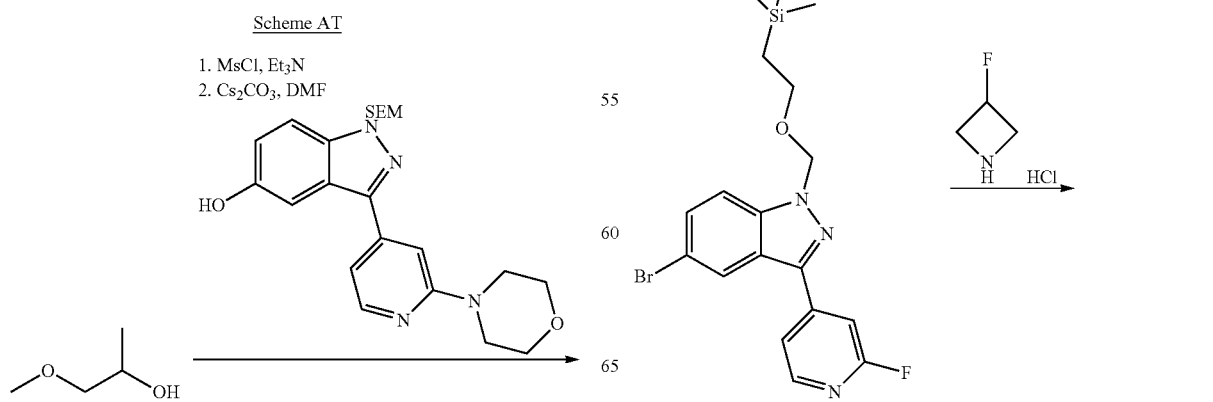

265
-continued

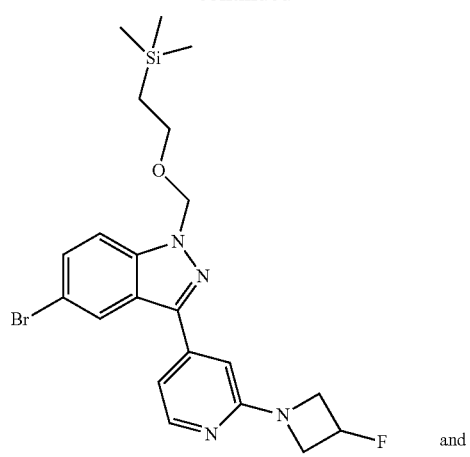

and

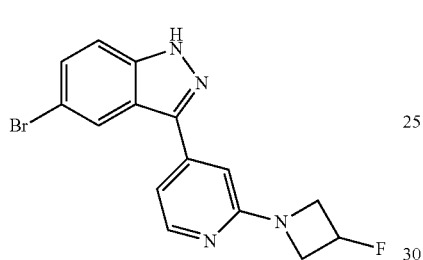

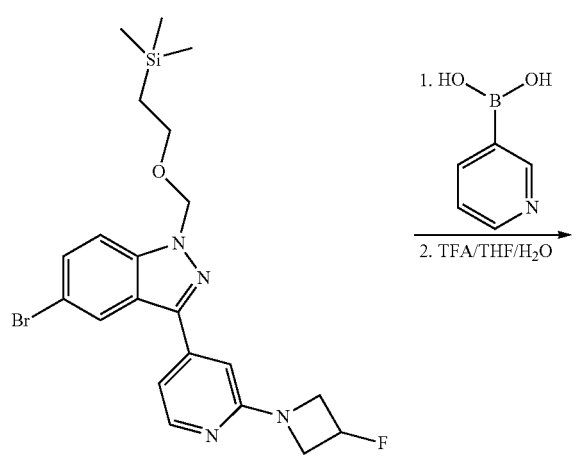

Example 306

266

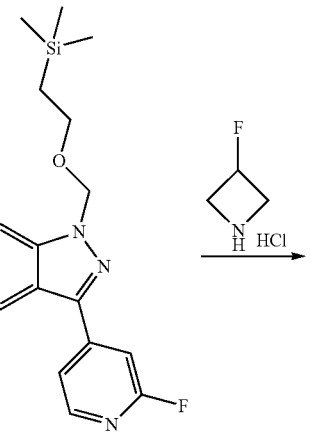

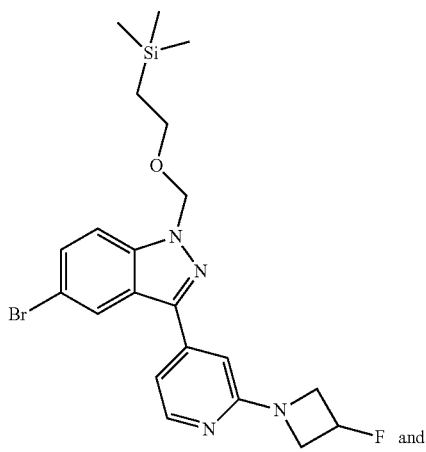

The intermediate prepared in Step 3 of Scheme D (600 mg, 1.42 mmol), 3-fluoroazetidine hydrochloride (475 mg, 4.26 mmol) and cesium carbonate (1.85 g, 5.68 mmol) were combined in DMSO (8 mL) in a microwave vial. The vial was sealed and the reaction was microwaved at 150° C. for 30 min. The reaction was then heated in an oil bath at 120° C. overnight. The reaction was cooled to room temperature and uncapped. The reaction mixture was partitioned between water and EtOAc. The layers were separated and the organic layer was dried over anhydrous $Na_2SO_4$, filtered and evaporated to afford a crude residue. The residue was purified via silica gel chromatography (gradient elution, 0-5% MeOH in $CH_2Cl_2$) to afford the desired product as well as the desired product with the SEM protecting group removed.

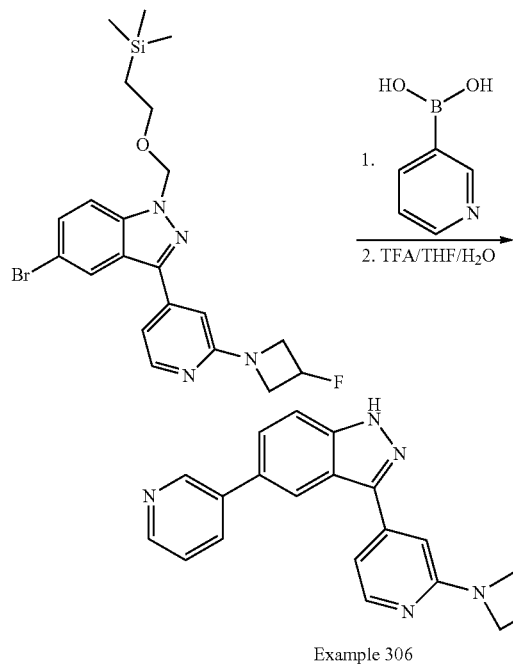

Example 306

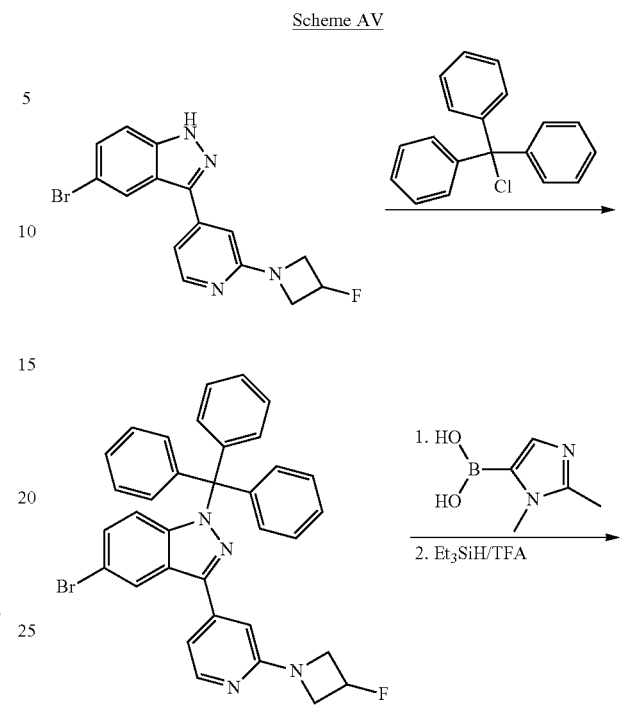

Scheme AV

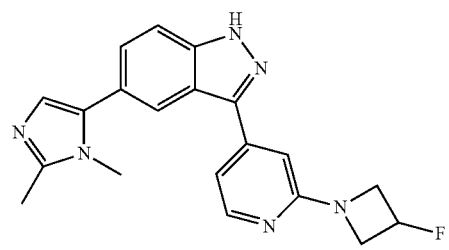

Example 307

The SEM-protected product from Step 1 (80 mg, 0.17 mmol), pyridin-3-ylboronic acid (41 mg, 0.34 mmol), Pd(dppf)Cl$_2$-DCM complex (27 mg, 0.034 mmol) and potassium carbonate (46 mg, 0.34 mmol) were combined in 1,4-dioxane (1.5 mL) and water (0.1 ml) in a microwave vial. The reaction was sealed and was microwaved at 110° C. for 3 h. The reaction was cooled to room temperature and filtered. The filtrate was concentrated. The resulting residue was dissolved in THF (1 mL). Trifluoroacetic acid (2 mL) and water (150 μl) were added and the reaction was microwaved at 105° C. for 1 h. The reaction was concentrated, 7N ammonia in MeOH (5 mL) was added and the reaction was concentrated again. The residue was purified via PTLC on silica gel to afford Example 306 (LCMS (ESI) m/z 346 (Ret.=1.66 min, LCMS method e)) as a white solid.

TABLE AU

Using a method similar to that outlined in Scheme AU, Step 1, and the appropriate fluoropyridine, the following intermediate was prepared:

| Intermediate Number | Fluoropyridine | Intermediate |
|---|---|---|
| AU1 | (structure) | (structure) |

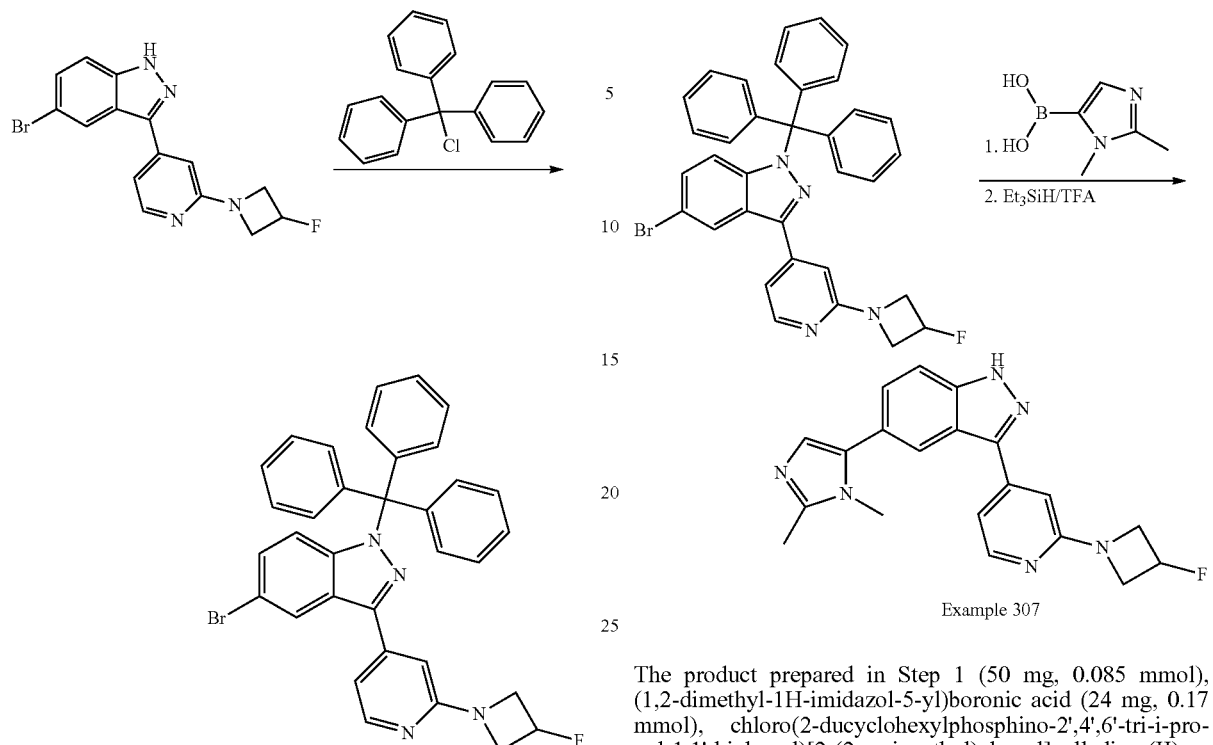

Step 2

Example 307

To a solution of the by-product from Step 1 of Scheme AU (130 mg, 0.37 mmol) in THF (4 mL) was added NaH (9 mg, 0.37 mmol), followed by trityl chloride (125 mg, 0.45 mmol). The resulting mixture was stirred at rt for 5 h. Water was added to the reaction mixture and the resulting solution was extracted with EtOAc. The organic layer was dried over anhydrous $Na_2SO_4$, filtered and evaporated to afford a crude residue which was purified via PTLC on silica gel to give the desired product as a yellow solid.

The product prepared in Step 1 (50 mg, 0.085 mmol), (1,2-dimethyl-1H-imidazol-5-yl)boronic acid (24 mg, 0.17 mmol), chloro(2-ducyclohexylphosphino-2',4',6'-tri-i-propyl-1,1'-biphenyl)[2-(2-aminoethyl)phenyl]palladium(II) methyl-t-butyl ether adduct (11 mg, 0.013 mmol) and potassium phosphate tribasic (36 mg, 0.17 mmol) were combined in 1,4-dioxane (2 mL) and water (100 µl). The resulting mixture was heated to 100° C. and stirred overnight. The reaction was cooled and filtered through a pad of Celite to remove the solids. The filtrate was concentrated and redissolved in TFA (2 mL). Triethylsilane (500 µl) was added and the reaction was stirred at rt for 10 min. Methylene chloride (1 mL) was added and the mixture was stirred overnight. The reaction was concentrated and the resulting residue was dissolved in 7N ammonia in MeOH (5 mL). The solution was concentrated and the resulting residue was purified via PTLC on silica gel to afford Example 307 (LCMS (ESI) m/z 363 (Ret.=1.64 min, LCMS method e)) as a yellow solid.

TABLE AV

Using the method outlined in Scheme AV, Step 1 and the requisite indazole, the following intermediate was prepared:

| Intermediate Number | Starting Halide | Intermediate |
|---|---|---|
| AV1 | | |

Scheme AW

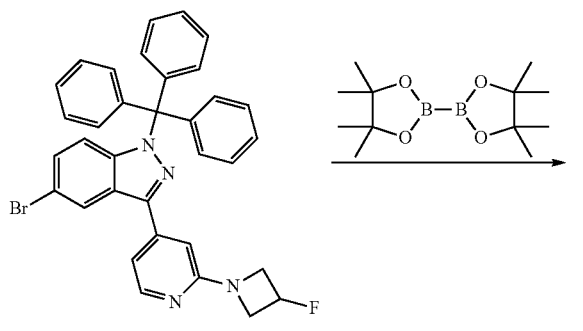

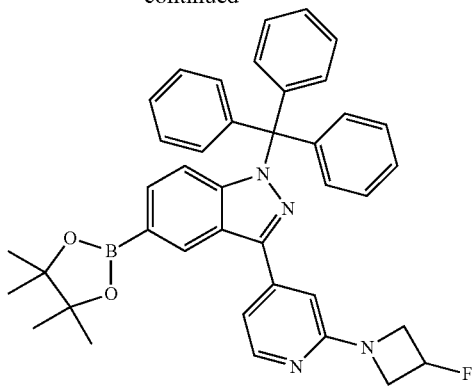

The product prepared in Step 1 of Scheme AV (90 mg, 0.15 mmol), bis(pinacolato)diboron (78 mg, 0.31 mmol), Pd(dppf)Cl$_2$·CH$_2$Cl$_2$ (25 mg, 0.031 mmol) and potassium acetate (45 mg, 0.46 mmol) were combined in 1,4-dioxane (2 mL). The reaction was sealed and microwaved at 110° C. for 3 h. The reaction was cooled and concentrated. Purification of the resulting residue via PTLC on silica gave the desired boronate as a yellow solid.

Step 2

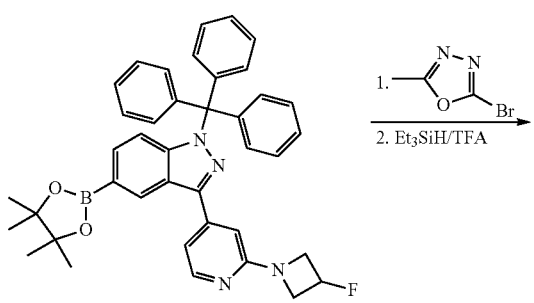

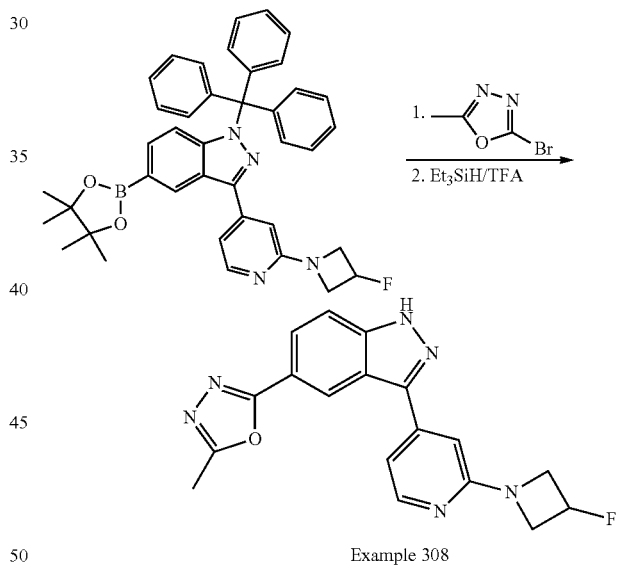

Example 308

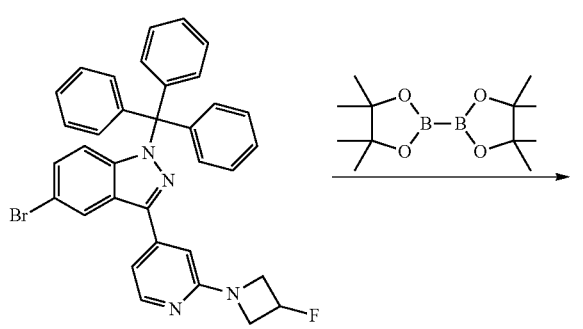

The product prepared in Step 1 (40 mg, 0.063 mmol), 2-bromo-5-methyl-1,3,4-oxadiazole (20 mg, 0.13 mmol), Pd(dppf)Cl$_2$·CH$_2$Cl$_2$ (10 mg, 0.013 mmol) and potassium acetate (15 mg, 0.16 mmol) were combined in 1,4-dioxane (2 mL) and water (100 µl). The reaction was sealed and microwaved at 110° C. for 3 h, then at 125° C. for 30 min. The reaction was cooled to room temperature, then concentrated to afford a residue, which was subsequently dissolved in TFA (2 mL). Triethylsilane (300 µl) was added and the reaction was stirred for 10 min. Dichloromethane (1 mL) was added and the reaction was stirred overnight. The reaction was concentrated and the residue was dissolved in 7N ammonia in MeOH (5 mL). The solution was evaporated and the resulting residue was purified via PTLC on silica gel to afford Example 308 (LCMS (ESI) m/z 351 (Ret.=1.81 min, LCMS method e)) as a yellow solid.

TABLE AW-1
Using the method outlined in Scheme AW, Step 1 and the requisite halide, the following intermediates were prepared
| Intermediate Number | Starting Halide | Intermediate |
|---|---|---|
| AW1 | 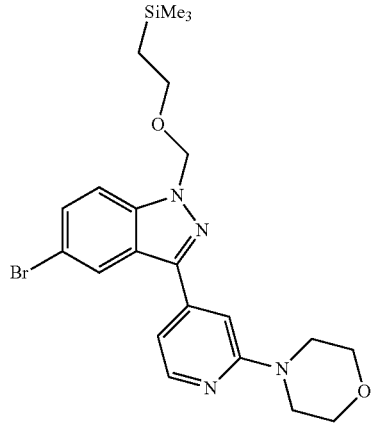 [SMILES: C[Si](C)(C)CCOCn1nc(-c2ccnc(N3CCOCC3)c2)c2cc(Br)ccc21] | 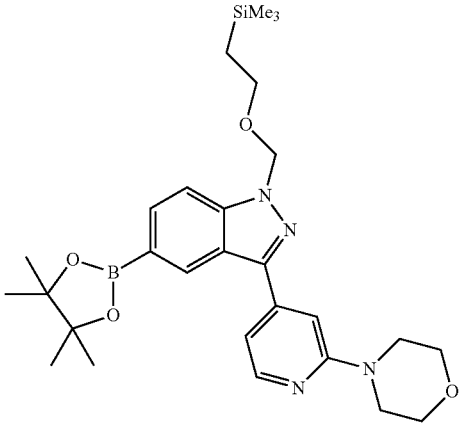 [SMILES: CC1(C)OB(c2ccc3c(c2)c(-c2ccnc(N4CCOCC4)c2)nn3COCC[Si](C)(C)C)OC1(C)C] |
| AW2 | 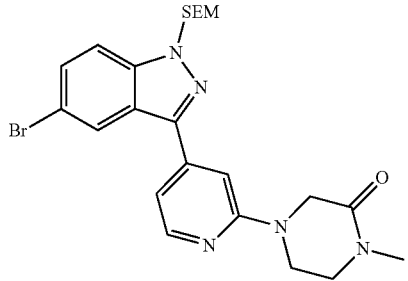 [SMILES: CN1CCN(c2cc(-c3nn(COCC[Si](C)(C)C)c4ccc(Br)cc34)ccn2)CC1=O] | 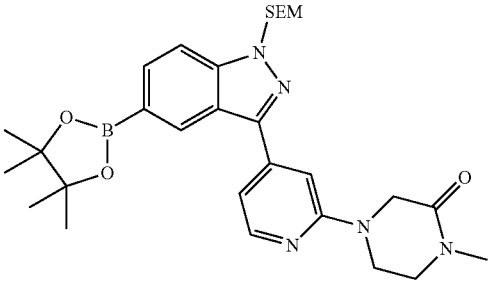 |
| AW3 | 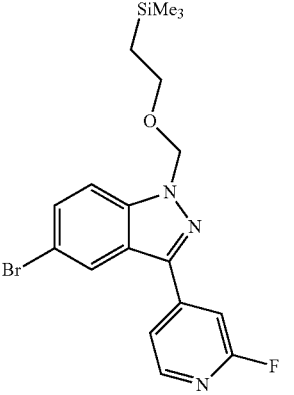 [SMILES: C[Si](C)(C)CCOCn1nc(-c2ccnc(F)c2)c2cc(Br)ccc21] | 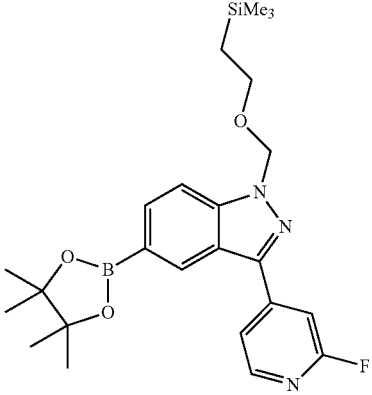 [SMILES: CC1(C)OB(c2ccc3c(c2)c(-c2ccnc(F)c2)nn3COCC[Si](C)(C)C)OC1(C)C] |
| AW4 | 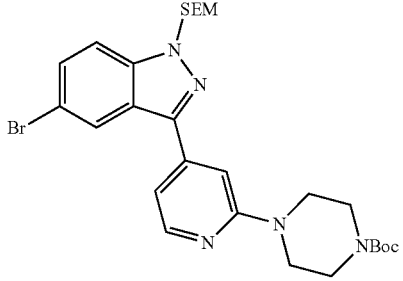 [SMILES: CC(C)(C)OC(=O)N1CCN(c2cc(-c3nn(COCC[Si](C)(C)C)c4ccc(Br)cc34)ccn2)CC1] | 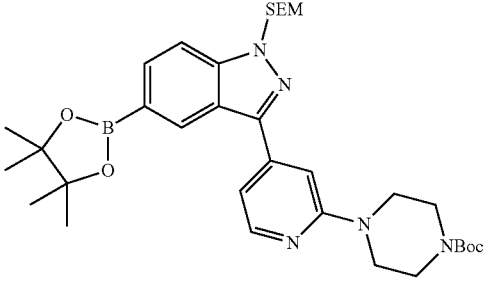 [SMILES: CC(C)(C)OC(=O)N1CCN(c2cc(-c3nn(COCC[Si](C)(C)C)c4ccc(B5OC(C)(C)C(C)(C)O5)cc34)ccn2)CC1] |

TABLE AW-1-continued

Using the method outlined in Scheme AW, Step 1 and the requisite halide, the following intermediates were prepared

| Intermediate Number | Starting Halide | Intermediate |
|---|---|---|
| AW5 | 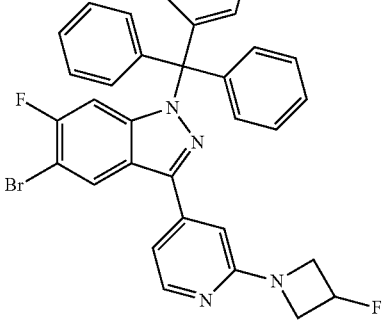 | 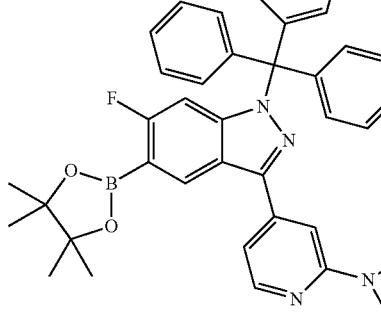 |
| AW6 | 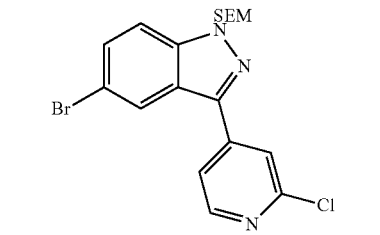 [SMILES: C[Si](C)(C)CCOCn1nc(-c2ccnc(Cl)c2)c2cc(Br)ccc21] | 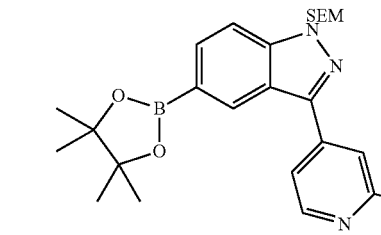 |
| AW7 | 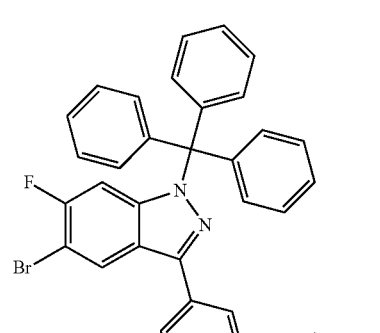 | 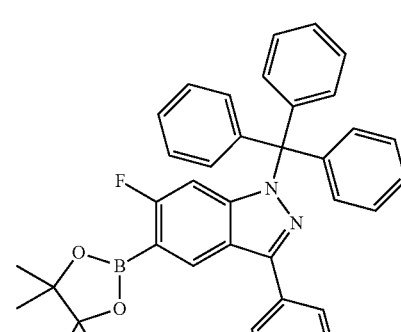 |

TABLE AW-2

Using the appropriate aryl halide and boronic ester and a coupling method similar to that outlined in Scheme AW, the following Examples were prepared:

| Ex | Structure | LCMS Cond. | RT (min) | m/z | LRRK2 IC$_{50}$ (nM) |
|---|---|---|---|---|---|
| 309 | | e | 1.50 | 350 | 1.8 |

TABLE AW-2-continued

Using the appropriate aryl halide and boronic ester and a coupling method similar to that outlined in Scheme AW, the following Examples were prepared:

| Ex | Structure | LCMS Cond. | RT (min) | m/z | LRRK2 IC$_{50}$ (nM) |
|---|---|---|---|---|---|
| 310 | 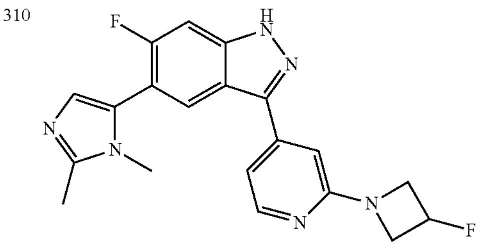 | e | 1.41 | 381 | 95 |

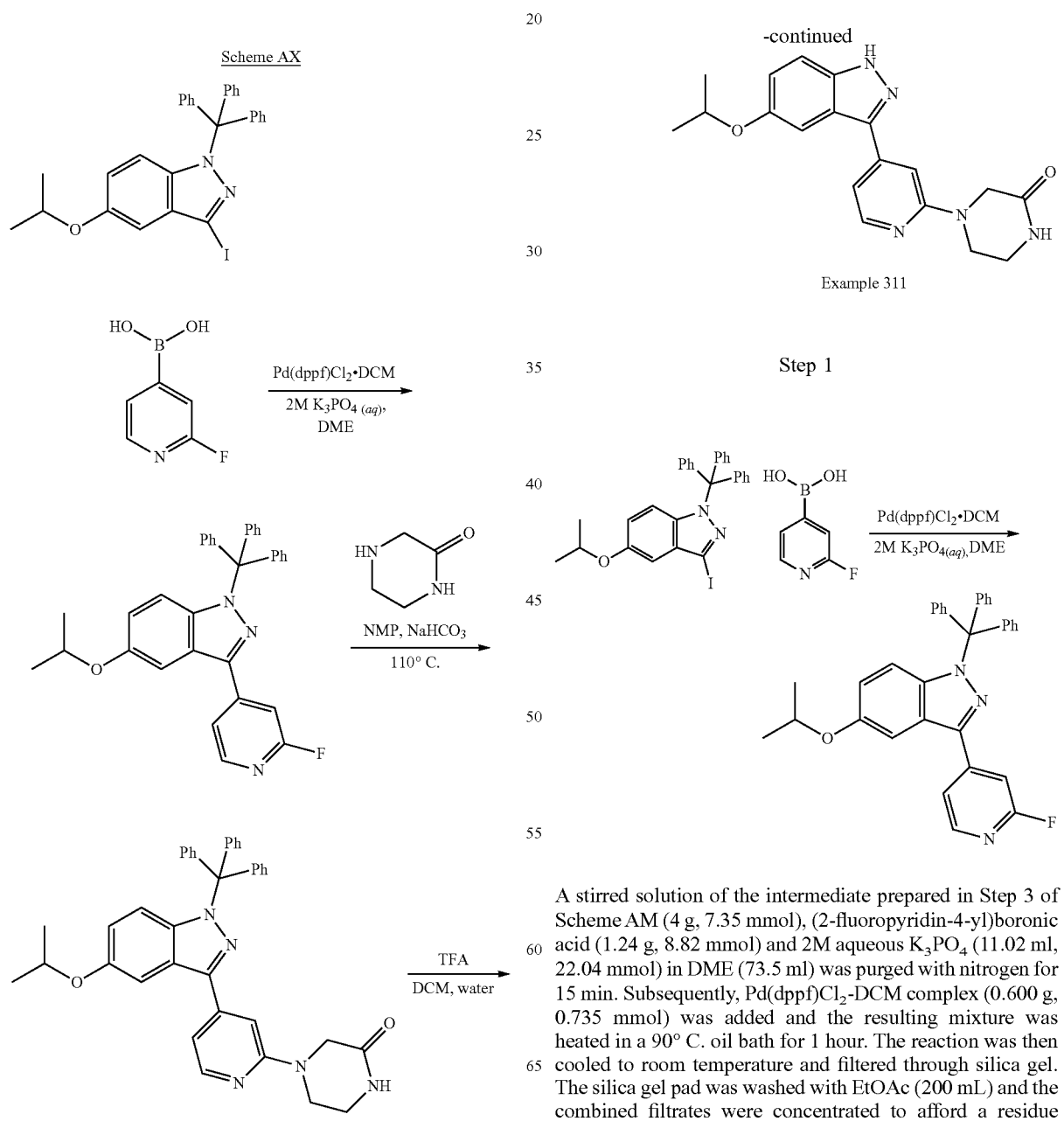

Example 311

Step 1

A stirred solution of the intermediate prepared in Step 3 of Scheme AM (4 g, 7.35 mmol), (2-fluoropyridin-4-yl)boronic acid (1.24 g, 8.82 mmol) and 2M aqueous K$_3$PO$_4$ (11.02 ml, 22.04 mmol) in DME (73.5 ml) was purged with nitrogen for 15 min. Subsequently, Pd(dppf)Cl$_2$-DCM complex (0.600 g, 0.735 mmol) was added and the resulting mixture was heated in a 90° C. oil bath for 1 hour. The reaction was then cooled to room temperature and filtered through silica gel. The silica gel pad was washed with EtOAc (200 mL) and the combined filtrates were concentrated to afford a residue which was purified by column chromatography on silica gel (ISCO RediSep Rf 80 g column) by gradient elution with 0% to 50% EtOAc in hexanes to give the desired product as a white solid.

Step 2

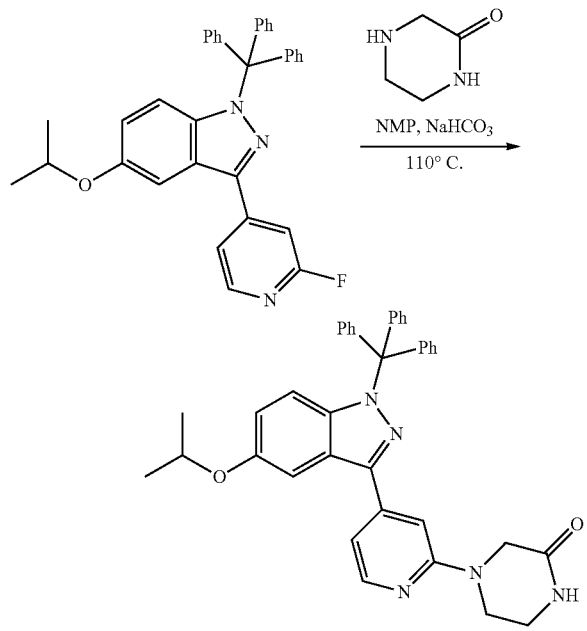

The compound prepared in Step 1 (850 mg, 1.66), piperazin-2-one (1.66 g, 16.55 mmol) and sodium bicarbonate (1.39 g, 16.55 mmol) were combined with NMP (6 mL) in a heavy-walled, glass screw-top reaction vessel. The vessel was sealed and heated for 3 days at 110° C. The reaction was then cooled, unsealed and diluted with water. The aqueous solution was extracted with EtOAc (×3). The combined organic layers were then washed with water (×2), brine, dried over anhydrous magnesium sulfate, filtered and concentrated under vacuum to leave a residue which was purified by silica gel chromatography (isocratic elution with 20:1 DCM: MeOH) to yield the desired product with some impurities present. Further purification via C18 reversed-phase MPLC (Biotage SP-1, gradient elution 0% to 100% MeCN in water with 0.1% TFA) afforded the desired product.

Step 3

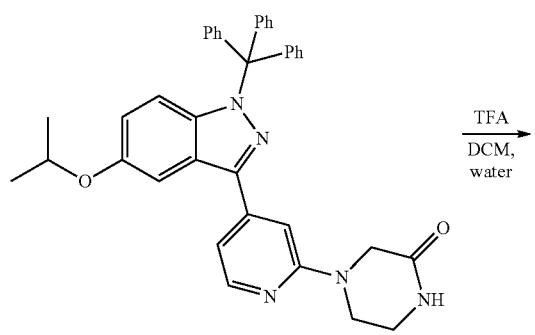

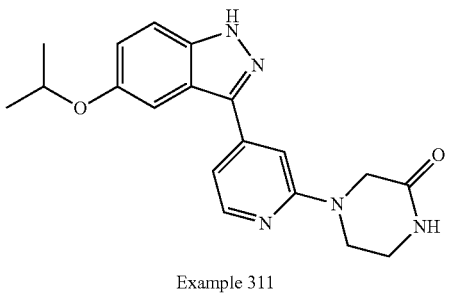

Example 311

To a solution of the product prepared in Step 2 (90 mg, 0.152 mmol) in CH$_2$Cl$_2$ (5 ml) was added water (0.5 ml) and TFA (2.5 ml). The resulting mixture was stirred at room temperature overnight. The reaction was then evaporated and partitioned between CH$_2$Cl$_2$ and saturated NaHCO$_3$ (aq). The organic layer was evaporated to afford a residue which was purified by C18 reversed-phase column chromatography (Biotage SP-1, MPLC, gradient elution, 100% water+0.1% TFA to 100% acetonitrile+0.1% TFA) to afford Example 311 (LCMS (ESI) m/z 352 (Ret.=1.84 min, LCMS method e)) as a solid TFA salt.

TABLE AX

Using the method outlined in Step 1 of Scheme AX, substituting 4-(4,4,5,5-tetramethyl-1,3,2-dioxaborolan-2-yl)pyridin-2-amine for (2-fluoropyridin-4-yl)boronic acid, the following intermediate was prepared

| Intermediate Number | Intermediate |
|---|---|
| AX1 | 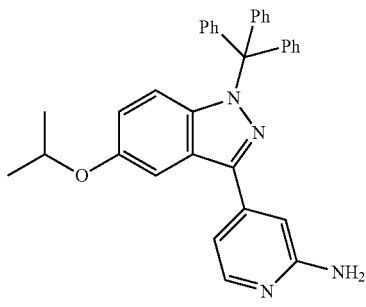 [SMILES: CC(C)Oc1ccc2c(c1)c(-c1ccnc(N)c1)nn2C(c1ccccc1)(c1ccccc1)c1ccccc1] |

Scheme AY

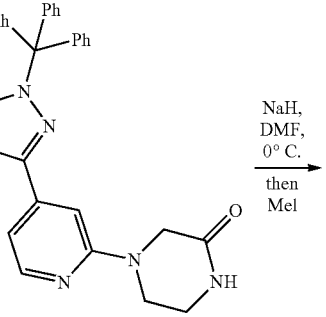

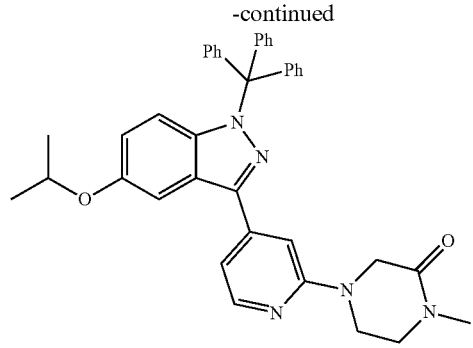

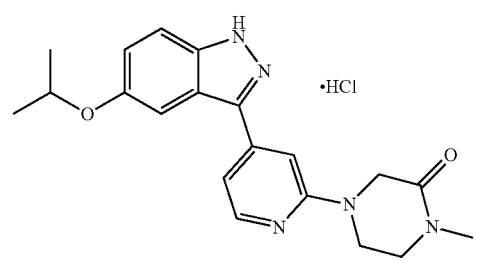

Example 312

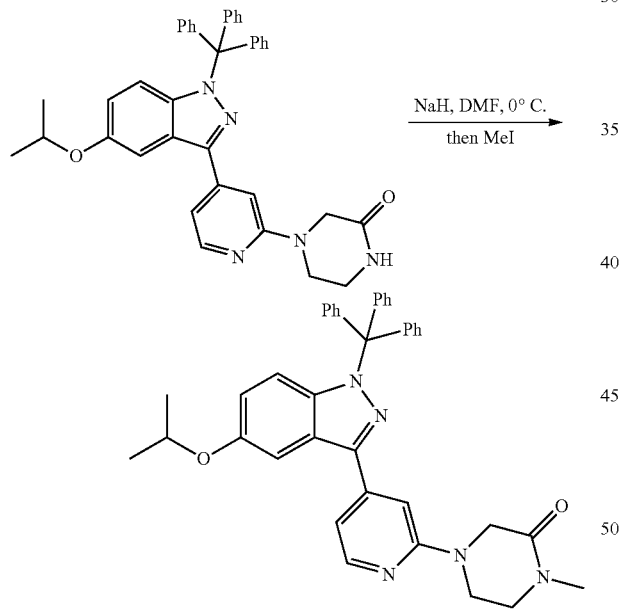

To a cold (0° C.), stirred suspension of NaH (5.05 mg, 0.126 mmol) in DMF (1 ml) was added a solution of the compound prepared in Step 2 of Scheme AX (50 mg, 0.084 mmol) in THF (0.2 ml). After 15 min at 0° C. MeI (10.53 µl, 0.168 mmol) was added in one portion and the mixture was stirred at 0° C. for 1 h and then at RT overnight. The reaction was quenched with water and extracted with EtOAc (×3). The combined organic layers were washed with brine (×2), dried over anhydrous magnesium sulfate, filtered and concentrated to leave a residue which was purified by PTLC (silica gel, eluted with 10:1 DCM:MeOH) to yield the desired product.

Step 2

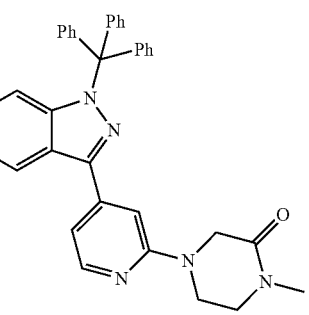

Example 312

A solution of the compound prepared in Step 1 (280 mg, 0.46 mmol) in a mixture of water (0.5 mL) and CH$_2$Cl$_2$ (5 mL) was treated with TFA (2.5 mL). The resulting mixture was stirred overnight at RT. The reaction was carefully quenched with NaHCO$_3$, diluted with water and extracted with CH$_2$Cl$_2$ (×3). The organic layers were dried over anhydrous magnesium sulfate, filtered and evaporated to afford a crude residue which was purified by silica gel column chromatography (isocratic elution, 10:1 CH$_2$Cl$_2$: MeOH). The resulting partially-purified material was subjected to C18 reversed-phase MPLC (Biotage SP-1, gradient elution 0% to 100% MeCN in water with 0.1% TFA) to afford Example 312 (LCMS (ESI) m/z 366 (Ret.=1.97 min, LCMS method e)).

Scheme AZ

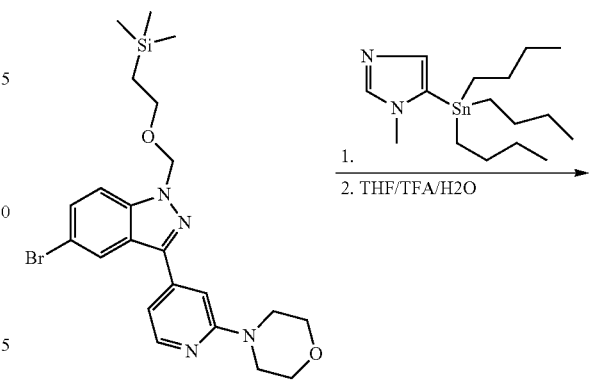

Example 313

Example 314

A solution of the compound prepared in Step 3, Scheme D (280 mg, 0.57 mmol), 1-methyl-5-(tributylstannyl)-1H-imidazole (340 mg, 0.92 mmol) and tetrakis(triphenylphosphine)palladium (0) (312 mg, 0.114 mmol) in toluene was heated at 110° C. overnight with stirring. The reaction was cooled, filtered and concentrated. The resulting residue was dissovled in a mixture of THF (1 mL), TFA (3 mL) and water (200 µl). The mixture was sealed and microwaved at 100° C. for 30 min. The reaction was cooled, unsealed and concentrated. The resulting residue was basified by the addition of 7N NH$_3$ in MeOH (10 mL). The solution was concentrated to afford a residue, which was subjected to PTLC on silica gel (5% 7N NH$_3$ in MeOH/DCM) to afford Example 313 (LCMS (ESI) m/z 361 (Ret.=1.56 min, LCMS method e)) as a white solid.

Scheme AAA

A solution of N-Iodosuccinimide (4.00 g, 12.4 mmol) and 5-bromo-indazole (2.00 g, 10.2 mmol) in MeCN (15 mL) was sealed in a glass microwave vessel. The vessel was heated in a microwave reactor for 20 minutes at 105° C. The reaction was cooled to room temperature and unsealed. Triethylamine (2 mL), Boc$_2$O (3.32 g, 15.2 mmol), DMAP (100 mg), methanol (10 mL) and CH$_2$Cl$_2$ (10 mL) were added to the reaction mixture. The resulting mixture was stirred at RT for 5 hours. Concentration of the reaction in vacuo afforded a crude residue which was subjected to silica gel chromatography (ISCO MPLC, gradient elution 0%-2% MeOH in CH$_2$Cl$_2$) to afford the desired product.

Step 2

-continued

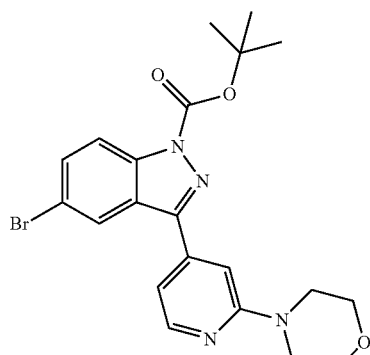

A stirred solution of the intermediate prepared in Step 1 (1 g, 2.37 mmol), (2-morpholinopyridin-4-yl)boronic acid (517 mg, 2.49 mmol), $K_2CO_3$ (11.02 ml, 22.04 mmol) and 1,1'-Pd(dppf)$Cl_2$-DCM complex (193 mg, 0.24 mmol) in THF (15 ml) and water (1 mL) in a sealed glass reaction vessel was heated at 80° C. for 4 hours. The reaction was then cooled to room temperature and partitioned between EtOAc and water. The layers were separated and the organic layer was dried over anhydrous sodium sulfate, filtered and evaporated to afford a residue which was purified by column chromatography on silica gel (ISCO MPLC, gradient elution, 0% to 2% MeOH in $CH_2Cl_2$) to give the desired product.

Step 3

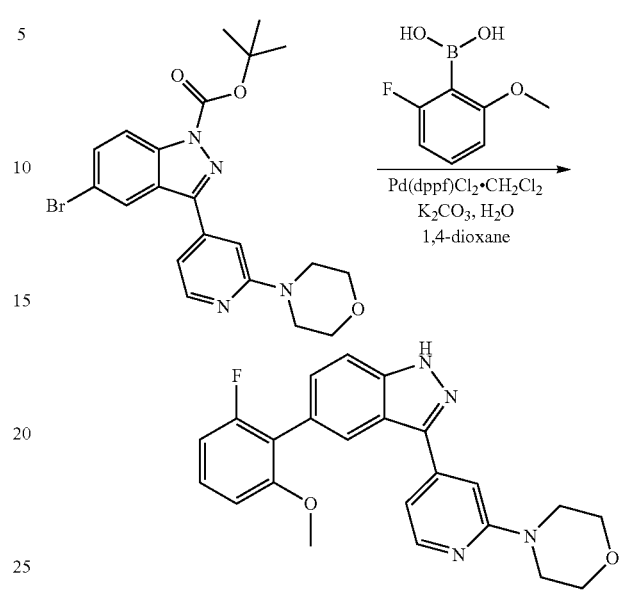

Example 314

The bromoindazole (60 mg, 0.131 mmol), 2-fluoro-6-methoxyphenylboronic acid (33 mg, 0.20 mmol), Pd(dppf)$Cl_2$.DCM complex (21 mg, 0.026 mmol) and potassium carbonate (36 mg, 0.26 mmol) were combined in a mixture of 1,4-dioxane (1.5 mL) and water (0.1 mL) in a microwave vial. The vial was sealed and heated in a microwave reactor at 110° C. for 2 h, then at 130° C. for 30 min. The reaction was cooled, unsealed and concentrated. The residue was purified via PTLC on silica gel to give Example 314 (LCMS (ESI) m/z 405 (Ret.=2.10 min, LCMS method e)) as a yellow solid.

TABLE AAA-1

Using the requisite boronic acid and a method similar to that outlined in Scheme AAA, the following Examples were prepared:

| Ex | Structure | LCMS Cond. | RT (min) | m/z | LRRK2 $IC_{50}$ (nM) |
|---|---|---|---|---|---|
| 315 | | e | 1.70 | 374 | 39 |

TABLE AAA-1-continued

Using the requisite boronic acid and a method similar to that outlined in Scheme AAA, the following Examples were prepared:

| Ex | Structure | LCMS Cond. | RT (min) | m/z | LRRK2 IC$_{50}$ (nM) |
|---|---|---|---|---|---|
| 316 | 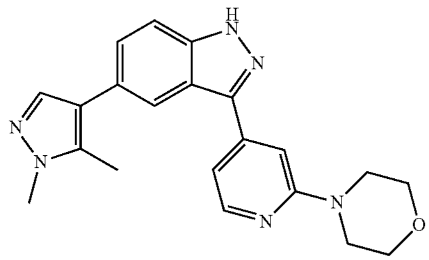 [SMILES: Cc1c(-c2ccc3[nH]nc(-c4ccnc(N5CCOCC5)c4)c3c2)cnn1C] | e | 1.92 | 375 | 2.1 |
| 317 | 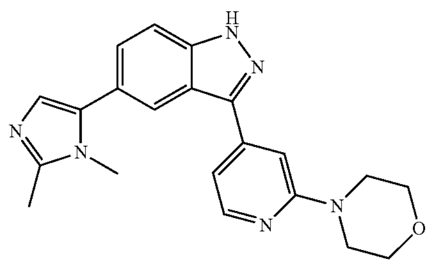 [SMILES: Cc1ncc(-c2ccc3[nH]nc(-c4ccnc(N5CCOCC5)c4)c3c2)n1C] | e | 1.61 | 375 | 1.4 |
| 318 | 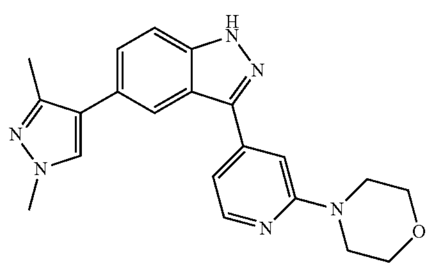 [SMILES: Cc1nn(C)cc1-c1ccc2[nH]nc(-c3ccnc(N4CCOCC4)c3)c2c1] | e | 1.89 | 375 | 17 |
| 319 | 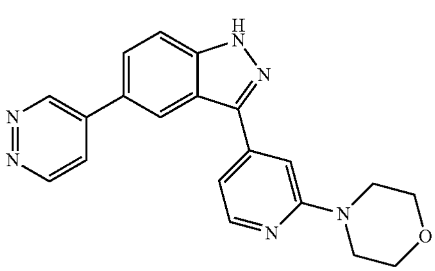 [SMILES: c1cc(-c2ccc3[nH]nc(-c4ccnc(N5CCOCC5)c4)c3c2)cnn1] | e | 1.75 | 359 | 8.2 |

TABLE AAA-1-continued

Using the requisite boronic acid and a method similar to that outlined in Scheme AAA, the following Examples were prepared:

| Ex | Structure | Cond. | LCMS RT (min) | m/z | LRRK2 IC$_{50}$ (nM) |
|---|---|---|---|---|---|
| 320 | 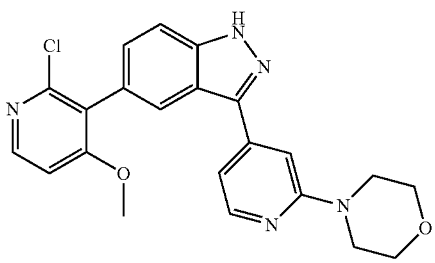 [SMILES: COc1ccnc(Cl)c1-c1ccc2[nH]nc(-c3ccnc(N4CCOCC4)c3)c2c1] | e | 1.89 | 422 | <0.60 |
| 321 | 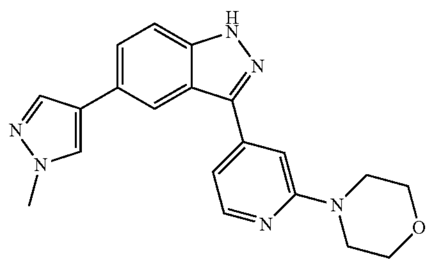 [SMILES: Cn1cc(-c2ccc3[nH]nc(-c4ccnc(N5CCOCC5)c4)c3c2)cn1] | e | 1.83 | 361 | <0.60 |
| 322 | 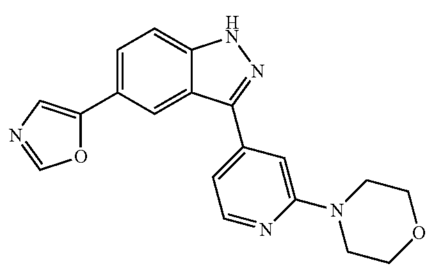 [SMILES: c1cc(-c2n[nH]c3ccc(-c4cncs4)cc23)cc(N2CCOCC2)n1] | f | 1.30 | 348 | 0.66 |

TABLE AAA-2

Using a method similar to that outlined in Scheme AAA with the following changes: Exchanging 5-bromo-6-fluoro-indazole for 5-bromo-indazole in Step 1, Exchanging 1,4-dioxane for THF and heating at 120° C. instead of 80° C. in Step 2 and Exchanging 4-methoxy-3-(4,4,5,5-tetramethyl-1,3,2-dioxaborolan-2-yl)pyridine for 2-fluoro-6-methoxyphenylboronic acid in Step 3, the following example was prepared:

| Ex | Structure | Cond. | LCMS RT (min) | m/z | LRRK2 IC$_{50}$ (nM) |
|---|---|---|---|---|---|
| 323 | 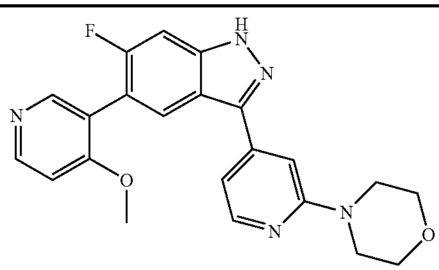 | i | 1.64 | 406 | <0.60 |

TABLE AAA-3

Using a method similar to that outlined in Scheme AAA Steps 1 and 2 with the following changes: Exchanging 5-bromo-6-fluoro-indazole for 5-bromo-indazole in Step 1 and exchanging 1,4-dioxane for THF and heating at 120° C. instead of 80° C. in Step 2, the following intermediate was prepared:

| Intermediate Number | Intermediate |
|---|---|
| AAA.1 | (structure) |

TABLE AAA-4

Using a method similar to that outlined in Steps 1 and 2 of Scheme AAA with the following changes: Exchanging 6,7-dihydro-1H-[1,4]dioxino[2,3-f]indazole for 5-bromo-indazole in Step 1 and exchanging $Cs_2CO_3$ for $K_2CO_3$ in Step 2, the following intermediate was prepared:

| Intermediate Number | Intermediate |
|---|---|
| AAA.2 | (structure) |

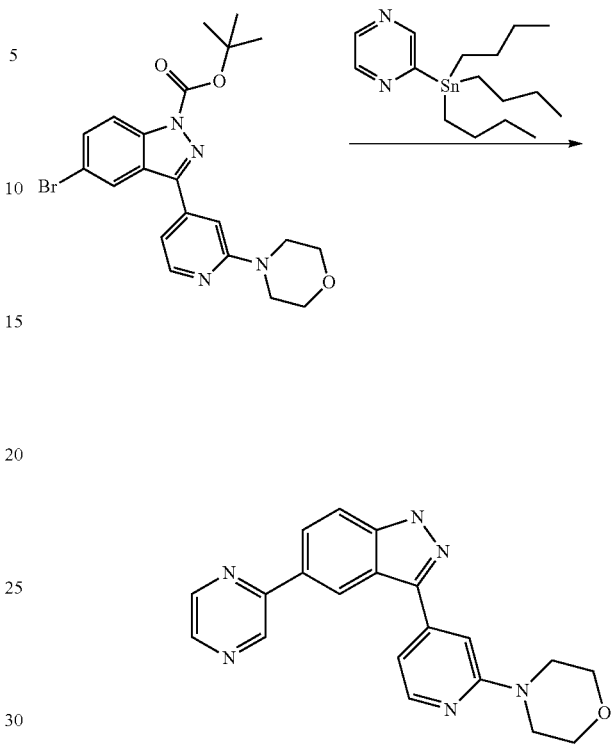

Scheme AAB

Example 324

A solution of the material prepared in Step 2 of Scheme AAA (50 mg, 0.11 mmol), 2-(tributylstannyl)pyrazine (80 mg, 0.22 mmol) and $PdCl_2(PPh_3)_2$ (15 mg, 0.022 mmol) in toluene (1.5 mL) was heated at 110° C. overnight with stirring. The reaction was cooled and concentrated to afford a residue, which was subjected to PTLC on silica gel to afford Example 324 (LCMS (ESI) m/z 359 (Ret.=1.90 min, LCMS method e)) as a yellow solid.

TABLE AAB

Using the requisite stannane and a method similar to that outlined in Scheme AAB, the following Examples were prepared:

| Ex | Structure | LCMS Cond. | RT (min) | m/z | LRRK2 $IC_{50}$ (nM) |
|---|---|---|---|---|---|
| 325 | (structure) | i | 2.15 | 348 | 6.9 |

TABLE AAB-continued
Using the requisite stannane and a method similar to that outlined in Scheme AAB, the following Examples were prepared:
| Ex | Structure | Cond. | RT (min) | m/z | LRRK2 IC$_{50}$ (nM) |
|---|---|---|---|---|---|
| 326 | | e | 1.75 | Calc'd 359.2 found: 359 | 6.4 |
| 327 | | e | 1.85 | Calc'd 364.1 Found: 364 | <0.60 |
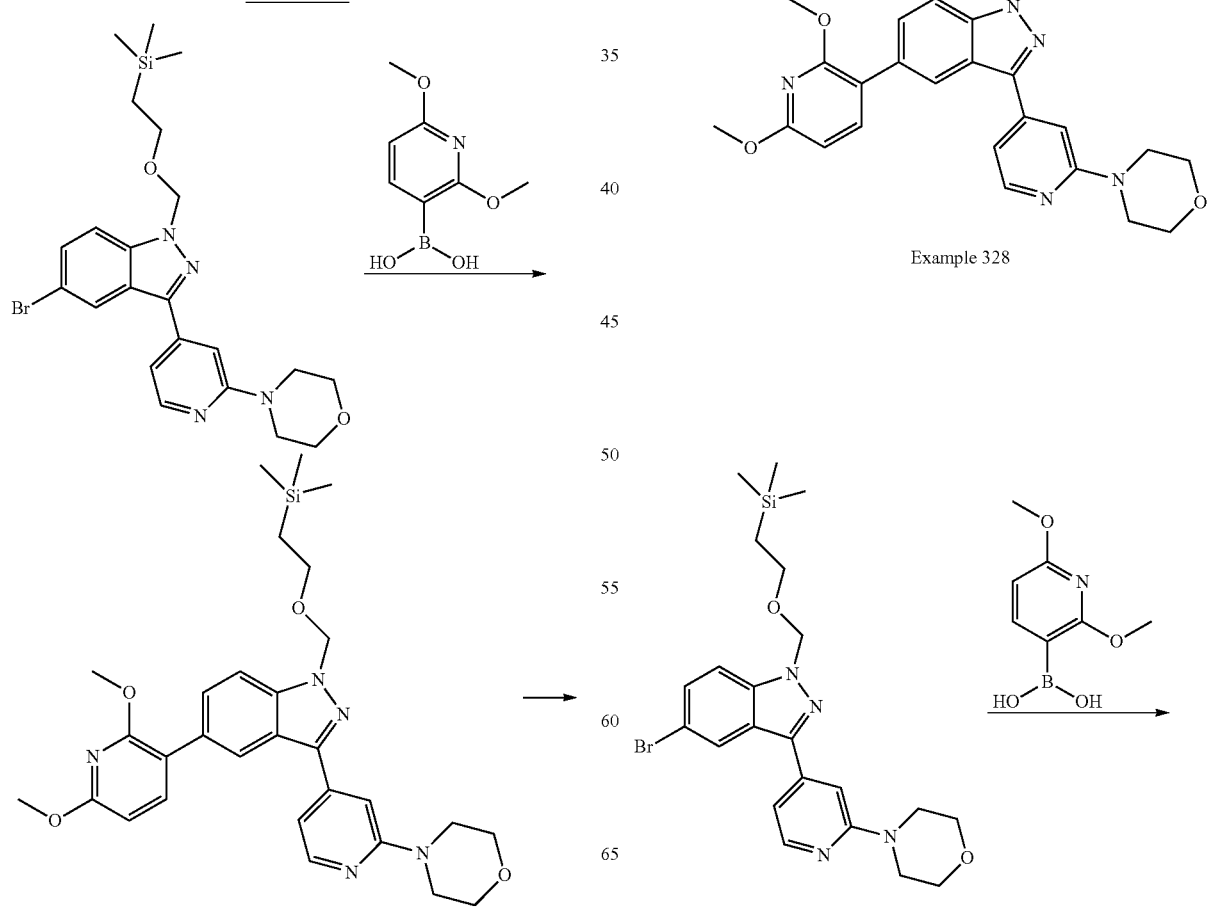
Example 328

-continued

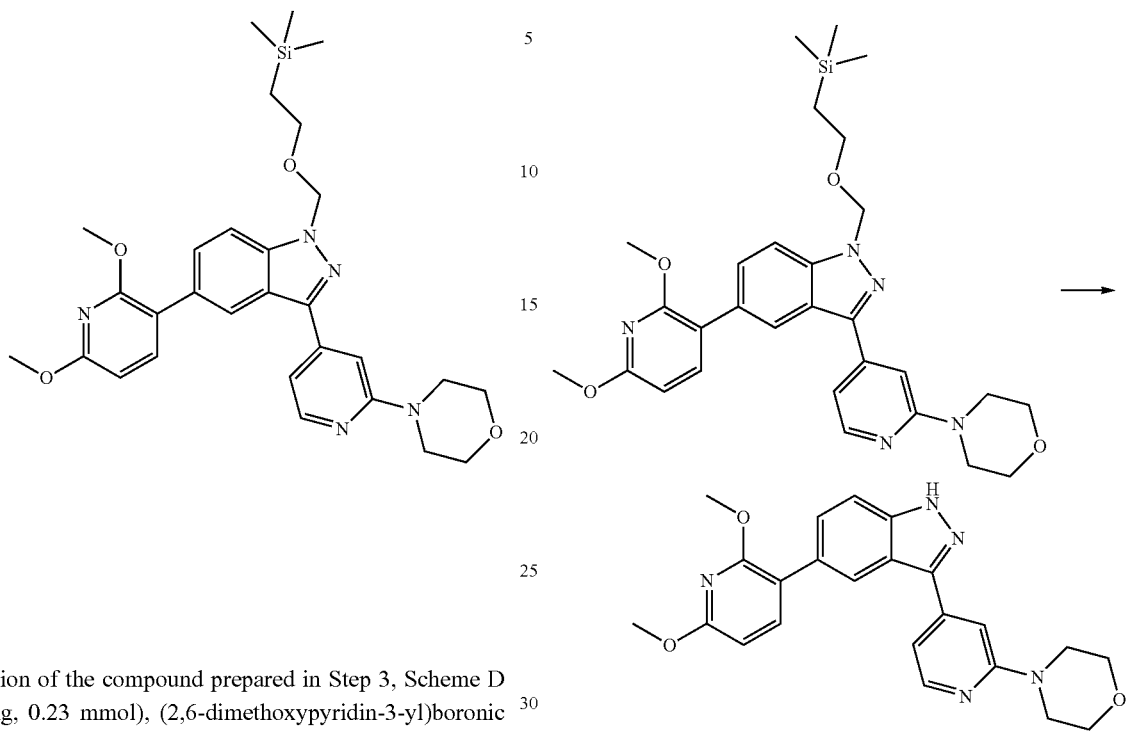

Example 328

A solution of the compound prepared in Step 3, Scheme D (110 mg, 0.23 mmol), (2,6-dimethoxypyridin-3-yl)boronic acid (62 mg, 0.34 mmol), Pd(dppf)Cl$_2$.DCM complex (33 mg, 0.045 mmol) and potassium carbonate (62 mg, 0.45 mmol) were combined in a mixture of 1,4-dioxane (3 mL) and water (0.3 mL). The resulting mixture was heated to 90° C. and stirred for 72 h. The reaction was filtered through a pad of Celite and the Celite pad was washed with CH$_2$Cl$_2$. The filtrate was evaporated to afford the crude product, which was taken on to the next step without further purification.

Step 2

The crude material from Step 1 was dissolved in 1.5 ml THF. To this solution was added 1 ml of TBAF (1.0M in THF) and the mixture was sealed and microwaved at 105° C. for 20 min. The reaction was cooled, unsealed and concentrated. The residue was purified via PTLC on silica gel (20% acetone in DCM) to afford Example 328 as a yellow solid (LCMS method e, Retention Time: 2.09 min, [M+H]+: calc: 418.2. found: 418).

TABLE AAC

Using the requisite boronic acid and a method similar to that outlined in Scheme AAC, the following Example was prepared:

| Ex | Structure | LCMS Cond. | RT (min) | m/z | LRRK2 IC$_{50}$ (nM) |
|---|---|---|---|---|---|
| 329 |  | e | 1.93 | 388 | 14 |

Scheme AAD

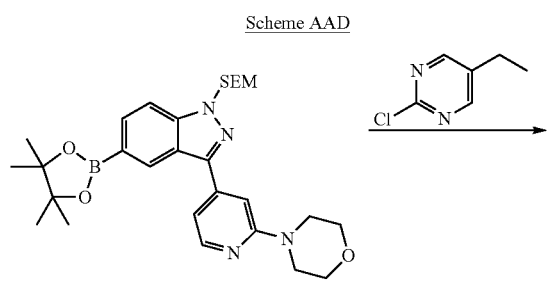

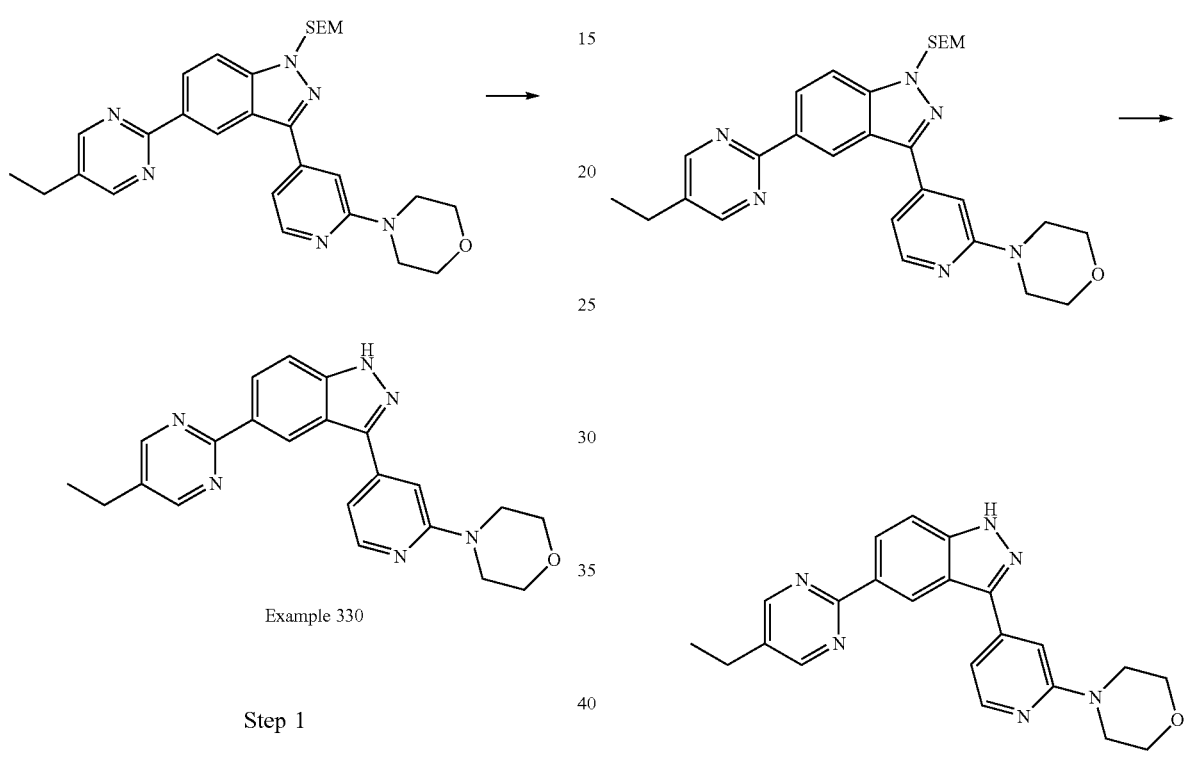

Example 330

Step 1

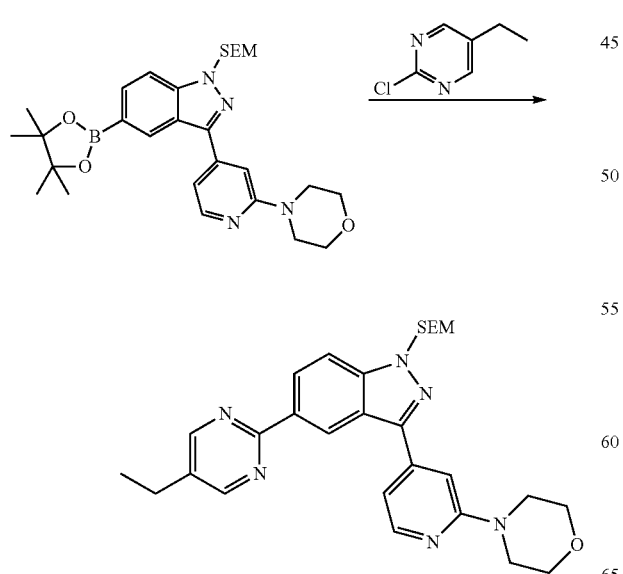

A solution of the Intermediate AW1 (82 mg, 0.15 mmol), 2-chloro-5-ethylpyrimidine (22 mg, 0.15 mmol), Pd(dppf)Cl₂.DCM complex (22 mg, 0.031 mmol) and cesium carbonate (149 mg, 0.46 mmol) were combined in THF (0.8 mL). The resulting mixture was sealed in a glass reaction vessel and was heated at 74° C. and stirred for 2.5 h. The reaction was cooled and concentrated to afford a residue which was purified via PTLC on silica gel (60% EtOAc in hexanes) followed by a second PTLC purification on silica gel (5% MeOH in DCM). The material was then subjected to PTLC purification on silica gel (50% EtOAc in DCM) to afford the desired product.

Example 330

The product prepared in Step 1 (42 mg, 0.081 mmol) was dissolved in 0.41 ml THF. To this solution was added TBAF (1.0M in THF, 0.081 mL, 0.081 mmol) and the mixture was sealed in a glass reaction vessel and was heated at 60° C. for 12 h, followed by stirring at room temperature for 72 h. An additional amount of TBAF (0.16 mL, 2 eq) was added, and the reaction was heated at 60° C. for 5 h. The reaction was cooled to room temperature, unsealed and concentrated. The residue was suspended in 4 mL of pH 7.4 pH K₃PO₄ buffer and was treated with 4 eq. aq. saturated NaClO₄ and stirred for 10 min. The resulting suspension was filtered and the filtrate was extracted twice with EtOAc. The combined organic layers were concentrated to afford a residue, which was purified by PTLC on silica gel (70% EtOAc in DCM) to afford a partially purified material which was subjected to PTLC on silica (30% acetone in hexanes) to afford Example 330 (LCMS (ESI) m/z 387 (Ret.=2.00 min, LCMS method e)).

TABLE AAD
Using the requisite aryl or heteroaryl halide, and a method similar to that outlined in Scheme AAD, the following Examples were prepared:
| Ex | Structure | LCMS Cond. | RT (min) | m/z | LRRK2 IC$_{50}$ (nM) |
|---|---|---|---|---|---|
| 331 | | e | 1.74 | 403 | 59 |
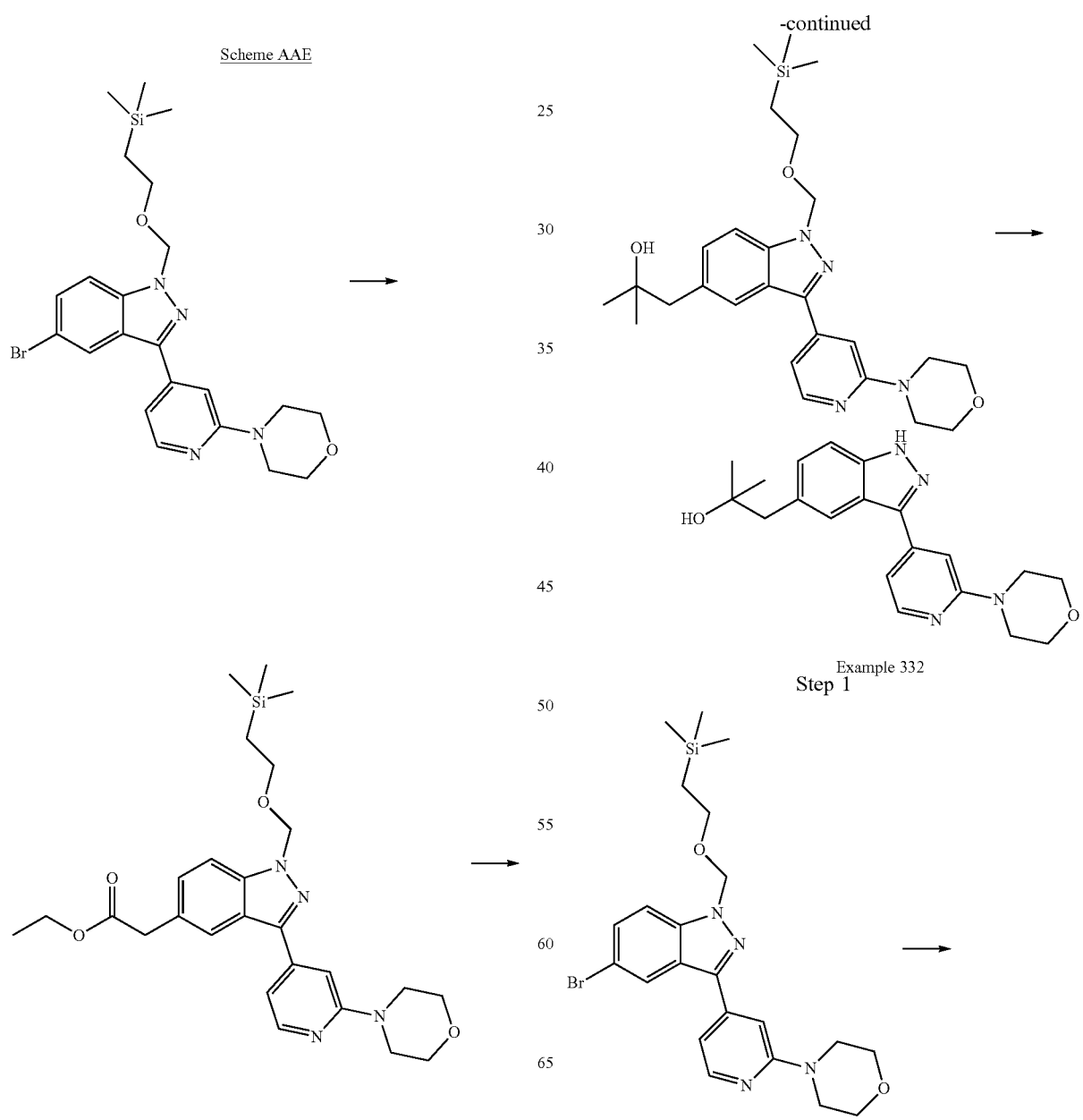
Example 332
Step 1

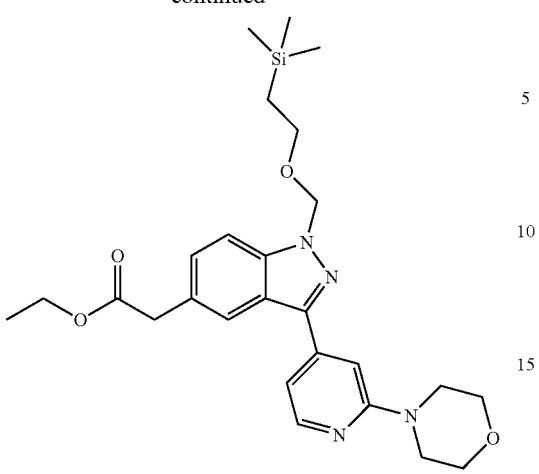

A solution of the compound prepared in Step 3, Scheme D (420 mg, 0.86 mmol), ethyl 3-oxobutanoate (223 mg, 1.72 mmol) palladium (II) acetate (15 mg, 0.069 mmol), di-tert-butyl(2'-methyl-[1,1'-biphenyl]-2-yl)phosphine (40 mg, 0.13 mmol) and K₃PO₄ (364 mg, 1.72 mmol) in toluene was sealed in a glass reaction vessel, heated to 115° C. and stirred for 3 days. The reaction was cooled to rt, unsealed and filtered through a pad of Celite. The Celite pad was washed with 5% MeOH in DCM. The combined filtrates were evaporated and the residue was subjected to PTLC on silica gel (50% EtOAc in hexane) to afford the desired product.

Step 2

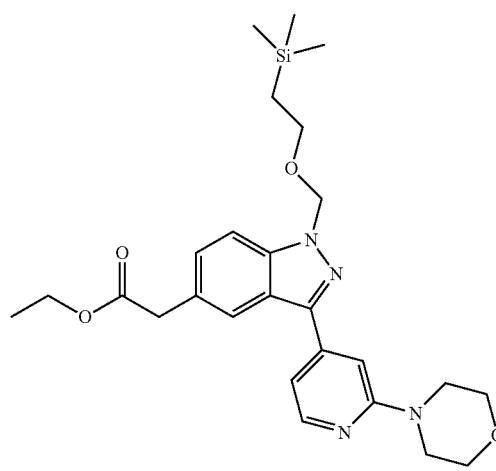

To a solution of the compound prepared in Step 1 (50 mg, 0.10 mmol) in THF (2 mL) was added MeMgBr (0.17 mL, 3M in diethyl ether) at room temperature. The reaction was stirred at rt for 3 hr. The reaction mixture was then partitioned between saturated aqueous NH₄Cl and EtOAc. The layers were separated and the organic layer was dried over anhydrous Na₂SO₄, filtered and evaporated. The resulting crude residue was purified via PTLC on silica gel to afford the desired product.

Step 3

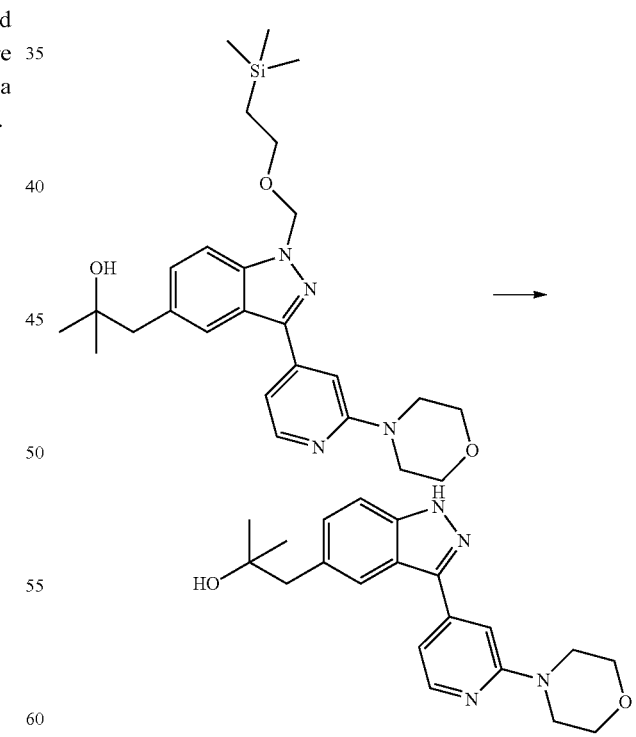

Example 332

A mixture of the product from Step 2 (40 mg) and TBAF (0.30 mL, 1M in THF) in THF (2 mL) was microwaved at 105° C. for 30 min. The reaction was cooled, unsealed and concentrated. The resulting residue was subjected to PTLC on silica gel (40% acetone in hexanes) to afford Example 332 (LCMS (ESI) m/z 353 (Ret.=1.85 min, LCMS method e)) as a yellow solid.

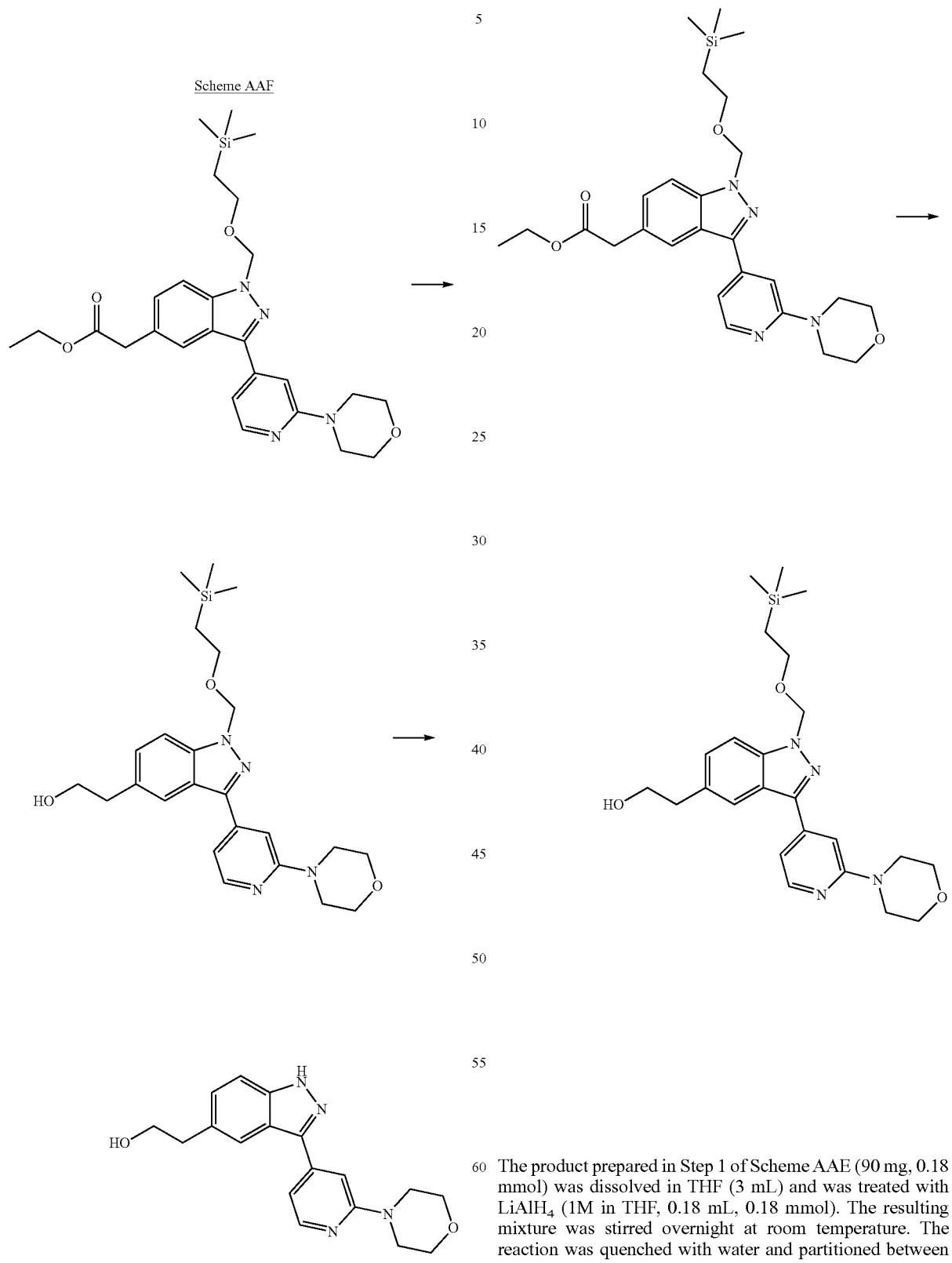

Step 1

The product prepared in Step 1 of Scheme AAE (90 mg, 0.18 mmol) was dissolved in THF (3 mL) and was treated with LiAlH$_4$ (1M in THF, 0.18 mL, 0.18 mmol). The resulting mixture was stirred overnight at room temperature. The reaction was quenched with water and partitioned between water and EtOAc. The organic layer was dried over anhydrous sodium sulfate, filtered and evaporated to afford the desired product as a yellow solid.

305

Step 2

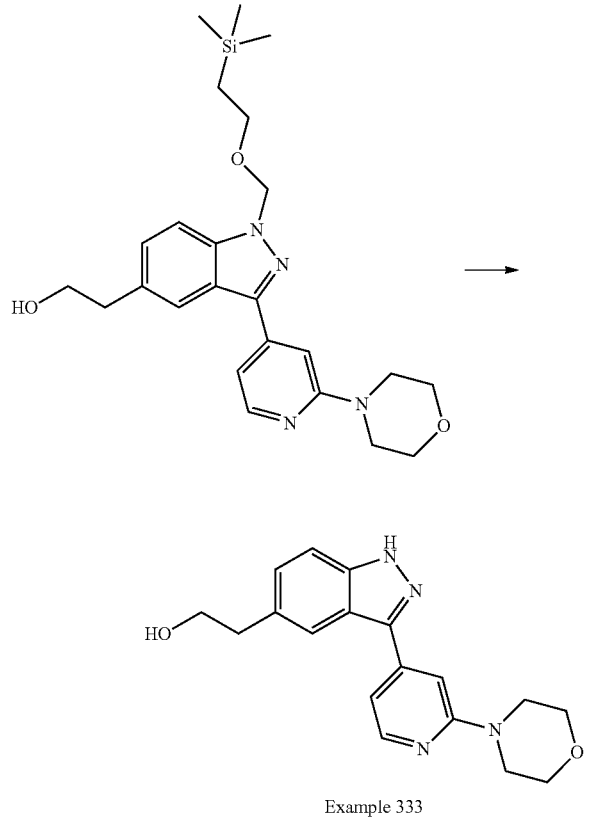

Example 333

Treatment of the product from Step 1 under conditions similar to that described in Step 3 of Scheme AAE afforded Example 333 (LCMS (ESI) m/z 325 (Ret.=1.75 min, LCMS method e)) as a white solid.

Scheme AAG

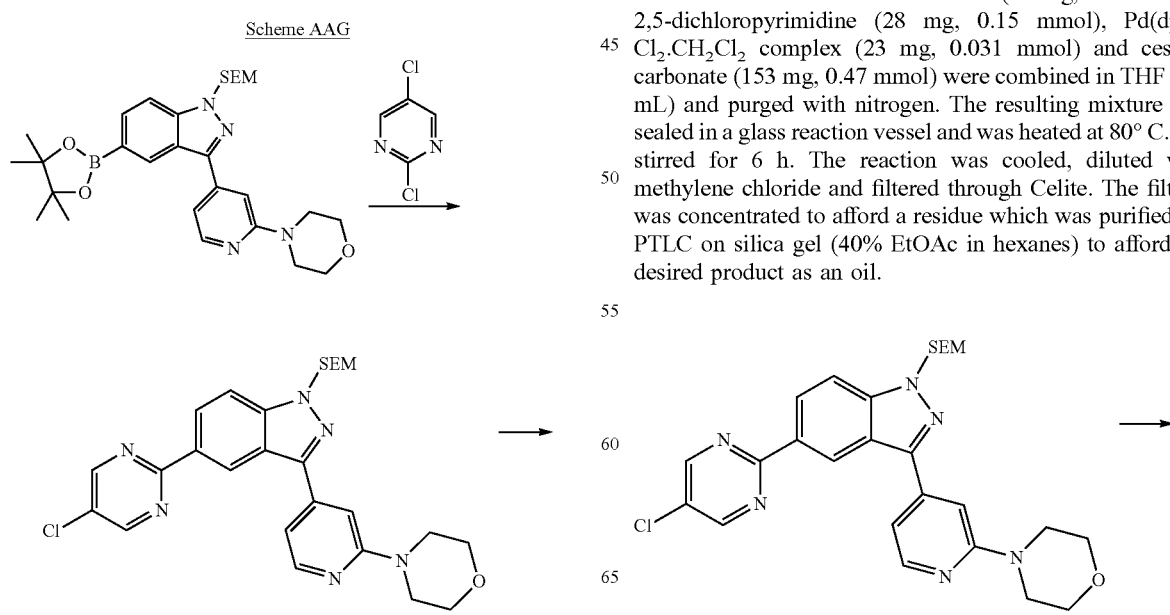

306

-continued

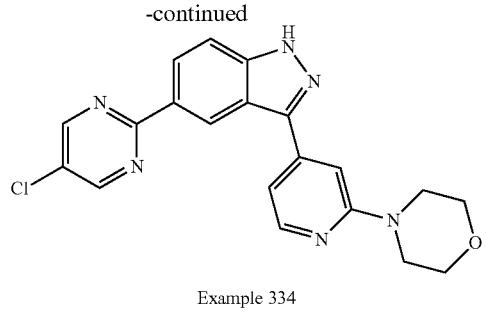

Example 334

Step 1

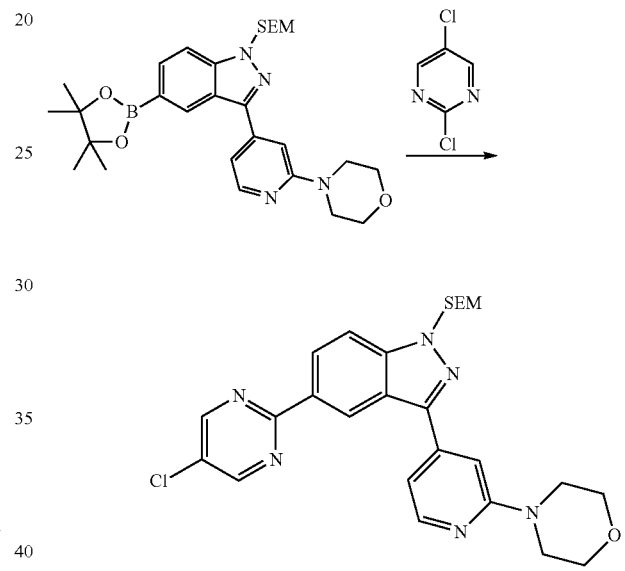

A solution of the Intermediate AW1 (84 mg, 0.16 mmol), 2,5-dichloropyrimidine (28 mg, 0.15 mmol), Pd(dppf) Cl$_2$.CH$_2$Cl$_2$ complex (23 mg, 0.031 mmol) and cesium carbonate (153 mg, 0.47 mmol) were combined in THF (0.8 mL) and purged with nitrogen. The resulting mixture was sealed in a glass reaction vessel and was heated at 80° C. and stirred for 6 h. The reaction was cooled, diluted with methylene chloride and filtered through Celite. The filtrate was concentrated to afford a residue which was purified via PTLC on silica gel (40% EtOAc in hexanes) to afford the desired product as an oil.

-continued

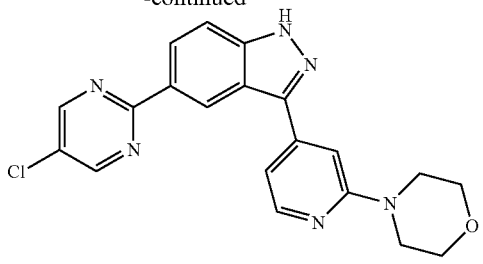

Example 334

The product from Step 1 (48 mg, 0.092 mmol) was dissolved in a combination of MeOH (0.9 mL) and THF (0.9 mL) and was treated with 4N HCl in 1,4-dioxane (0.46 mL). The reaction was sealed and heated at 80° C. for 16 h. Additional amounts of 4N HCl in 1,4-dioxane (0.46 mL), MeOH (0.25 mL) and THF (0.25 mL) were added. The reaction was sealed again and heated overnight at 80° C. The reaction was cooled to room temperature and diluted with $Et_2O$ which resulted in the formation of a precipitate. The solid was collected via filtration, washed with $Et_2O$ and partitioned between EtOAc and saturated aqueous $NaHCO_3$. The layers were separated and the aqueous layer was extracted twice with EtOAc. The organic layers were combined and concentrated to afford a crude residue which was purified via PTLC on silica gel (60% EtOAc in $CH_2Cl_2$) to afford Example 334 (LCMS (ESI) m/z 393 (Ret.=2.04 min, LCMS method e)) as a white solid.

TABLE AAG

Using the requisite aryl halide and boronic ester and a method similar to that outlined in Scheme AAG, the following Examples were prepared:

| Ex | Structure | LCMS Cond. | RT (min) | m/z | LRRK2 $IC_{50}$ (nM) |
|---|---|---|---|---|---|
| 335 | 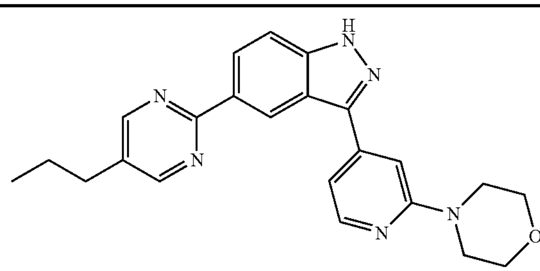 | e | 2.08 | 401 | 5.4 |
| 336 | 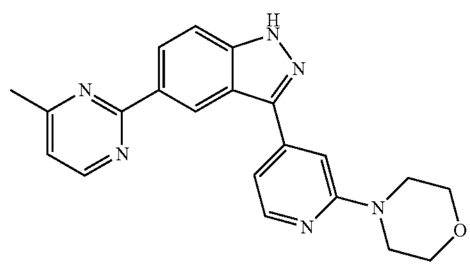 [SMILES: Cc1ccnc(-c2ccc3[nH]nc(-c4ccnc(N5CCOCC5)c4)c3c2)n1] | e | 1.93 | 373 | 33 |
| 337 | 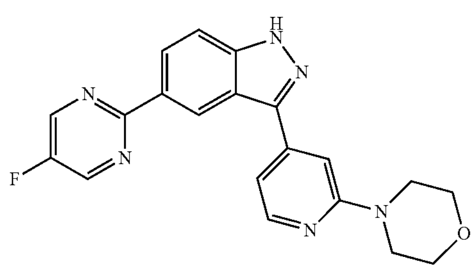 [SMILES: Fc1cnc(-c2ccc3[nH]nc(-c4ccnc(N5CCOCC5)c4)c3c2)nc1] | e | 1.97 | 377 | 42 |
| 338 | 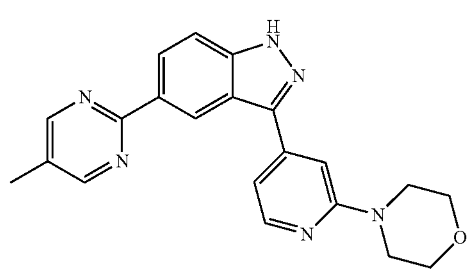 [SMILES: Cc1cnc(-c2ccc3[nH]nc(-c4ccnc(N5CCOCC5)c4)c3c2)nc1] | e | 1.96 | 373 | 8.9 |

TABLE AAG-continued

Using the requisite aryl halide and boronic ester and a method similar to that outlined in Scheme AAG, the following Examples were prepared:

| Ex | Structure | LCMS Cond. | RT (min) | m/z | LRRK2 IC$_{50}$ (nM) |
|---|---|---|---|---|---|
| 339 | 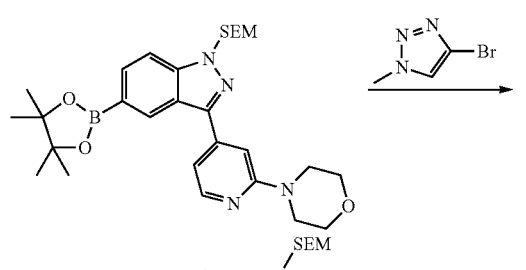 | e | 1.92 | 389 | 22 |

Scheme AAH

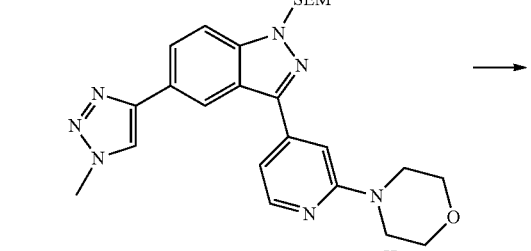

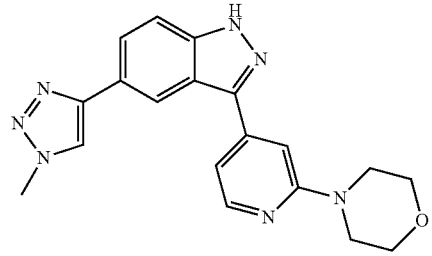

Example 340

Step 1

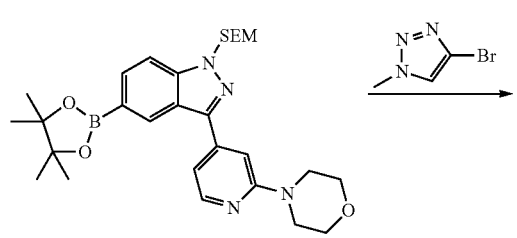

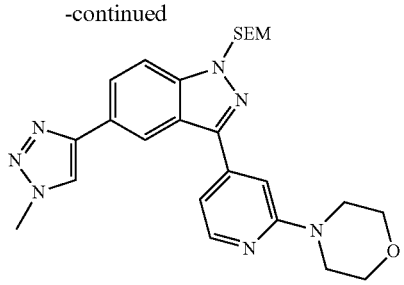

A solution of the Intermediate AW1 (110 mg, 0.21 mmol), 4-bromo-1-methyl-1H-1,2,3-triazole (50 mg, 0.31 mmol), Pd(dppf)Cl$_2$ (30 mg, 0.041 mmol) and potassium carbonate (57 mg, 0.41 mmol) were combined in 1,4-dioxane (1.5 mL). The resulting mixture was heated at 100° C. overnight. The reaction was cooled and the solids were removed via filtration. The filtrate was concentrated to afford the crude product, which was used in the next step without further purification.

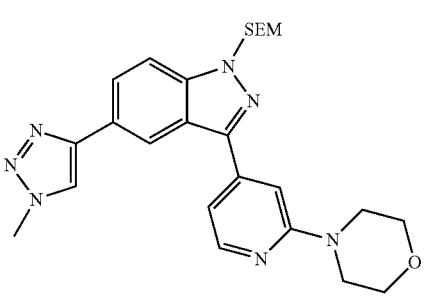

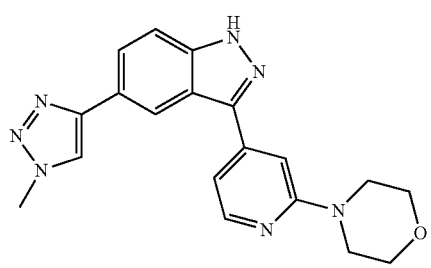

Example 340

The crude material prepared in Step 1 was dissolved in 1 ml THF. To this solution was added TFA (3 mL) and water (0.3 mL). The mixture was sealed in a glass reaction vessel and was heated at 100° C. for 2 h. The reaction was concentrated and the resulting residue was dissolved in 7M ammonia in methanol (5 mL). The mixture was then concentrated and the crude residue was subjected to PTLC on silica gel (5% (7M ammonia in methanol) in methylene chloride) to afford Example 340 (LCMS (ESI) m/z 362 (Ret.=1.78 min, LCMS method e)) was a yellow solid.

TABLE AAH

Using the requisite aryl bromide and boronic ester and a method similar to that outlined in Scheme AAH, the following Examples were prepared:

| Ex | Structure | LCMS Cond. | RT (min) | m/z | LRRK2 IC$_{50}$ (nM) |
|---|---|---|---|---|---|
| 341 | 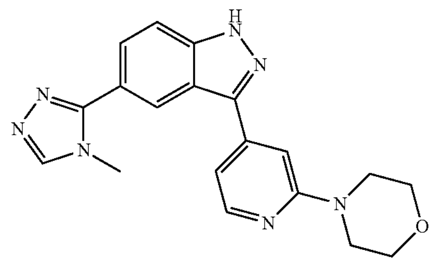 [SMILES: Cn1cnnc1-c1ccc2[nH]nc(-c3ccnc(N4CCOCC4)c3)c2c1] | e | 1.06 | 362 | 1.4 |

TABLE AAI

Using the appropriate aryl bromide and boronic ester and a coupling method similar to that outlined in Step 1 of Scheme AAH, followed by deprotection in a manner similar to that outlined in Step 2 of Scheme AAC, the following Example was prepared:

| Ex | Structure | LCMS Cond. | RT (min) | m/z | LRRK2 IC$_{50}$ (nM) |
|---|---|---|---|---|---|
| 342 | 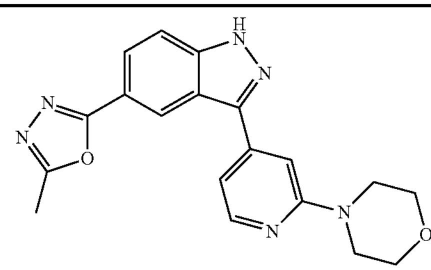 | e | 1.87 | 363 | 0.61 |

Scheme AAJ

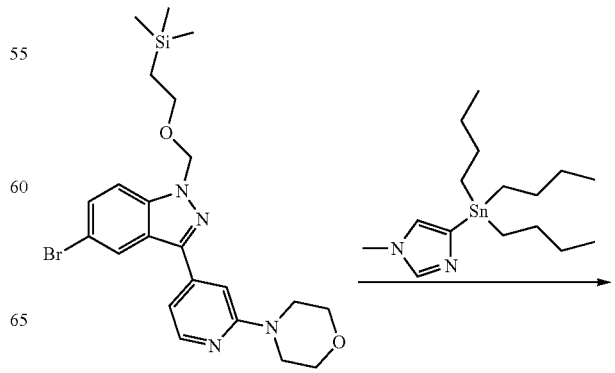

313
-continued

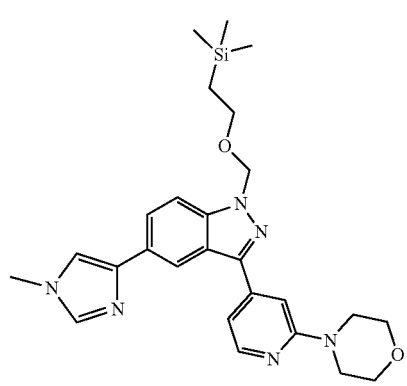

314
-continued

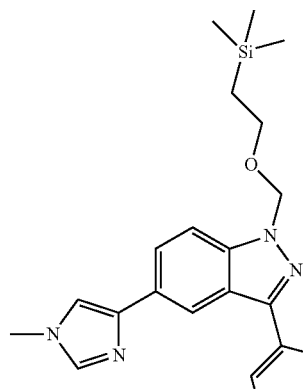

A solution of the compound prepared in Step 3, Scheme D (100 mg, 0.20 mmol), 1-methyl-4-(tributylstannyl)-1H-imidazole (152 mg, 0.41 mmol) and $PdCl_2(PPh_3)_2$) (22 mg, 0.031 mmol) in toluene (1.5 mL) was heated at 120° C. overnight with stirring. The reaction was cooled and concentrated to afford a residue, which was subjected to PTLC on silica gel to afford the desired product.

Step 2

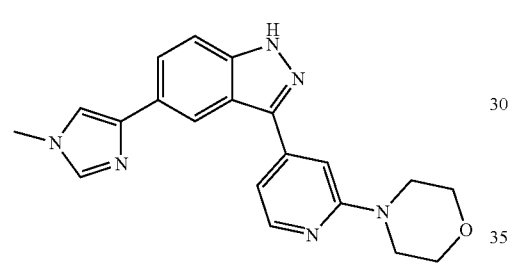

Example 343

Step 1

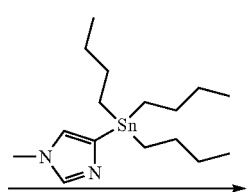

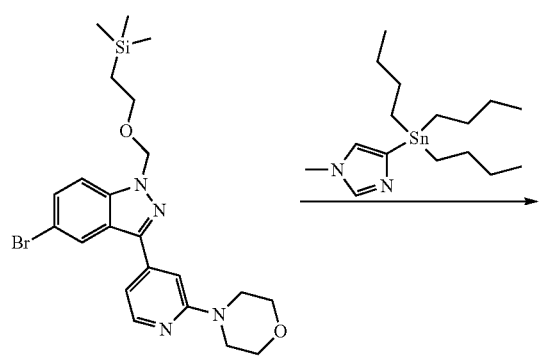

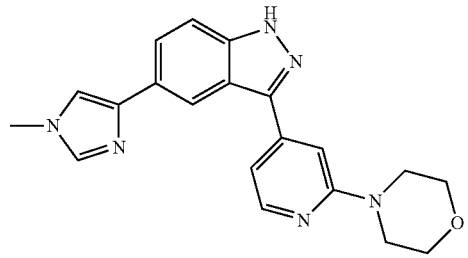

Example 343

Utilizing a method similar to that described in Scheme AAH, Step 2, Example 343 (LCMS (ESI) m/z 361 (Ret.=1.69 min, LCMS method e)) was afforded as a yellow solid.

TABLE AAK
Using the appropriate aryl halide and boronic ester and a coupling method similar to that outlined in Step 1 of Scheme AAC, followed by deprotection in a manner similar to that outlined in Step 2 of Scheme AAH, the following Examples were prepared:
| Ex | Structure | Cond. | LCMS RT (min) | m/z | LRRK2 IC$_{50}$ (nM) |
|---|---|---|---|---|---|
| 344 | | e | 1.82 | 347 | <0.60 |
| 345 | | e | 1.91 | 361 | 18 |
| 346 | | e | 1.83 | 347 | <0.60 |
Scheme AAL
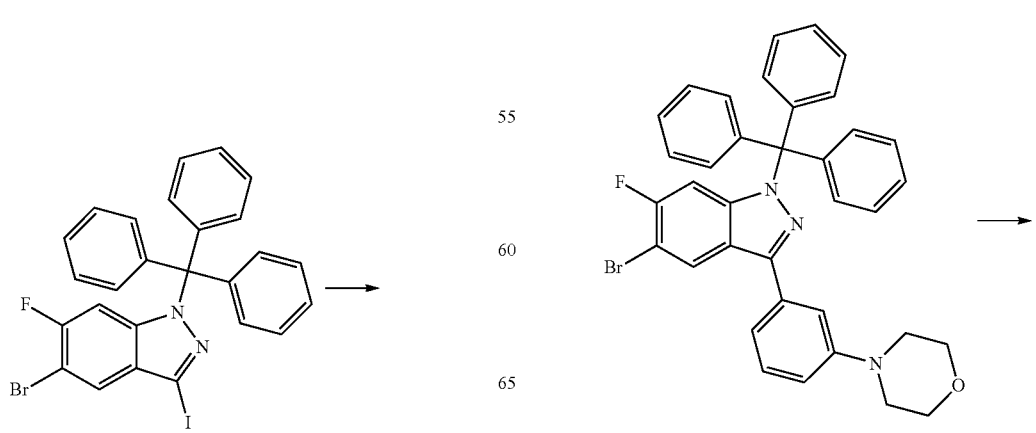

-continued

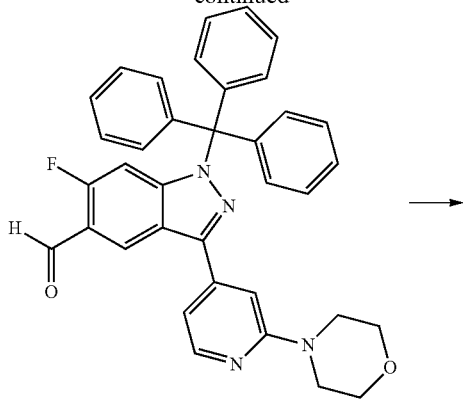

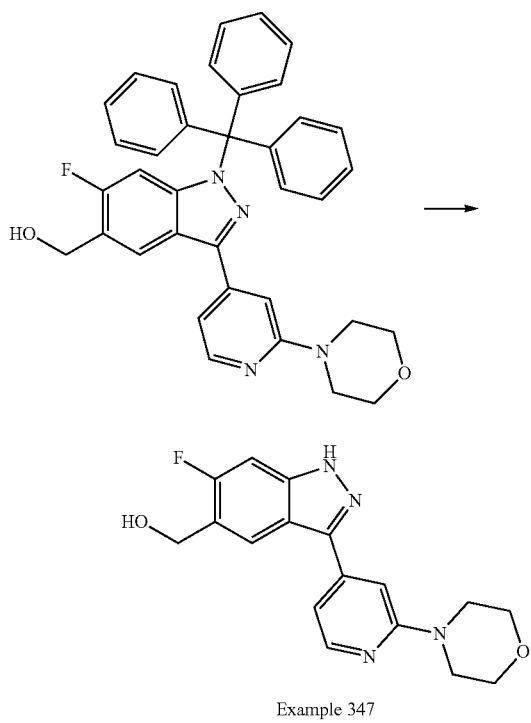

Example 347

Step 1

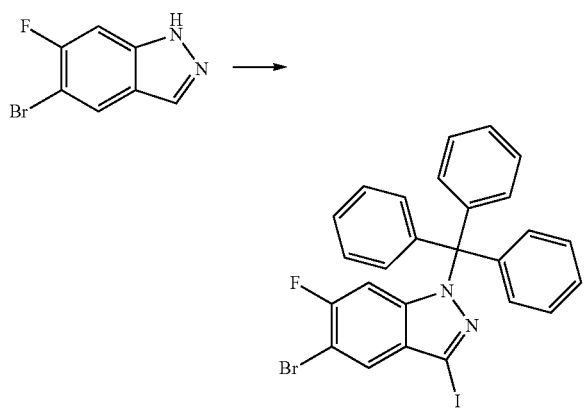

A solution of 5-bromo-6-fluoro-1H-indazole (2 g, 9.30 mmol) and N-iodosuccinimide (2.51 g, 11.16 mmol) were combined with acetonitrile (15 mL) in a sealed microwave vial. The reaction was heated in a microwave reactor at 105° C. for 30 min. The reaction was cooled, unsealed and concentrated to afford the crude iodide. The crude iodide was dissolved in 30 ml of DCM. Trityl chloride (3.89 g, 13.95 mmol) and triethylamine (1.88 g, 18.6 mmol) were added and the resulting mixture was stirred at rt for two days, then at 40° C. for 3 hr. The reaction was concentrated to afford a residue which was purified via silica gel chromatography (20% DCM in hexanes) to afford the desired product as a yellow solid.

Step 2

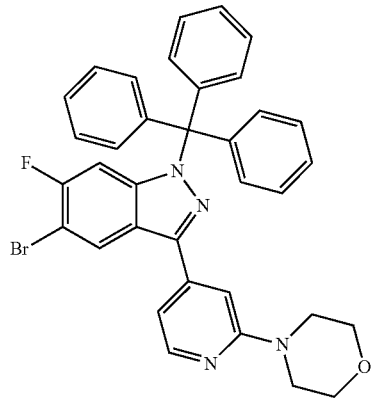

The product prepared in Step 1 (1.3 g, 2.23 mmol), (2-morpholinopyridin-4-yl)boronic acid (464 mg, 2.23 mmol), Pd(dppf)Cl$_2$.CH$_2$Cl$_2$ complex (182 mg, 0.22 mmol) and potassium carbonate (616 mg, 4.46 mmol) were combined in a mixture of 1,4-dioxane (10 mL) and water (1 mL) in a microwave vial. The vial was sealed and heated in a microwave reactor at 80° C. for 3 h. The reaction was cooled, unsealed and filtered through a pad of Celite. The filtrate was concentrated to afford a residue which was subjected to silica gel column chromatography (gradient elution 0% to 40% EtOAc in hexanes) to afford the desired product.

Step 3

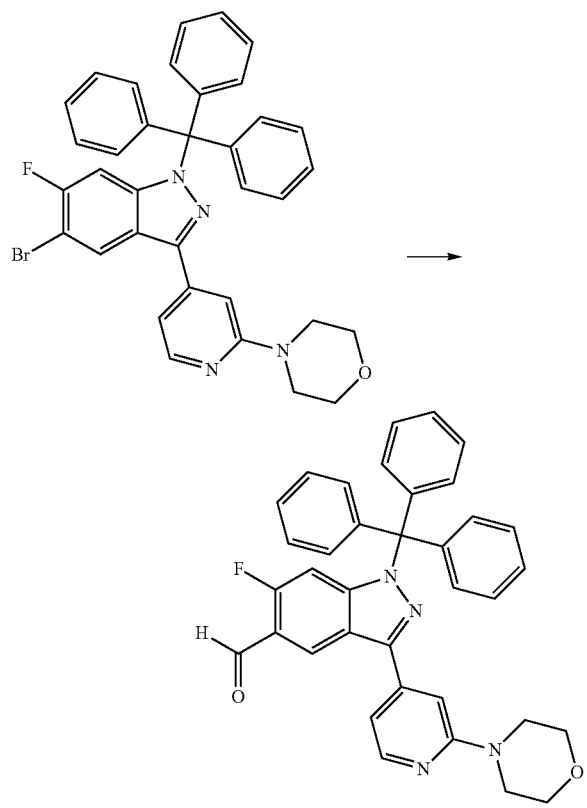

The product from Step 2 (200 mg, 0.32 mmol) was dissolved in THF (4 mL) and cooled to −78° C. To this solution was added n-BuLi (0.19 mL, 0.48 mmol). After stirring for 30 seconds at −78° C., DMF (118 mg, 1.61 mmol) was added and the reaction was stirred for 10 minutes at −78° C. The reaction was then stirred at 0° C. for 20 minutes. The reaction was partitioned between EtOAc and saturated aqueous ammonium chloride. The layers were separated and the organic layer was dried over anhydrous sodium sulfate, filtered and evaporated to afford the crude product, which was used in the next step without further purification.

Step 4

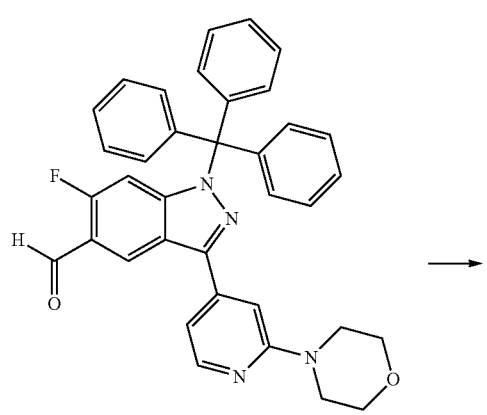

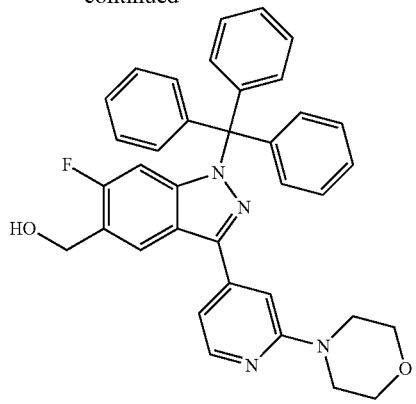

The compound prepared in Step 3 (190 mg, 0.26 mmol) was dissolved in a combination of THF (4 mL) and MeOH (4 mL) and was treated with sodium borohydride (15 mg, 0.39 mmol). After stirring at room temperature for 1 h, the reaction was partitioned between EtOAc and water. The layers were separated and the organic layer was dried over anhydrous sodium sulfate, filtered and evaporated to afford a crude residue which was subjected to PTLC on silica to afford the desired product as a white solid.

Step 5

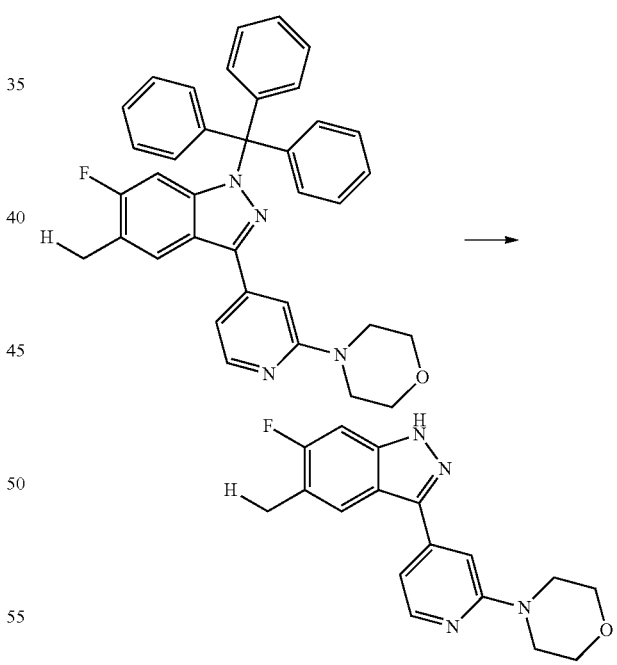

Example 347

The product from Step 4 (110 mg, 0.19 mmol) was dissolved in CH$_2$Cl$_2$ (1 mL) and treated with TFA (1 mL) followed by Et$_3$SiH (0.5 mL). The resulting reaction mixture was stirred at room temperature for 1 h. The reaction was concentrated to afford a crude residue, which was subjected to PTLC on silica gel [5% (7M ammonia in MeOH) in CH$_2$Cl$_2$] to afford Example 347 (LCMS (ESI) m/z 329 (Ret.=1.74 min, LCMS method e)) as a white solid.

TABLE AAL
Using a method similar to that outlined in Scheme AAL, Step 2, replacing (2-morpholinopyridin-4-yl)boronic acid with 2-fluoropyridine-4-boronic acid, the following intermediate was prepared:
| Intermediate Number | Intermediate |
| --- | --- |
| AAL1 | 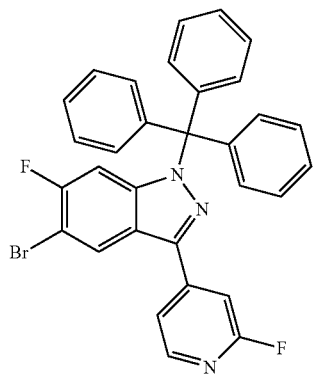 [SMILES: Fc1cc(-c2nn(C(c3ccccc3)(c3ccccc3)c3ccccc3)c3cc(F)c(Br)cc23)ccn1] |
Scheme AAM
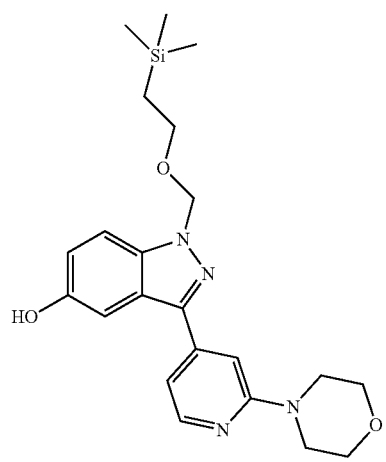
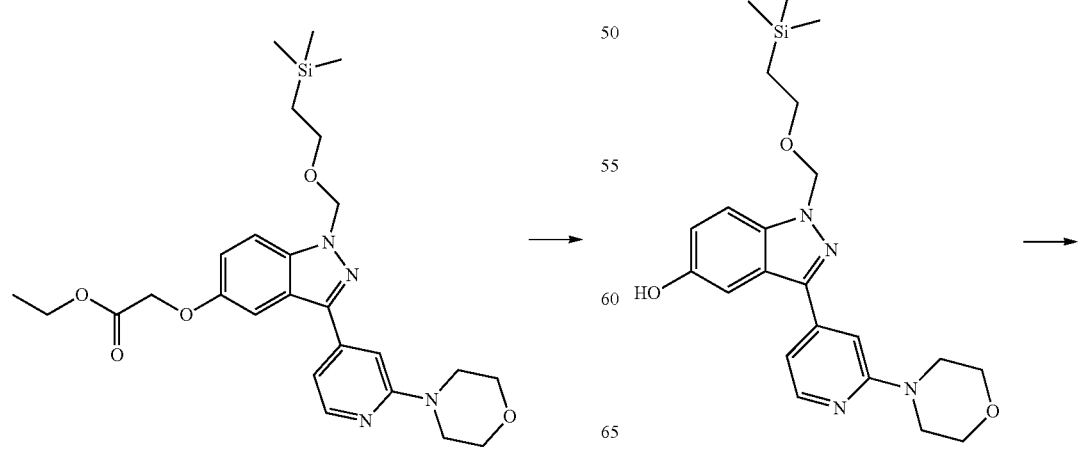
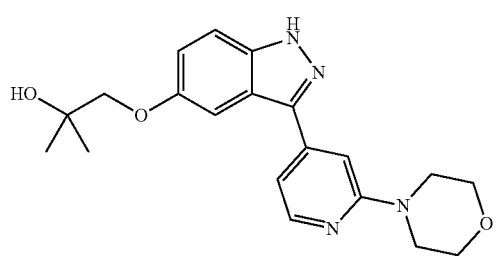
Example 348
Step 1

323
-continued

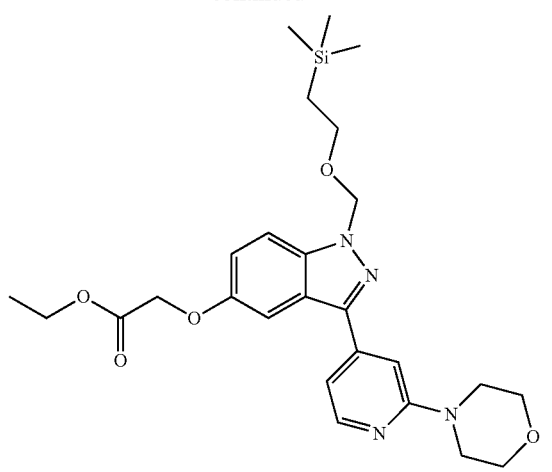

The material prepared in Scheme E, Step 3 (40 mg, 0.094 mmol) was combined with potassium carbonate (65 mg, 0.47 mmol) and ethyl iodoacetate (80 mg, 0.375 mmol) in DMF (2.5 mL). The resulting reaction mixture was stirred overnight at 90° C. The reaction was cooled and ethyl acetate (10 mL) was added to the reaction mixture. The resulting solids were removed via filtration and the filtrate was concentrated to afford the crude product, which was used in the next step without further purification.

Step 2

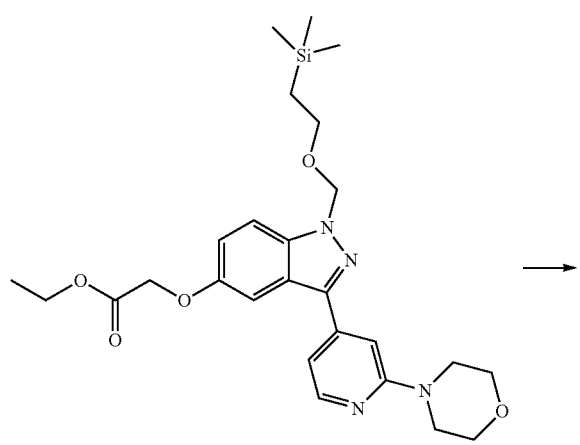

324
-continued

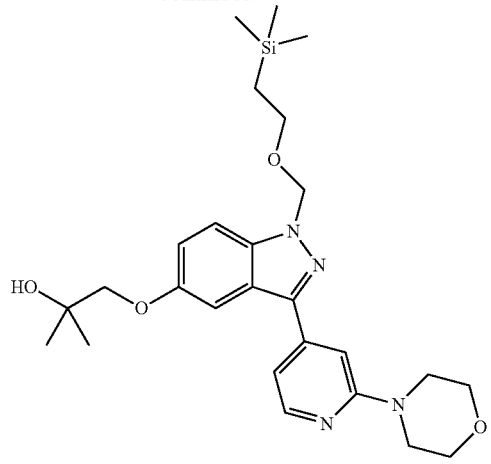

The crude material from Step 1 was dissolved in THF (3 mL) and was treated with methylmagnesium bromide (3M in THF, 0.16 mL). The reaction mixture was stirred at room temperature for 2 h. The reaction mixture was then partitioned between EtOAc and aqueous saturated ammonium chloride. The layers were separated and the organic layer was concentrated to afford a crude residue, which was subjected to PTLC on silica gel to afford the desired product as a solid.

Step 3

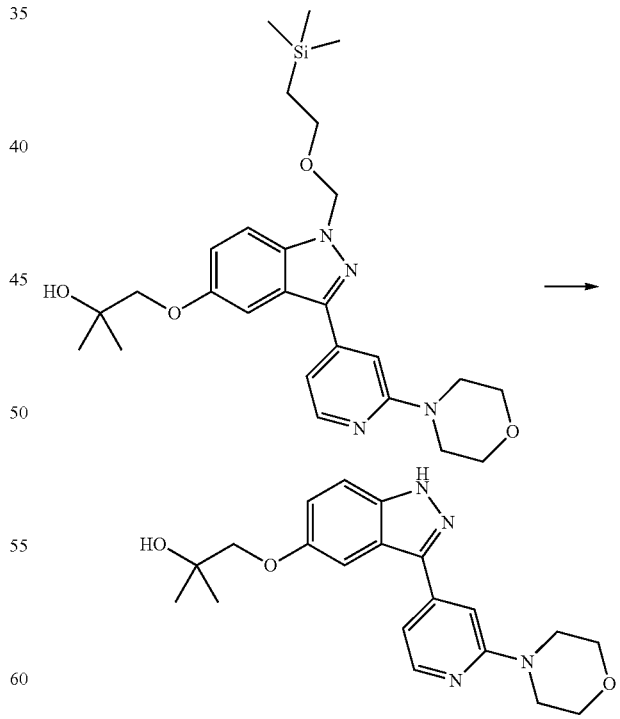

Example 348

The product from Step 2 was deprotected in a manner similar to that described in Scheme AAE, Step 3. The crude product was subjected to PTLC on silica gel (9:1 EtOAc:

hexanes) to afford Example 348 (LCMS (ESI) m/z 369 (Ret.=1.33 min, B128 short HCOOH)) as a yellow solid.

Step 1

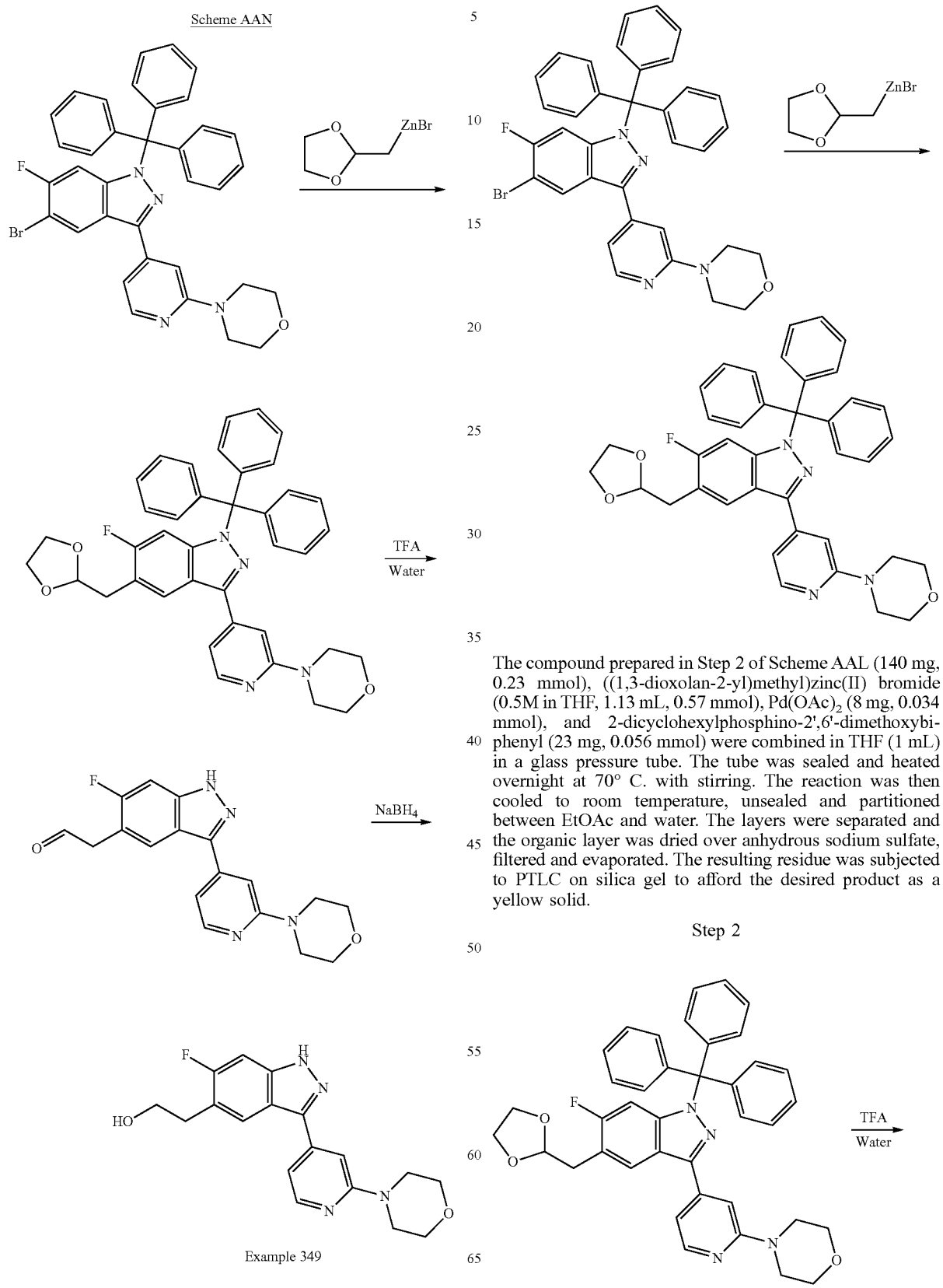

The compound prepared in Step 2 of Scheme AAL (140 mg, 0.23 mmol), ((1,3-dioxolan-2-yl)methyl)zinc(II) bromide (0.5M in THF, 1.13 mL, 0.57 mmol), Pd(OAc)$_2$ (8 mg, 0.034 mmol), and 2-dicyclohexylphosphino-2',6'-dimethoxybiphenyl (23 mg, 0.056 mmol) were combined in THF (1 mL) in a glass pressure tube. The tube was sealed and heated overnight at 70° C. with stirring. The reaction was then cooled to room temperature, unsealed and partitioned between EtOAc and water. The layers were separated and the organic layer was dried over anhydrous sodium sulfate, filtered and evaporated. The resulting residue was subjected to PTLC on silica gel to afford the desired product as a yellow solid.

Step 2

-continued

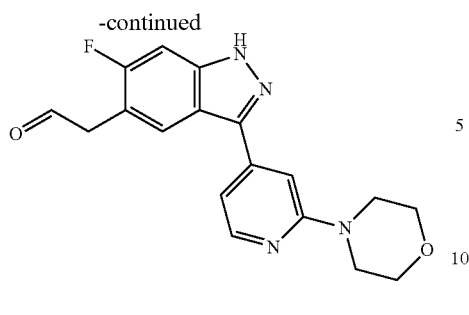

The product from Step 1 (70 mg, 0.11 mmol) was dissolved in a mixture of TFA (2 mL) and water (0.3 mL). The resulting solution was stirred for 3 h. The reaction was then concentrated to afford a crude residue, which was used in the next step without further purification.

Step 3

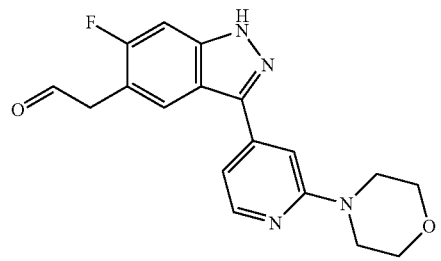

The crude product from Step 2 was dissolved in a mixture of MeOH (2 mL) and THF (2 mL). Sodium borohydride (42 mg, 1.12 mmol) was added and the reaction mixture was stirred at rt for 1 h. The reaction mixture was partitioned between EtOAc and saturated aqueous sodium bicarbonate. The layers were separated and the organic layer was concentrated in vacuo to afford a crude residue, which was subjected to PTLC on silica gel (5% MeOH in DCM) to afford Example 349 (LCMS (ESI) m/z 343 (Ret.=1.82 min, LCMS method e)) as a white solid.

Scheme AAO

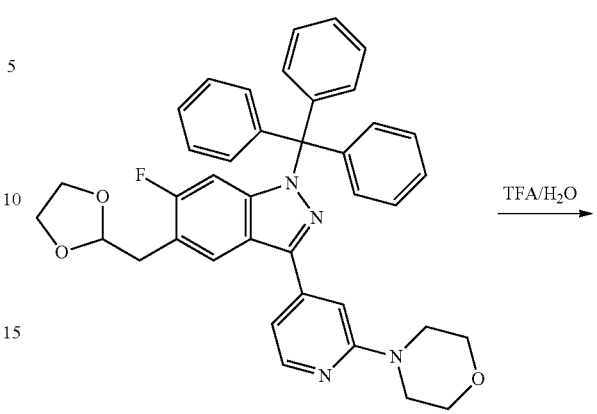

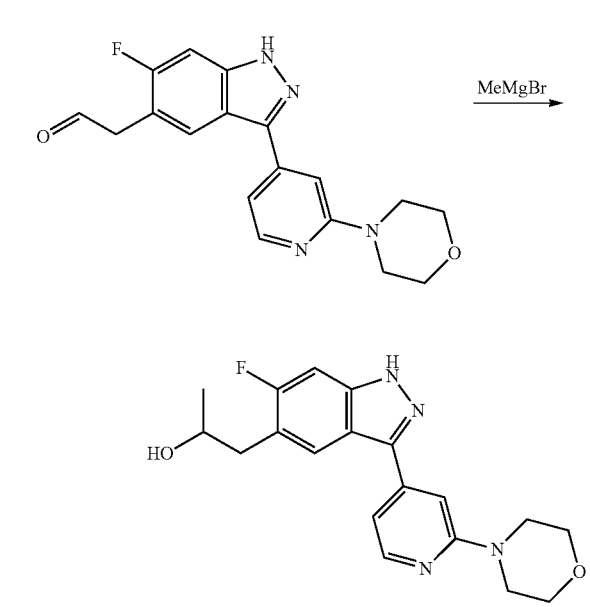

Example 350

Step 1

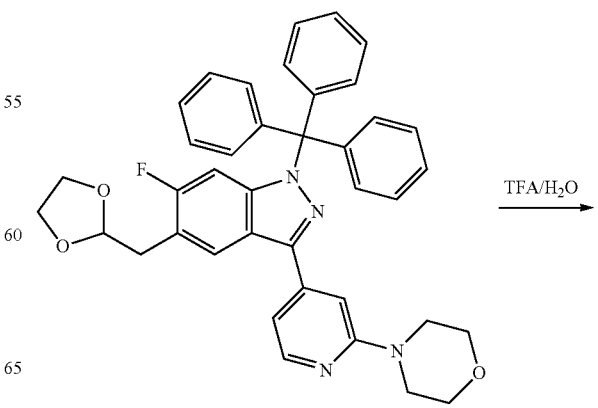

329

-continued

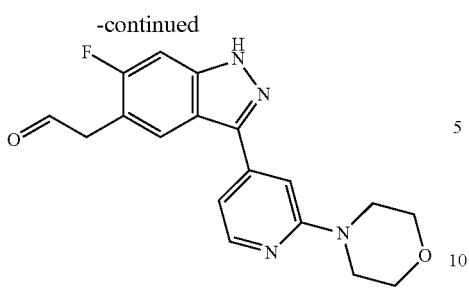

The product from Step 1 of Scheme AAN (40 mg, 0.11 mmol) was dissolved in a mixture of TFA (2 mL) and water (0.3 mL). The resulting solution was stirred for 3 h. The reaction was then concentrated to afford a crude residue, which was partitioned between 1N NaOH and EtOAc. The layers were separated and the organic layer was dried, filtered and concentrated in vacuo to afford a crude residue, which was used without further purification in the next step.

Step 2

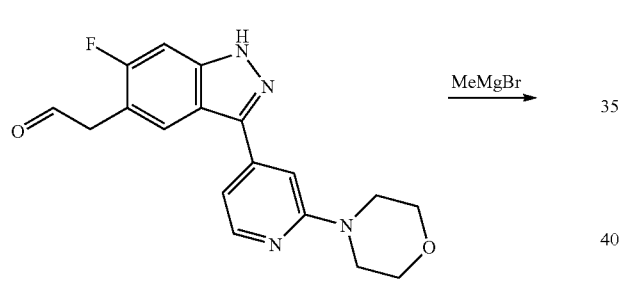

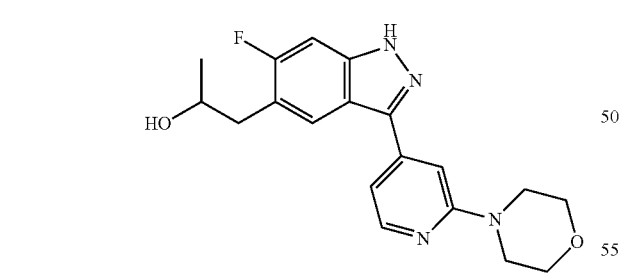

Example 350

The product from Step 1 was dissolved in THF (2 mL) and treated with methylmagnesium bromide (3M in THF, 0.11 mL, 0.32 mmol). The resulting mixture was stirred at rt for 1 h. The reaction mixture was partitioned between aqueous saturated ammonium chloride and EtOAc. The layers were

330 separated and the organic layer was concentrated in vacuo to afford a crude residue, which was subjected to PTLC on silica gel (5% MeOH in DCM) to afford Example 350 (LCMS (ESI) m/z 357 (Ret.=1.89 min, LCMS method e)) as a yellow solid.

Scheme AAP

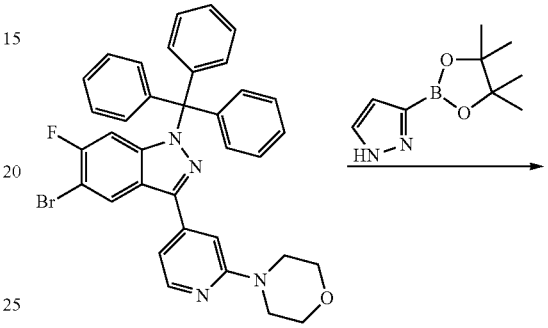

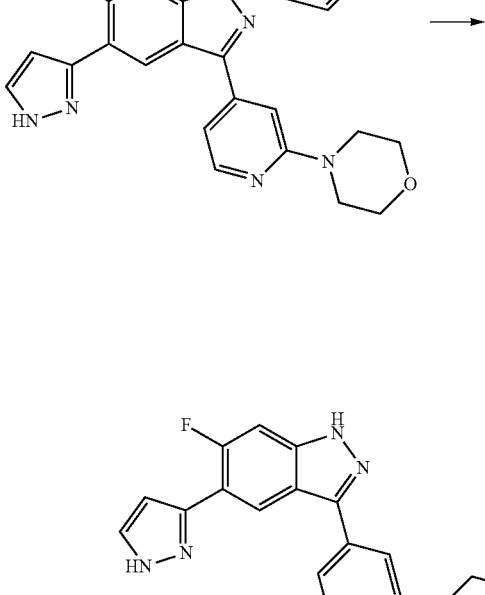

Example 351

Step 1

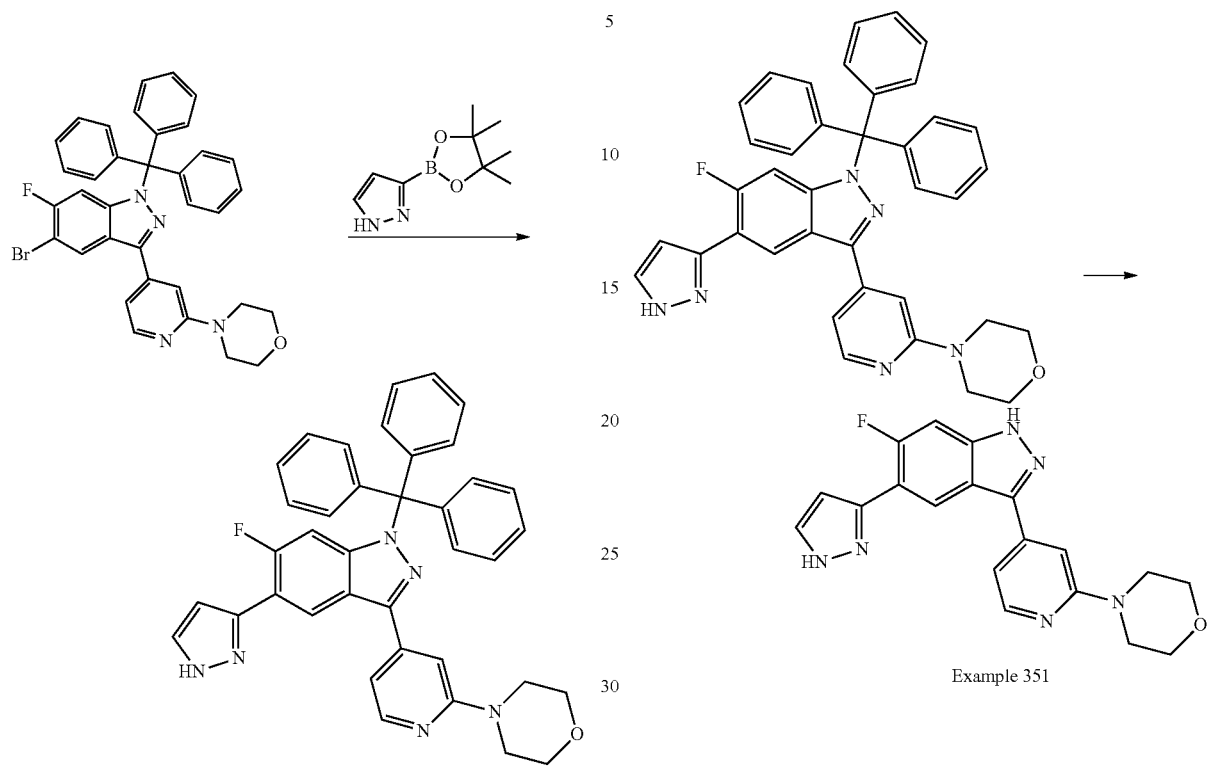

Step 2

Example 351

The compound prepared in Step 2 of Scheme AAL (50 mg, 0.081 mmol), 3-(4,4,5,5-tetramethyl-1,3,2-dioxaborolan-2-yl)-1H-pyrazole (31 mg, 0.16 mmol), potassium carbonate (22 mg, 0.16 mmol) Pd(dppf)Cl$_2$.CH$_2$Cl$_2$ complex (13 mg, 0.016 mmol) were combined in a mixture of 1,4-dioxane (1.5 mL) and water (0.1 mL) in a microwave vial. The vial was sealed and heated in a microwave reactor for 2 h at 130° C. with stirring. The reaction was then cooled to room temperature and unsealed. The reaction was concentrated to afford a crude residue.

The residue from Step 1 was dissolved in TFA (1.5 mL) and treated with Et$_3$SiH (0.5 mL). The resulting reaction mixture was stirred at room temperature for 10 minutes. Methylene chloride (1 mL) was added and the reaction was stirred at room temperature for 1 h. The reaction was concentrated to afford a crude residue, which was redissolved in 7M ammonia in MeOH (10 mL). The solution was concentrated to afford a crude residue, which was subjected to PTLC on silica gel (5% (7M ammonia in MeOH) in CH$_2$Cl$_2$) to afford Example 351 (LCMS (ESI) m/z 365 (Ret.=1.89 min, LCMS method e)) as a yellow solid.

TABLE AAP.1

Using the requisite boronic acid or boronic ester, and a method similar to that outlined in Scheme AAP, the following compounds were prepared:

| Ex | Structure | LCMS Cond. | RT (min) | m/z | LRRK2 IC$_{50}$ (nM) |
|---|---|---|---|---|---|
| 352 | | e | 1.93 | 379 | 12 |

TABLE AAP.2
Using the requisite bromoindazole, boronic acid or boronic ester, and a method similar to that outlined in Scheme AAP, replacing potassium carbonate with potassium acetate in Step 1, the following compounds were prepared:
| Ex | Structure | LCMS Cond. | RT (min) | m/z | LRRK2 IC$_{50}$ (nM) |
|---|---|---|---|---|---|
| 353 | | e | 1.85 | 367 | 4.6 |
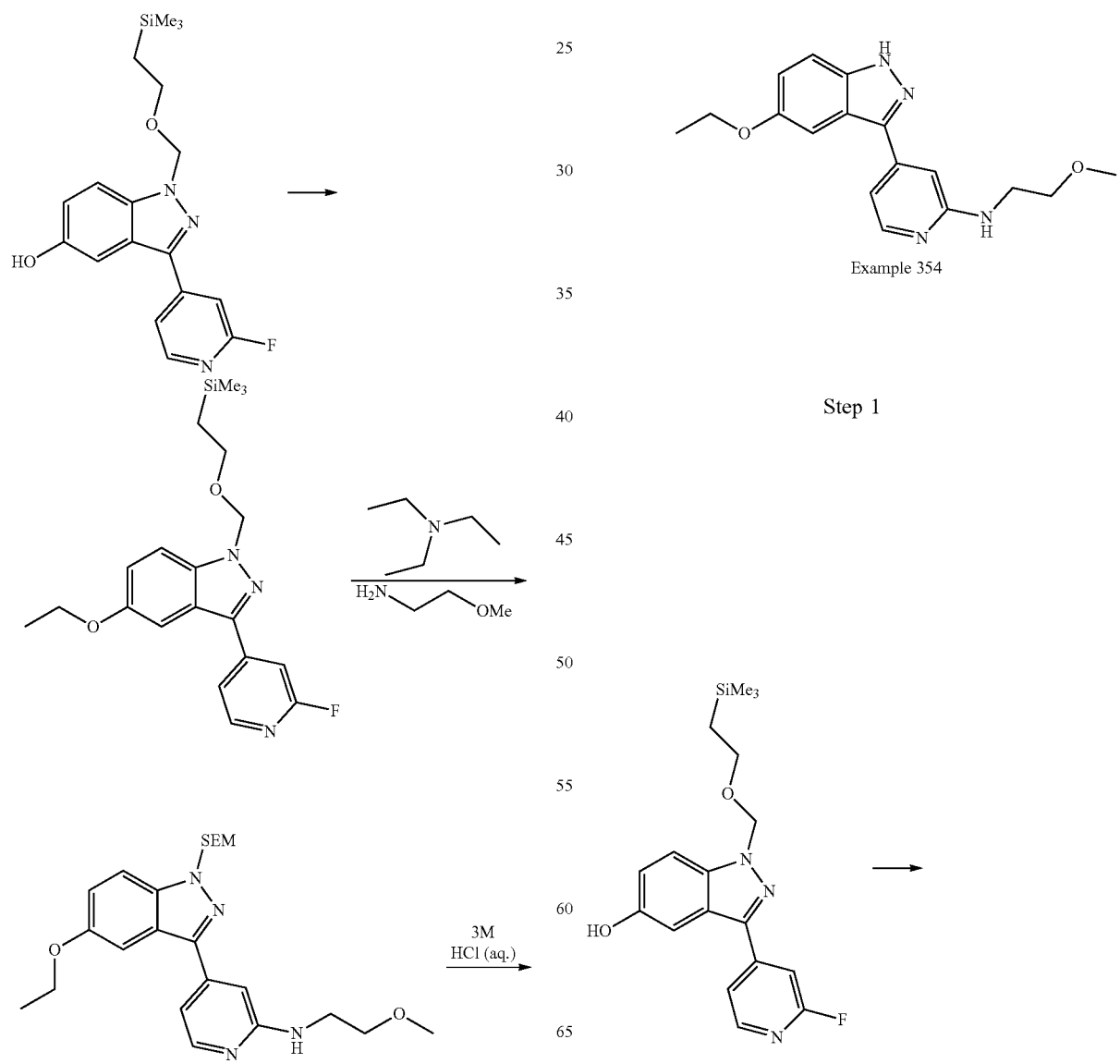
Example 354

-continued

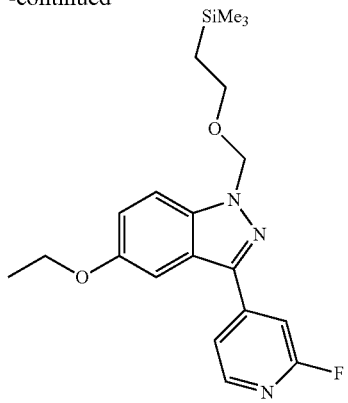

Cs₂CO₃ (1.40 g, 4.30 mmol) and iodoethane (191 µl, 2.358 mmol) were added to a stirred, room temperature mixture of the hydroxyindazole prepared in Step 2 of Scheme E (471 mg, 1.310 mmol) in DMF (5241 µl) and the mixture was stirred at room temperature for 4 h. The mixture was diluted with ethyl acetate (100 mL), washed with brine (3×100 mL), dried over anhydrous sodium sulfate, filtered and the solvent was evaporated under reduced pressure. The residue was purified by column chromatography on silica gel ISCO RediSep 40 g silica gel column, eluting with EtOAc/isohexane to give the desired product as a film.

Step 2

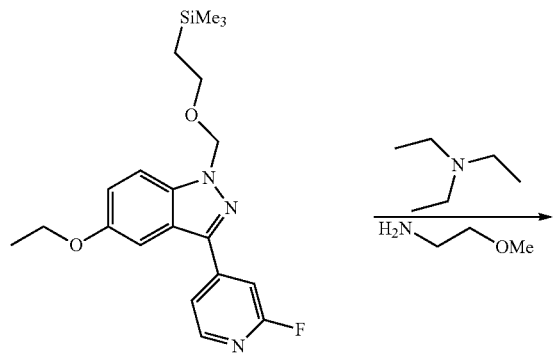

A solution of the product from Step 1 (97 mg, 0.25 mmol) in triethylamine (8 mL) was treated with 2-methoxyethylamine (0.26 mL, 2.99 mmol) and capped in a vial and heated at 130° C. overnight. An additional amount of 2-methoxyethylamine (1.3 mL) was added and heating was continued at 130° C. for 6 hours. An additional amount of 2-methoxyethylamine (3 mL) was added and heating was continued at 130° C. for 18 hours. An additional amount of 2-methoxyethylamine (3 mL) was added and heating was continued at 130° C. for 72 hours. The reaction was cooled to room temp and partitioned between EtOAc and water. The layers were separated and the organic layer was washed with water. The organic layer was dried over anhydrous MgSO₄, filtered and concentrated. The resulting residue was purified by C18 reversed-phase chromatography (gradient elution, 0% to 100% MeCN in water with 0.1% TFA) to afford the desired product as a TFA salt.

Step 3

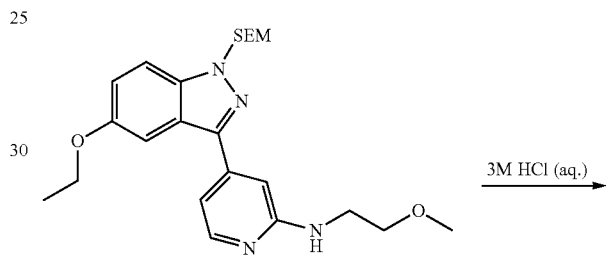

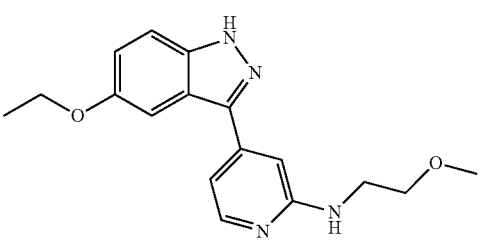

Example 354

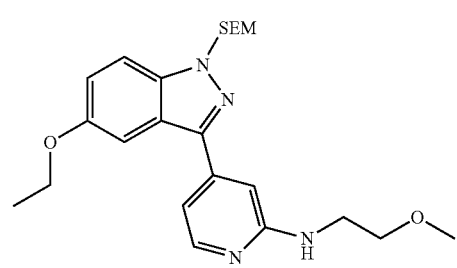

A solution of the product from Step 2 (100 mg, 0.23 mmol) in a mixture of EtOH (15 mL) and 3N HCl$_{(aq.)}$ (15 mL) was heated at 80° C. for 18 h. The reaction was then cooled to room temperature and concentrated in vacuo. The resulting residue was purified by C18 reversed-phase chromatography (gradient elution, 0% to 100% MeCN in water with 0.1% TFA) to afford Example 354 (LCMS (ESI) m/z 313 (Ret.=2.01 min, LCMS method e)) as a TFA salt.

TABLE AAQ-1

Using the requisite amine and fluoropyridine, and a method similar to that outlined in Scheme AAQ, the following compounds were prepared:

| Ex | Structure | LCMS Cond. | RT (min) | m/z | LRRK2 IC$_{50}$ (nM) |
|---|---|---|---|---|---|
| 355 | | e | 1.92 | 299 | 10 |
| 356 | | e | 2.06 | 327 | 10 |
| 357 | | e | 1.87 | 313 | 5.5 |
| 358 | | e | 1.90 | 313 | 16 |
| 359 | | e | 1.94 | 325 | 15 |

TABLE AAQ-1-continued

Using the requisite amine and fluoropyridine, and a method similar to that outlined in Scheme AAQ, the following compounds were prepared:

| Ex | Structure | LCMS Cond. | RT (min) | m/z | LRRK2 IC$_{50}$ (nM) |
|---|---|---|---|---|---|
| 360 | (5-ethoxy-1H-indazol-3-yl)-pyridine-piperazine-methylsulfonyl structure | e | 1.90 | 402 | <0.60 |
| 361 | (5-ethoxy-1H-indazol-3-yl)-pyridine-azetidine-OH-CF$_3$ structure | e | 1.98 | 379 | <0.60 |
| 362 | (5-ethoxy-1H-indazol-3-yl)-pyridine-N-methylpiperazine structure | e | 1.75 | 338 | 10 |

TABLE AAQ-2

Using the requisite amine and fluoropyridine, and a method similar to that outlined in Scheme AAQ, Step 2, the following intermediates were prepared:

| Intermediate Number | Starting Fluoropyridine | Intermediate |
|---|---|---|
| AAQ1 | 5-isopropoxy-1-(triphenylmethyl)-3-(2-fluoropyridin-4-yl)-1H-indazole | 5-isopropoxy-1-(triphenylmethyl)-3-(2-(4-(methylsulfonyl)piperazin-1-yl)pyridin-4-yl)-1H-indazole |

Scheme AAR
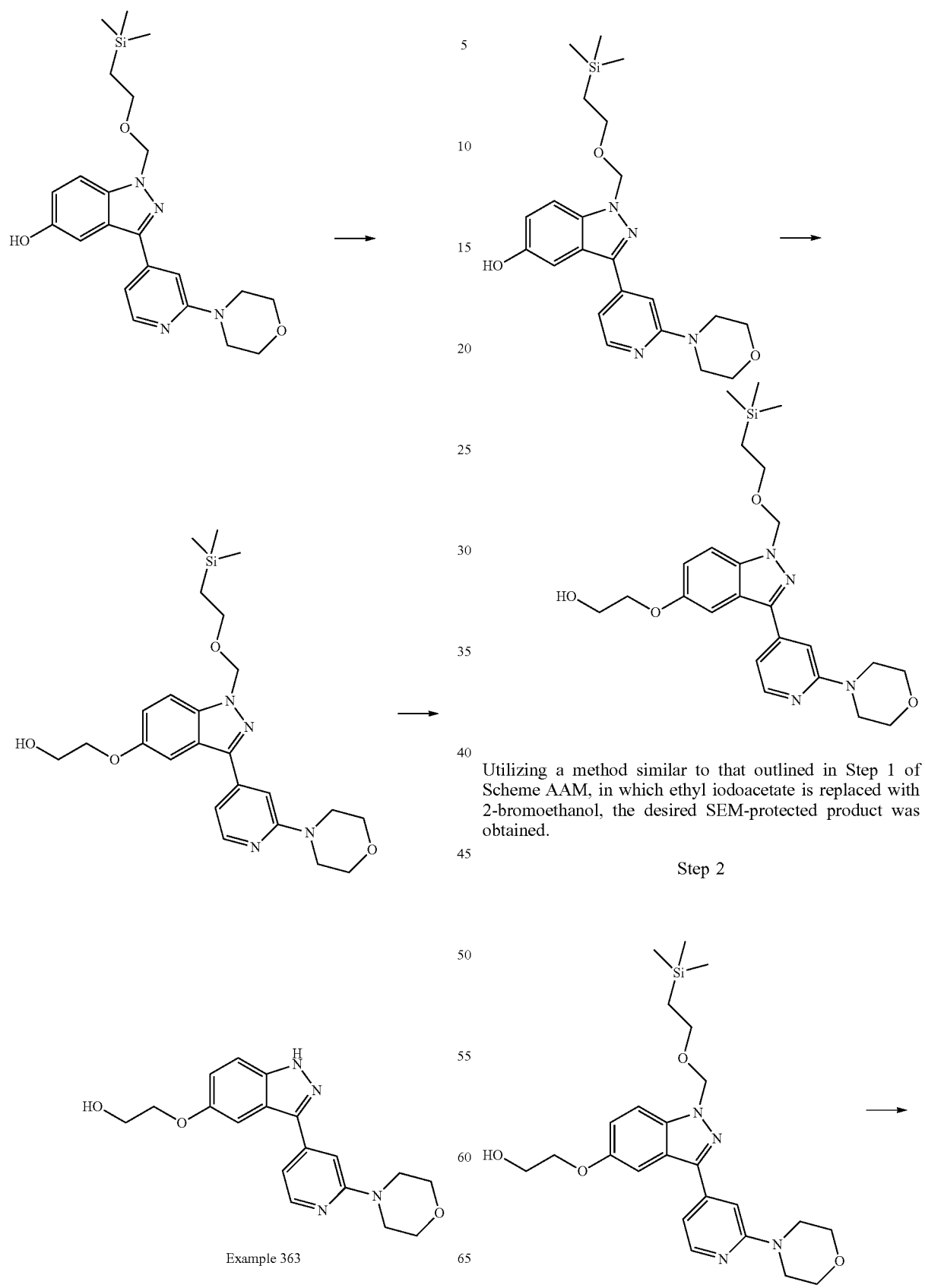
Utilizing a method similar to that outlined in Step 1 of Scheme AAM, in which ethyl iodoacetate is replaced with 2-bromoethanol, the desired SEM-protected product was obtained.
Step 2
Example 363

-continued
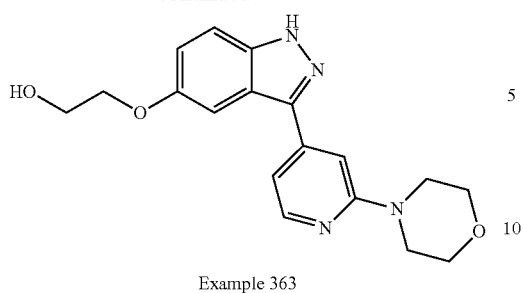
Example 363
The product from Step 1 was deprotected in a manner similar to that described in Scheme AAE, Step 3. The crude product was subjected to PTLC on silica gel (9:1 EtOAc: hexanes) to afford Example 363 (LCMS (ESI) m/z 341 (Ret.=1.20 min, B128 short HCOOH)) as a yellow solid.
Scheme AAS
-continued
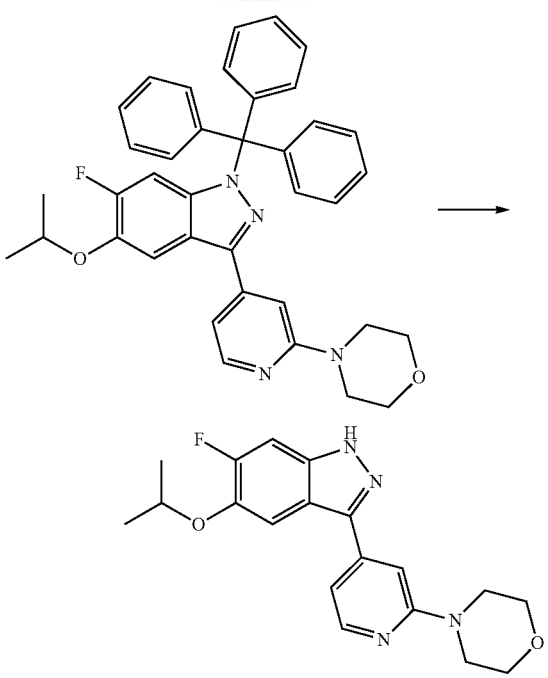
Example 364
Step 1
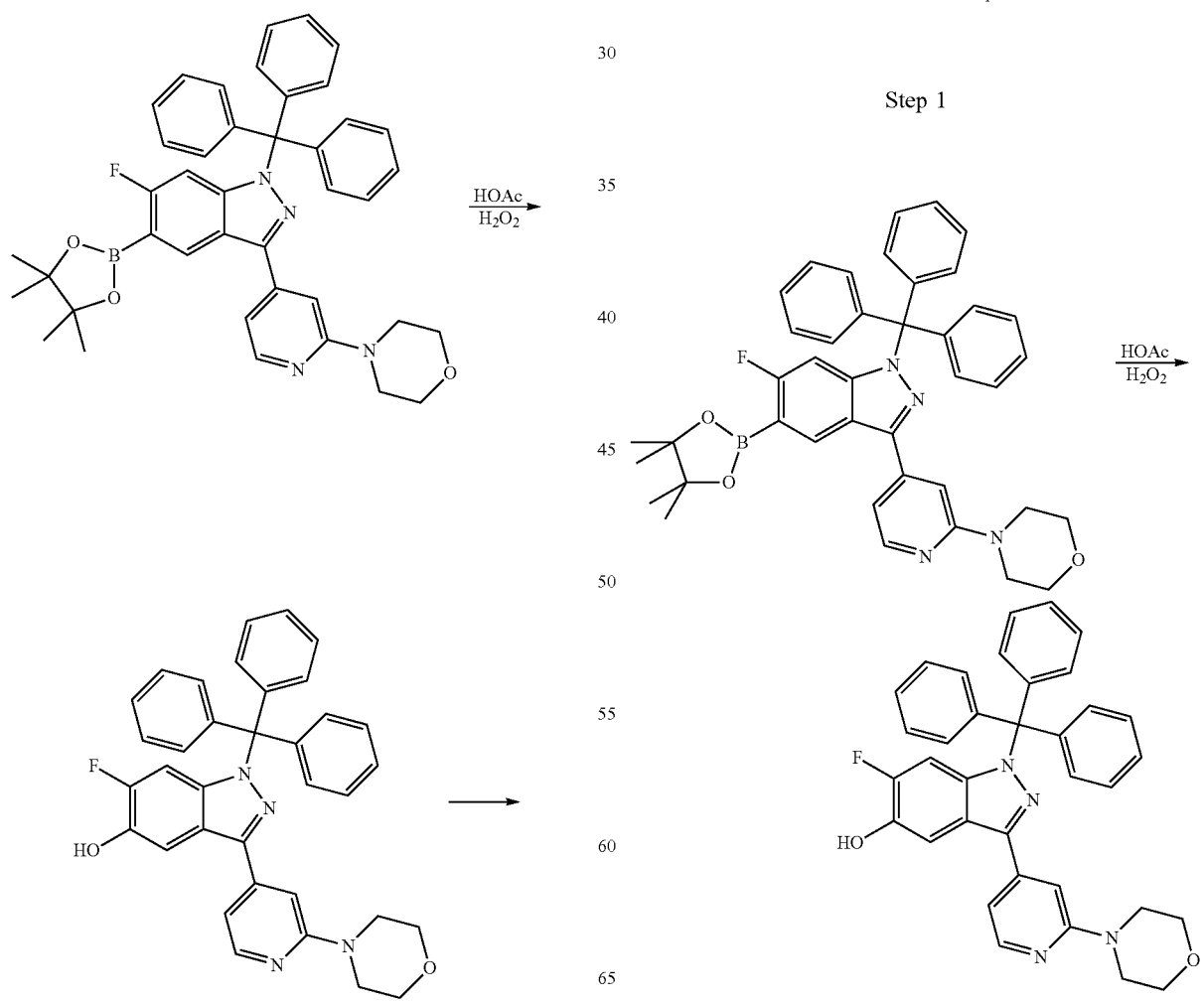

Utilizing Intermediate AW7 and a method similar to that described in Step 2 of Scheme E, the desired hydroxyindazole was prepared.

Step 2

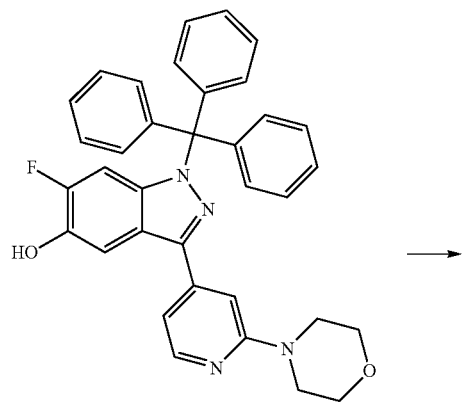

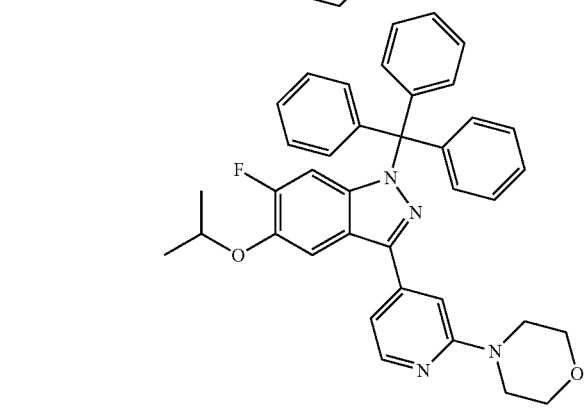

The product from Step 1 (50 mg, 0.090 mmol), 2-iodopropane (61 mg, 0.36 mmol) and cesium carbonate (117 mg, 0.36 mmol) were combined in DMF (1 mL) and stirred overnight at room temperature. The reaction was filtered and concentrated to afford a crude residue, which was used in the next step without further purification.

Step 3

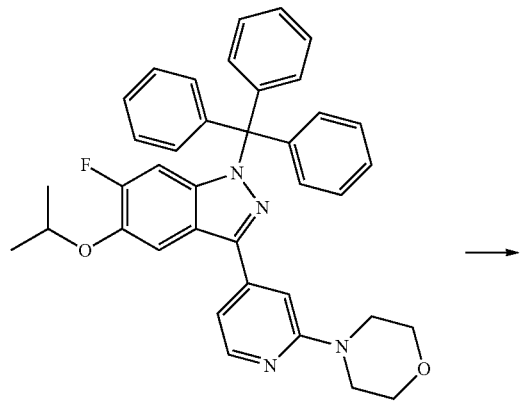

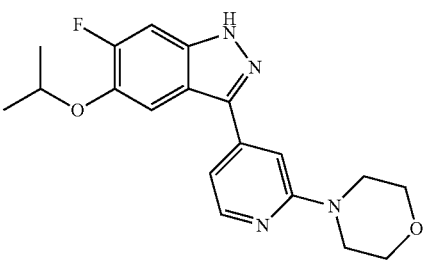

Example 364

The product from Step 2 was deprotected in a manner similar to that in Step 2 of Scheme AAP to afford Example 364 (LCMS (ESI) m/z 357 (Ret.=2.01 min, LCMS method e)) as a yellow solid.

Scheme AAT

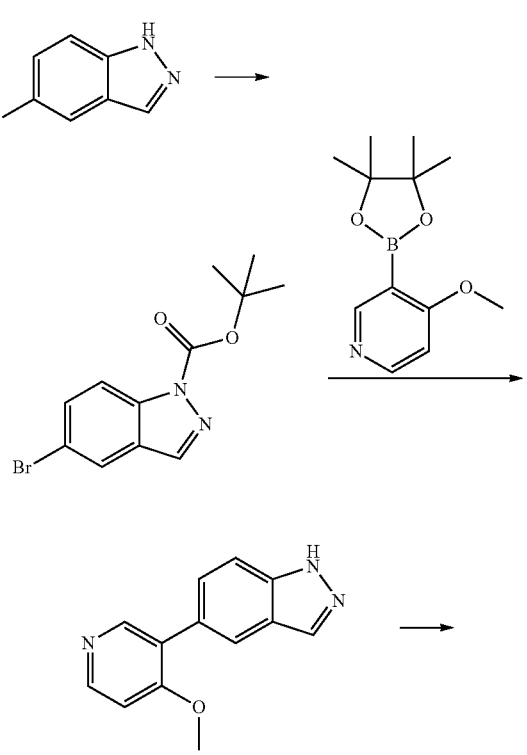

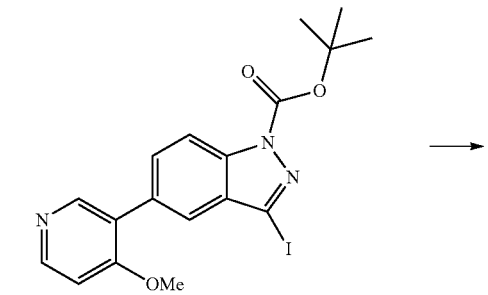

-continued

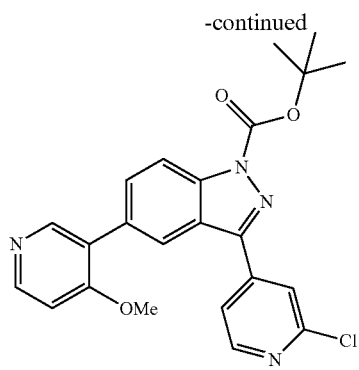

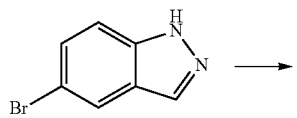

Example 365

Step 1

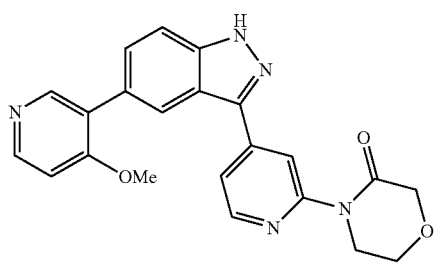

A solution of 5-bromoindazole (2 g, 10.2 mmol), Boc₂O (3.31 g, 15.2 mmol), DMAP (200 mg) and triethylamine (1.41 mL, 10.2 mmol) in 1:1 MeCN:MeOH (30 mL) was stirred at room temperature for 16 h. The reaction was then concentrated and subjected to silica gel chromatography (gradient elution, 0% to 30% EtOAc in hexanes) to afford the desired product.

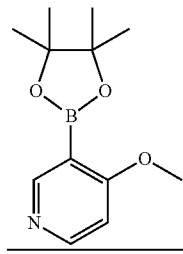

The product from Step 1 (3 g) was dissolved in 1,4-dioxane (25 mL). To this solution was added 4-methoxy-3-(4,4,5,5-tetramethyl-1,3,2-dioxaborolan-2-yl)pyridine (2.84 g), Pd(dppf)Cl₂ (824 mg), K₂CO₃ (2.78 g) and water (2 mL). The resulting mixture was stirred overnight at 100° C. The reaction was cooled to room temperature and partitioned between EtOAc and water. After the layers were separated, the organic layer was dried over anhydrous sodium sulfate, filtered and evaporated to afford a crude residue which was purified via silica gel chromatography to afford the desired product.

Step 3

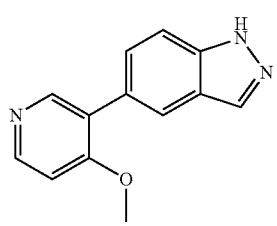

The compound prepared in Step 2 (987 mg, 1 eq) was combined with N-iodosuccinimide (1.7 g, 1.2 eq) in MeCN (15 mL) in a microwave reaction vessel and was subjected to microwave heating for 20 minutes at 110° C. The reaction was cooled to room temperature and the vessel unsealed. Ethanol (15 mL) and methylene chloride (15 mL) were added to the reaction, followed by Boc₂O (1.43 g, 1.5 eq), triethylamine (1 mL) and DMAP (600 mg). The resulting reaction mixture was stirred at room temperature for 72 h. The reaction was concentrated and the resulting residue was subjected to silica gel chromatography (gradient elution, 0-50% EtOAc in hexanes) to afford the desired product as a yellow solid.

Step 4

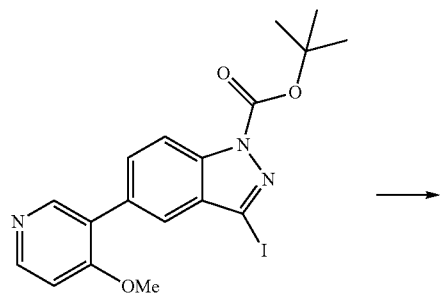

The product from Step 3 (600 mg, 1.33 mmol), (2-chloropyridin-4-yl)boronic acid (272 mg, 1.73 mmol), Pd(dppf)Cl$_2$·CH$_2$Cl$_2$ complex (163 mg, 0.199 mmol) and K$_2$CO$_3$ (368 mg, 2.66 mmol) were combined in 1,4-dioxane (4 mL) and water (0.3 mL). The mixture was heated overnight at 80° C. The reaction mixture was then heated in a microwave reactor for 2 hours. The reaction was cooled, filtered and concentrated to afford a crude residue, which was subjected to silica gel chromatography (gradient elution, 0-5% MeOH in CH$_2$Cl$_2$) to afford the desired product as a yellow solid.

Step 5

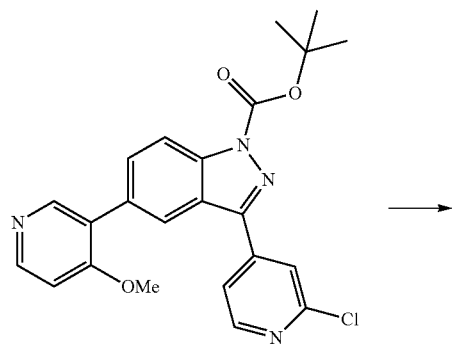

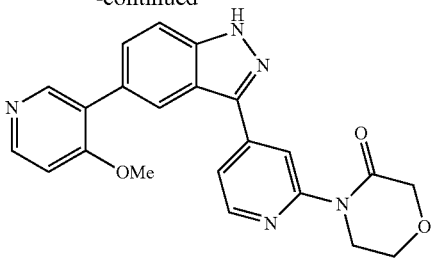

Example 365

The product from Step 4 (50 mg, 0.114 mmol), morpholin-3-one (23 mg, 0.23 mmol), 1,1'-bis(diphenylphosphino)ferrocene (13 mg, 0.023 mmol), Pd$_2$(dba)$_3$ (16 mg, 0.017 mmol) and Cs$_2$CO$_3$ (37 mg, 0.114 mmol) were combined in toluene (3 mL) and heated overnight at 115° C. The reaction was cooled to room temperature and concentrated. The resulting residue was subjected to PTLC on silica gel to afford Example 365 (LCMS (ESI) m/z 402 (Ret.=1.81 min, LCMS method e)) as a yellow solid.

Scheme AAU

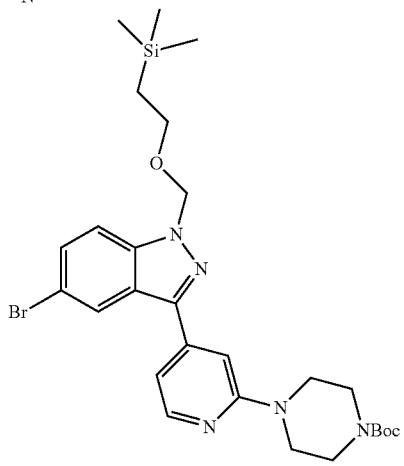

The intermediate prepared in Scheme D, Step 2 (663 g, 1.57 mol), and N-Boc-piperazine (2.92 g, 15.7 mmol) were combined in NMP (8 mL) in a glass, pressure vessel. The vessel was sealed and the reaction was heated at 100° C. overnight. The reaction was cooled to room temperature and uncapped. The reaction mixture was partitioned between water and EtOAc. The layers were separated and the organic layer was washed with water, dried over anhydrous MgSO₄, filtered and evaporated to afford a crude residue. The residue was purified via silica gel chromatography (5:1 hexanes: EtOAc) to afford the desired product as a colorless gum.

TABLE AAU

Utilizing a method similar to that outlined in Scheme AAU and the requisite starting materials, the following intermediates were prepared:

| Intermediate Number | Intermediate |
|---|---|
| AAU1 | (structure) |

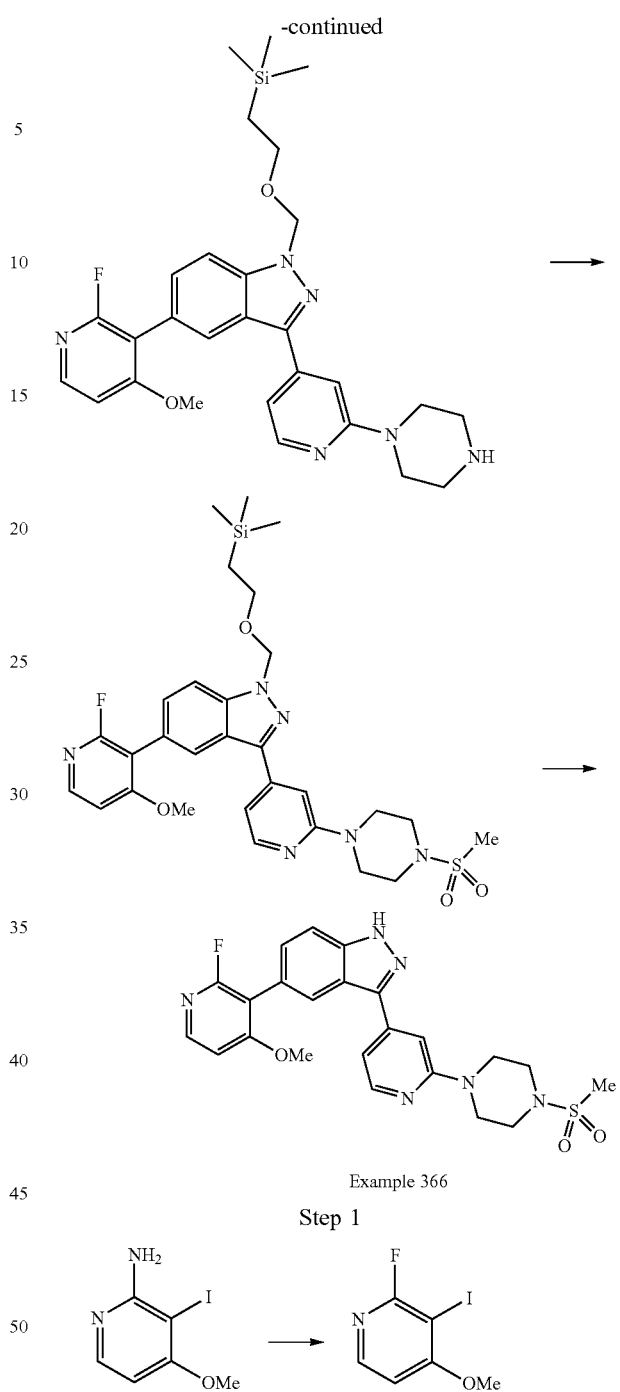

Example 366

Step 1

To a cold (−20° C.), stirred suspension of the 3-iodo-4-methoxypyridin-2-amine (2.5 g, 10 mmol) in HBF₄ (70 mL, 470 mmol) was added an aqueous solution of NaNO₂ (1.67 M, 6 mL, 10 mmol) over 20 min. The reaction turned green and then brown in color. The mixture was stirred at 0° C. for 3 h. The reaction was then carefully poured into a cold (0° C.) saturated solution of Na₂CO₃ (50 g) in H₂O (100 mL). The layer was then extracted with EtOAc (×3). The combined organic layers were dried over anhydrous MgSO₄, filtered, and concentrated under vacuum to leave a residue which was purified by column chromatography on silica gel (elution with 5:1 to 2:1 hexanes:ethyl acetate) to yield 2-fluoro-3-iodo-4-methoxypyridine as a light yellow solid.

Step 2

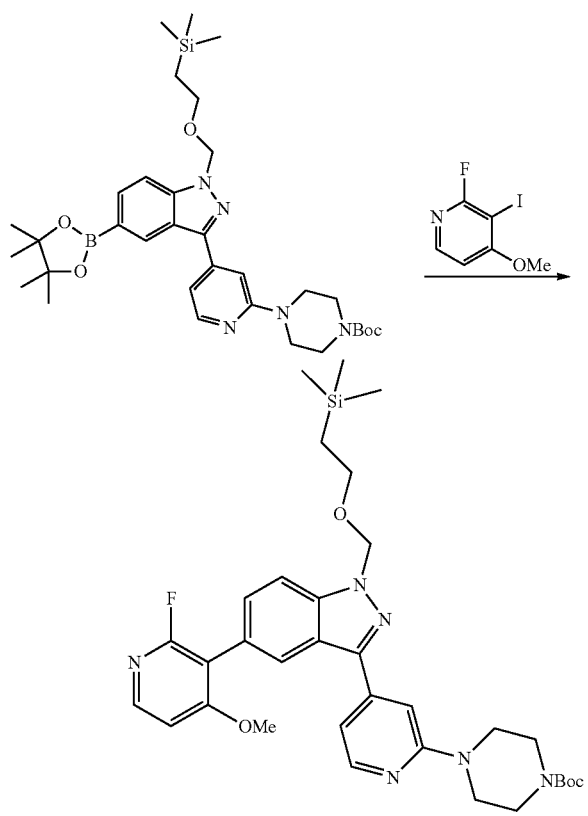
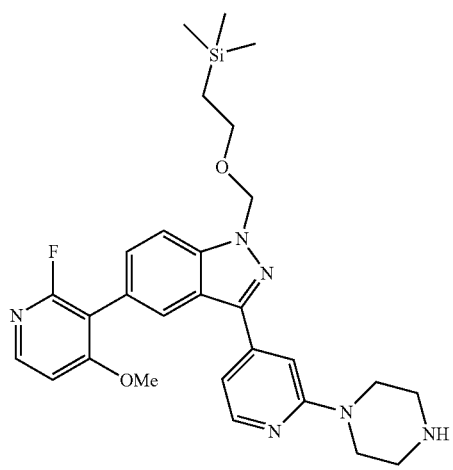

A suspension of the boronate ester (Intermediate AW4, 0.35 g, 0.55 mmol), 2-fluoro-3-iodo-4-methoxypyridine (209 mg, 0.826 mmol) and K₃PO₄ (351 mg, 1.65 mmol) in DME (6 ml) and H₂O (0.6 ml) was purged with argon for 15 min. Then 1,1'-Pd(dppf)Cl₂-DCM complex (45 mg, 0.055 mmol) was added and the mixture was heated at 105° C. for 15 h. The reaction was cooled to room temperature and the mixture was concentrated under vacuum. The resulting residue was re-dissolved in water and extracted with EtOAc (×2). The combined organic layers were dried over anhydrous MgSO₄, filtered, and concentrated under vacuum to leave a residue which was purified by column chromatography on silica gel (elution with 2:1 to 1:1 hexanes:ethyl acetate) to yield the desired product as a light yellow foam.

Step 3

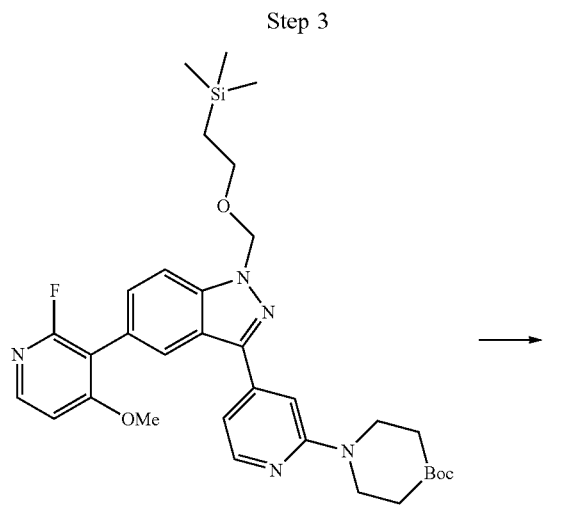

To a stirred solution of the product from Step 2 (100 mg, 0.158 mmol) in DCM (3 ml) was added HCl (4 M in dioxane, 0.5 mL) at RT and the mixture was stirred at RT for 1 h. The mixture was then cooled to 0° C. and the reaction was neutralized with Et₃N. The reaction was then concentrated under vacuum. To the residue was added EtOAc and the solid was filtered through a pad of celite. The filtrate was concentrated to give a residue which was directly used in the next step without further purification.

Step 4

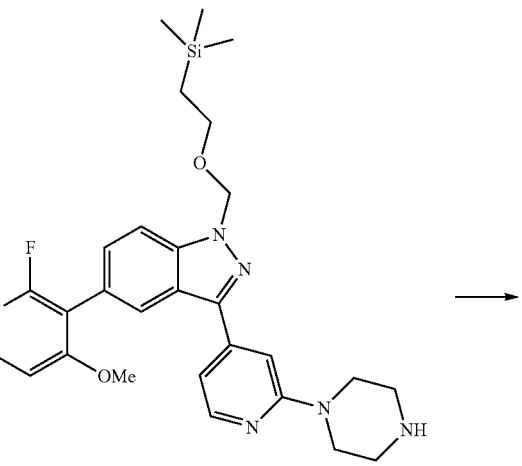

-continued

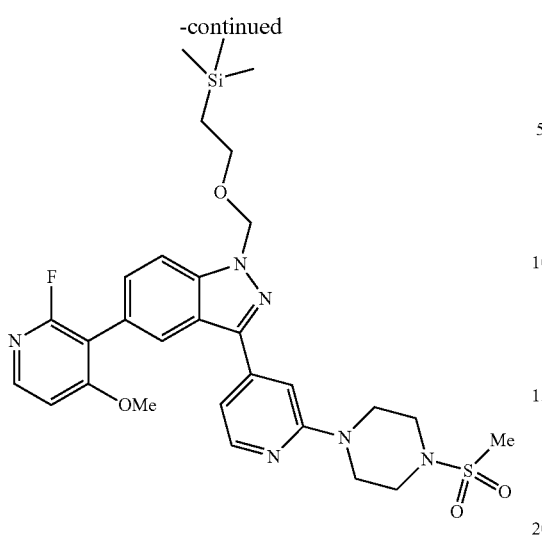

To a cold (0° C.), stirred solution of the material prepared in Step 3 (84 mg, 0.158 mmol) in DCM (2 ml) was added triethylamine (0.2 ml, 1.435 mmol) followed by methanesulfonyl chloride (0.025 ml, 0.316 mmol). The mixture was stirred at 0° C. for 2 h. Silica gel was added and a slurry was prepared, which was subjected to column chromatography on silica gel (elution with 100:1 to 30:1 DCM:MeOH) to yield the desired product as a colorless gel.

Step 5

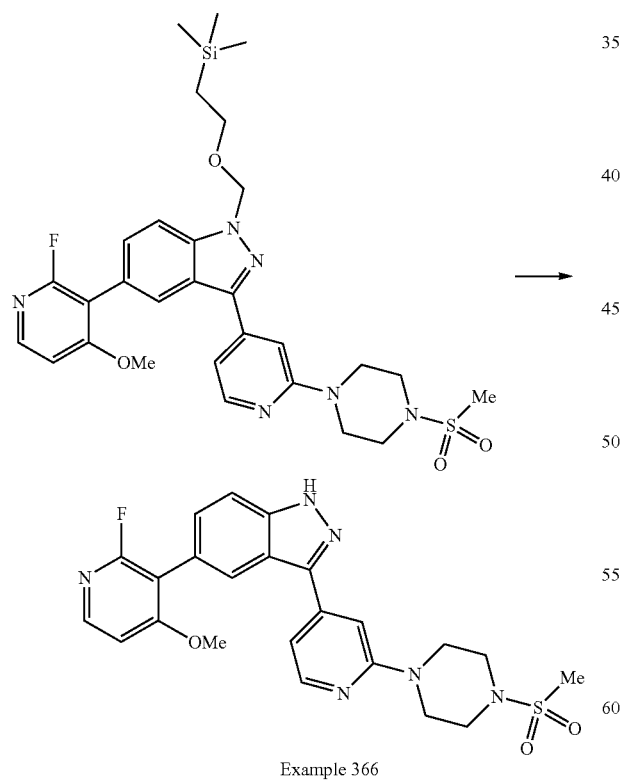

Example 366

To a stirred solution of the product from Step 4 (80 mg, 0.131 mmol) in DCM (1.5 mL) was added TFA (1.5 ml, 19.47 mmol) dropwise at RT. The mixture was stirred at RT for 5 h. The mixture was concentrated and the residue was redissolved in DCM (2 mL), MeOH (2 mL) and NH$_4$OH in H$_2$O (2 mL). The mixture was stirred overnight. The reaction was quenched with H$_2$O and extracted with DCM (×3). The combined organic layers were then dried over anhydrous MgSO$_4$, filtered, and concentrated under vacuum to leave a residue, which was purified via C18 reversed phase MPLC (Biotage SP-1, Analogix C18 column, gradient elution, 0% to 100% MeCN in water with 0.1% TFA) to afford Example 366 (LCMS (ESI) m/z 483 (Ret.=0.76 min, LCMS Method h)) as the TFA salt.

Scheme AAW

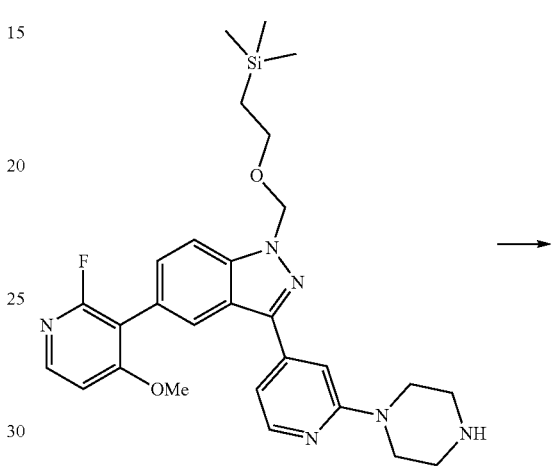

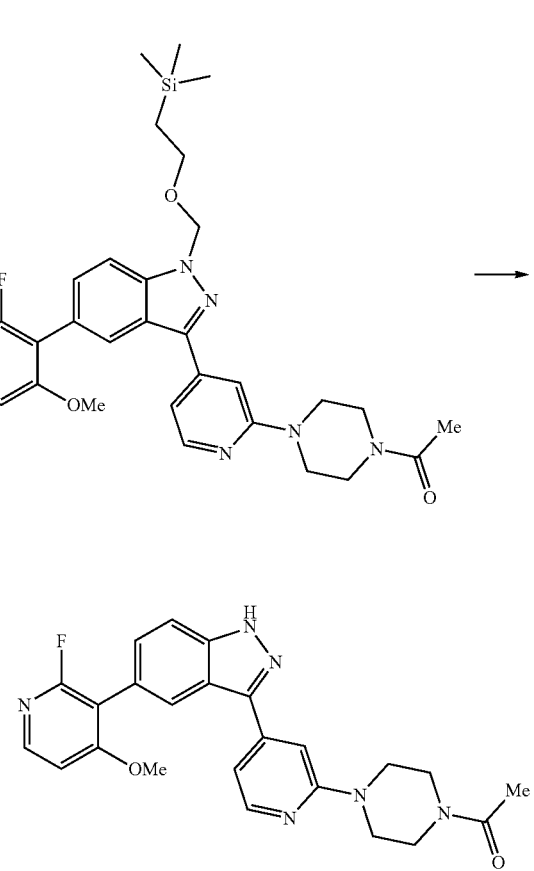

Example 367

Step 1

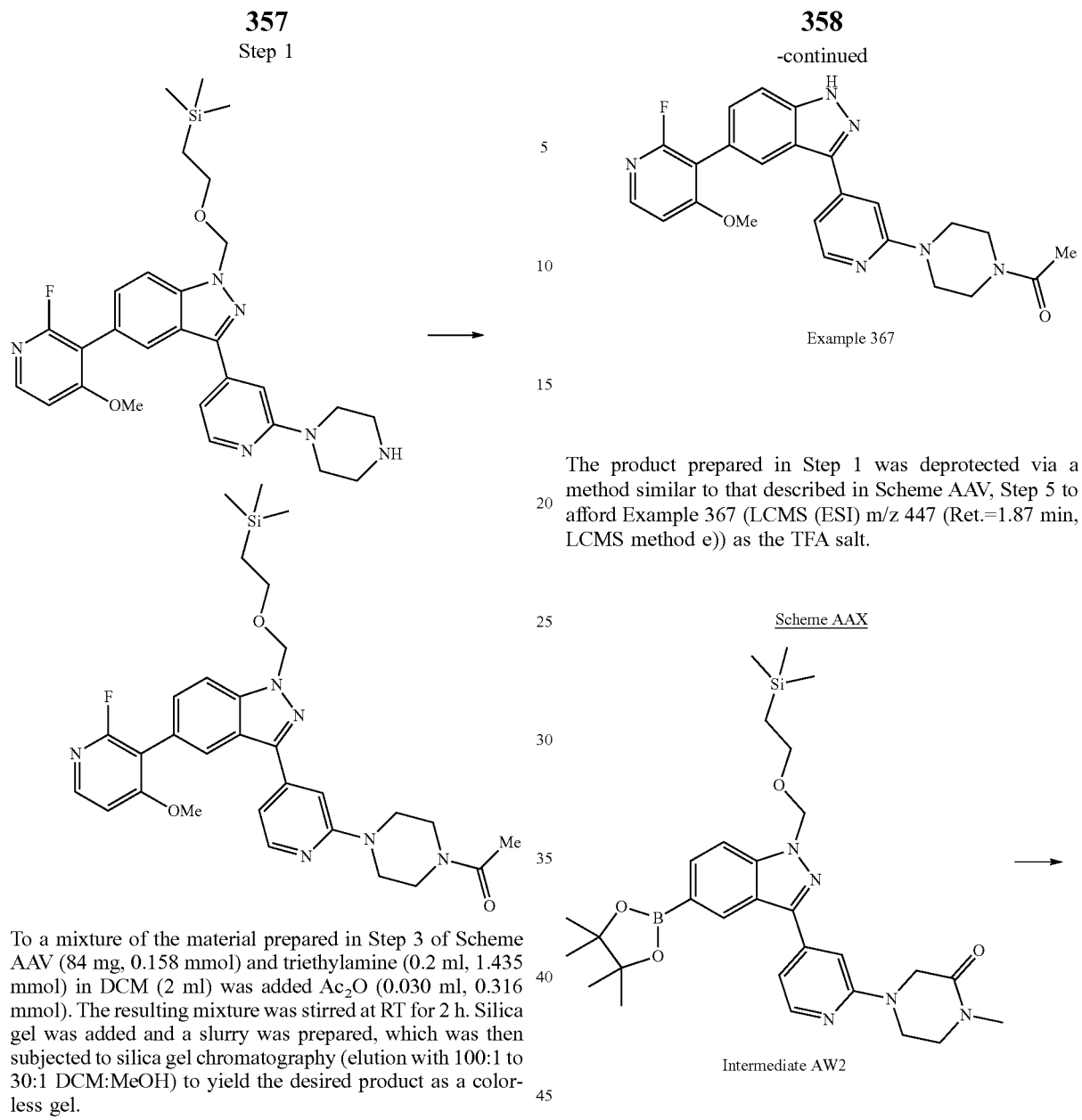

To a mixture of the material prepared in Step 3 of Scheme AAV (84 mg, 0.158 mmol) and triethylamine (0.2 ml, 1.435 mmol) in DCM (2 ml) was added Ac₂O (0.030 ml, 0.316 mmol). The resulting mixture was stirred at RT for 2 h. Silica gel was added and a slurry was prepared, which was then subjected to silica gel chromatography (elution with 100:1 to 30:1 DCM:MeOH) to yield the desired product as a colorless gel.

Step 2

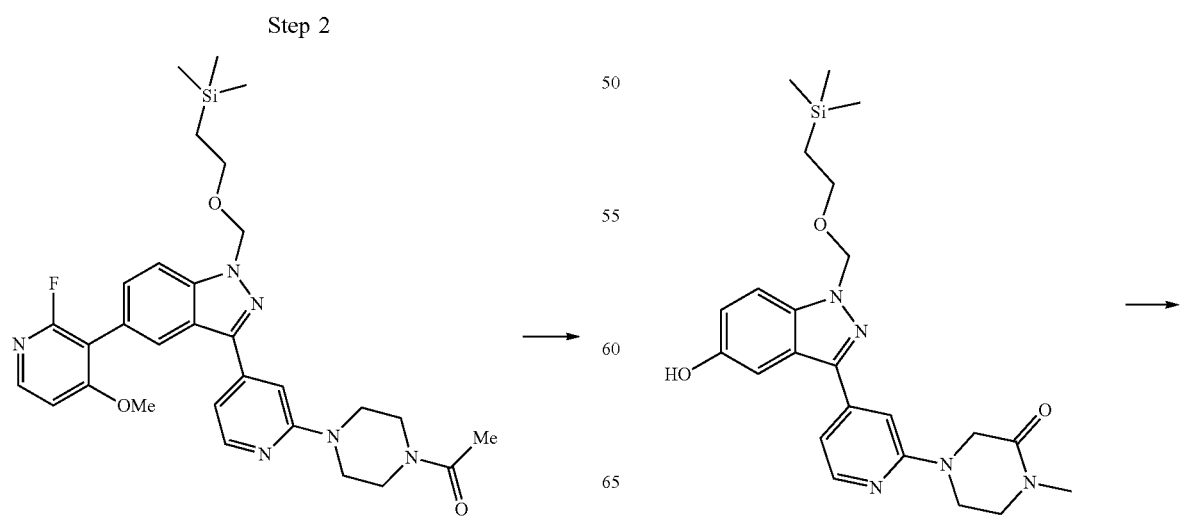

The product prepared in Step 1 was deprotected via a method similar to that described in Scheme AAV, Step 5 to afford Example 367 (LCMS (ESI) m/z 447 (Ret.=1.87 min, LCMS method e)) as the TFA salt.

Scheme AAX

Intermediate AW2

-continued

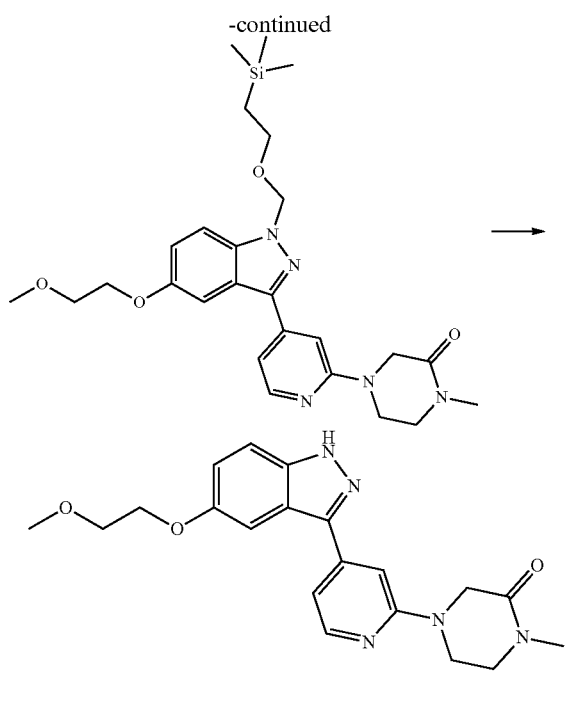

Example 368

Step 1

Intermediate AW2

Starting with Intermediate AW2 and utilizing a method similar to that described in Scheme E, Step 2, the desired hydroxyindazole was prepared.

Step 2

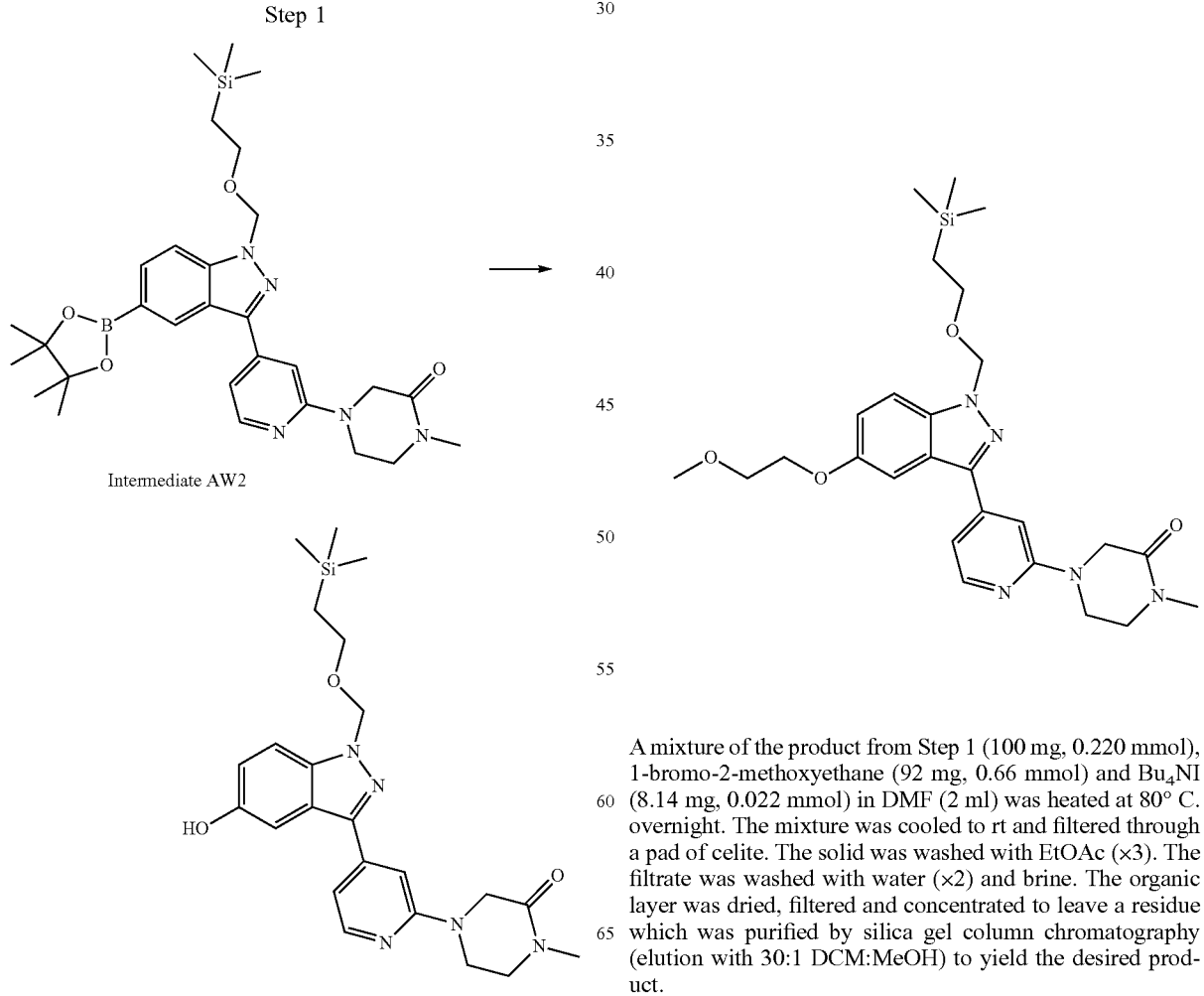

A mixture of the product from Step 1 (100 mg, 0.220 mmol), 1-bromo-2-methoxyethane (92 mg, 0.66 mmol) and Bu₄NI (8.14 mg, 0.022 mmol) in DMF (2 ml) was heated at 80° C. overnight. The mixture was cooled to rt and filtered through a pad of celite. The solid was washed with EtOAc (×3). The filtrate was washed with water (×2) and brine. The organic layer was dried, filtered and concentrated to leave a residue which was purified by silica gel column chromatography (elution with 30:1 DCM:MeOH) to yield the desired product.

Step 3
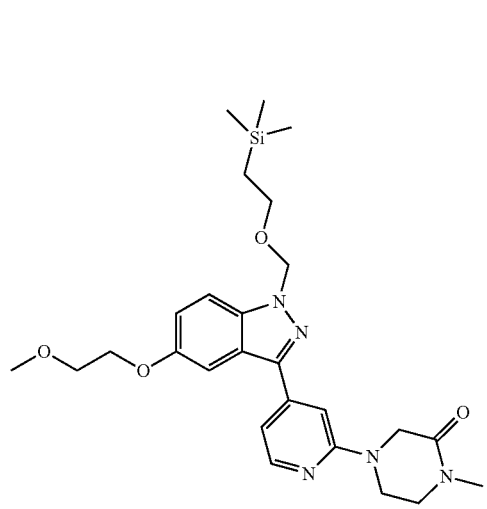
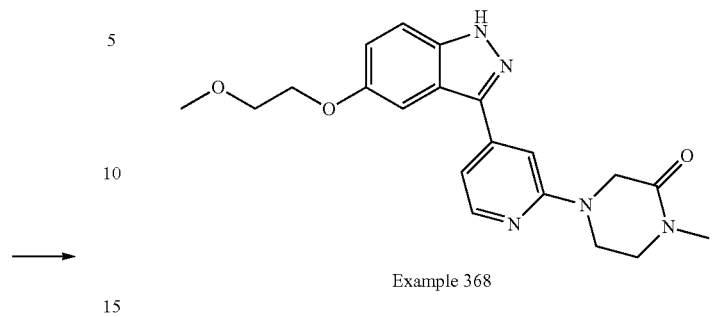
Example 368
The product prepared in Step 2 was deprotected via a method similar to that described in Scheme AAV, Step 5 to afford Example 368 (LCMS (ESI) m/z 382 (Ret.=1.85 min, LCMS method e)) as the TFA salt.
Scheme AAY
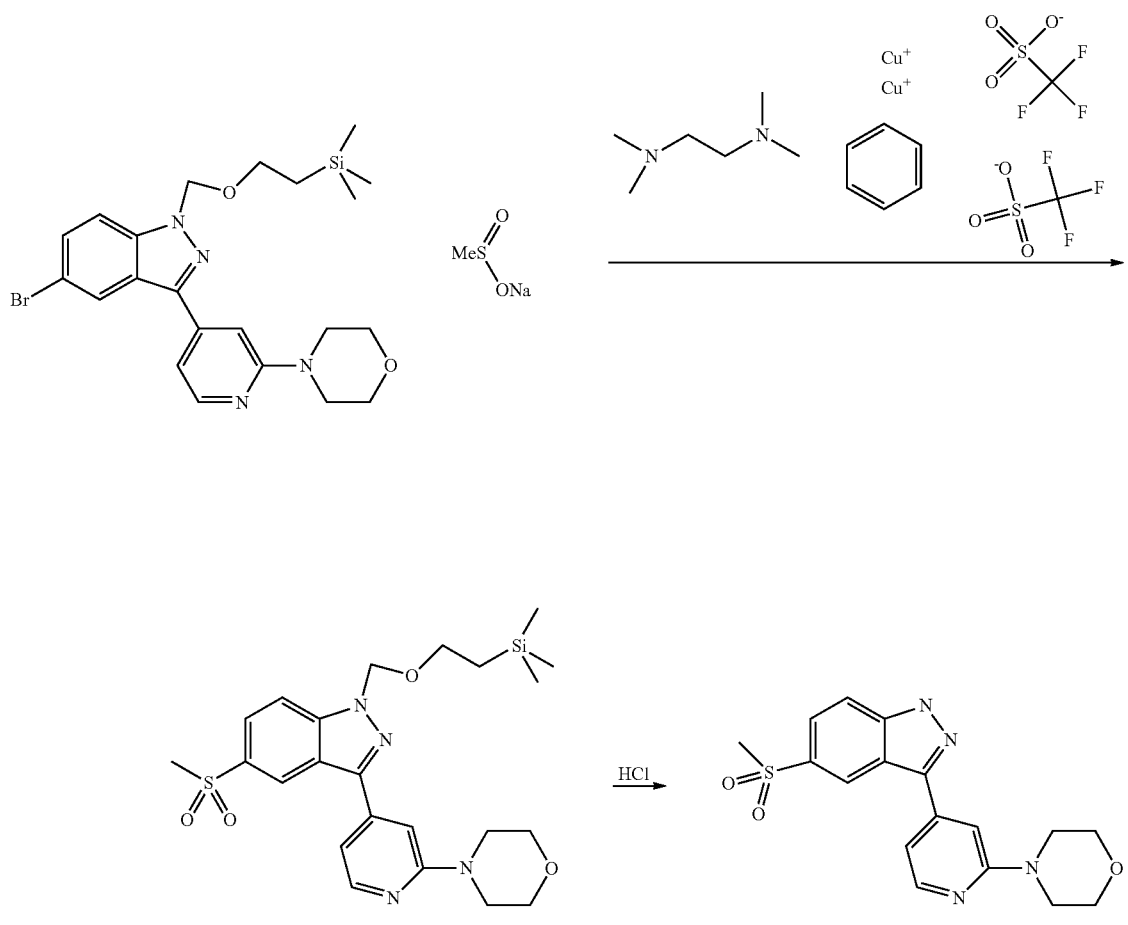
Example 369

Step 1

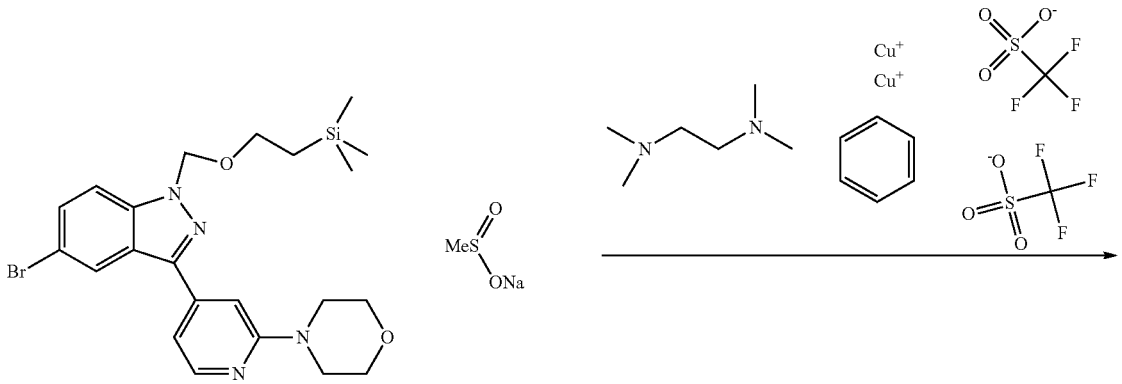

Step 2

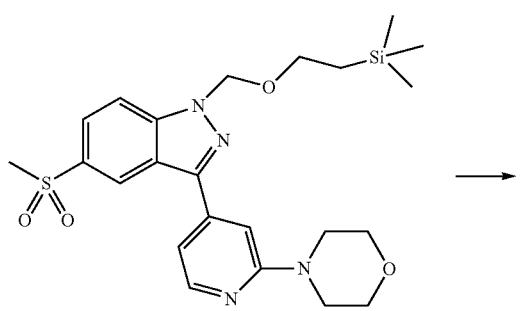

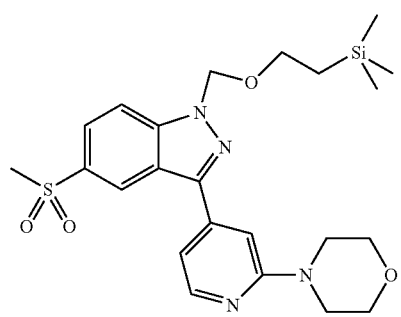

-continued

Example 369

A solution of the compound prepared in Step 3, Scheme D (377 mg, 0.77 mmol) was dissolved in of DMSO (1 mL), degassed with N$_2$ and added to a vial which contained N$^1$,N$^1$,N$^2$,N$^2$-tetramethylethane-1,2-diamine (17 mg, 0.15 mmol). Sodium methanesulfinate (189 mg, 1.85 mmol) and copper (I) triflate benzene complex (37 mg, 0.073 mmol) were added, then the vial was sealed and heated at 130° C. for 24 hours. The reaction was cooled to room temperature and filtered. The filtrate was partitioned between ethyl acetate and water. The organic layer was washed with brine (3×) then dried over anhydrous Na$_2$SO$_4$, filtered and evaporated. The resulting crude material was subjected to silica gel column chromatography to give the desired product.

To the product from Step 1 (150 mg, 0.31 mmol) in ethanol (6 ml) was added 6 ml of 3M HCl$_{(aq.)}$. The reaction was heated at 50° C. overnight, then heated at 80° C. for 24 hours. The reaction was evaporated. The resulting residue was dissolved in a mixture of methanol (8 ml), CH$_2$Cl$_2$ (6 ml) and concentrated aqueous ammonium hydroxide (6 ml) and stirred at room temperature for 72 hours. The reaction mixture was evaporated and the crude residue was purified by reversed phase MPLC, (Biotage SP1, Analogix 16 g C18 column, gradient elution with 100% water+0.1% TFA to 100% CH3CN+0.1% TFA over 32 min.). The pure fractions were combined to give Example 369 (LCMS (ESI) m/z 359 (Ret.=1.70 min, LCMS method e)) as a TFA salt.

TABLE AAY
Utilizing a method similar to that outlined in Scheme AAY and the requisite starting materials, the following examples were prepared:
| Ex | Structure | LCMS Cond. | RT (min) | m/z | LRRK2 IC$_{50}$ (nM) |
|---|---|---|---|---|---|
| 370 | | e | 1.77 | 299 | 18 |
| 371 | | e | 1.72 | 373 | 48 |
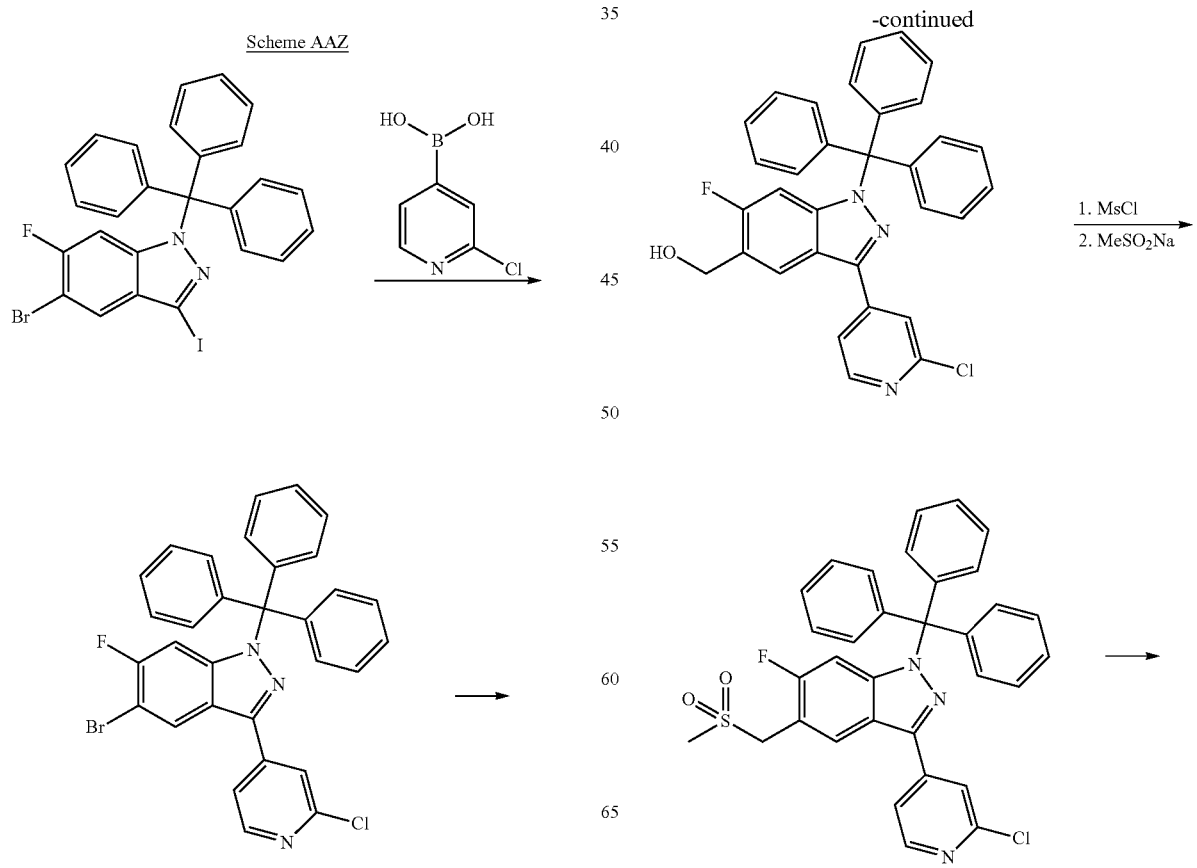

-continued

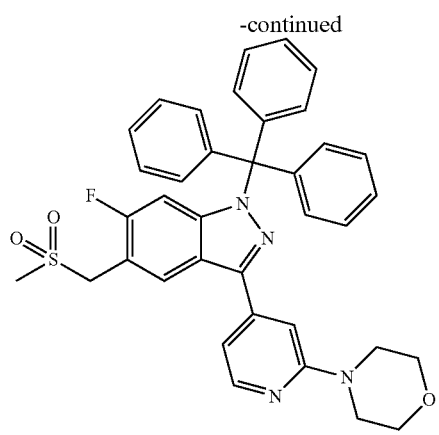

TFA/
H₂O
→

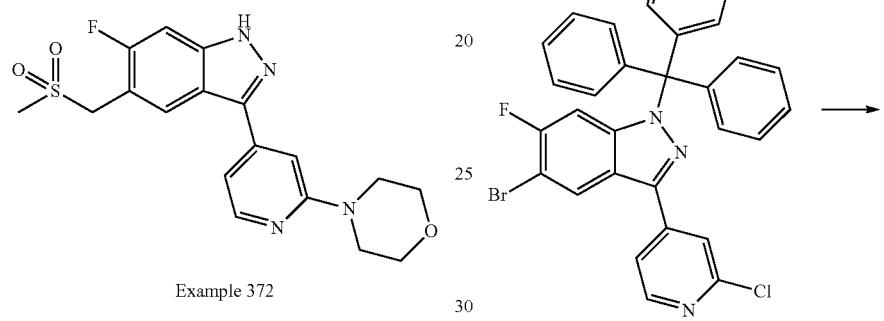

Example 372

Step 1

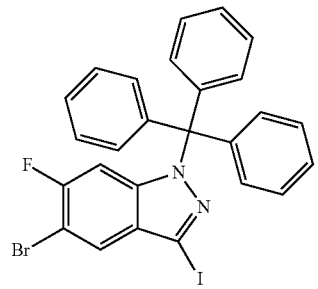

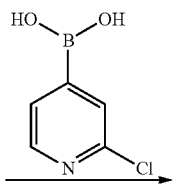

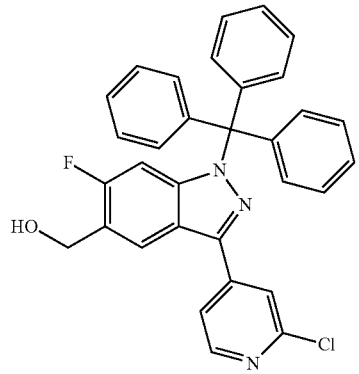

A mixture of the product from Step 1, Scheme AAL (1.0 g, 1.72 mmol), (2-chloropyridin-4-yl)boronic acid (0.297 g, 1.89 mmol), potassium carbonate (355 mg, 2.57 mmol) and 1,1'-Pd(dppf)Cl₂.DCM complex (0.210 g, 0.257 mmol) in 1,4-dioxane (10 ml) and Water (0.4 ml) was sealed in a glass microwave reaction vessel and heated in a microwave at 80° C. for 2 h. The reaction was cooled to room temperature, filtered and concentrated under vacuum to afford a crude residue which was purified by silica gel chromatography to yield the desired product as a yellow solid.

Step 2

The product from Step 1 (750 mg, 1.318 mmol) was dissolved in THF (10 ml) and cooled to −78° C., followed by addition of n-BuLi (2.5 M in hexanes, 0.79 mL, 1.98 mmol). The mixture was stirred at −78° C. for 1 min. N,N-Dimethylformamide (482 mg, 6.59 mmol) was added and the reaction was stirred at −78° C. for 1 h, then gradually warmed to rt and stirred overnight. The reaction was quenched with saturated aqueous NH₄Cl and the resulting mixture was extracted with ethyl acetate. The layers were separated and the organic layer was concentrated to afford a crude residue, which was purified via silica gel chromatography to afford the desired product.

Step 3

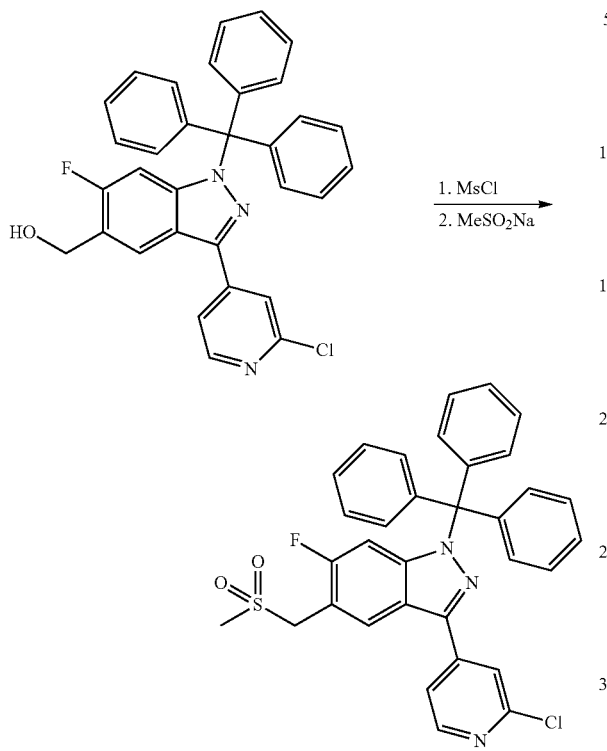

1. MsCl
2. MeSO$_2$Na

A solution of the product from Step 2 (200 mg, 0.385 mmol) in CH$_2$Cl$_2$ (3 ml) was treated with Et$_3$N (0.107 mL, 0.769 mmol) and MsCl (0.045 mL, 0.577 mmol). The resulting mixture was stirred at rt for 3 h. The reaction was then concentrated. The resulting residue was dissovled in DMSO (3 mL) and MeSO$_2$Na (393 mg, 3.85 mmol) was added. The reaction mixture was stirred at rt overnight. The reaction mixture was partitioned between water and EtOAc. The layers were separated and the organic layer was concentrated to afford a crude material which was subjected to PTLC on silica gel to afford the desired product as a yellow solid.

Step 4

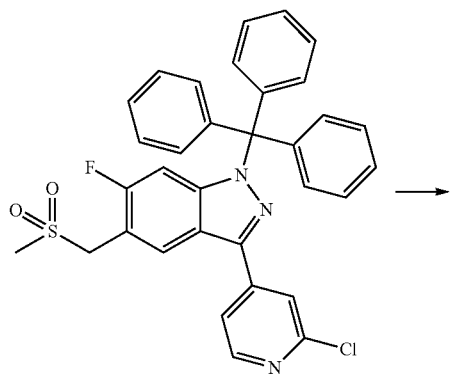

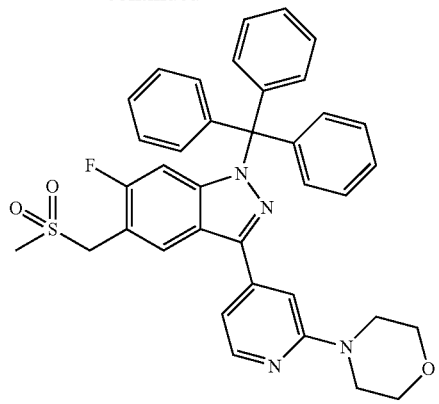

The product from Step 3 (105 mg, 0.180 mmol) and morpholine (629 mg, 7.22 mmol) were combined in DMSO (1 mL) in a microwave vial. The vial was sealed and heated in a microwave reactor at 205° C. for 30 min. The reaction was cooled, unsealed and partitioned between water and EtOAc. The organic layer was removed and evaporated to afford the crude product as a yellow solid which was taken on to the next step without further purification.

Step 5

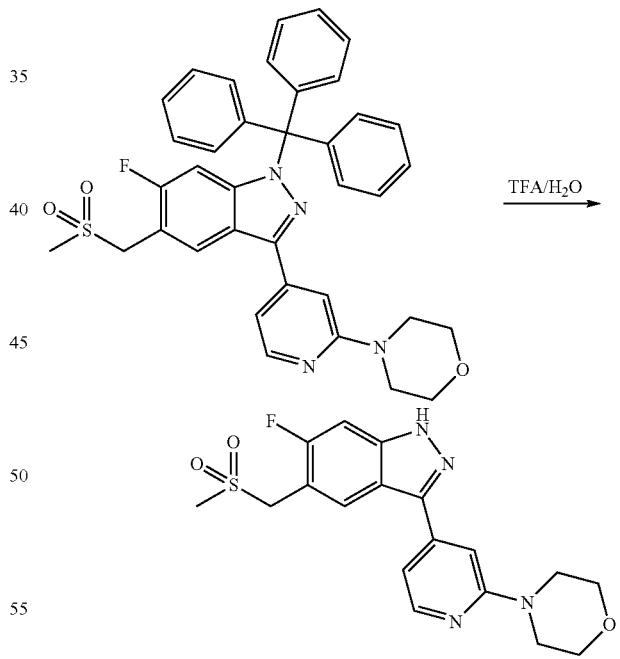

Example 372

The crude product from Step 4 was dissolved in a mixture of TFA (1.5 mL) and water (300 μl) and stirred at rt for 2 h. The reaction was then concentrated. The resulting residue was redissolved in MeOH (2 ml) and treated with 7N NH$_3$ in MeOH (2 mL). The mixture was subjected to PTLC on silica gel to afford Example 372 (LCMS (ESI) m/z 391 (Ret.=1.78 min, LCMS method e)) as a yellow solid.

Scheme AAAA

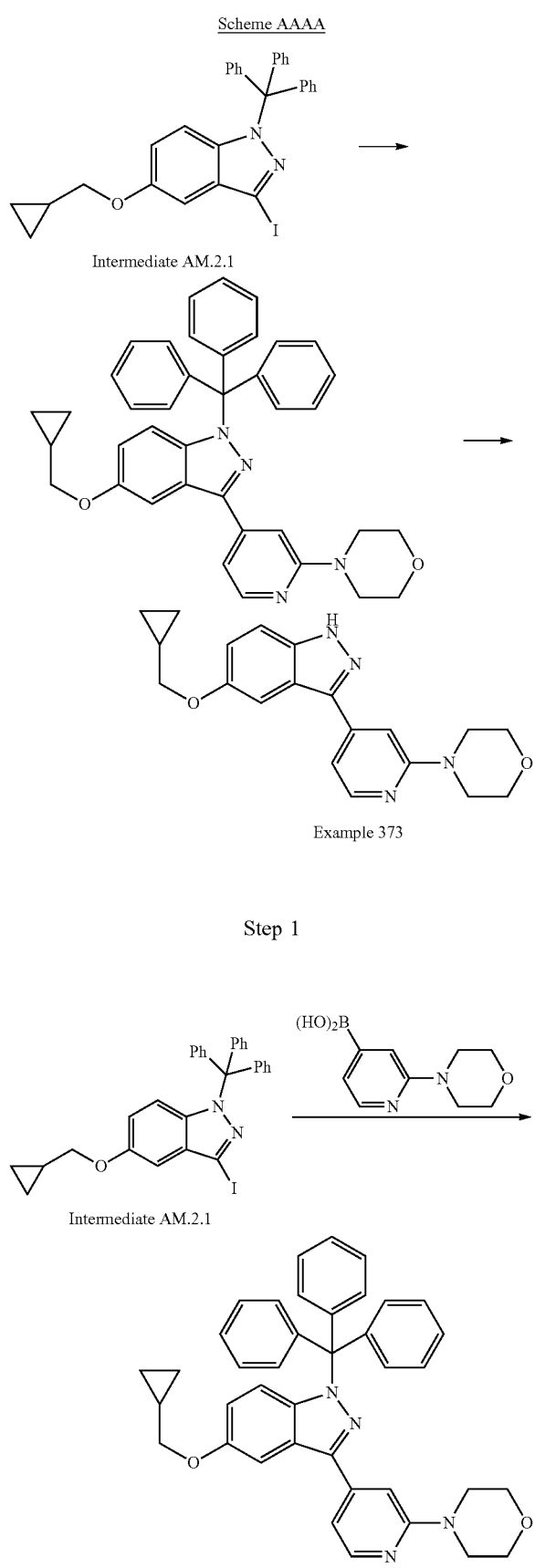

Intermediate AM.2.1

Step 1

Example 373

Intermediate AM.2.1 (167 mg, 0.30 mmol), (2-morpholinopyridin-4-yl)boronic acid (94 mg, 0.45 mmol) and $K_3PO_4$ (191 mg, 0.90 mmol) were combined in DME (4.0 mL) and water (0.4 mL) in a 6 mL microwave tube. The mixture was degassed by bubbling $N_2$ through the solution for 5 min. The catalyst, $PdCl_2(dppf)\cdot CH_2Cl_2$, (25 mg, 0.03 mmol) was added, and the cap was sealed. The tube was placed in a 110° C. oil bath and stirred. After 18 h heating, the dark mixture was allowed to cool and was partitioned between EtOAc (20 mL) and water (20 mL). The layers were separated and the aqueous layer was back-extracted with EtOAc. The combined EtOAc layers were washed with brine, dried over anhydrous $MgSO_4$, filtered and concentrated to afford a crude light purple foam. The material was subjected to PTLC on silica gel (2:1 hexanes:EtOAc, eluted off of silica gel with EtOAc) to afford the desired product as a colorless foam.

Step 2

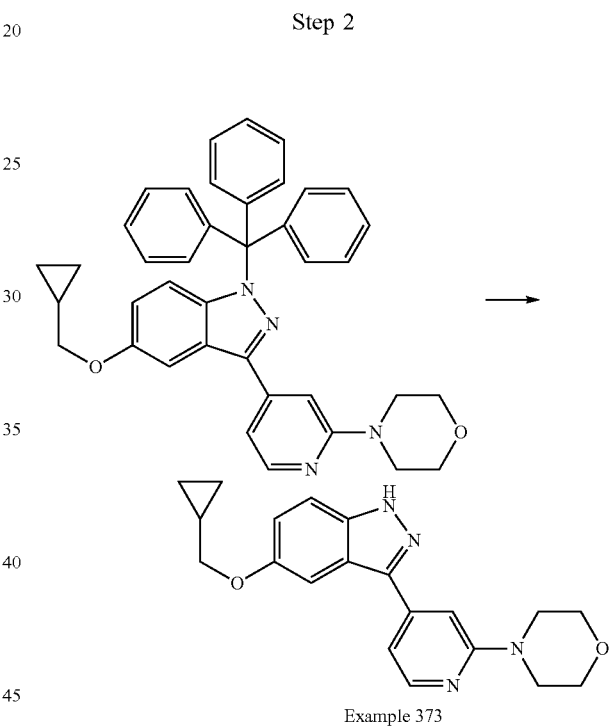

Example 373

To the compound prepared in Step 1 (67 mg, 0.11 mmol) and triethylsilane (0.19 mL, 1.20 mmol) in $CH_2Cl_2$ (2 mL) was added TFA (270 mg, 2.37 mmol) to give a pale orange soln. After 2 h, the solution was conc. to a yellow oil which crystallized. The residue was partitioned with EtOAc and 1N $NaHCO_3$ (aq.). The layers were separated and the organic layer was dried over anhydrous $MgSO_4$. The solution was filtered and concentrated to afford a partially crystalline gum. After standing overnight, the material was combined with 0.21 g triethylsilane in $CH_2Cl_2$ (3 mL), and TFA (0.41 g) was added. After 5 h, the reaction mixture was concentrated. The residue was partitioned with EtOAc and 1N $NaHCO_3$ (aq.). The layers were separated and the organic layer was dried over anhydrous $MgSO_4$. The solution was filtered and concentrated to afford a partially crystalline gum which was subjected to PTLC on silica gel (5% MeOH in $CH_2Cl_2$, eluted from silica with 10% MeOH in $CH_2Cl_2$) to afford Example 373 (LCMS (ESI) m/z 351 (Ret.=2.05 min, LCMS method e)) as beige crystals.

Scheme AAAB

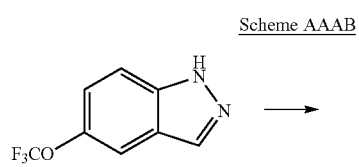

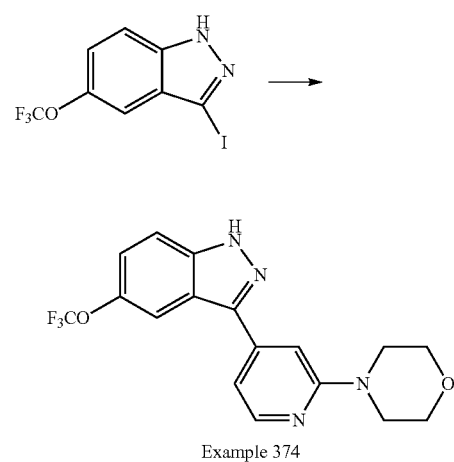

Example 374

Step 1

A solution of 5-(trifluoromethoxy)-1H-indazole (1.01 g, 5.00 mmol), iodine (2.03 g, 8.00 mmol) and K₂CO₃ (0.97 g, 7.02 mmol) in MeCN (20 mL) was stirred at room temperature in a capped reaction vessel for 18 h, Iodine (0.3 g) was added and the reaction was stirred at RT for 2 hours. Iodine (0.3 g) and K₂CO₃ (0.48 g) were added and the reaction was stirred for 4 h at RT. The reaction was concentrated and the resulting residue was partitioned between EtOAc and water. The layers were separated and the aqueous layer was extracted with EtOAc. The organic layers were combined, washed with 10% aq. Na₂S₂O₃, then brine. The organic layer was then dried over anhydrous magnesium sulfate, filtered and concentrated to afford the desired product, which was used in the next step without further purification.

Step 2

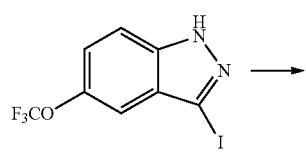

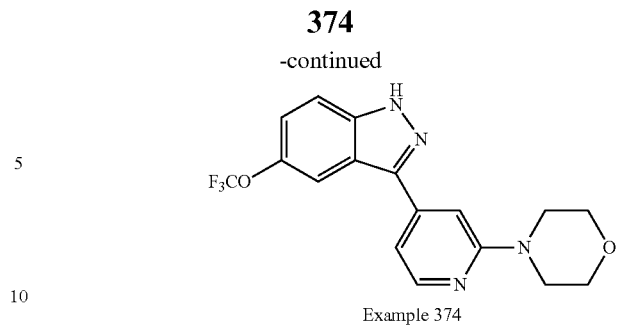

Example 374

The product from Step 1 (150 mg, 0.46 mmol), Boc₂O (120 mg, 0.55 mmol) and DMAP (10 mg) were combined in THF (2 mL) and stirred at RT for 2 h. To the reaction mixture was added, PdCl₂(dppf).CH₂Cl₂, (75 mg, 0.091 mmol), (2-morpholinopyridin-4-yl)boronic acid (133 mg, 0.64 mmol), K₂CO₃ (126 mg, 0.92 mmol) and water (0.1 mL). The resulting reaction mixture was sealed in a microwave reaction vial and heated in the microwave at 85° C. for 2 h. The reaction was cooled, unsealed and concentrated. The resulting residue was dissolved in a mixture of CH₂Cl₂ (3 mL) and 4N HCl in dioxane (2 mL). After stirring this mixture for 2 h, the volatiles were removed and the resulting residue was subjected to PTLC on silica gel (4% (7N ammonia in MeOH) in CH₂Cl₂) to afford Example 374 (LCMS (ESI) m/z 365 (Ret.=2.06 min, LCMS method e)) as a yellow solid.

TABLE AAAB

Utilizing a method similar to that outlined in Step 2 of Scheme AAAB, and the requisite startingmaterials, the following intermediate was prepared:

| Intermediate Number | Intermediate |
| --- | --- |
| AAAB1 | 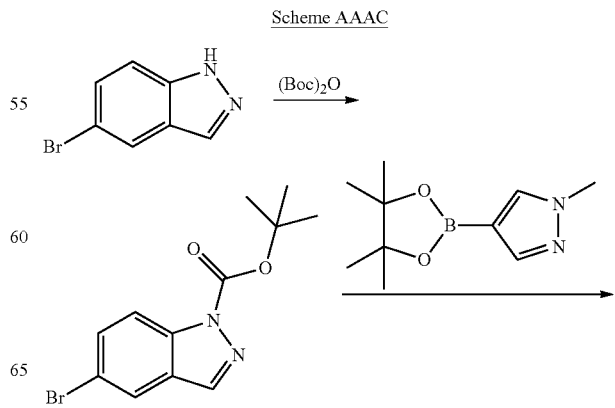 |

Scheme AAAC

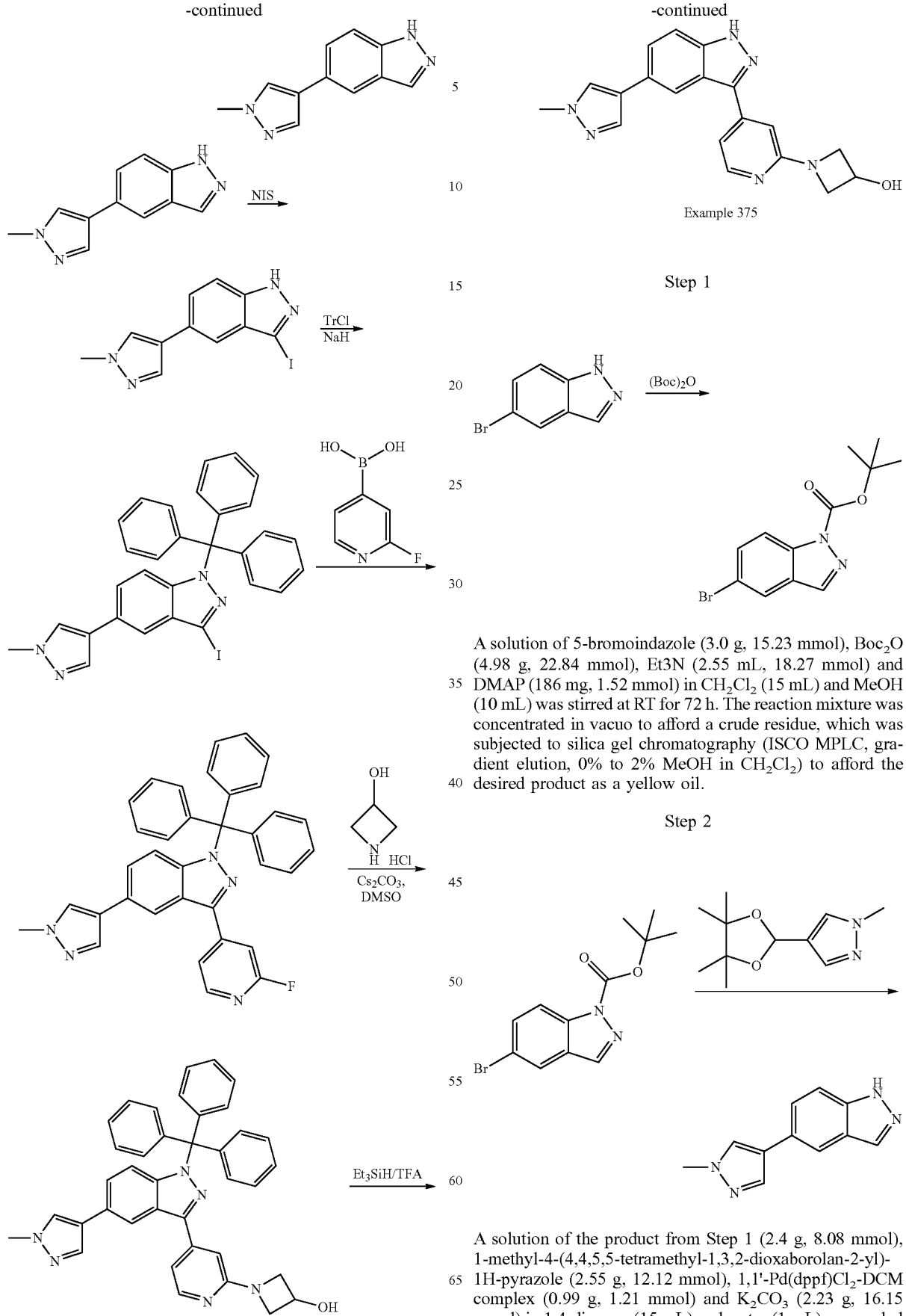

A solution of 5-bromoindazole (3.0 g, 15.23 mmol), Boc₂O (4.98 g, 22.84 mmol), Et3N (2.55 mL, 18.27 mmol) and DMAP (186 mg, 1.52 mmol) in CH₂Cl₂ (15 mL) and MeOH (10 mL) was stirred at RT for 72 h. The reaction mixture was concentrated in vacuo to afford a crude residue, which was subjected to silica gel chromatography (ISCO MPLC, gradient elution, 0% to 2% MeOH in CH₂Cl₂) to afford the desired product as a yellow oil.

Step 2

A solution of the product from Step 1 (2.4 g, 8.08 mmol), 1-methyl-4-(4,4,5,5-tetramethyl-1,3,2-dioxaborolan-2-yl)-1H-pyrazole (2.55 g, 12.12 mmol), 1,1'-Pd(dppf)Cl₂-DCM complex (0.99 g, 1.21 mmol) and K₂CO₃ (2.23 g, 16.15 mmol) in 1,4-dioxane (15 mL) and water (1 mL) was sealed in a microwave reaction vessel and heated in a microwave reactor for 2 h at 110° C. and 30 min. at 135° C. The reaction was then cooled, unsealed and filtered through a pad of Celite. The filter cake was washed with CH₂Cl₂ and the combined filtrates were concentrated to afford a crude residue. The resulting residue was dissolved in CH₂Cl₂ (15 mL) and MeOH (15 mL) and was treated with 4N HCl in 1,4-dioxane (15 mL). After stirring for 2 h at RT, the reaction mixture was concentrated. The resulting residue was dissolved in 7M ammonia in methanol, then concentrated. The resulting residue was subjected to silica gel chromatography (ISCO MPLC, gradient elution, 1% to 8% MeOH in CH₂Cl₂) to afford the desired product as a yellow solid.

Step 3

The product from Step 3 was dissolved in THF (30 mL). Sodium hydride (60% dispersion in mineral oil, 484 mg, 12.11 mmol) was added, followed by trityl chloride (3.38 g, 12.11 mmol). The resulting mixture was stirred at RT for 72 h. The reaction was then partitioned between EtOAc and water. The layers were separated and the organic layer was concentrated to afford a crude residue which was subjected to silica gel chromatography (ISCO MPLC, gradient elution, 20% to 50% EtOAc in hexanes) to afford the desired product as a yellow solid.

Step 5

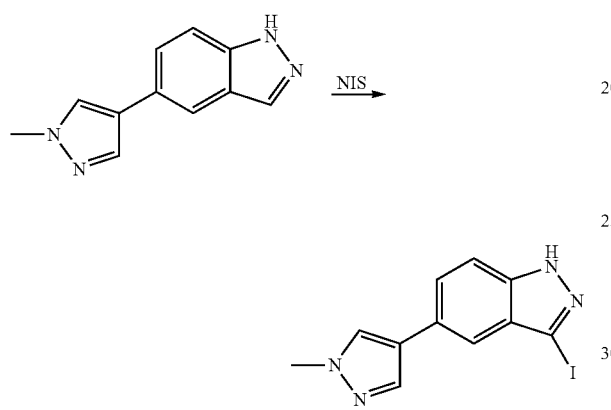

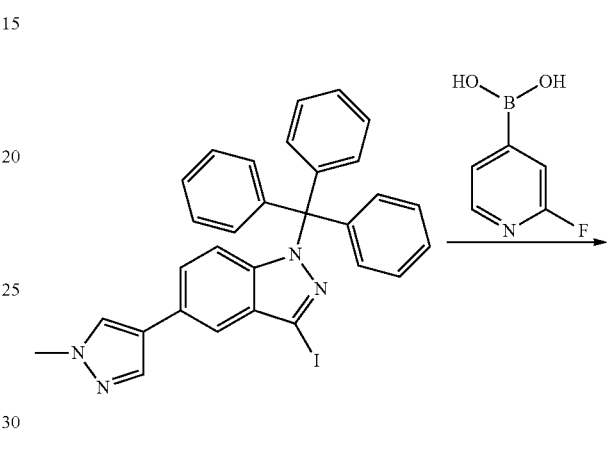

The product from Step 2 (1.2 g, 6.05 mmol) and NIS (2.04 g, 9.08 mmol) were combined in MeCN (15 mL) and DMF (15 mL). The resulting mixture was heated at 90° C. with stirring. The reaction was then cooled, concentrated and subjected to silica gel chromatography (ISCO MPLC, gradient elution, 0% to 5% MeOH in CH₂Cl₂ to afford the desired product as a yellow solid).

Step 4

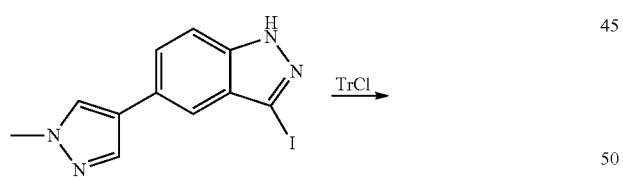

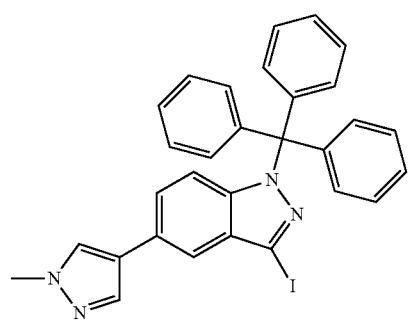

A solution of the product from Step 4 (670 mg, 1.18 mmol), (2-fluoropyridin-4-yl)boronic acid (250 mg, 1.77 mmol), Pd(dppf)Cl₂.DCM complex (145 mg, 0.18 mmol) and K₂CO₃ (327 mg, 2.37 mmol) in 1,4-dioxane (8 mL) and water (0.2 mL) was sealed in a microwave reaction vessel and heated in a microwave reactor for 2 h at 80° C. The reaction was then cooled, unsealed and concentrated to afford a crude residue. The resulting residue was subjected to silica gel chromatography (ISCO MPLC, gradient elution, 0% to 3% MeOH in CH₂Cl₂) to afford the desired product as a yellow solid.

Step 6

Step 7

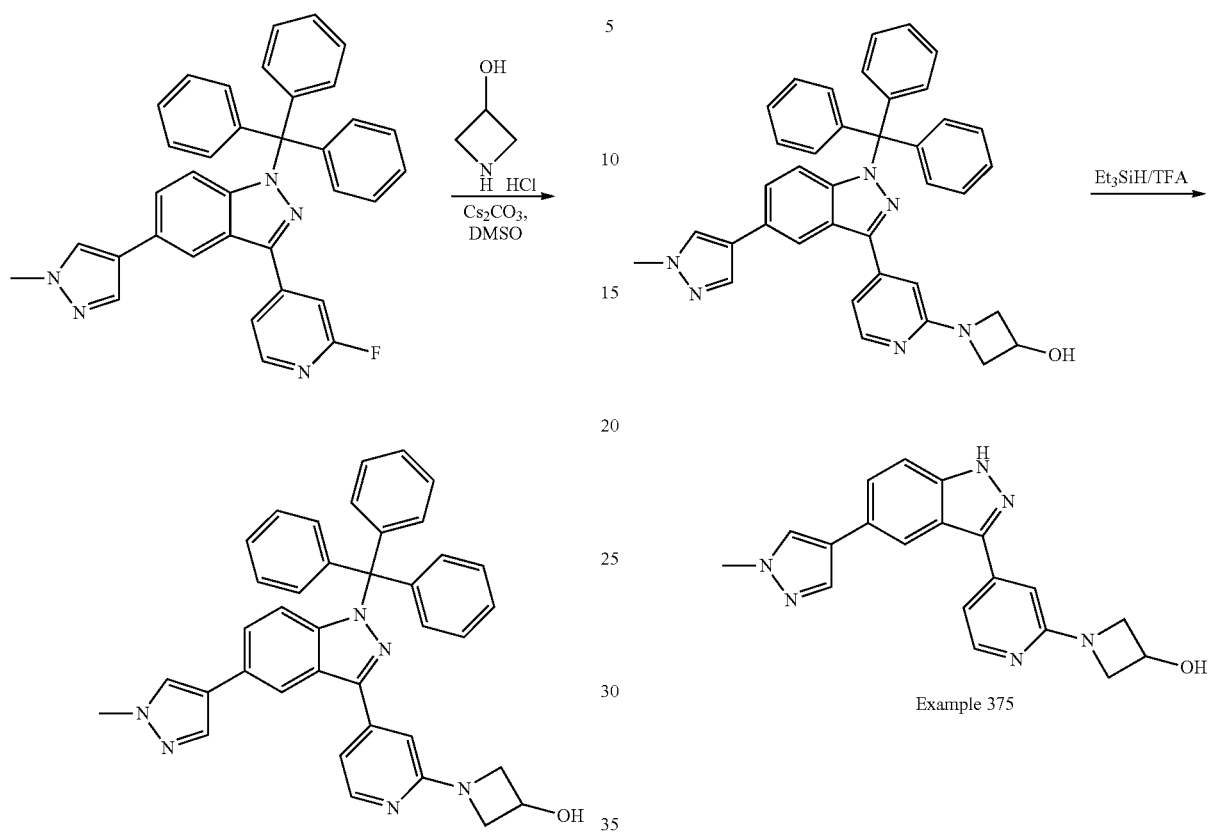

The product from Step 5 (120 mg, 0.22 mmol), azetidin-3-ol hydrochloride (196 mg, 1.79 mmol) and cesium carbonate (584 mg, 1.79 mmol) were combined in DMSO (1 mL) in a microwave vial. The resulting mixture was sealed and heated in a microwave reactor at 190° C. for 2 h. The reaction was cooled, unsealed, and filtered. The filtrate was subject to PTLC on silica gel (5% MeOH in $CH_2Cl_2$) to afford the desired product.

The product from Step 6 (80 mg) was dissolved in TFA (2 mL). Triethylsilane (0.5 mL) was added and the reaction was stirred for 10 minutes at RT. At that point $CH_2Cl_2$ (1 mL) was added and the reaction was stirred for 1 h at RT. The reaction was concentrated and the resulting solid was dissolved in 7M ammonia in MeOH (5 mL). The resulting material was subjected to PTLC on silica gel to give Example 375 (LCMS (ESI) m/z 347 (Ret.=1.86 min, LCMS method e)) as a yellow solid.

TABLE AAAC

Utilizing methods similar to that outlined in Scheme AAAC and the requisite starting amine, the following example was prepared:

| Ex | Structure | LCMS Cond. | RT (min) | m/z | LRRK2 IC$_{50}$ (nM) |
|---|---|---|---|---|---|
| 376 | | e | 1.96 | 349 | <0.60 |

Scheme AAAD

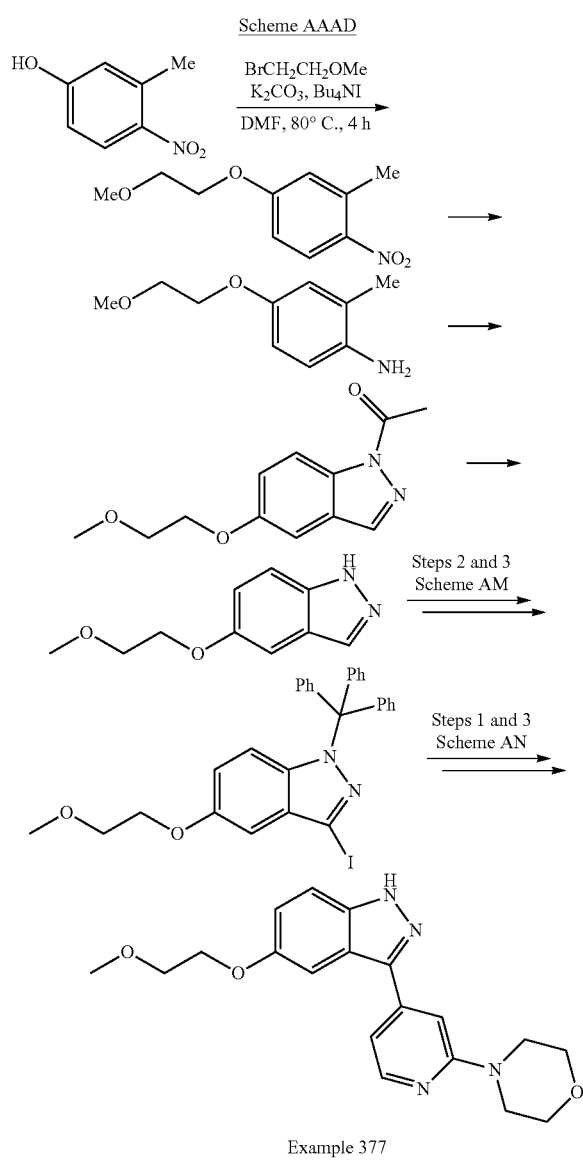

Example 377

Step 1

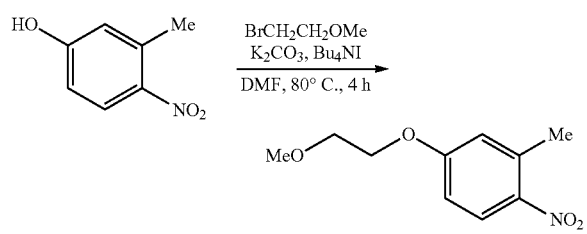

A solution of 3-methyl-4-nitrophenol (6.12 g, 40 mmol), 1-bromo-2-methoxyethane (8.34 g, 60 mmol), potassium carbonate (8.28 g, 60 mmol) and tetrabutylammonium iodide (1.48 g, 4.0 mmol) in DMF (50 mL) was heated in an 80° C. oil bath under nitrogen for 4 hours. The reaction was then cooled and filtered. The filter cake was washed with EtOAc and the combined filtrates were concentrated in vacuo. The crude material was partitioned between EtOAc (200 mL) and water (200 mL). The layers were separated and the organic layer was washed with water (200 mL) and brine, dried over anhydrous MgSO$_4$, filtered and concentrated to afford the desired product as a tan solid, which was used in the next step without further purification.

Step 2

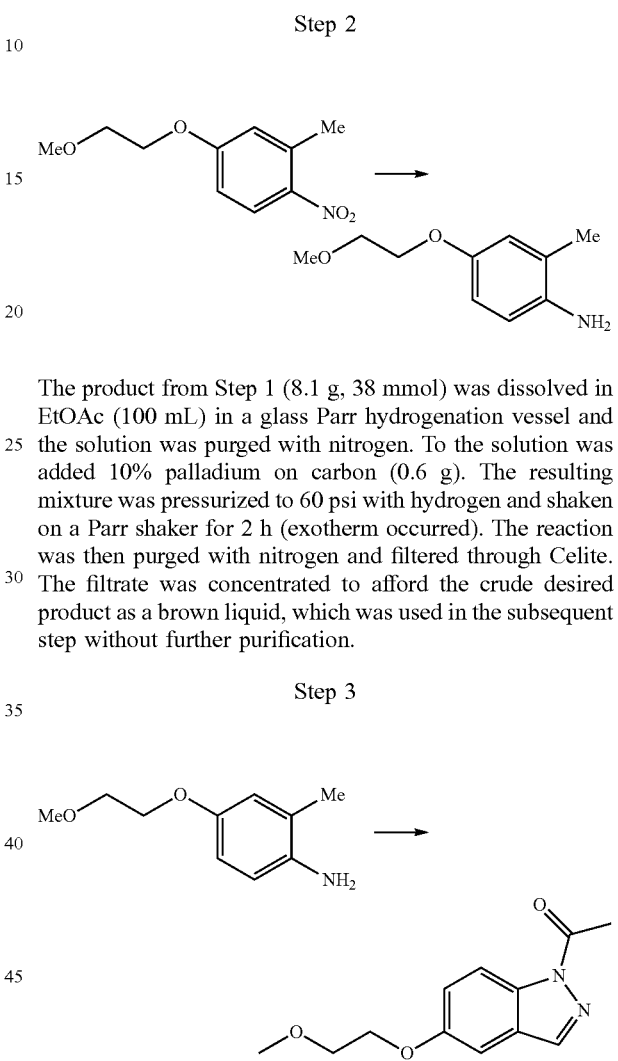

The product from Step 1 (8.1 g, 38 mmol) was dissolved in EtOAc (100 mL) in a glass Parr hydrogenation vessel and the solution was purged with nitrogen. To the solution was added 10% palladium on carbon (0.6 g). The resulting mixture was pressurized to 60 psi with hydrogen and shaken on a Parr shaker for 2 h (exotherm occurred). The reaction was then purged with nitrogen and filtered through Celite. The filtrate was concentrated to afford the crude desired product as a brown liquid, which was used in the subsequent step without further purification.

Step 3

The product from Step 2 (2.63 g, 14.5 mmol) was dissolved in CHCl$_3$ (25 mL). Potassium acetate (1.5 g, 15.3 mmol) was added and the mixture was cooled to 0° C. with an ice bath. Acetic anhydride (2.96 g, 29.1 mmol) was added slowly to the solution and the reaction was stirred for 10 minutes. The flask was removed from the ice bath and 18-crown-6 (0.77 g, 2.9 mmol) was added followed by isopentyl nitrite (3.74 g, 32 mmol). The reaction was then heated in a 70° C. oil bath with stirring under nitrogen for 23 h. The reaction was then allowed to cool to room temperature and was partitioned between CH$_2$Cl$_2$ (25 mL) and 1N aqueous NaHCO3 (25 mL). The layers were separated and the organic layer was washed with brine, dried over anhydrous magnesium sulfate, filtered and concentrated in vacuo to afford a dark red solid, which was subjected to silica gel chromatography (ISCO MPLC, gradient elution 0% to 100% EtOAc in hexanes) to afford the desired product as a light orange solid.

Step 4

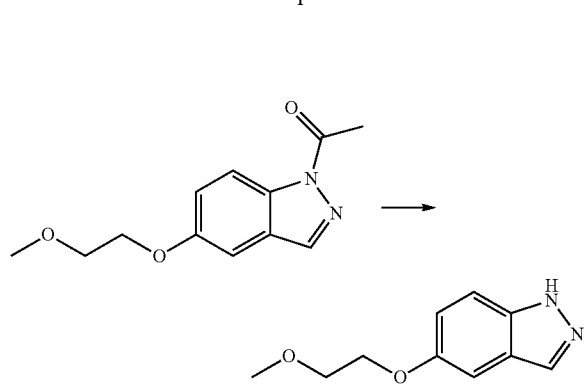

The product from Step 3 (0.94 g, 4.0 mmol) was combined in a solution of MeOH (25 mL), water (8 mL) and conc. HCl (8 mL) and warmed slightly to afford an orange solution. After stirring for 1 h, the reaction was concentrated to ~⅓ the volume and partitioned between 1N aqueous NaHCO3 (50 mL) and EtOAc (50 mL). Solid NaHCO$_3$ (5 g) was added to the biphasic mixture and the resulting mixture was stirred. The layers were separated and the organic layer was washed with brine, dried over anhydrous MgSO$_4$, filtered and concentrated to afford the desired product as a yellow/orange solid.

Step 5

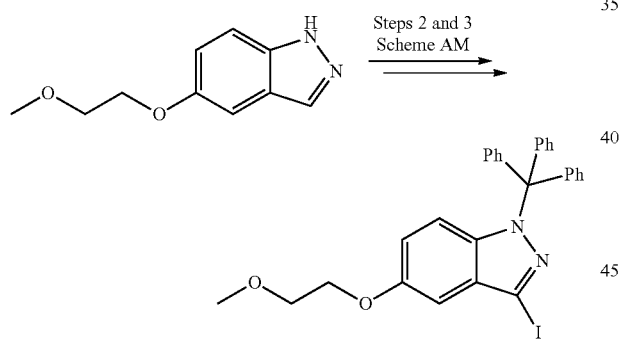

Utilizing the methods outlined in Steps 2 and 3 of Scheme AM, the product from Step 4 was converted to the desired trityl-protected iodoindazole.

Step 6

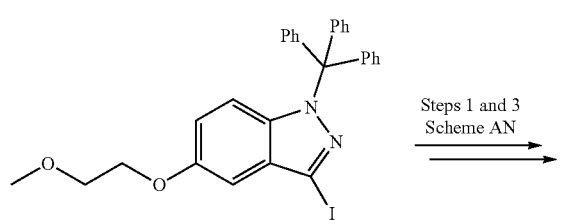

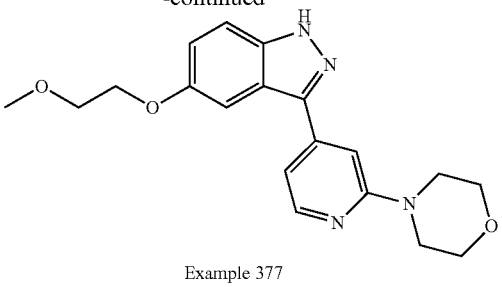

Example 377

Using a method similar to that outlined in Scheme AN, Step 1 (wherein (2-fluoropyridin-4-yl)boronic acid was replaced with (2-morpholinopyridin-4-yl)boronic acid), followed by a method similar to that outlined in Scheme AN, Step 3, Example 377 (LCMS (ESI) m/z 355 (Ret.=1.76 min, LCMS method e)) was prepared.

Scheme AAAE

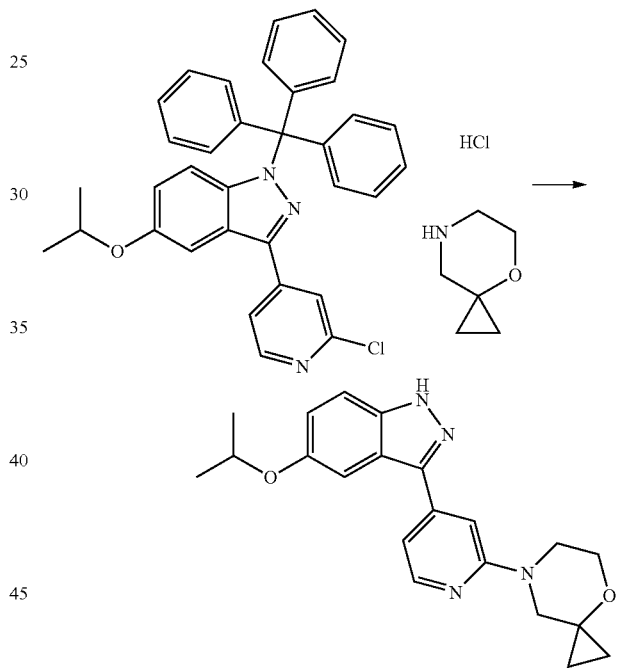

Example 378

A solution of the chloropyridine prepared in Step 4 of Scheme AM (250 mg, 0.472 mmol) in 1,4-dioxane (4 ml) was treated with sodium tert-butoxide (132 mg, 1.179 mmol), 4-oxa-7-azaspiro[2.5]octane hydrochloride (74.5 mg, 0.519 mmol), 1,3-bis(2,6-diisopropylphenyl)-imidazolidinium-chloride (40.3 mg, 0.094 mmol) and Pd$_2$(dba)$_3$ (43.2 mg, 0.047 mmol). The reaction was sealed and heated overnight at 100° C. The reaction was then cooled to room temperature. The reaction mixture was filtered. The filtrate was concentrated in vacuo and the resulting was dissolved in TFA (2 mL). Triethylsilane (0.5 mL) and CH$_2$Cl$_2$ (1 mL) were added and the reaction was stirred for 2 h at RT. The reaction was concentrated and the resulting solid was dissolved in 7M ammonia in MeOH (5 mL). The resulting material was subjected to PTLC on silica gel to give Example 378 (LCMS (ESI) m/z 387 (Ret.=1.90 min, LCMS method e)) as a yellow solid.

TABLE AAAE

Utilizing a method similar to that outlined in Scheme AAAE and the requisite starting amine and chloropyridine, the following examples were prepared:

| Ex | Structure | LCMS Cond. | RT (min) | m/z | LRRK2 IC$_{50}$ (nM) |
|---|---|---|---|---|---|
| 379 | 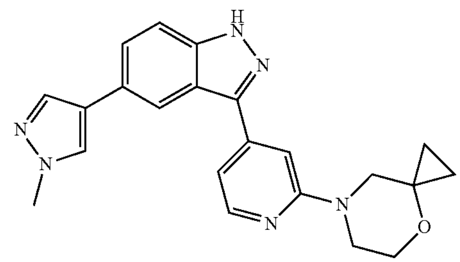 [SMILES: Cn1cc(-c2ccc3[nH]nc(-c4ccnc(N5CCOC6(CC6)C5)c4)c3c2)cn1] | e | 1.90 | 387 | 4.2 |
| 380 | 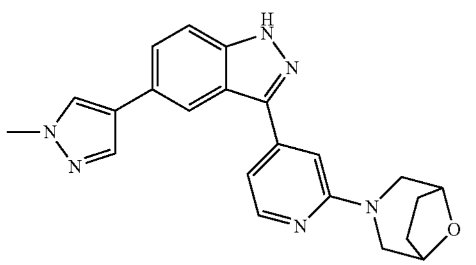 [SMILES: Cn1cc(-c2ccc3[nH]nc(-c4ccnc(N5CC6CCC(C5)O6)c4)c3c2)cn1] | e | 1.85 | 387 | 1.9 |
| 381 | 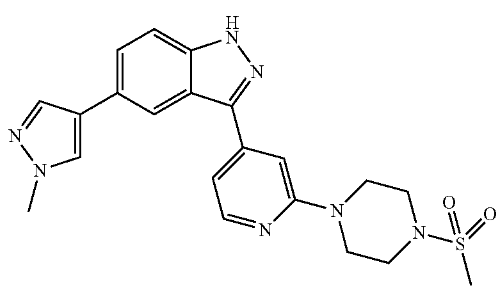 [SMILES: Cn1cc(-c2ccc3[nH]nc(-c4ccnc(N5CCN(S(C)(=O)=O)CC5)c4)c3c2)cn1] | i | 2.64 | 438 | 1.9 |

Scheme AAAF

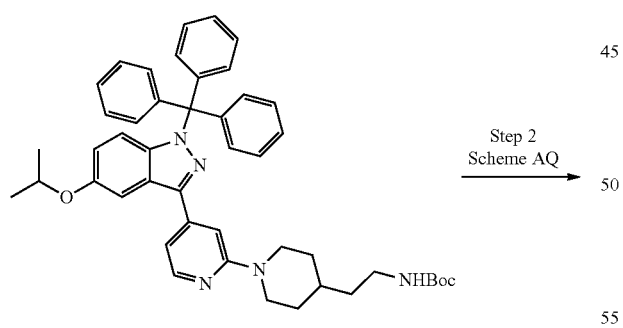

Intermediate AP.1

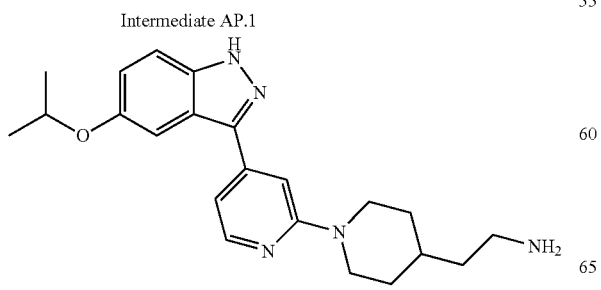

Example 382

Utilizing a method similar to that outlined in Step 2 of Scheme AQ, Intermediate AP.1 was converted to Example 382 (LCMS (ESI) m/z 380 (Ret.=1.87 min, LCMS method e)).

Scheme AAAG

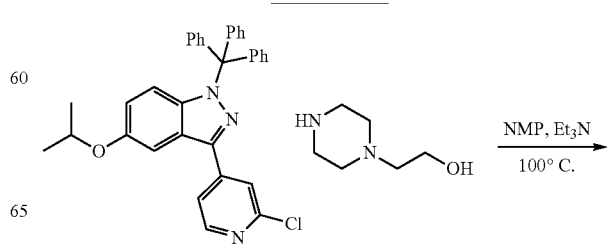

387
-continued

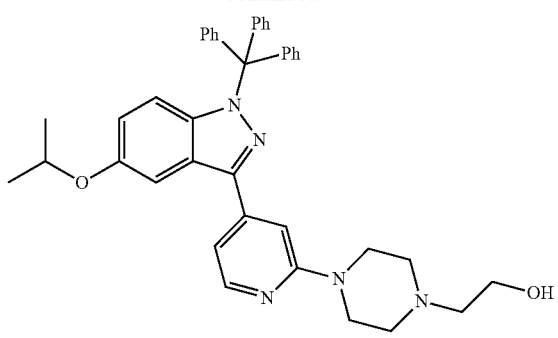

A solution of the chloropyridine prepared in Step 4 of Scheme AM (300 mg, 0.566 mmol), 2-(piperazin-1-yl)ethanol (737 mg, 5.66 mmol) and Et$_3$N (2 mL, 14.35 mmol) in NMP (2 mL) was sealed in a glass reaction vessel and heated 36 h at 100° C. The reaction was then cooled to room temperature. The reaction vessel was unsealed and the mixture was concentrated in vacuo. The resulting residue was subjected to silica gel chromatography (isocratic elution, 10:1 CH$_2$Cl$_2$:MeOH) to afford the desired product.

Scheme AAAH

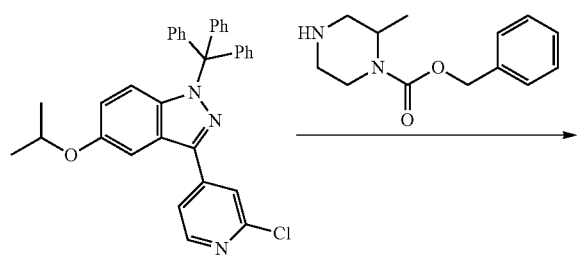

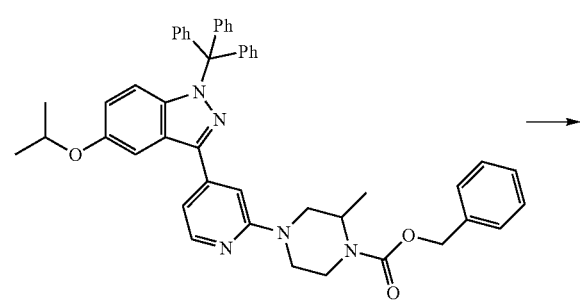

388
-continued

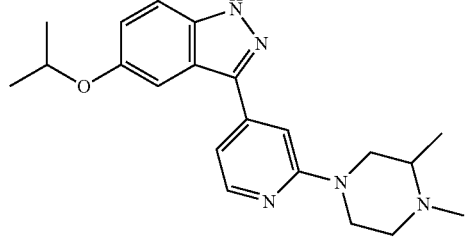

Example 384

Step 1

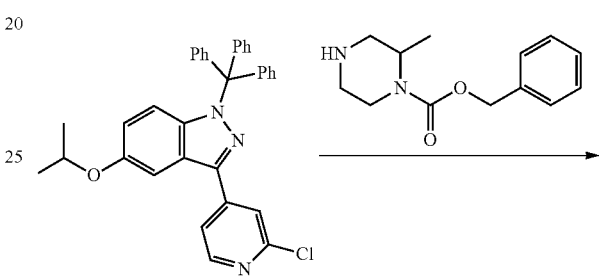

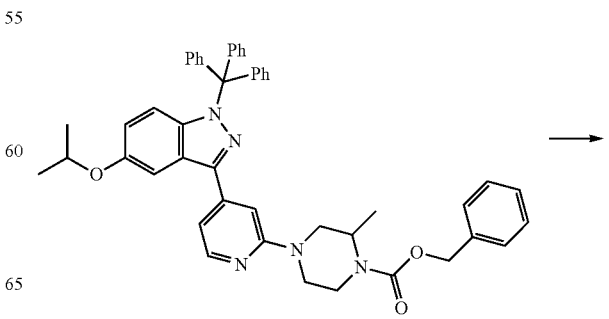

Utilizing a method similar to that described in Step 1 of Scheme AR, substituting 2-methoxyethanolamine with benzyl 2-methylpiperazine-1-carboxylate, the desired product was prepared.

Step 2

-continued

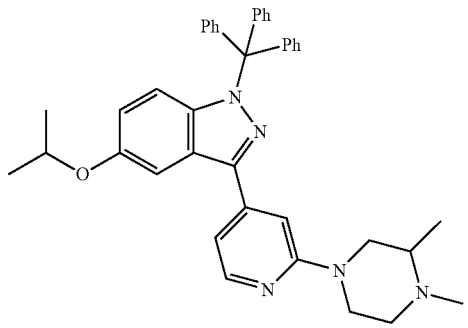

The product prepared in Step 1 (200 mg, 0.28 mmol) was dissolved in THF (3 mL) and added to a 0° C. suspension of lithium aluminum hydride (104 mg, 2.75 mmol) in THF (3 mL). The resulting mixture was heated at 60° C. for 6 h. The reaction was then cooled to 0° C. and diluted with Et$_2$O. An aqueous 1N NaOH solution (1 mL) was slowly added to the reaction mixture. The quenched reaction was stirred for 30 min. at RT. Anhydrous magnesium sulfate was added to the mixture, which was subsequently filtered. The filtrate was concentrated and the resulting residue was used in the next step without any further purification.

Step 3

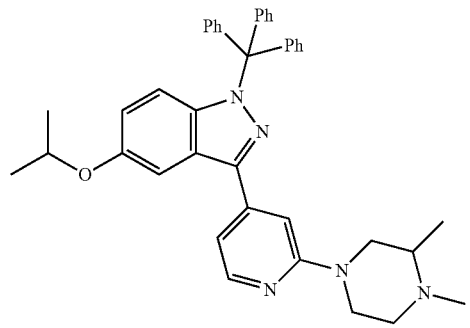

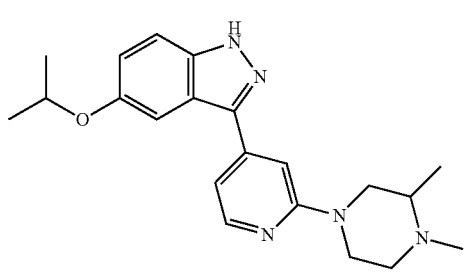

Example 384

Utilizing a method similar to that outlined in Step 2 of Scheme AR, the product from Step 2, Scheme AAAH was converted to Example 384 (LCMS (ESI) m/z 366 (Ret.=1.64 min, LCMS method g)).

Scheme AAAI

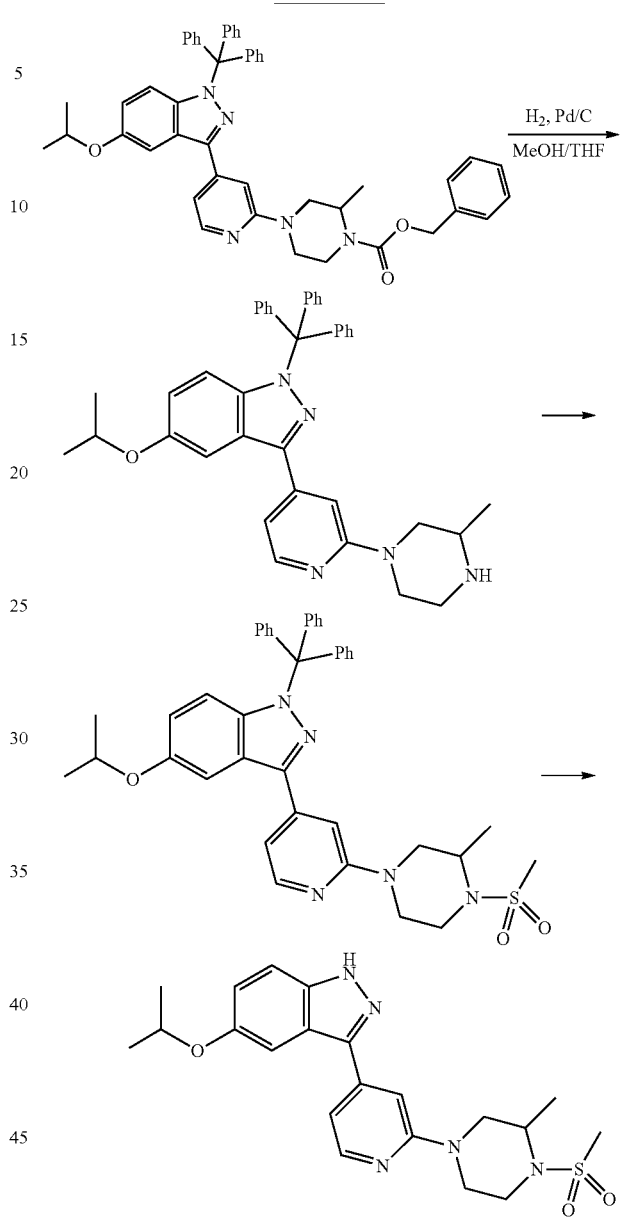

Example 385

Step 1

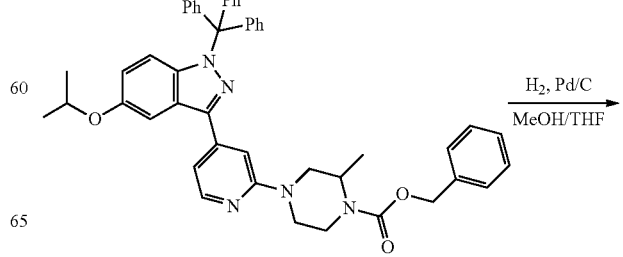

391

-continued

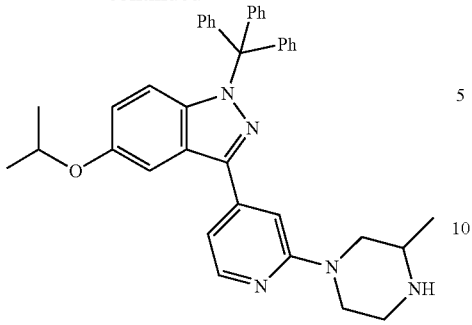

A mixture of the product from Scheme AAAH, Step 1 (1.2 g, 1.649 mmol) and 10% Pd/C (250 mg, 0.235 mmol) in Methanol (15 ml) and THF (5 ml) was stirred under a hydrogen atmosphere (1 atm) at RT overnight. The reaction was diluted with EtOAc and filtered through a pad of Celite. The filtrate was concentrated and the resulting residue was used directly in the next step without further purification.

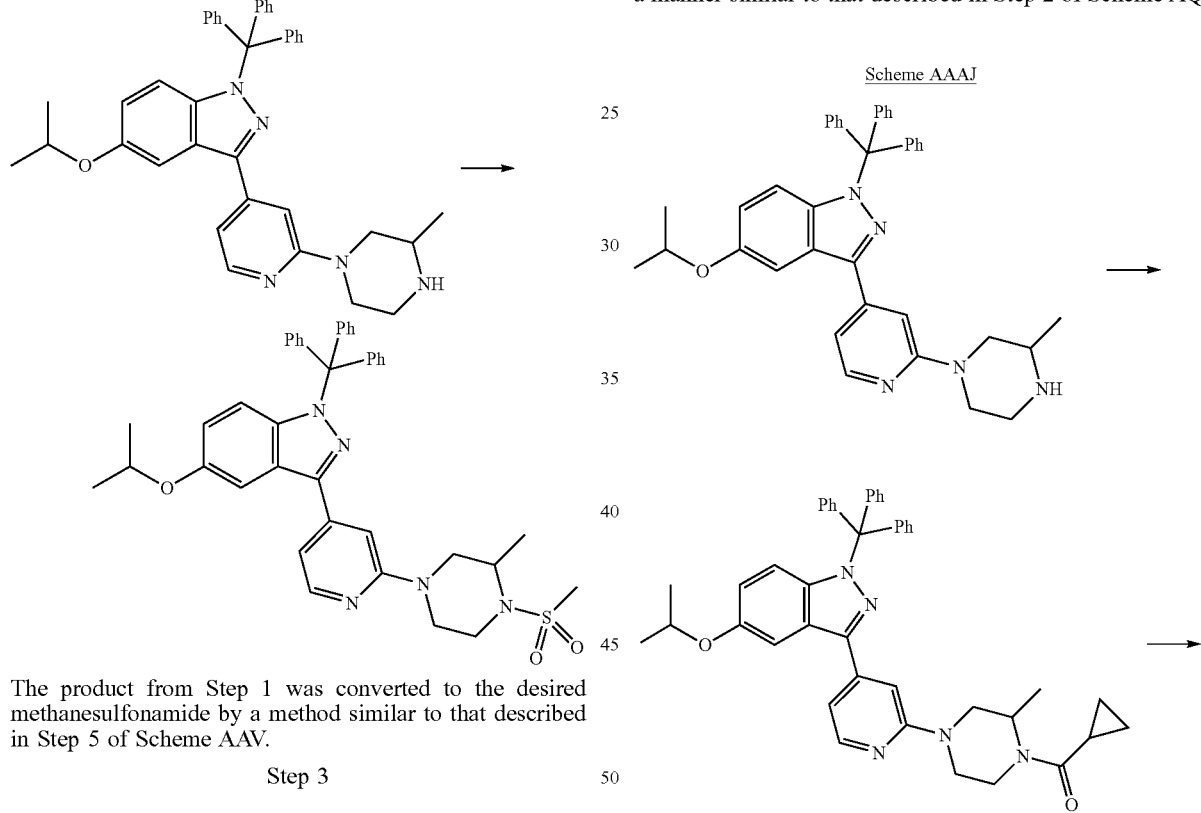

The product from Step 1 was converted to the desired methanesulfonamide by a method similar to that described in Step 5 of Scheme AAV.

Step 3

392

-continued

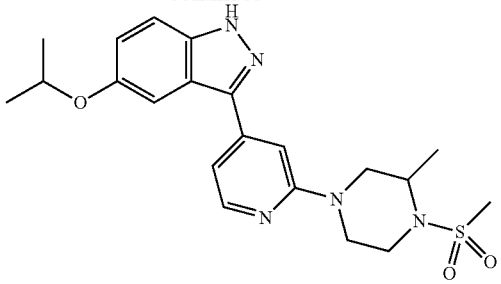

Example 385

The product from Step 2 was converted to Example 385 (LCMS (ESI) m/z 430 (Ret.=1.98 min, LCMS method e)) in a manner similar to that described in Step 2 of Scheme AQ.

Scheme AAAJ

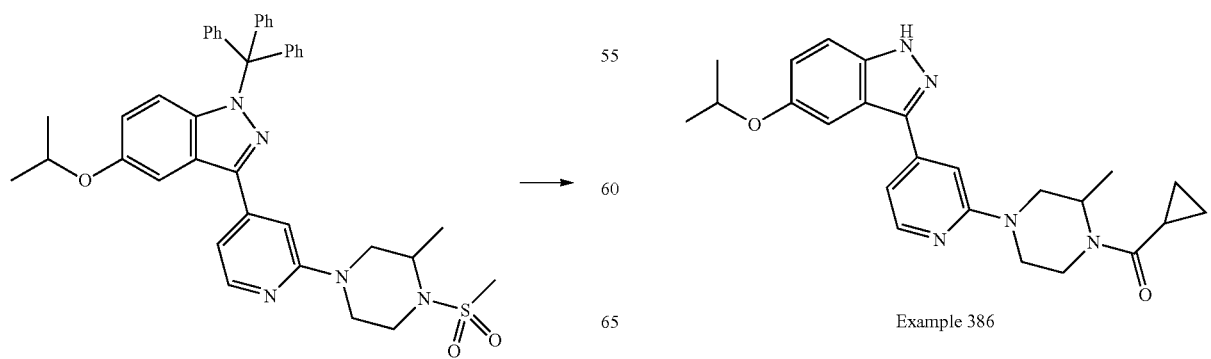

Example 386

393

Step 1

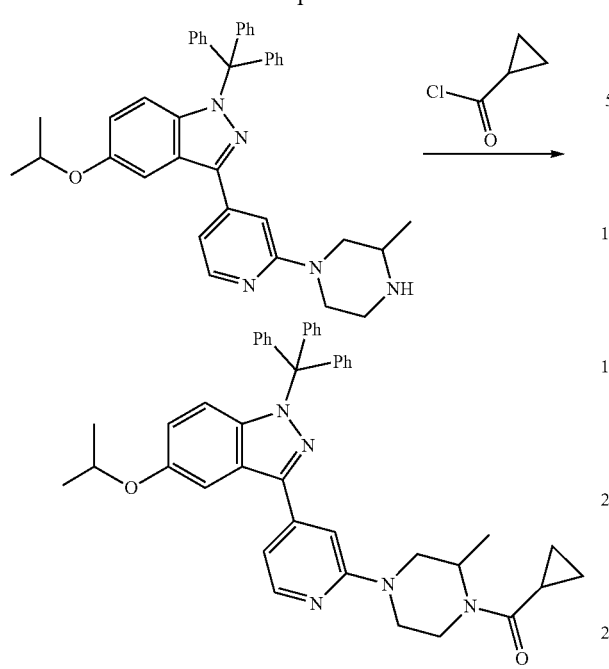

The product prepared in Step 1, Scheme AAAI (80 mg, 0.135 mmol), Et₃N (0.094 mL, 0.674 mmol) and cyclopropanecarbonyl chloride (0.024 mL, 0.269 mmol) were combined in CH₂Cl₂ (2.5 mL) stirred at 0° C. for 2 h. The reaction was quenched with water and extracted with DCM (×3). The combined organic layers were dried, filtered and concentrated to leave a residue which was purified by silica gel column chromatography (elution with 1:1 hexanes: EtOAc) to yield the desired product.

Step 2

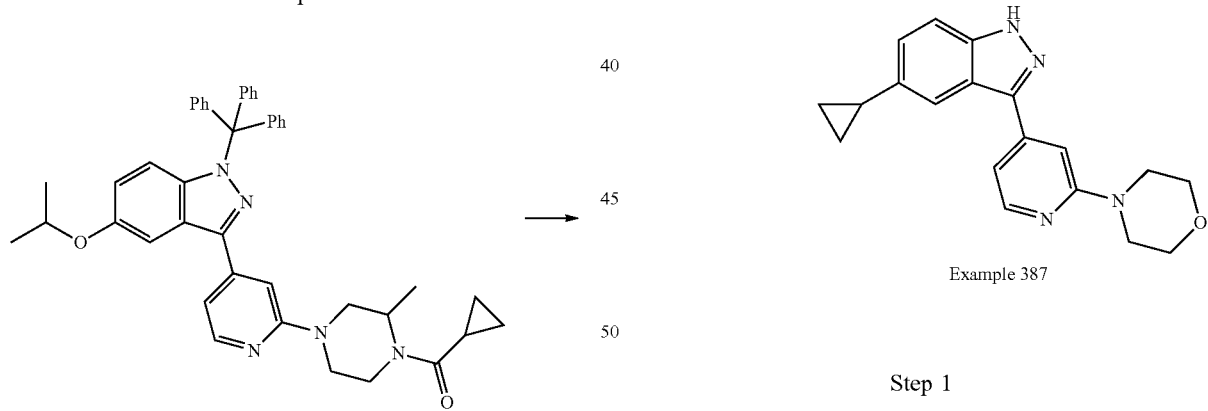

Example 386

The product from Step 2 was deprotected in a manner similar to that described in Step 2 of Scheme AQ to provide Example 386 (LCMS (ESI) m/z 420 (Ret.=2.01 min, LCMS method e)).

Scheme AAAK

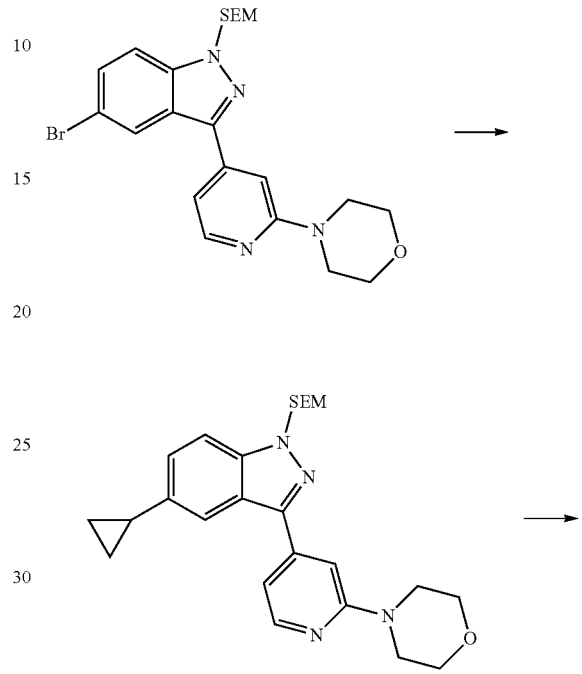

Example 387

Step 1

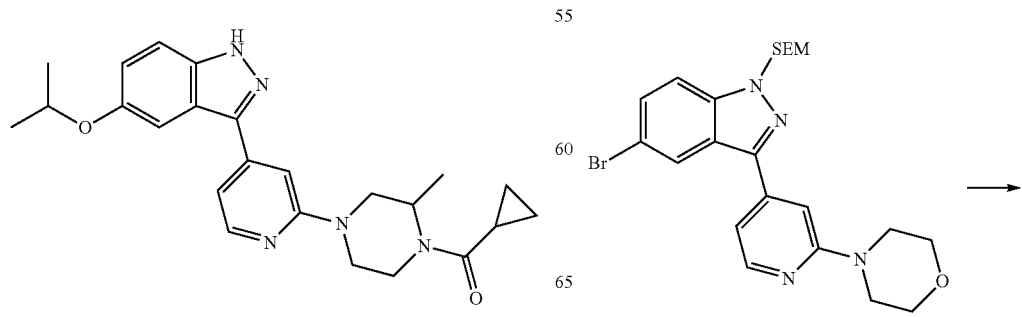

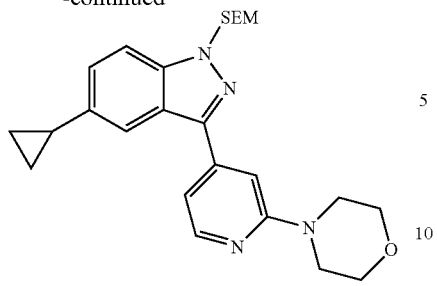

A solution of the compound prepared in Step 3, Scheme D (204 mg, 0.417 mmol), $K_3PO_4$ (292 mg, 1.375 mmol), $Pd(PPh_3)_4$ (10 mg, 0.008 mmol) and potassium cyclopropyltrifluoroborate (74 mg, 0.50 mmol) in toluene (1.5 mL) and water (0.5 mL) was sealed in a microwave tube and heated in a microwave reactor for 1 h at 150° C. The reaction was cooled and unsealed and the reaction mixture was partitioned between EtOAc and brine. The layers were separated and the organic layer was concentrated to afford a crude residue, which was subjected to reversed-phase column chromatography (Biotage SP1 MPLC, Analogix 55 g $C_{18}$ MPLC column, gradient elution 0% to 100% MeCN in water w/ 0.1% TFA) to give the desired product.

Step 2

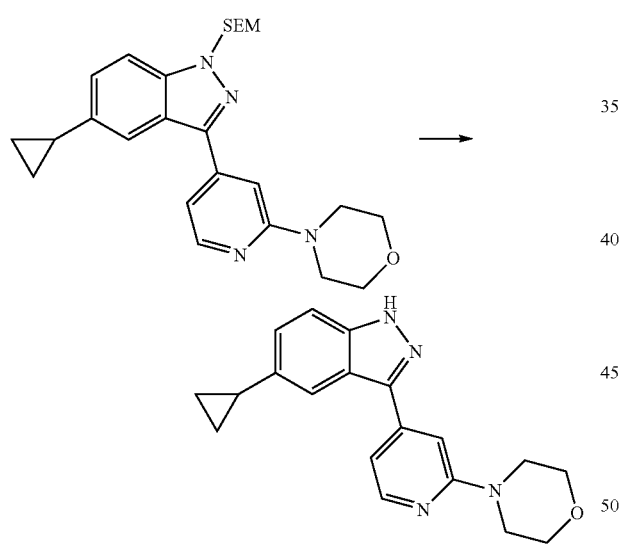

Example 387

A solution of the product from Step 1 (70 mg, 0.16 mmol) in a mixture of EtOH (5 mL) and 3N $HCl_{(aq.)}$ (5 mL) was heated at 80° C. for 24 h. The reaction was then cooled to room temperature and concentrated in vacuo. The resulting residue was dissolved in a mixture of methylene chloride (4 ml), methanol (6 ml) and conc. ammonium hydroxide (4 ml) and stirred overnight at room temp. The mixture was then concentrated in vacuo. The resulting residue was purified by C18 reversed-phase chromatography (Biotage SP1 MPLC, Analogix 55 g $C_{18}$ MPLC column, gradient elution, 0% to 100% MeCN in water with 0.1% TFA) to afford Example 387 (LCMS (ESI) m/z 321 (Ret.=1.94 min, LCMS method e)) as a TFA salt.

Scheme AAAL

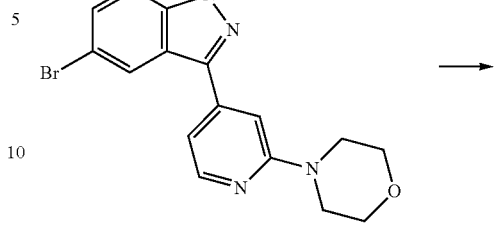

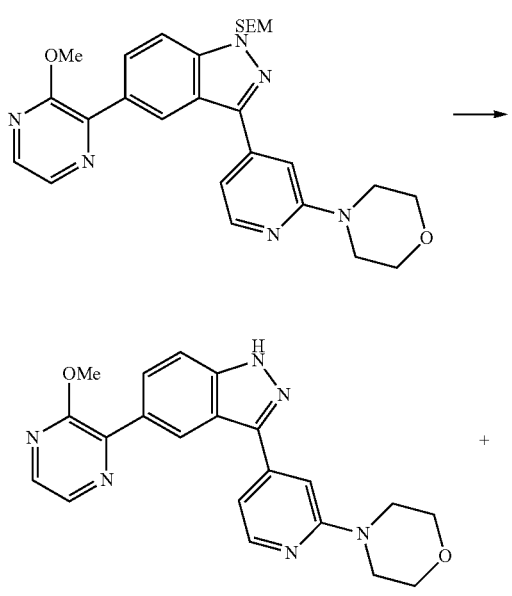

Example 388

Example 389

Step 1

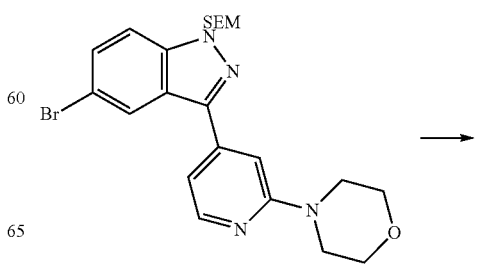

-continued

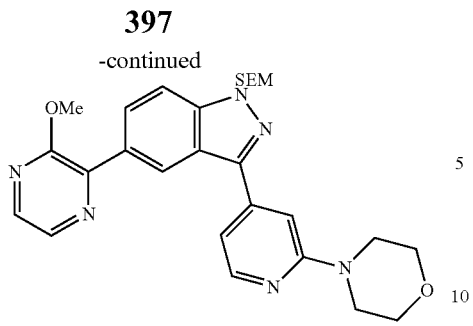

To a stirred, −30° C. mixture of 2.2 M n-BuLi in hexanes (1.045 ml, 2.300 mmol) in THF (10 mL) was added 2,2,6,6-tetramethylpiperidine (0.407 ml, 2.400 mmol). The resulting mixture was stirred at 0° C. for 15 min. The mixture was then cooled to −78° C. and a solution of 2-methoxypyrazine (0.097 ml, 1.00 mmol) in THF (4 mL) was added dropwise. The mixture was stirred at −78° C. for 30 min. Freshly prepared 0.5 M zinc chloride in THF (4.00 ml, 2.00 mmol) was then added dropwise and the resulting solution was warmed to room temperature over 30 minutes. The compound prepared in Step 3, Scheme D (204 mg, 0.417 mmol) (0.587 g, 1.200 mmol) in THF (5 mL) was added to the heteroaryl zinc mixture and the reaction was stirred at 50° C. for 18 h. The reaction was poured into a mixture of 20% aqueous sodium citrate and EtOAc and stirred for 15 min. The aqueous layer was discarded and the organic layer was washed with brine, dried over anhydrous Na₂SO₄, filtered and evaporated to afford a residue which was purified by column chromatography on silica gel (ISCO RediSep 40 g silica gel column), using gradient elution (0% to 50% EtOAc in hexanes) to afford the desired product.

Step 2

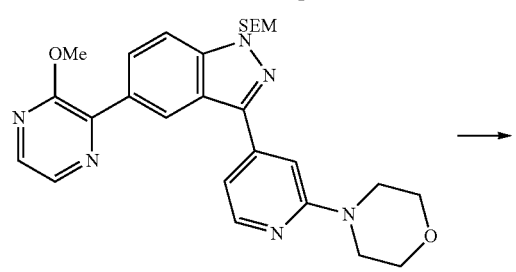

→

-continued

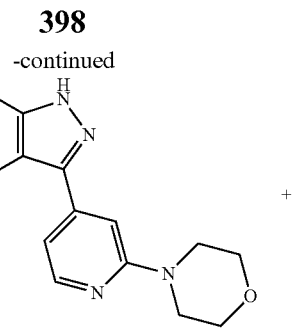

Example 388

+

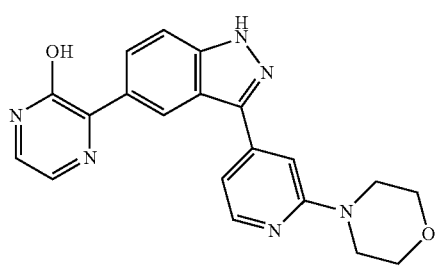

Example 389

3N HCl (aq.) (15 ml, 45.0 mmol) was added to a stirred room temperature mixture of The product from Step 1 (235 mg, 0.453 mmol) was dissolved in Ethanol (15 ml) and treated with 3N HCl (aq.) (15 ml, 45.0 mmol). The resulting mixture was stirred at 80° C. for 18 h. The reaction mixture was then cooled and evaporated under reduced pressure.

Dichloromethane (10 ml), NH₄OH (6 ml, 43.1 mmol) and MeOH (10 ml, 247 mmol) were added to the crude residue and the resulting mixture was stirred at room temperature for 72 h. The reaction mixture was then evaporated under reduced pressure. The resulting residue was dissolved in DMSO, split into two batches and purified by reversed-phase column chromatography (Biotage SP1 MPLC, Analogix 100 g SF25 C18 column), eluting with a gradient of Acetonitrile/Water+0.1% TFA from 0% to 100% MeCN to give afford both Example 388 (LCMS (ESI) m/z 389 (Ret.=1.90 min, LCMS method e)) and Example 389 (LCMS (ESI) m/z 375 (Ret.=1.69 min, LCMS method e)).

TABLE AAAL

Utilizing a method similar to that outlined in Scheme AAAL and 2-ethoxy-pyrazine in place of 2-methoxypyrazine, the following example was prepared:

| Ex | Structure | Cond. | RT (min) | m/z | LRRK2 IC$_{50}$ (nM) |
|---|---|---|---|---|---|
| 390 | 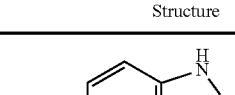 | e | 1.96 | 403 | 1.6 |

Scheme AAAM

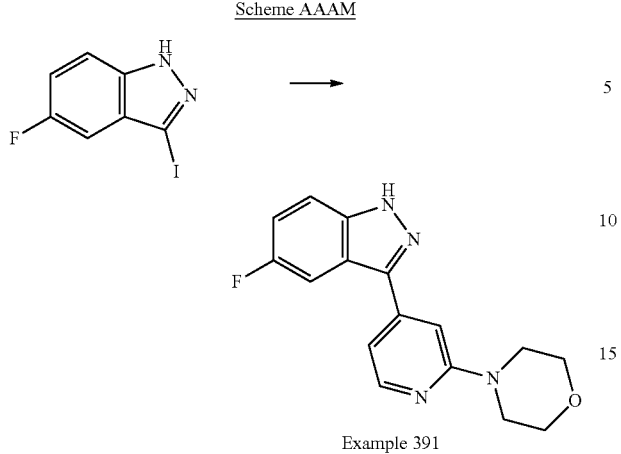

Example 391

To a solution of 5-fluoro-3-iodoindazole (100 mg, 0.382 mmol) in DME (3.816 mL) was added [2-(4-Morpholinyl)-4-pyridinyl]-boronic acid (95 mg, 0.458 mmol), 2M aqueous Na$_2$CO$_3$ (0.572 mL, 1.145 mmol), PdCl$_2$(PPh$_3$)$_2$ (26.8 mg, 0.038 mmol), and the solution was stirred at 90° C. for 16 h. The mixture was cooled and concentrated in vacuo. The crude residue was purified by PTLC using a 1000 micron silica gel plate eluting with (methanol 5%, dichloromethane) to provide Example 391 (LCMS (ESI) m/z 299 (Ret.=1.93 min, LCMS method e)) as a tan solid.

Scheme AAAN

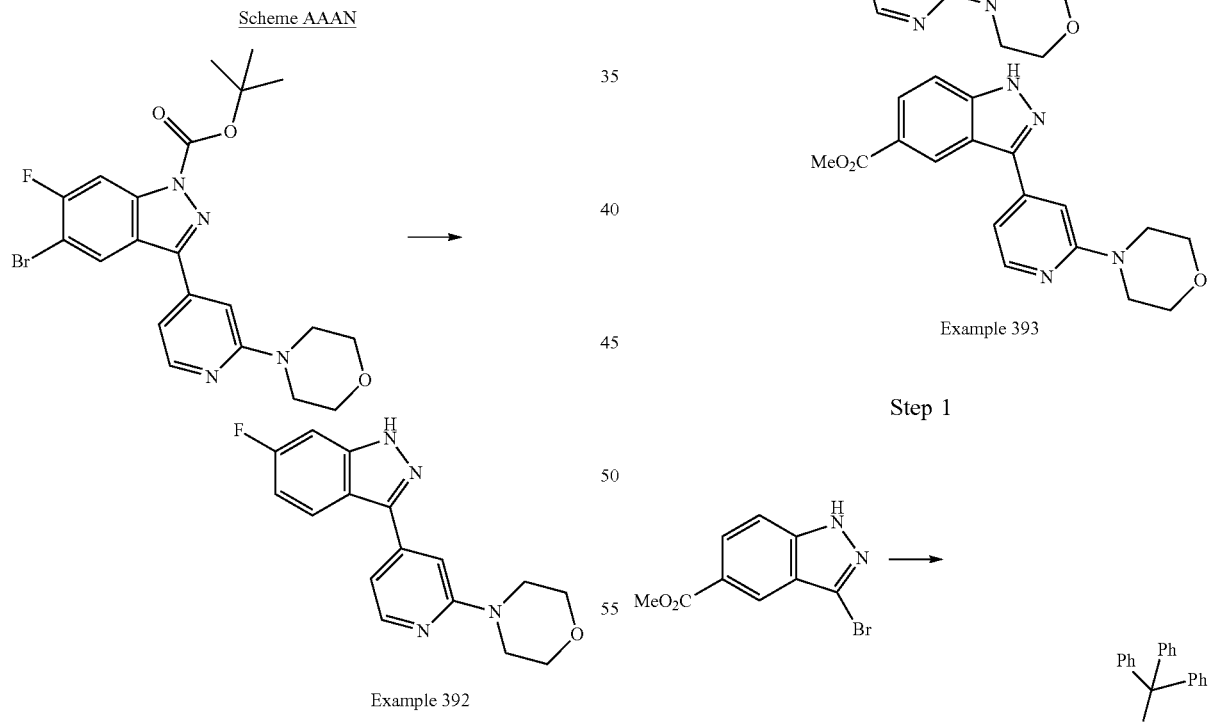

Example 392

A solution of Intermediate AAA.1 (130 mg, 0.272 mmol) in THF (5 mL) was cooled to −78° C. and treated with a solution of n-BuLi (0.409 mmol). After stirring at −78° C. for 1 h, DMF (50 mg, 0.68 mmol) was added and the reaction was stirred overnight at room temperature. The reaction was quenched with saturated aqueous ammonium chloride and partitioned with EtOAc. The layers were separated and the organic layer was dried over anhydrous sodium sulfate, filtered and concentrated to afford a crude residue which was subjected to PTLC on silica gel (50% EtOAc in hexanes) to afford Example 392 (LCMS (ESI) m/z 299 (Ret.=1.35 min, B128short HCOOH)).

Scheme AAAO

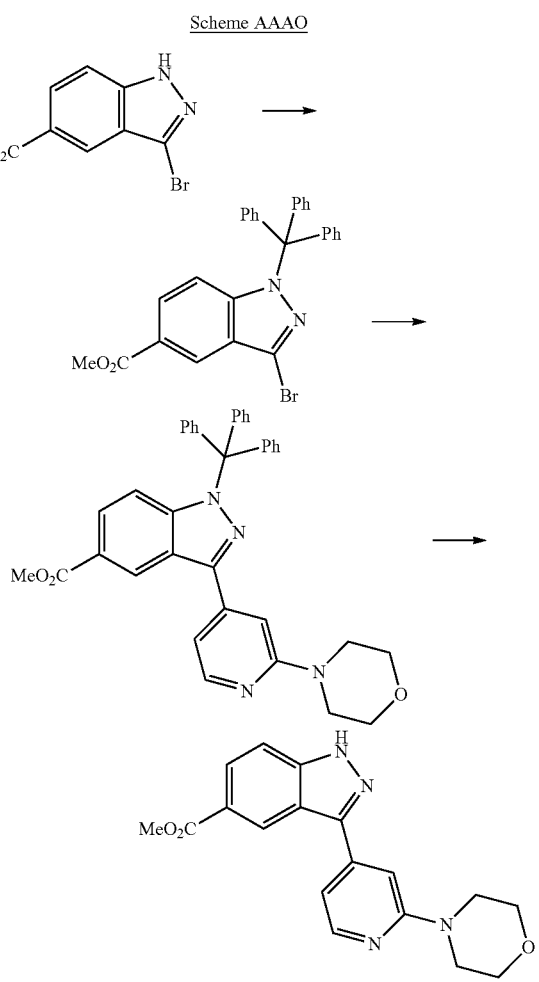

Example 393

Step 1

Sodium hydride (60% by wt. in mineral oil, 47.0 mg, 1.176 mmol) was added to a 0° C. solution of methyl 3-bromo- 1H-indazole-5-carboxylate (250 mg, 0.980 mmol) in THF (3 ml) and the resulting mixture was stirred for 35 min. trityl chloride (287 mg, 1.029 mmol) was then added and the mixture was stirred at the same temperature for 1 h and further stirred at rt for 45 min. The reaction mixture was ice-cooled again, and NH$_4$Cl (sat. aq.) was added and the mixture was extracted with EtOAc. The organic layer was washed with water and brine, dried over anhydrous MgSO$_4$, filtered and concentrated to afford a residue which was purified on silica gel (gradient elution, EtOAc/hexanes) to afford the desired product as a white solid.

Step 2

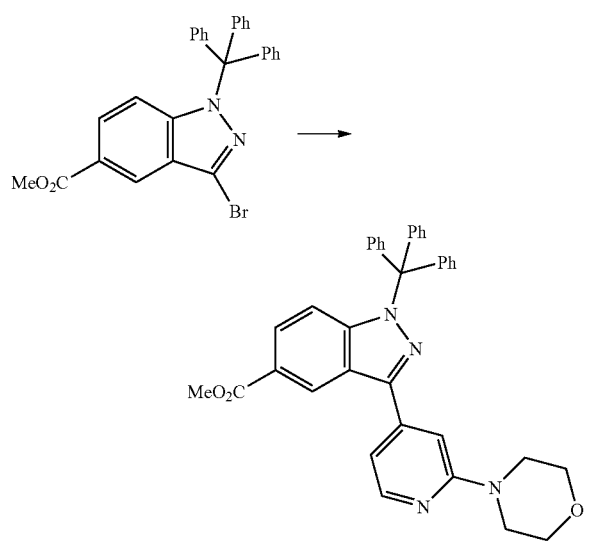

To a solution of the product from Step 1 (500 mg, 1.005 mmol) in DME (10.05 mL) was added B-[2-(4-Morpholinyl)-4-pyridinyl]-boronic acid (251 mg, 1.206 mmol), 2M aqueous Na$_2$CO$_3$ (4.674 mL, 9.35 mmol), and PdCl$_2$(PPh$_3$)$_2$ (70.6 mg, 0.101 mmol). The solution was saturated with N2 gas by bubbling for 5 minutes and the mixture was heated at 90° C. for 16 h in a sealed tube. The mixture was cooled and unsealed. Water (50 mL) was added and the mixture was extracted with ethyl acacate (150 mL). The combined organic fractions were dried over anhydrous MgSO$_4$, filtered and evaporated under reduced pressure. The resulting residue was purified by column chromatography on silica gel [120 g column], eluting with EtOAc/hexanes to give the desired product as a light tan solid.

Step 3

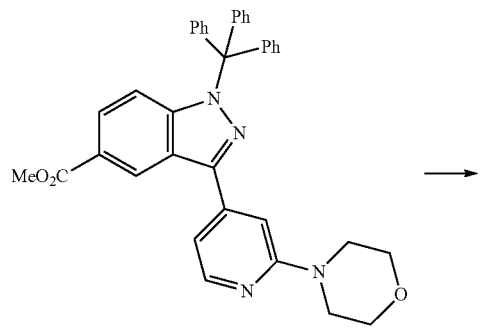

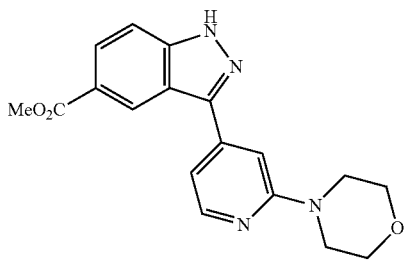

Example 393

To a solution of EtMgBr (1.056 mL, 3.17 mmol) in diethyl ether (5.471 mL) at −78° C. was added Ti(OiPr)$_4$ (0.290 mL, 0.990 mmol), followed by addition of the product from Step 2 (575 mg, 0.990 mmol). The temperature was raised to 0° C. over 1 h and stirred for another 1 h. A solution of 10% sulfuric acid was added (enough to make everything soluble) at 0° C. The mixture was partitioned with dichloromethane (100 mL). The layers were separated and the organic layer was washed with water, dried over anhydrous MgSO$_4$, filtered and evaporated under reduced pressure to provide a crude solid. The crude material was purified by PTLC, using a 1000 micron silica gel plate eluting with 10% methanol in dichloromethane to provide Example 393 (LCMS (ESI) m/z 339 (Ret.=1.87 min, LCMS method e)) as a tan solid.

Schemne AAAP

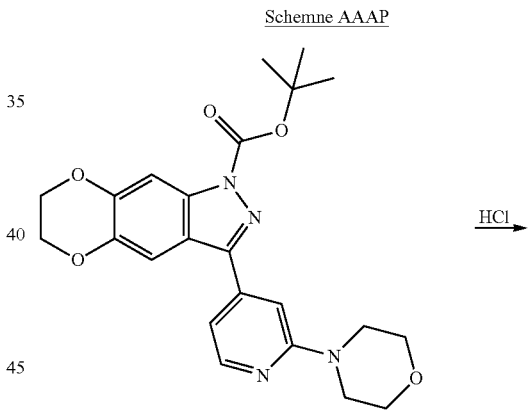

Intermediate AAA.2

Example 394

Intermediate AAA.2 (120 mg, 0.274 mmol) was treated with 4N HCl in dioxane (3 mL) at rt for 3 h. The reaction was concentrated. The resulting residue was purified via gradient C18 chromatography [ISCO MPLC, 0-100% water in acetonitrile with 0.1% TFA] which furnished Example 394 (LCMS method f, Retention time: 1.58, m/z [M+H]$^+$: 339).

Scheme AAAQ

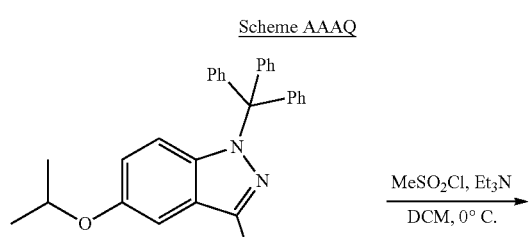

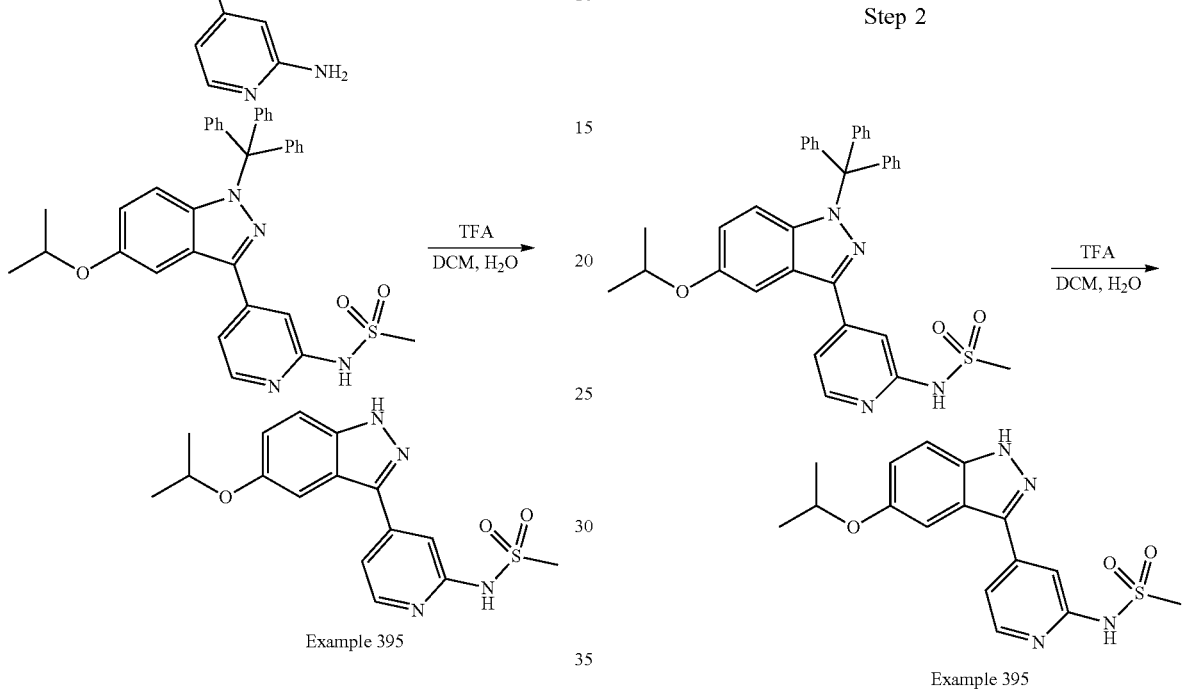

Step 1

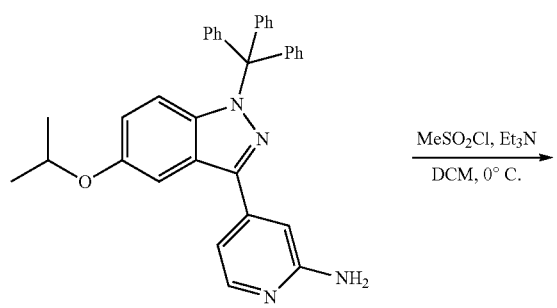

To a cold (0° C.), stirred solution of Intermediate AX1 (100 mg, 0.196 mmol) in DCM (2 ml) were added Et₃N (0.055 ml, 0.392 mmol) and methanesulfonyl chloride (0.018 ml, 0.235 mmol) successively. The reaction was stirred at 0° C. for 30 min. The reaction was quenched with water and extracted with DCM (×3). The organic layers were combined and concentrated to afford a crude residue, which was subjected to silica gel column chromatography (isocratic elution with 20:1 DCM:MeOH) to afford the desired product.

Step 2

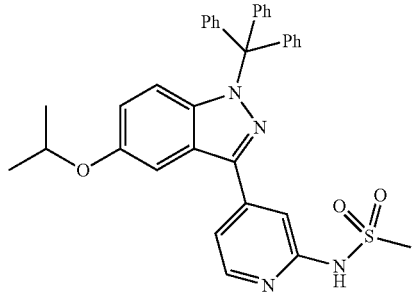

Trifluoroacetic acid (1.5 ml, 130 mmol) was added to a stirred, room temperature mixture of the product from Step 1 (36 mg, 0.061 mmol) in water (0.3 ml) and dichloromethane (3 ml). The resulting mixture was stirred at room temperature for 5 h.

The reaction was neutralized with saturated aqueous sodium bicarbonate solution and extracted with $CH_2Cl_2$ three times. The organic layers were combined and evaporated to give a crude product which was purified by C18 reversed-phase column chromatography (Biotage SP1 MPLC, Analogix C18 column, gradient elution 0% to 100% MeCN in water w/ 0.1% TFA) to afford Example 395 (LCMS method e, Retention time: 1.98 min, m/z $[M+H]^+$: 347).

Scheme AAAR

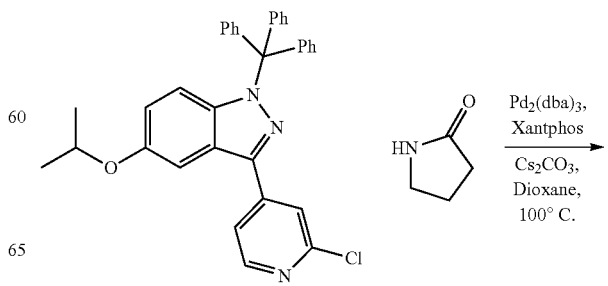

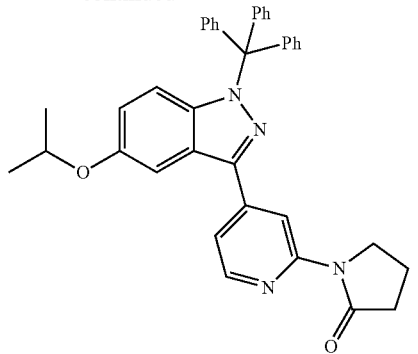 [SMILES: CC(C)Oc1ccc2c(c1)c(-c1ccnc(N3CCOC3=O)c1)nn2C(c1ccccc1)(c1ccccc1)c1ccccc1]

A solution of the chloropyridine prepared in Step 4 of Scheme AM (300 mg, 0.566 mmol), pyrrolidin-2-one (48 mg, 0.566 mmol), Pd$_2$(dba)$_3$ (26 mg, 0.028 mmol), Xantphos (49 mg, 0.085 mmol) and cesium carbonate (277 mg, 0.849 mmol) in 1,4-dioxane (1.2 mL) was purged with argon and heated at 100° C. for 20 h. The reaction mixture was concentrated and the resulting residue was subjected to silica gel chromatography (gradient elution, 2:1 to 1:1 hexanes:EtOAc) to afford the desired product.

TABLE AAAR

Utilizing a method similar to that outlined in Scheme AAAR and the requisite starting materials, the following intermediate was prepared:

| Intermediate Number | Intermediate |
|---|---|
| AAAR1 | 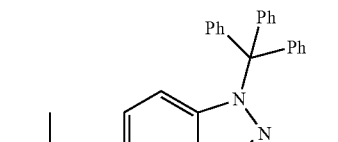 |

Scheme AAAS

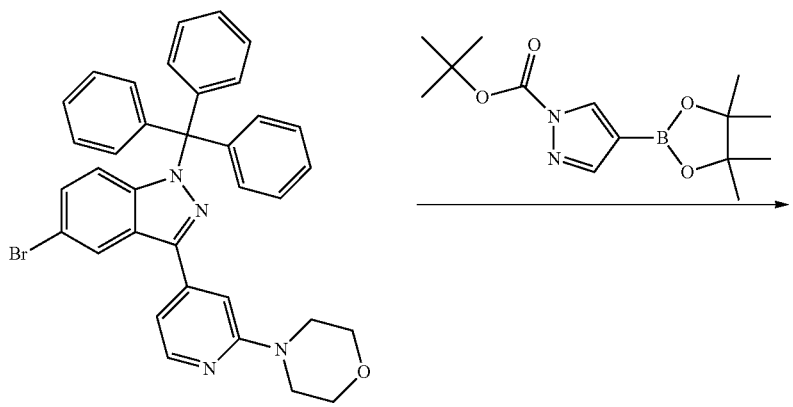

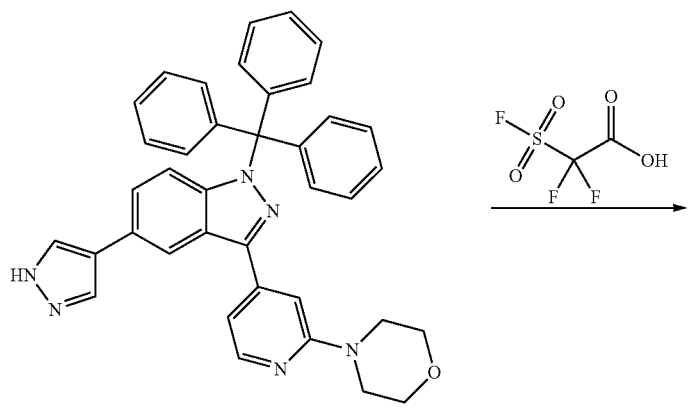

-continued

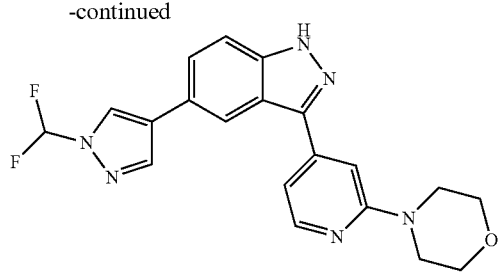

Example 396

Step 1

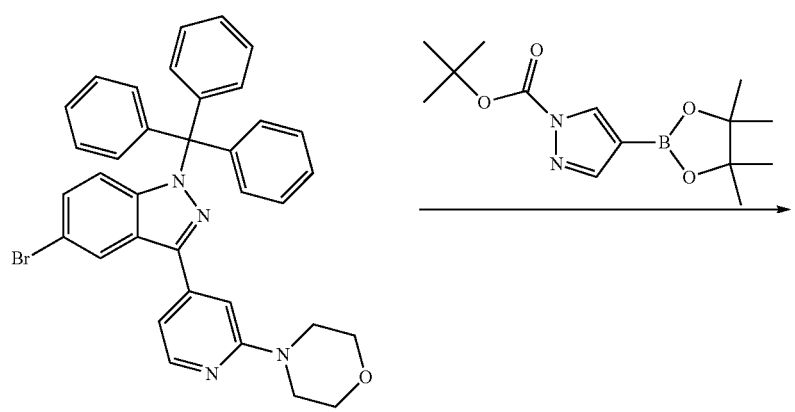

Intermediate AV1 (1.20 g, 1.995 mmol), 1-Boc pyrazole-4-boronic acid pinacol ester-(880 mg, 2.99 mmol), Pd(dppf)Cl$_2$ (292 mg, 0.399 mmol) and K$_2$CO$_3$ (551 mg, 3.99 mmol) were combined in 1,4-dioxane (8 mL) and water (0.3 mL) in a glass microwave vessel. The reaction vessel was sealed and heated overnight in a 100° C. oil bath. The reaction was then microwaved at 140° C. for 30 minutes. The reaction was then filtered and concentrated to afford a residue which was subjected to silica gel chromatography via ISCO MPLC to afford the desired product.

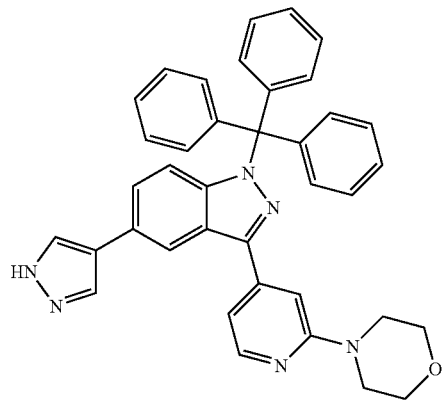

Step 2

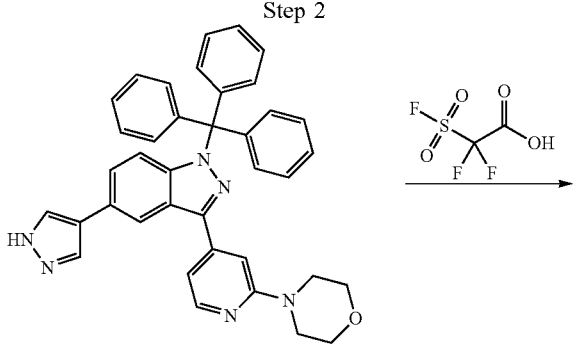

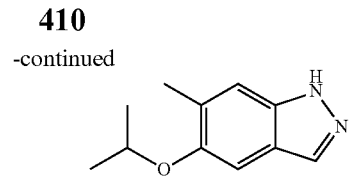

Example 396

The product from Step 1 (110 mg, 0.187 mmol) was combined with sodium sulfate (5.31 mg, 0.037 mmol) and 2,2-difluoro-2-(fluorosulfonyl)acetic acid (66.6 mg, 0.039 mL, 0.374 mmol) in MeCN (3 mL). The reaction was then stirred for 6 h at RT. The reaction mixture was then concentrated and dissolved in a mixture of TFA (0.5 mL) and CH₂Cl₂ (1 mL). The reaction was stirred for 2 h at RT, then concentrated in vacuo. The residue was dissolved in 7M ammonia in MeOH (5 mL) and subjected to PTLC to afford Example 396 (LCMS method e, Retention time: 1.91 min., m/z [M+H]+=397) as a yellow solid.

Scheme AAAT

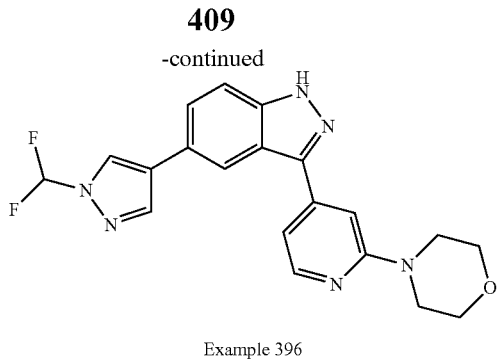

Example 397

Step 1

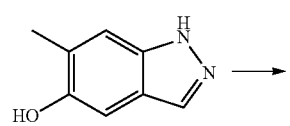

A solution of 6-methyl-1H-indazol-5-ol (1.50 g, 10.12 mmol), Boc₂O (2.43 g, 11.14 mmol) and DMAP (124 mg, 1.012 mmol) in DMF (10 mL) was stirred overnight at room temperature. Cesium carbonate and 2-iodopropane were added to the reaction and the resulting mixture was stirred overnight at RT. The reaction mixture was filtered and the filtrate was concentrated. Trifluoroacetic acid (10 mL) was added and the mixture was stirred for 30 min. The reaction mixture was concentrated in vacuo and the resulting residue was partitioned between EtOAc and saturated aqueous sodium bicarbonate. The layers were separated and the organic layer was concentrated to afford a residue, which was subjected to silica gel chromatography via ISCO MPLC to afford the desired product as a yellow solid.

Step 2

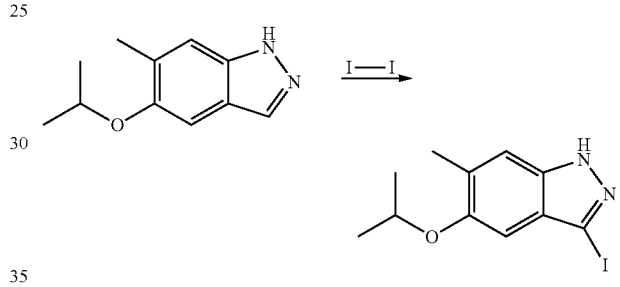

Utilizing a method similar to that described in Step 2 of Scheme AM, the product prepared in Step 1 of Scheme AAAT was converted to the desired iodoindazole.

Step 3

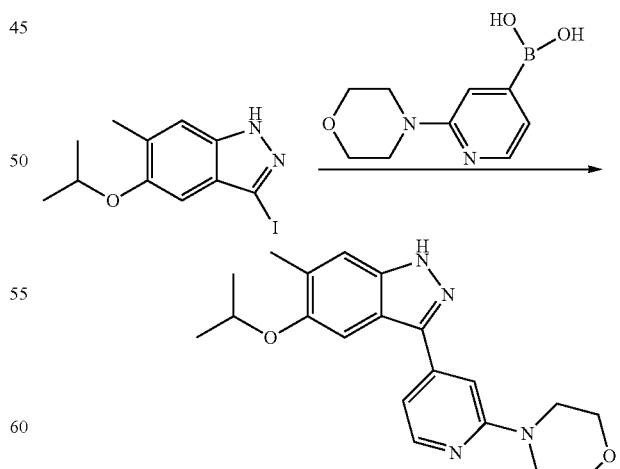

Example 397

A solution of the product from Step 2 (50 mg, 0.158 mmol) B-[2-(4-morpholino)-4-pyridinyl]-boronic acid (66 mg, 0.31606 mmol), potassium phosphate tribasic (67 mg mL, 0.316 mmol), and 1,1'-bis(di-tert-butylphosphono)ferrocene palladium dichloride (20.6 mg, 0.032 mmol) in 1,4-dioxane (2 mL) and water (0.2 mL) was heated at 90° C. for 16 h. The reaction was cooled subjected to PTLC on silica gel to afford Example 397 (LCMS method e, Retention time: 2.05 min., m/z [M+H]+=353) as a yellow solid.

Scheme AAAU

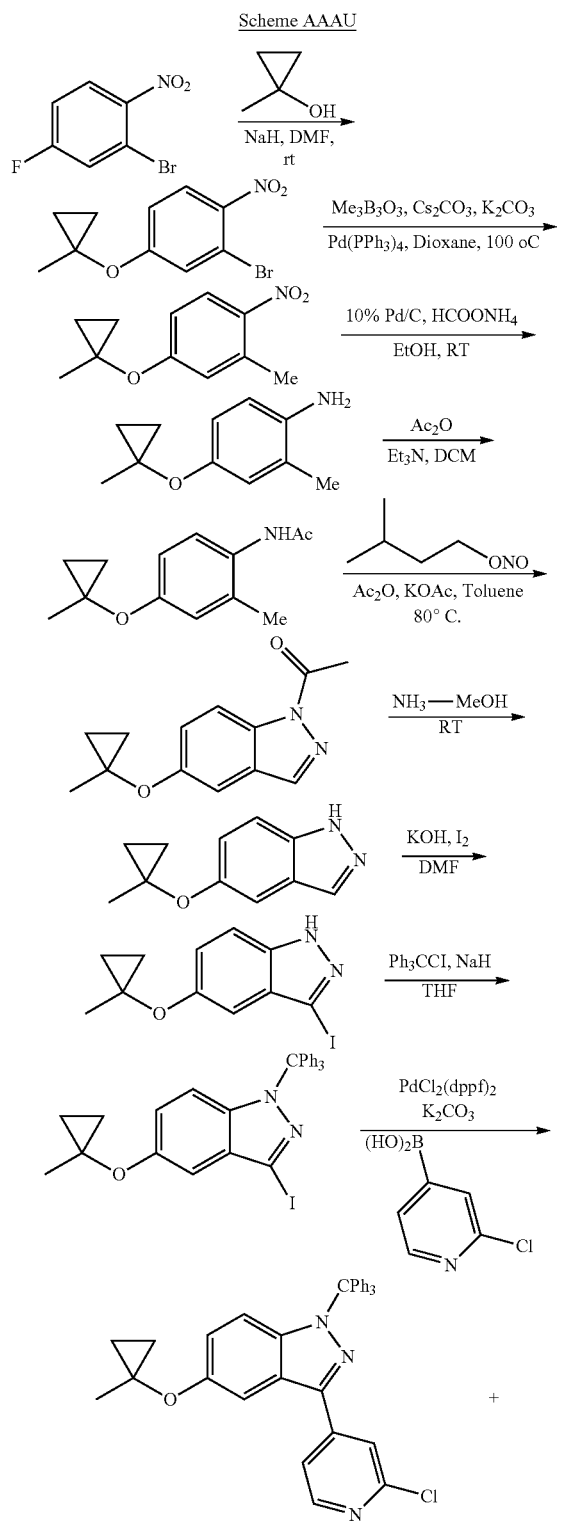

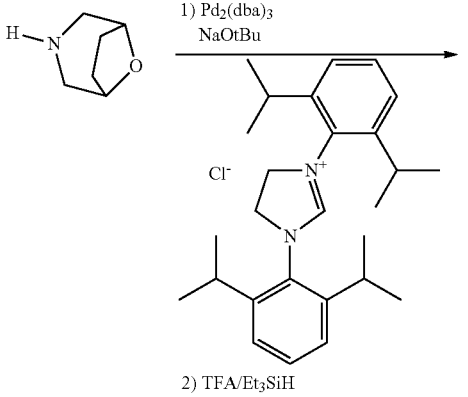

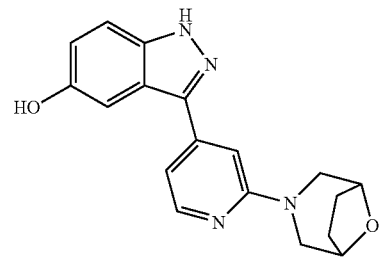

Example 398

Step 1

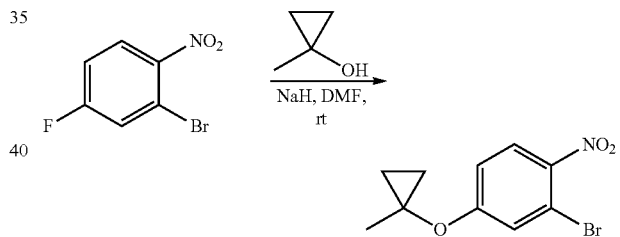

To a cold (0° C.), stirred mixture of 2-bromo-4-fluoronitrobenzene (10.0 g, 45.5 mmol) and 1-methylcyclopropanol (3.61 g, 50.0 mmol) in DMF (200 ml) was added NaH (2.36 g of 60% in oil, 59.1 mmol) in portions. Once the addition was complete the cold bath was removed and the mixture was stirred at rt for 5 h. The reaction was quenched with water and extracted with EtOAc (×3). The combined organic layers were washed with water (×3), brine (×2), dried, filtered and concentrated to leave an oil which was purified by column chromatography (elution with 100:0 to 20:1 hexane:EtOAc) to yield the desired product as a light yellow oil.

Step 2

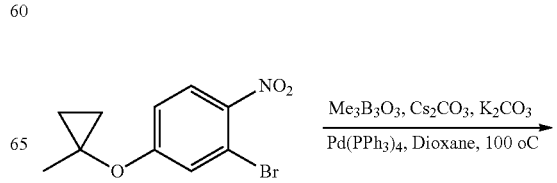

-continued

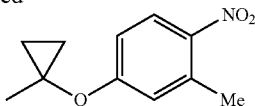

To a stirred mixture of ether (2.0 g, 7.35 mmol), K₂CO₃ (2.03 g, 14.70 mmol) and Cs₂CO₃ (2.39 g, 7.35 mmol) in Dioxane (110 ml) was purged Ar for 15 min. Then trimethylboraxine (2.26 ml, 16.17 mmol) and Pd(Ph₃P)₄ (0.85 g, 0.74 mmol) were added and the mixture was heated at 100° C. overnight. The reaction was cooled to room temperature and concentrated under vacuum. To this residue was added 10:1 hex:EtOAc (500 mL) and filtered through a pad of silica. The solid was washed with a mixture of hexane:EtOAc (1 L of 10:1 hexane:EtOAc) solution. The filtrate was concentrated under vacuum to provide the desired product, which was used in the next step without further purification.

Step 3

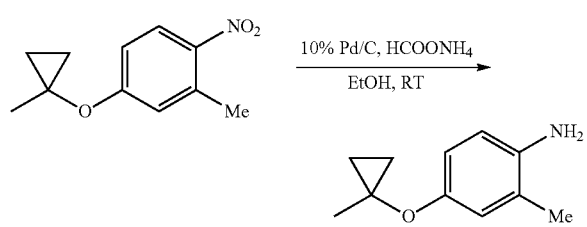

The nitro derivative was dissolved in absolute EtOH (110 mL). To this solution were added 10% Pd/C (0.782 g, 0.735 mmol) and ammonium formate (5.56 g, 88.0 mmol) and the mixture was stirred at room temperature for 5 h. To this solution was added a solution containing 5:1 hexane:EtOAc (500 mL) and the mixture was filtered through a pad of silica. The filtrate was concentrated and the residue was purified by column chromatography (elution with 10:1 to 5:1 hexane:EtOAc) to yield the desired amine as a dark brown oil.

Step 4

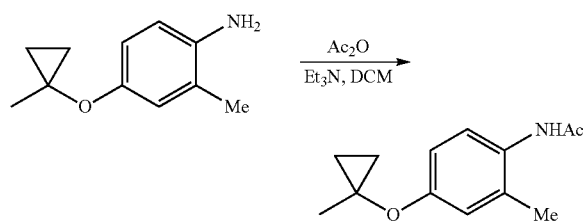

To a cold (0° C.), stirred mixture of amine (1.4 g, 7.90 mmol) and triethylamine (2.20 ml, 15.80 mmol) in CH₂Cl₂ (12 ml) was added Ac₂O (1.12 ml, 11.85 mmol). The mixture was slowly warmed to room temperature and stirred overnight. Silica gel was added and the mixture was evaporated to leave a slurry which was then purified by column chromatography (elution with 1:1 hexane:EtOAc) to yield the desired acetamide as a colorless gum.

Step 5

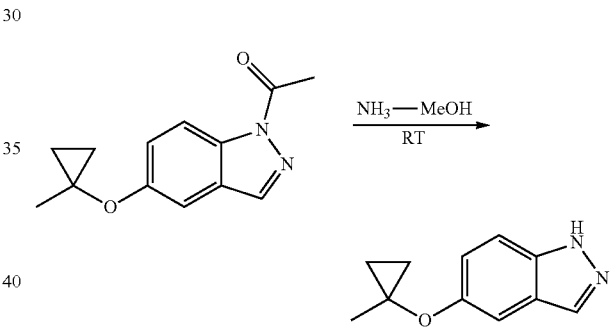

To a stirred solution of the acetamide (1.76 g, 8.03 mmol) in toluene (42 ml) were added KOAc (1.182 g, 12.04 mmol) and Ac₂O (3.48 ml, 36.9 mmol). Then the mixture was heated to 80° C. when isoamyl nitrite (4.49 ml, 32.1 mmol) was added dropwise and the resulting mixture was heated at 80° C. overnight. The insoluble material was filtered through a pad of celite and the filtrate was concentrated to leave a residue which was purified by column chromatography (elution with 20:1 hexane:EtOAc) to yield the desired product as a yellow solid.

Step 6

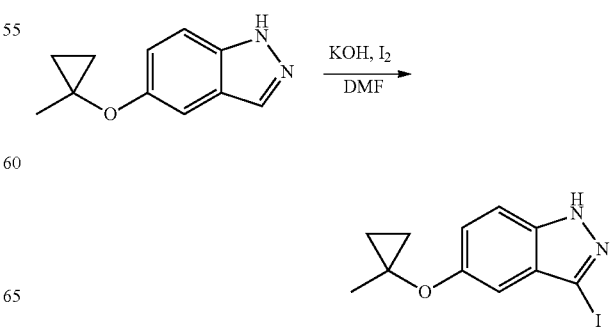

To a stirred suspension of the N-acetyl indazole (6.5 g, 28.2 mmol) in MeOH (20 mL) was added NH3 (20.16 ml of 7M solution, 141.0 mmol) and the mixture was stirred at RT for 2 h. The reaction was concentrated and the residue was purified by column chromatography (elution with 5:1 to 1:1 hexane:EtOAc) to yield the desired indazole as a yellow solid.

Step 7

To a stirred solution of indazole (5.0 g, 26.6 mmol) in DMF (50 ml) was added KOH (5.96 g, 106 mmol) followed by I$_2$ (13.48 g, 53.1 mmol). The mixture was stirred at room temperature for 3 h before being quenched with a saturated aqueous solution of Na$_2$S$_2$O$_3$ followed by addition of water. The resulting layer was extracted with EtOAc (×4). The combined organic layers were dried over MgSO$_4$, filtered and concentrated under vacuum to leave a residue which was purified by column chromatography (elution with 10:1 to 1:1 hexane:EtOAc) to yield the iodide as a yellow solid.

Step 8

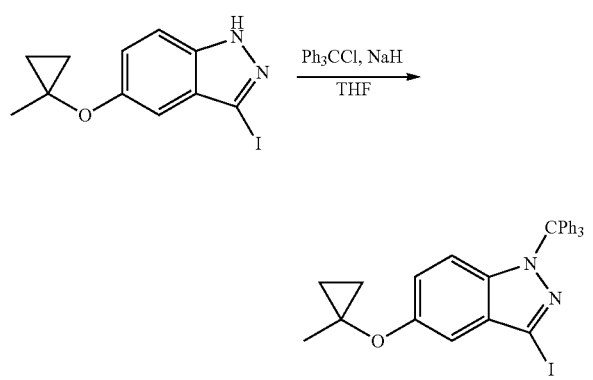

To a cold (0° C.), stirred solution of iodide (5.1 g, 16.24 mmol) in THF (50 ml) was added NaH (0.779 g, 19.48 mmol) in portions. After the addition was complete the mixture was stirred at 0° C. for 15 min when trityl chloride (4.98 g, 17.86 mmol) was added in one portion. The resulting mixture was then slowly warmed to room temperature and stirred at room temperature for 4 h. The reaction was quenched with water and extracted with DCM (×3). The combined organic layers were dried over MgSO$_4$, filtered and concentrated to leave a residue which was purified by column chromatography (elution with 100% DCM) to yield the desired product as an off-white solid.

Step 9

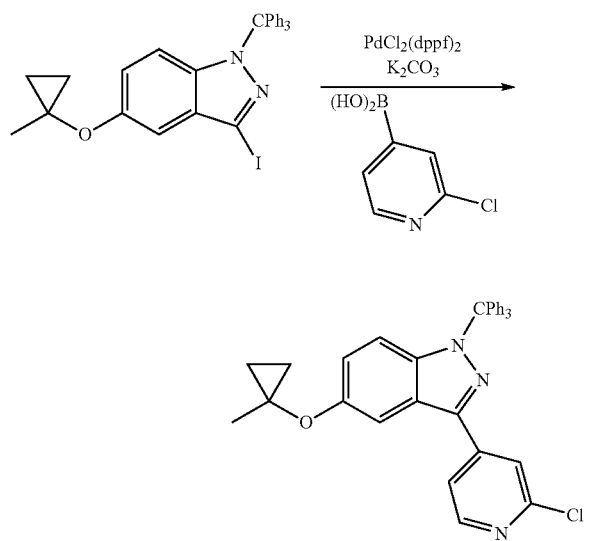

The iodide was reacted with (2-chloropyridin-4-yl)boronic acid using conditions outlined in Step 3 of Scheme A which provided the desired chloro-pyridine.

Step 10

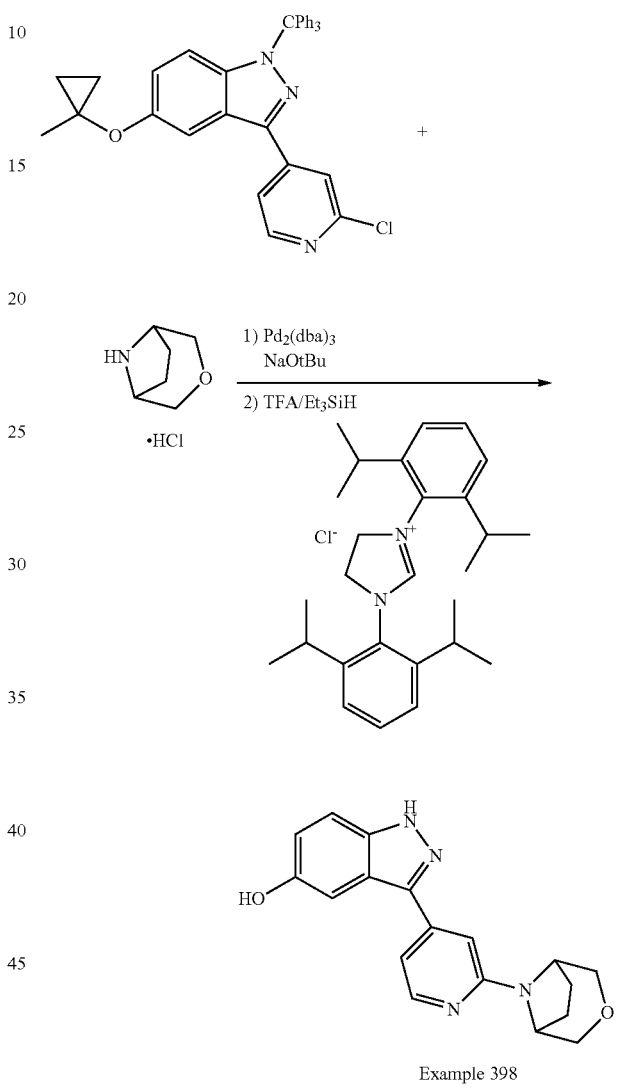

Example 398

The chloro-pyridine (100 mg, 0.18 mmol), 3-oxa-8-azabicyclo[3.2.1]octane hydrochloride (41 mg, 0.28 mmol), 1,3-bis(2,6-diisopropylphenyl)-4,5-dihydro-1H-imidazol-3-ium chloride (23 mg, 0.055 mmol), Pd$_2$(dba)$_3$ (34 mg, 0.037 mmol), and NaOtBu (53 mg, 0.55 mmol) were taken up in 2 ml of dioxane in a sealed tube. The solution was heated at 100° C. for 24 h. The solution was cooled, unsealed, filtered and concentrated. The residue was treated with 2 ml of TFA, 0.5 ml of Et$_3$SiH and 1 mL CH$_2$Cl$_2$. After stirring at RT for 4 h, the solution was concentrated. The residue was treated with 5 ml of 7 NH$_3$ in MeOH, and the resulting solution was concentrated. The residue was purified via PTLC to provide Example 398 (LCMS (ESI) m/z 323 (Ret.=1.74 min, LCMS method e))) as a yellow solid.

417
Scheme AAAV
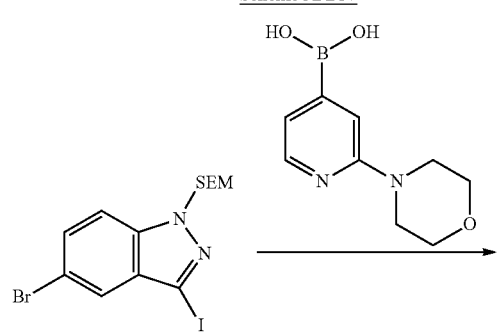
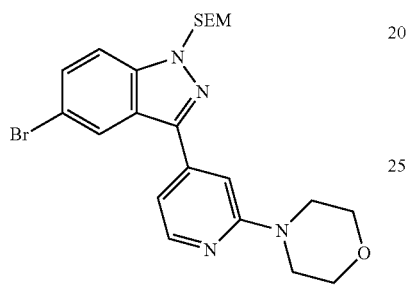
Intermediate AAAV.1
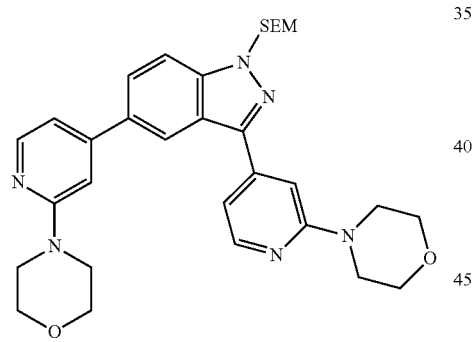
Intermediate AAAV.2
418
-continued
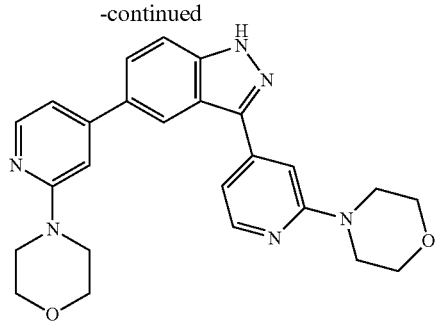
Example 399
Step 1
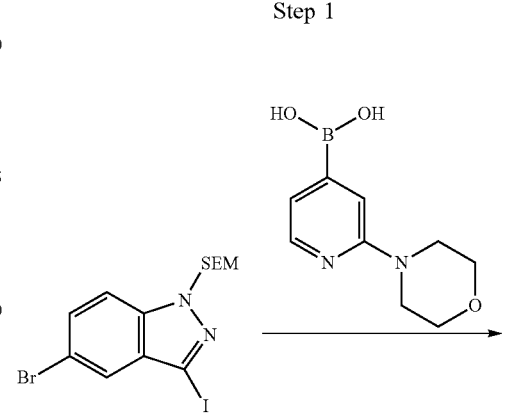
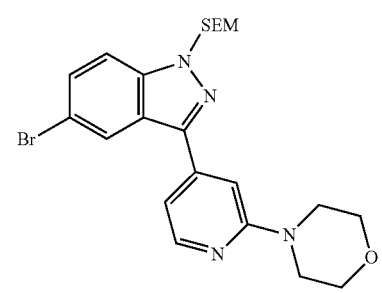
Intermediate AAAV.1
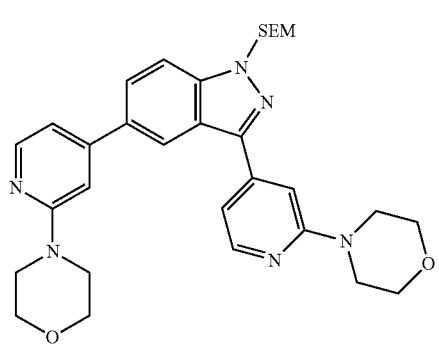
Intermediate AAAV.2
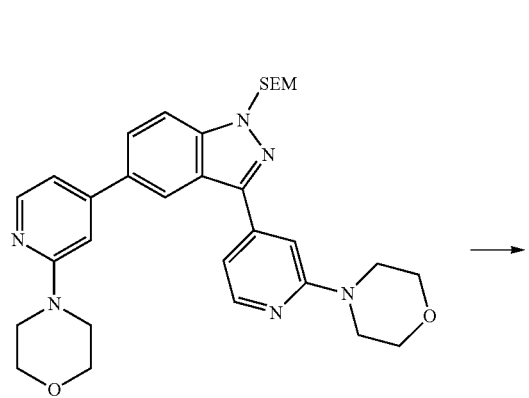
Intermediate AAAV.2

419

To a solution of the iodide prepared in Step 1 of Scheme D (2.0 g, 4.41 mmol) in THF (20 mL) at rt was added (2-morpholinopyridin-4-yl)boronic acid (1.1 g, 5.30 mmol), $Cs_2CO_3$ (4.31 g, 13.24 mmol), and $Pd(dppf)Cl_2$ (323 mg, 0.44 mmol) under nitrogen. The mixture (in a closed 40 mL vial) was heated at 80° C. for 1.5 hrs. The mixture was diluted with DCM and filtered. The resulting filtrate was concentrated to afford a residue, which was purified via reversed-phase C18 MPLC [ISCO, gradient elution: 0% to 100% acetonitrile in water with 0.1% TFA] to afford Intermediate AAAV.1 and Intermediate AAAV.2.

Step 2

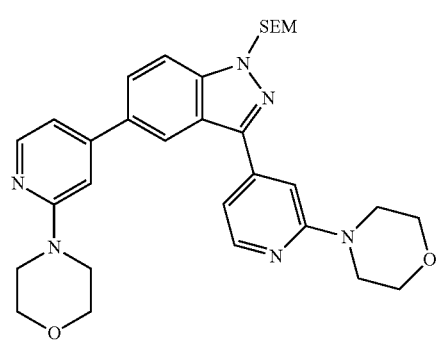

Intermediate AAAV.2

420

-continued

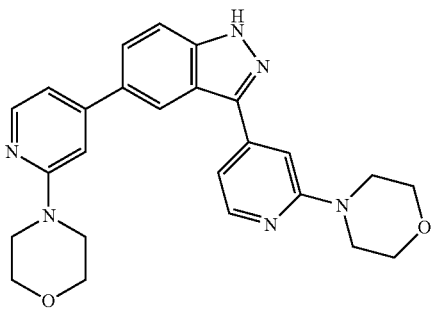

Example 399

A solution of Intermediate AAAV.2 (80 mg, 0.14 mmol) and TBAF (1M in THF, 0.279 mL) in THF (2 mL) was sealed in a glass reaction vessel and heated at 105° C. for 1.5 h. The reaction was then cooled to RT, unsealed and concentrated. The resulting residue was purified via reversed-phase C18 MPLC [ISCO, gradient elution: 0% to 100% acetonitrile in water with 0.1% TFA] to afford Example 399 (LCMS (ESI) m/z 443 (Ret.=1.74 min, LCMS method e)) as a white solid.

Scheme AAAW

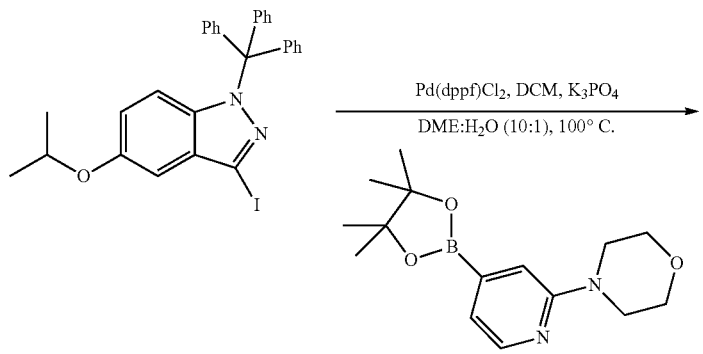

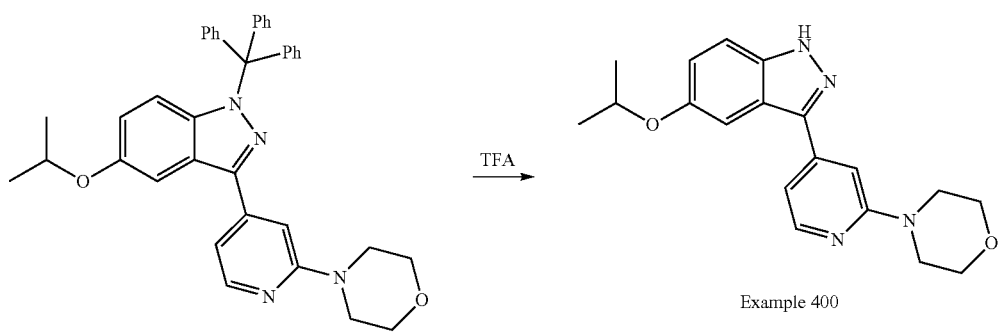

Example 400

Step 1

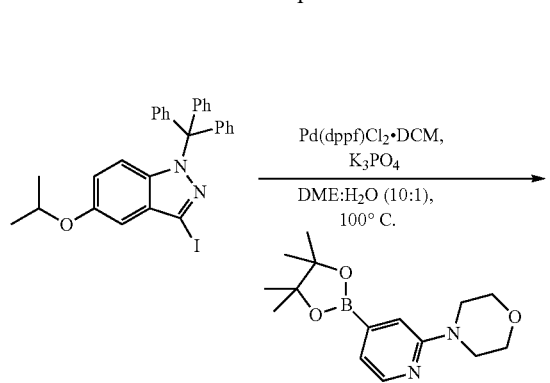

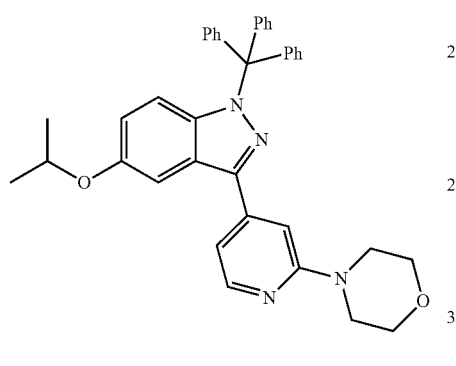

The iodo indazole (1.5 g, 2.7 mmol), boronic ester (0.96 g, 3.3 mmol), and 4.1 ml of a 2 M aqueous solution of K₃PO₄ were taken up in 30 ml of DME. The resulting solution was degassed with nitrogen for 5 minutes. 1,1'-Bis (diphenylphosphino)ferrocene-palladium(II) dichloride-dichloromethane complex (225 mg, 0.27 mmol) was added, and the resulting mixture was heated to 90° C. for 30 minutes. The mixture was filtered through a pad of Celite. The Celite was rinsed with EtOAc. The solution was concentrated. The residue was purified via gradient flash chromatography (0-50% EtOAc in hexanes, SiO₂) which provided 980 mg of the pyridiyl indazole as a yellow foam.

Step 2

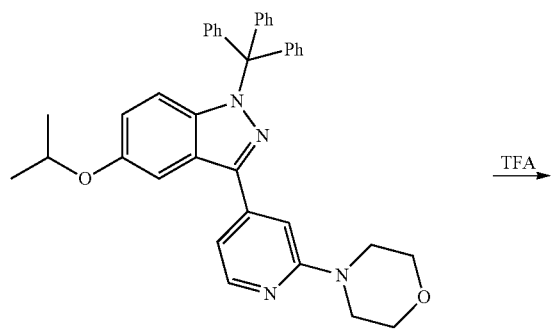

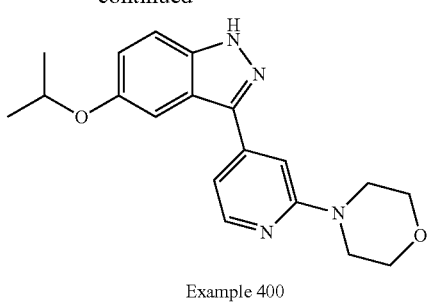

Example 400

The trityl protected indazole (980 mg, 1.69 mmol) was taken up in 10 ml of DCM. TFA (11 ml) was added, and the resulting solution was stirred at RT for 4 hours. The reaction was concentrated. The residue was partitioned between DCM and sat. NaHCO₃ (aq.). The organic layer was dried over Na₂SO₄, filtered, and concentrated. The residue was purified via gradient flash chromatography (0-50% EtOAc in DCM, SiO₂) which provided 523 mg Example 400 (LCMS (ESI) m/z 339 (Ret.=1.96 min, LCMS method e)) as a white solid.

Scheme AAAX

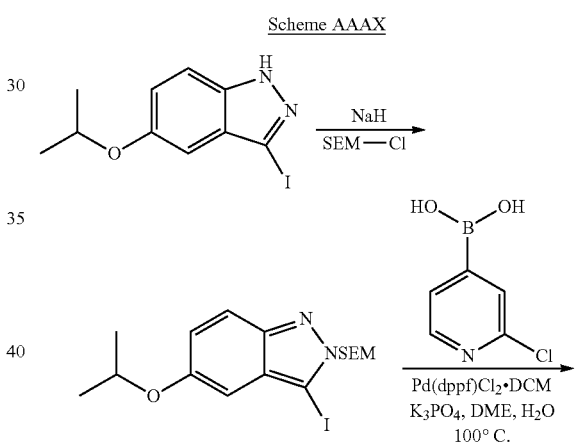

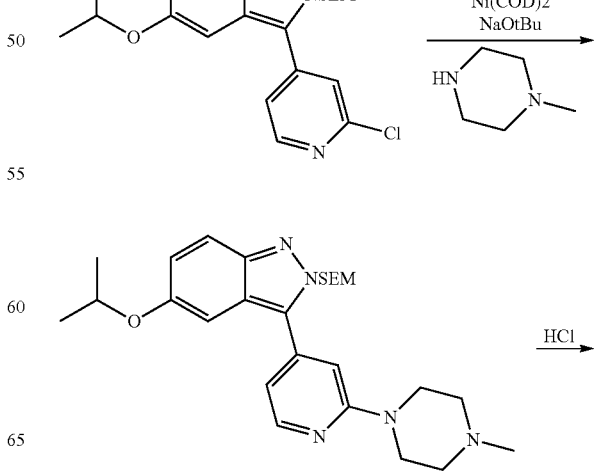

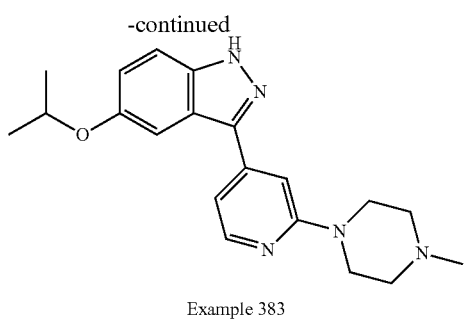

Example 383

Step 1

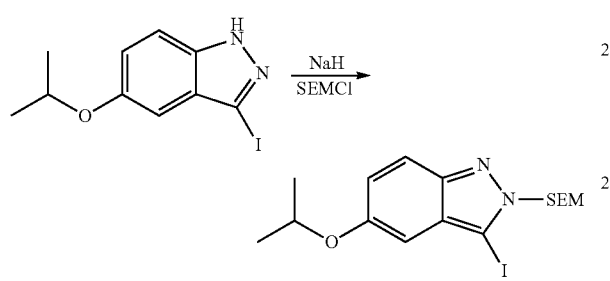

The iodo indazole (3 g, 9.9 mmol) was taken up in THF (15 ml) at 0° C. 2-(Trimethylsilyl)ethoxymethyl chloride (2.1 ml, 11.9 mmol) was added, and the reaction was allowed to warm to RT. The solution was stirred at RT for 12 hours. The solution was partitioned between water and DCM. The aqueous layer was extracted with DCM. The combined organic layers were dried (MgSO$_4$), filtered, and concentrated. The residue was purified via gradient flash chromatography (100/1 to 20/1 hexanes/EtOAc, SiO$_2$) which provided the SEM protected indazole.

Step 2

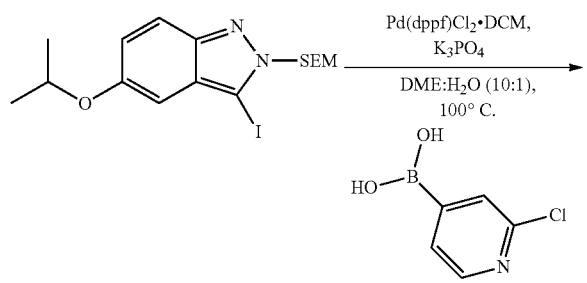

The iodo indazole (2.86 g, 6.6 mmol), boronic acid (1.35 g, 8.58 mmol), and K$_3$PO$_4$(4.2 g, 19.8 mmol) were taken up in 30 ml of DME and 6 ml of water. The resulting solution was degassed with argon for 15 minutes. 1,1'-Bis(diphenylphosphino)ferrocene-palladium(II) dichloride-dichloromethane complex (540 mg, 0.66 mmol) was added, and the resulting mixture was heated to 105° C. for 16 hours. The mixture was cooled and filtered through a pad of Celite. The Celite was rinsed with EtOAc. The solution was concentrated. The residue was purified via gradient flash chromatography (10/1 to 5/1 hexanes/EtOAc, SiO$_2$) which provided 2.4 g of the pyridyl indazole as a white solid.

Step 3

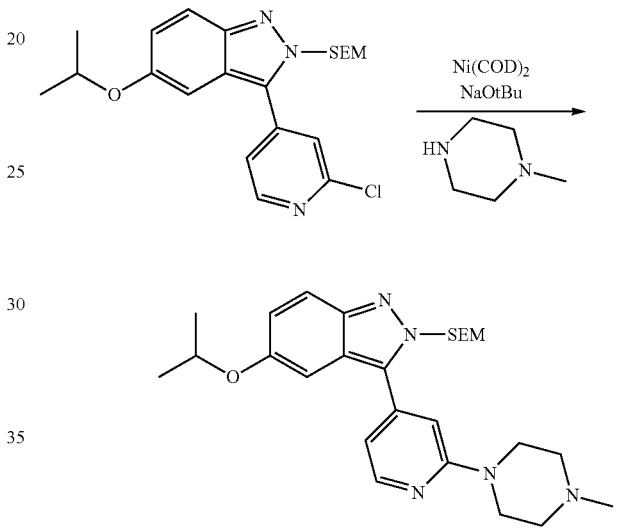

The chloro-indazole (150 mg, 0.36 mmol), N-methyl piperazine (54 mg, 0.54 mmol), NaOtBu (69 mg, 0.72 mmol), 1,3-Bis(2,6-diisopropylphenyl)-imidazolidinium-chloride (30.7 mg, 0.072 mmol) and Ni(COD)$_2$ (10 mg, 0.048 mmol, 0.1 eq) were talem up in 1,4-Dioxane (2 ml). The resulting solution was degassed with argon for 15 minutes. The mixture was heated at 80° C. for 3 hours. The mixture was cooled, diluted with DCM, and filtered through a pad of Celite. The filtrate was concentrated. The residue was purified by column chromatography (elution with 20:1 DCM:MeOH) to yield the desired product.

Step 4

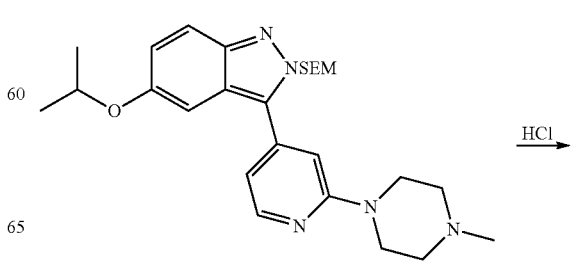

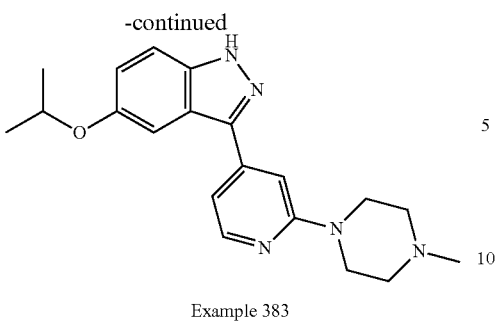

Example 383

To a stirred solution of the SEM protected indazole (88 mg, 0.183 mmol) in DCM (2 ml) was added HCl (1 ml, 4.0 M). The mixture was stirred at RT for 5 h. The reaction was neutralized with sat NaHCO₃ solution and extracted with DCM (×3). The combined organic layers were dried (MgSO₄), filtered, and concentrated. The residue was purified by flash chromatography (elution with 10:1 DCM:MeOH, SiO₂) which provided Example 383 as a yellow foam (LCMS Method e: retention time: 1.89 minutes, [M+H]⁺: calc.: 352.2. found: 352).

Biological Assays

The data presented for the 5 mM and Km ATP LanthaScreen™ Assay represents mean IC₅₀ values based on several test results and may have reasonable. deviations depending on the specific conditions and reagents used. Reagents for the LRRK2 5 mM and Km ATP LanthaScreen™ Assay were purchased from Life Technologies Corporation.

LRRK2 5 mM ATP LanthaScreen™ Assay
a) 400 nl of a 1:2.15 serial dilution of test compound (98 µM top assay concentration) is spotted via Labcyte Echo to certain wells in a 384 well black, untreated plate. Control wells contain 400 nl of either DMSO or 400 nl of a known inhibitor in DMSO.
b) 10 µl of a 2.5 nM LRRK2(G2019S mutation, GST-LRRK2(amino acids 970-2527)) enzyme solution in 1× assay buffer (50 mM Tris pH 8.5, 10 mM MgCl₂, 0.01% Brij-35, 1.0 mM EGTA, 2 mM DTT, 0.05 mM NaVO₄) is added to all wells.
c) A 30 minute room temperature incubation is followed by addition of 10 µl of 800 nM fluorescein labeled LRRKtide peptide substrate and 10 mM ATP solution in 1× assay buffer to all wells.
d) After a 35 minute room temperature incubation, 20 µl of TR-FRET Dilution Buffer (Invitrogen PV3756B) containing 4 nM Tb-labeled anti-phospho LRRKtide antibody and 20 mM EDTA is added to all wells.
e) Plates are incubated at room temperature for 1 hour and read on an Envision™ multi-mode plate reader with LanthaScreen™ settings. Results are analysed using Assay Data Analyzer.

LRRK2 Km ATP LanthaScreen™ Assay
a) 400 nl of a 1:2.15 serial dilution of test compound (98 µM top assay concentration) is spotted via Labcyte Echo to certain wells in a 384 well black, untreated plate. Control wells contain 400 nl of either DMSO or 400 nl of a known inhibitor in DMSO.
b) 10 µl of a 2.5 nM LRRK2(G2019S mutation, GST-LRRK2(amino acids 970-2527)) enzyme solution in 1× assay buffer (50 mM Tris pH 8.5, 10 mM MgCl₂, 0.01% Brij-35, 1 mM EGTA, 2 mM DTT, 0.05 mM NaVO₄) is added to all wells.
c) A 30 minute room temperature incubation is followed by addition of 10 µl of 800 nM fluorescein labeled LRRKtide peptide substrate and 186 µM ATP solution in 1× assay buffer to all wells.
d) After a 60 minute room temperature incubation, 20 µl of TR-FRET Dilution Buffer (Invitrogen PV3756B) containing 4 nM Tb-labeled anti-phospho LRRKtide antibody and 20 mM EDTA is added to all wells.
e) Plates are incubated at room temperature for 1 hour and read on an Envision™ multi-mode plate reader with LanthaScreen™ settings. Results are analysed using Assay Data Analyzer.

The following Table illustrates LRRK2 Km LanthaScreen™ results for analogs prepared.

| Ex | Structure | LRRK2 IC₅₀ (nM) |
|---|---|---|
| 1 | 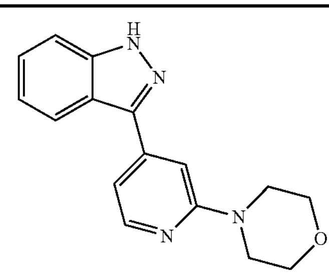 | 16 |
| 75 | 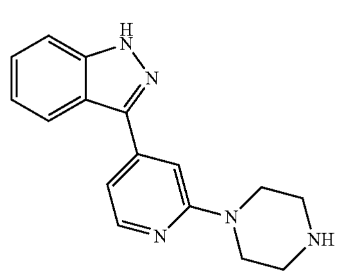 [SMILES: c1ccc2c(-c3ccnc(N4CCNCC4)c3)n[nH]c2c1] | 80 |

-continued

| Ex | Structure | LRRK2 IC$_{50}$ (nM) |
|---|---|---|
| 76 | 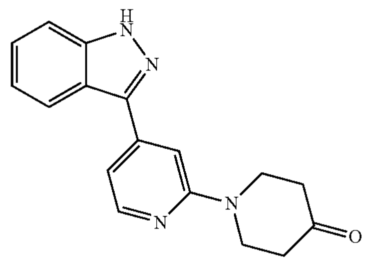 [SMILES: O=C1CCN(c2cc(-c3n[nH]c4ccccc34)ccn2)CC1] | 45 |
| 77 | 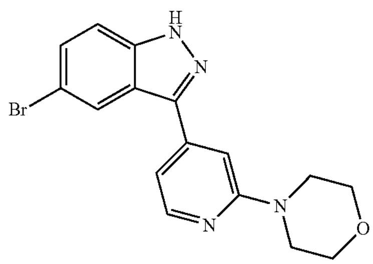 [SMILES: Brc1ccc2[nH]nc(-c3ccnc(N4CCOCC4)c3)c2c1] | 11 |
| 78 | 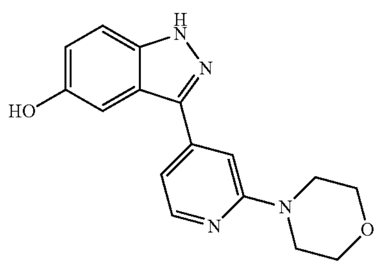 [SMILES: Oc1ccc2[nH]nc(-c3ccnc(N4CCOCC4)c3)c2c1] | 5.3 |
| 79 | 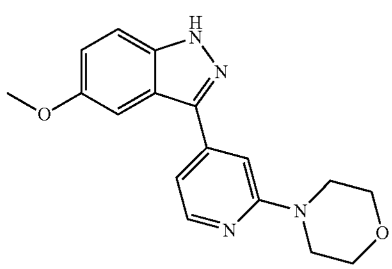 [SMILES: COc1ccc2[nH]nc(-c3ccnc(N4CCOCC4)c3)c2c1] | 7.4 |
| 85 | 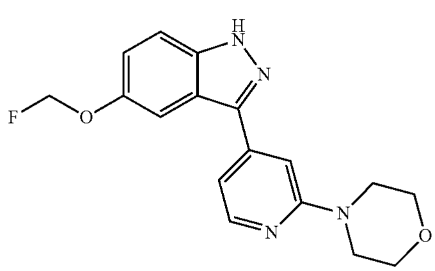 [SMILES: FCOc1ccc2[nH]nc(-c3ccnc(N4CCOCC4)c3)c2c1] | 10.2 |

-continued

| Ex | Structure | LRRK2 IC$_{50}$ (nM) |
|---|---|---|
| 86 | 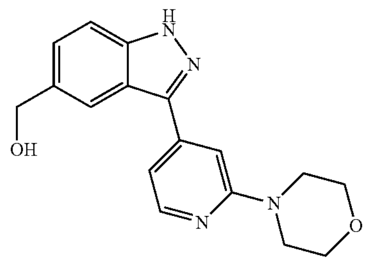 [SMILES: OCc1ccc2[nH]nc(-c3ccnc(N4CCOCC4)c3)c2c1] | 16.4 |
| 87 | 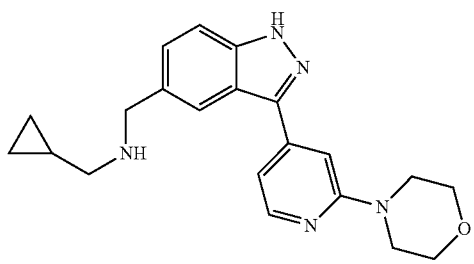 [SMILES: c1cc(-c2n[nH]c3ccc(CNCC4CC4)cc23)cc(N2CCOCC2)n1] | 424 |
| 97 | 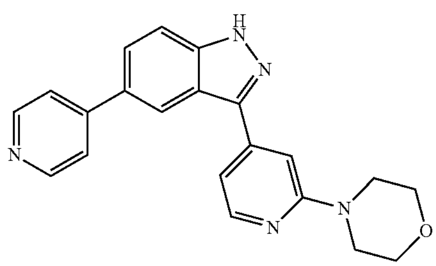 [SMILES: c1cc(-c2ccc3[nH]nc(-c4ccnc(N5CCOCC5)c4)c3c2)ccn1] | 13.7 |
| 98 | 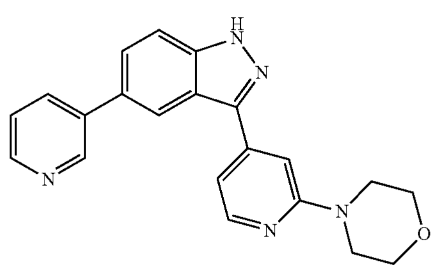 [SMILES: c1cncc(-c2ccc3[nH]nc(-c4ccnc(N5CCOCC5)c4)c3c2)c1] | 3.4 |
| 99 | 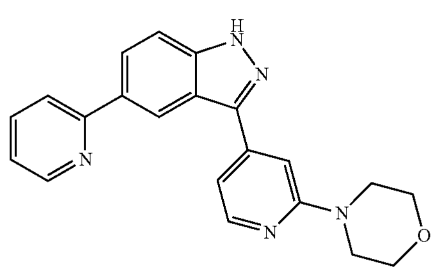 [SMILES: c1ccc(-c2ccc3[nH]nc(-c4ccnc(N5CCOCC5)c4)c3c2)nc1] | 13.7 |

-continued

| Ex | Structure | LRRK2 IC$_{50}$ (nM) |
|---|---|---|
| 100 | 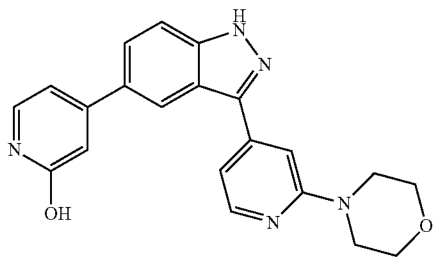 [SMILES: Oc1cc(-c2ccc3[nH]nc(-c4ccnc(N5CCOCC5)c4)c3c2)ccn1] | 3.4 |
| 103 | 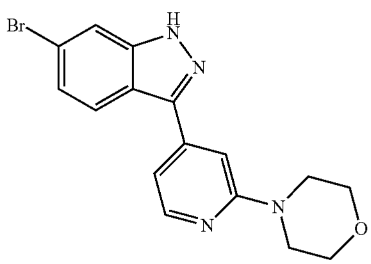 [SMILES: Brc1ccc2c(-c3ccnc(N4CCOCC4)c3)n[nH]c2c1] | 19 |
| 104 | 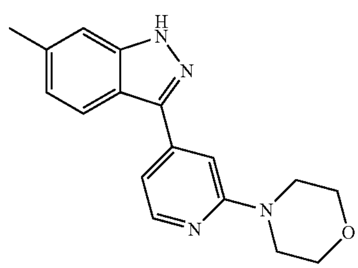 [SMILES: Cc1ccc2c(-c3ccnc(N4CCOCC4)c3)n[nH]c2c1] | 35 |
| 105 | 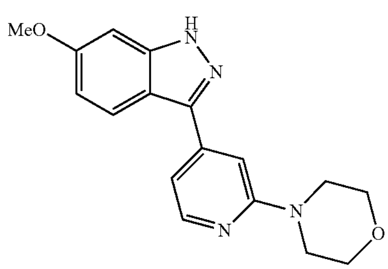 [SMILES: COc1ccc2c(-c3ccnc(N4CCOCC4)c3)n[nH]c2c1] | 30 |
| 106 | 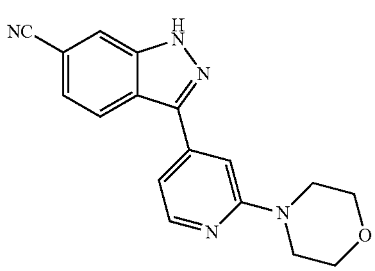 [SMILES: N#Cc1ccc2c(-c3ccnc(N4CCOCC4)c3)n[nH]c2c1] | 49 |

-continued
| Ex | Structure | LRRK2 IC$_{50}$ (nM) |
|---|---|---|
| 107 | 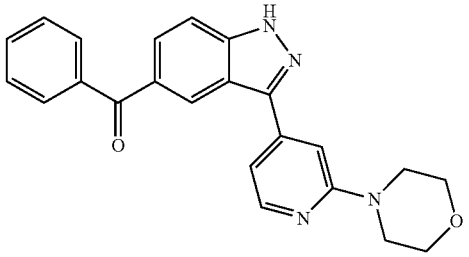 [SMILES: O=C(c1ccccc1)c1ccc2[nH]nc(-c3ccnc(N4CCOCC4)c3)c2c1] | 3.4 |
| 108 | 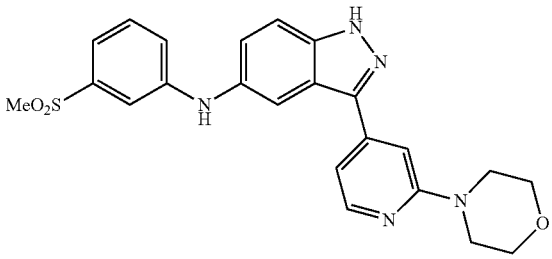 [SMILES: CS(=O)(=O)c1cccc(Nc2ccc3[nH]nc(-c4ccnc(N5CCOCC5)c4)c3c2)c1] | 9.3 |
| 113 | 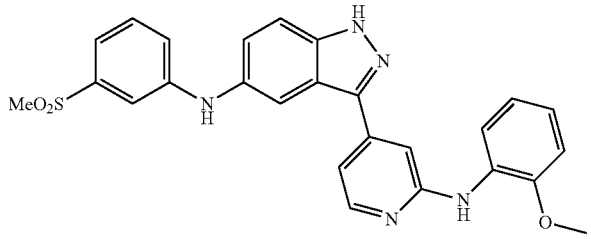 [SMILES: COc1ccccc1Nc1cc(-c2n[nH]c3ccc(Nc4cccc(S(C)(=O)=O)c4)cc23)ccn1] | 422 |
| 114 | 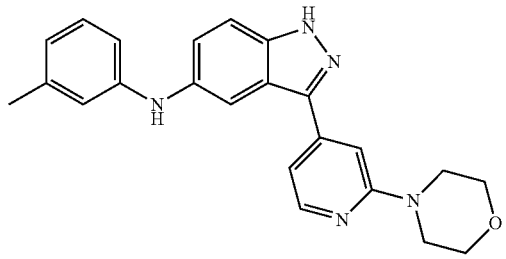 [SMILES: Cc1cccc(Nc2ccc3[nH]nc(-c4ccnc(N5CCOCC5)c4)c3c2)c1] | 28.7 |
| 115 | 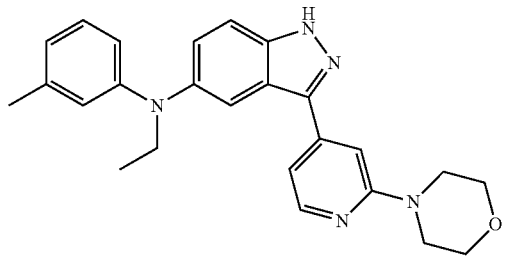 [SMILES: CCN(c1cccc(C)c1)c1ccc2[nH]nc(-c3ccnc(N4CCOCC4)c3)c2c1] | 1575 |

-continued
| Ex | Structure | LRRK2 IC$_{50}$ (nM) |
|---|---|---|
| 116 | 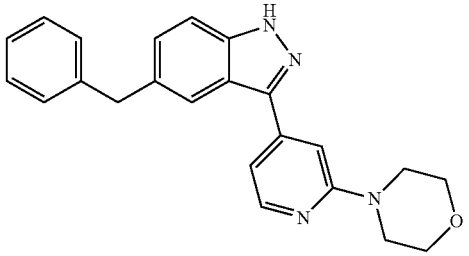 [SMILES: c1ccc(Cc2ccc3[nH]nc(-c4ccnc(N5CCOCC5)c4)c3c2)cc1] | 45 |
| 117 | 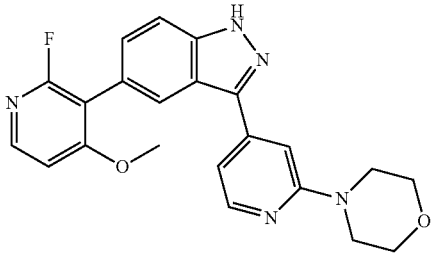 [SMILES: COc1ccnc(F)c1-c1ccc2[nH]nc(-c3ccnc(N4CCOCC4)c3)c2c1] | 3.4 |
| 118 | 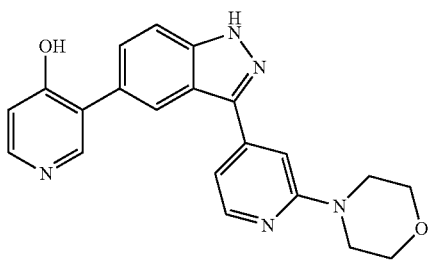 [SMILES: Oc1ccncc1-c1ccc2[nH]nc(-c3ccnc(N4CCOCC4)c3)c2c1] | 70 |
| 119 | 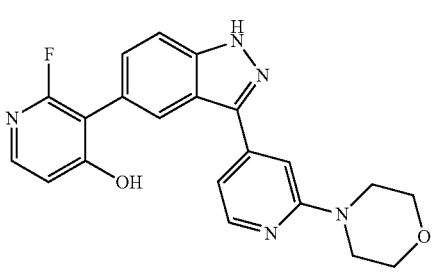 [SMILES: Oc1ccnc(F)c1-c1ccc2[nH]nc(-c3ccnc(N4CCOCC4)c3)c2c1] | 34 |
| 120 | 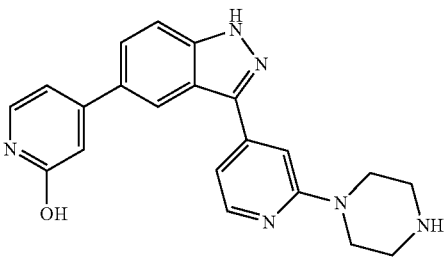 [SMILES: Oc1cc(-c2ccc3[nH]nc(-c4ccnc(N5CCNCC5)c4)c3c2)ccn1] | 3.4 |

-continued

| Ex | Structure | LRRK2 IC$_{50}$ (nM) |
|---|---|---|
| 124 | 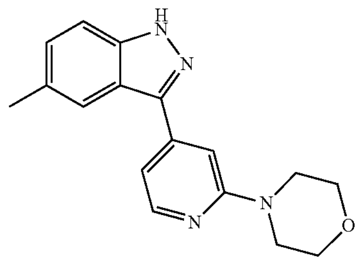 [SMILES: Cc1ccc2[nH]nc(-c3ccnc(N4CCOCC4)c3)c2c1] | 9.6 |
| 125 | 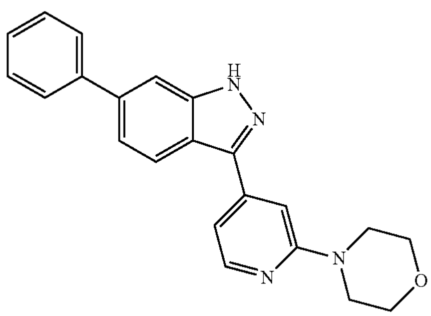 [SMILES: c1ccc(-c2ccc3c(-c4ccnc(N5CCOCC5)c4)n[nH]c3c2)cc1] | 34 |
| 126 | 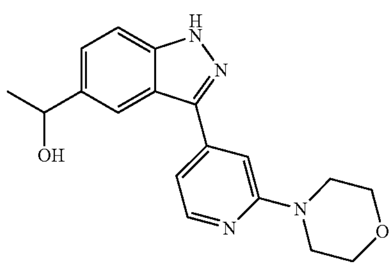 [SMILES: CC(O)c1ccc2[nH]nc(-c3ccnc(N4CCOCC4)c3)c2c1] | 9.9 |
| 313 | 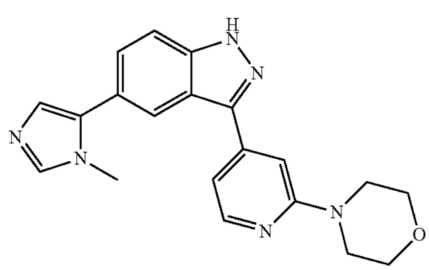 [SMILES: Cn1cncc1-c1ccc2[nH]nc(-c3ccnc(N4CCOCC4)c3)c2c1] | <0.6 |
| 314 | 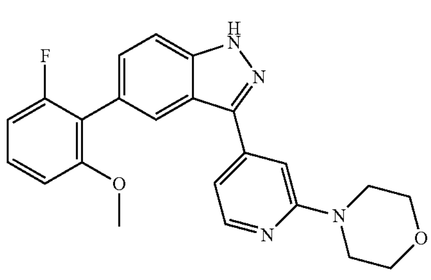 [SMILES: COc1cccc(F)c1-c1ccc2[nH]nc(-c3ccnc(N4CCOCC4)c3)c2c1] | <0.6 |

US 9,440,952 B2
439
-continued
| Ex | Structure | LRRK2 IC$_{50}$ (nM) |
|---|---|---|
| 328 | 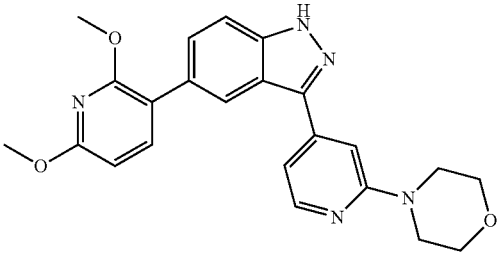 [SMILES: COc1ccc(-c2ccc3[nH]nc(-c4ccnc(N5CCOCC5)c4)c3c2)c(OC)n1] | 189 |
| 348 | 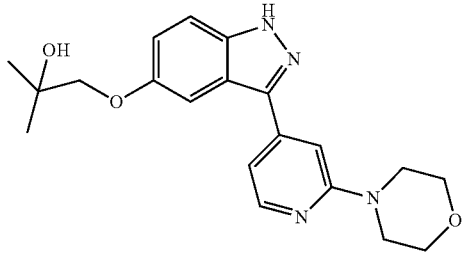 [SMILES: CC(C)(O)COc1ccc2[nH]nc(-c3ccnc(N4CCOCC4)c3)c2c1] | 14 |
| 363 | 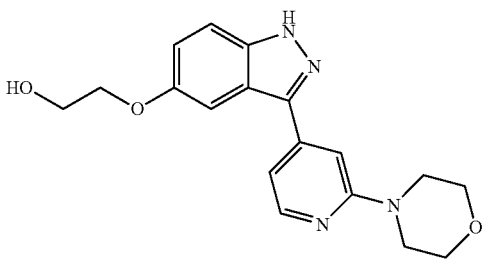 [SMILES: OCCOc1ccc2[nH]nc(-c3ccnc(N4CCOCC4)c3)c2c1] | 9.3 |
| 392 | 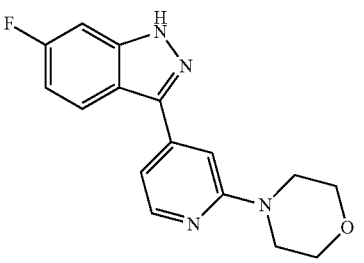 [SMILES: Fc1ccc2c(-c3ccnc(N4CCOCC4)c3)n[nH]c2c1] | 32 |
| 399 | 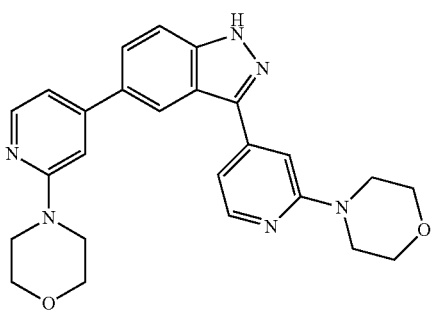 [SMILES: c1cc(-c2ccc3[nH]nc(-c4ccnc(N5CCOCC5)c4)c3c2)cc(N2CCOCC2)n1] | 74 |
440

-continued

| Ex | Structure | LRRK2 IC$_{50}$ (nM) |
|---|---|---|
| 366 | 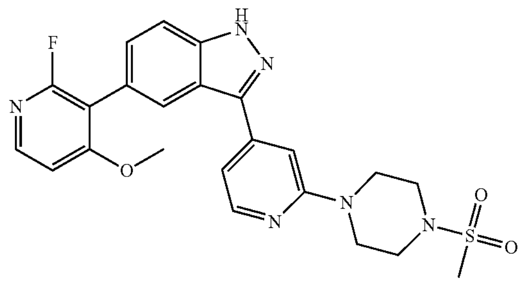 [SMILES: COc1ccnc(F)c1-c1ccc2[nH]nc(-c3ccnc(N4CCN(S(C)(=O)=O)CC4)c3)c2c1] | <0.6 |
| 367 | 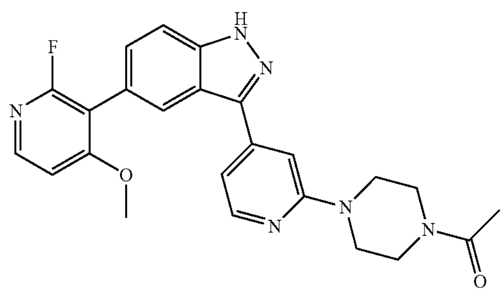 [SMILES: COc1ccnc(F)c1-c1ccc2[nH]nc(-c3ccnc(N4CCN(C(C)=O)CC4)c3)c2c1] | <0.6 |
| 330 | 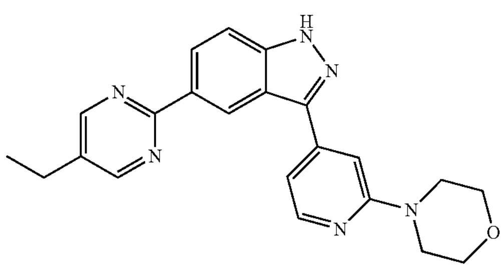 [SMILES: CCc1cnc(-c2ccc3[nH]nc(-c4ccnc(N5CCOCC5)c4)c3c2)nc1] | 5.6 |
| 393 | 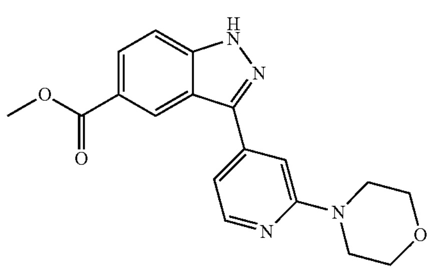 [SMILES: COC(=O)c1ccc2[nH]nc(-c3ccnc(N4CCOCC4)c3)c2c1] | 15 |
| 333 | 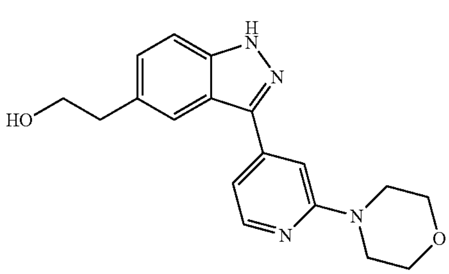 [SMILES: OCCc1ccc2[nH]nc(-c3ccnc(N4CCOCC4)c3)c2c1] | 30 |

-continued

| Ex | Structure | LRRK2 IC$_{50}$ (nM) |
|---|---|---|
| 332 | 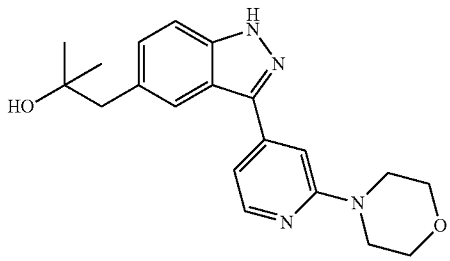 [SMILES: CC(C)(O)Cc1ccc2[nH]nc(-c3ccnc(N4CCOCC4)c3)c2c1] | 93 |
| 347 | 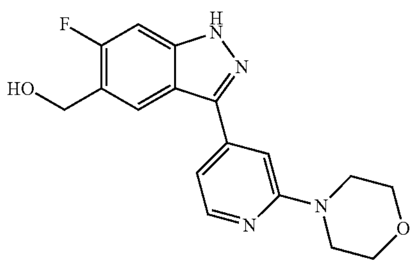 [SMILES: OCc1cc2c(-c3ccnc(N4CCOCC4)c3)n[nH]c2cc1F] | 38 |
| 364 | 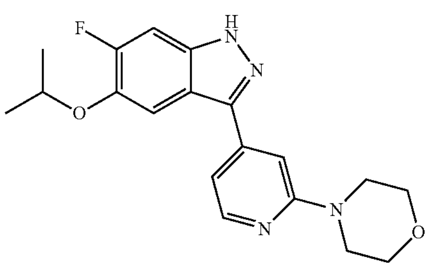 [SMILES: CC(C)Oc1cc2c(-c3ccnc(N4CCOCC4)c3)n[nH]c2cc1F] | 1.9 |
| 334 | 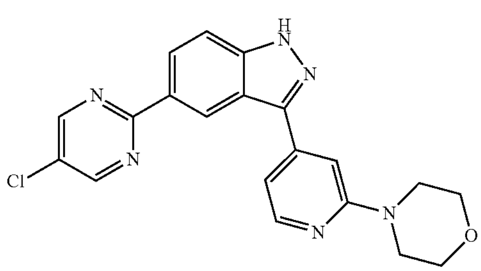 [SMILES: Clc1cnc(-c2ccc3[nH]nc(-c4ccnc(N5CCOCC5)c4)c3c2)nc1] | 52 |
| 365 | 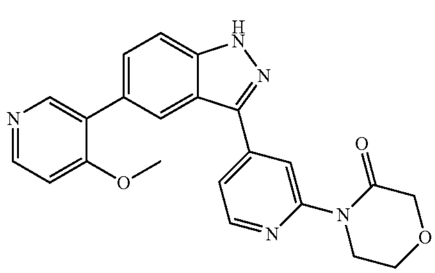 [SMILES: COc1ccncc1-c1ccc2[nH]nc(-c3ccnc(N4CCOCC4=O)c3)c2c1] | 17 |

-continued

| Ex | Structure | LRRK2 IC$_{50}$ (nM) |
|---|---|---|
| 377 | 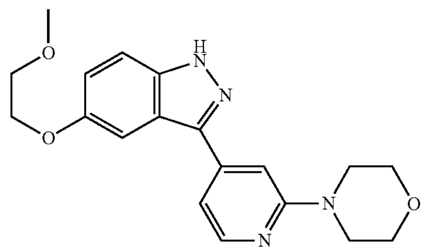 [SMILES: COCCOc1ccc2[nH]nc(-c3ccnc(N4CCOCC4)c3)c2c1] | 70 |
| 312 | 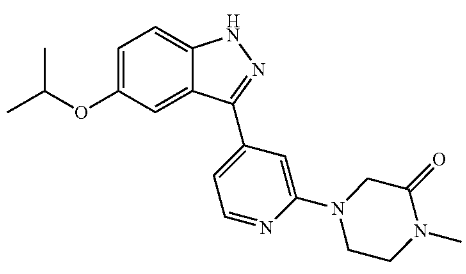 [SMILES: CC(C)Oc1ccc2[nH]nc(-c3ccnc(N4CCN(C)C(=O)C4)c3)c2c1] | 2.6 |
| 368 | 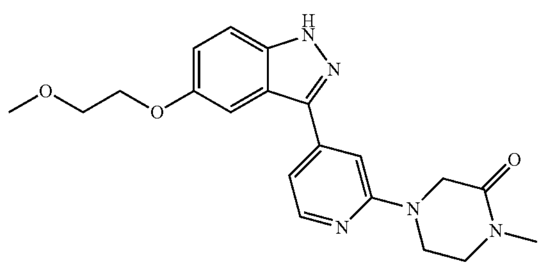 | 30 |
| 349 | 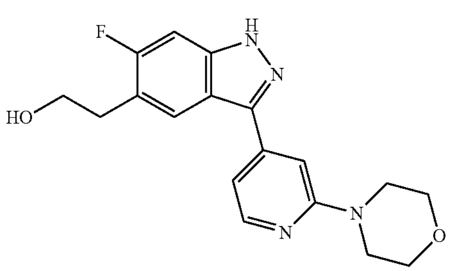 [SMILES: OCCc1cc2c(-c3ccnc(N4CCOCC4)c3)n[nH]c2cc1F] | 27 |
| 350 | 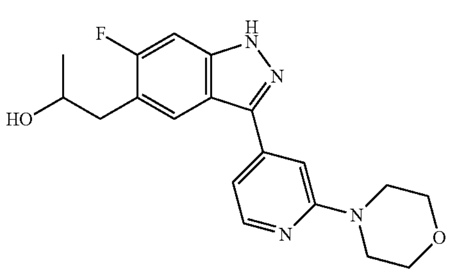 [SMILES: CC(O)Cc1cc2c(-c3ccnc(N4CCOCC4)c3)n[nH]c2cc1F] | 76 |

-continued

| Ex | Structure | LRRK2 IC$_{50}$ (nM) |
|---|---|---|
| 372 | 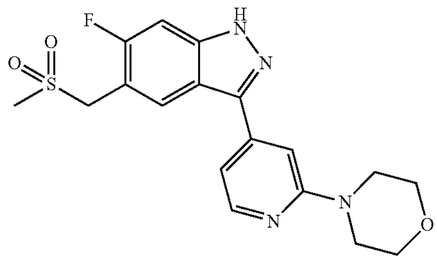 [SMILES: CS(=O)(=O)Cc1cc2c(-c3ccnc(N4CCOCC4)c3)n[nH]c2cc1F] | 1215 |
| 280 | 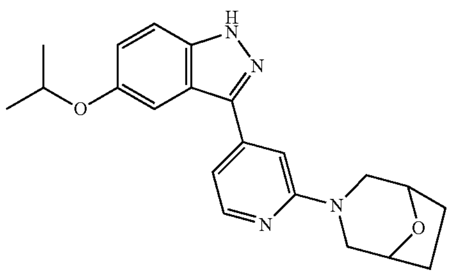 [SMILES: CC(C)Oc1ccc2[nH]nc(-c3ccnc(N4CC5CCC(C4)O5)c3)c2c1] | 5.0 |
| 391 | 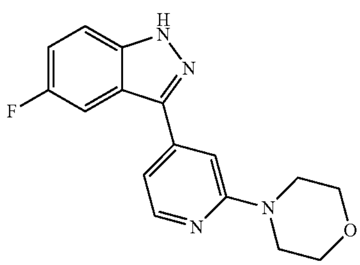 [SMILES: Fc1ccc2[nH]nc(-c3ccnc(N4CCOCC4)c3)c2c1] | 61 |
| 283 | 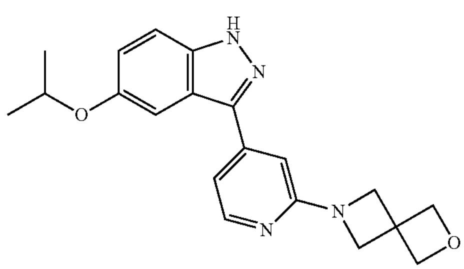 [SMILES: CC(C)Oc1ccc2[nH]nc(-c3ccnc(N4CC5(COC5)C4)c3)c2c1] | 5.9 |
| 373 | 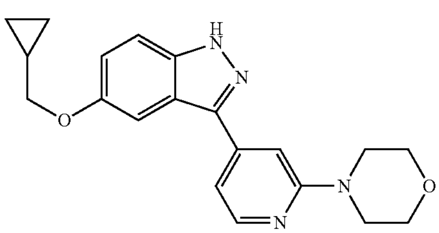 [SMILES: c1cc(-c2n[nH]c3ccc(OCC4CC4)cc23)cc(N2CCOCC2)n1] | 84 |
| 343 | 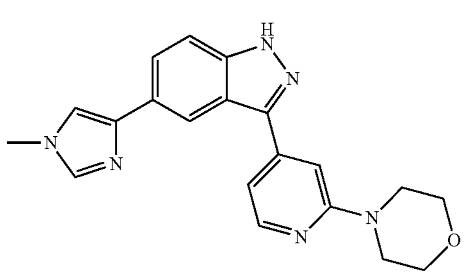 [SMILES: Cn1cnc(-c2ccc3[nH]nc(-c4ccnc(N5CCOCC5)c4)c3c2)c1] | 4.9 |

-continued

| Ex | Structure | LRRK2 IC$_{50}$ (nM) |
|---|---|---|
| 324 | 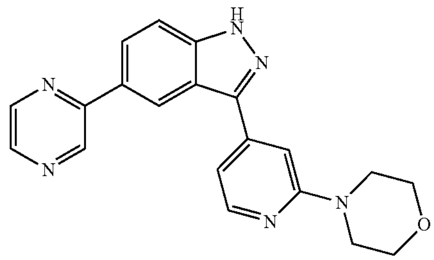 [SMILES: c1cnc(-c2ccc3[nH]nc(-c4ccnc(N5CCOCC5)c4)c3c2)cn1] | 1.1 |
| 351 | 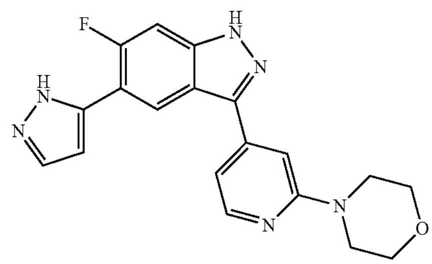 [SMILES: Fc1cc2[nH]nc(-c3ccnc(N4CCOCC4)c3)c2cc1-c1ccn[nH]1] | 1.1 |
| 354 | 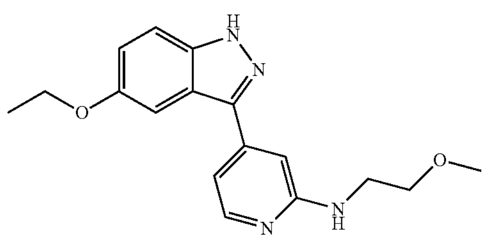 [SMILES: CCOc1ccc2[nH]nc(-c3ccnc(NCCOC)c3)c2c1] | 6.2 |
| 374 | 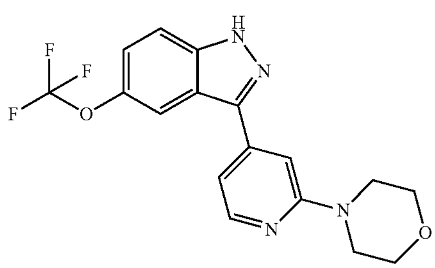 [SMILES: FC(F)(F)Oc1ccc2[nH]nc(-c3ccnc(N4CCOCC4)c3)c2c1] | 28 |
| 292 | 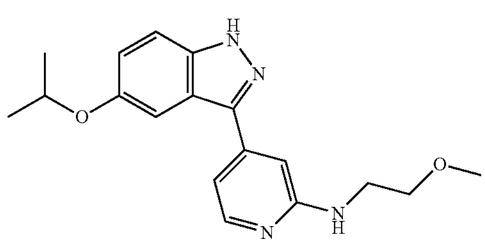 [SMILES: COCCNc1cc(-c2n[nH]c3ccc(OC(C)C)cc23)ccn1] | 5.9 |
| 375 | 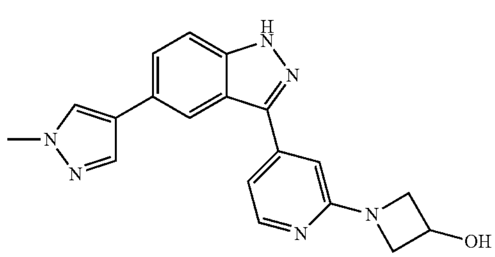 [SMILES: Cn1cc(-c2ccc3[nH]nc(-c4ccnc(N5CC(O)C5)c4)c3c2)cn1] | <0.6 |

-continued
| Ex | Structure | LRRK2 IC$_{50}$ (nM) |
|---|---|---|
| 340 | 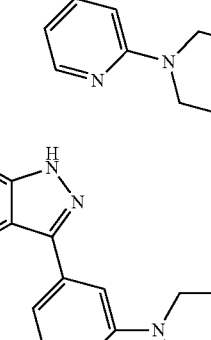 | 1.1 |
| 369 | 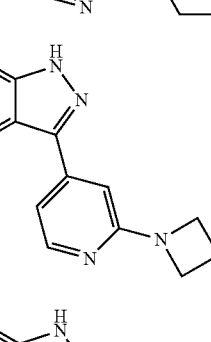 | 109 |
| 308 | 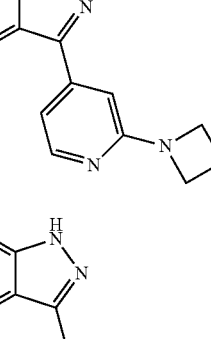 | 4.9 |
| 306 | 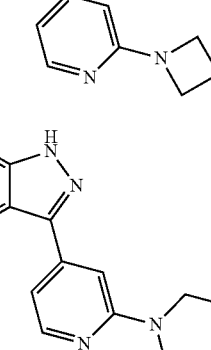 | 2.9 |
| 307 | 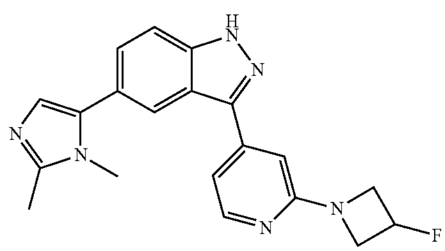 [SMILES: Cc1ncc(-c2ccc3[nH]nc(-c4ccnc(N5CC(F)C5)c4)c3c2)n1C] | 2.1 |
| 311 | 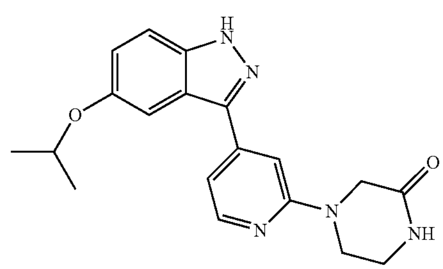 [SMILES: CC(C)Oc1ccc2[nH]nc(-c3ccnc(N4CCNC(=O)C4)c3)c2c1] | <0.6 |

-continued

| Ex | Structure | LRRK2 IC$_{50}$ (nM) |
|---|---|---|
| 394 | 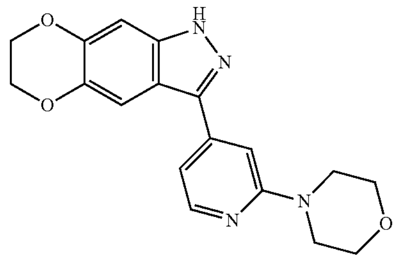 [SMILES: c1cc(-c2n[nH]c3cc4c(cc23)OCCO4)cc(N2CCOCC2)n1] | 12 |
| 388 | 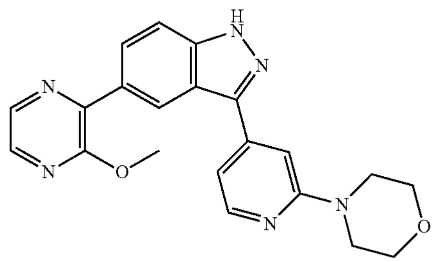 [SMILES: COc1nccnc1-c1ccc2[nH]nc(-c3ccnc(N4CCOCC4)c3)c2c1] | 38 |
| 389 | 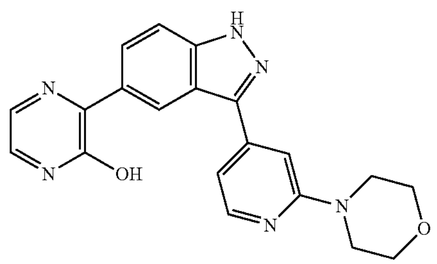 [SMILES: Oc1nccnc1-c1ccc2[nH]nc(-c3ccnc(N4CCOCC4)c3)c2c1] | <0.6 |
| 387 | 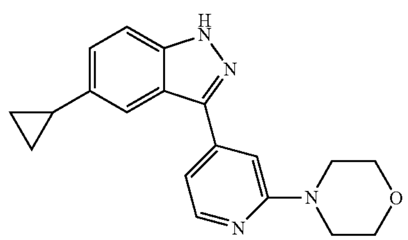 [SMILES: c1cc(-c2n[nH]c3ccc(C4CC4)cc23)cc(N2CCOCC2)n1] | 6.0 |
| 384 | 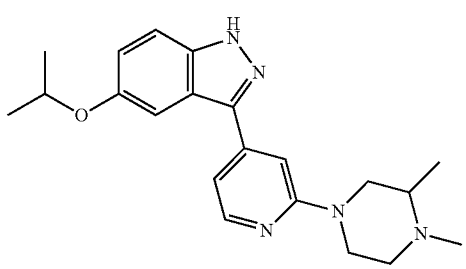 [SMILES: CC(C)Oc1ccc2[nH]nc(-c3ccnc(N4CCN(C)C(C)C4)c3)c2c1] | 2.2 |
| 285 | 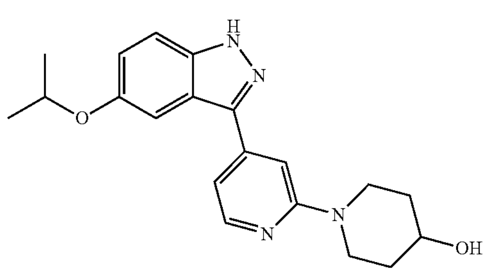 [SMILES: CC(C)Oc1ccc2[nH]nc(-c3ccnc(N4CCC(O)CC4)c3)c2c1] | 3.8 |

-continued

| Ex | Structure | LRRK2 IC$_{50}$ (nM) |
|---|---|---|
| 305 | 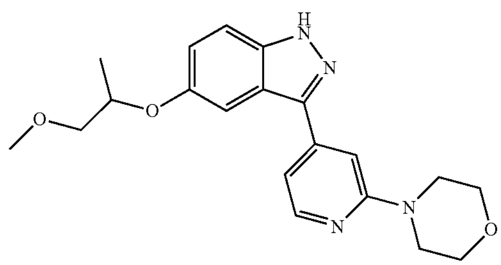 [SMILES: COCC(C)Oc1ccc2[nH]nc(-c3ccnc(N4CCOCC4)c3)c2c1] | 5.4 |
| 385 | 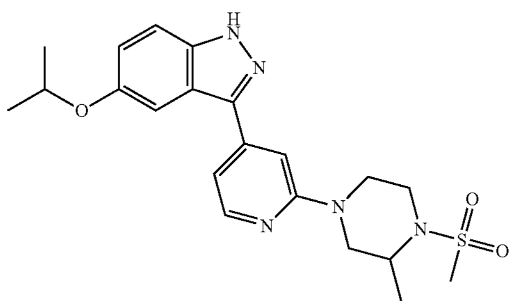 [SMILES: CC(C)Oc1ccc2[nH]nc(-c3ccnc(N4CCN(S(C)(=O)=O)C(C)C4)c3)c2c1] | 2.2 |
| 386 | 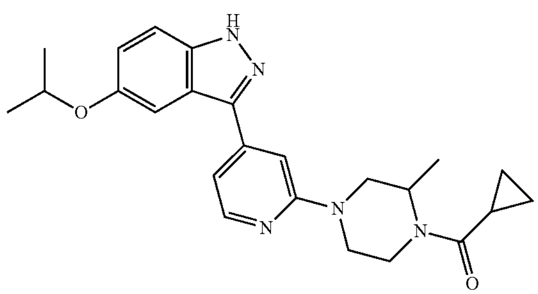 [SMILES: CC(C)Oc1ccc2[nH]nc(-c3ccnc(N4CCN(C(=O)C5CC5)C(C)C4)c3)c2c1] | 2.8 |
| 395 | 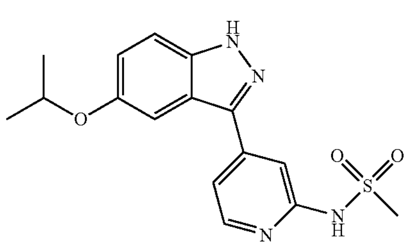 [SMILES: CC(C)Oc1ccc2[nH]nc(-c3ccnc(NS(C)(=O)=O)c3)c2c1] | 20 |
| 286 | 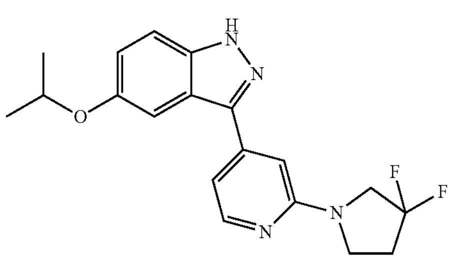 [SMILES: CC(C)Oc1ccc2[nH]nc(-c3ccnc(N4CCC(F)(F)C4)c3)c2c1] | 5.5 |

-continued

| Ex | Structure | LRRK2 IC$_{50}$ (nM) |
|---|---|---|
| 396 | 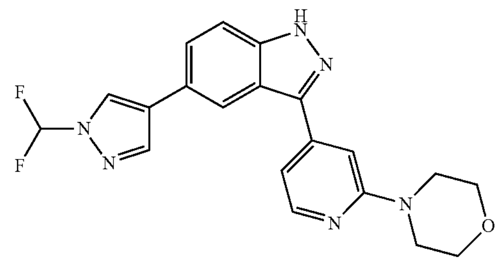 [SMILES: FC(F)n1cc(-c2ccc3[nH]nc(-c4ccnc(N5CCOCC5)c4)c3c2)cn1] | 2.8 |
| 382 | 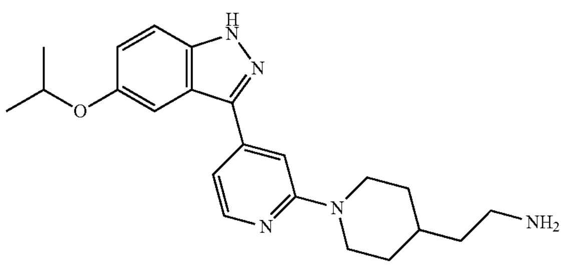 [SMILES: CC(C)Oc1ccc2[nH]nc(-c3ccnc(N4CCC(CCN)CC4)c3)c2c1] | 6.8 |
| 398 | 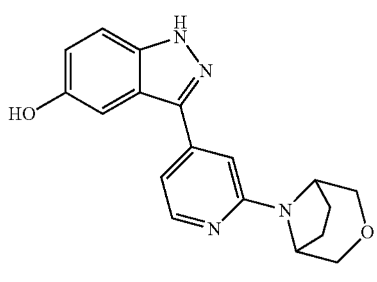 [SMILES: Oc1ccc2[nH]nc(-c3ccnc(N4C5CCC4COC5)c3)c2c1] | 69 |
| 397 | 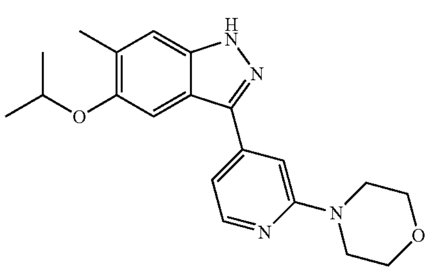 [SMILES: Cc1cc2[nH]nc(-c3ccnc(N4CCOCC4)c3)c2cc1OC(C)C] | 167 |
| 400 | 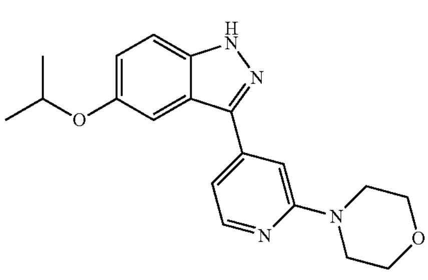 [SMILES: CC(C)Oc1ccc2[nH]nc(-c3ccnc(N4CCOCC4)c3)c2c1] | 1.9 |

-continued

| Ex | Structure | LRRK2 IC$_{50}$ (nM) |
|---|---|---|
| 378 | 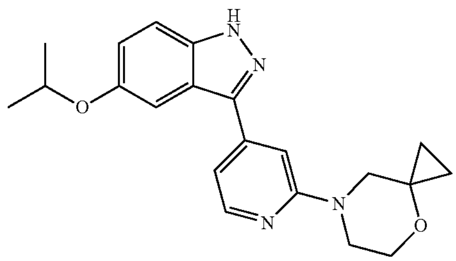 [SMILES: CC(C)Oc1ccc2[nH]nc(-c3ccnc(N4CCOC5(CC5)C4)c3)c2c1] | 7.5 |
| 304 | 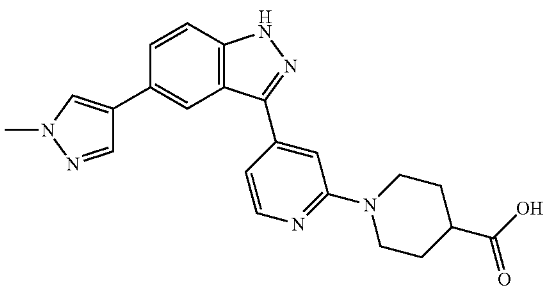 [SMILES: Cn1cc(-c2ccc3[nH]nc(-c4ccnc(N5CCC(C(=O)O)CC5)c4)c3c2)cn1] | 3.6 |
| 383 | 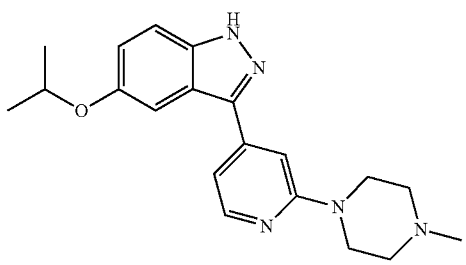 [SMILES: CC(C)Oc1ccc2[nH]nc(-c3ccnc(N4CCN(C)CC4)c3)c2c1] | 0.75 |

TABLE A 5 mM ATP LanthaScreen ™ Assay Data of representative compounds

In the table below, representive examples are provided with their respective IC$_{50}$ in the 5 mM ATP LanthaScreen ™ Assay. Preferred compounds have an IC$_{50}$ less than 1 μM in the 5 mM ATP LanthaScreen ™ Assay.

| Example | IC$_{50}$ (nM) |
|---|---|
| 321 | 12 |
| 121 | 16 |
| 400 | 14 |
| 316 | 8.0 |
| 383 | 22 |
| 289 | 16 |
| 376 | 23 |
| 311 | 14 |
| 285 | 15 |
| 268 | 6.0 |
| 381 | 24 |

TABLE B

Kinase selectivity of representative compounds
Kinase selectivity was performed using Z'-LYTE ™ or Adapta ® assay platforms available from Life Technologies Corporation. Values in Table B are percent inhibition in the presence of the indicated concentration of the example.

| | | Test Conc (μM) | | | |
|---|---|---|---|---|---|
| Kinase | Assay Platform | 0.100 Ex 381 | 1 Ex 400 | 0.100 Ex 383 | 1 Ex 289 |
| AURKB (Aurora B) | A | 13 | 9 | 8 | 23 |
| BRAF V599E | A | 11 | 51 | — | 64 |
| CDK1/cyclin B | A | 26 | 29 | 5 | 18 |
| CHEK2 (CHK2) | A | 19 | 16 | — | 26 |
| CLK2 | A | 91 | 47 | 26 | 49 |
| DYRK1A | A | 78 | 9 | 8 | 12 |
| IRAK1 | B | 20 | 11 | 2 | 6 |
| JAK3 | A | 4 | 49 | 7 | 29 |
| MAPK1 (ERK2) | A | 11 | 41 | 10 | 55 |
| MAPK8 (JNK1) | A | 25 | 72 | — | 54 |

A—Z-LYTE ™;
B—Adapta ®

LCMS Conditions a—Mobile Phase: A: 95% water, 5% ACN (0.05% TFA): B: ACN (0.05% TFA); Gradient: 94:6 to 2:98 (A:B) over 3.65 min; 2:98 (A:B) for 0.3 min; 2:98 to 94:6 (A:B) over 0.03 min; 94:6 (A:B) 0.02 min. Flow rate: 1.0 ml/min; Column: YMC pro C18 (2.0×20 mm, 5 μM)

b—Mobile Phase: A: 95% water, 5% ACN (0.05% TFA): B: ACN (0.05% TFA); Gradient: 95:5 to 1:99 (A:B) over 1.3 min; 1:99 (A:B) for 0.6 min; 1:99 to 95:5 (A:B) over 0.1 min; 95:5 (A:B) 0.5 min. Flow rate: 1.0 ml/min; Column: Aquity UPLC BEH C18 (1.0×50 mm, 1.7 μM)

c—Mobile Phase: A: 95% water, 5% ACN (0.05% TFA): B: ACN (0.05% TFA); Gradient: 100:0 to 0:100 (A:B) over 3.3 min (Flow rate: 1.5 ml/min); 0:100 (A:B) for 0.4 min (Flow rate: 1.75 ml); 0:100 to 100:0 (A:B) over 0.05 min (Flow rate: 2 ml/min); 100/0 (A:B) 0.75 min. (Flow rate: 2 ml/min); Column: YMC pro C18 (2.0×20 mm, 5 μM)

d—Gradient 5:95 to 100:0 MeCN (0.1% NH$_4$OH): water (0.1% NH$_4$OH) over 1.4 min; Waters Acquity UPLC, column: Waters BEH-C18, 1.7 um, 2.1×50 mm 1 mL/min flow rate.

e—Agilent 6140 Quadruple Easy Access LC/MS; Column: Agilent Zorbax SB-C18, 3.0×50 mm, 1.8 μm; Solvent A: Water with 0.1% TFA; Solvent B: acetonitrile with 0.1% TFA; Flow Rate: 1 mL/min; Dual wavelength UV Detection at 220 nm and 254 nm; Gradient: 10% Solvent B to 95% Solvent B over 1.5 min., isocratic at 95% Solvent B for 1.2 min., gradient to 10% Solvent B over 0.1 min., isocratic at 10% Solvent B for 0.8 min.

f—Agilent 6140 Quadruple Easy Access LC/MS; Column: Agilent Zorbax SB-C18, 3.0×50 mm, 1.8 μm; Solvent A: Water with 0.05% TFA and 0.5% acetic acid; Solvent B: acetonitrile with 0.05% TFA and 0.5% acetic acid; Flow Rate: 1 mL/min; Dual wavelength UV Detection at 220 nm and 254 nm; Gradient: 10% Solvent B to 95% Solvent B over 1.5 min., isocratic at 95% Solvent B for 1.2 min., gradient to 10% Solvent B over 0.1 min., isocratic at 10% Solvent B for 0.8 min.

g—Agilent 6140 Quadruple Easy Access LC/MS; Column: Agilent Zorbax SB-C18, 3.0×50 mm, 1.8 μm; Solvent A: Water with 0.05% TFA and 0.5% acetic acid; Solvent B: acetonitrile with 0.05% TFA and 0.5% acetic acid; Flow Rate: 1 mL/min; Dual wavelength UV Detection at 220 nm and 254 nm; Isocratic elution at 10% Solvent B over 0.1 min., gradient elution: 10% Solvent B to 99% Solvent B over 1.9 min., isocratic elution at 99% Solvent B for 1.9 min., gradient to 10% Solvent B over 0.1 min., isocratic at 10% Solvent B for 0.5 min.

h—Agilent 6140 Quadruple Easy Access LC/MS; Column: Agilent Zorbax SB-C18, 3.0×50 mm, 1.8 μm; Solvent A: Water with 0.05% TFA and 0.5% acetic acid; Solvent B: acetonitrile with 0.05% TFA and 0.5% acetic acid; Flow Rate: 1 mL/min; Dual wavelength UV Detection at 220 nm and 254 nm; Gradient elution: 10% Solvent B to 95% Solvent B over 1.0 min., isocratic elution at 95% Solvent B for 0.36 min., gradient to 10% Solvent B over 0.02 min., isocratic at 10% Solvent B for 0.32 min.

i—Agilent 6140 Quadruple Easy Access LC/MS; Column: Supelco Ascentis Express C18, 3.0×100 mm, 2.7 μm; Solvent A: Water with 0.05% TFA; Solvent B: Acetonitrile with 0.05% TFA; Flow Rate: 1 mL/min; UV Detection: DAD 200-400 nm; Gradient elution: 10% Solvent B to 99% Solvent B over 4.0 min.

j—Agilent 6140 Quadruple Easy Access LC/MS; Column: Supelco Ascentis Express C18, 3.0×50 mm, 2.7 μM; Solvent A: Water with 0.05% TFA; Solvent B: Acetonitrile with 0.05% TFA; Flow Rate: 1.25 mL/min; UV Detection: DAD 200-400 nm; Gradient elution: 10% Solvent B to 99% Solvent B over 1.5 min.

The invention claimed is:

1. A compound of the formula:

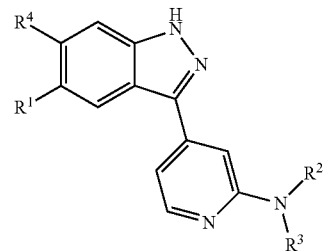

wherein $R^1$ is selected from the group consisting of:
a) hydrogen,
b) halo,
c) cyano,
d) hydroxyl,
e) $C_{2-6}$ alkenyl, which is optionally substituted with one to three substitutents independently selected from the group consisting of halo, cyano and $R^5$;
f) $OC_{2-6}$ alkenyl, which is optionally substituted with one to three substitutents independently selected from the group consisting of halo, cyano and $R^5$;
g) $R^5$,
h) $OR^5$,
i) $R^7$,
j) $S(O)_m R^5$,
k) $S(O)_m R^7$,
l) $(C=O)R^7$,
m) $(C=O)R^5$,
n) $(C=O)OR^5$, and
o) $NR^c R^d$;

$R^2$ is selected from the group consisting of hydrogen and $C_{1-6}$ alkyl, which is optionally substituted with one to three substitutents independently selected from the group consisting of:
a) halo,
b) cyano,
c) $R^5$,
d) $R^7$,
e) $OR^5$, and
f) $NR^c R^d$;

$R^3$ is selected from the group consisting of:
a) hydrogen,
b) $C_{1-6}$ alkyl, which is optionally substituted with one to three substitutents independently selected from the group consisting of halo, cyano, $OR^5$ and $NR^c R^d$,
c) $C_{3-8}$ cycloalkyl, which is optionally substituted with one to three substitutents independently selected from the group consisting of halo, cyano, $OR^5$ and $NR^c R^d$,
e) heteroaryl, which is optionally substituted with one to three substitutents independently selected from the group consisting of halo, cyano, oxo, $R^5$, $OR^5$ and $NR^c R^d$,
f) $C_{4-8}$ cycloalkenyl, which is optionally substituted with one to three substitutents independently selected from the group consisting of halo, cyano, $OR^5$ and $NR^c R^d$,
g) $(C=O)R^7$,
h) $(C=O)R^5$,
i) $S(O)_m R^5$, and
j) $S(O)_m R^7$;

or $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) $OR^5$,
e) $NR^cR^d$,
f) $SO_3H$,
g) $S(O)_mR^5$,
h) $S(O)_mR^7$
i) $R^5$,
j) $R^6$,
k) $R^7$,
l) $(C=O)R^5$,
m) $(C=O)OR^5$,
n) $(C=O)R^7$, and
o) $(C=O)NR^cR^d$;

$R^4$ is selected from the group consisting of hydrogen, halo, cyano, $OR^5$, aryl, heteroaryl, $C_{3-8}$ cycloalkyl, $C_{4-8}$ cycloalkenyl, $C_{4-8}$ heterocyclyl and $C_{1-6}$ alkyl, which is optionally substituted with one to three substituents independently selected from the group consisting of halo, cyano, $OC_{1-3}$ alkyl, $NR^cR^d$ and hydroxyl;

or $R^1$ and $R^4$ are taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) $R^5$, and
e) $R^7$;

$R^5$ is selected from the group consisting of hydrogen and $C_{1-6}$ alkyl, which is optionally substituted with one to three substituents independently selected from the group consisting of:
a) halo,
b) hydroxyl,
c) $OC_{1-6}$ alkyl,
d) $NR^cR^d$,
e) $(C=O)NR^cR^d$,
f) $S(O)_mR^8$,
g) $S(O)_mR^7$,
h) $R^7$ and
i) $OR^7$;

$R^6$ is $C_{1-6}$ alkyl, which is optionally substituted with one to three substituents independently selected from the group consisting of halo and hydroxyl;

or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of:
a) halo,
b) oxo,
c) cyano,
d) hydroxyl,
e) $C_{1-3}$ alkyl, which is optionally substituted with one to three halo,
f) $C_{3-8}$ cycloalkyl,
g) $OC_{1-3}$ alkyl, which is optionally substituted with one to three halo, and
h) $OC_{3-8}$ cycloalkyl;

$R^7$ is selected from the group consisting of $C_{4-8}$ heterocyclyl, $C_{3-8}$ cycloalkyl, $C_{4-8}$ cycloalkenyl, aryl or heteroaryl,
wherein said heteroaryl of $R^7$ is selected from the group consisting of benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline, and wherein said heterocyclyl, cycloalkyl, cycloalkenyl, aryl and heteroaryl groups are optionally substituted with one to three substituents independently selected from the group consisting of:
a) halo,
b) cyano,
c) hydroxyl,
d) oxo,
e) $C_{1-3}$ alkyl, which is optionally substituted with one to four substituents independently selected from the group consisting of hydroxyl, halo, cyano, heterocyclyl, $OC_{1-3}$ alkyl and $NR^cR^d$,
f) $OC_{1-3}$ alkyl, which is optionally substituted with one to four substituents independently selected from the group consisting of hydroxyl, halo, cyano, heterocyclyl, $OC_{1-3}$ alkyl $R^cR^d$ and aryl,
g) $C_{3-8}$ cycloalkyl, which is optionally substituted with one to four substituents independently selected from the group consisting of hydroxyl, halo, cyano, heterocyclyl, $OC_{1-3}$ alkyl and $R^cR^d$,
h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
i) heteroaryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
j) heterocyclyl, which is optionally substituted with one to four substituents independently selected from the group consisting of hydroxyl, halo, cyano, $OC_{1-3}$ alkyl and $NR^cR^d$,
k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$;

$R^8$ is hydrogen or $C_{1-6}$ alkyl, which is optionally substituted with one to three substituents independently selected from the group consisting of:
a) halo,
b) cyano, c) hydroxyl,
d) $OC_{1-3}$ alkyl, which is optionally substituted with one to four substituents independently selected from the group consisting of hydroxyl, halo and $NR^cR^d$, and
e) $C_{3-8}$ cycloalkyl;

$R^c$ is selected from the group consisting of:
  a) hydrogen and
  b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}alkyl)_2$, $OC_{1-6}$ alkyl, and $C_{3-8}$ cycloalkyl;

$R^d$ is selected from the group consisting of:
  a) hydrogen,
  b) $C_{3-8}$ cycloalkyl,
  c) $C_{3-6}$ heterocyclyl,
  d) $C_{1-3}$ alkyl,
  e) (C=O)$C_{1-3}$ alkyl,
  f) aryl, and
  g) heteroaryl;

wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl;

or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl;

m is an integer from zero to two,
or a pharmaceutically acceptable salt thereof.

2. The compound of claim 1 wherein $R^1$ is selected from the group consisting of $R^5$, $OR^5$ and $R^7$, or a pharmaceutically acceptable salt thereof.

3. The compound of claim 2 wherein $R^1$ is selected from the group consisting of $OR^5$ and $R^7$, or a pharmaceutically acceptable salt thereof.

4. The compound of claim 3 wherein $R^1$ is selected from the group consisting of $OC_{1-3}$ alkyl, aryl and heteroaryl, wherein said aryl and heteroaryl groups are optionally substituted with one to three substituents independently selected from the group consisting of halo, hydroxyl, $C_{1-3}$ alkyl and $OC_{1-3}$ alkyl, or a pharmaceutically acceptable salt thereof.

5. The compound of claim 4 wherein $R^4$ is selected from the group consisting of: hydrogen and halo, or a pharmaceutically acceptable salt thereof.

6. The compound of claim 5 wherein $R^2$ and $R^3$ are taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) cyano,
  d) $OR^5$,
  e) $NR^cR^d$,
  f) $SO_3H$,
  g) $S(O)_mR^5$,
  h) $S(O)_mR^7$,
  i) $R^5$,
  j) $R^6$,
  k) $R^7$,
  l) (C=O)$R^5$,
  m) (C=O)$OR^5$,
  n) (C=O)$R^7$, and
  o) (C=O)$NR^cR^d$;
or a pharmaceutically acceptable salt thereof.

7. The compound of claim 6 wherein $R^2$ and $R^3$ are taken together with the atoms to which they are attached to form a 6 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  (a) halo,
  b) oxo,
  c) $OR^5$,
  d) $NR^cR^d$,
  e) $S(O)_mR^5$,
  f) $S(O)_mR^7$,
  g) $R^5$,
  h) $R^6$,
  i) $R^7$,
  j) (C=O)$R^5$,
  k) (C=O)$OR^5$, and
  l) (C=O)$R^7$,
or a pharmaceutically acceptable salt thereof.

8. A compound selected from

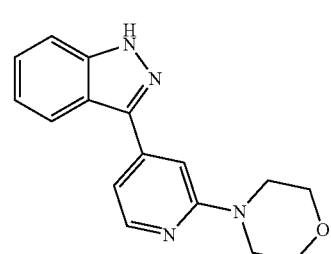

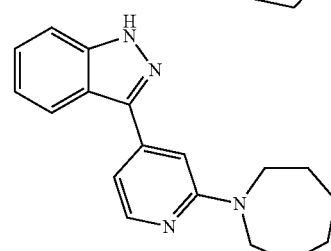

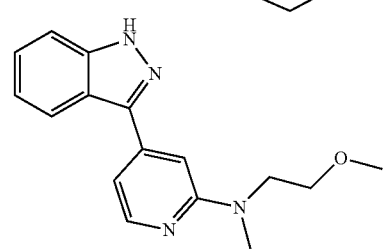

467
-continued
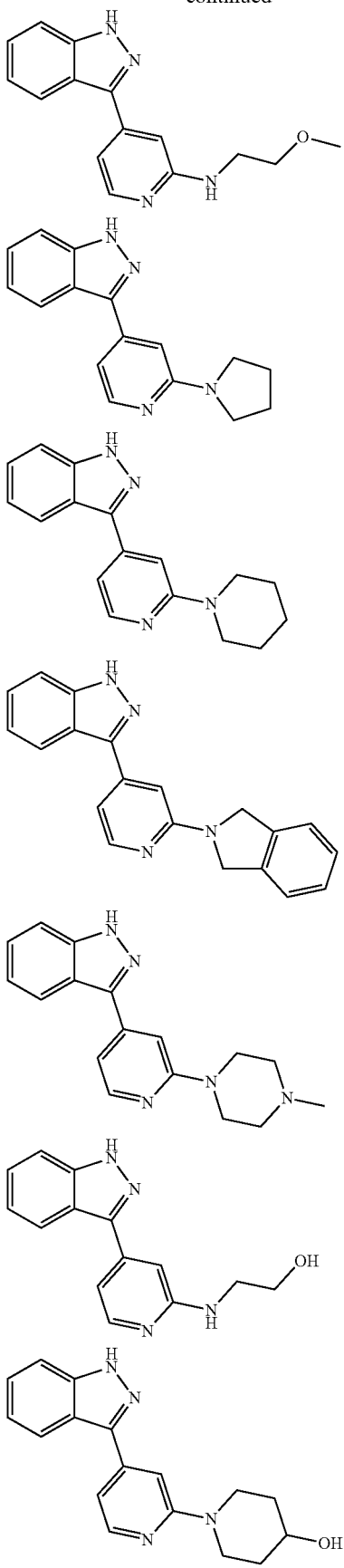
468
-continued
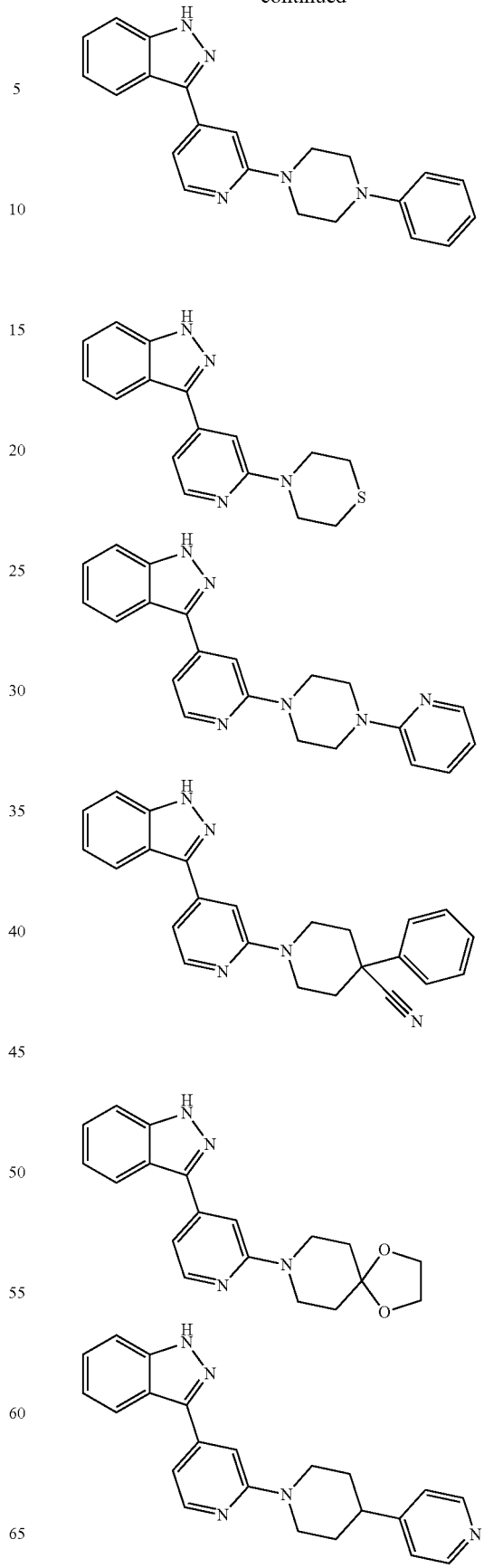

469
-continued
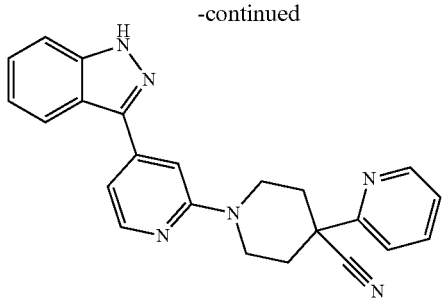
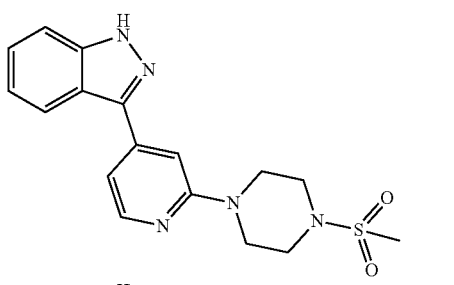
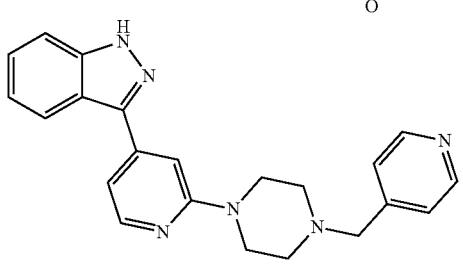
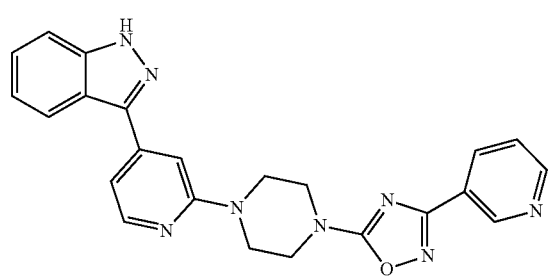
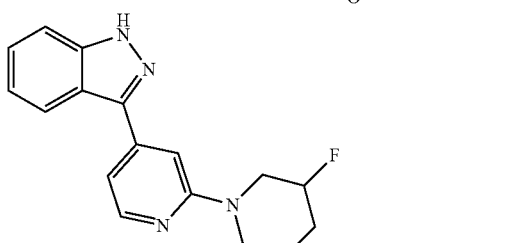
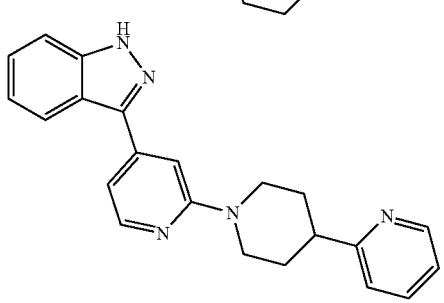
470
-continued
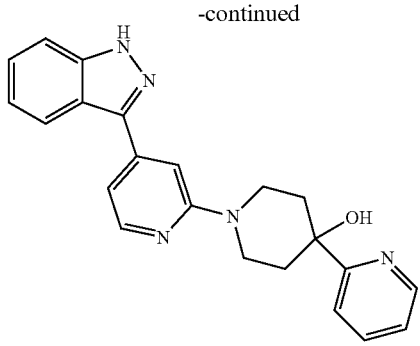
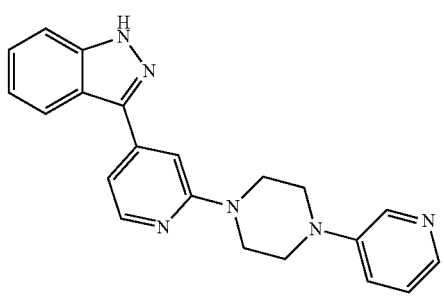
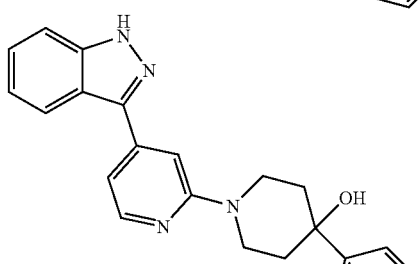
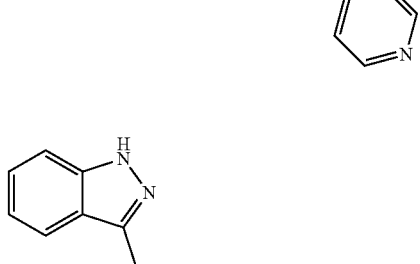
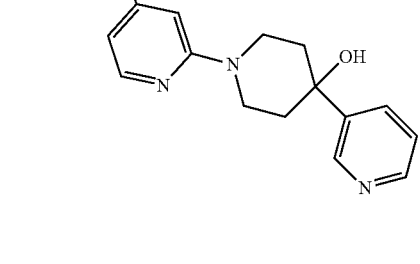
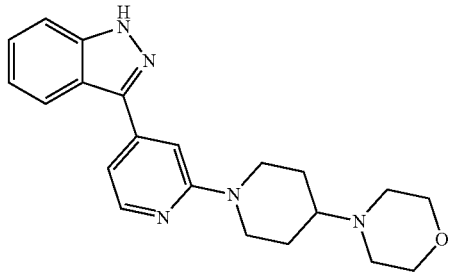

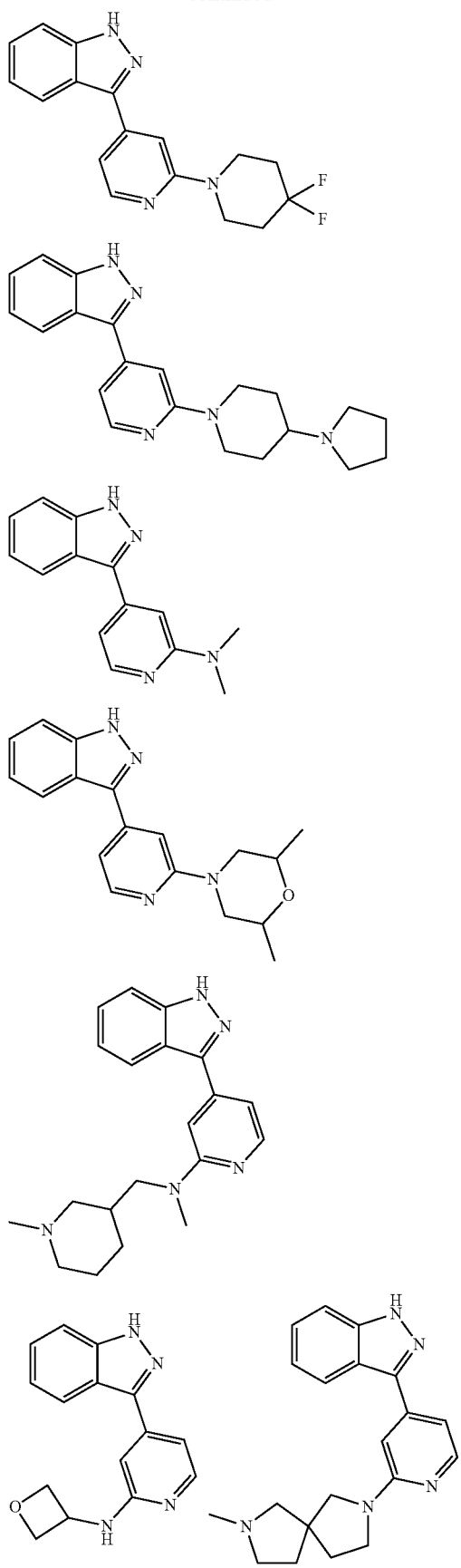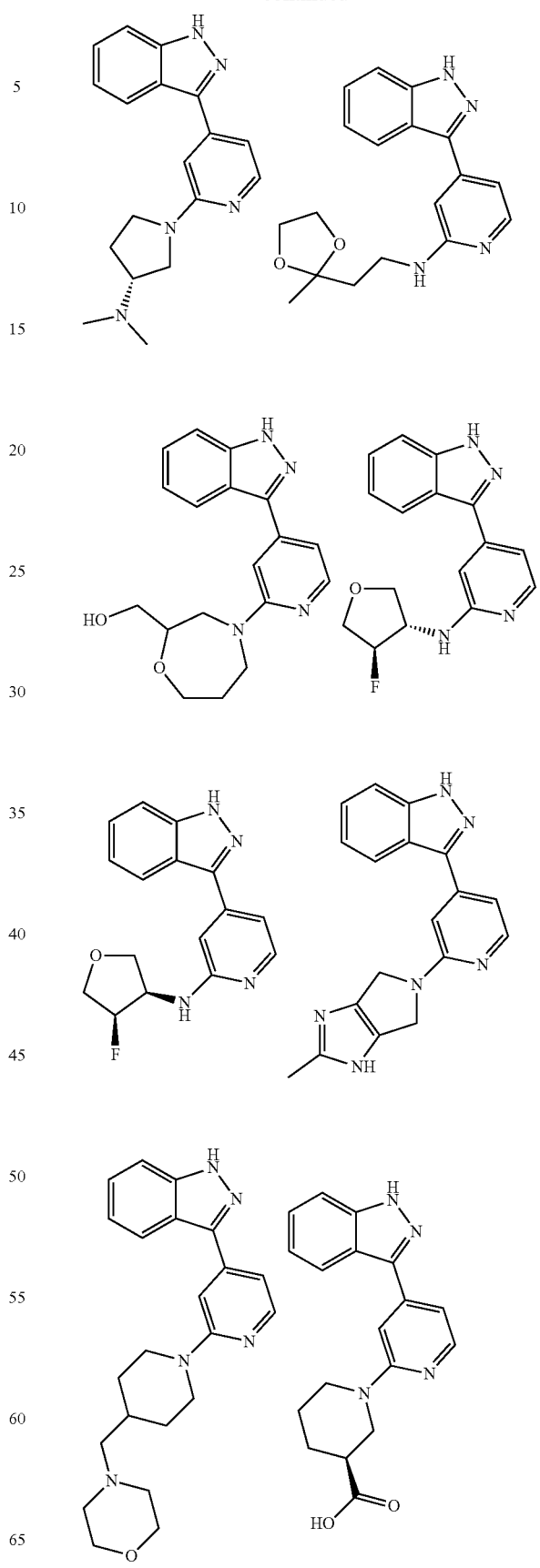

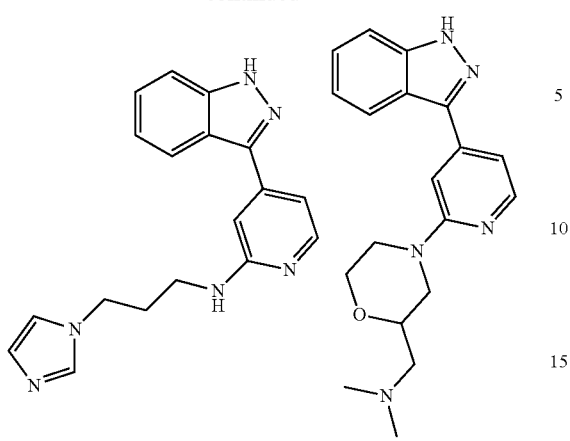
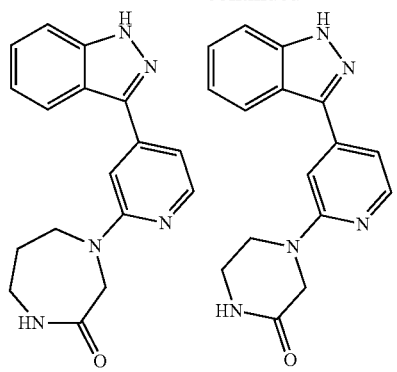
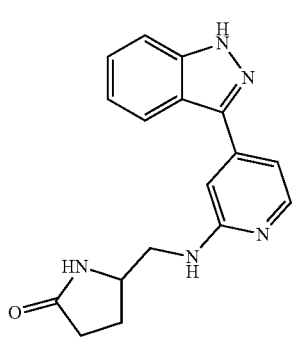
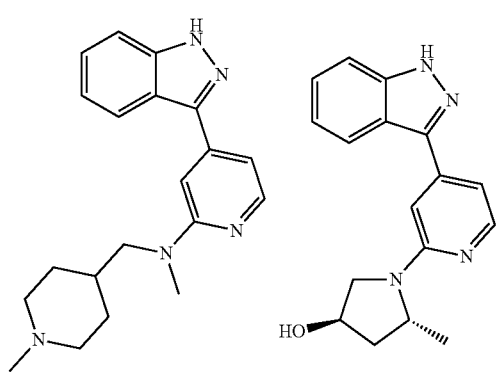
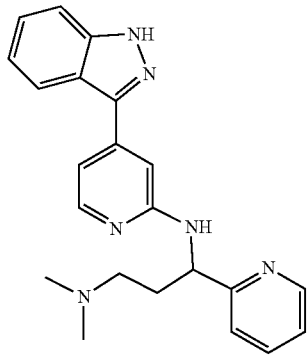
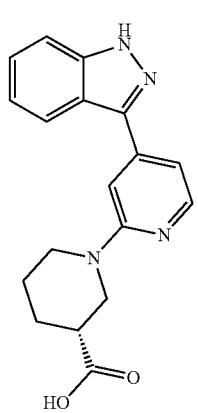
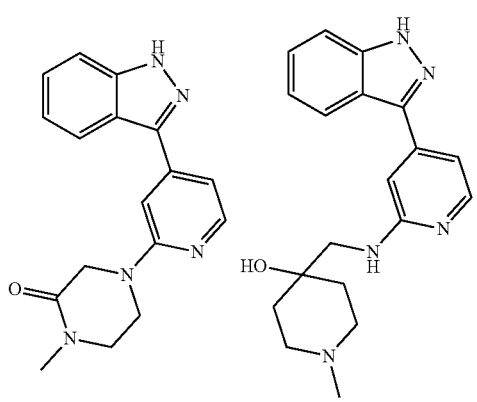
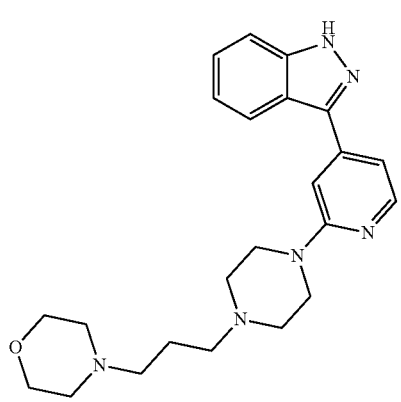

475
-continued
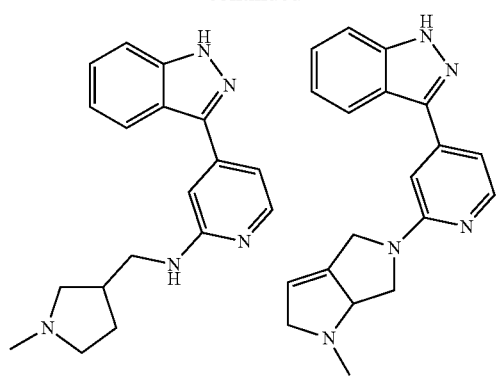
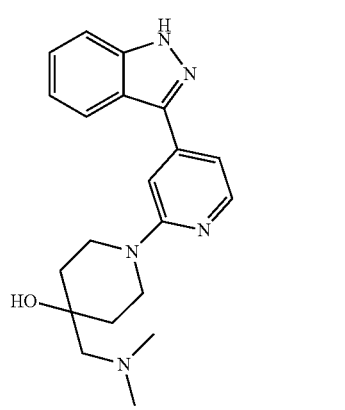
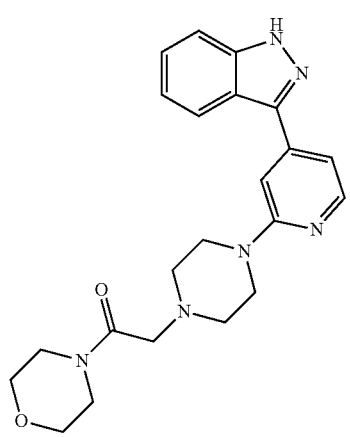
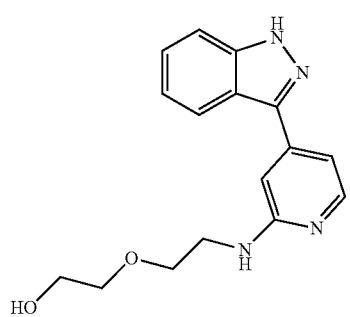
476
-continued
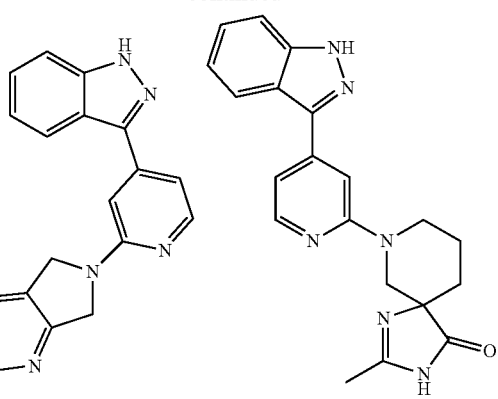
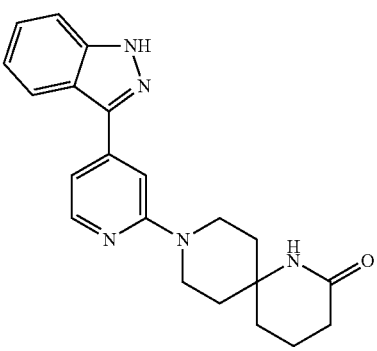
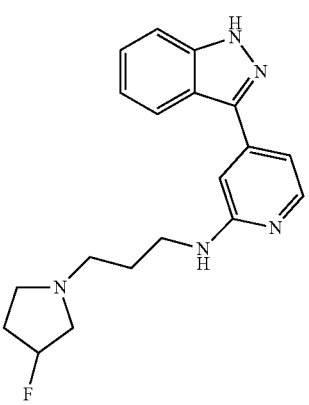
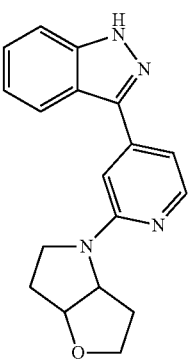

477
-continued
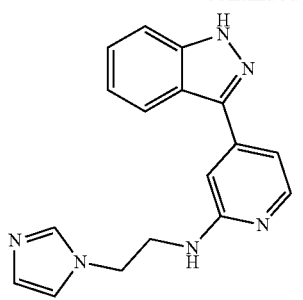
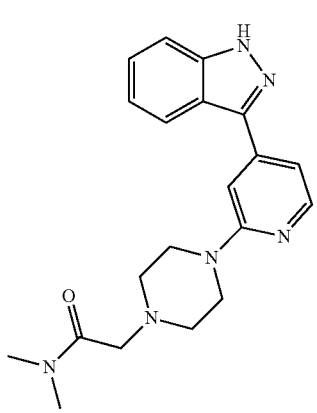
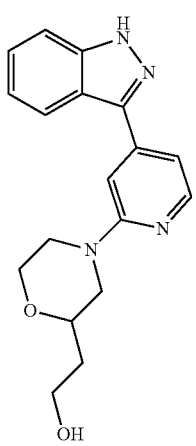
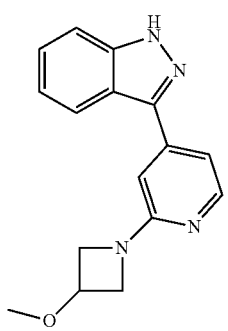
478
-continued
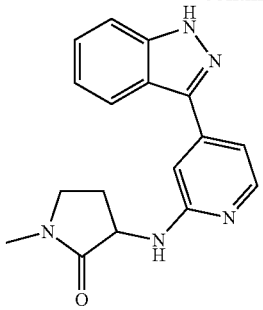
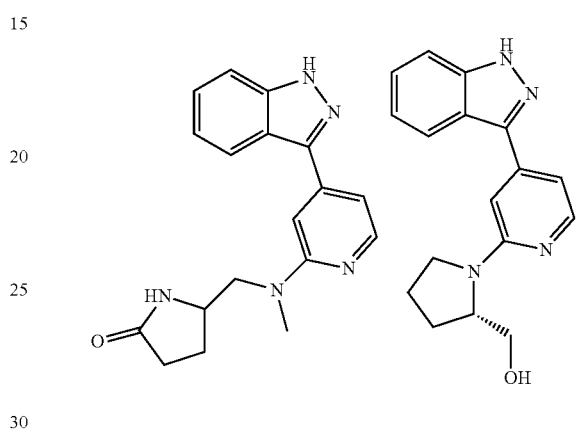
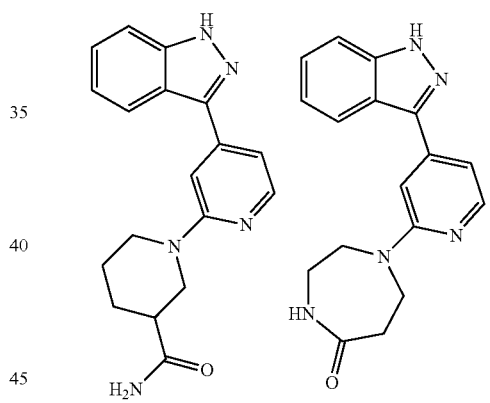
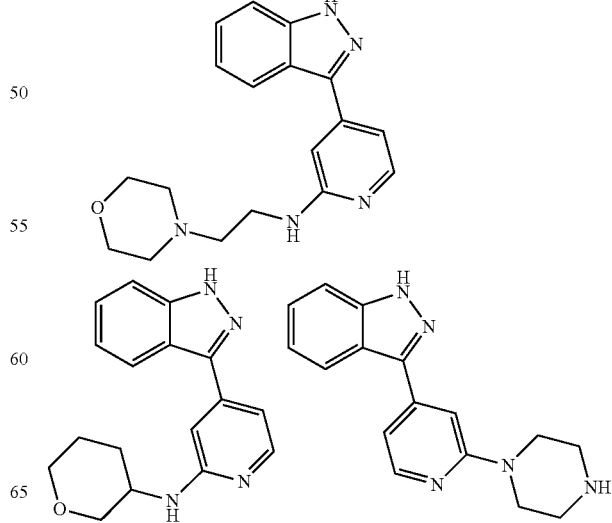

479
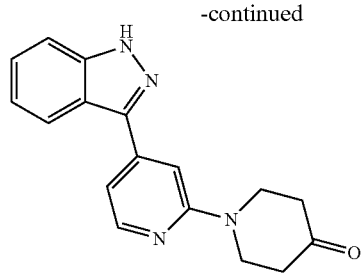
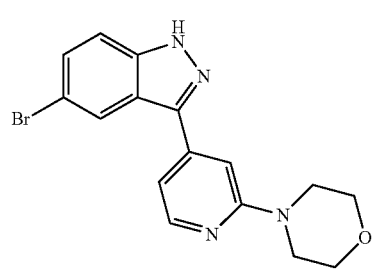
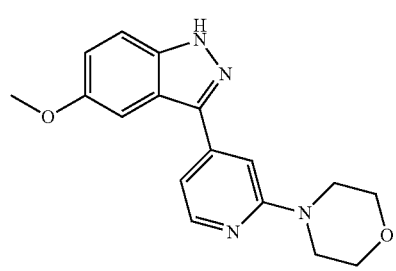
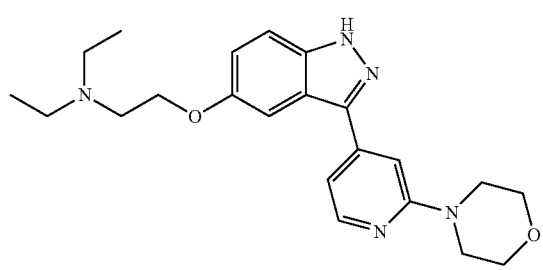
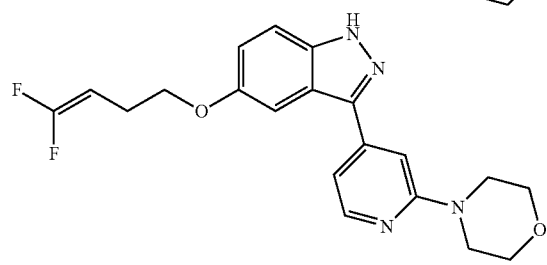
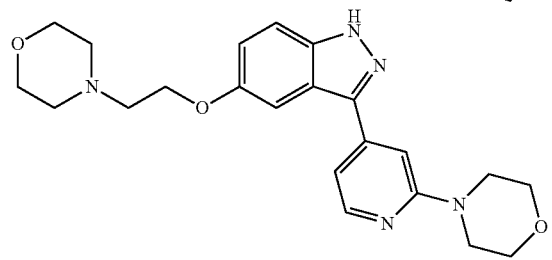
480
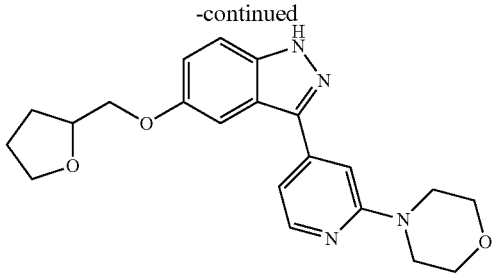
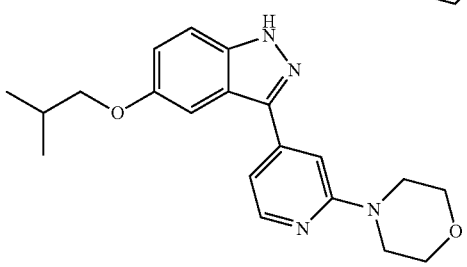
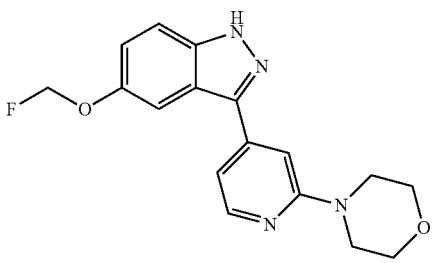
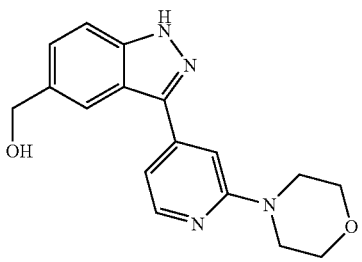
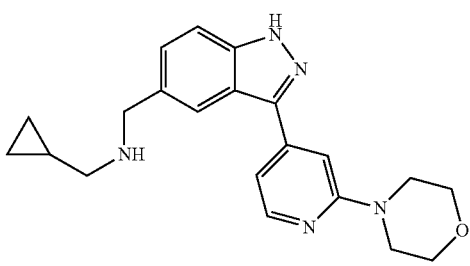
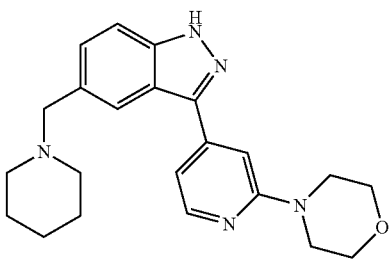

| 481 | 482 |
|---|---|
| -continued | -continued |
| 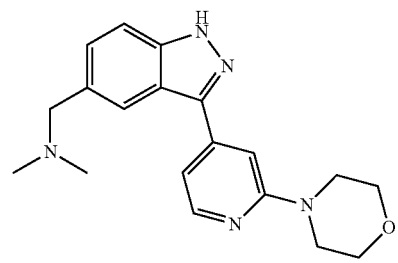 | 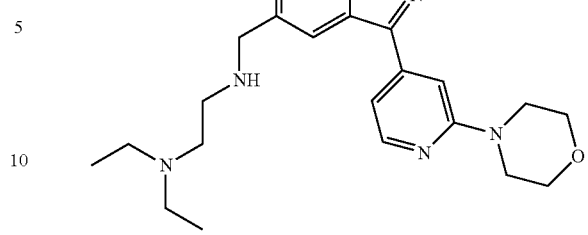 |
| 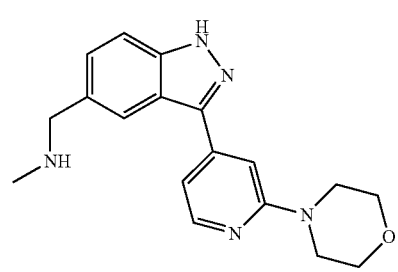 | 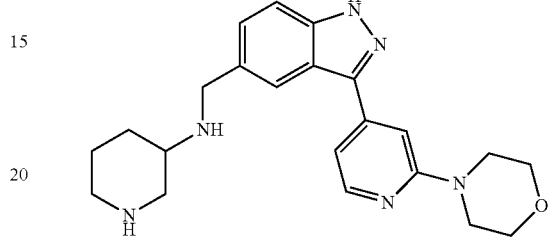 |
| 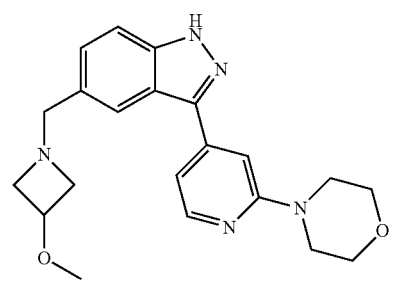 | 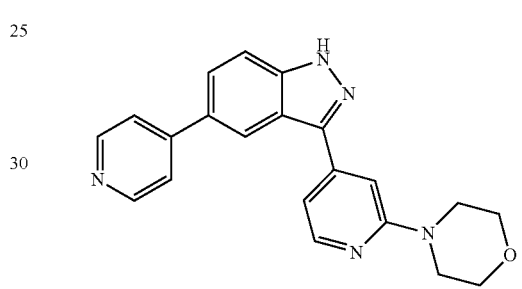 |
| 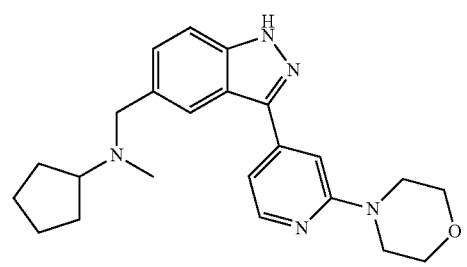 | 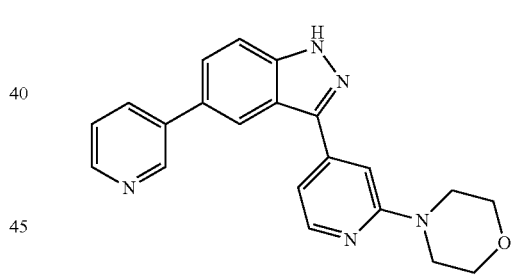 |
| 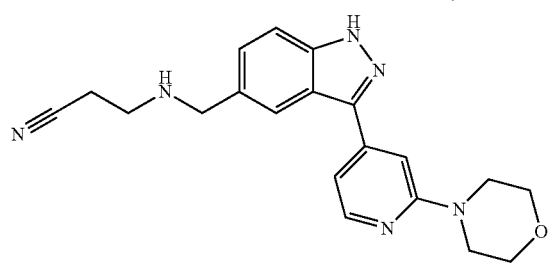 | 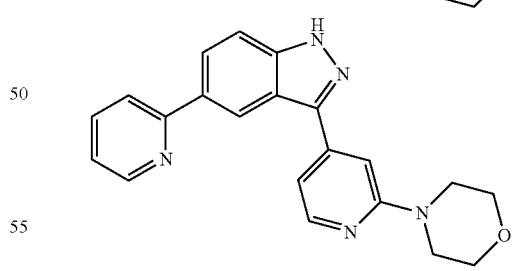 |
| 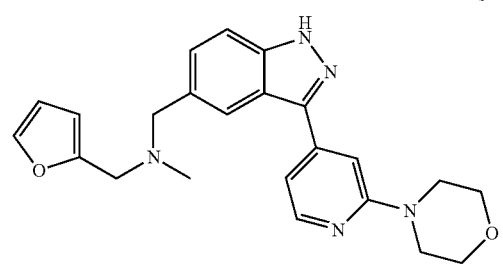 | 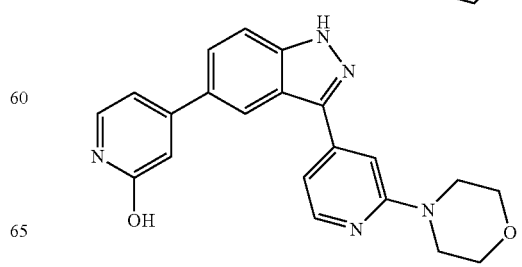 |

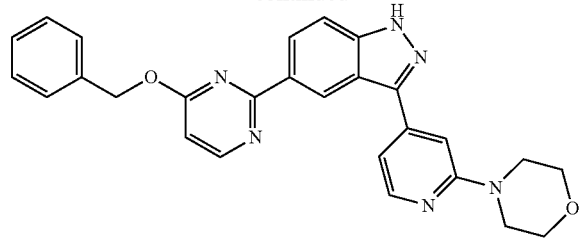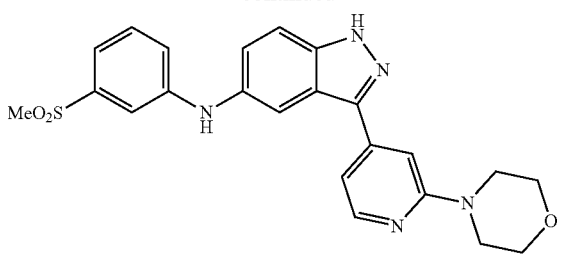

485
-continued
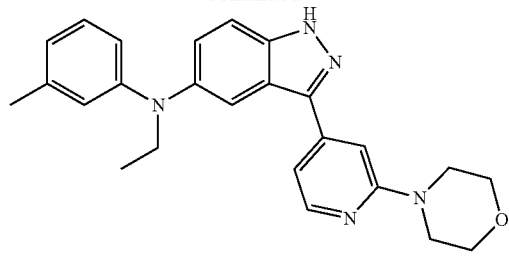
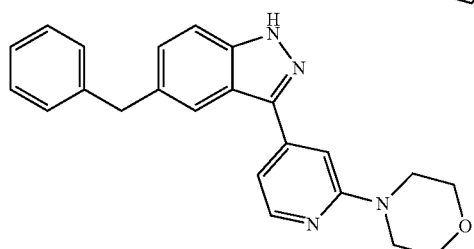
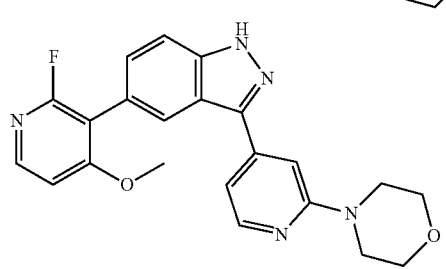
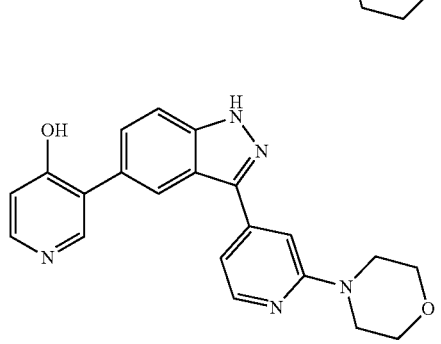
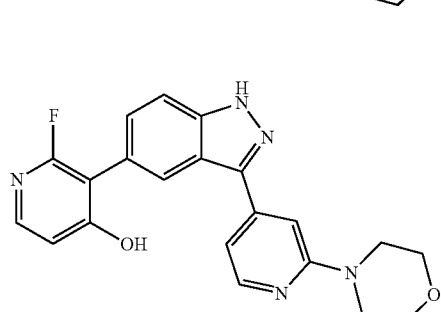
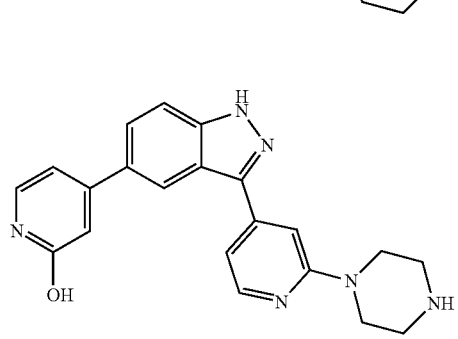
486
-continued
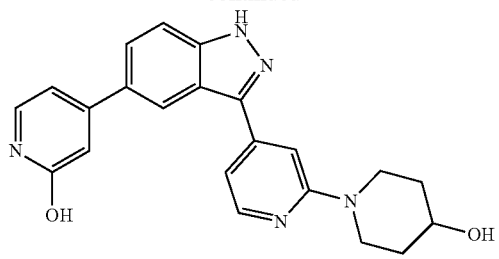
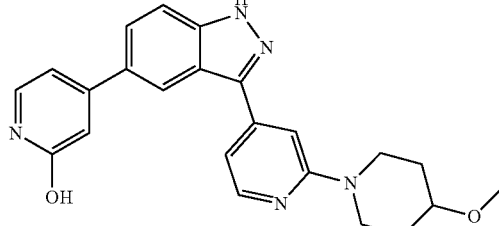
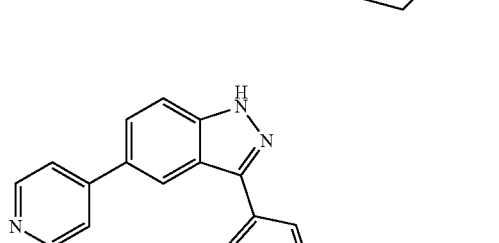
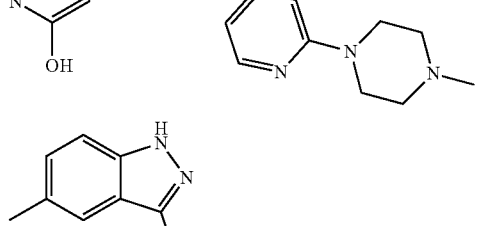
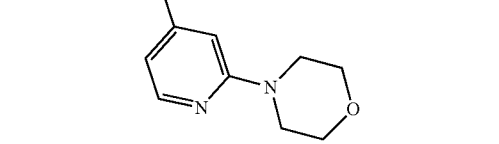
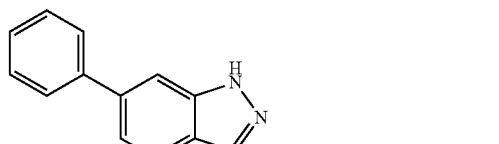
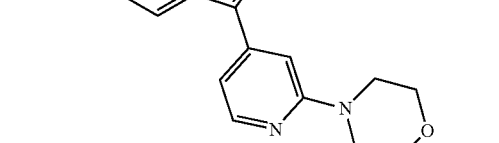
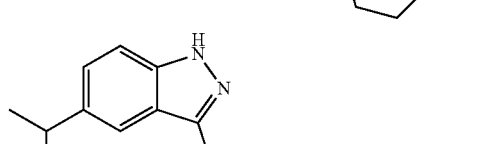
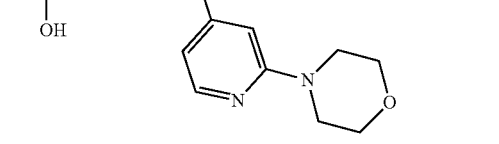

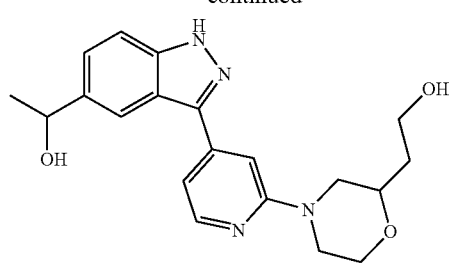
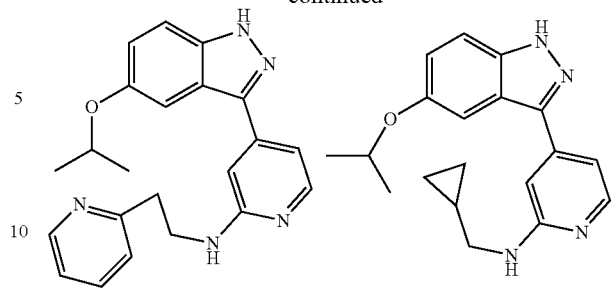

489
-continued
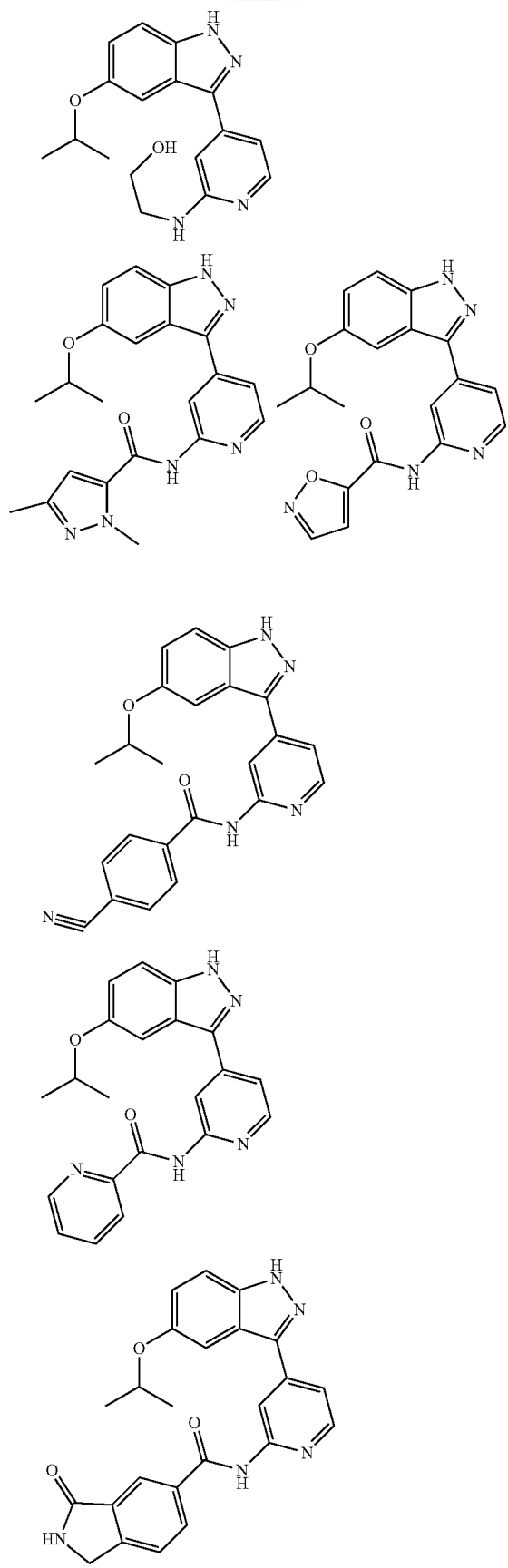
490
-continued
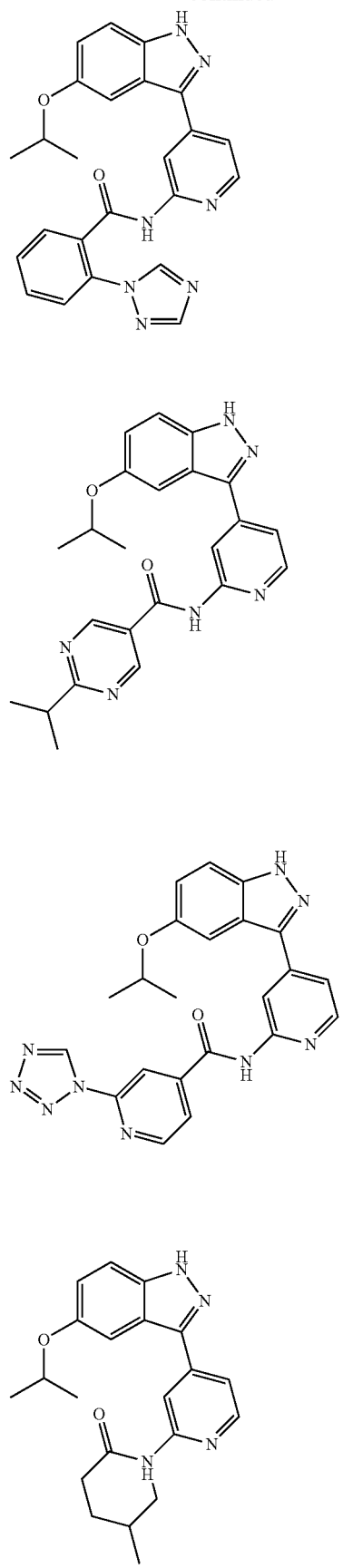

491
-continued
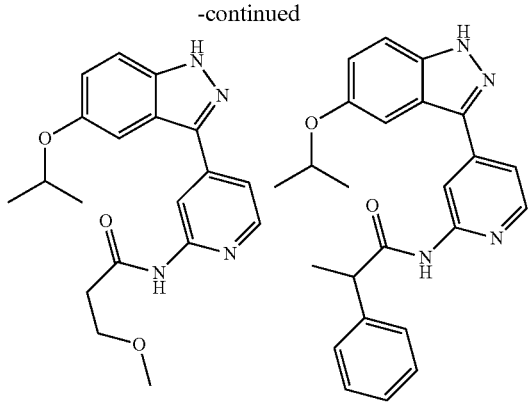
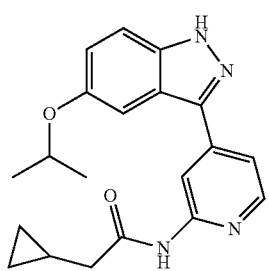
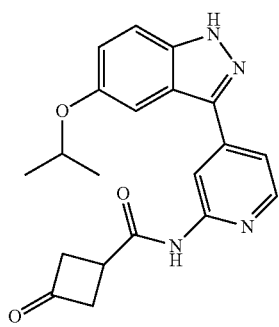
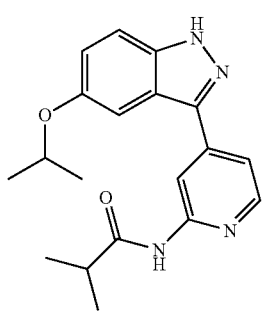
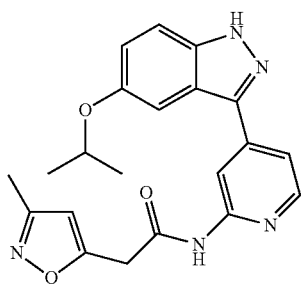
492
-continued
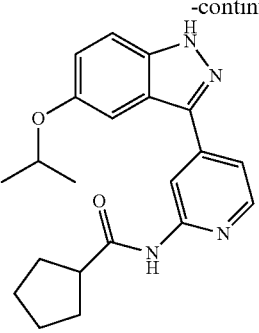
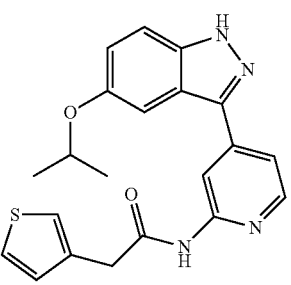
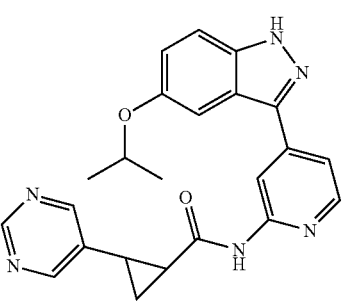
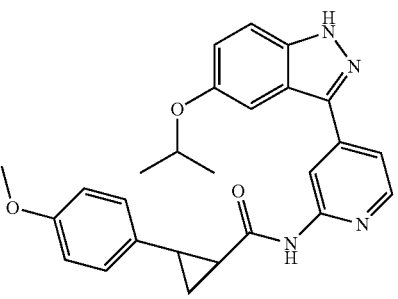
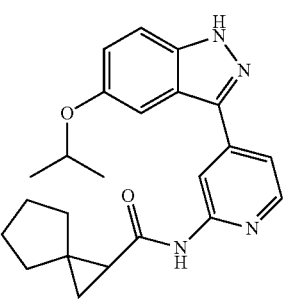

493
-continued
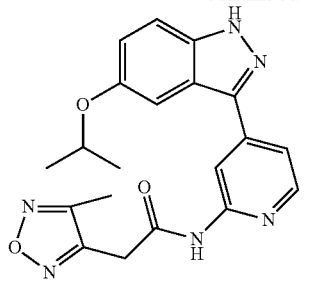
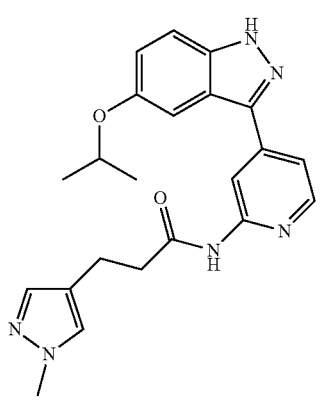
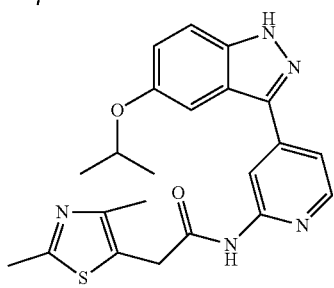
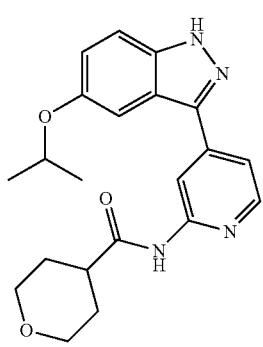
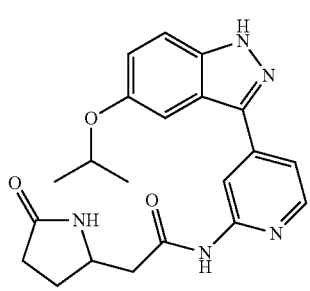
494
-continued
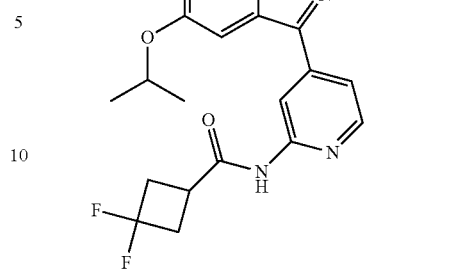
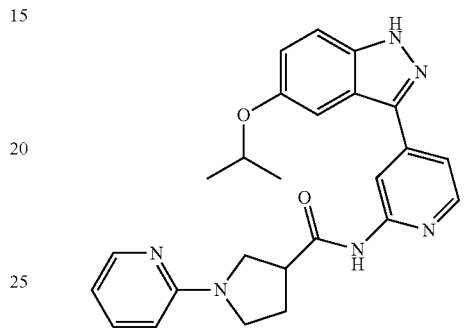
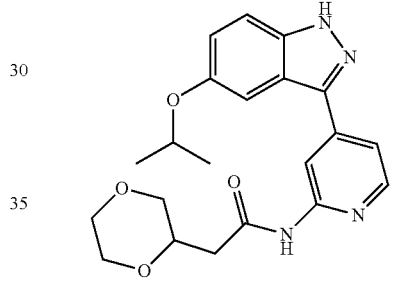
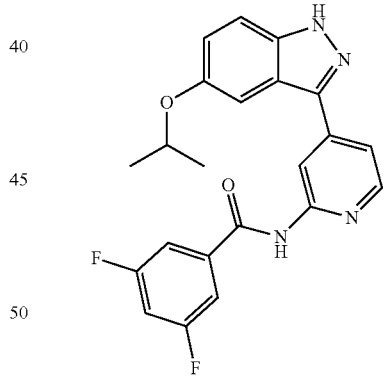
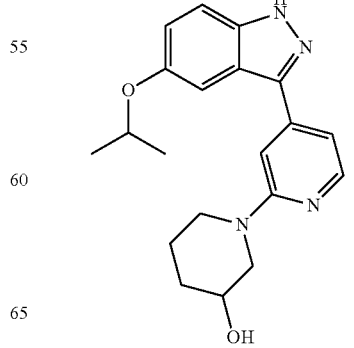

495
-continued
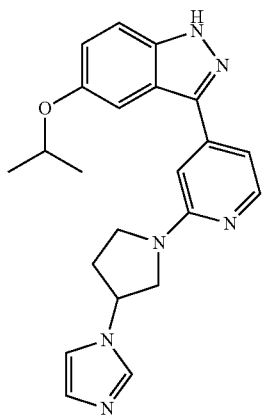
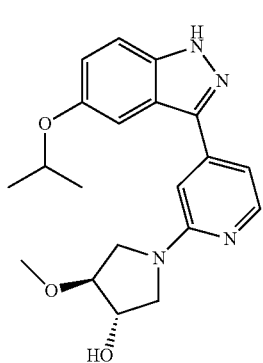
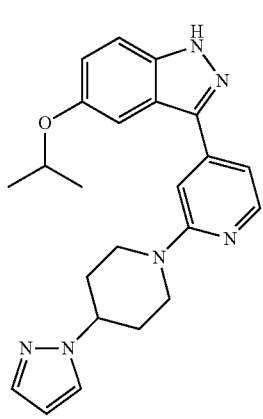
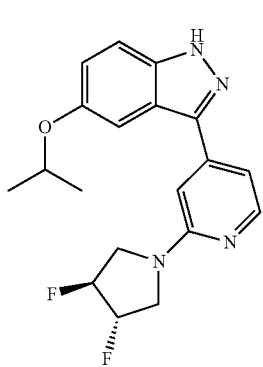
496
-continued
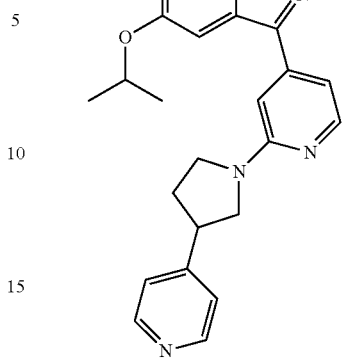
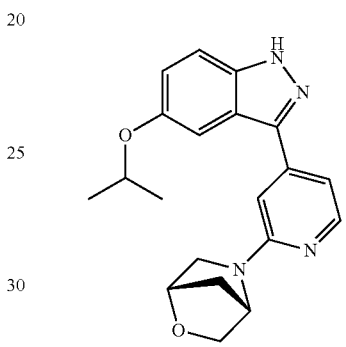
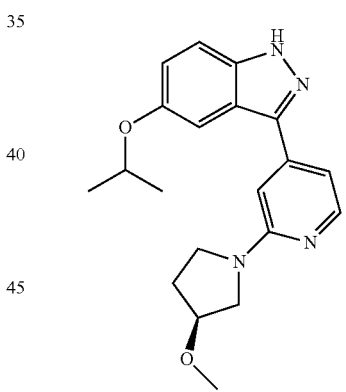
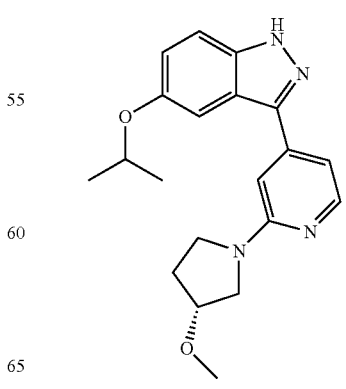

497
-continued
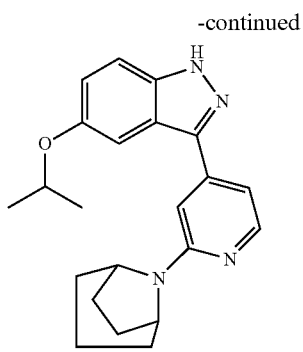
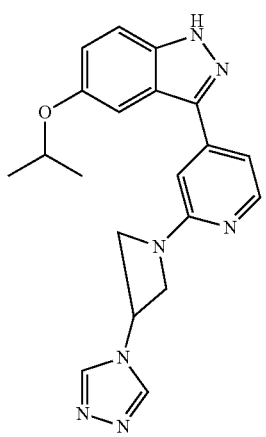
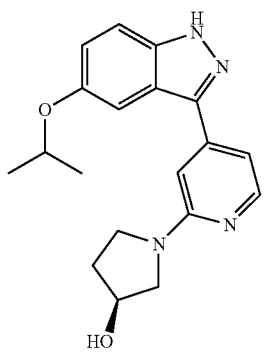
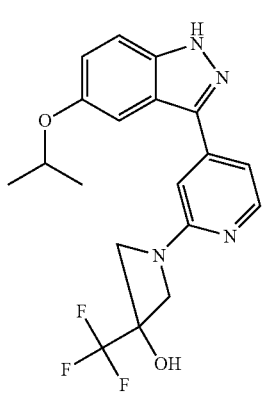
498
-continued
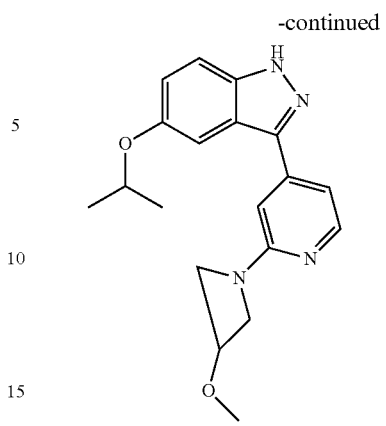
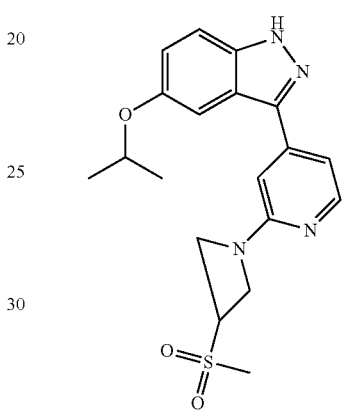
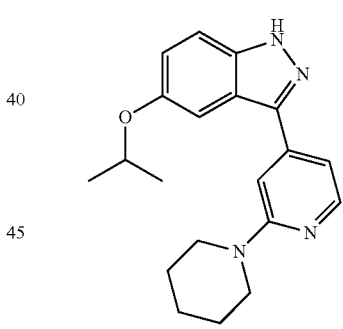
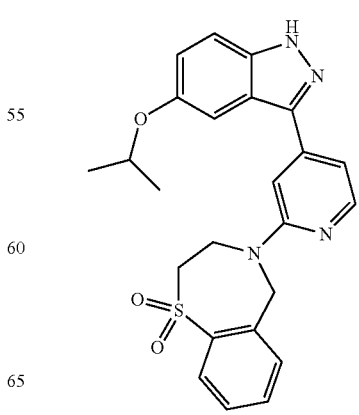

499
-continued
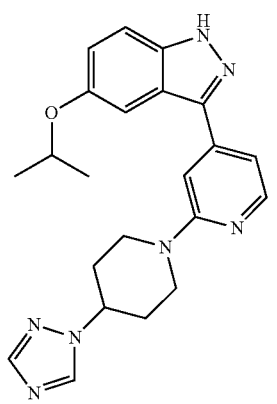
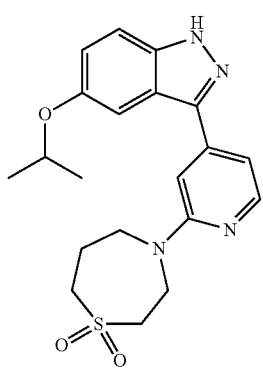
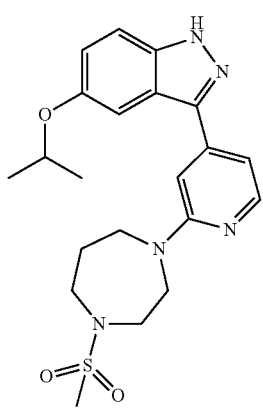
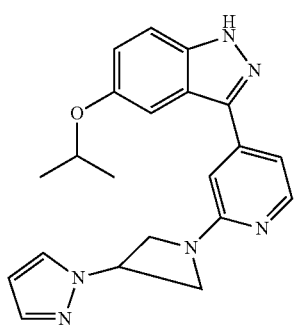
500
-continued
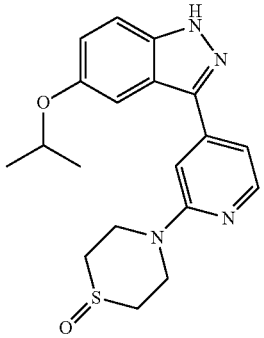
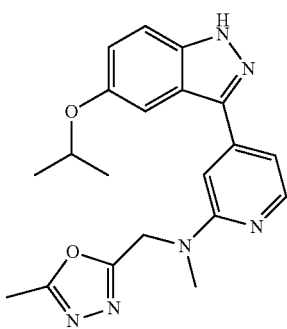
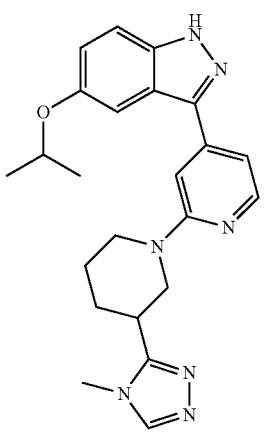
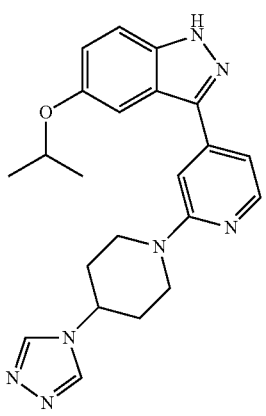

501
-continued
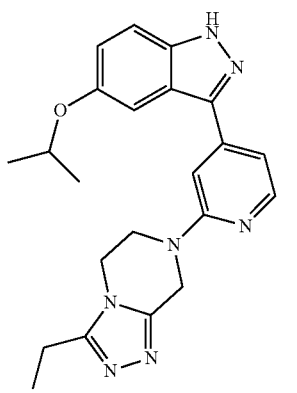
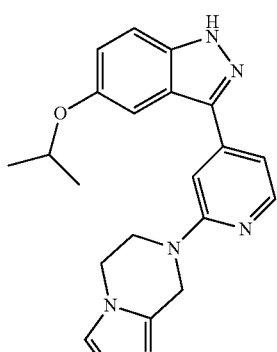
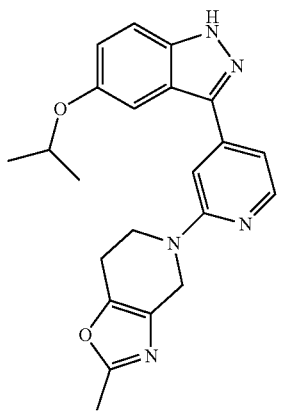
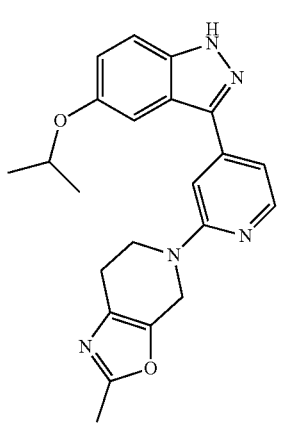
502
-continued
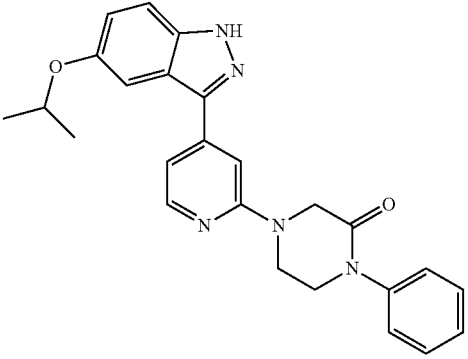
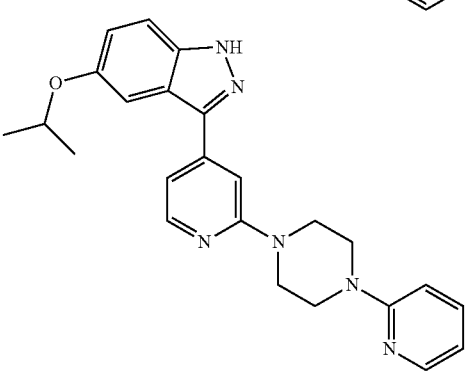
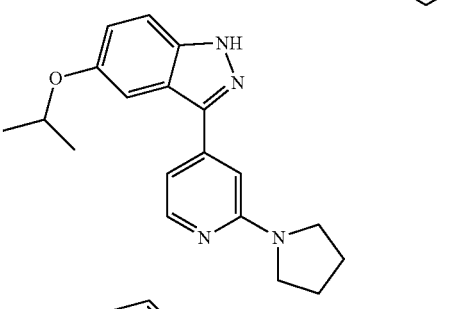
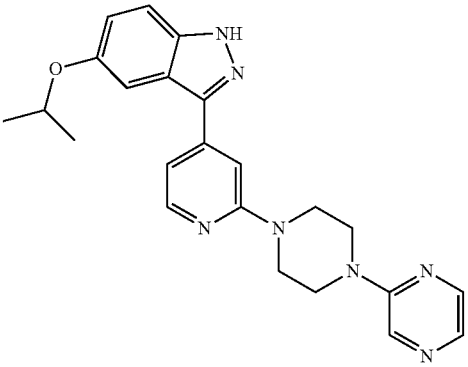
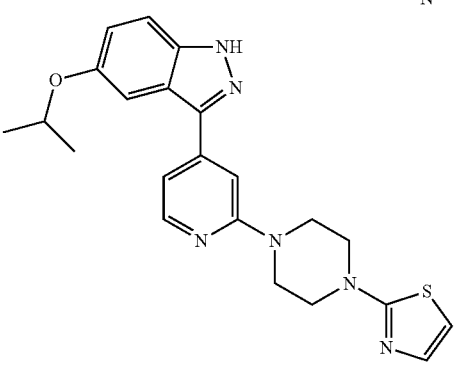

503
-continued
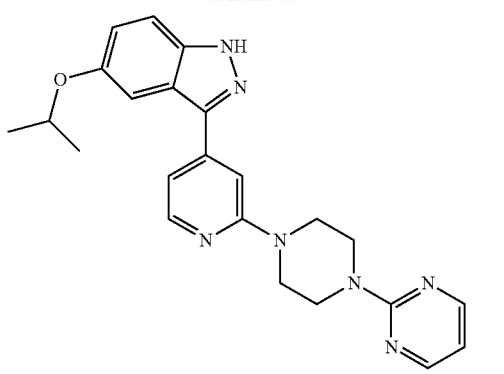
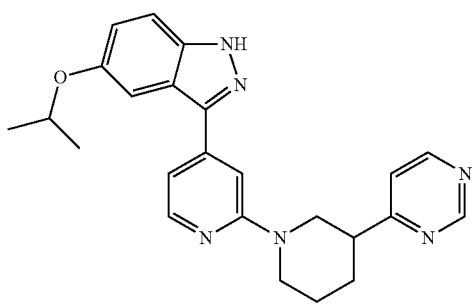
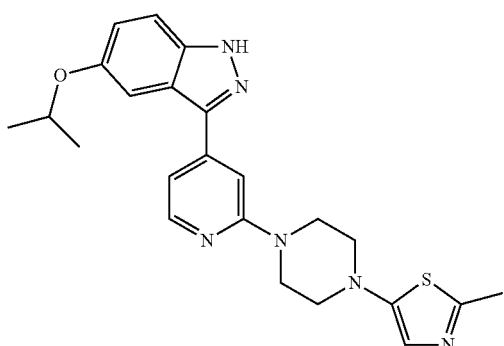
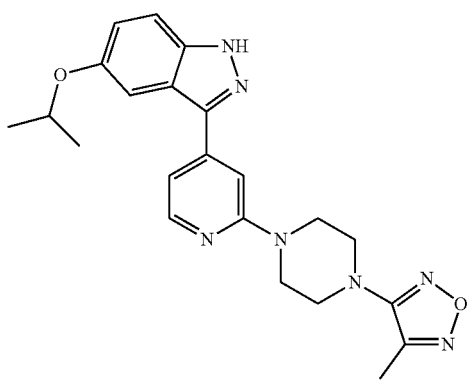
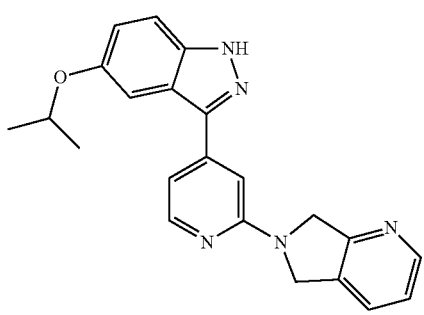
504
-continued
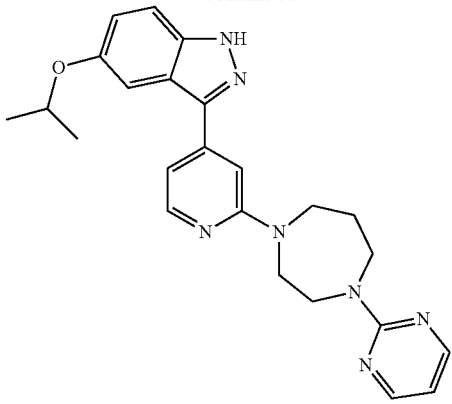
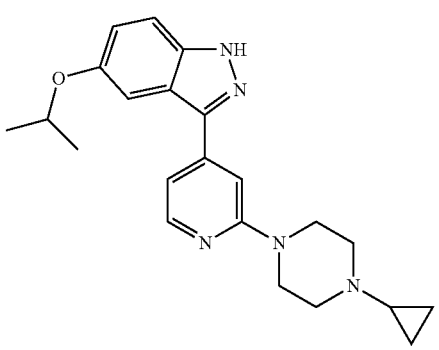
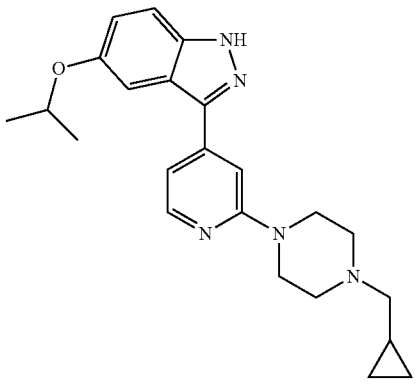
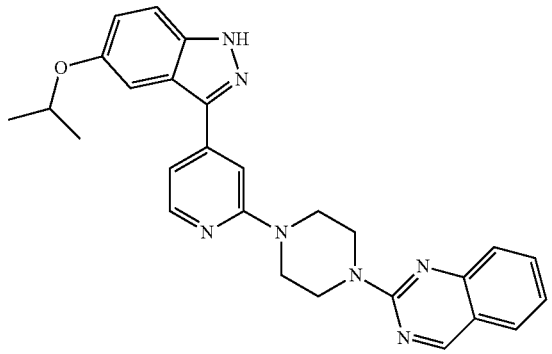

505
-continued
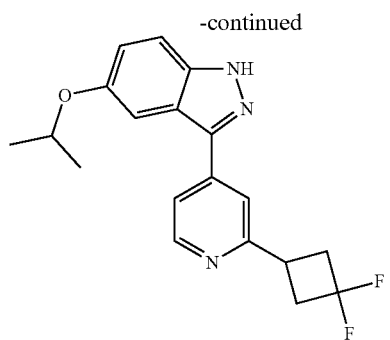
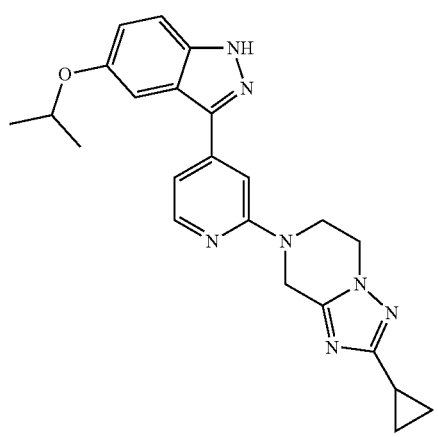
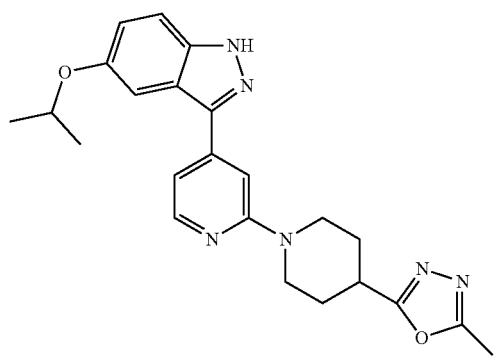
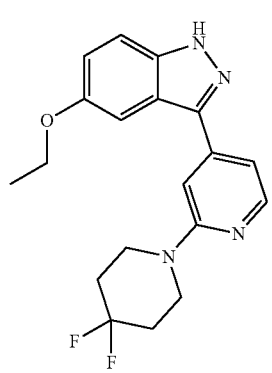
506
-continued
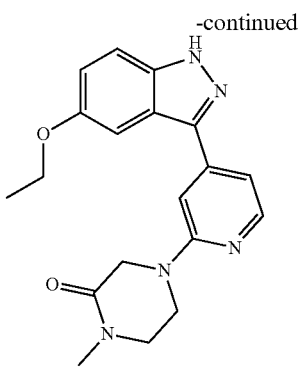
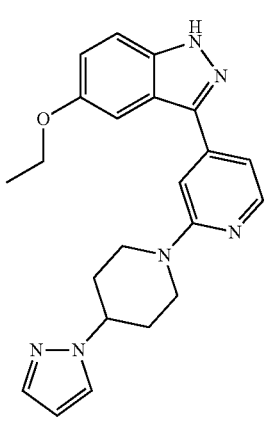
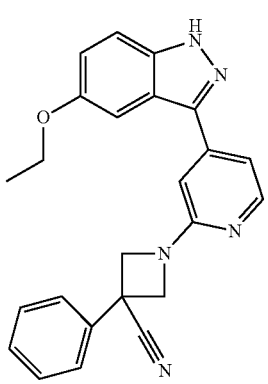
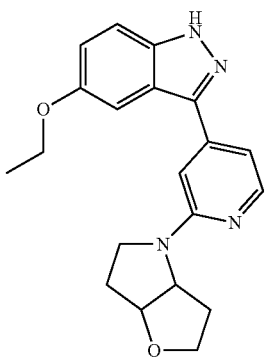

507
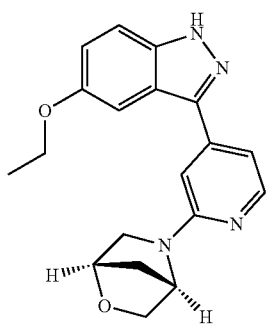
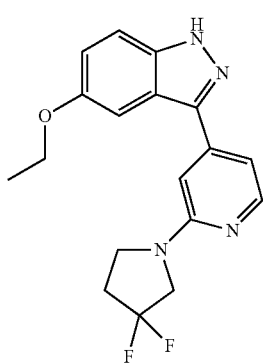
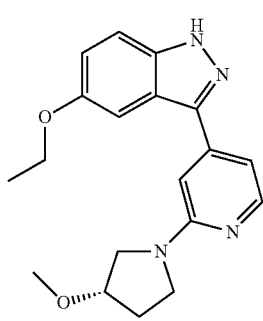
508
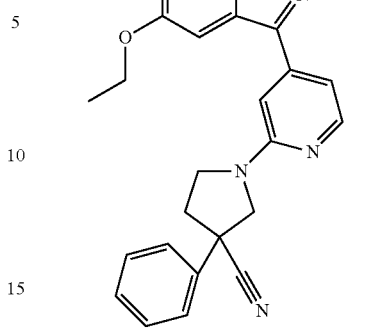
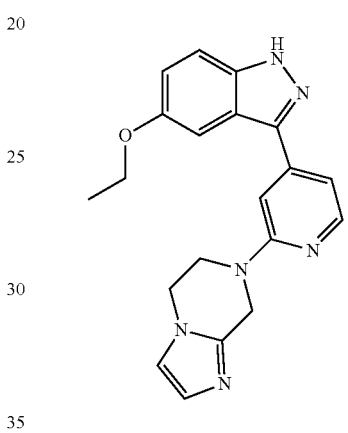
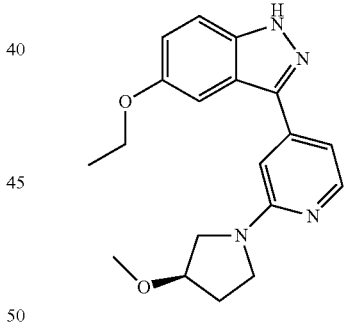
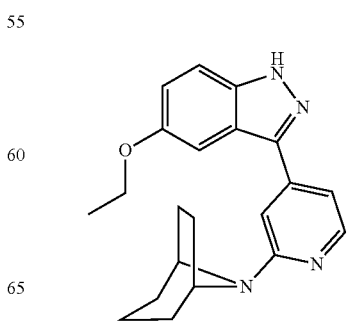

509
-continued
510
-continued
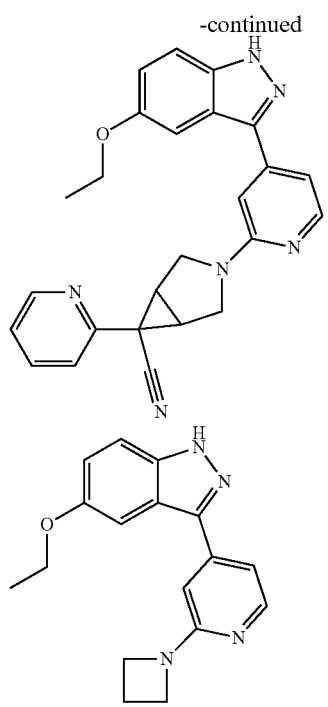
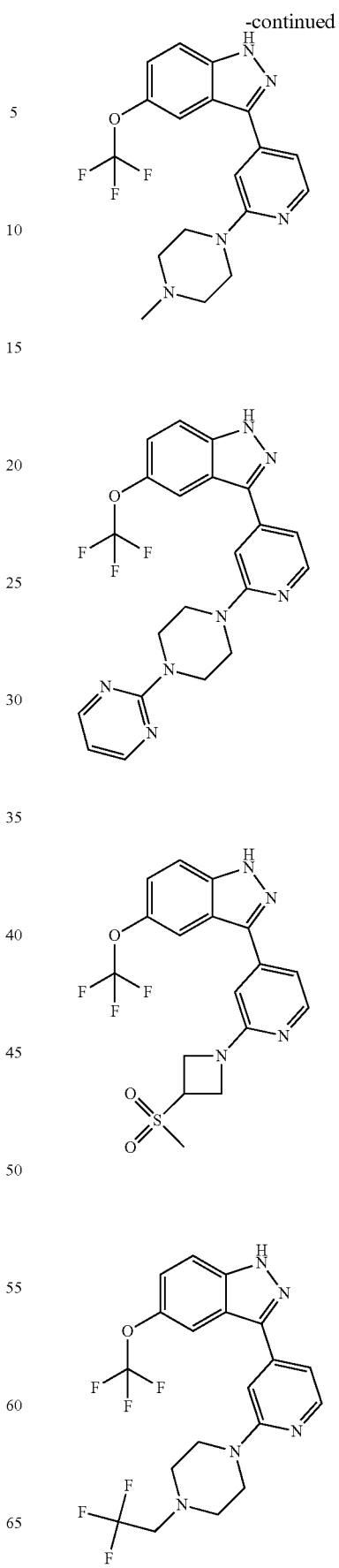

511
-continued
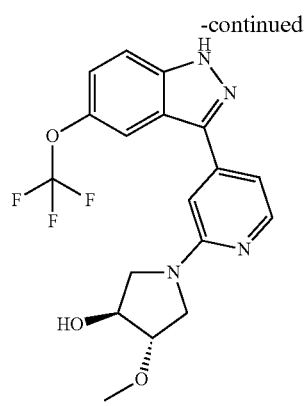
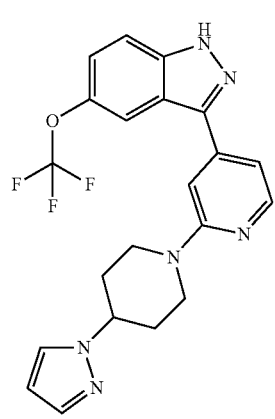
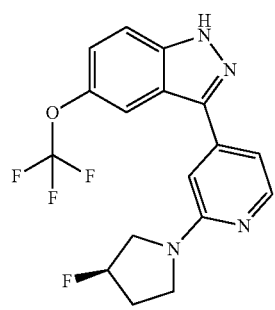
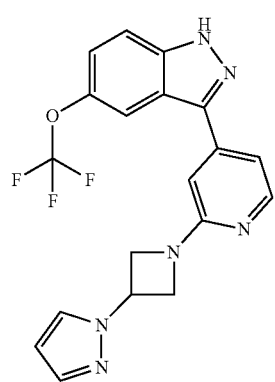
512
-continued
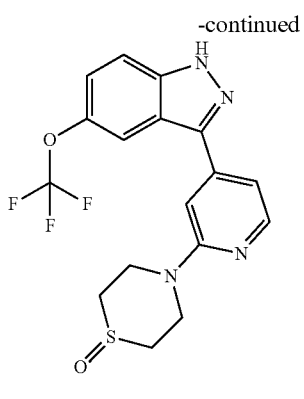
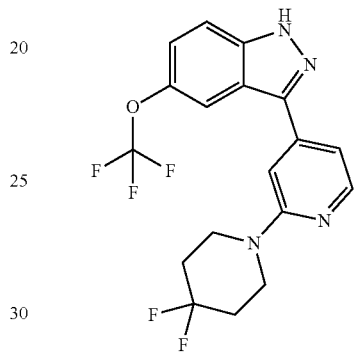
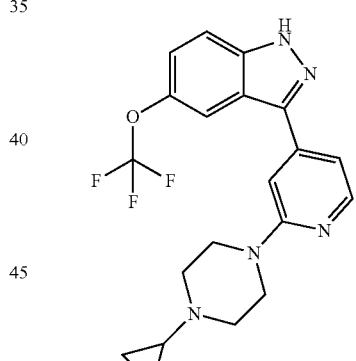
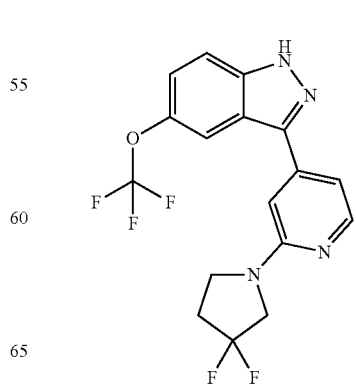

513
-continued
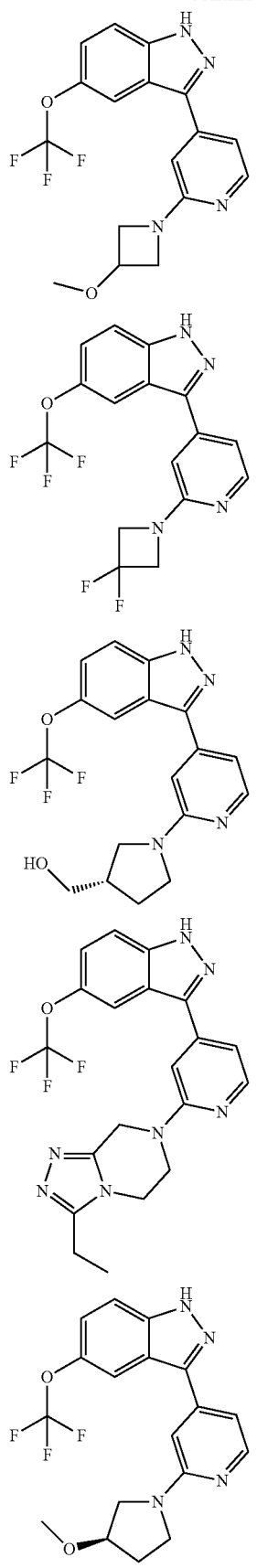
514
-continued
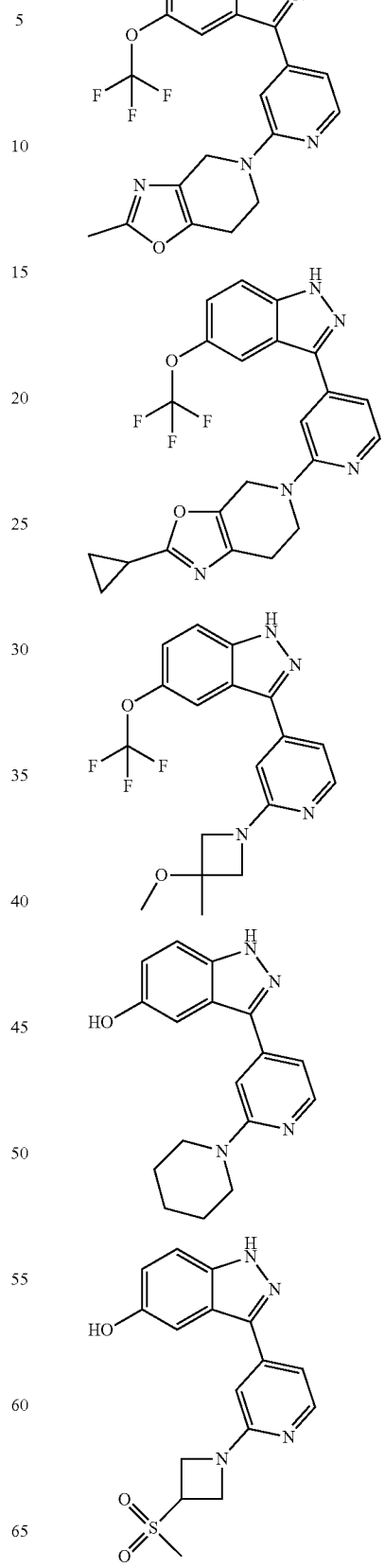

515
-continued
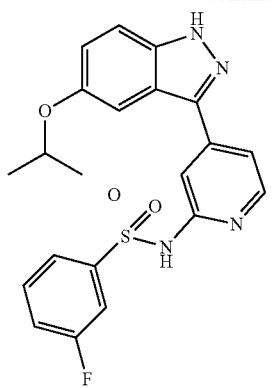
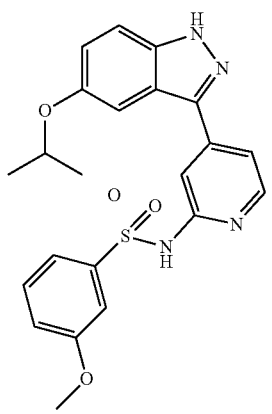
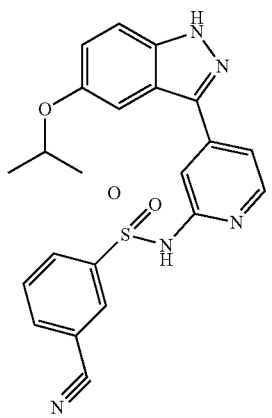
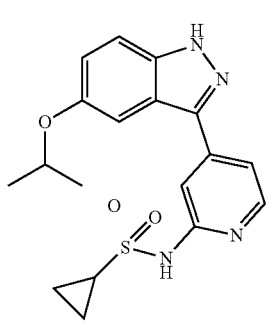
516
-continued
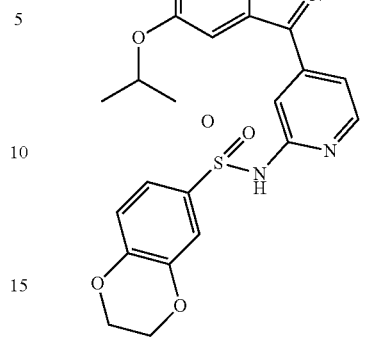
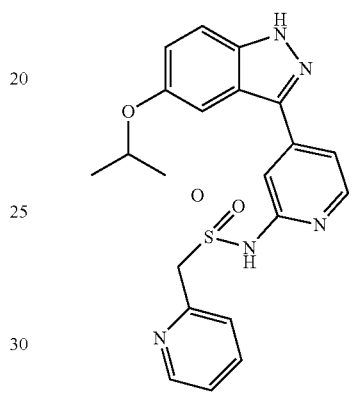
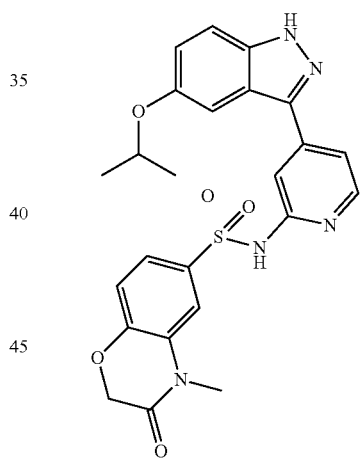
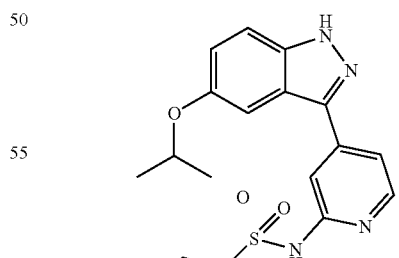

517
-continued
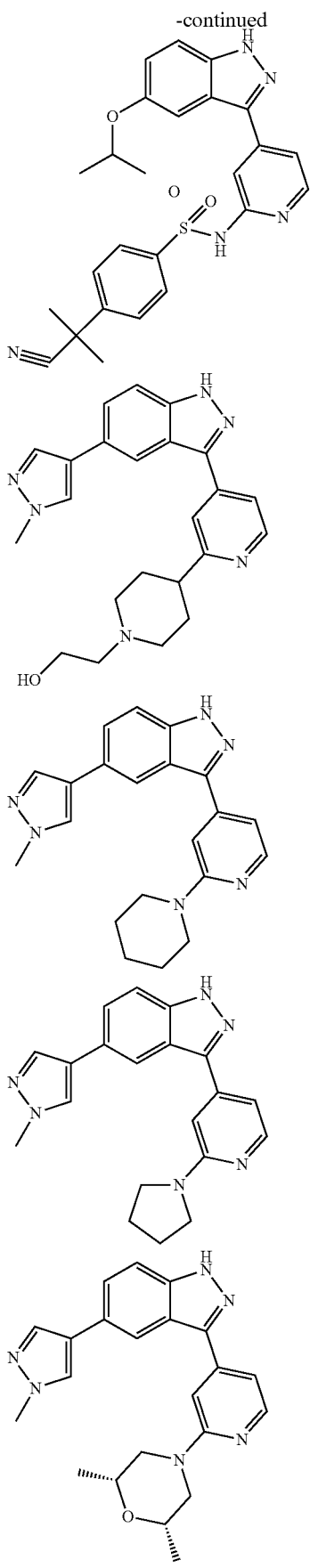
518
-continued
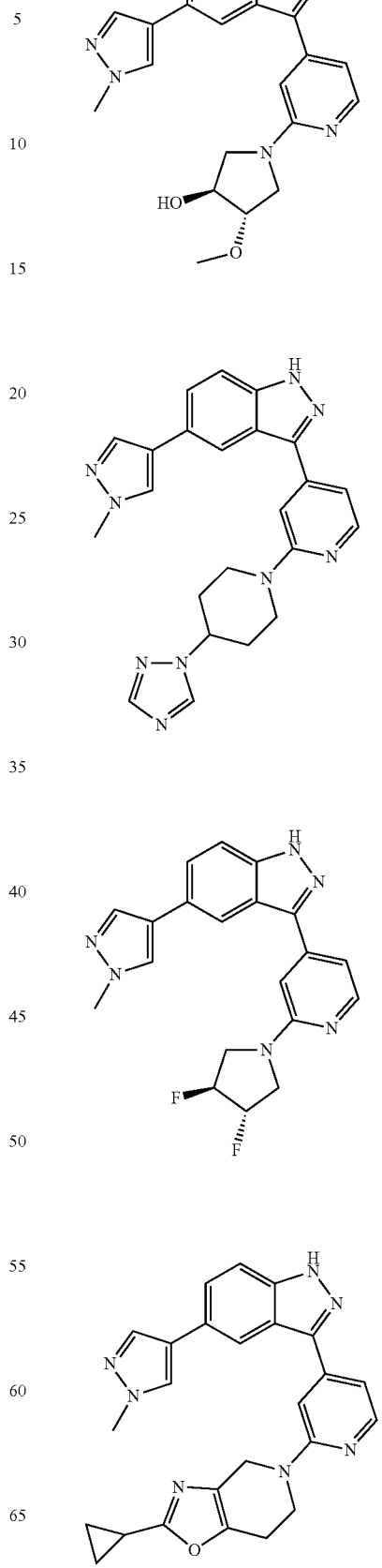

519
-continued
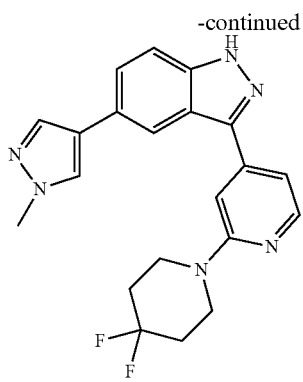
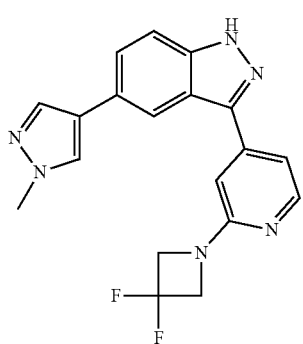
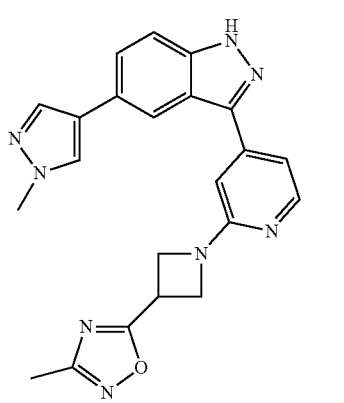
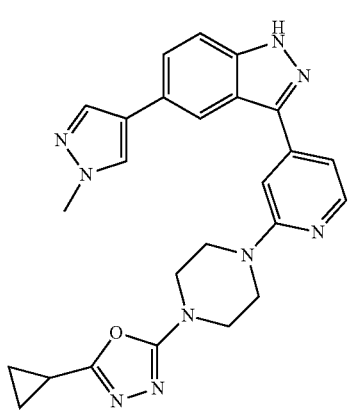
520
-continued
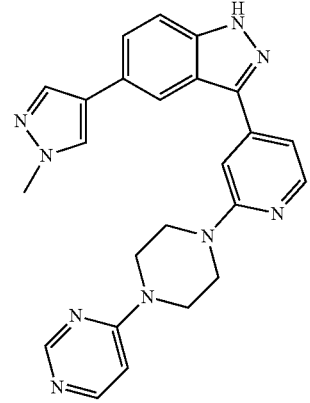

521
-continued
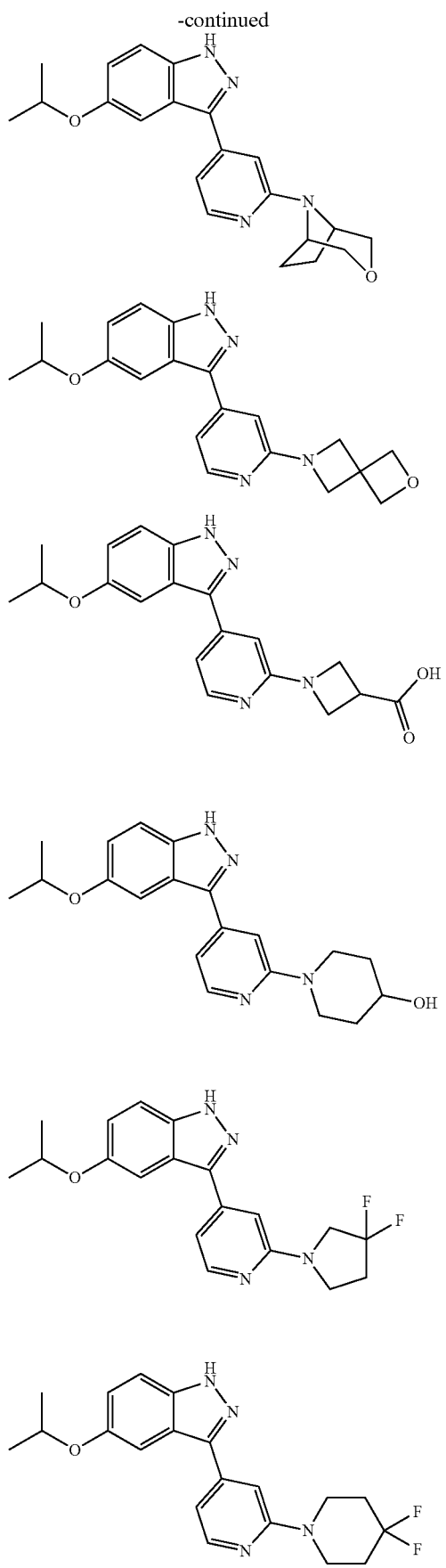
522
-continued
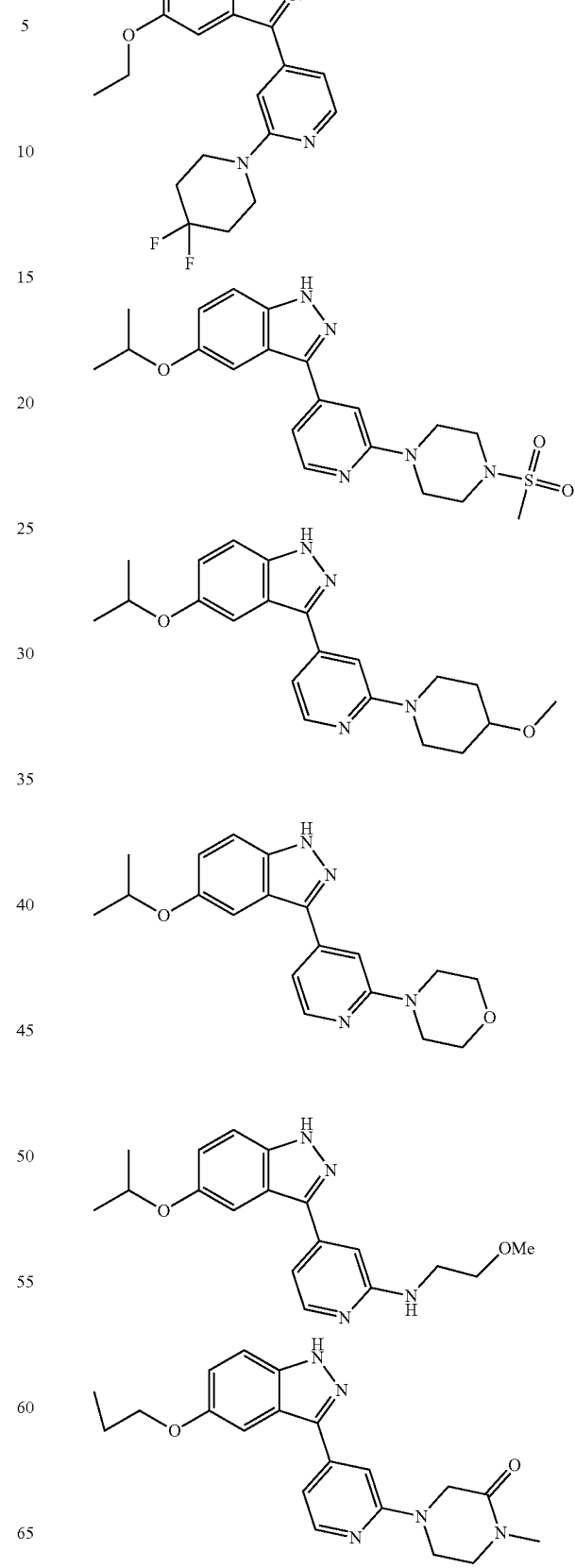

523
-continued
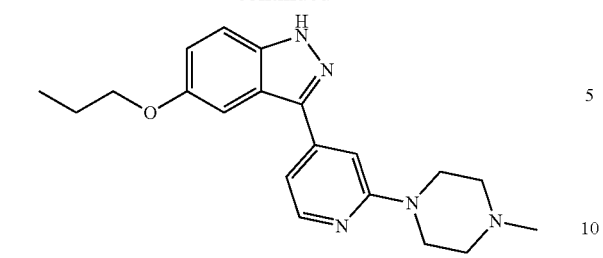
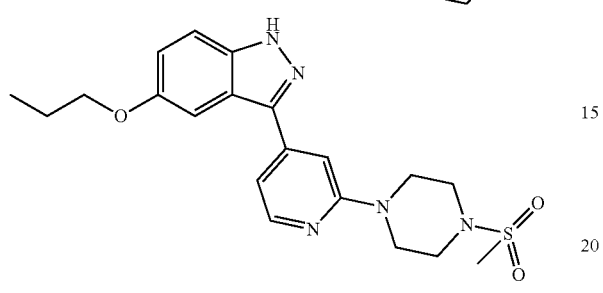
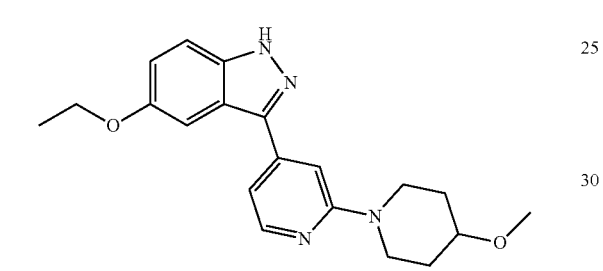
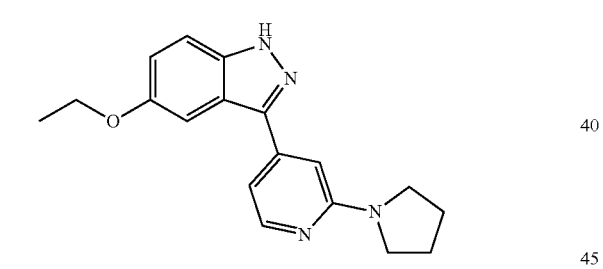
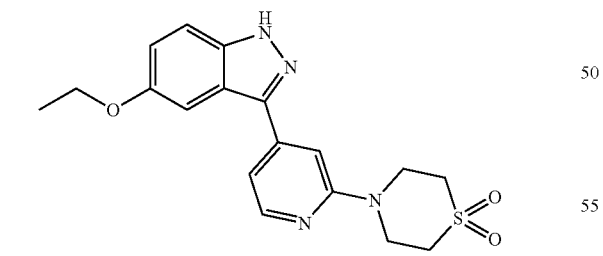
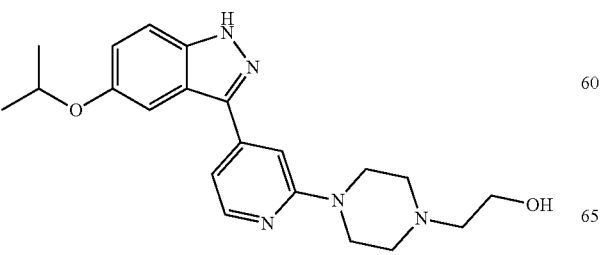
524
-continued
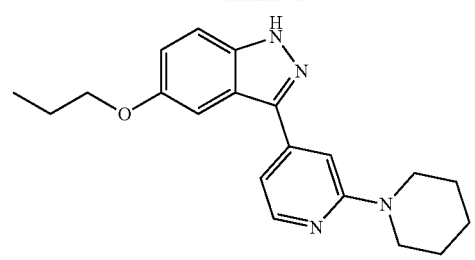
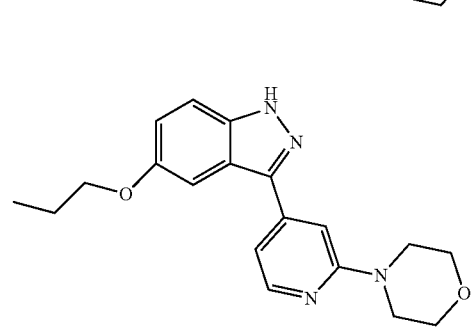
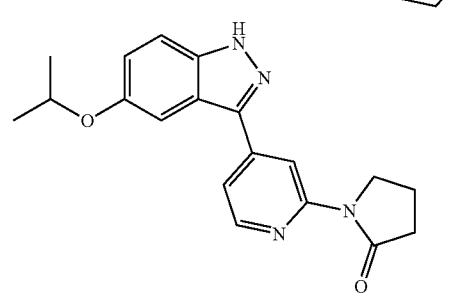
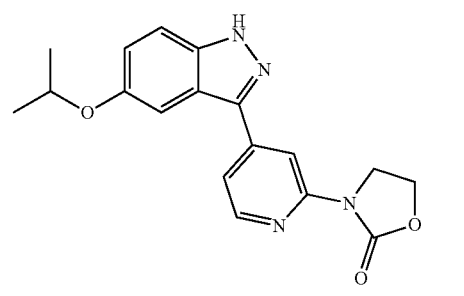
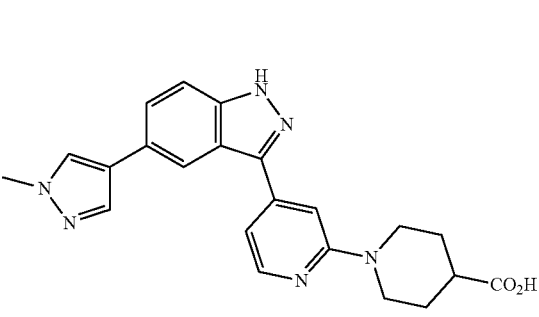
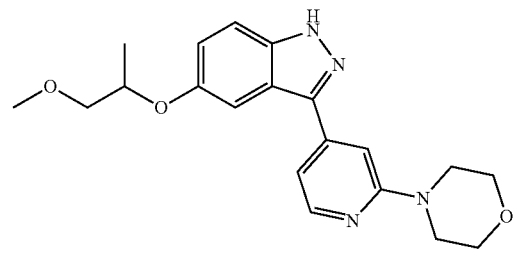

525
-continued
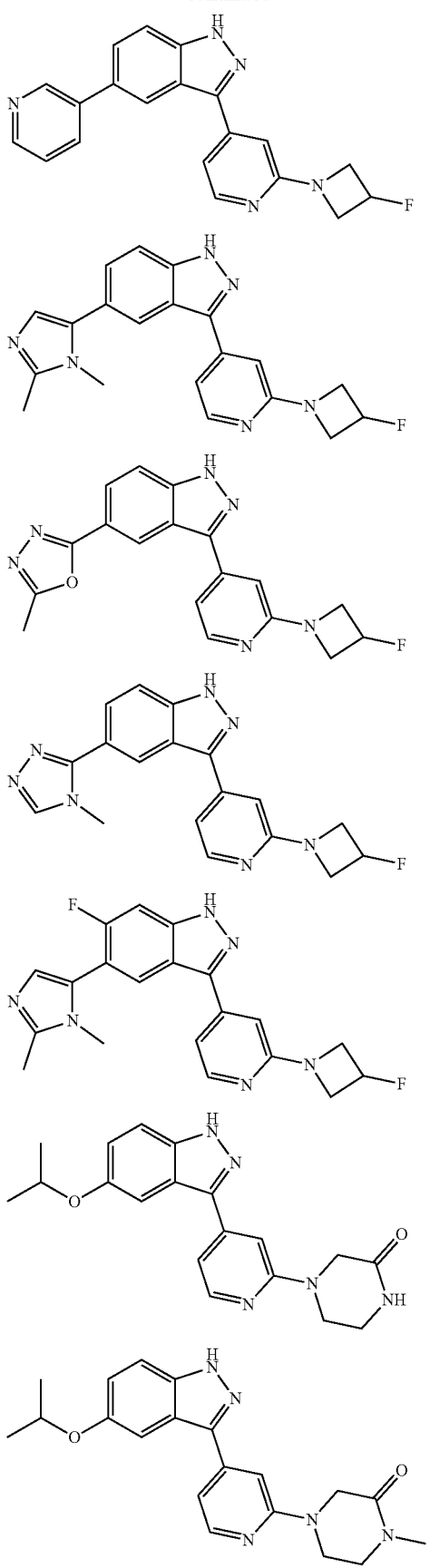
526
-continued
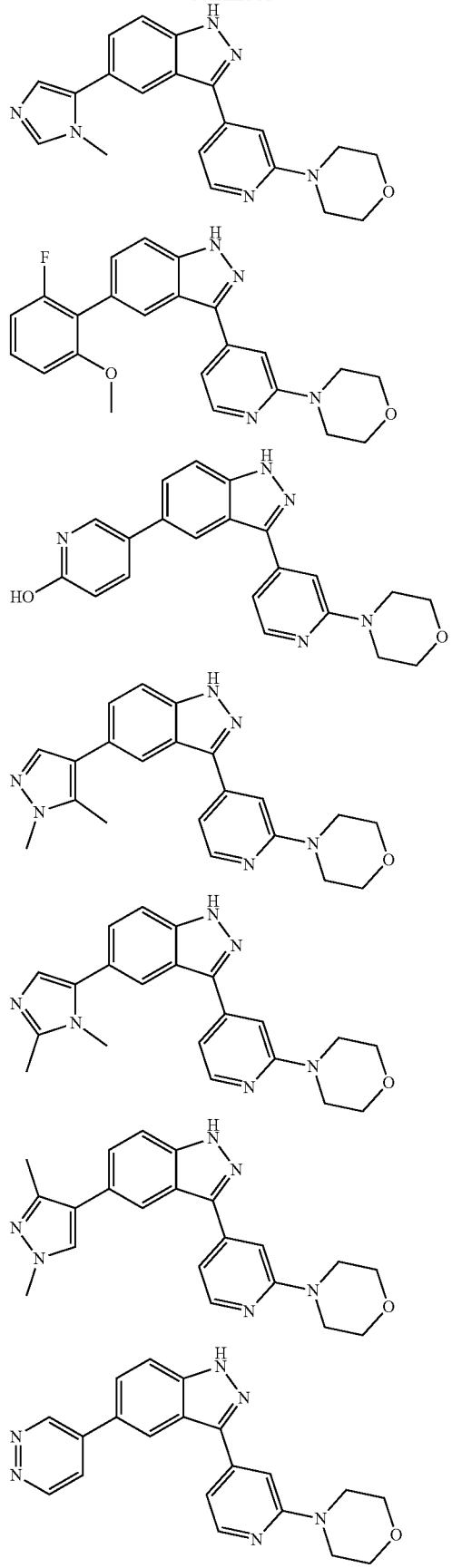

527
-continued
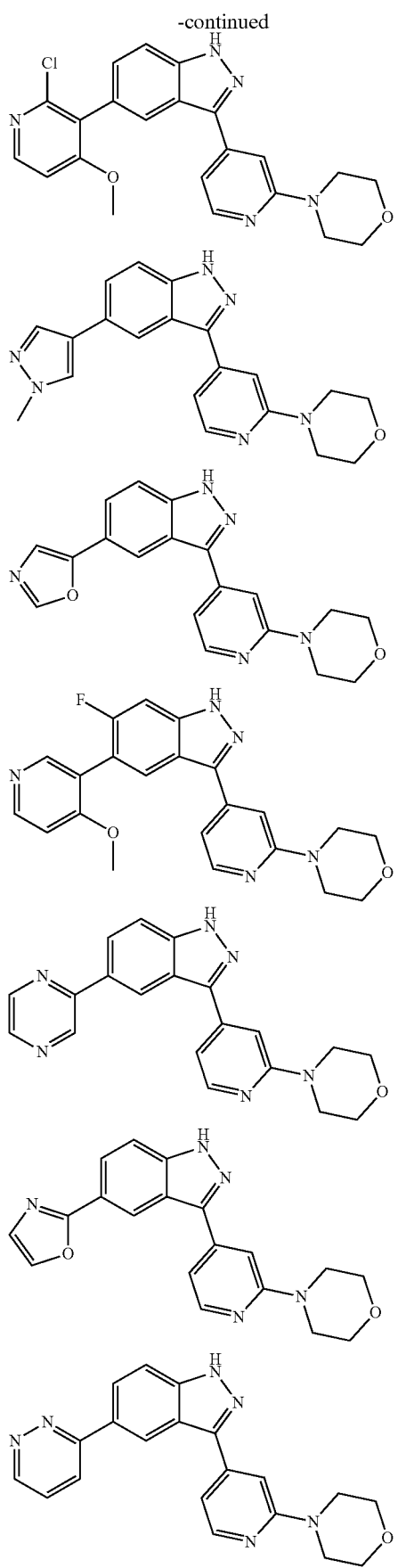
528
-continued
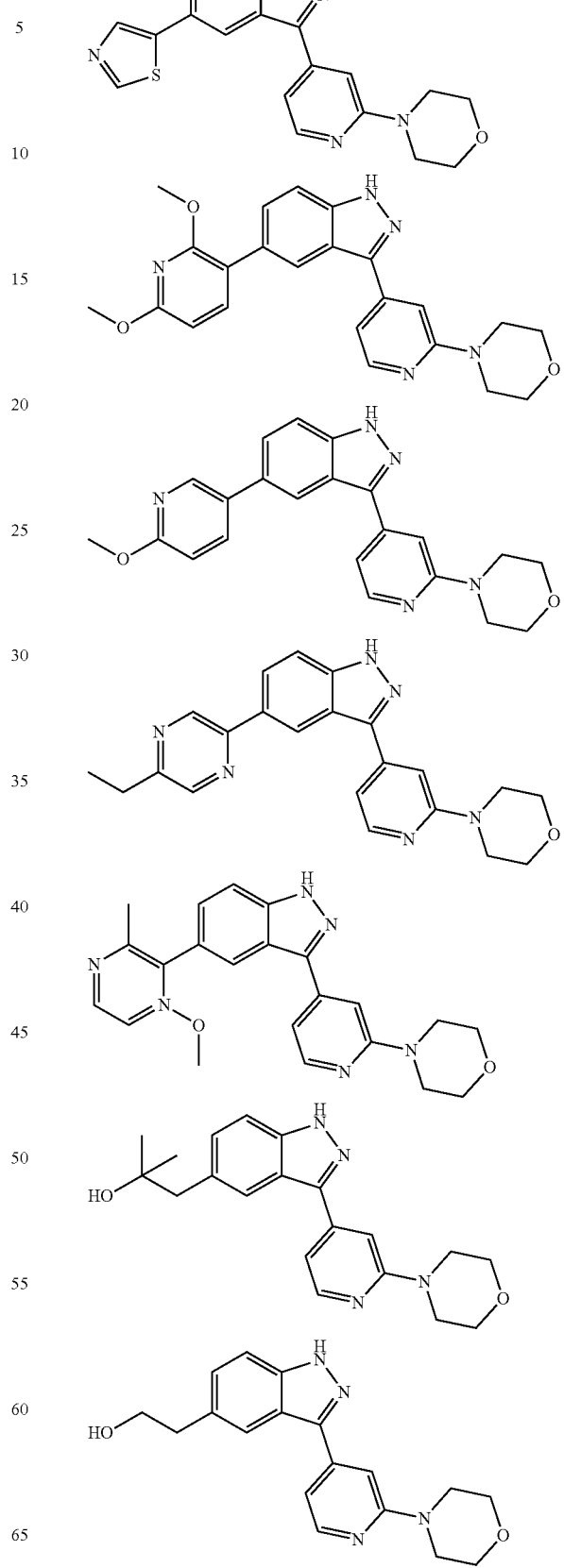

529
-continued
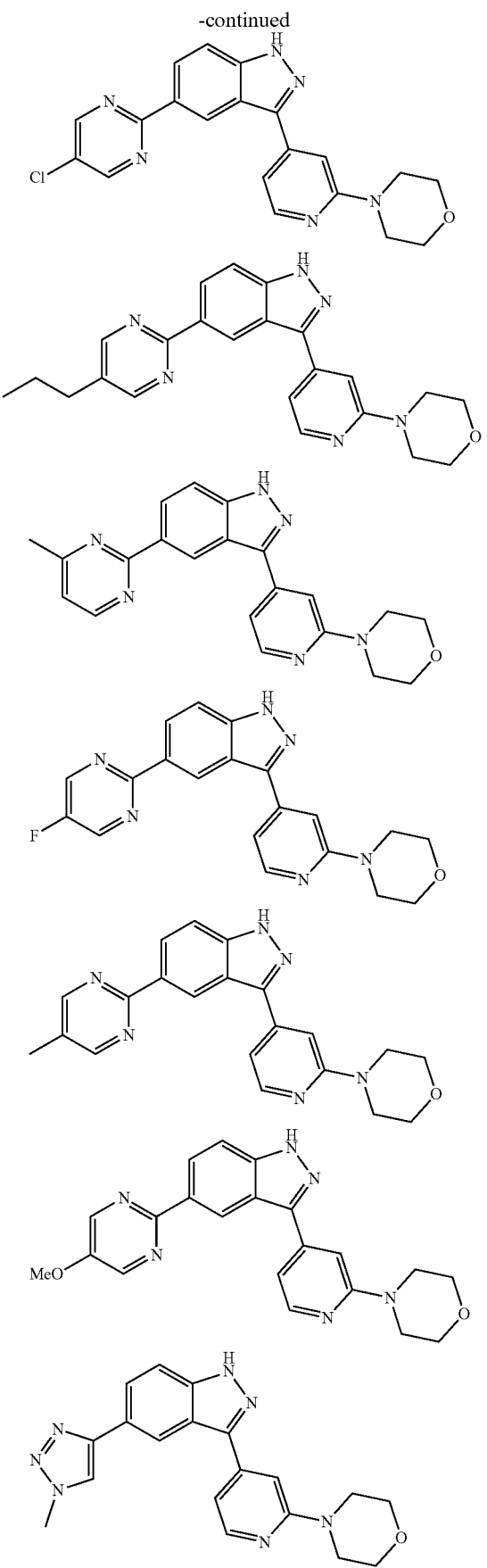
530
-continued
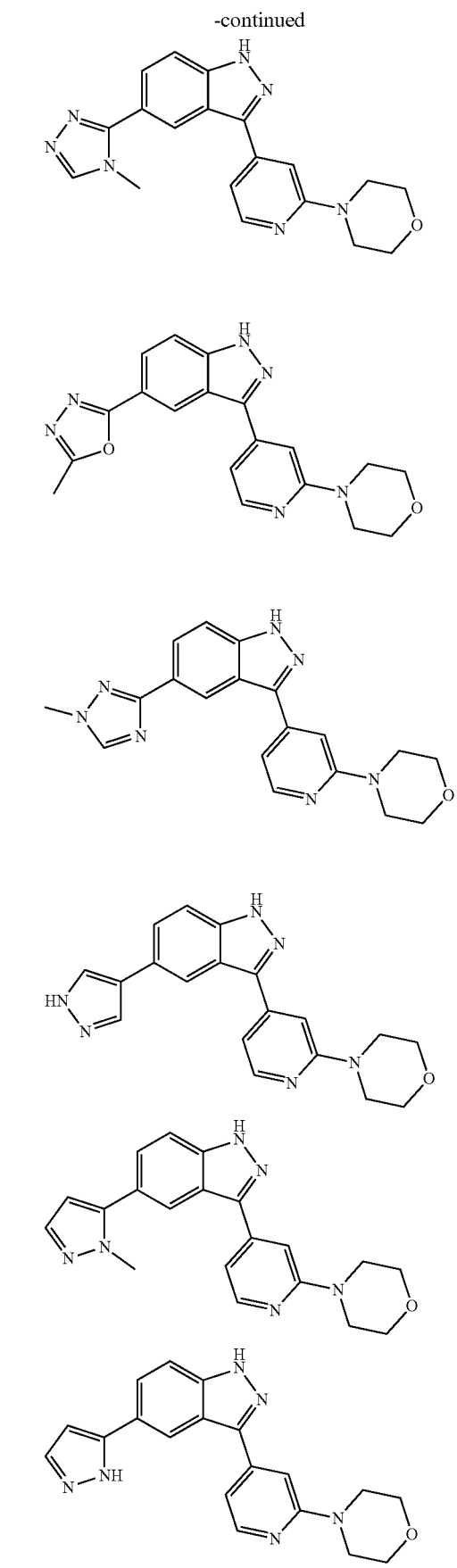

531
-continued
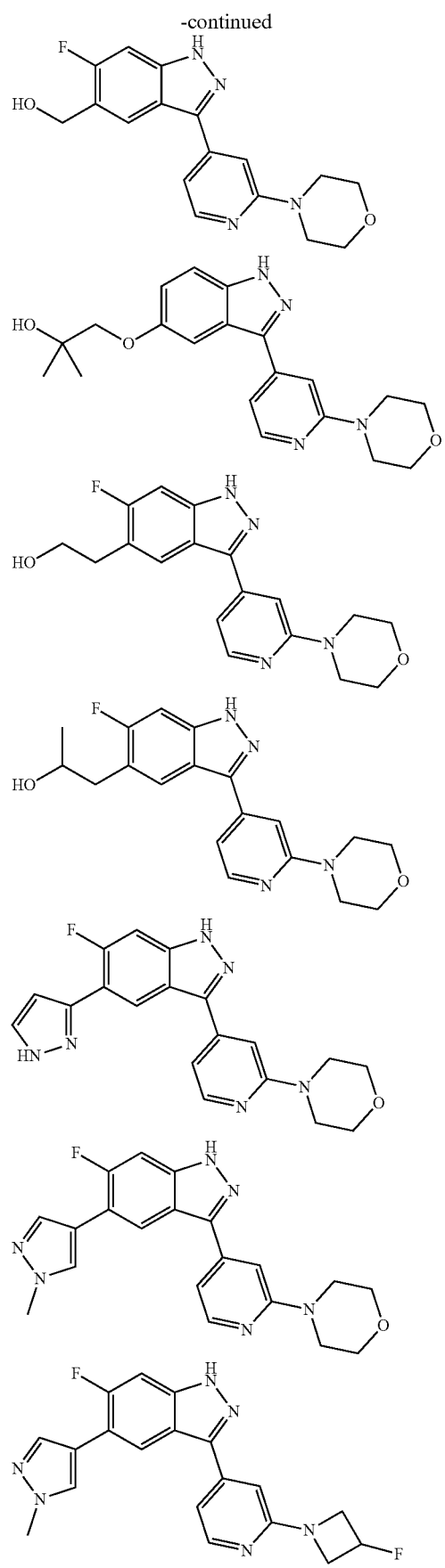
532
-continued
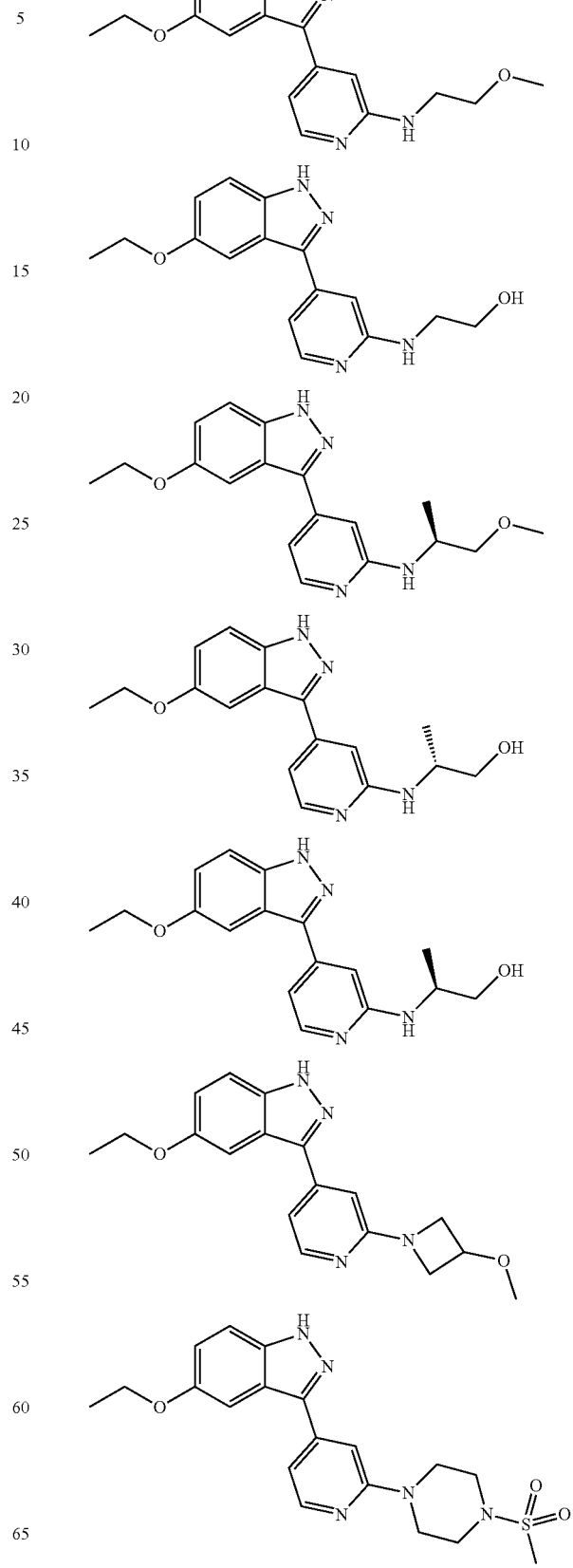

533
-continued
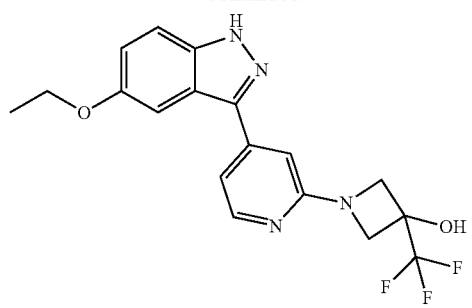
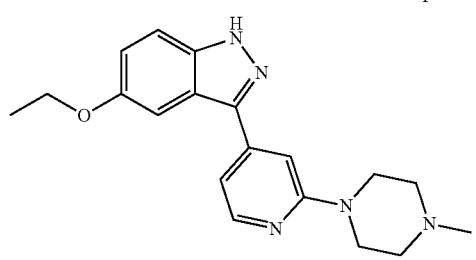
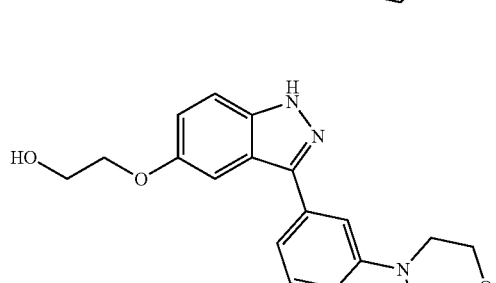
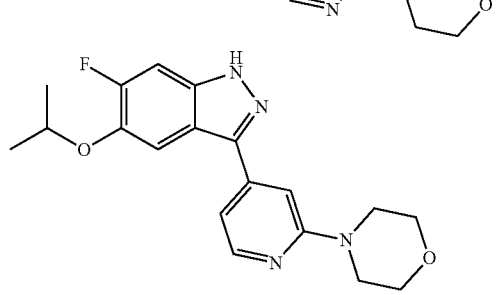
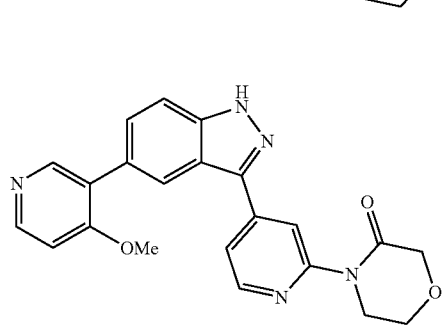
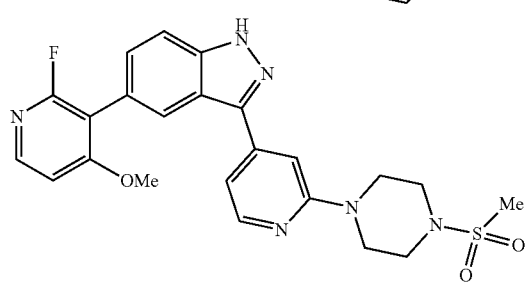
534
-continued
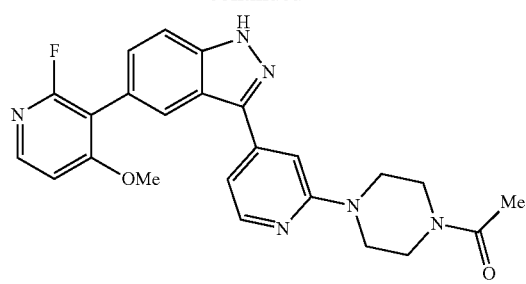
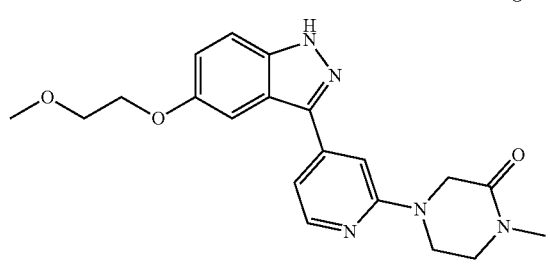
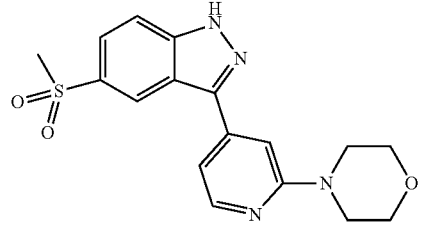
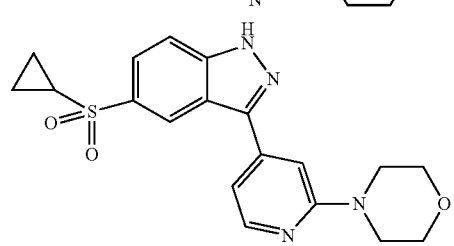
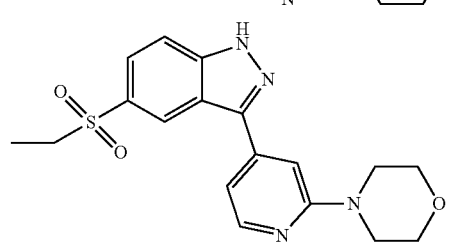
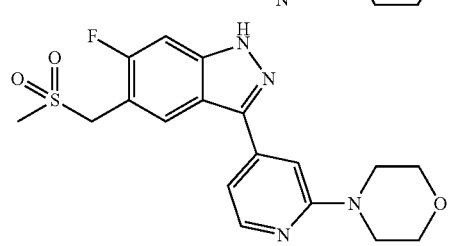
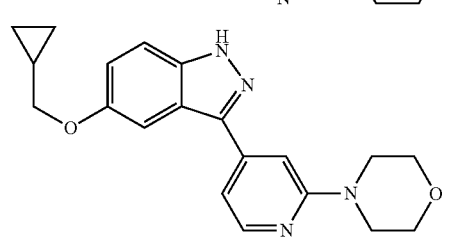

535
-continued
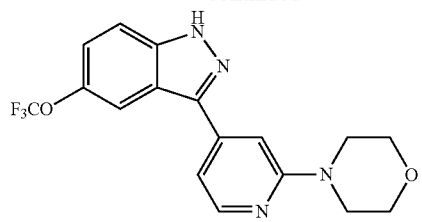
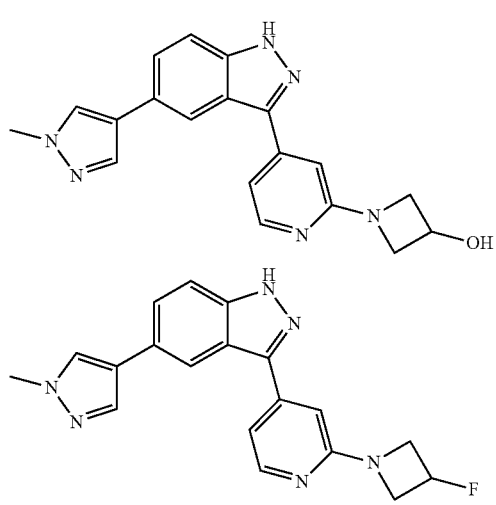
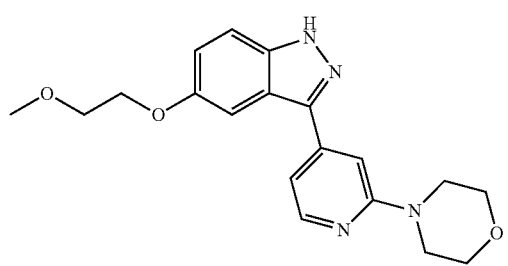
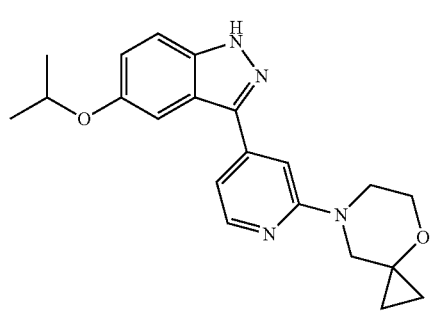
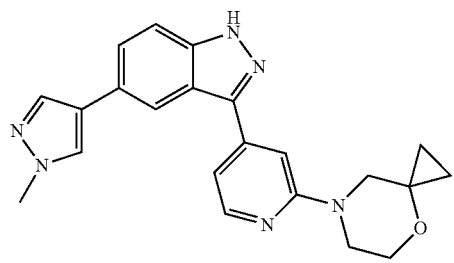
536
-continued
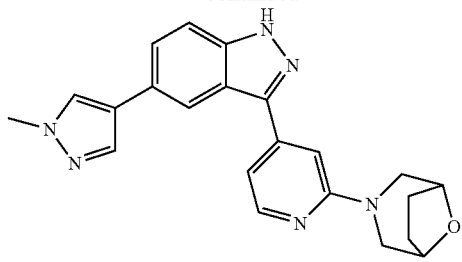
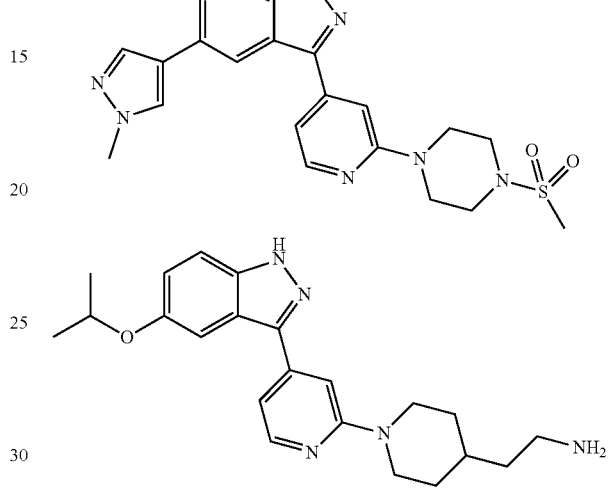
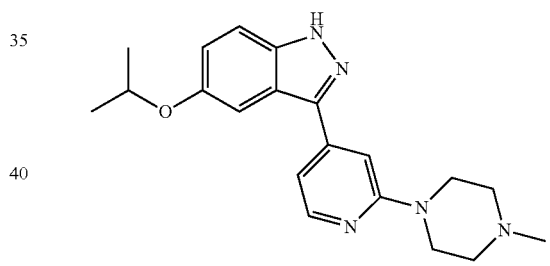
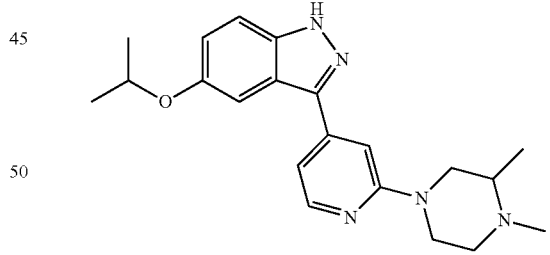
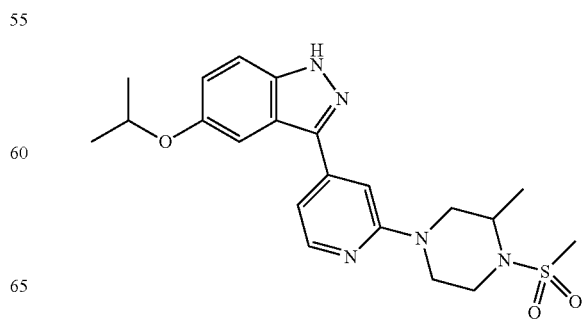

537
-continued
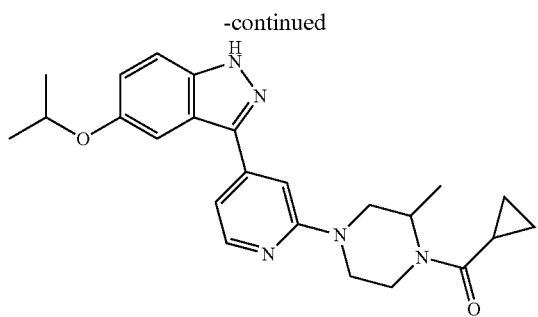
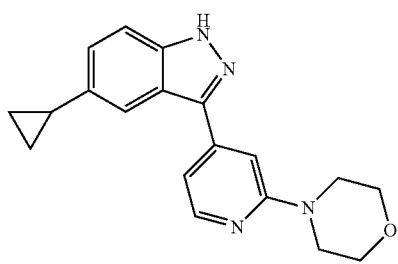
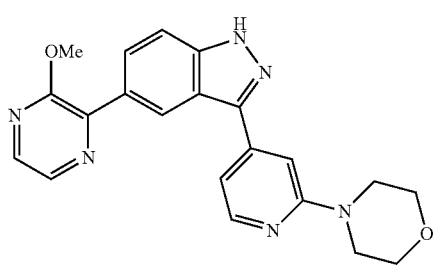
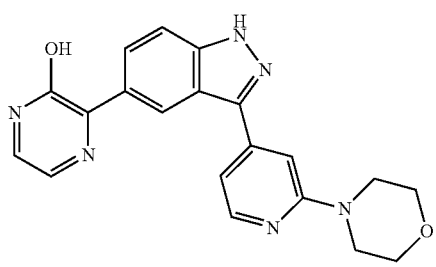
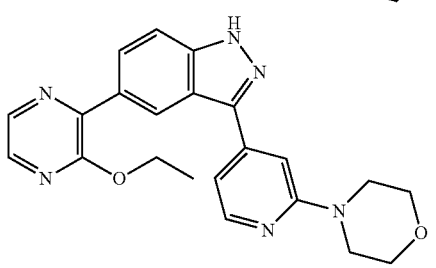
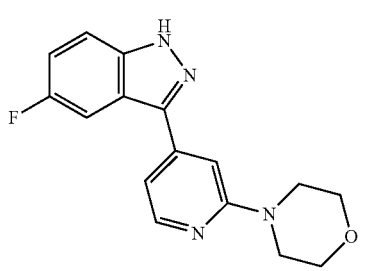
538
-continued
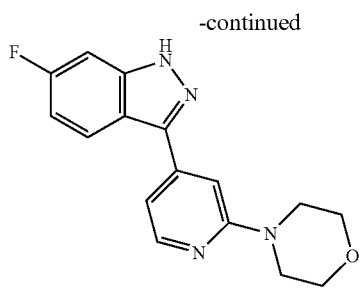
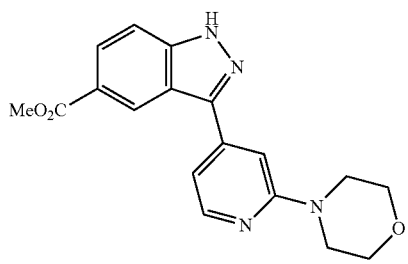
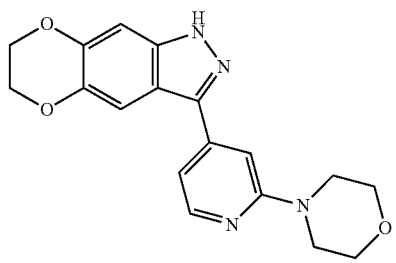
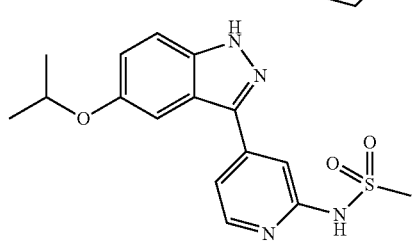
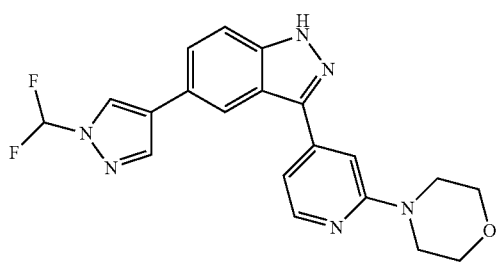
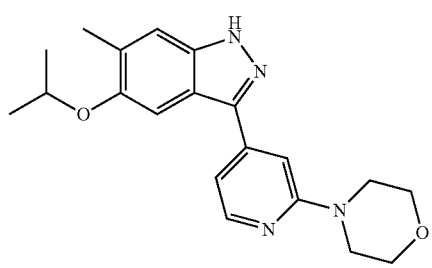

-continued
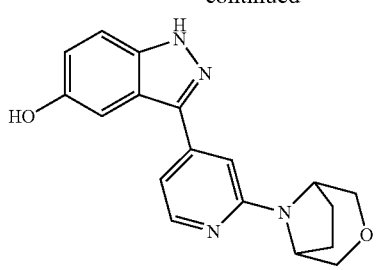
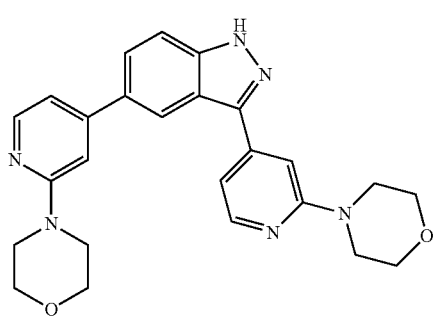
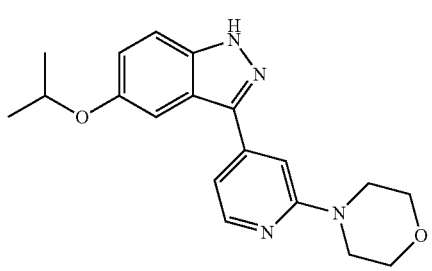
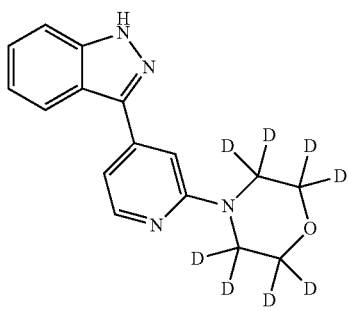
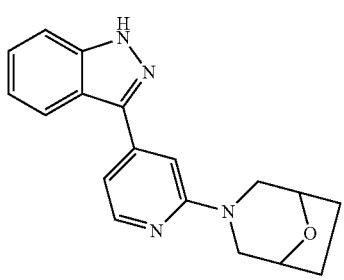
or a pharmaceutically acceptable salt thereof.
9. The compound of claim 8 selected from
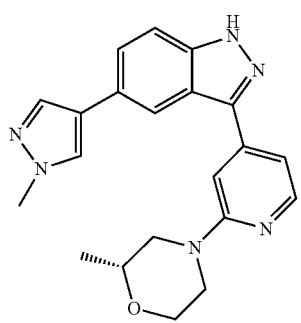
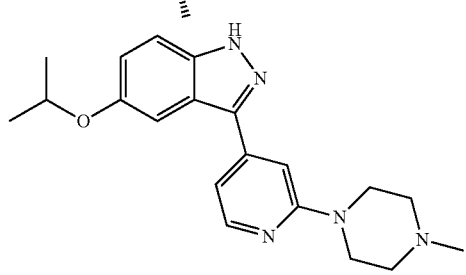
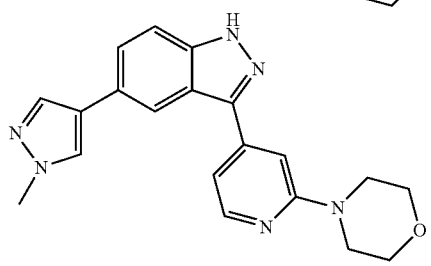
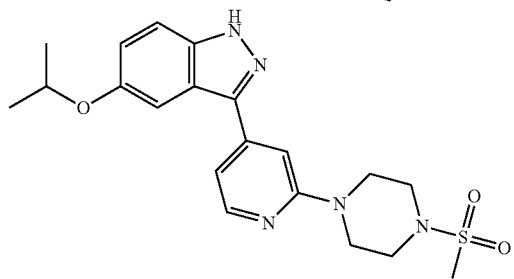
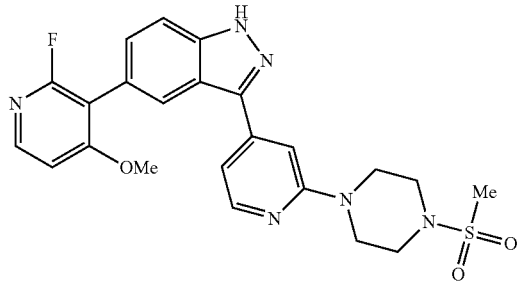
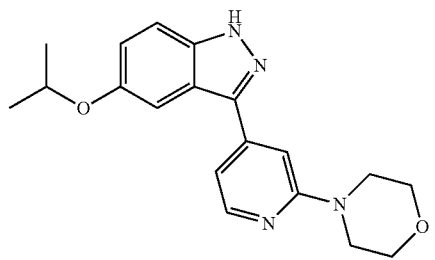

-continued

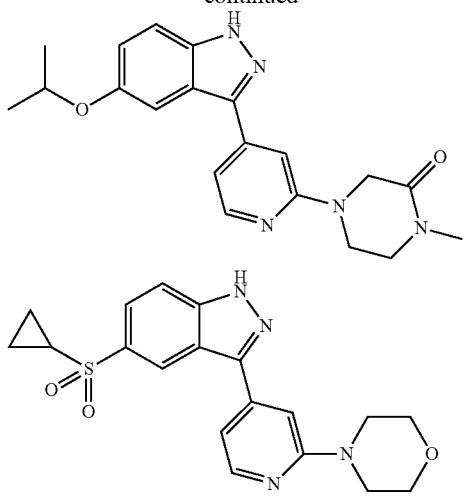

or a pharmaceutically acceptable salt thereof.

10. The compound of claim 9 selected from

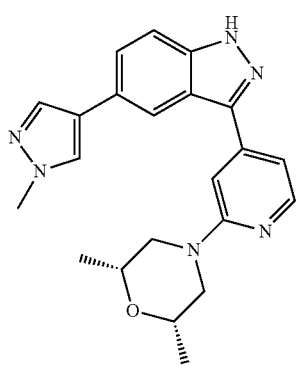

or a pharmaceutically acceptable salt thereof.

11. The compound of claim 9 selected from

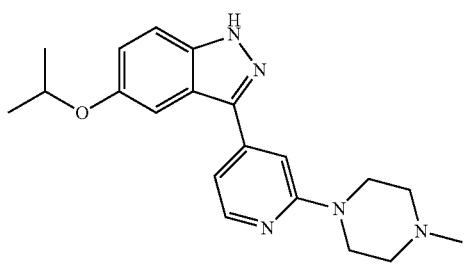 [SMILES: CC(C)Oc1ccc2[nH]nc(-c3ccnc(N4CCN(C)CC4)c3)c2c1]

or a pharmaceutically acceptable salt thereof.

12. The compound of claim 9 selected from

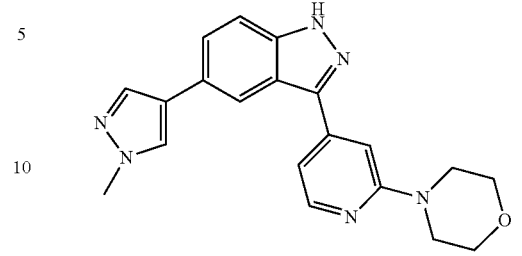

or a pharmaceutically acceptable salt thereof.

13. The compound of claim 9 selected from

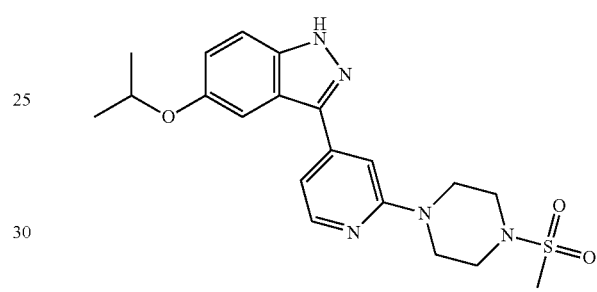

or a pharmaceutically acceptable salt thereof.

14. The compound of claim 9 selected from

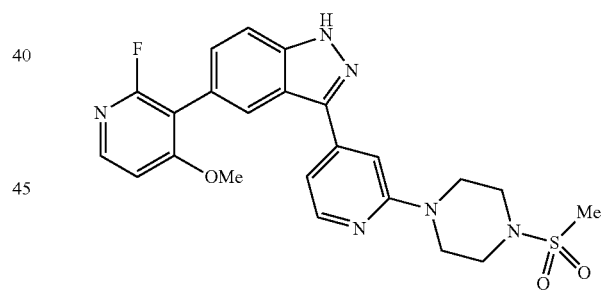

or a pharmaceutically acceptable salt thereof.

15. The compound of claim 9 selected from

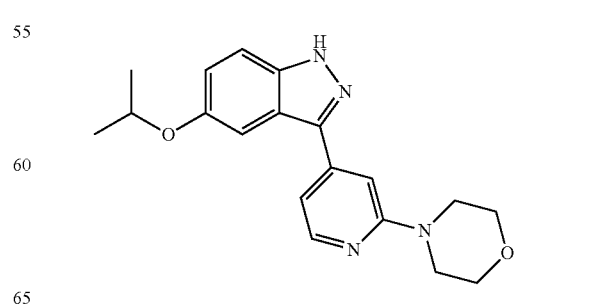

or a pharmaceutically acceptable salt thereof.

16. The compound of claim 9 selected from

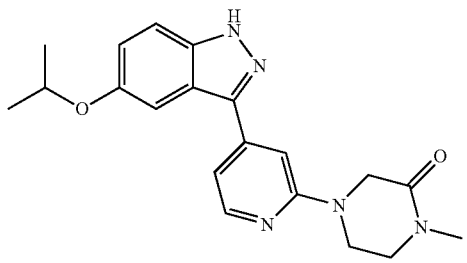 [SMILES: CC(C)Oc1ccc2[nH]nc(-c3ccnc(N4CCN(C)C(=O)C4)c3)c2c1]

or a pharmaceutically acceptable salt thereof.

17. The compound of claim 9 selected from

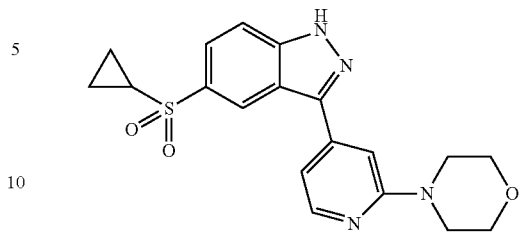

or a pharmaceutically acceptable salt thereof.

18. A pharmaceutical composition comprising a compound of claim 1, and a pharmaceutically acceptable carrier.

19. A method for the treatment of Parkinson's Disease comprising administering a compound of claim 1, or a pharmaceutical composition thereof, to a patient in need thereof.

* * * * *